United States Patent
Amiri et al.

(10) Patent No.: US 7,728,010 B2
(45) Date of Patent: *Jun. 1, 2010

(54) SUBSTITUTED BENZ-AZOLES AND METHODS OF THEIR USE AS INHIBITORS OF RAF KINASE

(75) Inventors: Payman Amiri, Walnut Creek, CA (US); Wendy Fantl, San Francisco, CA (US); Teresa Hansen, Danville, CA (US); Barry Haskell Levine, Lafayette, CA (US); Christopher McBride, Oakland, CA (US); Daniel J Poon, Oakland, CA (US); Savithri Ramurthy, Walnut Creek, CA (US); Paul A Renhowe, Danville, CA (US); Cynthia M Shafer, El Sobrante, CA (US); Sharadha Subramanian, San Ramon, CA (US); Leonard Sung, Irvine, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 947 days.

This patent is subject to a terminal disclaimer.

(21) Appl. No.: 11/282,939

(22) Filed: Nov. 18, 2005

(65) Prior Publication Data

US 2007/0299039 A1 Dec. 27, 2007

Related U.S. Application Data

(62) Division of application No. 10/405,945, filed on Mar. 31, 2003, now Pat. No. 7,071,216.

(60) Provisional application No. 60/369,066, filed on Mar. 29, 2002.

(51) Int. Cl.
*A61K 31/423* (2006.01)
*A61K 31/4439* (2006.01)
*C07D 263/58* (2006.01)
*C07D 413/12* (2006.01)

(52) U.S. Cl. .................... 514/338; 514/375; 546/271.7; 548/222

(58) Field of Classification Search ....................... None
See application file for complete search history.

(56) References Cited

U.S. PATENT DOCUMENTS

| 6,211,177 B1 | 4/2001 | Sperl |
| 6,248,771 B1 | 6/2001 | Shenoy |
| 6,399,603 B1 | 6/2002 | Jacobs |
| 6,417,194 B1 | 7/2002 | Fox |

FOREIGN PATENT DOCUMENTS

| EP | 1346982 A1 | 9/2003 |
| WO | 0021927 A2 | 4/2000 |
| WO | 0062778 A1 | 10/2000 |
| WO | 0166539 A1 | 9/2001 |
| WO | 0242273 A2 | 5/2002 |
| WO | 0244156 A2 | 6/2002 |
| WO | 02053534 A1 | 7/2002 |
| WO | 02076960 A1 | 10/2002 |
| WO | 02094808 A1 | 11/2002 |
| WO | 03053939 A1 | 7/2003 |
| WO | 03074515 A1 | 9/2003 |
| WO | 03082272 A1 | 10/2003 |
| WO | 2004085425 A1 | 10/2004 |

OTHER PUBLICATIONS

Kruse, L.I., et al., "Synthesis, Tubulin Binding, Antineoplastic Evaluation, and Structure-Activity Relationship of Oncodazole Analogues," J. Med. Chem. 32:409-417, 1989.
Notice of Reasons for Rejection mailed Sep. 29, 2009, in corresponding Application JP No. 2003-579810, filed Mar. 31, 2003.

*Primary Examiner*—Laura L. Stockton
(74) *Attorney, Agent, or Firm*—Christensen O'Connor Johnson Kindness PLLC; George Dohmann

(57) ABSTRACT

New substituted benz-azole compounds, compositions and methods of inhibition of Raf kinase activity in a human or animal subject are provided. The new compounds compositions may be used either alone or in combination with at least one additional agent for the treatment of a Raf kinase mediated disorder, such as cancer.

40 Claims, No Drawings

SUBSTITUTED BENZ-AZOLES AND METHODS OF THEIR USE AS INHIBITORS OF RAF KINASE

CROSS-REFERENCE TO RELATED APPLICATION

This application is a divisional of U.S. application Ser. No. 10/405,945, filed Mar. 31, 2003, now U.S. Pat. No. 7,071,216, which claims the benefit of U.S. Provisional Application No. 60/369,066, filed Mar. 29, 2002, each incorporated herein by reference in its entirety.

FIELD OF THE INVENTION

The present invention relates to new substituted benz-azole-like compounds and pharmaceutically acceptable salts, esters or prodrugs thereof, compositions of the new compounds together with pharmaceutically acceptable carriers, and uses of the new compounds, either alone or in combination with at least one additional therapeutic agent, in the prophylaxis or treatment of cancer.

BACKGROUND OF THE INVENTION

The Raf serine/threonine kinases are essential components of the Ras/Mitogen-Activated Protein Kinase (MAPK) signaling module that controls a complex transcriptional program in response to external cellular stimuli. Raf genes code for highly conserved serine-threonine-specific protein kinases which are known to bind to the ras oncogene. They are part of a signal transduction pathway believed to consist of receptor tyrosine kinases, p21 ras, Raf protein kinases, Mek1 (ERK activator or MAPKK) kinases and ERK (MAPK) kinases, which ultimately phosphorylate transcription factors. In this pathway Raf kinases are activated by Ras and phosphorylate and activate two isoforms of Mitogen-Activated Protein Kinase (called Mek1 and Mek2), that are dual specificity threonine/tyrosine kinases. Both Mek isoforms activate Mitogen Activated Kinases 1 and 2 (MAPK, also called Extracellular Ligand Regulated Kinase 1 and 2 or Erk1 and Erk2). The MAPKs phosphorylate many substrates including transcription factors and in so doing set up their transcriptional program. Raf kinase participation in the Ras/MAPK pathway influences and regulates many cellular functions such as proliferation, differentiation, survival, oncogenic transformation and apoptosis.

Both the essential role and the position of Raf in many signaling pathways have been demonstrated from studies using deregulated and dominant inhibitory Raf mutants in mammalian cells as well as from studies employing biochemical and genetic techniques model organisms. In many cases, the activation of Raf by receptors that stimulate cellular tyrosine phosphorylation is dependent on the activity of Ras, indicating that Ras functions upstream of Raf. Upon activation, Raf-1 then phosphorylates and activates Mek1, resulting in the propagation of the signal to downstream effectors, such as MAPK (mitogen-activated protein kinase) (Crews et al. (1993) Cell 74:215). The Raf serine/threonine kinases are considered to be the primary Ras effectors involved in the proliferation of animal cells (Avruch et al. (1994) Trends Biochem. Sci. 19:279).

Raf kinase has three distinct isoforms, Raf-1 (c-Raf), A-Raf, and B-Raf, distinguished by their ability to interact with Ras, to activate MAPK kinase pathway, tissue distribution and sub-cellular localization (Marias et. Al., Biochem. J. 351: 289-305, 2000; Weber et. al., Oncogene 19:169-176, 2000; Pritchard et. al., Mol. Cell. Biol. 15:6430-6442, 1995). Raf kinases are activated by Ras and phosphorylate and activate two isoforms of Mitogen-Activated Protein Kinase (called Mek1 and Mek2) that are dual specificity threonine/tyrosine kinases. Both Mek isoforms activate Mitogen Activated Kinases 1 and 2 (MAPK, also called Extracellular Ligand Regulated Kinase 1 and 2 or Erk1 and Erk2). The MAPKs phosphorylate many substrates including cytosolic proteins and ETS family of transcription factors. Raf kinase participation in the Ras/MAPK pathway influences and regulates many cellular functions such as proliferation, differentiation, survival, cell cycle progression and apoptosis.

Activating mutation of one of the Ras genes can be seen in ~20% of all tumors and the Raf/MEK/ERK pathway is activated in ~30% of all tumors (Bos et. al., Cancer Res. 49:4682-4689, 1989) (Hoshino et. al., Oncogene 18:813-822, 1999). Recent studies have shown that B-Raf mutation in the skin nevi is a critical step in the initiation of melanocytic neoplasia (Pollock et. al., Nature Genetics 25: 1-2, 2002). Furthermore, most recent studies have emerged that activating mutation in the kinase domain of B-Raf occurs in ~66% of melanomas, 12% of colon carcinoma and 14% of liver cancer (Davies et. al., Nature 417:949-954, 2002) (Yuen et. al., Cancer Research 62:6451-6455, 2002) (Brose et. al., Cancer Research 62:6997-7000, 2002).

Inhibitors of Raf/MEK/ERK pathway at the level of Raf kinases can potentially be effective as therapeutic agents against tumors with over-expressed or mutated receptor tyrosine kinases, activated intracellular tyrosine kinases, tumors with aberrantly expressed Grb2 (an adapter protein that allows stimulation of Ras by the Sos exchange factor) as well as tumors harboring activating mutations of Raf itself. In the early clinical trails inhibitor of Raf-1 kinase that also inhibit B-Raf have shown promise as therapeutic agents in cancer therapy (Crump, Current Pharmaceutical Design 8: 2243-2248, 2002; Sebastien et. al., Current Pharmaceutical Design 8: 2249-2253, 2002).

Disruption of Raf expression in cell lines through the application of RNA antisense technology has been shown to suppress both Ras and Raf-mediated tumorigenicity (Kolch et al., Nature 349:416-428, 1991; Monia et al., Nature Medicine 2(6):668-675, 1996).

Several Raf kinase inhibitors have been described as exhibiting efficacy in inhibiting tumor cell proliferation in vitro and/or in vivo assays (see, e.g., U.S. Pat. Nos. 6,391,636, 6,358,932, 6,037,136, 5,717,100, 6,458,813, 6,204,467, and 6,268,391). Other patents and patent applications suggest the use of Raf kinase inhibitors for treating leukemia (see, e.g., U.S. Pat. Nos. 6,268,391, and 6,204,467, and published U.S. Patent Application Nos. 20020137774; 20020082192; 20010016194; and 20010006975), or for treating breast cancer (see, e.g., U.S. Pat. Nos. 6,358,932, 5,717,100, 6,458,813, 6,268,391, and 6,204,467, and published U.S. Patent Application No. 20010014679).

SUMMARY OF THE INVENTION

New substituted benz-azole compounds and pharmaceutically acceptable salts thereof or esters having a solubility enhancing moieties or prodrugs thereof are provided of the formula (I):

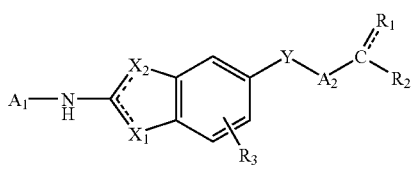
(I)

wherein, $X_1$ and $X_2$ are independently selected from =N—, —$NR_4$—, —O— or —S—, provided that if $X_1$ is —$NR_4$—, —O— or —S—, then $X_2$ is =N—, or if $X_2$ is —$NR_4$—, —O— or —S—, then $X_2$ is =N—, and both $X_1$ and $X_2$ are not =N—;

Y is O or S;

$A_1$ is substituted or unsubstituted alkyl, cycloalkyl, heterocycloalkyl, aryl, polycyclic aryl, polycyclic arylalkyl, heteroaryl, biaryl, heteroarylaryl, heteroarylheteroaryl, cycloalkylalkyl, heterocycloalkylalkyl, arylalkyl, heteroarylalkyl, biarylalkyl, or heteroarylarylalkyl;

$A_2$ is substituted or unsubstituted heteroaryl;

$R_1$ is O or H, and $R_2$ is $NR_5R_6$ or hydroxyl; or $R_1$ is taken together with $R_2$ to form a substituted or unsubstituted heterocycloalkyl or heteroaryl group; wherein, the dashed line represents a single or double bond;

$R_3$ is hydrogen, halogen, loweralkyl, or loweralkoxy;

$R_4$ is hydrogen, hydroxyl, alkylamino, dialkylamino or alkyl;

$R_5$ and $R_6$ are independently selected from hydrogen, and substituted or unsubstituted alkyl, alkoxyalkyl, aminoalkyl, amidoalkyl, acyl, cycloalkyl, heterocycloalkyl, aryl, heteroaryl, alkyloxyalkylheterocyclo, and heteroarylalkyl; or $R_5$ and $R_6$ are taken together to form substituted or unsubstituted heterocyclo or heteroaryl; and the pharmaceutically acceptable salts, esters and prodrugs thereof.

In other embodiments, new substituted benz-azole compounds are provided of the formula (II):

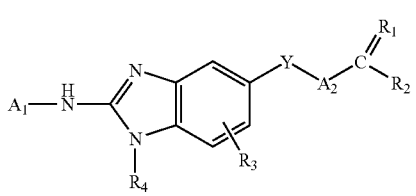
(II)

wherein and Y, $Ar_1$, $Ar_2$, $R_1$, $R_2$, $R_3$ and $R_4$ are as defined above; and the pharmaceutically acceptable salts, esters, and prodrugs thereof.

In other embodiments, new substituted benz-azole compounds are provided of the formula (III):

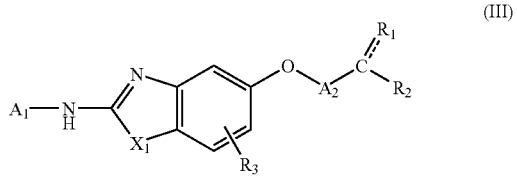
(III)

wherein $X_1$, $Ar_1$, $Ar_2$, $R_1$, $R_2$ and $R_3$ are as defined above; and the pharmaceutically acceptable salts, esters, tautomers and prodrugs thereof.

In other embodiments, new substituted benz-azole compounds are provided of the formula (IV):

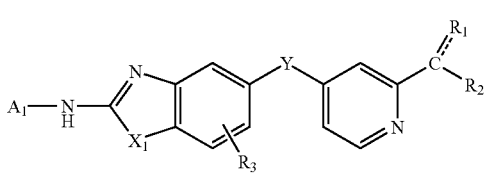
(IV)

wherein $X_1$, Y, $Ar_1$, $R_1$, $R_2$ and $R_3$ are as defined above; and the pharmaceutically acceptable salts, esters, tautomers and prodrugs thereof.

In yet other embodiments, new substituted benz-azole compounds are provided of the formula (V):

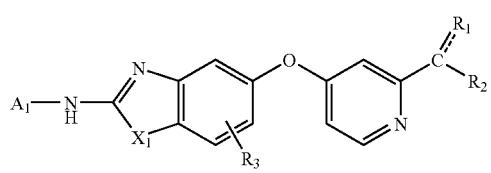
(V)

wherein $X_1$, $Ar_1$, $R_1$, $R_2$ and $R_3$ are as defined above; and the pharmaceutically acceptable salts, esters, tautomers and prodrugs thereof.

In other aspects, the present invention provides methods for treating Raf related disorders in a human or animal subject in need of such treatment comprising administering to said subject an amount of a compound of formula (I), (II), (III), (IV) or (V) effective to reduce or prevent tumor growth in the subject.

In yet other aspects, the present invention provides methods for treating Raf related disorders in a human or animal subject in need of such treatment comprising administering to said subject an amount of a compound of formula (I), (II), (III), (IV) or (V) effective to reduce or prevent tumor growth in the subject in combination with at least one additional agent for the treatment of cancer.

In yet other aspects, the present invention provides therapeutic compositions comprising at least one compound of formula (I), (II), (III), (IV) or (V) in combination with one or more additional agents for the treatment of cancer, as are commonly employed in cancer therapy.

The compounds of the invention are useful in the treatment of cancers, including carcinomas (e.g., of the lungs, pancreas, thyroid, bladder or colon), myeloid disorders (e.g., myeloid leukemia) and adenomas (e.g., villous colon adenoma).

The invention further provides compositions, methods of use, and methods of manufacture as described in the detailed description of the invention.

DETAILED DESCRIPTION OF THE PREFERRED EMBODIMENT

In accordance with one aspect of the present invention, new substituted benz-azole compounds and pharmaceutically acceptable salts, esters or prodrugs thereof are provided of the formula (I):

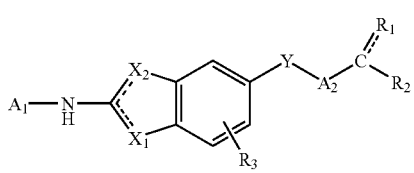

(I)

wherein, $X_1$ and $X_2$ are independently selected from $=N-$, $-NR_4-$, $-O-$ or $-S-$, provided that if $X_1$ is $-NR_4-$, $-O-$ or $-S-$, then $X_2$ is $=N-$, or if $X_2$ is $-NR_4-$, $-O-$ or $-S-$, then $X_1$ is $=N-$, and both $X_1$ and $X_2$ are not $=N-$; Y is O or S;

Y is O or S;

$A_1$ is substituted or unsubstituted alkyl, cycloalkyl, heterocycloalkyl, aryl, polycyclic aryl, polycyclic arylalkyl, heteroaryl, biaryl, heteroarylaryl, heteroarylheteroaryl, cycloalkylalkyl, heterocycloalkylalkyl, arylalkyl, heteroarylalkyl, biarylalkyl, or heteroarylarylalkyl;

$A_2$ is substituted or unsubstituted heteroaryl;

$R_1$ is O or H, and $R_2$ is $NR_5R_6$ or hydroxyl; or $R_1$ is taken together with $R_2$ to form a substituted or unsubstituted heterocycloalkyl or heteroaryl group; wherein, the dashed line represents a single or double bond;

$R_3$ is hydrogen, halogen, loweralkyl, or loweralkoxy;

$R_4$ is hydrogen, hydroxyl, alkylamino, dialkylamino or alkyl;

$R_5$ and $R_6$ are independently selected from hydrogen, and substituted or unsubstituted alkyl, alkoxyalkyl, aminoalkyl, amidoalkyl, acyl, cycloalkyl, heterocycloalkyl, aryl, heteroaryl, alkyloxyalkylheterocyclo, and heteroarylalkyl; or $R_5$ and $R_6$ are taken together to form substituted or unsubstituted heterocyclo or heteroaryl; and the pharmaceutically acceptable salts, esters and prodrugs thereof.

In other embodiments, new substituted benz-azole compounds are provided of the formula (II):

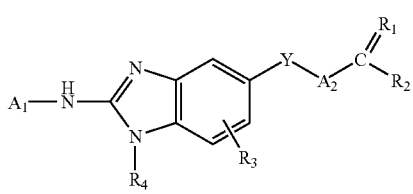

(II)

wherein and Y, $Ar_1$, $Ar_2$, $R_1$, $R_2$, $R_3$ and $R_4$ are as defined above; and the pharmaceutically acceptable salts, esters, and prodrugs thereof.

In other embodiments, new substituted benz-azole compounds are provided of the formula (III):

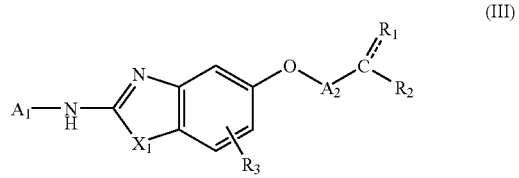

(III)

wherein $X_1$, $Ar_1$, $Ar_2$, $R_1$, $R_2$ and $R_3$ are as defined above; and the pharmaceutically acceptable salts, esters, tautomers and prodrugs thereof.

In other embodiments, new substituted benz-azole compounds are provided of the formula (IV):

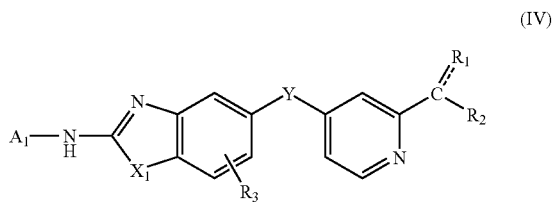

(IV)

wherein $X_1$, Y, $Ar_1$, $R_1$, $R_2$ and $R_3$ are as defined above; and the pharmaceutically acceptable salts, esters, tautomers and prodrugs thereof.

In yet other embodiments, new substituted benz-azole compounds are provided of the formula (V):

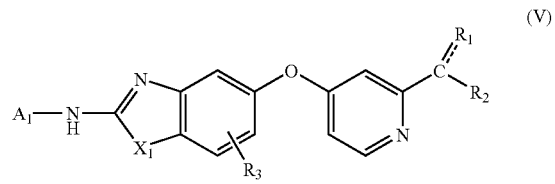

(V)

wherein $X_1$, $Ar_1$, $R_1$, $R_2$ and $R_3$ are as defined above; and the pharmaceutically acceptable salts, esters, tautomers and prodrugs thereof.

In another aspect, the present invention provides methods of treating human or animal subjects suffering from a Raf related disorder, such as cancer. Thus, the present invention provides methods of treating a human or animal subject in need of such treatment comprising administering to the subject a therapeutically effective amount of a compound of formula I, II, III, IV or V above, either alone or in combination with other anticancer agents.

In other aspects, the present invention provides methods for treating Raf related disorders in a human or animal subject in need of such treatment comprising administering to said subject an amount of a compound of formula (I), (II), (III), (IV) or (V) effective to reduce or prevent tumor growth in the subject.

In yet other aspects, the present invention provides methods for treating Raf related disorders in a human or animal subject in need of such treatment comprising administering to said subject an amount of a compound of formula (I), (II), (III), (IV) or (V) effective to reduce or prevent tumor growth in the subject in combination with at least one additional agent for the treatment of cancer. A number of suitable anticancer agents to be used as combination therapeutics are contemplated for use in the methods of the present invention. Indeed, the present invention contemplates, but is not limited to, administration of numerous anticancer agents such as: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons [e.g. IFN-a, etc.] and interleukins [e.g. IL-2, etc.], etc.); adoptive immunotherapy agents; hematopoietic growth factors; agents that induce tumor cell differentiation (e.g. all-trans-retinoic acid, etc.); gene therapy reagents; antisense therapy reagents and nucleotides; tumor vaccines; inhibitors of angiogenesis, and the like. Numerous other examples of chemotherapeutic compounds and anticancer therapies suitable for coadministration with the disclosed compounds of formula (I), (II), (III), (IV) or (V) are known to those skilled in the art.

In preferred embodiments, anticancer agents to be used in combination with compounds of the present invention comprise agents that induce or stimulate apoptosis. Agents that induce apoptosis include, but are not limited to, radiation (e.g., W); kinase inhibitors (e.g., Epidermal Growth Factor Receptor [EGFR] kinase inhibitor, Vascular Growth Factor Receptor [VGFR] kinase inhibitor, Fibroblast Growth Factor Receptor [FGFR] kinase inhibitor, Platelet-derived Growth Factor Receptor [PGFR] I kinase inhibitor, and Bcr-Abl kinase inhibitors such as STI-571, Gleevec, and Glivec]); antisense molecules; antibodies [e.g., Herceptin and Rituxan]; anti-estrogens [e.g., raloxifene and tamoxifen]; anti-androgens [e.g., flutamide, bicalutamide, finasteride, aminoglutethamide, ketoconazole, and corticosteroids]; cyclooxygenase 2 (COX-2) inhibitors [e.g., Celecoxib, meloxicam, NS-398, and non-steroidal antiinflammatory drugs (NSAIDs)]; and cancer chemotherapeutic drugs [e.g., irinotecan (Camptosar), CPT-11, fludarabine (Fludara), dacarbazine (DTIC), dexamethasone, mitoxantrone, Mylotarg, VP-16, cisplatinum, 5-FU, Doxrubicin, Taxotere or taxol]; cellular signaling molecules; ceramides and cytokines; and staurosprine, and the like.

In other aspects, the present invention provides pharmaceutical compositions comprising at least one compound of formula I, II, III, IV or V together with a pharmaceutically acceptable carrier suitable for administration to a human or animal subject, either alone or together with other anticancer agents.

In other aspects, the present invention provides methods of manufacture of compounds of formula I, II, III, IV or V as described herein.

In yet other aspects, the present invention provides compounds which are inhibitors of the enzyme raf kinase. Since the enzyme is a downstream effector of $p21^{ras}$, the instant inhibitors are useful in pharmaceutical compositions for human or veterinary use where inhibition of the raf kinase pathway is indicated, e.g., in the treatment of tumors and/or cancerous cell growth mediated by raf kinase. In particular, the compounds are useful in the treatment of human or animal, e.g., murine cancer, since the progression of these cancers is dependent upon the ras protein signal transduction cascade and therefore is susceptible to treatment by interruption of the cascade by inhibiting raf kinase activity. Accordingly, the compounds of the invention are useful in treating solid cancers, such as, for example, carcinomas (e.g., of the lungs, pancreas, thyroid, bladder or colon, myeloid disorders (e.g., myeloid leukemia) or adenomas (e.g., villous colon adenoma).

"Raf inhibitor" is used herein to refer to a compound that exhibits an $IC_{50}$ with respect to Raf Kinase activity of no more than about 100 μM and more typically not more than about 50 μM, as measured in the Raf/Mek Filtration Assay described generally hereinbelow. Preferred isoforms of Raf Kinase in which the compounds of the present invention will be shown to inhibit, include A-Raf, B-Raf, and C-Raf (Raf-1). "$IC_{50}$" is that concentration of inhibitor which reduces the activity of an enzyme (e.g., Raf kinase) to half-maximal level. Representative compounds of the present invention have been discovered to exhibit inhibitory activity against Raf. Compounds of the present invention preferably exhibit an $IC_{50}$ with respect to Raf of no more than about 10 μM, more preferably, no more than about 5 μM, even more preferably not more than about 1 μM, and most preferably, not more than about 200 nM, as measured in the Raf kinase assays described herein.

As used herein, the term "benz-azoles" includes benzimidazoles, benzothiazoles and benzoxazoles.

The phrase "alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$—CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. Thus the phrase alkyl groups includes primary alkyl groups, secondary alkyl groups, and tertiary alkyl groups. Preferred alkyl groups include straight and branched chain alkyl groups and cyclic alkyl groups having 1 to 12 carbon atoms.

As used herein "loweralkyl" includes both substituted or unsubstituted straight or branched chain alkyl groups having from 1 to 6 carbon atoms. Representative loweralkyl groups include, for example, methyl, ethyl, propyl, isopropyl, n-butyl, tert-butyl, neopentyl, trifluoromethyl, pentafluoroethyl and the like. Loweralkyl groups may be substituted, such as with halo, hydroxy, amino, nitro and/or cyano groups, and the like. Representative of halo-substituted and hydroxy-substituted loweralkyl include chloromethyl, trichloromethyl, chloroethyl, hydroxyethyl, and the like. Other suitable substituted loweralkyl moieties include, for example, aralkyl, aminoalkyl, aminoaralkyl, carbonylaminoalkyl, alkylcarbonylaminoalkyl, arylcarbonylaminoalkyl, aralkylcarbonylaminoalkyl, aminoalkoxyalkyl and arylaminoalkyl.

"Loweralkoxy" as used herein refers to RO— wherein R is loweralkyl. Representative examples of loweralkoxy groups include methoxy, ethoxy, t-butoxy, trifluoromethoxy and the like.

As used herein, the term "halogen" or "halo" refers to chloro, bromo, fluoro and iodo groups. "Haloalkyl" refers to an alkyl radical substituted with one or more halogen atoms.

The term "haloloweralkyl" refers to a loweralkyl radical substituted with one or more halogen atoms. The term "haloalkoxy" refers to an alkoxy radical substituted with one or more halogen atoms. The term "haloloweralkoxy" refers to a loweralkoxy radical substituted with one or more halogen atoms.

"Amino" refers herein to the group —$NH_2$. The term "alkylamino" refers herein to the group —NRR' where R and R' are each independently selected from hydrogen or a lower alkyl. The term "arylamino" refers herein to the group —NRR' where R is aryl and R' is hydrogen, a lower alkyl, or an aryl. The term "aralkylamino" refers herein to the group —NRR' where R is a lower aralkyl and R' is hydrogen, a loweralkyl, an aryl, or a loweraralkyl.

The term "alkoxyalkyl" refers to the group -alk$_1$-O-alk$_2$ where alk$_1$ is alkyl or alkenyl, and alk$_2$ is alkyl or alkenyl. The term "loweralkoxyalkyl" refers to an alkoxyalkyl where alk$_1$ is loweralkyl or loweralkenyl, and alk$_2$ is loweralkyl or loweralkenyl. The term "aryloxyalkyl" refers to the group -alkyl-O-aryl. The term "aralkoxyalkyl" refers to the group -alkylenyl-O-aralkyl, where aralkyl is a loweraralkyl.

The term "alkoxyalkylamino" refers herein to the group —NR-(alkoxyalkyl), where R is typically hydrogen, loweralkyl, or loweralkyl. The term "aminoloweralkoxyalkyl" refers herein to an aminoalkoxyalkyl in which the alkoxyalkyl is a loweralkoxyalkyl.

The term "aminocarbonyl" refers herein to the group —C(O)—$NH_2$. "Substituted aminocarbonyl" refers herein to the group —C(O)—NRR' where R is loweralkyl and R' is hydrogen or a loweralkyl. The term "arylaminocarbonyl" refers herein to the group —C(O)—NRR' where R is an aryl and R' is hydrogen, loweralkyl or aryl. "aralkylaminocarbonyl" refers herein to the group —C(O)—NRR' where R is loweraralkyl and R' is hydrogen, loweralkyl, aryl, or loweraralkyl.

"Aminosulfonyl" refers herein to the group —S(O)$_2$—$NH_2$. "Substituted aminosulfonyl" refers herein to the group —S(O)$_2$—NRR' where R is loweralkyl and R' is hydrogen or a loweralkyl. The term "aralkylaminosulfonlyaryl" refers herein to the group aryl-S(O)$_2$—NH-aralkyl, where the aralkyl is loweraralkyl.

"Carbonyl" refers to the divalent group —C(O)—.

"Carbonyloxy" refers generally to the group —C(O)—O. Such groups include esters, —C(O)—O—R, where R is loweralkyl, cycloalkyl, aryl, or loweraralkyl. The term "carbonyloxycycloalkyl" refers generally herein to both an "carbonyloxycarbocycloalkyl" and an "carbonyloxyheterocycloalkyl", i.e., where R is a carbocycloalkyl or heterocycloalkyl, respectively. The term "arylcarbonyloxy" refers herein to the group —C(O)—O-aryl, where aryl is a mono- or polycyclic, carbocycloaryl or heterocycloaryl. The term "aralkylcarbonyloxy" refers herein to the group —C(O)—O-aralkyl, where the aralkyl is loweraralkyl.

The term "sulfonyl" refers herein to the group —$SO_2$—. "Alkylsulfonyl" refers to a substituted sulfonyl of the structure —$SO_2$R— in which R is alkyl. Alkylsulfonyl groups employed in compounds of the present invention are typically loweralkylsulfonyl groups having from 1 to 6 carbon atoms in its backbone structure. Thus, typical alkylsulfonyl groups employed in compounds of the present invention include, for example, methylsulfonyl (i.e., where R is methyl), ethylsulfonyl (i.e., where R is ethyl), propylsulfonyl (i.e., where R is propyl), and the like. The term "arylsulfonyl" refers herein to the group —$SO_2$-aryl. The term "aralkylsulfonyl" refers herein to the group —$SO_2$-aralkyl, in which the aralkyl is loweraralkyl. The term "sulfonamido" refers herein to —$SO_2NH_2$.

As used herein, the term "carbonylamino" refers to the divalent group —NH—C(O)— in which the hydrogen atom of the amide nitrogen of the carbonylamino group can be replaced a loweralkyl, aryl, or loweraralkyl group. Such groups include moieties such as carbamate esters (—NH—C(O)—O—R) and amides —NH—C(O)—O—R, where R is a straight or branched chain loweralkyl, cycloalkyl, or aryl or loweraralkyl. The term "loweralkylcarbonylamino" refers to alkylcarbonylamino where R is a loweralkyl having from 1 to about 6 carbon atoms in its backbone structure. The term "arylcarbonylamino" refers to group —NH—C(O)—R where R is an aryl. Similarly, the term "aralkylcarbonylamino" refers to carbonylamino where R is a lower aralkyl. As used herein, the term "aminocarbonyl" refers to the divalent group —C(O)—NH— in which the hydrogen atom of the amide nitrogen of the carbonylamino group can be replaced a loweralkyl, aryl, or loweraralkyl group, as described above.

As used herein, the term "guanidino" or "guanidyl" refers to moieties derived from guanidine, $H_2N$—C(=NH)—$NH_2$. Such moieties include those bonded at the nitrogen atom carrying the formal double bond (the "2"-position of the guanidine, e.g., diaminomethyleneamino, $(H_2N)_2$C=NH—) and those bonded at either of the nitrogen atoms carrying a formal single bond (the "1-" and/or "3"-positions of the guandine, e.g., $H_2N$—C(=NH)—NH—). The hydrogen atoms at any of the nitrogens can be replaced with a suitable substituent, such as loweralkyl, aryl, or loweraralkyl.

As used herein, the term "amidino" refers to the moieties R—C(=N)—NR'— (the radical being at the "$N^1$" nitrogen) and R(NR')C=N— (the radical being at the "$N^2$" nitrogen), where R and R' can be hydrogen, loweralkyl, aryl, or loweraralkyl.

"Cycloalkyl" refers to a mono- or polycyclic, heterocyclic or carbocyclic alkyl substituent. Typical cycloalkyl substituents have from 3 to 8 backbone (i.e., ring) atoms in which each backbone atom is either carbon or a heteroatom. The term "heterocycloalkyl" refers herein to cycloalkyl substituents that have from 1 to 5, and more typically from 1 to 4 heteroatoms in the ring structure. Suitable heteroatoms employed in compounds of the present invention are nitrogen, oxygen, and sulfur. Representative heterocycloalkyl moieties include, for example, morpholino, piperazinyl, piperadinyl and the like. Carbocycloalkyl groups are cycloalkyl groups in which all ring atoms are carbon. When used in connection with cycloalkyl substituents, the term "polycyclic" refers herein to fused and non-fused alkyl cyclic structures.

The term "substituted heterocycle" or "heterocyclic group" or heterocycle as used herein refers to any 3- or 4-membered ring containing a heteroatom selected from nitrogen, oxygen, and sulfur or a 5- or 6-membered ring containing from one to three heteroatoms selected from the group consisting of nitrogen, oxygen, or sulfur; wherein the 5-membered ring has 0-2 double bonds and the 6-membered ring has 0-3 double bonds; wherein the nitrogen and sulfur atom maybe optionally oxidized; wherein the nitrogen and sulfur heteroatoms maybe optionally quarternized; and including any bicyclic group in which any of the above heterocyclic rings is fused to a benzene ring or another 5- or 6-membered heterocyclic ring independently defined above. The term "heterocycle" thus includes rings in which nitrogen is the heteroatom as well as partially and fully-saturated rings. Preferred heterocycles include, for example: diazapinyl, pyrryl, pyrrolinyl, pyrrolidinyl, pyrazolyl, pyrazolinyl, pyrazolidinyl, imidazoyl, imidazolinyl, imidazolidinyl, pyridyl, piperidinyl, pyrazinyl, piperazinyl, N-methyl piperazinyl, azetidinyl, N-methylazetidinyl, pyrimidinyl, pyridazinyl, oxazolyl, oxazolidinyl, isoxazolyl, isoazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl and benzothienyl.

Heterocyclic moieties can be unsubstituted or monosubstituted or disubstituted with various substituents independently selected from hydroxy, halo, oxo (C=O), alkylimino (RN=, wherein R is a loweralkyl or loweralkoxy group), amino, alkylamino, dialkylamino, acylaminoalkyl, alkoxy, thioalkoxy, polyalkoxy, loweralkyl, cycloalkyl or haloalkyl.

The heterocyclic groups may be attached at various positions as will be apparent to those having skill in the organic and medicinal chemistry arts in conjunction with the disclosure herein.

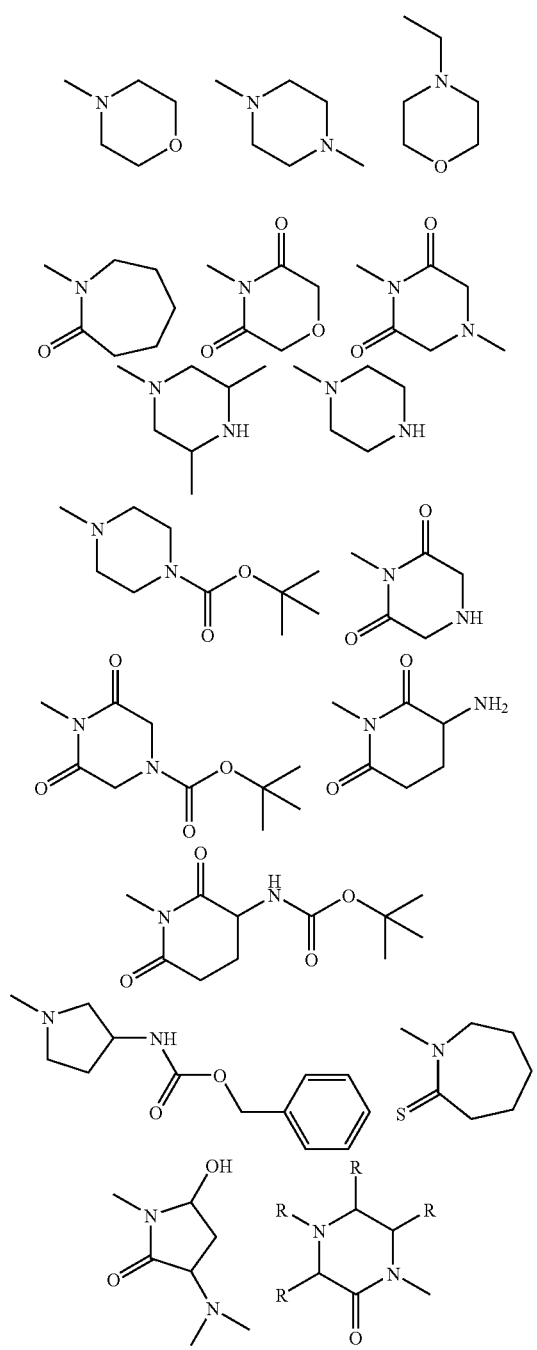

where R is H or a heterocyclic substituent, as described herein.

Representative heterocyclics include, for example, imidazolyl, pyridyl, piperazinyl, azetidinyl, thiazolyl, furanyl, triazolyl benzimidazolyl, benzothiazolyl, benzoxazolyl, quinolinyl, isoquinolinyl, quinazolinyl, quinoxalinyl, phthalazinyl, indolyl, naphthpyridinyl, indazolyl, and quinolizinyl.

"Aryl" refers to optionally substituted monocyclic and polycyclic aromatic groups having from 3 to 14 backbone carbon or hetero atoms, and includes both carbocyclic aryl groups and heterocyclic aryl groups. Carbocyclic aryl groups are aryl groups in which all ring atoms in the aromatic ring are carbon. The term "heteroaryl" refers herein to aryl groups having from 1 to 4 heteroatoms as ring atoms in an aromatic ring with the remainder of the ring atoms being carbon atoms. When used in connection with aryl substituents, the term "polycyclic aryl" refers herein to fused and non-fused cyclic structures in which at least one cyclic structure is aromatic, such as, for example, benzodioxozolo (which has a heterocyclic structure fused to a phenyl group, i.e.,

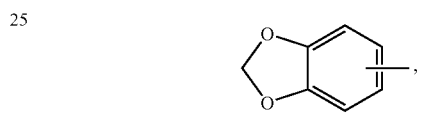

naphthyl, and the like. Exemplary aryl moieties employed as substituents in compounds of the present invention include phenyl, pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, and the like.

"Aralkyl" refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

Representative heteroaryl groups include, for example, those shown below. These heteroaryl groups can be further substituted and may be attached at various positions as will be apparent to those having skill in the organic and medicinal chemistry arts in conjunction with the disclosure herein.

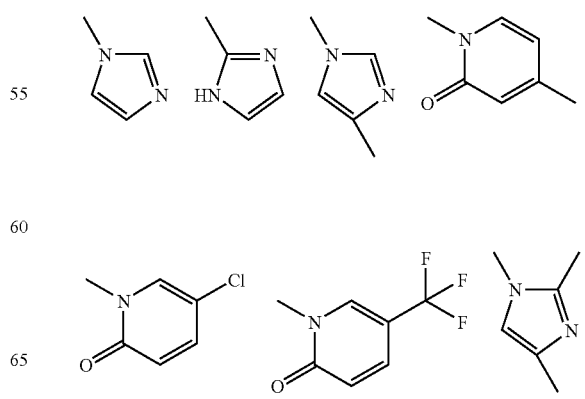

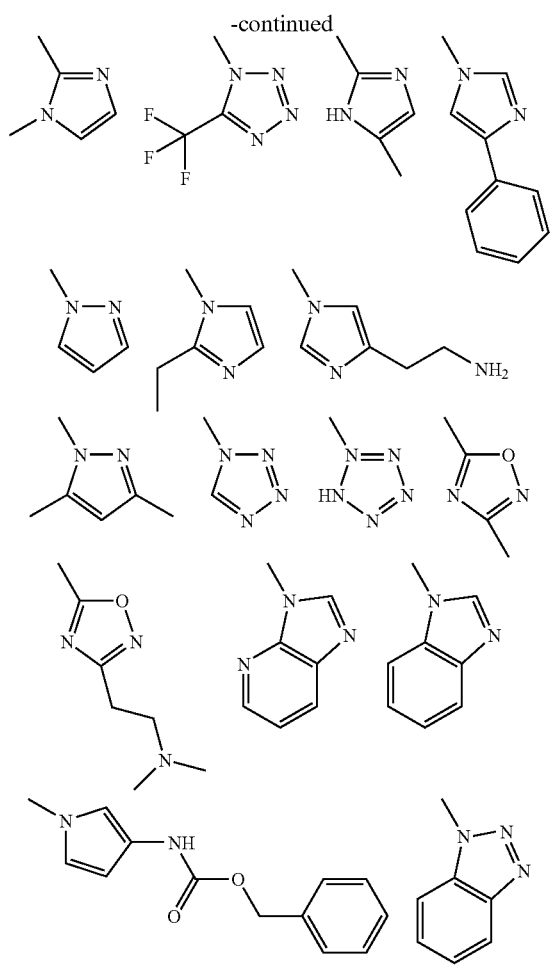

-continued

Representative heteroaryl's include, for example, imidazolyl, pyridyl, piperazinyl, azetidinyl, thiazolyl, triazolyl benzimidazolyl, benzothiazolyl, and benzoxazolyl.

The term "biaryl" refers to a group or substituent to which two aryl groups, which are not condensed to each other, are bound. Exemplary biaryl compounds include, for example, phenylbenzene, diphenyldiazene, 4-methylthio-1-phenylbenzene, phenoxybenzene, (2-phenylethynyl)benzene, diphenyl ketone, (4-phenylbuta-1,3-diynyl)benzene, phenylbenzylamine, (phenylmethoxy)benzene, and the like. Preferred optionally substituted biaryl groups include: 2-(phenylamino)-N-[4-(2-phenylethynyl)-phenyl]acetamide, 1,4-diphenylbenzene, N-[4-(2-phenylethynyl)phenyl]-2-[benzylamino]acetamide, 2-amino-N-[4-(2-phenylethynyl)phenyl]propanamide, 2-amino-N-[4-(2-phenylethynyl)phenyl]acetamide, 2-(cyclopropylamino)-N-[4-(2-phenylethynyl)-phenyl]acetamide, 2-(ethylamino)-N-[4-(2-phenylethynyl)phenyl]acetamide, 2-[(2-methylpropyl)amino]-N-[4-(2-phenylethynyl)phenyl]acetamide, 5-phenyl-2H-benzo-[d]1,3-dioxolene, 2-chloro-1-methoxy-4-phenylbenzene, 2-[(imidazolylmethyl)amino]-N-[4-(2-phenylethynyl)phenyl]acetamide, 4-phenyl-1-phenoxybenzene, N-(2-aminoethyl)-[4-(2-phenylethynyl)phenyl]carboxamide, 2-{[(4-fluorophenyl)methyl]amino}-N-[4-(2-phenylethynyl)phenyl]acetamide, 2-{[(4-methylphenyl)methyl]amino}-N-[4-(2-phenylethynyl)phenyl]acetamide, 4-phenyl-1-(trifluoromethyl)benzene, 1-butyl-4-phenylbenzene, 2-(cyclohexylamino)-N-[4-(2-phenylethynyl)phenyl]acetamide, 2-(ethylmethylamino)-N-[4-(2-phenylethynyl)phenyl]acetamide, 2-(butylamino)-N-[4-(2-phenylethynyl)phenyl]acetamide, N-[4-(2-phenylethynyl)phenyl]-2-(4-pyridylamino)acetamide, N-[4-(2-phenylethynyl)phenyl]-2-(quinuclidin-3-ylamino)acetamide, N-[4-(2-phenylethynyl)phenyl]pyrrolidin-2-ylcarboxamide, 2-amino-3-methyl-N-[4-(2-phenylethynyl)-phenyl]butanamide, 4-(4-phenylbuta-1,3-diynyl)phenylamine, 2-(dimethylamino)-N-[4-(4-phenylbuta-1,3-diynyl)phenyl]acetamide, 2-(ethylamino)-N-[4-(4-phenylbuta-1,3-diynyl)phenyl]acetamide, 4-ethyl-1-phenylbenzene, 1-[4-(2-phenylethynyl)phenyl]ethan-1-one, N-(1-carbamoyl-2-hydroxypropyl)[4-(4-phenylbuta-1,3-diynyl)phenyl]carboxamide, N-[4-(2-phenylethynyl)phenyl]propanamide, 4-methoxyphenyl phenyl ketone, phenyl-N-benzamide, (tert-butoxy)-N-[(4-phenylphenyl)methyl]carboxamide, 2-(3-phenylphenoxy)ethanehydroxamic acid, 3-phenylphenyl propanoate, 1-(4-ethoxyphenyl)-4-methoxybenzene, and [4-(2-phenylethynyl)phenyl]pyrrole.

The term "heteroarylaryl" refers to a biaryl group where one of the aryl groups is a heteroaryl group. Exemplary heteroarylaryl groups include, for example, 2-phenylpyridine, phenylpyrrole, 3-(2-phenylethynyl)pyridine, phenylpyrazole, 5-(2-phenylethynyl)-1,3-dihydropyrimidine-2,4-dione, 4-phenyl-1,2,3-thiadiazole, 2-(2-phenylethynyl)pyrazine, 2-phenylthiophene, phenylimidazole, 3-(2-piperazinylphenyl)-furan, 3-(2,4-dichlorophenyl)-4-methylpyrrole, and the like. Preferred optionally substituted heteroarylaryl groups include: 5-(2-phenylethynyl)pyrimidine-2-ylamine, 1-methoxy-4-(2-thienyl)benzene, 1-methoxy-3-(2-thienyl)benzene, 5-methyl-2-phenylpyridine, 5-methyl-3-phenylisoxazole, 2-[3-(trifluoromethyl)phenyl]furan, 3-fluoro-5-(2-furyl)-2-methoxy-1-prop-2-enylbenzene, (hydroxyimino)(5-phenyl(2-thienyl))methane, 5-[(4-methylpiperazinyl)methyl]-2-phenylthiophene, 2-(4-ethylphenyl)thiophene, 4-methylthio-1-(2-thienyl)benzene, 2-(3-nitrophenyl)thiophene, (tert-butoxy)-N-[(5-phenyl(3-pyridyl))methyl]carboxamide, hydroxy-N-[(5-phenyl(3-pyridyl))methyl]-amide, 2-(phenylmethylthio)pyridine, and benzylimidazole.

The term "heteroarylheteroaryl" refers to a biaryl group where both of the aryl groups is a heteroaryl group. Exemplary heteroarylheteroaryl groups include, for example, 3-pyridylimidazole, 2-imidazolylpyrazine, and the like. Preferred optionally substituted heteroarylheteroaryl groups include: 2-(4-piperazinyl-3-pyridyl)furan, diethyl(3-pyrazin-2-yl(4-pyridyl))amine, and dimethyl {2-[2-(5-methylpyrazin-2-yl)ethynyl](4-pyridyl)}amine.

"Optionally substituted" or "substituted" refers to the replacement of hydrogen with a monovalent or divalent radical. Suitable substitution groups include, for example, hydroxyl, nitro, amino, imino, cyano, halo, thio, sulfonyl, thioamido, amidino, imidino, oxo, oxamidino, methoxamidino, imidino, guanidino, sulfonamido, carboxyl, formyl, loweralkyl, haloloweralkyl, loweralkyamino, haloloweralkylamino, loweralkoxy, haloloweralkoxy, loweralkoxyalkyl, alkylcarbonyl, aminocarbonyl, arylcarbonyl, aralkylcarbonyl, heteroarylcarbonyl, heteroaralkylcarbonyl, alkylthio, aminoalkyl, cyanoalkyl, aryl and the like.

The substitution group can itself be substituted. The group substituted onto the substitution group can be carboxyl, halo; nitro, amino, cyano, hydroxyl, loweralkyl, loweralkoxy, aminocarbonyl, —SR, thioamido, —SO$_3$H, —SO$_2$R or cycloalkyl, where R is typically hydrogen, hydroxyl or loweralkyl.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substitutents can be straight chain, branched or cyclic arrangements of covalently bonded carbon or heteroatoms.

As used herein, the term "carboxy-protecting group" refers to a carbonyl group which has been esterified with one of the commonly used carboxylic acid protecting ester groups employed to block or protect the carboxylic acid function while reactions involving other functional sites of the compound are carried out. In addition, a carboxy protecting group can be attached to a solid support whereby the compound remains connected to the solid support as the carboxylate until cleaved by hydrolytic methods to release the corresponding free acid. Representative carboxy-protecting groups include, for example, loweralkyl esters, secondary amides and the like.

As used herein, the term "pharmaceutically acceptable salts" refers to the nontoxic acid or alkaline earth metal salts of the compounds of Formula I. These salts can be prepared in situ during the final isolation and purification of the compounds of Formula I, or by separately reacting the base or acid functions with a suitable organic or inorganic acid or base, respectively. Representative salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylpropionate, picrate, pivalate, propionate, succinate, sulfate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "cancer" refers to cancer diseases that can be beneficially treated by the inhibition of Raf kinase, including, for example, solid cancers, such as carcinomas (e.g., of the lungs, pancreas, thyroid, bladder or colon), myeloid disorders (e.g., myeloid leukemia) and adenomas (e.g., villous colon adenoma).

In illustrative embodiments of the invention, $Ar_1$ may be, for example, phenyl which may be substituted by one or more substitutents selected from the group consisting of hydroxyl, nitro, cyano, halo, and substituted or unsubstituted amino, imino, thio, sulfonyl, thioamido, amidino, imidino, oxo, oxamidino, methoxamidino, imidino, guanidino, sulfonamido, carboxyl, formyl, loweralkyl, haloloweralkyl, loweralkyamino, haloloweralkylamino, loweralkoxy, haloloweralkoxy, loweralkoxyalkyl, alkylcarbonyl, aminocarbonyl, loweralkylaminocarbonyl, heterocycloalkylloweralkylaminocarbonyl, carboxylloweralkylaminocarbonyl, arylcarbonyl, aralkylcarbonyl, heteroarylcarbonyl, heteroaralkylcarbonyl, alkylthio, aminoalkyl, cyanoalkyl, aryl and the like. In other illustrative embodiments of the invention, $Ar_2$ may be, for example, pyridyl, which may be substituted by one or more substitutents selected from the group consisting of hydroxyl, nitro, cyano, halo, and substituted or unsubstituted amino, imino, thio, sulfonyl, thioamido, amidino, imidino, oxo, oxamidino, methoxamidino, imidino, guauidino, sulfonamido, carboxyl, formyl, loweralkyl, haloloweralkyl, loweralkyamino, haloloweralkylamino, loweralkoxy, haloloweralkoxy, loweralkoxyalkyl, alkylcarbonyl, aminocarbonyl, loweralkylaminocarbonyl, heterocycloalkylloweralkylaminocarbonyl, carboxylloweralkylaminocarbonyl, arylcarbonyl, aralkylcarbonyl, heteroarylcarbonyl, heteroaralkylcarbonyl, alkylthio, aminoalkyl, cyanoalkyl, aryl and the like.

In representative embodiments of the invention, the compounds of the invention include, for example, 4-[(2-{[4-chloro-3-(trifluoromethyl)phenyl]amino}-1H-benzimidazol-6-yl)oxy]-N-methylpyridine-2-carboxamide, 4-({2-[(3-chlorophenyl)amino]-1H-benzimidazol-6-yl}oxy)-N-methylpyridine-2-carboxamide, 4-({2-[(4-bromophenyl)

amino]-1H-benzimidazol-6-yl}oxy)-N-methylpyridine-2-carboxamide, 4-({2-[(3-chloro-4-fluorophenyl)amino]-1H-benzimidazol-6-yl}oxy)-N-methylpyridine-2-carboxamide, N-methyl-4-{[2-(phenylamino)-1H-benzimidazol-6-yl]oxy}pyridine-2-carboxamide, 4-[(2-{[4-bromo-2-(trifluoromethyl)phenyl]amino}-1H-benzimidazol-6-yl)oxy]-N-methylpyridine-2-carboxamide, N-methyl-4-({2-[(2-methylpropyl)amino]-1H-benzimidazol-6-yl}oxy)pyridine-2-carboxamide, 4-[(2-{[4-(dimethylamino)naphthalen-1-yl]-amino}-1H-benzimidazol-6-yl)oxy]-N-methylpyridine-2-carboxamide, N-methyl-4-({2-[(4-nitrophenyl)amino]-1H-benzimidazol-6-yl}oxy)pyridine-2-carboxamide, N-methyl-4-({2-[(phenylcarbonyl)amino]-1H-benzimidazol-6-yl}oxy)pyridine-2-carboxamide, N-methyl-4-({2-[(phenylmethyl)amino]-1H-benzimidazol-6-yl}oxy)pyridine-2-carboxamide, methyl 4-{[6-({2-[(methylamino)carbonyl]pyridin-4-yl}oxy)-1H-benzimidazol-2-yl]amino}benzoate, 4-({2-[(4-chlorophenyl)amino]-1H-benzimidazol-6-yl}oxy)-N-methylpyridine-2-carboxamide, 4-[(2-{[2-(ethyloxy)phenyl]amino}-1H-benzimidazol-6-yl)oxy]-N-methylpyridine-2-carboxamide, N-methyl-4-({2-[(2-morpholin-4-ylethyl)amino]-1H-benzimidazol-6-yl}oxy)pyridine-2-carboxamide, 4-({2-[(4-iodophenyl)amino]-1H-benzimidazol-6-yl}oxy)-N-methylpyridine-2-carboxamide, N-methyl-4-[(2-{[4-(trifluoromethyl)phenyl]amino}-1H-benzimidazol-6-yl)oxy]pyridine-2-carboxamide, 4-({2-[(furan-2-ylmethyl)amino]-1H-benzimidazol-6-yl}oxy)-N-methylpyridine-2-carboxamide, 4-({2-[(4-bromo-3-methylphenyl)amino]-1H-benzimidazol-6-yl}oxy)-N-methylpyridine-2-carboxamide, 4-({2-[(4-acetylphenyl)amino]-1H-benzimidazol-6-yl}-oxy)-N-methylpyridine-2-carboxamide, N-methyl-4-({2-[(2,4,6-trimethylphenyl)amino]-1H-benzimidazol-6-yl}oxy)pyridine-2-carboxamide, 4-[(2-{[4-(1,1-dimethylethyl)phenyl]amino}-1H-benzimidazol-6-yl)oxy]-N-methylpyridine-2-carboxamide, 4-({2-[(2-bromophenyl)amino]-1H-benzimidazol-6-yl}oxy)-N-methylpyridine-2-carboxamide, 4-({2-[(3-bromophenyl)amino]-1H-benzimidazol-6-yl}oxy)-N-methylpyridine-2-carboxamide, 4-({2-[(2-chlorophenyl)amino]-1H-benzimidazol-6-yl}oxy)-N-methylpyridine-2-carboxamide, methyl 3-{[6-({2-[(methylamino)carbonyl]pyridin-4-yl}oxy)-1H-benzimidazol-2-yl]amino}thiophene-2-carboxylate, 4-({2-[(4-bromophenyl)amino]-1H-benzimidazol-6-yl}oxy)-N-{(3R,5R)-5-[(methyloxy)methyl]pyrrolidin-3-yl}pyridine-2-carboxamide, 4-({2-[(4-bromophenyl)amino]-1-methyl-1H-benzimidazol-5-yl}oxy)-N-methylpyridine-2-carboxamide, 4-[(2-{[4-chloro-3-(trifluoromethyl)phenyl]amino}-1-methyl-1H-benzimidazol-5-yl)oxy]-N-methylpyridine-2-carboxamide, N-methyl-4-[(1-methyl-2-{[4-(trifluoromethyl)phenyl]amino}-1H-benzimidazol-5-yl)oxy]pyridine-2-carboxamide, 4-({2-[(4-bromophenyl)amino]-1-methyl-1H-benzimidazol-5-yl}oxy)-N-ethylpyridine-2-carboxamide, 4-({2-[(4-bromophenyl)amino]-1-methyl-1H-benzimidazol-5-yl}oxy)-N-(2-hydroxyethyl)pyridine-2-carboxamide, 4-({2-[(4-bromophenyl)amino]-1-methyl-1H-benzimidazol-5-yl}oxy)-N,N-dimethylpyridine-2-carboxamide, 4-({2-[(4-bromophenyl)amino]-1-methyl-1H-benzimidazol-5-yl}oxy)-N-(2,2,2-trifluoroethyl)pyridine-2-carboxamide, N-(4-bromophenyl)-1-methyl-5-{[2-(pyrrolidin-1-ylcarbonyl)pyridin-4-yl]oxy)}-1H-benzimidazol-2-amine, ethyl (3R)-3-(methyloxy)-4-[({4-[(2-{[4-(trifluoromethyl)phenyl]amino}-1H-benzimidazol-5-yl)oxy]pyridin-2-yl}-carbonyl)amino]piperidine-1-carboxylate, 4-({2-[(4-bromophenyl)amino]-1-methyl-1H-benzimidazol-5-yl}oxy)-N-[2-(dimethylamino)ethyl]pyridine-2-carboxamide, 4-({2-[(4-bromophenyl)amino]-1-methyl-1H-benzimidazol-5-yl}oxy)-N-(tetrahydrofuran-2-ylmethyl)pyridine-2-carboxamide, 4-({2-[(4-bromophenyl)amino]-1-methyl-1H-benzimidazol-5-yl}oxy)-N-(2-morpholin-4-ylethyl)pyridine-2-carboxamide, 4-({2-[(4-bromophenyl)amino]-1-methyl-1H-benzimidazol-5-yl}oxy)-N-(piperidin-4-ylmethyl)pyridine-2-carboxamide, 5-({2-[(3-aminopyrrolidin-1-yl)carbonyl]pyridin-4-yl}oxy)-N-(4-bromophenyl)-1-methyl-1H-benzimidazol-2-amine, 4-({2-[(4-bromophenyl)amino]-1-methyl-1H-benzimidazol-5-yl}oxy)-N-[1-(diphenylmethyl)azetidin-3-yl]pyridine-2-carboxamide, 4-({2-[(4-bromophenyl)amino]-1-methyl-1H-benzimidazol-5-yl}oxy)-N-piperidin-3-ylpyridine-2-carboxamide, 4-({2-[(4-bromophenyl)amino]-1-methyl-1H-benzimidazol-5-yl}oxy)-N-(1,3-thiazol-2-yl)pyridine-2-carboxamide, and 4-({2-[(4-bromophenyl)amino]-1-methyl-1H-benzimidazol-5-yl}oxy)-N-[(1-ethylpyrrolidin-2-yl)methyl]pyridine-2-carboxamide, (4-{2-[(4-bromophenyl)amino]benzothiazol-5-yloxy}(2-pyridyl))-N-methylcarboxamide, (4-{2-[(4-bromophenyl)amino]benzoxazol-5-yloxy}-(2-pyridyl))-N-methylcarboxamide, and other representative compounds set forth in the Examples.

In other aspects, the present invention relates to the processes for preparing the compounds of Formulas I, II, III, IV and V and to the synthetic intermediates useful in such processes.

The compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, as well as single diastereomers of the compounds of the invention are included in the present invention. The terms "S" and "R" configuration, as used herein, are as defined by the IUPAC 1974 RECOMMENDATIONS FOR SECTION E, FUNDAMENTAL STEREOCHEMISTRY, *Pure Appl. Chem.* 45:13-30 (1976). The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the CHEMICAL ABSTRACTS INDEX GUIDE-APPENDIX IV (1987) paragraph 203.

The present invention also relates to the processes for preparing the compounds of the invention and to the synthetic intermediates useful in such processes, as described in detail below.

Synthetic Methods

Compounds of the invention containing a benzimidazole core may be prepared using a number of methods familiar to one of skill in the art. In one method, suitably functionalized diamines may be coupled with various thioisocyanates to form the intermediate thioureas. Cyclization to form the benzimidazole moiety may be effected under known conditions such as with treatment carbodiimides or alkyl halides as in the following schemes.

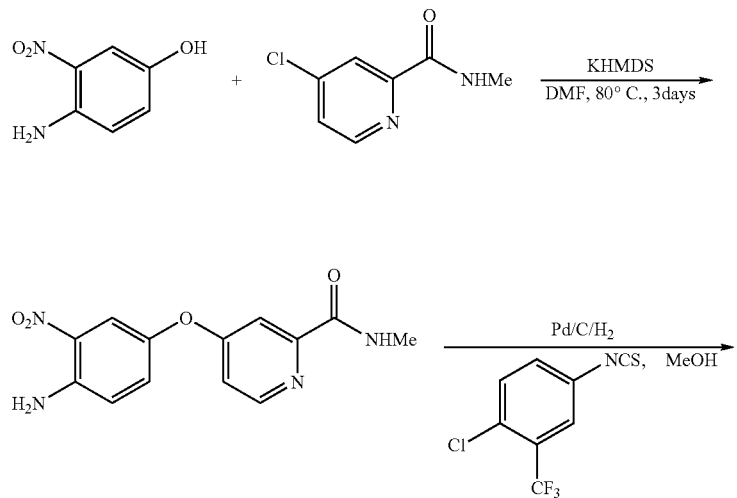
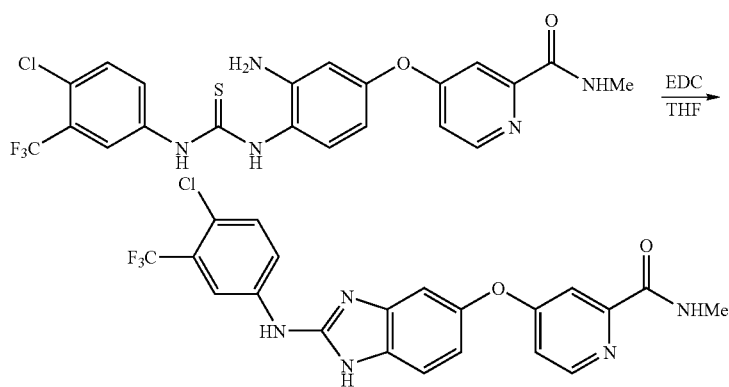
Scheme:
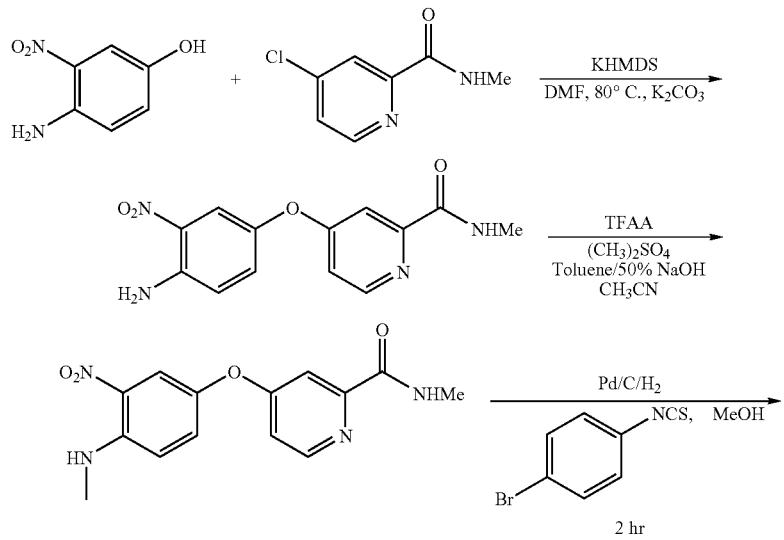

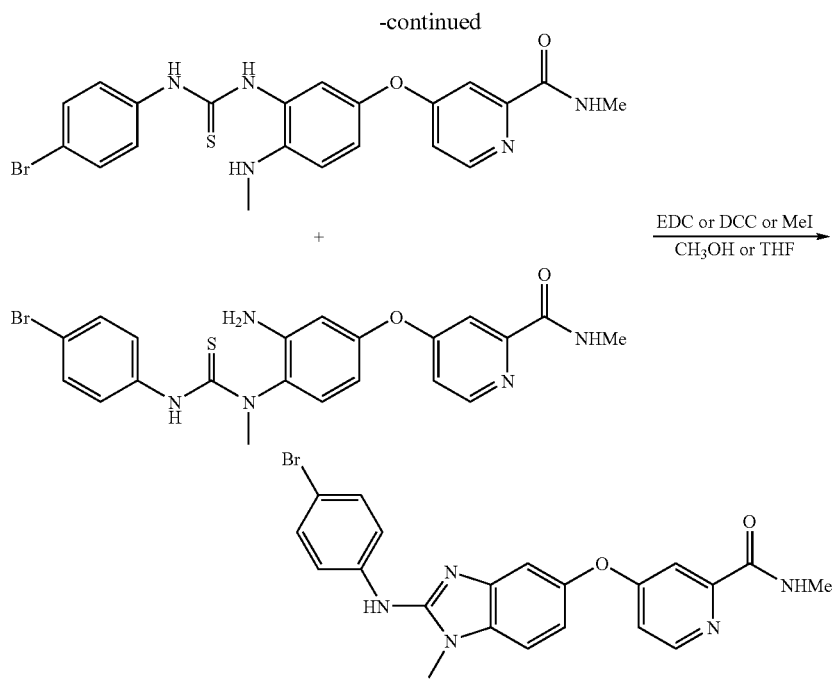
Scheme:
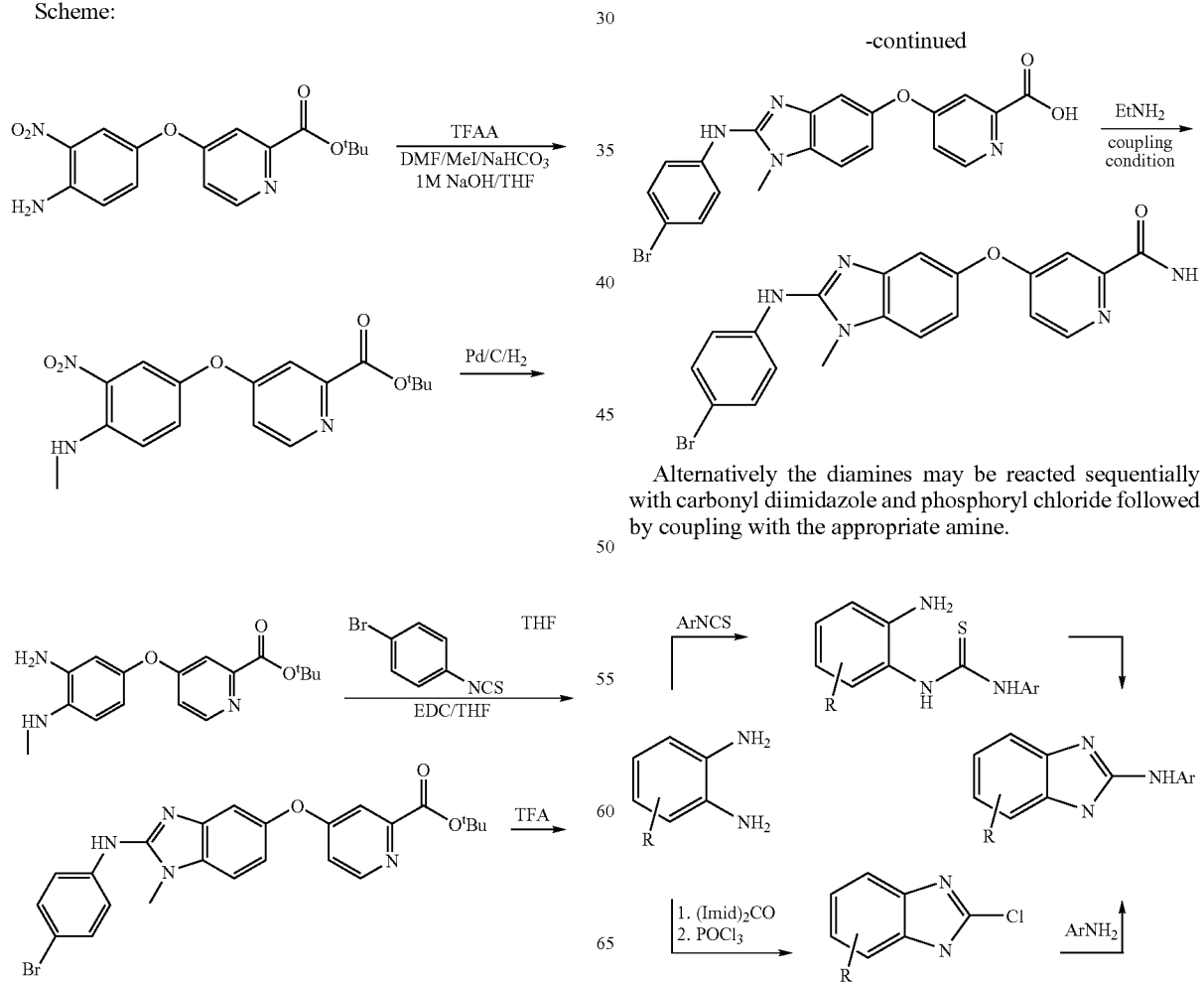
Alternatively the diamines may be reacted sequentially with carbonyl diimidazole and phosphoryl chloride followed by coupling with the appropriate amine.

Compounds containing the oxazole structure may similarly be prepared according to the methods above or according to other known general procedures. Haviv et al. (*J. Med. Chem.* 1988, 31:1719) describes a procedure for assembling oxazole cores wherein a hydroxy aniline is treated with ethyl potassium xanthate. The resulting sulfuryl benzoxazole may then be chlorinated and coupled with an amine.

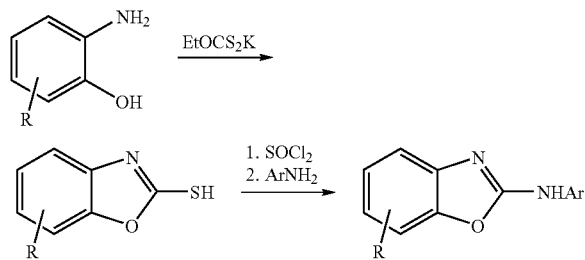

Compounds containing a benzothiazole core may also be prepared according to known methods. An ortho-halothioisocyanate may be reacted with an amine to form a thiourea. Reduction with NaH then allows formation of the thiazole ring.

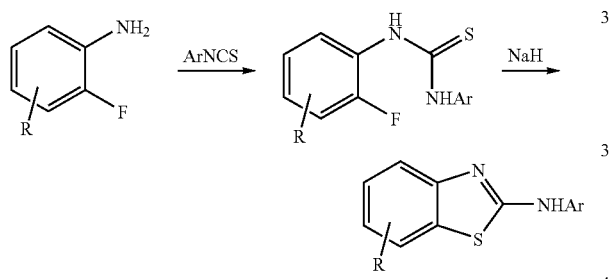

Benzothiazoles may generally be substituted in accordance with the present invention, such as through the following synthetic pathway:

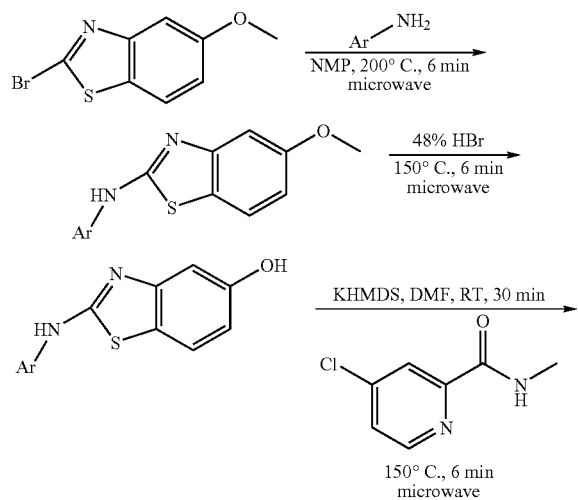

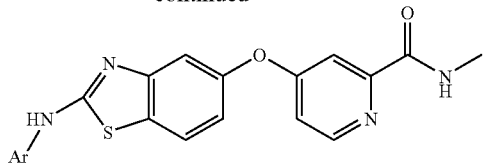

Benzoxzoles may generally be synthesized through the following pathway:

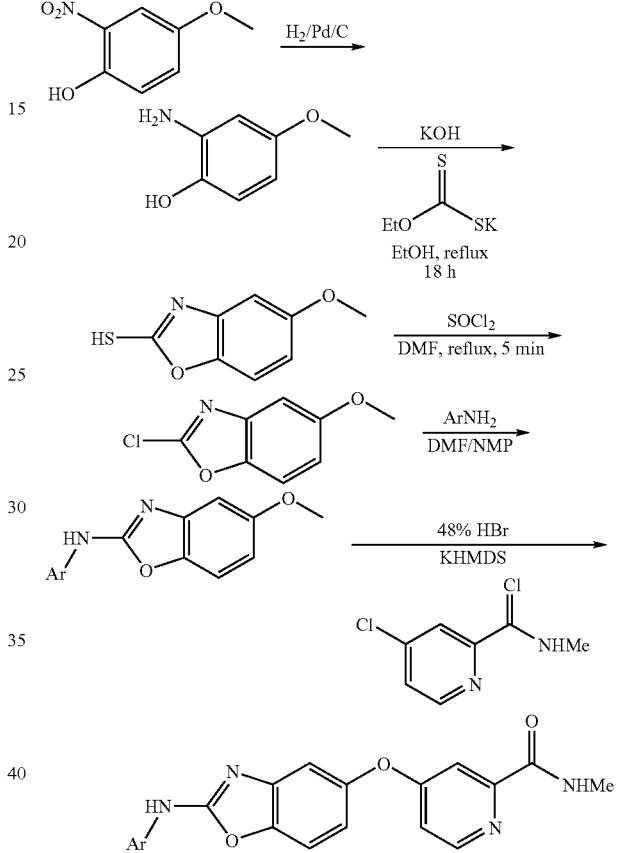

The compounds of the invention are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

Effective amounts of the compounds of the invention generally include any amount sufficient to detectably inhibit Raf activity by any of the assays described herein, by other Raf kinase activity assays known to those having ordinary skill in the art or by detecting an inhibition or alleviation of symptoms of cancer.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose.

The compounds of the present invention may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq. (1976).

While the compounds of the invention can be administered as the sole active pharmaceutical agent, they can also be used in combination with one or more other agents used in the treatment of cancer. Representative agents useful in combination with the compounds of the invention for the treatment of cancer include, for example, irinotecan, topotecan, gemcitabine, 5-fluorouracil, leucovorin carboplatin, cisplatin, taxanes, tezacitabine, cyclophosphamide, vinca alkaloids, imatinib (Gleevec), anthracyclines, rituximab, trastuzumab, as well as other cancer chemotherapeutic agents.

The above compounds to be employed in combination with the compounds of the invention will be used in therapeutic amounts as indicated in the *Physicians' Desk Reference* (PDR) 47th Edition (1993), which is incorporated herein by reference, or such therapeutically useful amounts as would be known to one of ordinary skill in the art.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

Antiestrogens, such as tamoxifen, inhibit breast cancer growth through induction of cell cycle arrest, that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to antiestrogen resistance (Donovan et al, *J. Biol. Chem.* 276:40888, 2001). As reported by Donovan et al., inhibition of MAPK signaling through treatment with MEK inhibitor changed the phosphorylation status of p27 in hormone refractory breast cancer cell lines and in so doing restored hormone sensitivity. Accordingly, in one aspect, the compounds of formulas (I), (II), (III), (IV) and (V) may be used in the treatment of hormone dependent cancers, such as breast and prostate cancers, to reverse hormone resistance commonly seen in these cancers with conventional anticancer agents.

In hematological cancers, such as chronic myelogenous leukemia (CML), chromosomal translocation is responsible for the constitutively activated BCR-AB1 tyrosine kinase. The afflicted patients are responsive to Geevec, a small molecule tyrosine kinase inhibitor, as a result of inhibition of Ab1 kinase activity. However, many patients with advanced stage disease respond to Gleevec initially, but then relapse later due to resistance-conferring mutations in the Ab1 kinase domain. In vitro studies have demonstrated that BCR-Av1 employs the Raf kinase pathway to elicit its effects. In addition, inhibiting more than one kinase in the same pathway provides additional protection against resistance-conferring mutations. Accordingly, in another aspect of the invention, the compounds of formulas (I), (II), (III), (IV) and (V) are used in combination with at least one additional agent, such as Gleevec, in the treatment of hematological cancers, such as chronic myelogenous leukemia (CML), to reverse or prevent resistance to the at least one additional agent.

The present invention will be understood more readily by reference to the following examples, which are provided by way of illustration and are not intended to be limiting of the present invention.

Representative side chains for use in the compounds of the following examples may generally be prepared in accordance with the following procedures:

Example 1

Synthesis of 4-[(2-{[4-chloro-3-(trifluoromethyl) phenyl]amino}-1H-benzimidazol-6-yl)oxy]-N-methylpyridine-2-carboxamide The compound 4-[(2-{[4-chloro-3-(trifluoromethyl)phenyl]amino}-1H-benzimidazol-6-yl)oxy]-N-methylpyridine-2-carboxamide was synthesized as follows:

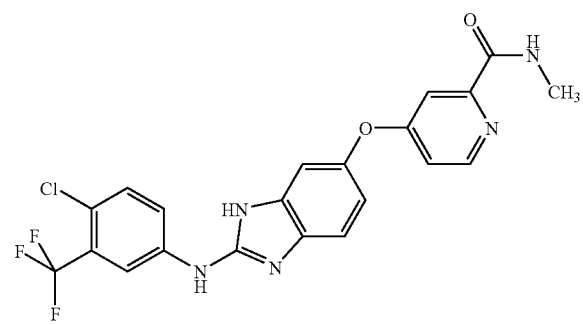

Step 1. Synthesis of 4-[(4-amino-3-nitrophenyl)oxy]-N-methylpyridine-2-carboxamide A mixture containing 4-amino-3-nitrophenol (1 eq) and potassium bis(trimethylsilyl)amide (2 eq) was stirred in dimethylformamide for 2 hours at room temperature. To this mixture was added (4-chloro(2-pyridyl))-N-methylcarboxamide (1 eq) and potassium carbonate (1.2 eq) and stirred at 90° C. for 3 days. The reaction mixture was then concentrated and partitioned between ethyl acetate and water. The organic layer was separated and washed with brine, dried, filtered, and concentrated in vacuum to give brown solid. Purification on silica gel (2% triethyl amine/50% ethyl acetate in hexane) gave 4-[(4-amino-3-nitrophenyl)oxy]-N-methylpyridine-2-carboxamide as an orange solid. The product gave satisfactory NMR. HPLC, 3.39 min; MS: MH+=289.

Step 2. Synthesis of 4-[(3,4-diaminophenyl)oxy]-N-methylpyridine-2-carboxamide

The mixture containing [4-(3-amino-4-nitrophenoxy)(2-pyridyl)]-N— in methanol with catalytic amount of 10% Pd/C was hydrogenated until disappearance of the yellow color to yield the product amine. HPLC, 2.5 mins; MS: MH+=259.

Step 3. Synthesis of 4-[(2-{[4-chloro-3-(trifluoromethyl)phenyl]amino}-1H-benzimidazol-6-yl)oxy]-N-methylpyridine-2-carboxamide The mixture containing 4-[(3,4-diaminophenyl)oxy]-N-methylpyridine-2-carboxamide (1 eq) and 4-chloro-3-(trifluoromethyl)benzeneisothiocyanate (1 eq) in tetrahydrofuran was stirred at room temperature for 16 hours to give the corresponding thiourea. To the resulting mixture was added 1-ethyl-3-(3-dimethylaminopropyl)carbodiimide hydrochloride (2 eq) and the mixture was stirred for another 10 hours. The mixture was concentrated and partitioned between ethyl acetate and water. The organic layer was washed with brine and dried. Purification on HPLC gave 4-[(2-{[4-chloro-3-(trifluoromethyl)phenyl]amino}-1H-benzimidazol-6-yl)oxy]-N-methylpyridine-2-carboxamide. MS: MH+=462

Examples 2-108

The compounds shown in the following Table 1 (Examples 2-108) were prepared from following the procedure described for Example 1.

TABLE 1

| Example | Structure | Name | MH+ |
|---|---|---|---|
| 2 | 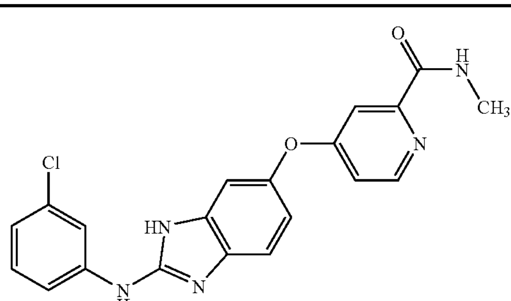 | 4-({2-[(3-chlorophenyl)amino]-1H-benzimidazol-6-yl}oxy)-N-methyl-pyridine-2-carboxamide | 394 |

TABLE 1-continued

| Example | Name | MH+ |
|---|---|---|
| 3 | 4-({2-[(4-bromophenyl)amino]-1H-benzimidazol-6-yl}oxy)-N-methylpyridine-2-carboxamide | 440 |
| 4 | 4-({2-[(3-chloro-4-fluorophenyl)-amino]-1H-benzimidazol-6-yl}-oxy)-N-methylpyridine-2-carboxamide | 412 |
| 5 | N-methyl-4-{[2-(phenylamino)-1H-benzimidazol-6-yl]oxy}-pyridine-2-carboxamide | 360 |
| 6 | 4-[(2-{[4-bromo-2-(trifluoro-methyl)phenyl]amino}-1H-benzimidazol-6-yl)oxy]-N-methyl-pyridine-2-carboxamide | 508 |
| 7 | N-methyl-4-({2-[(2-methylpropyl)-amino]-1H-benzimidazol-6-yl}-oxy)pyridine-2-carboxamide | 340 |

TABLE 1-continued

| Example | Structure | Name | MH+ |
| --- | --- | --- | --- |
| 8 | 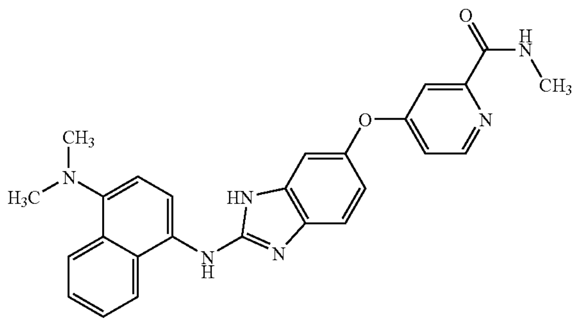 | 4-[(2-{[4-(dimethylamino)-naphthalen-1-yl]amino}-1H-benzimidazol-6-yl)oxy]-N-methyl-pyridine-2-carboxamide | 453 |
| 9 | 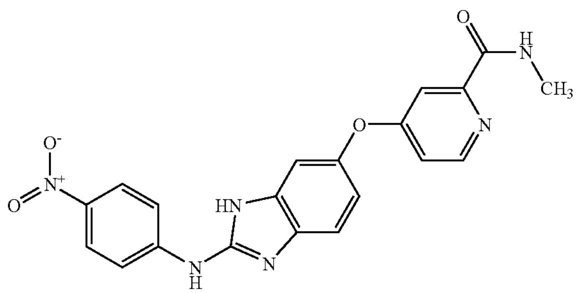 | N-methyl-4-({2-[(4-nitrophenyl)-amino]-1H-benzimidazol-6-yl}-oxy)pyridine-2-carboxamide | 405 |
| 10 | 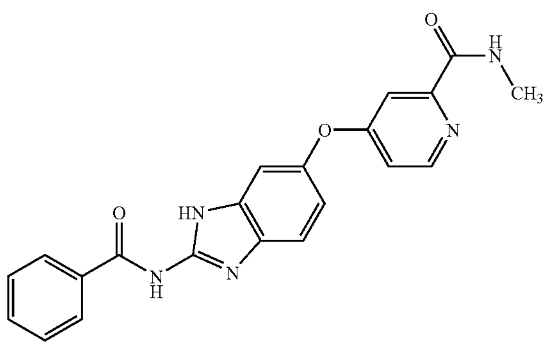 | N-methyl-4-({2-[(phenylcarbonyl)-amino]-1H-benzimidazol-6-yl}-oxy)pyridine-2-carboxamide | 388 |
| 11 | 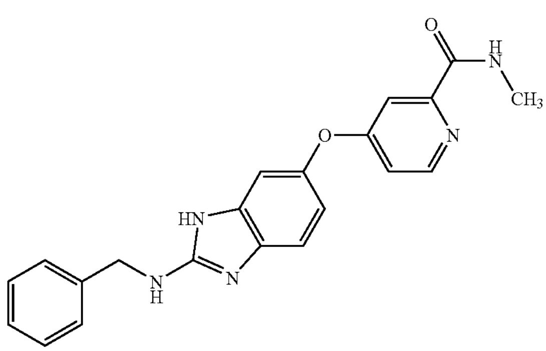 | N-methyl-4-({2-[(phenylmethyl)-amino]-1H-benzimidazol-6-yl}-oxy)pyridine-2-carboxamide | 374 |
| 12 | 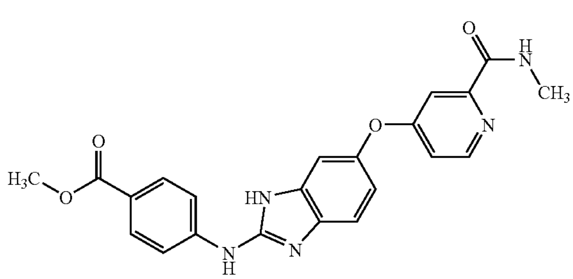 | methyl 4-{[6-({2-[(methylamino)-carbonyl]pyridin-4-yl}oxy)-1H-benzimidazol-2-yl]amino}benzoate | 418 |

TABLE 1-continued

| Example | Structure | Name | MH+ |
|---|---|---|---|
| 13 | 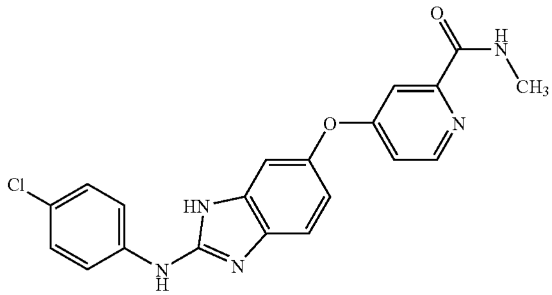 | 4-({2-[(4-chlorophenyl)amino]-1H-benzimidazol-6-yl}oxy)-N-methyl-pyridine-2-carboxamide | 394 |
| 14 | 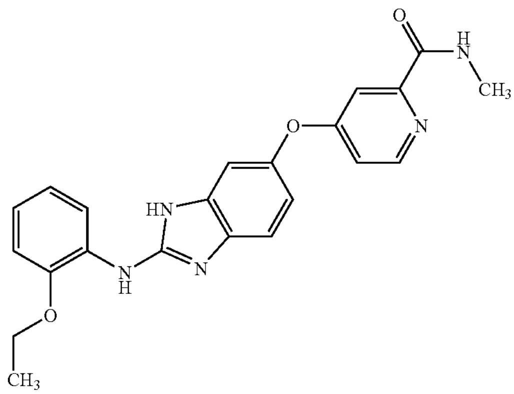 | 4-[(2-{[2-(ethyloxy)phenyl]-amino}-1H-benzimidazol-6-yl)-oxy]-N-methylpyridine-2-carboxamide | 404 |
| 15 | 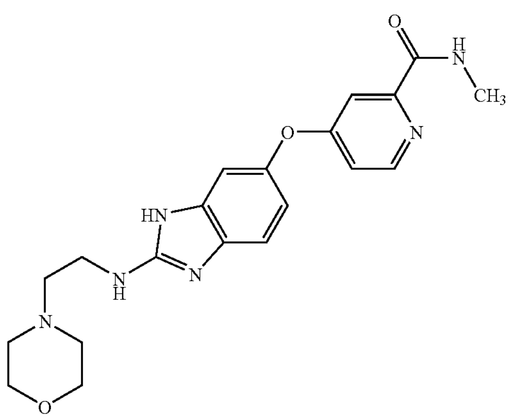 | N-methyl-4-({2-[(2-morpholin-4-ylethyl)amino]-1H-benzimidazol-6-yl}oxy)pyridine-2-carboxamide | 397 |
| 16 | 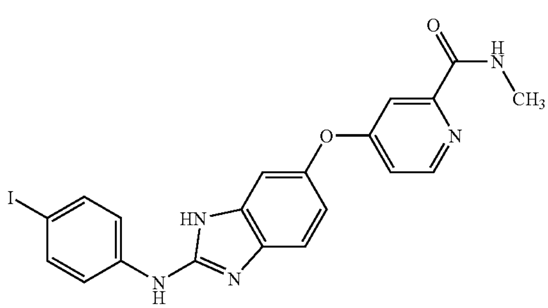 | 4-({2-[(4-iodophenyl)amino]-1H-benzimidazol-6-yl}oxy)-N-methyl-pyridine-2-carboxamide | 486 |

TABLE 1-continued

| Example | Structure | Name | MH+ |
|---|---|---|---|
| 17 | 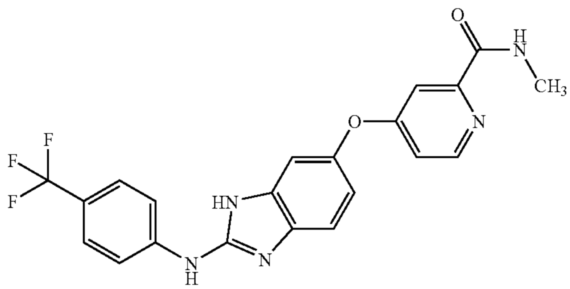 | N-methyl-4-[(2-{[4-(trifluoro-methyl)phenyl]amino}-1H-benzimidazol-6-yl)oxy]pyridine-2-carboxamide | 428 |
| 18 | 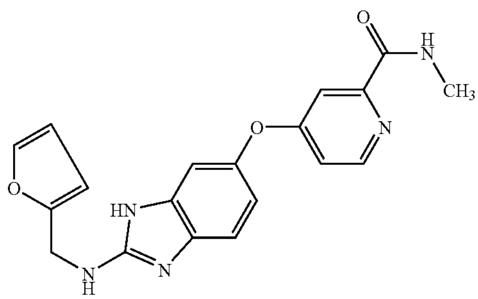 | 4-({2-[(furan-2-ylmethyl)amino]-1H-benzimidazol-6-yl}oxy)-N-methylpyridine-2-carboxamide | 364 |
| 19 | 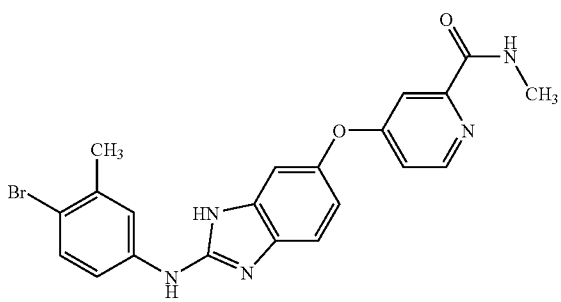 | 4-({2-[(4-bromo-3-methylphenyl)-amino]-1H-benzimidazol-6-yl}-oxy)-N-methylpyridine-2-carboxamide | 453 |
| 20 | 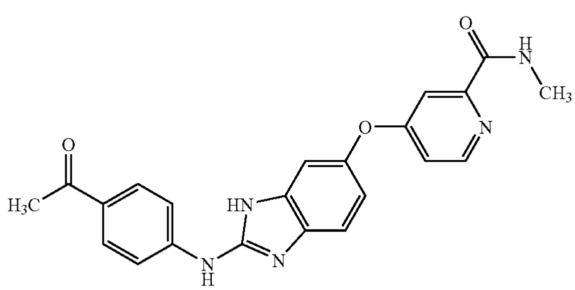 | 4-({2-[(4-acetylphenyl)amino]-1H-benzimidazol-6-yl}oxy)-N-methyl-pyridine-2-carboxamide | 402 |
| 21 | 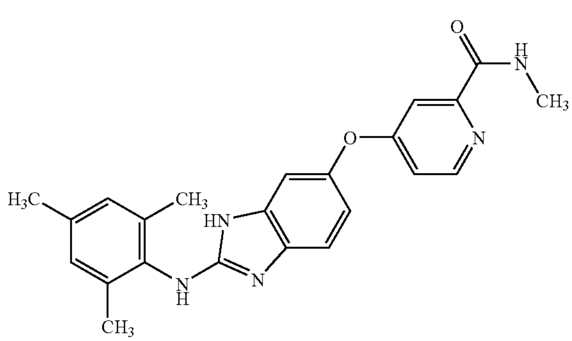 | N-methyl-4-({2-[(2,4,6-trimethyl-phenyl)amino]-1H-benzimidazol-6-yl}oxy)pyridine-2-carboxamide | 402 |

TABLE 1-continued

| Example | Structure | Name | MH+ |
|---|---|---|---|
| 22 | 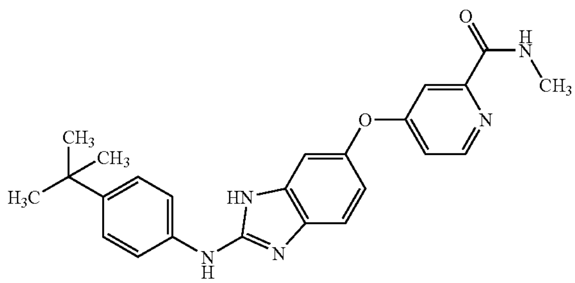 | 4-[(2-{[4-(1,1-dimethylethyl)-phenyl]amino}-1H-benzimidazol-6-yl)oxy]-N-methylpyridine-2-carboxamide | 416 |
| 23 | 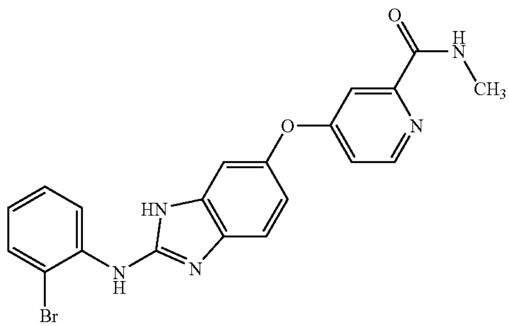 | 4-({2-[(2-bromophenyl)amino]-1H-benzimidazol-6-yl}oxy)-N-methylpyridine-2-carboxamide | 440 |
| 24 | 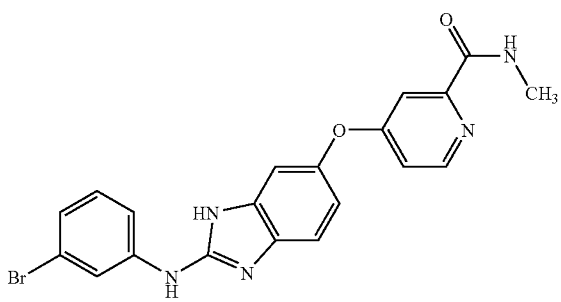 | 4-({2-[(3-bromophenyl)amino]-1H-benzimidazol-6-yl}oxy)-N-methylpyridine-2-carboxamide | 440 |
| 25 | 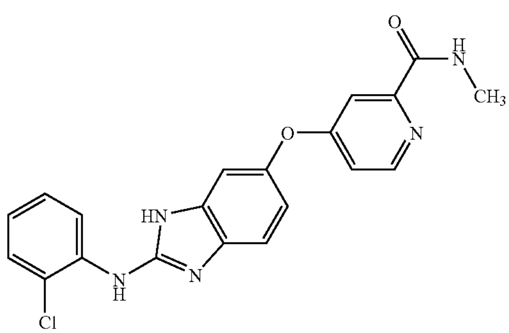 | 4-({2-[(2-chlorophenyl)amino]-1H-benzimidazol-6-yl}oxy)-N-methyl-pyridine-2-carboxamide | 394 |
| 26 | 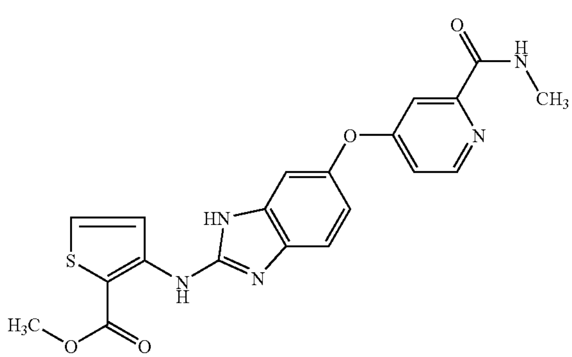 | methyl 3-{[6-({2-[(methylamino)-carbonyl]pyridin-4-yl}oxy)-1H-benzimidazol-2-yl]amino}-thiophene-2-carboxylate | 424 |

TABLE 1-continued

| Example | Structure | Name | MH+ |
|---|---|---|---|
| 27 | 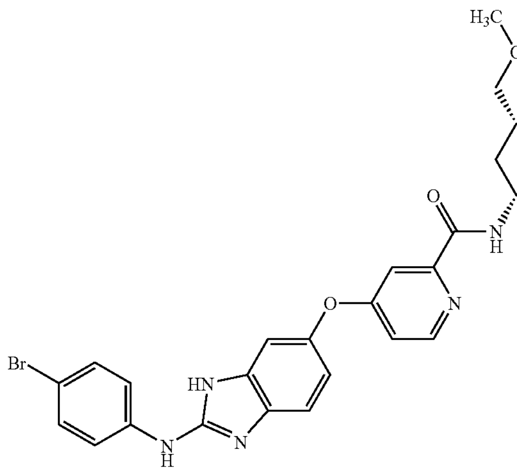 | 4-({2-[(4-bromophenyl)amino]-1H-benzimidazol-6-yl}oxy)-N-{(3R,5R)-5-[(methyloxy)methyl]-pyrrolidin-3-yl}pyridine-2-carboxamide | 539 |
| 28 | 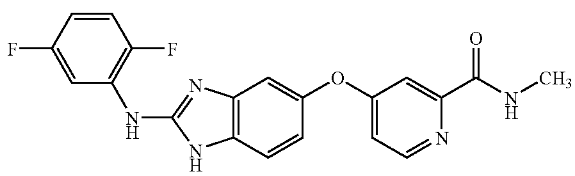 | (4-{2-[(2,5-difluorophenyl)amino]-benzimidazol-5-yloxy}(2-pyridyl))-N-methylcarboxamide | 395.3 |
| 29 | 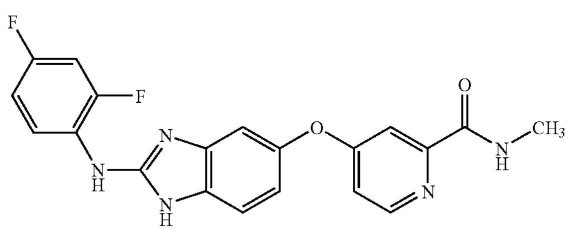 | (4-{2-[(2,4-difluorophenyl)amino]-benzimidazol-5-yloxy}(2-pyridyl))-N-methylcarboxamide | 395.3 |
| 30 | 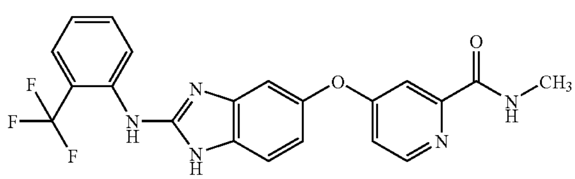 | N-methyl[4-(2-{[2-(trifluoromethyl)phenyl]amino}-benzimidazol-5-yloxy)(2-pyridyl)]-carboxamide | 427.3 |
| 31 | 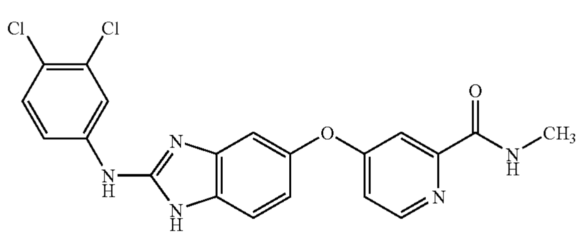 | (4-{2-[(3,4-dichlorophenyl)amino]-benzimidazol-5-yloxy}(2-pyridyl))-N-methylcarboxamide | 428.2 |
| 32 | 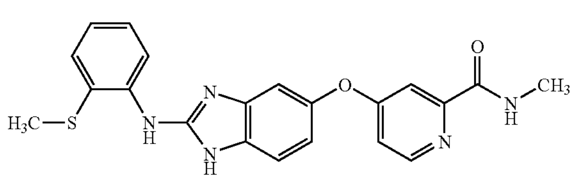 | N-methyl(4-{2-[(2-methylthio-phenyl)amino]benzimidazol-5-yloxy}(2-pyridyl))carboxamide | 405.4 |

TABLE 1-continued

| Example | Structure | Name | MH+ |
|---|---|---|---|
| 33 | 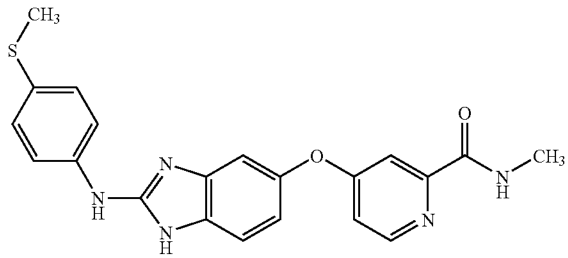 | N-methyl(4-{2-[(4-methylthiophenyl)amino]benzimidazol-5-yloxy}(2-pyridyl))carboxamide | 405.4 |
| 34 | 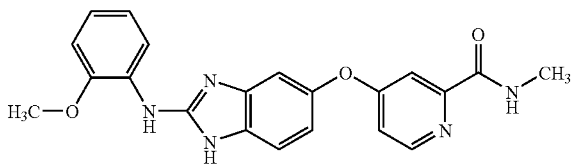 | (4-{2-[(2-methoxyphenyl)amino]-benzimidazol-5-yloxy}(2-pyridyl))-N-methylcarboxamide | 389.4 |
| 35 | 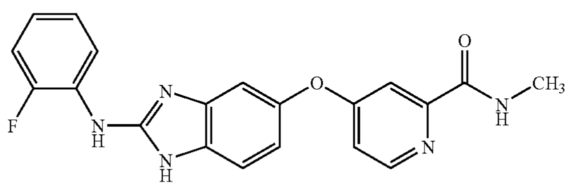 | (4-{2-[(2-fluorophenyl)amino]-benzimidazol-5-yloxy}(2-pyridyl))-N-methylcarboxamide | 377.3 |
| 36 | 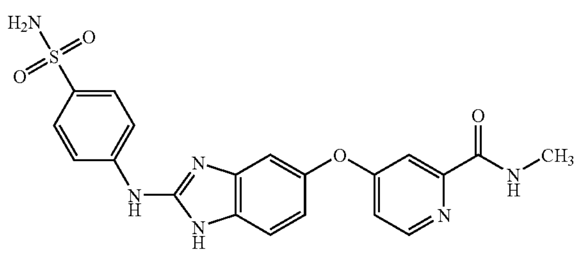 | N-methyl(4-{2-[(4-sulfamoylphenyl)amino]benzimidazol-5-yloxy}(2-pyridyl))carboxamide | 438.4 |
| 37 | 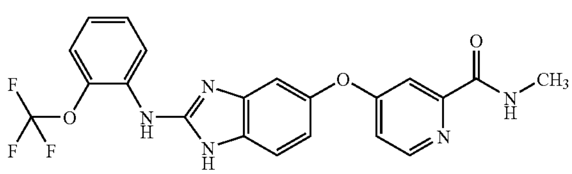 | N-methyl[4-(2-{[2-(trifluoromethoxy)phenyl]amino}-benzimidazol-5-yloxy)(2-pyridyl)]-carboxamide | 443.3 |
| 38 | 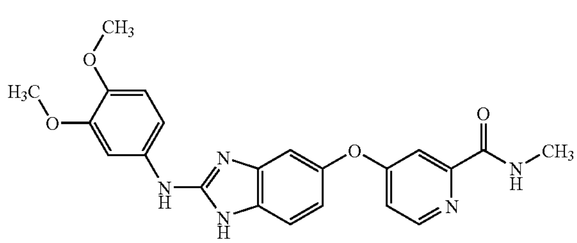 | (4-{2-[(3,4-dimethoxyphenyl)-amino]benzimidazol-5-yloxy}(2-pyridyl))-N-methylcarboxamide | 419.4 |
| 39 | 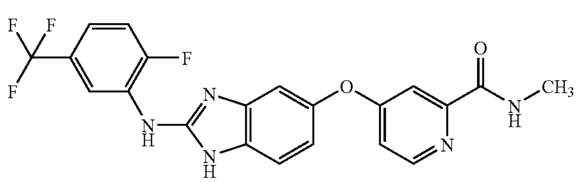 | [4-(2-{[2-fluoro-5-(trifluoromethyl)phenyl]amino}-benzimidazol-5-yloxy)(2-pyridyl)]-N-methylcarboxamide | 445.3 |

TABLE 1-continued

| Example | Structure | Name | MH+ |
|---|---|---|---|
| 40 | 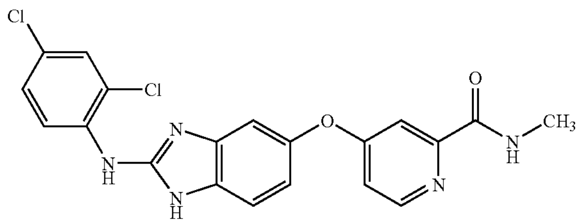 | (4-{2-[(2,4-dichlorophenyl)amino]-benzimidazol-5-yloxy}(2-pyridyl))-N-methylcarboxamide | 428.2 |
| 41 | 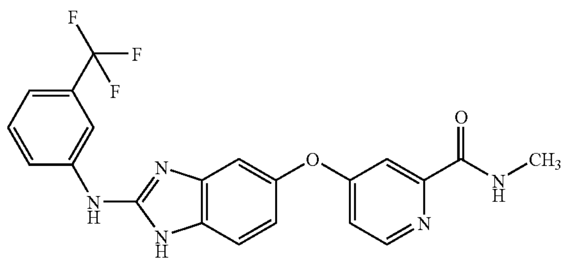 | N-methyl[4-(2-{[3-trifluoro-methyl)phenyl]amino}-benzimidazol-5-yloxy)(2-pyridyl)]-carboxamide | 427.3 |
| 42 | 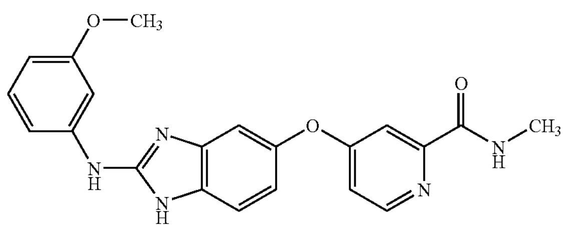 | (4-{2-[(3-methoxyphenyl)amino]-benzimidazol-5-yloxy}(2-pyridyl))-N-methylcarboxamide | 389.4 |
| 43 | 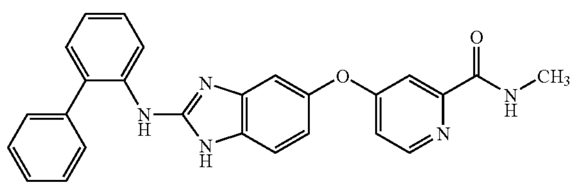 | N-methyl(4-{2-[(2-phenylphenyl)-amino]benzimidazol-5-yloxy}(2-pyridyl))carboxamide | 435.4 |
| 44 | 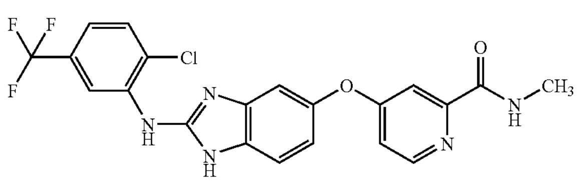 | [4-(2-{[2-chloro-5-(trifluoro-methyl)phenyl]amino}-benzimidazol-5-yloxy)(2-pyridyl)]-N-methylcarboxamide | 461.8 |
| 45 | 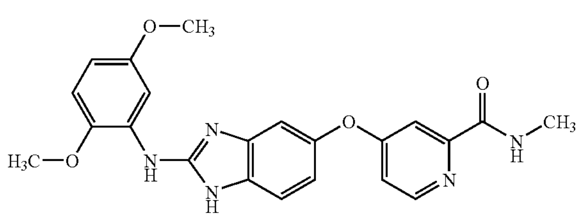 | (4-{2-[(2,5-dimethoxyphenyl)-amino]benzimidazol-5-yloxy}(2-pyridyl))-N-methylcarboxamide | 419.4 |
| 46 | 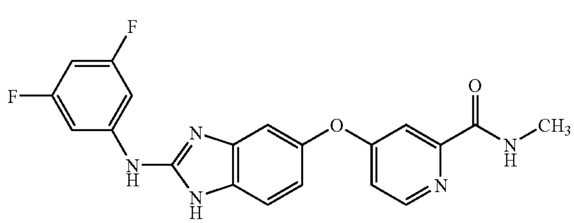 | (4-{2-[(3,5-difluorophenyl)amino]-benzimidazol-5-yloxy}(2-pyridyl))-N-methylcarboxamide | 395.3 |

TABLE 1-continued

| Example | Name | MH+ |
|---|---|---|
| 47 | (4-{2-[(2-ethylphenyl)amino]-benzimidazol-5-yloxy}(2-pyridyl))-N-methylcarboxamide | 387.4 |
| 48 | (4-{2-[(3,5-difluorophenyl)amino]-benzimidazol-5-yloxy}(2-pyridyl))-N-methylcarboxamide | 395.4 |
| 49 | [4-(2-{[3,5-bis(trifluoromethyl)-phenyl]amino}benzimidazol-5-yloxy)(2-pyridyl)]-N-methyl-carboxamide | 495.4 |
| 50 | (4-{2-[(2-methoxy-5-methylphenyl)amino]-benzimidazol-5-yloxy}(2-pyridyl))-N-methylcarboxamide | 403.4 |
| 51 | (4-{2-[(4-bromophenyl)amino]-1-methylbenzimidazol-6-yloxy}(2-pyridyl))-N-methylcarboxamide | 452.3 |
| 52 | N-methyl[4-(2-{[2-(methylethyl)phenyl]amino}benzimidazol-5-yloxy)(2-pyridyl)]carboxamide | 401.4 |
| 53 | (4-{2-[(2-methoxy-4-nitrophenyl)-amino]benzimidazol-5-yloxy}(2-pyridyl))-N-methylcarboxamide | 434.4 |
| 54 | (4-{2-[(3,5-dimethoxyphenyl)-amino]benzimidazol-5-yloxy}(2-pyridyl))-N-methylcarboxamide | 420.1 |

TABLE 1-continued

| Example | Structure | Name | MH+ |
| --- | --- | --- | --- |
| 55 | 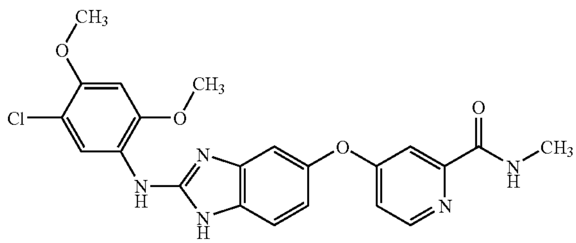 | (4-{2-[(5-chloro-2,4-dimethoxy-phenyl)amino]benzimidazol-5-yloxy}(2-pyridyl))-N-methyl carboxamide | 454.1 |
| 56 | 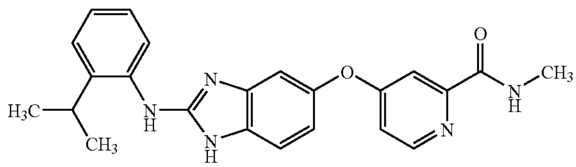 | N-methyl-4-[(2-{[2-(1-methyl-ethyl)phenyl]amino}-1H-benzimidazol-5-yl)oxy]pyridine-2-carboxamide | 402.5 |
| 57 | 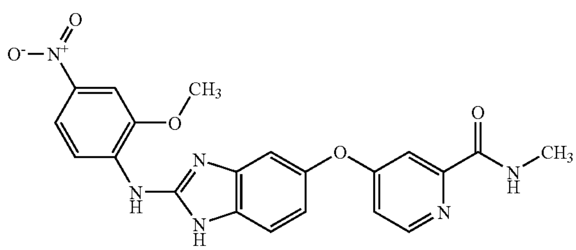 | N-methyl-4-[(2-{[2-(methyloxy)-4-nitrophenyl]amino}-1H-benzimidazol-5-yl)oxy]pyridine-2-carboxamide | 435.4 |
| 58 | 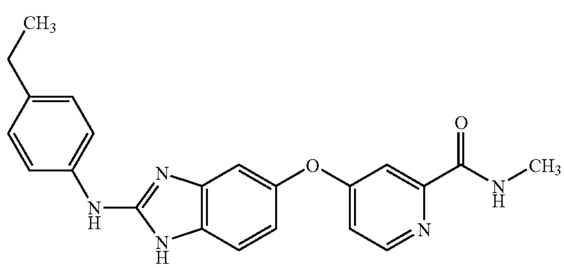 | 4-({2-[(4-ethylphenyl)amino]-1H-benzimidazol-5-yl}oxy)-N-methyl-pyridine-2-carboxamide | 388.4 |
| 59 | 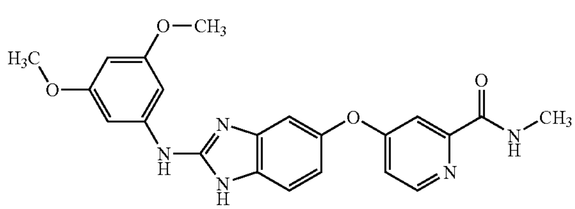 | 4-[(2-{[3,5-bis(methyloxy)phenyl]-amino}-1H-benzimidazol-5-yl)-oxy]-N-methylpyridine-2-carboxamide | 420.4 |
| 60 | 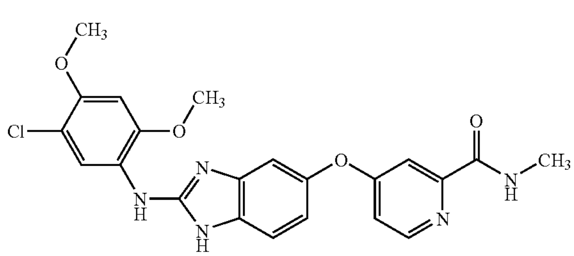 | 4-[(2-{[5-chloro-2,4-bis(methyl-oxy)phenyl]amino}-1H-benzimidazol-5-yl)oxy]-N-methyl-pyridine-2-carboxamide | 454.9 |

TABLE 1-continued

| Example | Name | MH+ |
|---|---|---|
| 61 | 4-({2-[(4-cyclohexylphenyl)-amino]-1H-benzimidazol-5-yl}-oxy)-N-methylpyridine-2-carboxamide | 442.5 |
| 62 | 4-({2-[(3,4-difluorophenyl)amino]-1H-benzimidazol-5-yl}oxy)-N-methylpyridine-2-carboxamide | 396.4 |
| 63 | 4-({2-[(3,4-dimethylphenyl)-amino]-1H-benzimidazol-5-yl}-oxy)-N-methylpyridine-2-carboxamide | 388.4 |
| 64 | 4-({2-[(4-bromo-3-chlorophenyl)-amino]-1H-benzimidazol-5-yl}-oxy)-N-methylpyridine-2-carboxamide | 473.7 |
| 65 | 4-({2-[(4-butylphenyl)amino]-1H-benzimidazol-5-yl}oxy)-N-methyl-pyridine-2-carboxamide | 416.5 |
| 66 | N-methyl-4-[(2-{[4-(1-methyl-ethyl)phenyl]amino}-1H-benzimidazol-5-yl)oxy]pyridine-2-carboxamide | 402.5 |

TABLE 1-continued

| Example | Structure | Name | MH+ |
|---|---|---|---|
| 67 | 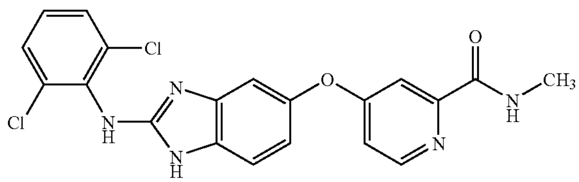 | 4-({2-[(2,6-dichlorophenyl)amino]-1H-benzimidazol-5-yl}oxy)-N-methylpyridine-2-carboxamide | 429.3 |
| 68 | 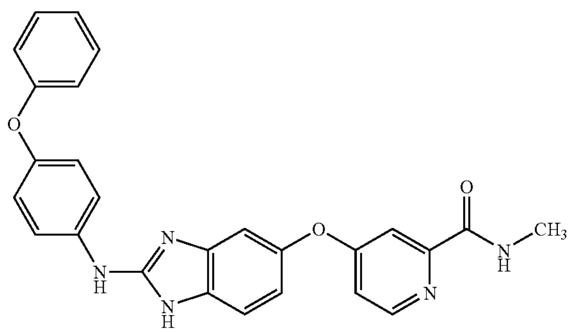 | N-methyl-4-[(2-{[4-(phenyloxy)phenyl]amino}-1H-benzimidazol-5-yl)oxy]pyridine-2-carboxamide | 452.5 |
| 69 | 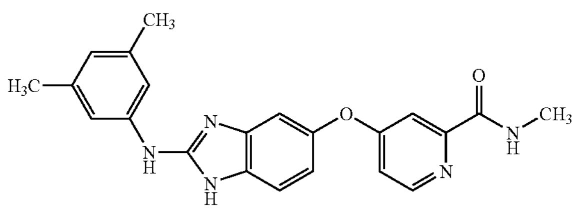 | 4-({2-[(3,5-dimethylphenyl)amino]-1H-benzimidazol-5-yl}oxy)-N-methylpyridine-2-carboxamide | 388.4 |
| 70 | 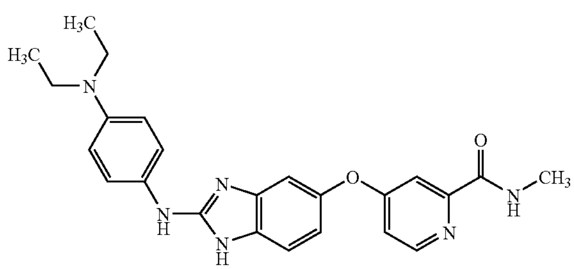 | 4-[(2-{[4-diethylamino)phenyl]amino}-1H-benzimidazol-5-yl)oxy]-N-methylpyridine-2-carboxamide | 431.5 |
| 71 | 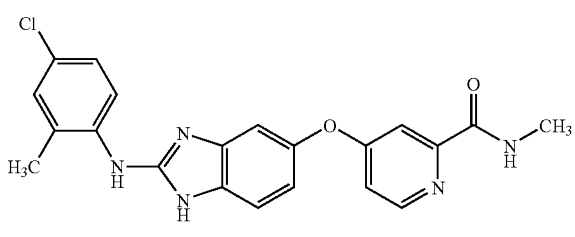 | 4-({2-[(4-chloro-2-methylphenyl)amino]-1H-benzimidazol-5-yl}oxy)-N-methylpyridine-2-carboxamide | 408.9 |
| 72 | 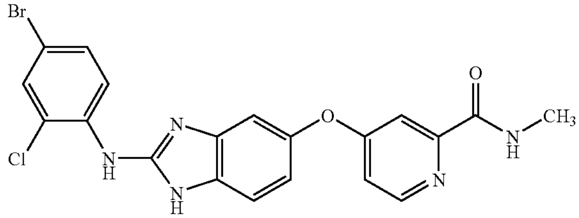 | 4-({2-[(4-bromo-2-chlorophenyl)amino]-1H-benzimidazol-5-yl}oxy)-N-methylpyridine-2-carboxamide | 473.7 |

TABLE 1-continued

| Example | Structure | Name | MH+ |
|---|---|---|---|
| 73 | 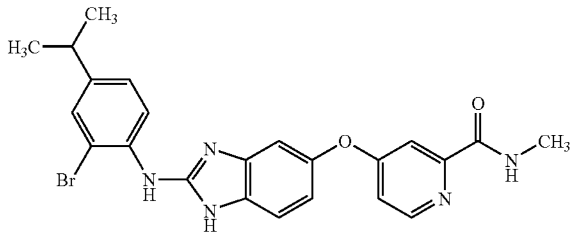 | 4-[(2-{[2-bromo-4-(1-methyl-ethyl)phenyl]amino}-1H-benzimidazol-5-yl)oxy]-N-methyl-pyridine-2-carboxamide | 481.4 |
| 74 | 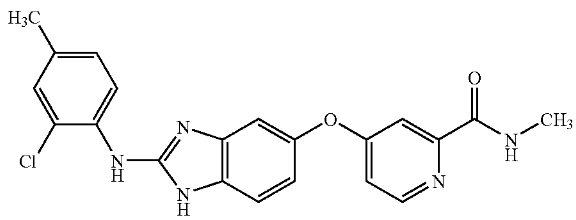 | 4-({2-[(2-chloro-4-methylphenyl)-amino]-1H-benzimidazol-5-yl}-oxy)-N-methylpyridine-2-carboxamide | 408.9 |
| 75 | 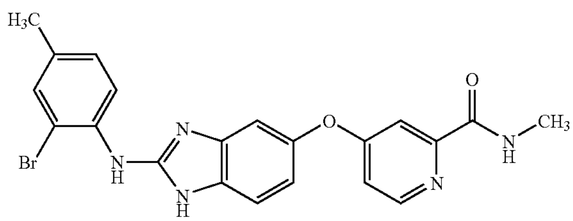 | 4-({2-[(2-bromo-4-methylphenyl)-amino]-1H-benzimidazol-5-yl}-oxy)-N-methylpyridine-2-carboxamide | 453.3 |
| 76 | 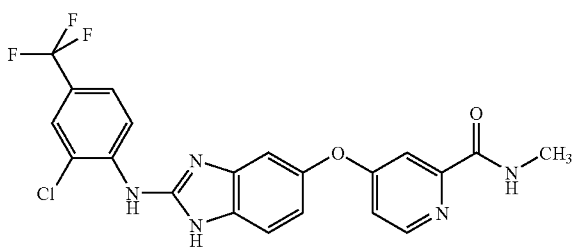 | 4-[(2-{[2-chloro-4-(trifluoro-methyl)phenyl]amino}-1H-benzimidazol-5-yl)oxy]-N-methylpyridine-2-carboxamide | 462.8 |
| 77 | 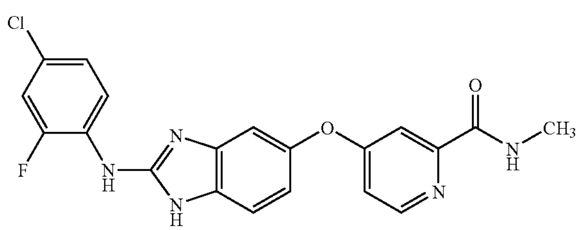 | 4-({2-[(4-chloro-2-fluorophenyl)-amino]-1H-benzimidazol-5-yl}-oxy)-N-methylpyridine-2-carboxamide | 412.8 |
| 78 | 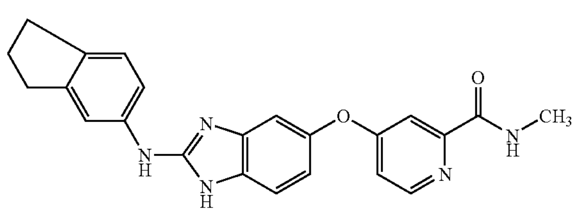 | 4-{[2-(2,3-dihydro-1H-inden-5-ylamino)-1H-benzimidazol-5-yl]-oxy}-N-methylpyridine-2-carboxamide | 400.5 |
| 79 | 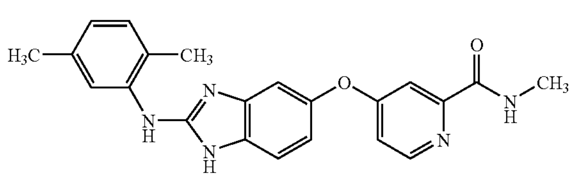 | 4-({2-[(2,5-dimethyphenyl)-amino]-1H-benzimidazol-5-yl}-oxy)-N-methylpyridine-2-carboxamide | 388.4 |

TABLE 1-continued

| Example | Structure | Name | MH+ |
|---|---|---|---|
| 80 | 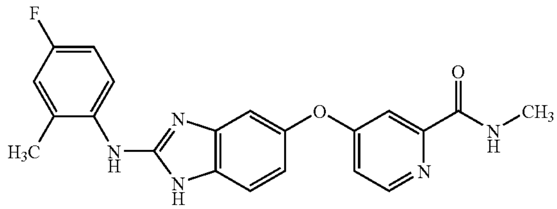 | 4-({2-[(4-fluoro-2-methylphenyl)-amino]-1H-benzimidazol-5-yl}-oxy)-N-methylpyridine-2-carboxamide | 392.4 |
| 81 | 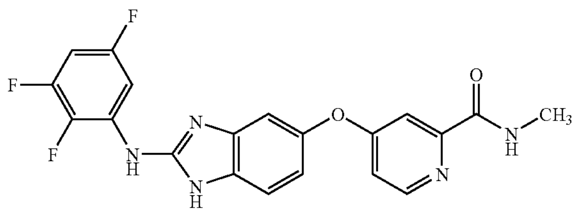 | N-methyl-4-({2-[(2,3,5-trifluoro-phenyl)amino]-1H-benzimidazol-5-yl}oxy)pyridine-2-carboxamide | 414.4 |
| 82 | 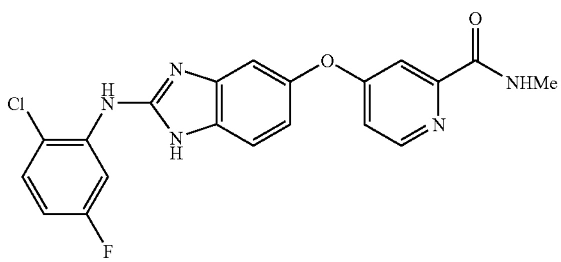 | 4-({2-[(2-chloro-5-fluorophenyl)-amino]-1H-benzimidazol-5-yl}-oxy)-N-methylpyridine-2-carboxamide | 412.8 |
| 83 | 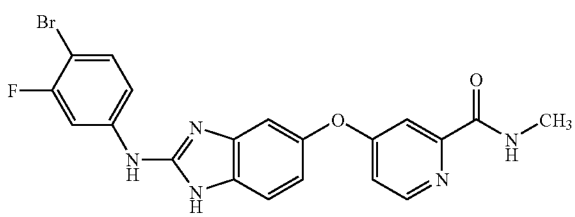 | 4-({2-[(4-bromo-3-fluorophenyl)-amino]-1H-benzimidazol-5-yl}-oxy)-N-methylpyridine-2-carboxamide | 457.3 |
| 84 | 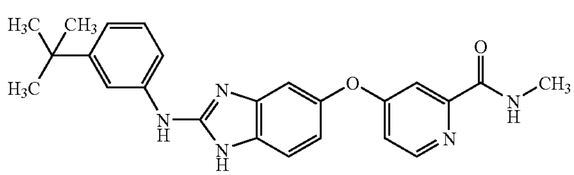 | 4-[(2-{[3-(1,1-dimethylethyl)-phenyl]amino}-1H-benzimidazol-5-yl)oxy]-N-methylpyridine-2-carboxamide | 416.5 |
| 85 | 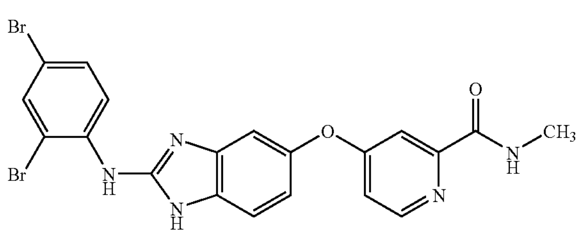 | 4-({2-[(2,4-dibromophenyl)-amino]-1H-benzimidazol-5-yl}-oxy)-N-methylpyridine-2-carboxamide | 518.2 |
| 86 | 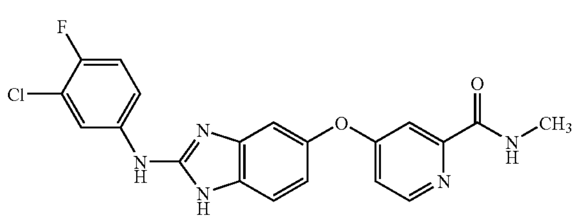 | 4-({2-[(3-chloro-4-fluorophenyl)-amino]-1H-benzimidazol-5-yl}-oxy)-N-methylpyridine-2-carboxamide | 412.8 |

TABLE 1-continued

| Example | Structure | Name | MH+ |
|---|---|---|---|
| 87 | 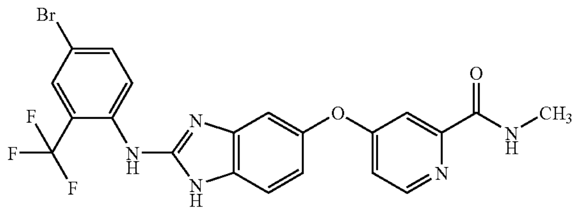 | 4-[(2-{[4-bromo-2-(trifluoromethyl)phenyl]amino}-1H-benzimidazol-5-yl)oxy]-N-methylpyridine-2-carboxamide | 507.3 |
| 88 | 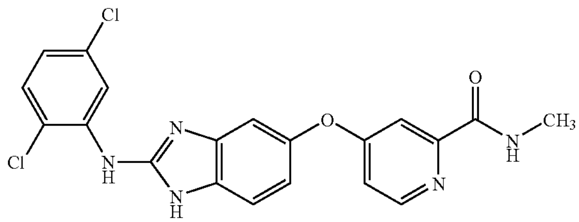 | 4-({2-[(2,5-dichlorophenyl)amino]-1H-benzimidazol-5-yl}oxy)-N-methylpyridine-2-carboxamide | 429.3 |
| 89 | 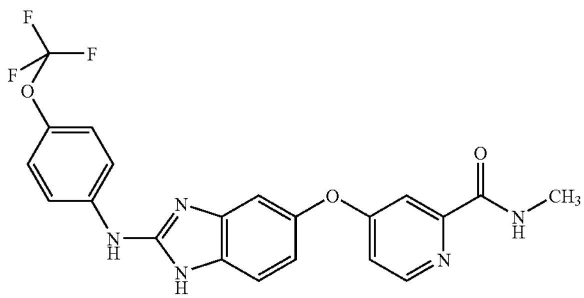 | N-methyl-4-{[2-({4-[(trifluoromethyl)oxy]phenyl}amino)-1H-benzimidazol-5-yl]oxy}pyridine-2-carboxamide | 444.4 |
| 90 | 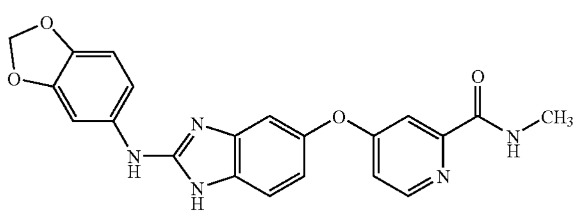 | 4-{[2-(1,3-benzodioxol-5-ylamino)-1H-benzimidazol-5-yl]oxy}-N-methylpyridine-2-carboxamide | 404.4 |
| 91 | 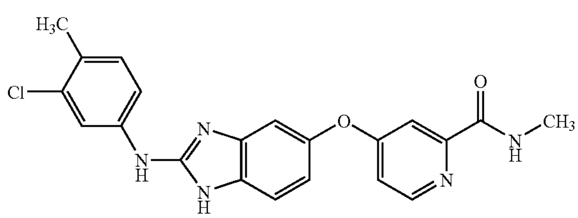 | 4-({2-[(3-chloro-4-methylphenyl)amino]-1H-benzimidazol-5-yl}oxy)-N-methylpyridine-2-carboxamide | 408.9 |
| 92 | 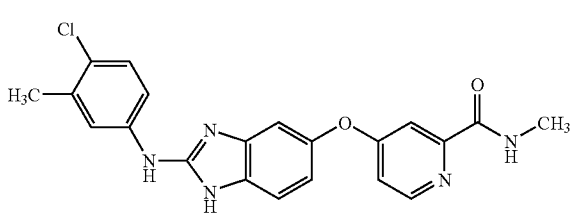 | 4-({2-[(4-chloro-3-methylphenyl)amino]-1H-benzimidazol-5-yl}oxy)-N-methylpyridine-2-carboxamide | 408.9 |

TABLE 1-continued

| Example | Structure | Name | MH+ |
|---|---|---|---|
| 93 | 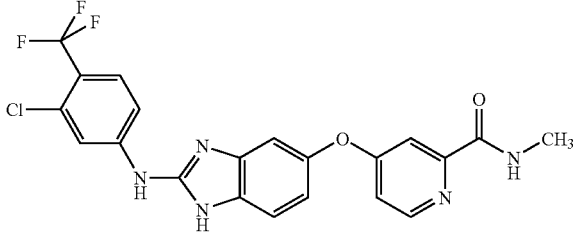 | 4-[(2-{[3-chloro-4-(trifluoro-methyl)phenyl]amino}-1H-benzimidazol-5-yl)oxy]-N-methyl-pyridine-2-carboxamide | 462.8 |
| 94 | 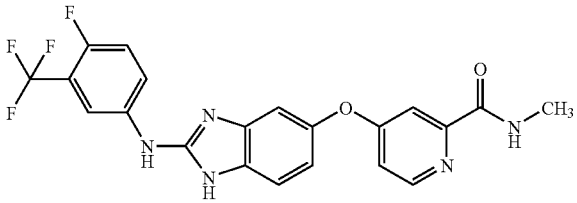 | 4-[(2-{[4-fluoro-3-(trifluoro-methyl)phenyl]amino}-1H-benzimidazol-5-yl)oxy]-N-methyl-pyridine-2-carboxamide | 446.4 |
| 95 | 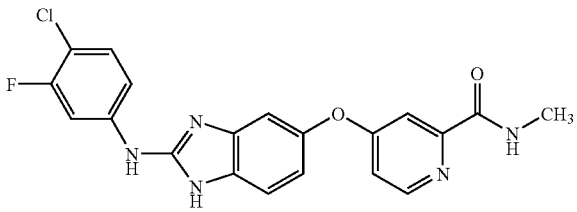 | 4-({2-[(4-chloro-3-fluorophenyl)amino]-1H-benzimidazol-5-yl}-oxy)-N-methylpyridine-2-carboxamide | 412.8 |
| 96 | 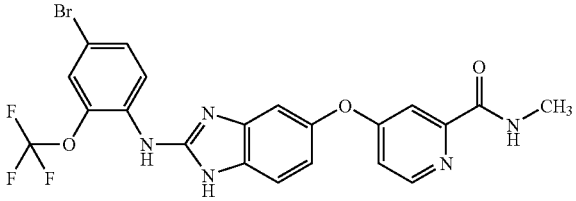 | 4-{[2-({4-bromo-2-[(trifluoro-methyl)oxy]phenyl}amino)-1H-benzimidazol-5-yl]oxy}-N-methyl-pyridine-2-carboxamide | 523.3 |
| 97 | 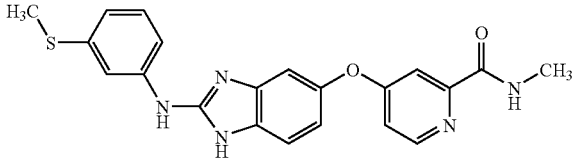 | N-methyl-4-[(2-{[3-(methylthio)-phenyl]amino}-1H-benzimidazol-5-yl)oxy]pyridine-2-carboxamide | 406.5 |
| 98 | 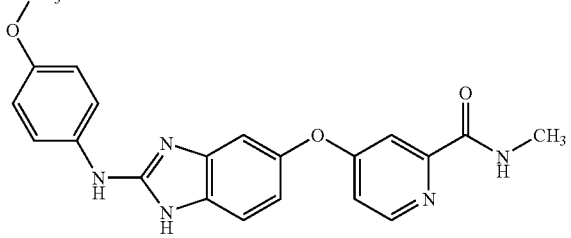 | N-methyl-4-[(2-{[4-(methyloxy)-phenyl]amino}-1H-benzimidazol-5-yl)oxy]pyridine-2-carboxamide | 390.4 |
| 99 | 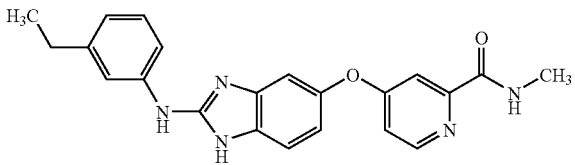 | 4-({2-[(3-ethylphenyl)amino]-1H-benzimidazol-5-yl}oxy)-N-methyl-pyridine-2-carboxamide | 388.4 |

TABLE 1-continued

| Example | Structure | Name | MH+ |
|---|---|---|---|
| 100 | 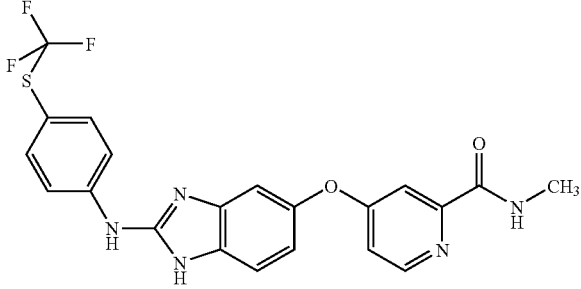 | N-methyl-4-{[2-({4-[(trifluoro-methyl)thio]phenyl}amino)-1H-benzimidazol-5-yl]oxy}pyridine-2-carboxamide | 460.4 |
| 101 | 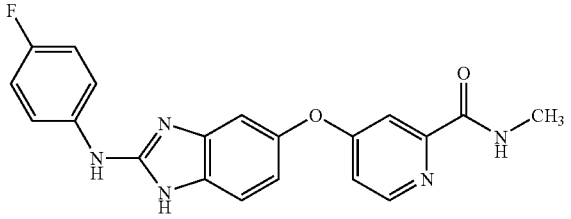 | 4-({2-[(4-fluorophenyl)amino]-1H-benzimidazol-5-yl}oxy)-N-methyl-pyridine-2-carboxamide | 378.4 |
| 102 | 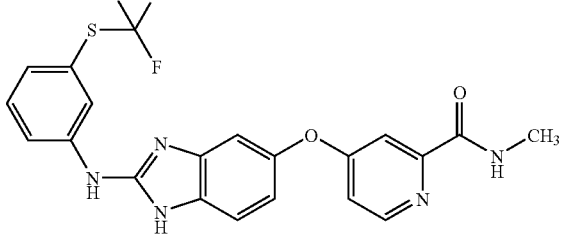 | N-methyl-4-{[2-({3-[(trifluoro-methyl)thio]phenyl}amino)-1H-benzimidazol-5-yl]oxy}pyridine-2-carboxamide | 460.4 |
| 103 | 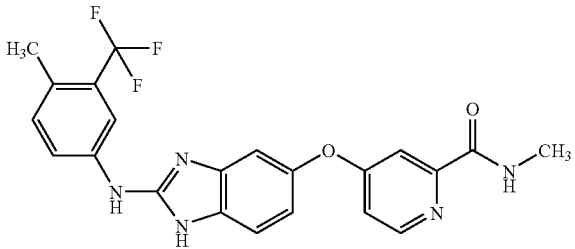 | N-methyl-4-[(2-{[4-methyl-3-(trifluoromethyl)phenyl]amino}-1H-benzimidazol-5-yl)oxy]-pyridine-2-carboxamide | 442.4 |
| 104 | 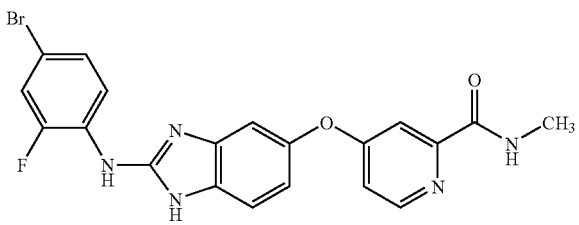 | 4-({2-[(4-bromo-2-fluorophenyl)-amino]-1H-benzimidazol-5-yl}-oxy)-N-methylpyridine-2-carboxamide | 457.3 |
| 105 | 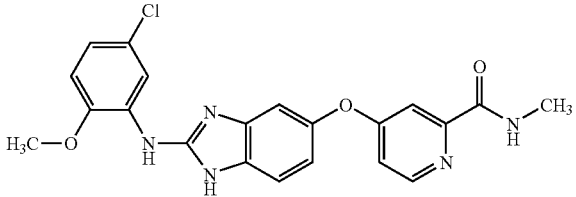 | 4-[2-{[5-chloro-2-(methyloxy)-phenyl]amino}-1H-benzimidazol-5-yl)oxy]-N-methylpyridine-2-carboxamide | 424.9 |

TABLE 1-continued

| Example | Structure | Name | MH+ |
|---|---|---|---|
| 106 | 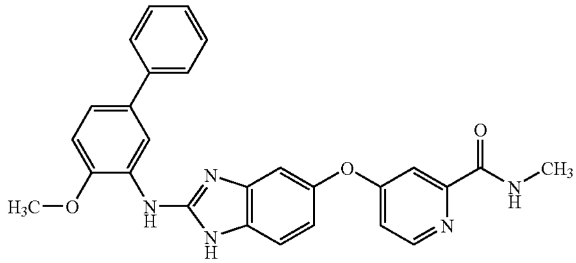 | N-methyl-4-[(2-{[4-(methyloxy)-1,1'-biphenyl-3-yl]amino}-1H-benzimidazol-5-yl)oxy]pyridine-2-carboxamide | 466.5 |
| 107 | 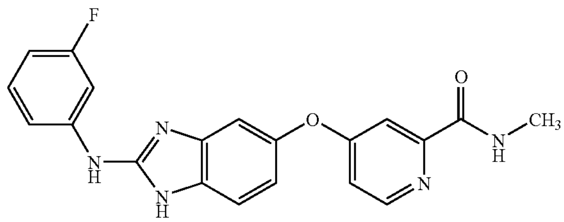 | 4-({2-[(3-fluorophenyl)amino]-1H-benzimidazol-5-yl}oxy)-N-methyl-pyridine-2-carboxamide | 378.4 |
| 108 | 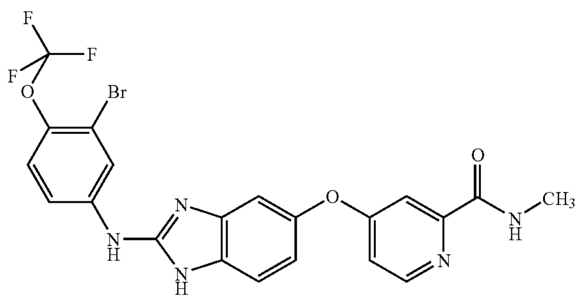 | 4-{[2-({3-bromo-4-[(trifluoromethyl)oxy]phenyl}amino)-1H-benzimidazol-5-yl]oxy}-N-methyl-pyridine-2-carboxamide | 523.3 |

Example 109

Synthesis of (4-{2-[(4-bromophenyl)amino]-benzothiazol-5-yloxy}(2-pyridyl))-N-methylcarboxamide

Step 1. Synthesis of 2-bromo-5-methoxybenzothiazole

A solution of bromine (3.6 eq) in chloroform (0.75M) was added dropwise over a of 1 hr to a stirred suspension of 5-methoxy-2-mercaptobenzothiazole (1 eq) in form at 0° C. The mixture was stirred for 30 min before it was added slowly to water and stirred for further 20 min. The mixture was filtered to remove a cream solid. The organic phase was dried and evaporated to leave a brown solid. The brown solid was dissolved in ether and filtered. The residue was washed with ether and the filtrate and washings were combined and evaporated, chromatographed (4:1 hexanes and ethyl acetate) to give the title compound as a pale yellow solid. MS: MH+=244

Step 2. Synthesis of (4-bromophenyl)(5-methoxybenzothiazol-2-yl)amine

The mixture containing 2-bromo-5-methoxybenzthiazole (1 eq), 4-Bromoaniline (2 eq) and disopropylethylamine was subjected to microwave in NMP at 220° C. The resultant mixture was concentrated and partitioned between ethyl acetate and water. The organic layer was washed with brine and dried. Purification on silica gel gave the desired product. MS: MH+=335

Step 3. Synthesis of 2-[(4-bromophenyl)amino]benzothiazol-5-ol

The mixture of (4-bromophenyl)(5-methoxybenzothiazol-2-yl)amine and hydrobromic acid (48%) was subjected to the microwave at 150° C. for 6 mins to yield the desired product. MS: MH+=321

Step 4. Synthesis of (4-{2-[(4-bromophenyl)amino]benzothiazol-5-yloxy}(2-pyridyl))-N-methylcarboxamide The mixture containing 2-[(4-bromophenyl)amino]benzothiazol-5-ol (1 eq), Potassiumbis(trimethylsilyl)amide (4 eq), was stirred in dimethylformamide for 30 min at room temperature. To this mixture was added (4-chloro(2-pyridyl)-N-methylcarboxamide (1 eq) and Potassium carbonate (1.2 eq) and microwaved for 6 mins at 150° C. The reaction mixture was then concentrated and partitioned between ethyl acetate and water. The organic layer was separated and washed with brine, dried, filtered and concentrated. Purification on Prep LC yielded the desired product. MS: MH+=455

Each of the Examples 110-119 shown in the following Table 2 were synthesized according to the procedure described in Example 109:

TABLE 2

| Example | Structure | Name | MH+ |
|---|---|---|---|
| 110 | 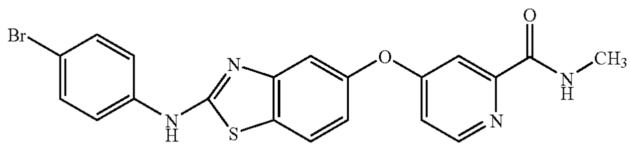 | (4-{2-[(4-bromophenyl)amino]-benzothiazol-5-yloxy}(2-pyridyl))-N-methylcarboxamide | 455 |
| 111 | 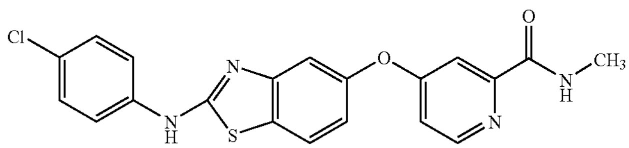 | (4-{2-[(4-chlorophenyl)amino]-benzothiazol-5-yloxy}(2-pyridyl))-N-methylcarboxamide | 411.1 |
| 112 | 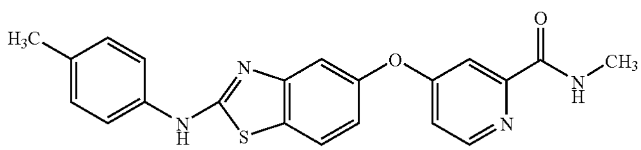 | N-methyl(4-{2-[(4-methylphenyl)-amino]benzothiazol-5-yloxy}(2-pyridyl))carboxamide | 391.1 |
| 113 | 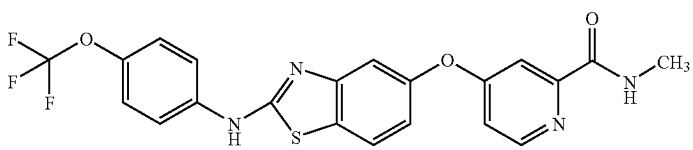 | N-methyl[4-(2-{[4-trifluoro-methoxy)phenyl]amino}-benzothiazol-5-yloxy)(2-pyridyl)]-carboxamide | 461.1 |
| 114 | 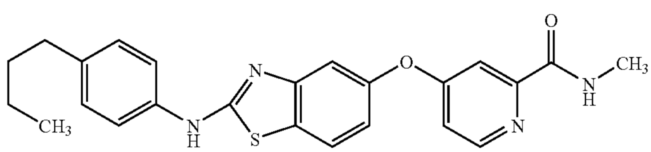 | (4-{2-[(4-butylphenyl)amino]-benzothiazol-5-yloxy}(2-pyridyl))-N-methylcarboxamide | 433.2 |
| 115 | 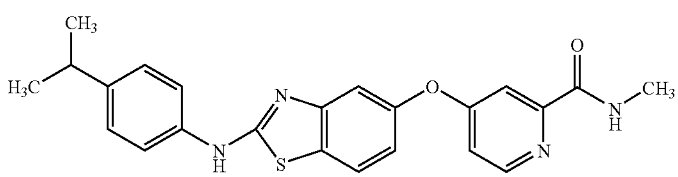 | N-methyl[4-(2-{[4-(methylethyl)-phenyl]amino}benzothiazol-5-yloxy)(2-pyridyl)]carboxamide | 419.2 |
| 116 | 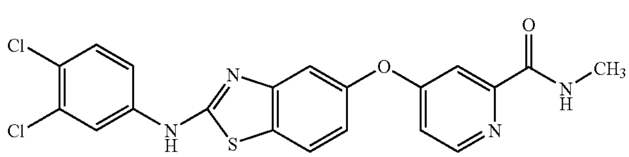 | (4-{2-[(3,4-dichlorophenyl)amino]-benzothiazol-5-yloxy}(2-pyridyl))-N-methylcarboxamide | 445 |
| 117 | 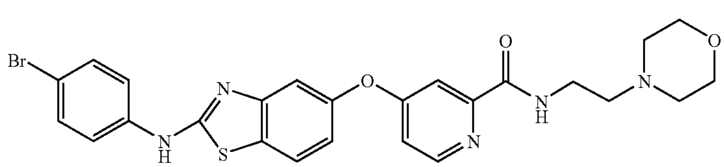 | (4-{2-[(4-bromophenyl)amino]-benzothiazol-5-yloxy}(2-pyridyl))-N-(2-morpholin-4-ylethyl)-carboxamide | 554.1 |
| 118 | Chiral | N-((3R)pyrrolidin-3-yl)(4-{2-[(4-bromophenyl)amino]benzothiazol-5-yloxy}(2-pyridyl)carboxamide | 510 |

| Example | Structure | Name | MH+ |
|---|---|---|---|
| 119 | 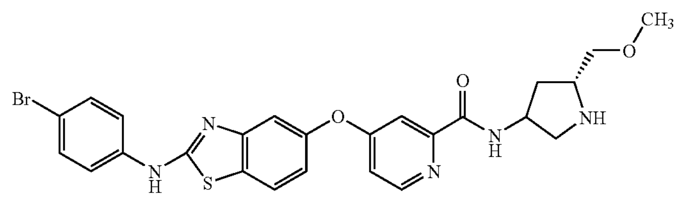 | N-[(3R,5R)-5-(methoxymethyl)-pyrrolidin-3-yl](4-{2-[(4-bromophenyl)amino]benzothiazol | 554.1 |

Example 120a

Synthesis of 4-({2-[(4-bromophenyl)amino]-1-methyl-1H-benzimidazol-5-yl}oxy)-N-methylpyridine-2-carboxamide The compound 4-({2-[(4-bromophenyl)amino]-1-methyl-1H-benzimidazol-5-yl}oxy)-N-methylpyridine-2-carboxamide was synthesized as follows:

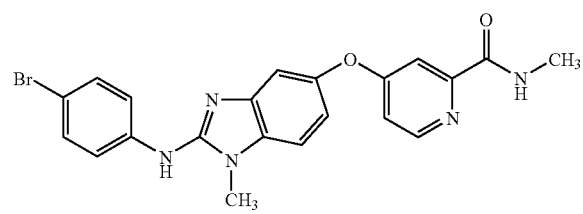

Step 1. Synthesis of 4-{[3-amino-4-(methylamino)phenyl]oxy}-N-methylpyridine-2-carboxamide A solution of 4-[(4-amino-3-nitrophenyl)oxy]-N-methylpyridine-2-carboxamide (1 eq) in methylene chloride was treated with trifluoroacetic anhydride (1 eq) and stirred for 10 minutes at 0° C. The mixture was quenched with saturated NaHCO3 solution. The organic layer was separated and washed with water, brine, dried and evaporated. MS: MH+=385.2.

To a solution of the trifluoroacetamide (1 eq) in a mixture of toluene, acetonitrile and sodium hydroxide solution (50%) was added benzyltrimethylammonium chloride (1 eq) and dimethyl sulfate (1.2 eq). The biphasic mixture was stirred overnight at room temperature and evaporated. The mixture was taken up in ethyl acetate, washed with water, brine, dried and evaporated. The crude product was purified by column chromatography eluting with 1:1 hexanes and ethylacetate followed by 2% triethylamine in 1:1 hexanes and ethyl acetate followed by 2% triethylamine in 1:1 hexanes and ethyl acetate to afford N-methyl-4-{[4-(methylamino)-3-nitrophenyl]oxy}pyridine-2-carboxamide as a reddish orange solid. MS: MH+=303.1.

The solution of nitromethylaniline in methanol was treated with 5% palladium on carbon and stirred under hydrogen atmosphere for 15 min. (until the disappearance of yellow coloration) at room temperature. The mixture was filtered and the filtrate was concentrated to provide 0.36 g of the diamine 4-{[3-amino-4-(methylamino)phenyl]oxy}-N-methylpyridine-2-carboxamide. MS: MH+=273.3.

Step 2. Synthesis of 4-({2-[(4-bromophenyl)amino]-1-methyl-1H-benzimidazol-5-yl}oxy)-N-methylpyridine-2-carboxamide A solution of the diamine 4-{[3-amino-4-(methylamino)phenyl]oxy}-N-methylpyridine-2-carboxamide (1 eq) in methanol was treated with 4-bromophenylisothiocyanate (1 eq) and stirred at 60° C.-65° C. for 2 hours. The reaction mixture was cooled down to room temperature and methyl iodide (1 eq) was added and stirred overnight at 60° C. The reaction was cooled to room temperature, evaporated, taken up in ethyl acetate, and washed with water and brine, dried, and evaporated under reduced pressure. Column chromatography using a gradient solvent system of hexanes and ethyl acetate and either 1:1 methylene chloride and acetone or 5% methanol in methylene chloride yielded the product as a half white powder. MS: MH+=452.3

Example 120b

Alternative Synthesis of 4-({2-[(4-bromophenyl)amino]-1-methyl-1H-benzimidazol-5-yl}oxy)-N-methylpyridine-2-carboxamide

Step 1. Synthesis of N-methyl{4-[4-(methylamino)-3-aminophenoxy](2-pyridyl)}carboxamide

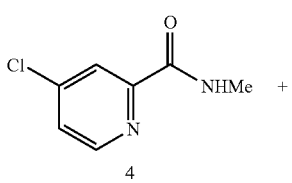

4

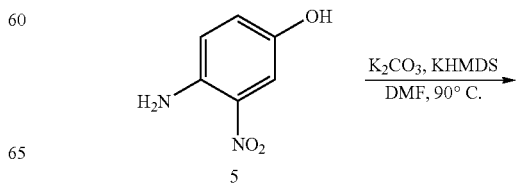

5

-continued

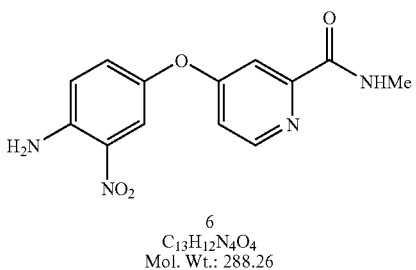

6
C₁₃H₁₂N₄O₄
Mol. Wt.: 288.26

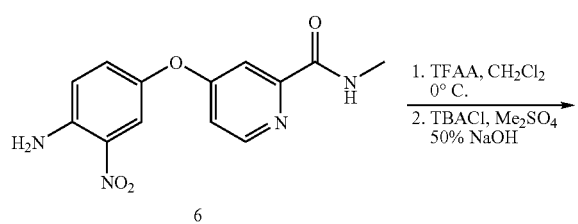

6

1. TFAA, CH₂Cl₂
 0° C.
2. TBACl, Me₂SO₄
 50% NaOH

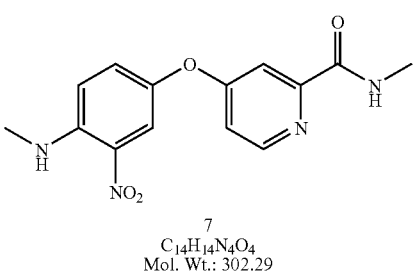

7
C₁₄H₁₄N₄O₄
Mol. Wt.: 302.29

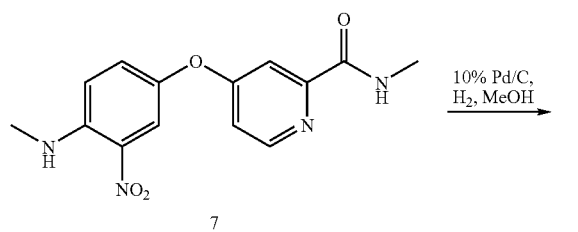

7

10% Pd/C,
H₂, MeOH

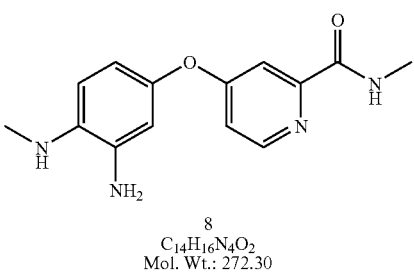

8
C₁₄H₁₆N₄O₂
Mol. Wt.: 272.30

A mixture containing 4-amino-3-nitrophenol 5 (1.0 g, 6.4 mmol), potassium bis(trimethylsilyl)amide (2.58 g, 12.8 mmol) was stirred in DMF (50 ml) for 2 hours at rt. To this mixture was added (4-chloro(2-pyridyl))-N-methylcarboxamide 4 (1.09 g, 6.4 mmol) and potassium carbonate (0.5 g, 7.6 mmol) and stirred at 90° C. overnight. The reaction mixture was then concentrated and partitioned between ethyl acetate and water. The organic layer was separated and washed with brine (2×10 ml), dried, filtered and concentrated in vacuum to give brown solid. Purification on silica gel with 2% triethyl amine in 50% ethyl acetate in hexane gave 1.3 g (yield, 72%) of [4-(4-amino-3-nitrophenoxy)(2-pyridyl)]-N-methylcarboxamide 6 as an orange solid: ¹H NMR (300 MHz, CDCl₃) δ 8.40 (d, J=5.6 Hz, 1H), 7.99 (br s, 1H), 7.90 (d, J=2.7 Hz, 1H), 7.64 (d, J=2.7 Hz, 1H), 7.17 (dd, J=2.7, 9.0 Hz, 1H), 6.95 (ddd, J=0.7, 2.5, 5.6 Hz, 1H), 6.89 (d, J=9.0 Hz, 1H), 6.18 (br s, 2H), 3.00 (d, J=5.1 Hz, 3H); mp 208-210° C. dec; LCMS m/z 289.2 (MH⁺), t$_R$=1.92 min.

A 500 mL three neck round bottom flask fitted with a mechanical stirrer was charged with nitroaniline 6 (10.0 g, 34.8 mmol) and CH₂Cl₂ (175 ml). The resulting suspension was cooled to 0° C. and TFAA (9.5 mL, 14.1 g, 67.0 mmol) was added over 16 h while allowing the cooling bath to expire.[2] After the reaction was judged complete by TLC,[3] TBACl (5.2 g, 17.5 mmol)[4] and dimethyl sulfate (6.7 mL, 8.9 g, 70.0 mmol) were added followed by 50% aqueous NaOH solution (140 mL). The resulting reaction mixture was cooled with an ice bath, and stirred vigorously for 1.5 h at rt.[3,5,6] The reaction was then poured over ice water and the resulting phases were partitioned and separated. The aqueous phase was extracted with CH₂Cl₂ (3×100 mL) and the combined organic layers were washed with brine (2×100 mL), dried (MgSO₄), and concentrated. The crude residue was purified by recrystallization (1:3 ethanol-water) to give 8.36 g (27.7 mmol, 79%) of 7 as fine red needles: ¹H NMR (300 MHz, CDCl₃) δ 8.40 (dd, J=0.5, 4.9 Hz, 1H), 8.07 (br d, J=3.7 Hz, 1H), 7.98 (br s, 1H), 7.95 (d, J=2.9 Hz, 1H), 7.62 (dd, J=0.5, 2.9 Hz, 1H), 7.27 (ddd, J=0.5, 2.9, 9.3 Hz, 1H), 6.98 (dd, J=2.7, 5.6 Hz, 1H), 6.92 (d, J=9.3 Hz, 1H), 3.07 (d, J=5.1 MHz, 3H), 3.00 (d, J=5.1 Hz, 3H); ¹³C NMR (75 MHz, CDCl₃) δ 166.6, 164.6, 152.6, 150.0, 144.8, 142.2, 130.6, 118.9, 115.5, 114.2, 109.7, 30.2, 26.4; mp 164-166° C. LCMS m/z 303.4 (MH⁺), t$_R$=2.37 min.

A suspension of nitroaniline 7 (5.0 g, 16.5 mmol) in methanol was sparged with N₂ for 20 min after which 10% Pd/C (0.88 g, 0.8 mmol) was added. The reaction was purged with H₂ and maintained under a H₂ atmosphere overnight at room temperature. The reaction was purged with N₂ and filtered through Celite. The collected solids were washed with EtOAc (3×50 mL), and the combined organic layers were dried (MgSO₄) and concentrated to afford 4.35 g (16.0 mmol, 97%) of an off white solid as 8: ¹H NMR (300 MHz, CDCl₃) δ 8.30 (d, J=5.5 Hz, 1H), 7.99 (br s, 1H), 7.67 (d, J=2.5 Hz, 1H), 6.91 (dd, J=2.5, 5.5 Hz, 1H), 6.62 (d, J=8.5 Hz, 1H), 6.53 (dd, J=2.5, 8.5 Hz, 1H), 6.44 (d, J=2.5 Hz, 1H), 2.98 (d, J=5.2 Hz, 3H), 2.86 (s, 3H); ¹³C NMR (75 MHz, CDCl₃) δ 167.4, 164.9, 152.2, 149.6, 146.0, 136.6, 136.3, 114.0, 112.3, 112.0, 110.2, 109.0, 31.6, 26.5; mp 153-156° C. dec.; LCMS m/z 273.3 (MH⁺), t$_R$=1.66 min.

Step 2. Synthesis of (4-{2-[(4-bromophenyl)amino]-1-methylbenzimidazol-5-yloxy}(2-pyridyl))-N-methylcarboxamide crude residue was purified by trituration in hot toluene to furnish 2.22 g (4.95 mmol, 49%) of a tan solid as 1: $^1$H NMR (300 MHz, CDCl$_3$) δ 8.38 (d, J=5.8 Hz, 1H), 8.07 (br d, J=4.7 Hz, 1H), 7.61 (d, J=2.5 Hz, 1H), 7.44 (app dd, J=8.8, 20.6 Hz,

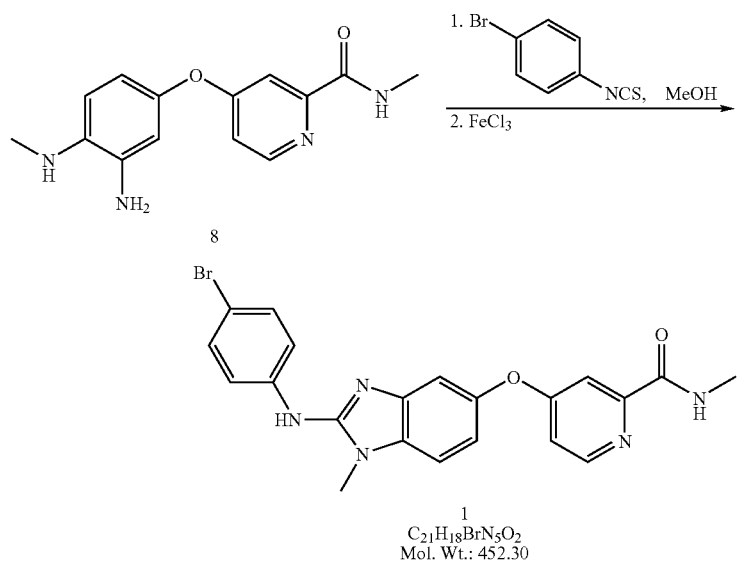

A 250 mL round bottom flask was charged with 4-bromophenylisothiocyanate[1] (2.17 g, 10.1 mmol), diamine 8 (2.74 g, 10.1 mmol), and MeOH (40 mL) and the reaction was maintained at rt overnight. Ferric chloride (2.43 g, 15 mmol) was added and the resulting red reaction mixture was stirred overnight. The reaction was partitioned with EtOAc (100 mL) and water (100 mL), and filtered through Celite. The layers were separated and the aqueous phase was neutralized (pH=7) with saturated Na$_2$CO$_3$ solution. The resulting aqueous phase was extracted with EtOAc (100 mL) and the mixture was filtered through Celite. The phases were separated and the aqueous phase was again extracted and filtered. The combined organic layers were washed with brine (250 mL), dried (MgSO$_4$), and concentrated to give a brown solid. The 4H), 7.05 (m, 3H), 6.78 (dd, J=2.2, 8.5 Hz, 1H), 3.51 (s, 3H), 3.00 (d, J=5.2 Hz, 3H); mp 251-254° C. dec.; LCMS m/z 452.2 (MH$^+$), t$_R$=2.17 min.

Examples 121-384

The compounds shown in the following Table 3 (Examples 121-384) were prepared from following the procedure described for Example 120a.

TABLE 3

| Example | Structure | Name | MH+ |
|---|---|---|---|
| 121 | 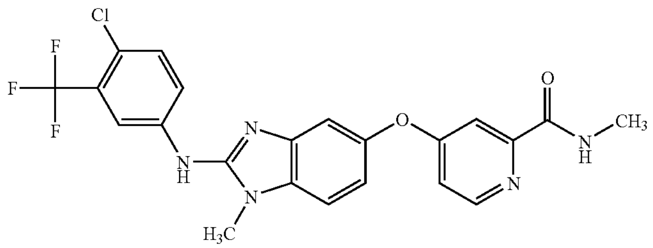 | 4-[(2-{[4-chloro-3-(trifluoromethyl)phenyl]amino}-1-methyl-1H-benzimidazol-5-yl)-oxy]-N-methylpyridine-2-carboxamide | 476.1 |
| 122 | 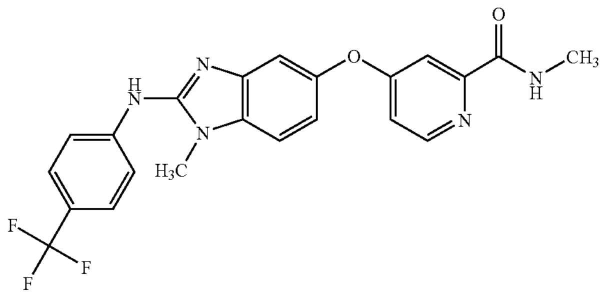 | N-methyl-4-[(1-methyl-2-{[4-(trifluoromethyl)phenyl]amino}-1H-benzimidazol-5-yl)oxy]-pyridine-2-carboxamide | 442 |
| 123 | 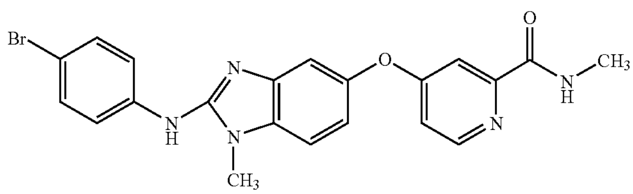 | (4-{2-[(4-bromophenyl)amino]-1-methylbenzimidazol-5-yloxy}(2-pyridyl))-N-methylcarboxamide | 452.0 |
| 124 | 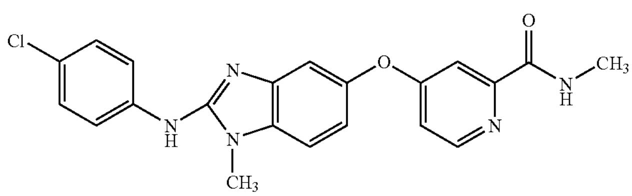 | (4-{2-[(4-chlorophenyl)amino]-1-methylbenzimidazol-5-yloxy}-(2-pyridyl))-N-methylcarboxamide | 408.1 |
| 125 | 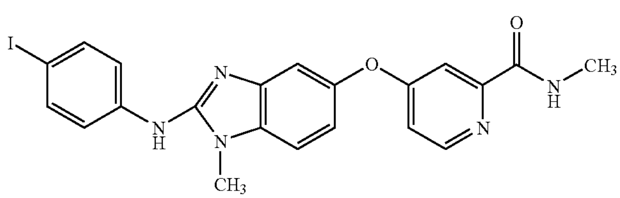 | (4-{2-[(4-iodophenyl)amino]-1-methylbenzimidazol-5-yloxy}(2-pyridyl))-N-methylcarboxamide | 500.1 |
| 126 | 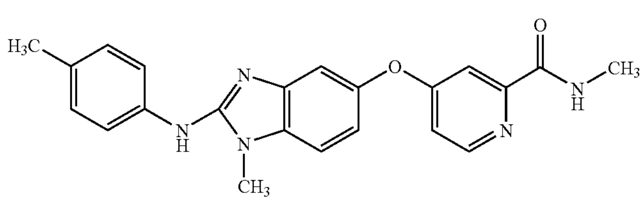 | N-methyl(4-{1-methyl-2-[(4-methylphenyl)amino]benzimidazol-5-yloxy}(2-pyridyl))carboxamide | 388.2 |
| 127 | 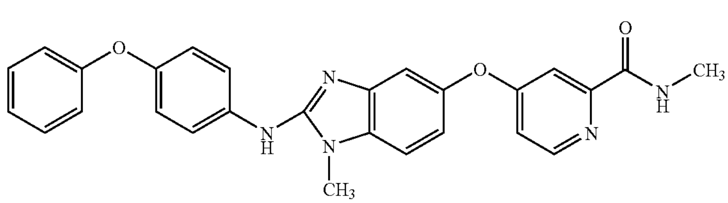 | N-methyl(4-{1-methyl-2-[(4-phenoxyphenyl)amino]benzimidazol-5-yloxy}(2-pyridyl))-carboxamide | 466.2 |

TABLE 3-continued

| Example | Structure | Name | MH+ |
|---|---|---|---|
| 128 | 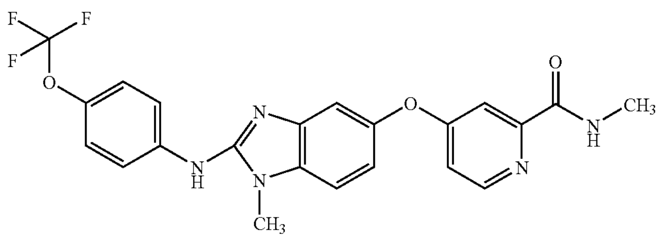 | N-methyl[4-(1-methyl-2-{[4-(trifluoromethoxy)phenyl]amino}benzimidazol-5-yloxy)(2-pyridyl)]carboxamide | 458.2 |
| 129 | 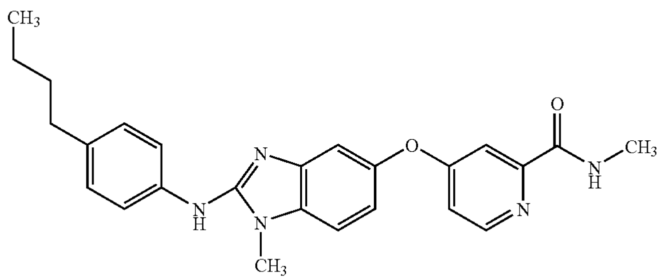 | (4-{2-[(4-butylphenyl)amino]-1-methylbenzimidazol-5-yloxy}(2-pyridyl))-N-methylcarboxamide | 430.2 |
| 130 | 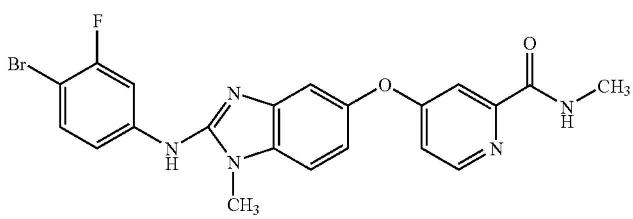 | (4-{2-[(4-bromo-3-fluorophenyl)amino]-1-methylbenzimidazol-5-yloxy}(2-pyridyl))-N-methylcarboxamide | 470.1 |
| 131 | 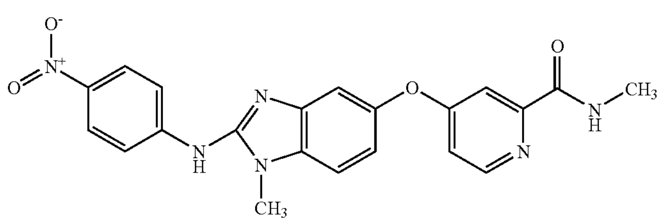 | N-methyl(4-{1-methyl-2-[(4-nitrophenyl)amino]benzimidazol-5-yloxy}(2-pyridyl))-carboxamide | 419.2 |
| 132 | 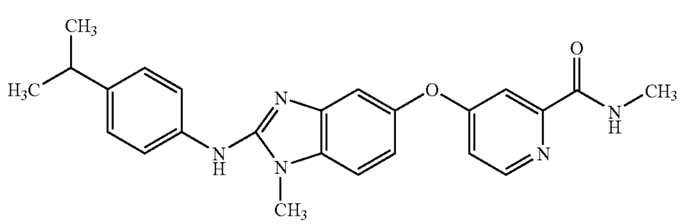 | N-methyl[4-(1-methyl-2-{[4-(methylethyl)phenyl]amino}benzimidazol-5-yloxy)(2-pyridyl)]-carboxamide | 416.3 |
| 133 | 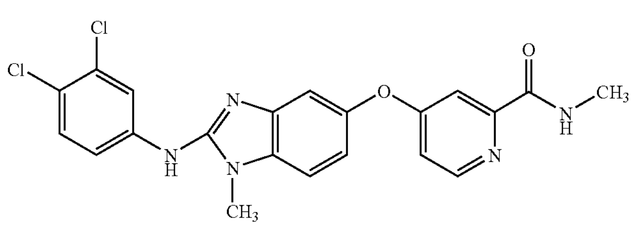 | (4-{2-[(3,4-dichlorophenyl)amino]-1-methylbenzimidazol-5-yloxy}(2-pyridyl))-N-methyl-carboxamide | 442.1 |

TABLE 3-continued

| Example | Structure | Name | MH+ |
|---|---|---|---|
| 134 | 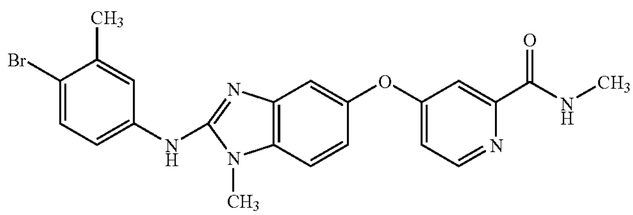 | (4-{2-[(4-bromo-3-methyl-phenyl)amino]-1-methyl-benzimidazol-5-yloxy}(2-pyridyl))-N-methylcarboxamide | 466.1 |
| 135 | 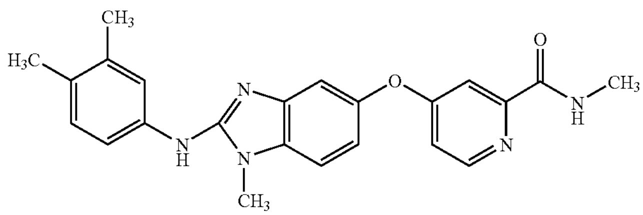 | (4-{2-[(3,4-dimethylphenyl)-amino]-1-methylbenzimidazol-5-yloxy}(2-pyridyl))-N-methyl-carboxamide | 402.2 |
| 136 | 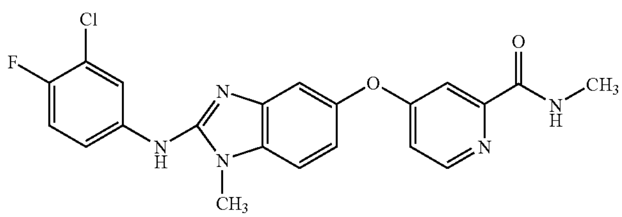 | (4-{2-[(3-chloro-4-fluoro phenyl)amino]-1-methyl-benzimidazol-5-yloxy}(2-pyridyl))-N-methylcarboxamide | 426.1 |
| 137 | 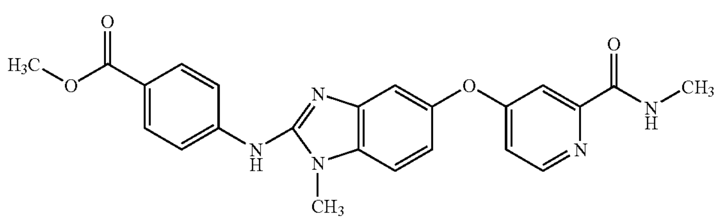 | methyl 4-({1-methyl-5-[2-(N-methylcarbamoyl)(4-pyridyl-oxy)]benzimidazol-2-yl}amino)-benzoate | 432.2 |
| 138 | 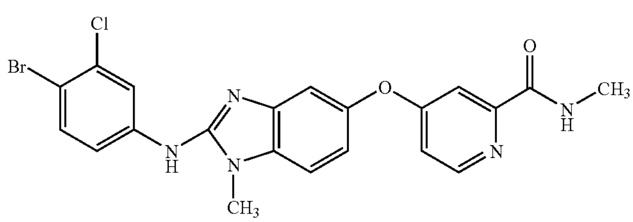 | (4-{2-[(4-bromo-3-chloro-phenyl)amino]-1-methyl-benzimidazol-5-yloxy}(2-pyridyl))-N-methylcarboxamide | 486.0 |
| 139 | 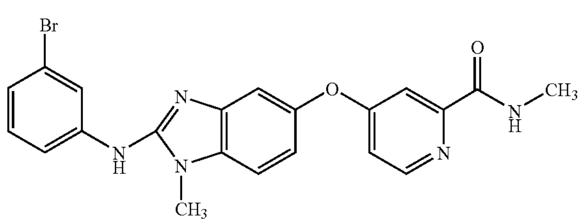 | (4-{2-[(3-bromophenyl)amino]-1-methylbenzimidazol-5-yl-oxy}(2-pyridyl))-N-methyl-carboxamide | 452.1 |
| 140 | 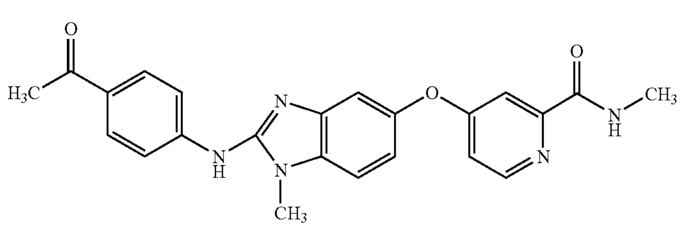 | (4-{2-[(4-acetylphenyl)amino]-1-methylbenzimidazol-5-yloxy}-(2-pyridyl))-N-methylcarboxamide | 416.2 |

TABLE 3-continued

| Example | Structure | Name | MH+ |
|---|---|---|---|
| 141 | 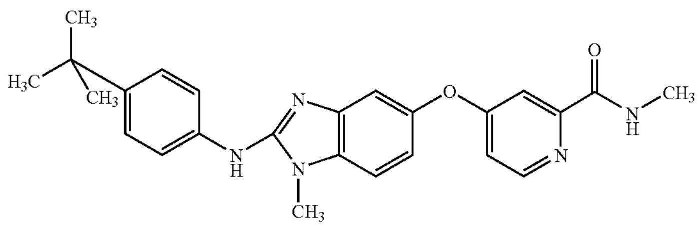 | [4-(2-{[4-(tert-butyl)phenyl]-amino}-1-methylbenzimidazol-5-yloxy)(2-pyridyl)]-N-methyl-carboxamide | 430.2 |
| 142 | 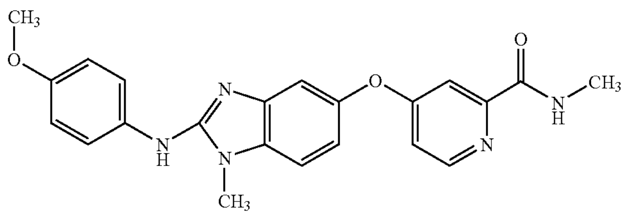 | (4-{2-[(4-methoxyphenyl)-amino]-1-methylbenzimidazol-5-yloxy}(2-pyridyl))-N-methyl-carboxamide | 404.2 |
| 143 | 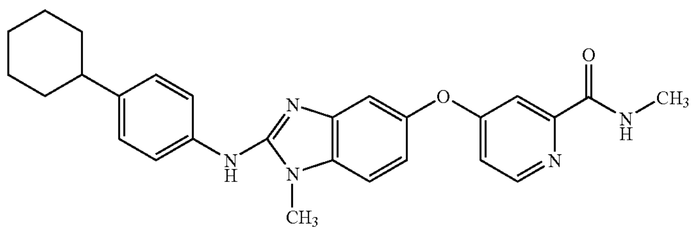 | (4 {2-[(4-cyclohexylphenyl)-amino]-1-methylbenzimidazol-5-yloxy}(2-pyridyl))-N-methyl-carboxamide | 456.2 |
| 144 | 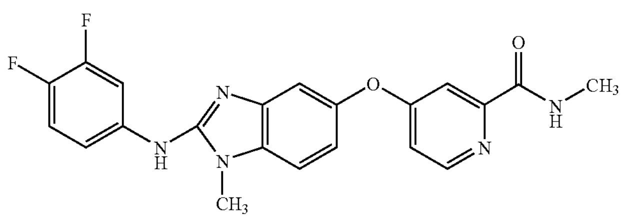 | (4-{2-[(3,4-difluorophenyl)-amino]-1-methylbenzimidazol-5-yloxy}(2-pyridyl))-N-methyl-carboxamide | 410.2 |
| 145 | 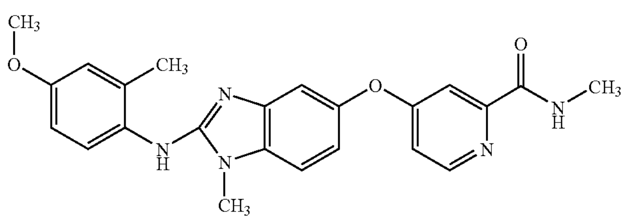 | (4-{2-[(4-methoxy-2-methyl-phenyl)amino]-1-methyl-benzimidazol-5-yloxy}(2-pyridyl))-N-methylcarboxamide | 418.2 |
| 146 | 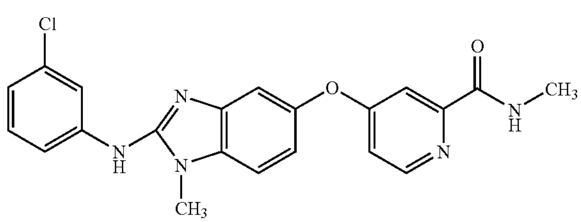 | (4-{2-[(3-chlorophenyl)amino]-1-methylbenzimidazol-5-yloxy}(2-pyridyl))-N-methyl-carboxamide | 408.1 |
| 147 | 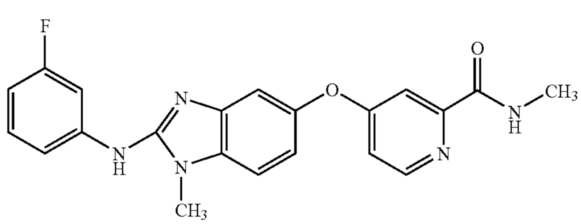 | (4-{2-[(3-fluorophenyl)amino]-1-methylbenzimidazol-5-yloxy}-(2-pyridyl))-N-methylcarboxamide | 392.2 |

TABLE 3-continued

| Example | Name | MH+ |
|---|---|---|
| 148 | 4-({1-methyl-5-[2-(N-methyl-carbamoyl)(4-pyridyloxy)]-benzimidazol-2-yl}amino)-benzoic acid | 418.2 |
| 149 | N-methyl{4-[1-methyl-2-(phenylcarbonylamino)-benzimidazol-5-yloxy](2-pyridyl)}carboxamide | 402.2 |
| 150 | [4-(2-{[2-chloro-5-(trifluoro-methyl)phenyl]amino}-1-methylbenzimidazol-5-yloxy)(2-pyridyl)]-N-methylcarboxamide | 476.1 |
| 151 | (4-{2-[(2,5-dimethoxyphenyl)-amino]-1-methylbenzimidazol-5-yloxy}(2-pyridyl))-N-methyl-carboxamide | 434.2 |
| 152 | (4-{2-[(2,4-difluorophenyl)-amino]-1methylbenzimidazol-5-yloxy}(2-pyridyl))-N-methyl-carboxamide | 410.2 |
| 153 | (4-{2-[(3,5-difluorophenyl)-amino]-1-methylbenzimidazol-5-yloxy}(2-pyridyl))-N-methyl-carboxamide | 410.2 |

TABLE 3-continued

| Example | Structure | Name | MH+ |
|---|---|---|---|
| 154 | 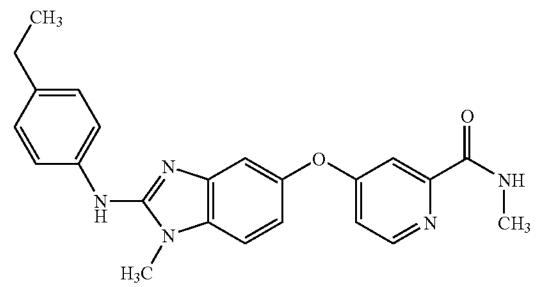 | (4-{2-[(4-ethylphenyl)amino]-1-methylbenzimidazol-5-yloxy}(2-pyridyl))-N-methylcarboxamide | 402.2 |
| 155 | 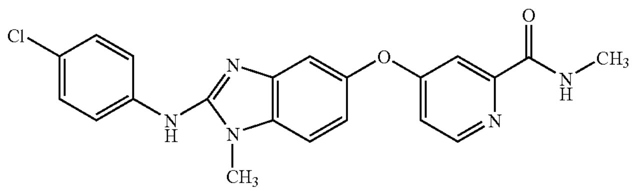 | (4-{2-[(4-chlorophenyl)amino]-1-methylbenzimidazol-5-yloxy}-(2-pyridyl))-N-methylcarboxamide | 408.1 |
| 156 | 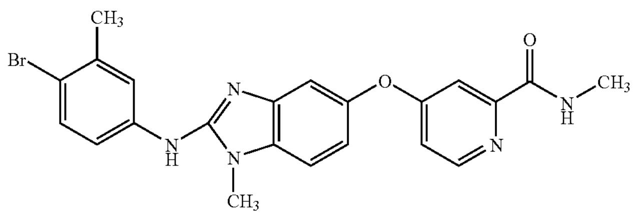 | (4-{2-[(4-bromo-3-methyl-phenyl)amino]-1-methyl-benzimidazol-5-yloxy}(2-pyridyl))-N-methylcarboxamide | 466.1 |
| 157 | 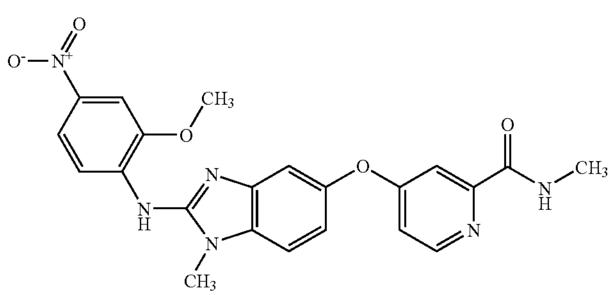 | (4-{2-[(2-methoxy-4-nitro-phenyl)amino]-1-methyl-benzimidazol-5-yloxy}(2-pyridyl))-N-methylcarboxamide | 448.4 |
| 158 | 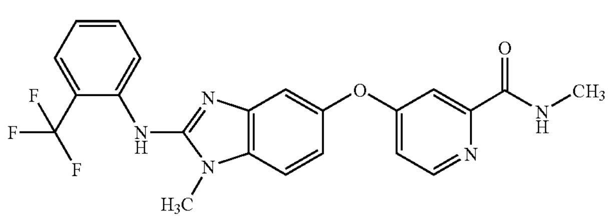 | N-methyl[4-(1-methyl-2-{[2-(tri-fluoro-methyl)phenyl]amino}benzimidazol-5-yloxy)(2-pyridyl)]-carboxamide | 441.4 |
| 159 | 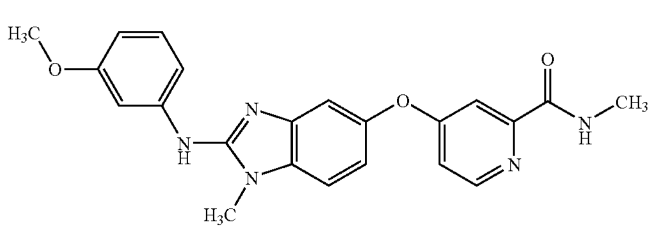 | (4-{2-[(3-methoxyphenyl)-amino]-1-methylbenzimidazol-5-yloxy}(2-pyridyl))-N-methyl-carboxamide | 403.4 |

TABLE 3-continued

| Example | Structure | Name | MH+ |
|---|---|---|---|
| 160 | 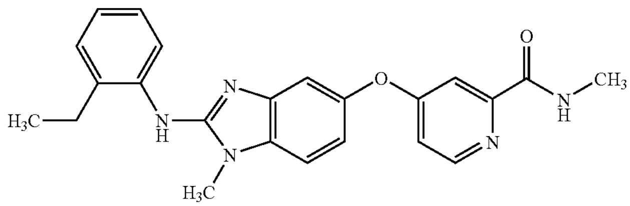 | (4-{2-[(2-ethylphenyl)amino]-1-methylbenzimidazol-5-yloxy}(2-pyridyl))-N-methylcarboxamide | 401.4 |
| 161 | 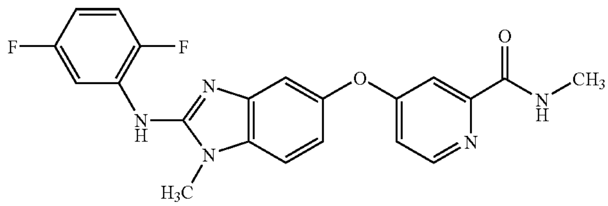 | (4-{2-[(2,5-difluorophenyl)-amino]-1-methylbenzimidazol-5-yloxy}(2-pyridyl))-N-methyl-carboxamide | 409.3 |
| 162 | 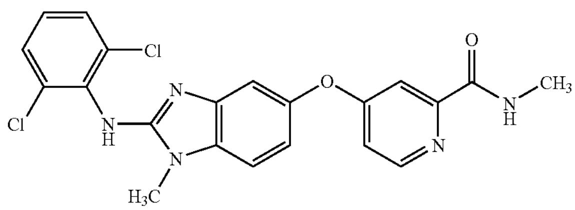 | (4-{2-[(2,6-dichlorophenyl)-amino]-1-methylbenzimidazol-5-yloxy}(2-pyridyl))-N-methyl-carboxamide | 442.3 |
| 163 | 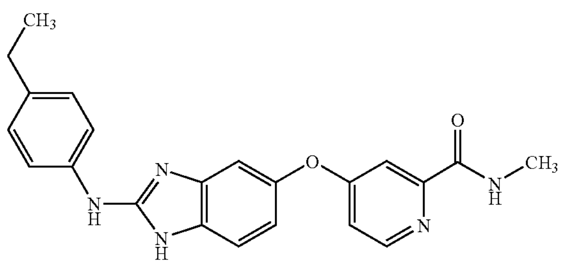 | (4-{2-[(4-ethylphenyl)amino]-benzimidazol-5-yloxy}(2-pyridyl))-N-methylcarboxamide | 388.2 |
| 164 | 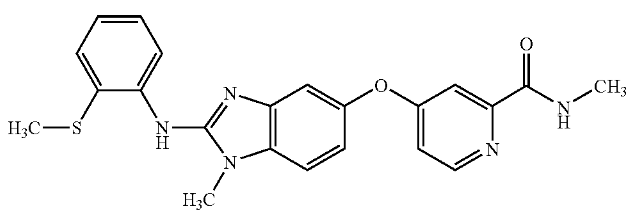 | N-methyl(4-{1-methyl-2-[(2-methylthiophenyl)amino]-benzimidazol-5-yloxy}(2-pyridyl))carboxamide | 420.1 |
| 165 | 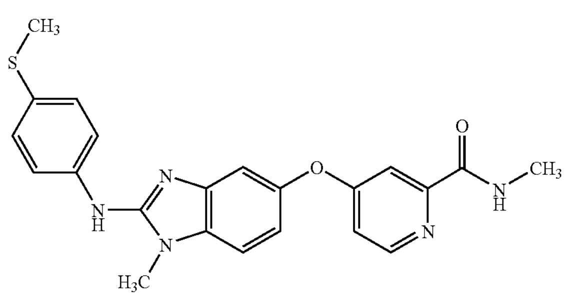 | N-methyl(4-{1-methyl-2-[(4-methylthiophenyl)amino]-benzimidazol-5-yloxy}(2-pyridyl))carboxamide | 420.1 |

TABLE 3-continued

| Example | Structure | Name | MH+ |
|---|---|---|---|
| 166 | 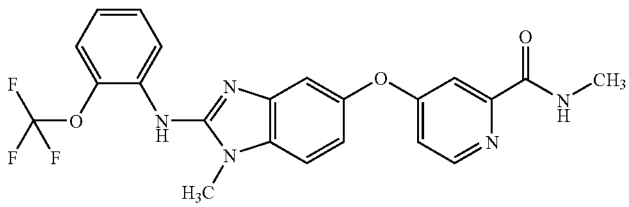 | N-methyl[4-(1-methyl-2-{[2-(trifluoromethoxy)phenyl]-amino}benzimidazol-5-yloxy)(2-pyridyl)]carboxamide | 458.1 |
| 167 | 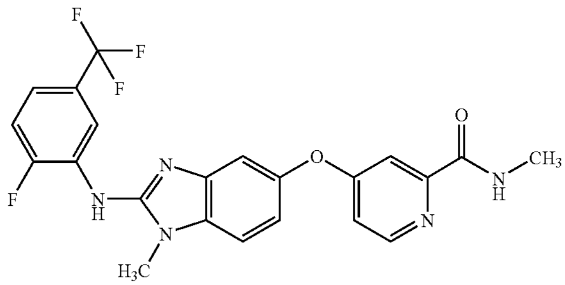 | [4-(2-{[2-fluoro-5-(trifluoro-methyl)phenyl]amino}-1-methylbenzimidazol-5-yloxy)(2-pyridyl)]-N-methylcarboxamide | 460.1 |
| 168 | 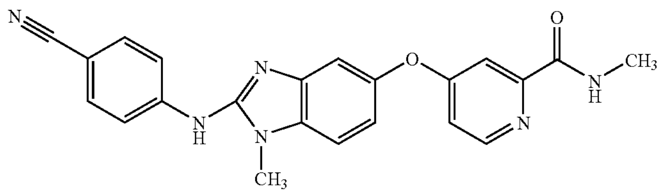 | (4-{2-[(4-cyanophenyl)amino]-1-methylbenzimidazol-5-yloxy}-(2-pyridyl))-N-methylcarboxamide | 399.1 |
| 169 | 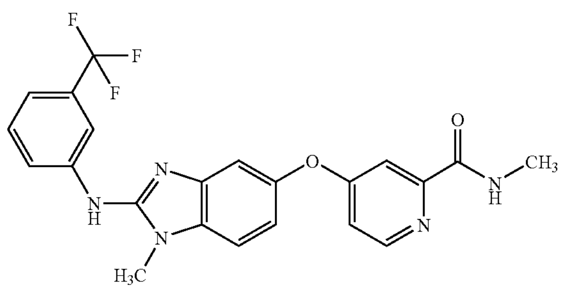 | N-methyl[4-(1-methyl-2-{[3-(trifluoromethyl)phenyl]amino}-benzimidazol-5-yloxy)(2-pyridyl)]carboxamide | 442.1 |
| 170 | 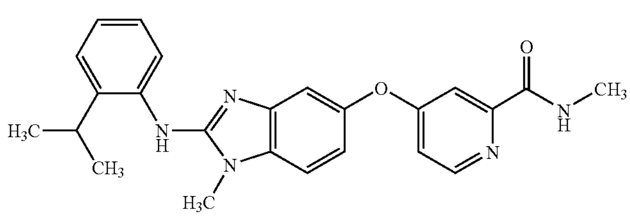 | N-methyl[4-(1-methyl-2-{[2-(methylethyl)phenyl]amino}-benzimidazol-5-yloxy)(2-pyridyl)]carboxamide | 416.2 |
| 171 | 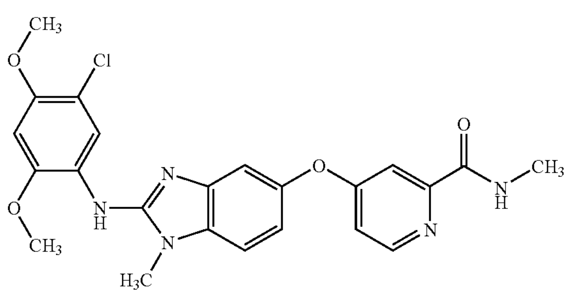 | (4-{2-[(5-chloro-2,4-dimethoxy-phenyl)amino]-1-methyl-benzimidazol-5-yloxy}(2-pyridyl))-N-methylcarboxamide | 468.2 |

TABLE 3-continued

| Example | Name | MH+ |
|---|---|---|
| 172 | N-methyl(4-{1-methyl-2-[(2-phenylphenyl)amino]benzimidazol-5-yloxy}(2-pyridyl))-carboxamide | 450.2 |
| 173 | (4-{2-[(3-ethylphenyl)amino]-1-methylbenzimidazol-5-yloxy}(2-pyridyl))-N-methylcarboxamide | 402.2 |
| 174 | (4-{2-[(2-fluorophenyl)amino]-1-methylbenzimidazol-5-yloxy}-(2-pyridyl))-N-methylcarboxamide | 392.1 |
| 175 | (4-{2-[(4-bromophenyl)amino]-1-ethylbenzimidazol-5-yloxy}(2-pyridyl))-N-methylcarboxamide | 466.1 |
| 176 | (4-{2-[(4-aminophenyl)amino]-1-methylbenzimidazol-5-yloxy}-(2-pyridyl))-N-methylcarboxamide | 389.2 |
| 177 (synthesis as in Ex 1) | N-methyl[4-(1-methyl-2-{[4-(methylamino)phenyl]amino}-benzimidazol-5-yloxy)(2-pyridyl)]carboxamide | 403.2 |
| 178 (synthesis as in Ex 1) | [4-(2-{[4-(dimethylamino)-phenyl]amino}-1-methyl-benzimidazol-5-yloxy)(2-pyridyl)]-N-methylcarboxamide | 417.2 |

TABLE 3-continued

| Example | Structure | Name | MH+ |
|---|---|---|---|
| 179 | 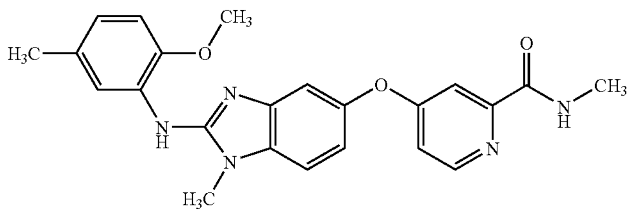 | N-methyl-4-[(1-methyl-2-{[5-methyl-2-(methyloxy)phenyl]-amino}-1H-benzimidazol-5-yl)oxy]pyridine-2-carboxamide | 418.5 |
| 180 | 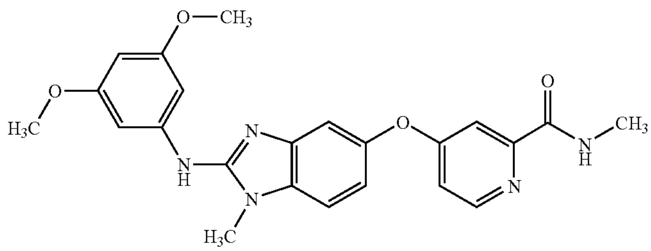 | 4-[(2-{[3,5-bis(methyloxy)-phenyl]amino}-1-methyl-1H-benzimidazol-5-yl)oxy]-N-methylpyridine-2-carboxamide | 434.5 |
| 181 | 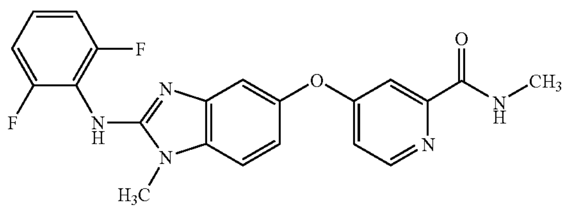 | 4-({2-[(2,6-difluorophenyl)-amino]-1-methyl-1H-benzimidazol-5-yl}oxy)-N-methyl-pyridine-2-carboxamide | 410.4 |
| 182 | 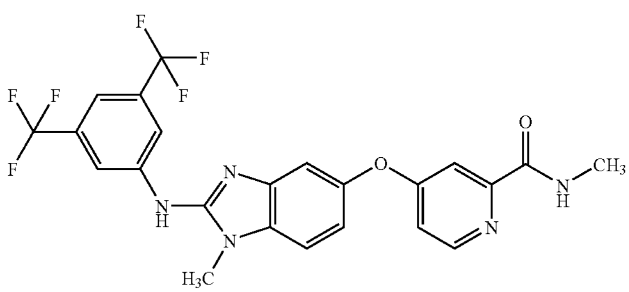 | 4-[(2-{[3,5-bis(trifluoromethyl)-phenyl]amino}-1-methyl-1H-benzimidazol-5-yl)oxy]-N-methylpyridine-2-carboxamide | 510.4 |
| 183 | 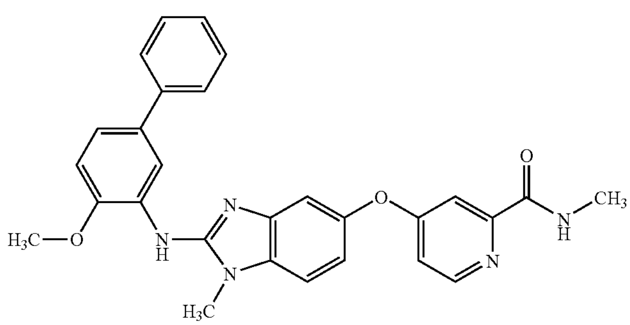 | N-methyl-4-[(1-methyl-2-{[4-(methyloxy)-1,1'-biphenyl-3-yl]-amino}-1H-benzimidazol-5-yl)-oxy]pyridine-2-carboxamide | 480.5 |
| 184 | 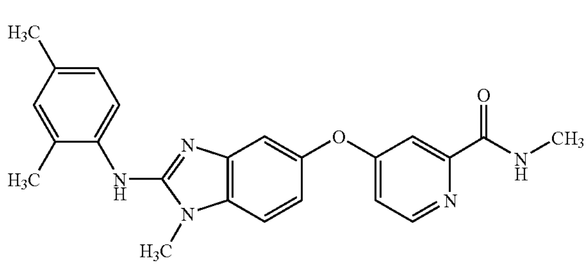 | 4-({2-[(2,4-dimethylphenyl)-amino]-1-methyl-1H-benzimidazol-5-yl}oxy)-N-methylpyridine-2-carboxamide | 402.5 |

TABLE 3-continued

| Example | Structure | Name | MH+ |
|---|---|---|---|
| 185 | 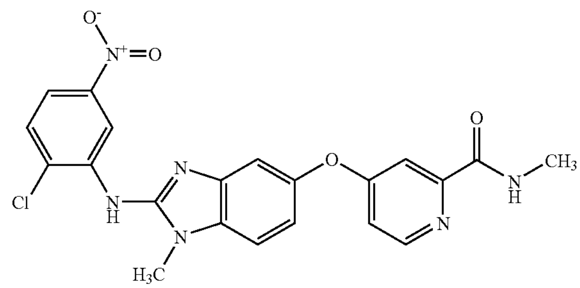 | 4-({2-[(2-chloro-5-nitrophenyl)-amino]-1-methyl-1H-benzimidazol-5-yl}oxy)-N-methyl-pyridine-2-carboxamide | 453.9 |
| 186 | 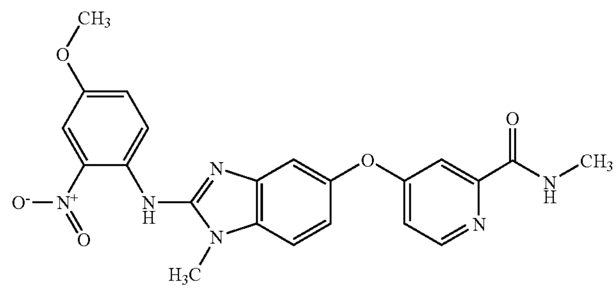 | N-methyl-4-[(1-methyl-2-{[4-(methyloxy)-2-nitrophenyl]-amino}-1H-benzimidazol-5-yl)oxy]pyridine-2-carboxamide | 449.4 |
| 187 | 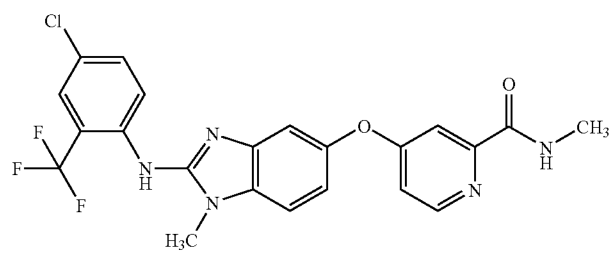 | 4-[(2-{[4-chloro-2-(trifluoro-methyl)phenyl]amino}-1-methyl-1H-benzimidazol-5-yl)-oxy]-N-methylpyridine-2-carboxamide | 476.9 |
| 188 | 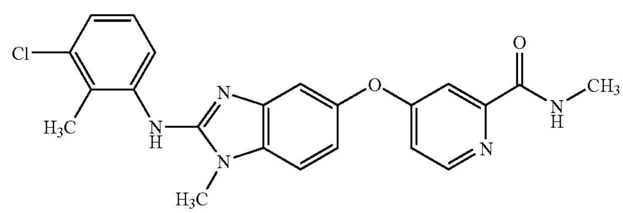 | 4-({2-[(3-chloro-2-methyl-phenyl)amino]-1-methyl-1H-benzimidazol-5-yl}oxy)-N-methylpyridine-2-carboxamide | 422.9 |
| 189 | 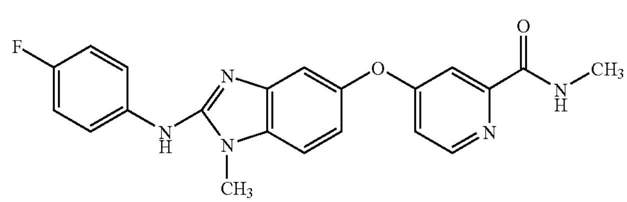 | 4-({2-[(4-fluorophenyl)amino]-1-methyl-1H-benzimidazol-5-yl}oxy)-N-methylpyridine-2-carboxamide | 392.4 |
| 190 | 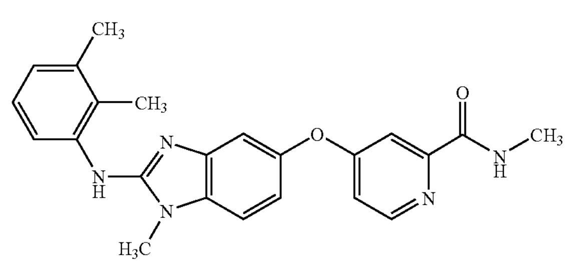 | 4-({2-[(2,3-dimethylphenyl)-amino]-1-methyl-1H-benzimidazol-5-yl}oxy)-N-methylpyridine-2-carboxamide | 402.5 |

TABLE 3-continued

| Example | Structure | Name | MH+ |
|---|---|---|---|
| 191 | 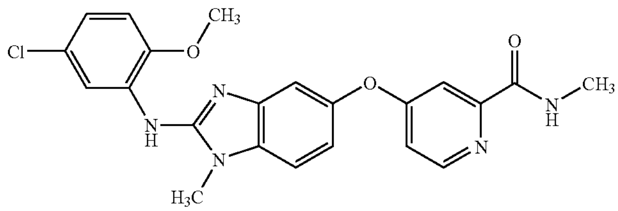 | 4-[(2-{[5-chloro-2-(methyloxy)-phenyl]amino}-1-methyl-1H-benzimidazol-5-yl)oxy]-N-methylpyridine-2-carboxamide | 438.9 |
| 192 | 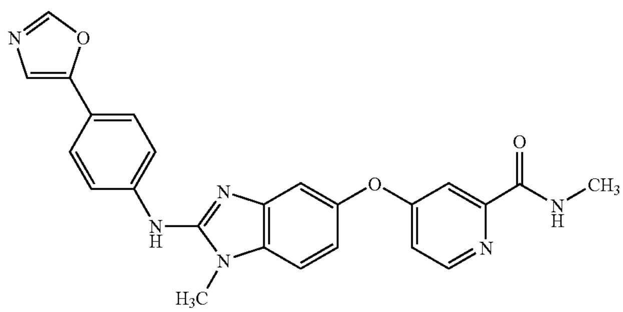 | N-methyl-4-[(1-methyl-2-{[4-(1,3-oxazol-5-yl)phenyl]amino}-1H-benzimidazol-5-yl)oxy]-pyridine-2-carboxamide | 441.5 |
| 193 | 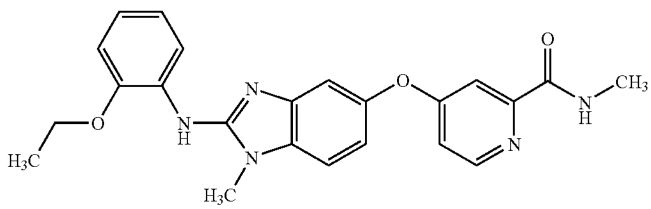 | 4-[(2-{[2-(ethyloxy)phenyl]-amino}-1-methyl-1H-benzimidazol-5-yl)oxy]-N-methyl-pyridine-2-carboxamide | 418.5 |
| 194 | 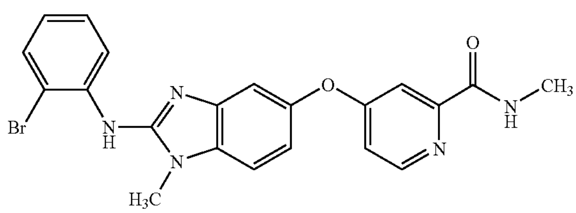 | 4-({2-[(2-bromophenyl)amino]-1-methyl-1H-benzimidazol-5-yl}oxy)-N-methylpyridine-2-carboxamide | 453.3 |
| 195 | 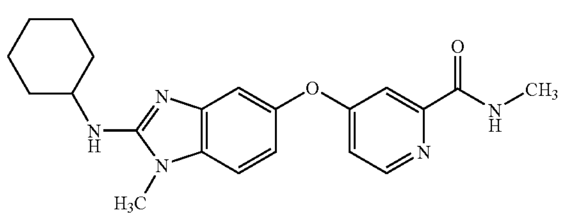 | 4-{[2-(cyclohexylamino)-1-methyl-1H-benzimidazol-5-yl]-oxy}-N-methylpyridine-2-carboxamide | 380.5 |
| 196 | 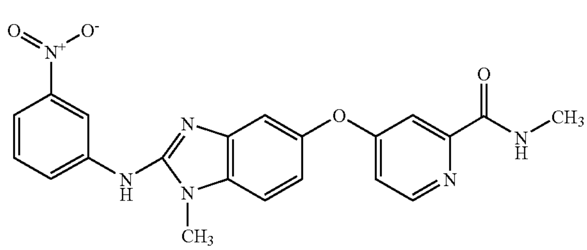 | N-methyl-4-({1-methyl-2-[(3-nitrophenyl)amino]-1H-benzimidazol-5-yl}oxy)pyridine-2-carboxamide | 419.4 |

TABLE 3-continued

| Example | Structure | Name | MH+ |
|---|---|---|---|
| 197 | 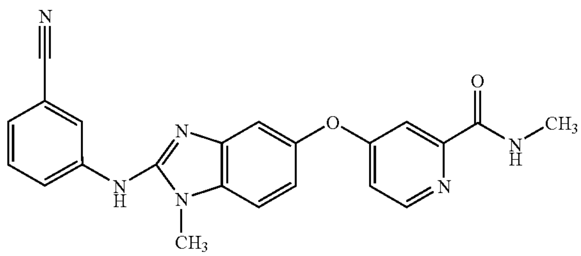 | 4-({2-[(3-cyanophenyl)amino]-1-methyl-1H-benzimidazol-5-yl}oxy)-N-methylpyridine-2-carboxamide | 399.4 |
| 198 | 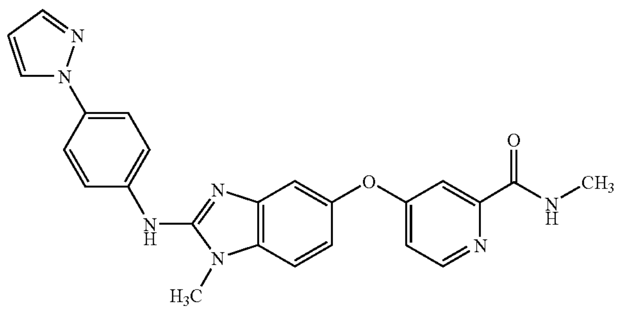 | N-methyl-4-[(1-methyl-2-{[4-(1H-pyrazol-1-yl)phenyl]-amino}-1H-benzimidazol-5-yl)-oxy]pyridine-2-carboxamide | 440.5 |
| 199 | 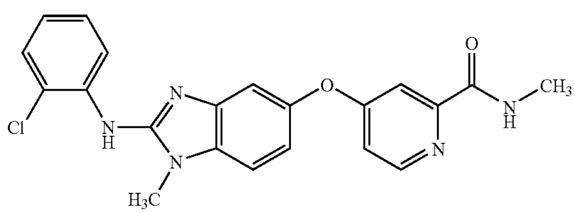 | 4-({2-[(2-chlorophenyl)amino]-1-methyl-1H-benzimidazol-5-yl}oxy)-N-methylpyridine-2-carboxamide | 408.9 |
| 200 | 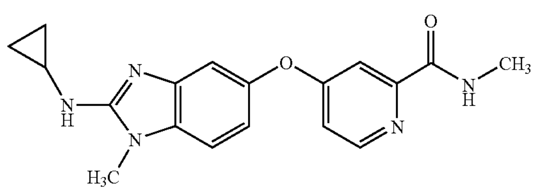 | 4-{[2-(cyclopropylamino)-1-methyl-1H-benzimidazol-5-yl]-oxy}-N-methylpyridine-2-carboxamide | 338.4 |
| 201 | 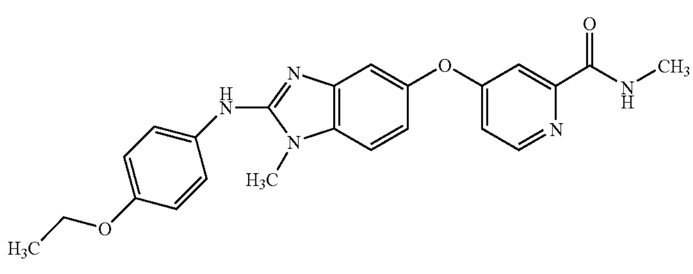 | 4-[(2-{[4-(ethyloxy)phenyl]-amino}-1-methyl-1H-benzimidazol-5-yl)oxy]-N-methylpyridine-2-carboxamide | 418.5 |
| 202 | 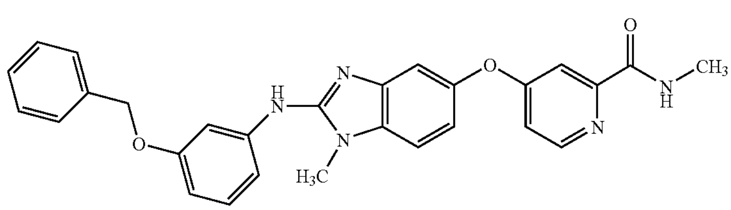 | N-methyl-4-{[1-methyl-2-({3-[(phenylmethyl)oxy]phenyl}amino)-1H-benzimidazol-5-yl]oxy}-pyridine-2-carboxamide | 480.5 |

TABLE 3-continued

| Example | Structure | Name | MH+ |
|---|---|---|---|
| 203 | 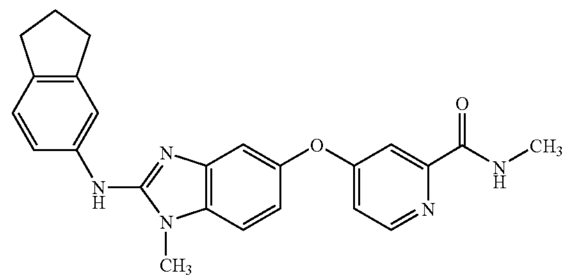 | 4-{[2-(2,3-dihydro-1H-inden-5-ylamino)-1-methyl-1H-benzimidazol-5-yl]oxy}-N-methylpyridine-2-carboxamide | 414.5 |
| 204 | 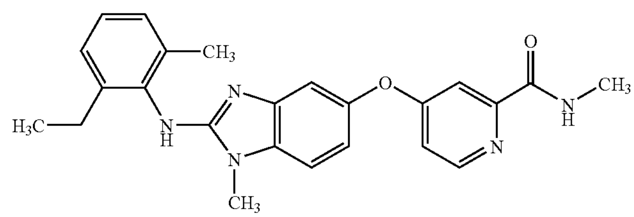 | 4-({2-[(2-ethyl-6-methylphenyl)-amino]-1-methyl-1H-benzimidazol-5-yl}oxy)-N-methylpyridine-2-carboxamide | 416.5 |
| 205 | 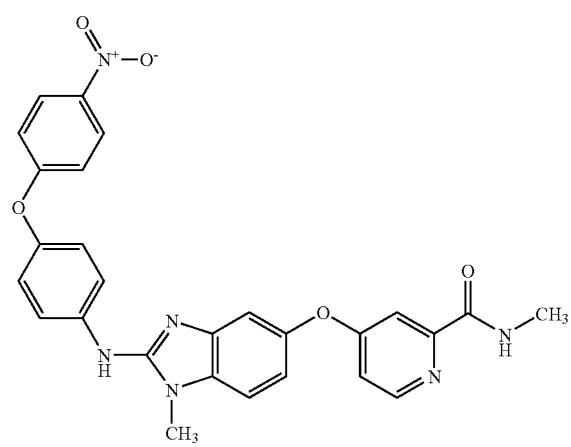 | N-methyl-4-{[1-methyl-2-({4-[(4-nitrophenyl)oxy]phenyl}-amino)-1H-benzimidazol-5-yl]-oxy}pyridine-2-carboxamide | 511.5 |
| 206 | 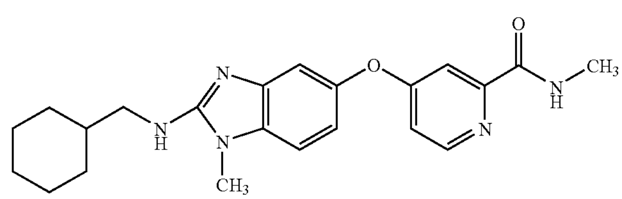 | 4-({2-[(cyclohexylmethyl)-amino]-1-methyl-1H-benzimidazol-5-yl}oxy)-N-methylpyridine-2-carboxamide | 394.5 |
| 207 | 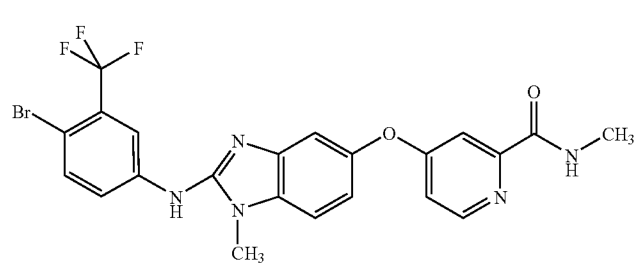 | 4-[(2-{[4-bromo-3-(trifluoromethyl)phenyl]amino}-1-methyl-1H-benzimidazol-5-yl)oxy]-N-methylpyridine-2-carboxamide | 521.3 |

TABLE 3-continued

| Example | Structure | Name | MH+ |
|---|---|---|---|
| 208 | 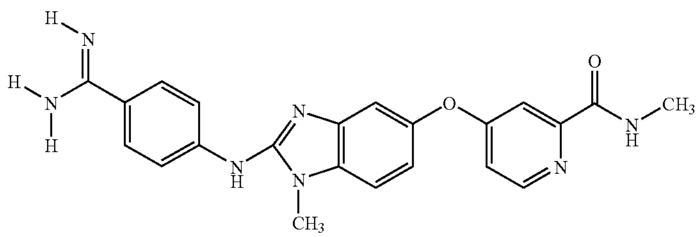 | 4-{[2-({4-[(Z)-amino(imino)-methyl]phenyl}amino)-1-methyl-1H-benzimidazol-5-yl]oxy}-N-methylpyridine-2-carboxamide | 416.5 |
| 209 | 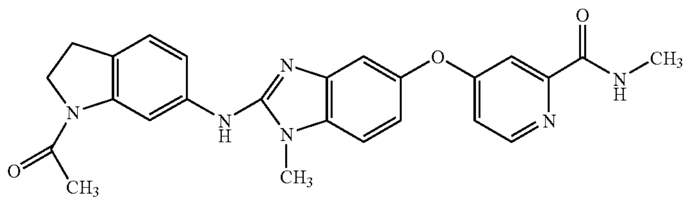 | 4-({2-[(1-acetyl-2,3-dihydro-1H-indol-6-yl)amino]-1-methyl-1H-benzimidazol-5-yl}oxy)-N-methylpyridine-2-carboxamide | 457.5 |
| 210 | 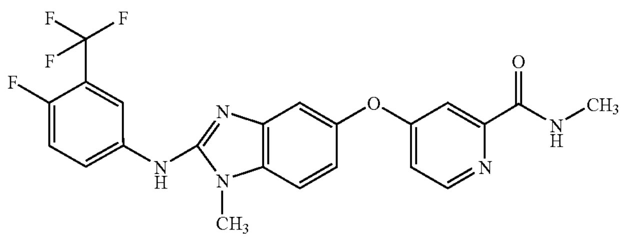 | 4-[(2-{[4-fluoro-3-(trifluoro-methyl)phenyl]amino}-1-methyl-1H-benzimidazol-5-yl)oxy]-N-methylpyridine-2-carboxamide | 460.4 |
| 211 | 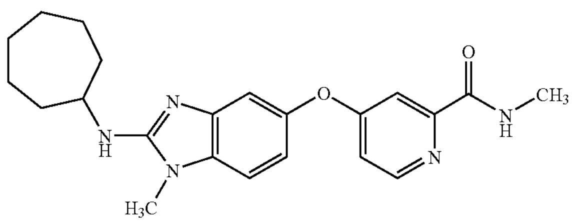 | 4-{[2-(cycloheptylamino)-1-methyl-1H-benzimidazol-5-yl]-oxy}-N-methylpyridine-2-carboxamide | 394.5 |
| 212 | 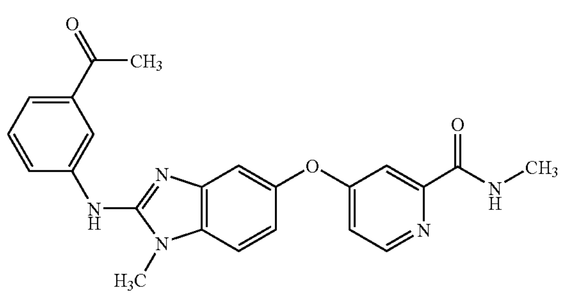 | 4-({2-[(3-acetylphenyl)amino]-1-methyl-1H-benzimidazol-5-yl}oxy)-N-methylpyridine-2-carboxamide | 416.5 |
| 213 | 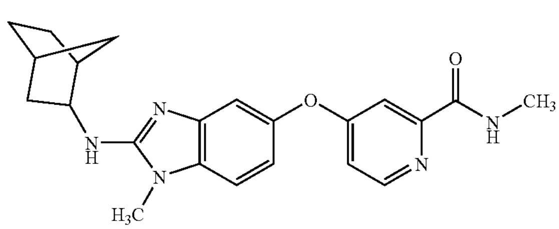 | 4-{[2-(bicyclo[2.2.1]hept-2-ylamino)-1-methyl-1H-benzimidazol-5-yl]oxy}-N-methylpyridine-3-carboxamide | 392.5 |

TABLE 3-continued

| Example | Structure | Name | MH+ |
|---|---|---|---|
| 214 | 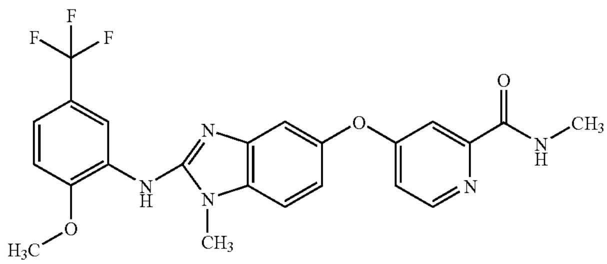 | N-methyl-4-[(1-methyl-2-{[2-(methyloxy)-5-(trifluoromethyl)-phenyl]amino}-1H-benzimidazol-5-yl)oxy]pyridine-2-carboxamide | 472.4 |
| 215 | 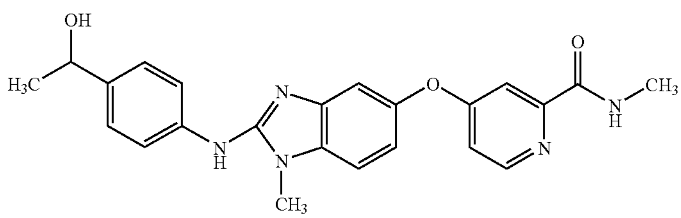 | 4-[(2-{[4-(1-hydroxyethyl)-phenyl]amino}-1-methyl-1H-benzimidazol-5-yl)oxy]-N-methylpyridine-2-carboxamide | 418.5 |
| 216 | 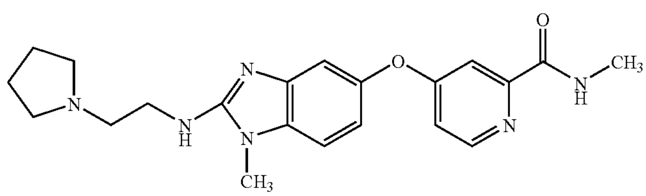 | N-methyl-4-({1-methyl-2-[(2-pyrrolidin-1-ylethyl)amino]-1H-benzimidazol-5-yl}oxy)pyridine-2-carboxamide | 395.5 |
| 217 | 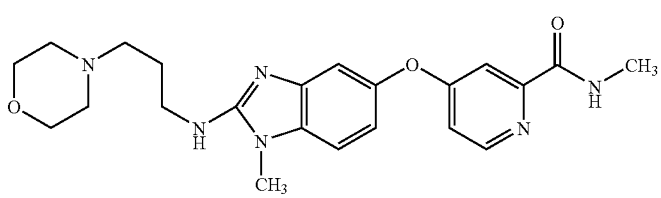 | N-methyl-4-({1-methyl-2-[(3-morpholin-4-ylpropyl)amino]-1H-benzimidazol-5-yl}oxy)-pyridine-2-carboxamide | 425.5 |
| 218 | 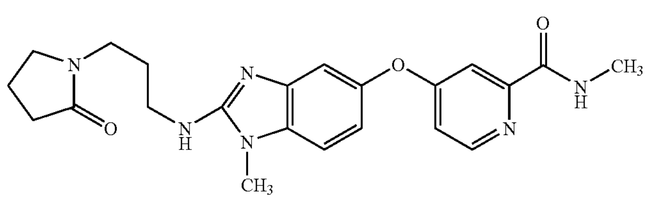 | N-methyl-4-[(1-methyl-2-{[3-(2-oxopyrrolidin-1-yl)propyl]-amino}-1H-benzimidazol-5-yl)oxy]pyridine-2-carboxamide | 423.5 |
| 219 | 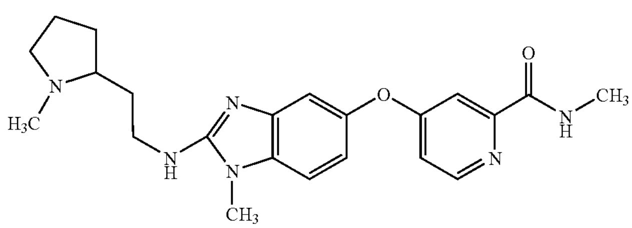 | N-methyl-4-[(1-methyl-2-{[2-(1-methylpyrrolidin-2-yl)ethyl]-amino}-1H-benzimidazol-5-yl)oxy]pyridine-2-carboxamide | 409.5 |
| 220 | 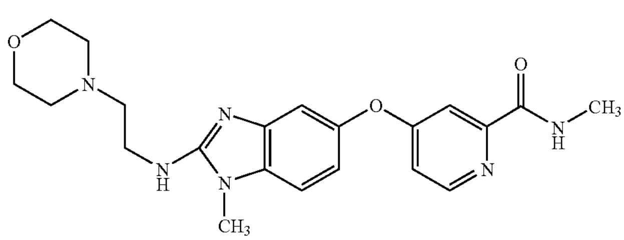 | N-methyl-4-({1-methyl-2-[(2-morpholin-4-ylethyl)amino]-1H-benzimidazol-5-yl}oxy)pyridine-2-carboxamide | 411.5 |

TABLE 3-continued

| Example | Structure | Name | MH+ |
|---|---|---|---|
| 221 | 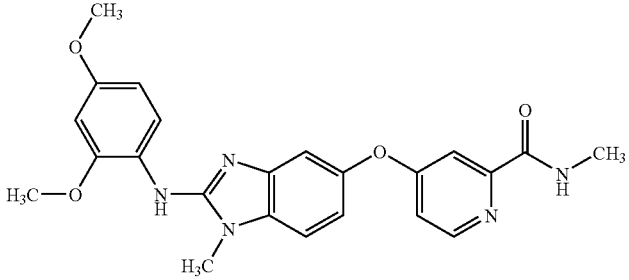 | 4-[(2-{[2,4-bis(methyloxy)-phenyl]amino}-1-methyl-1H-benzimidazol-5-yl)oxy]-N-methylpyridine-2-carboxamide | 434.5 |
| 222 | 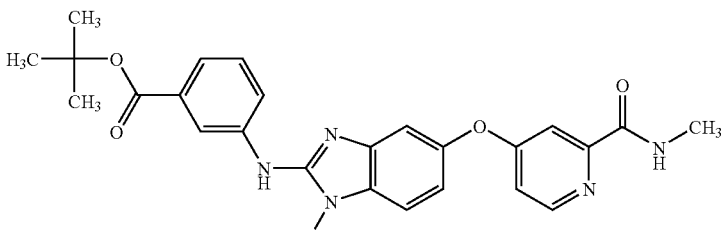 | 1,1-dimethylethyl 3-{[1-methyl-5-({2-[(methylamino)carbonyl]-pyridin-4-yl}oxy)-1H-benzimidazol-2-yl]amino}benzoate | 474.5 |
| 223 | 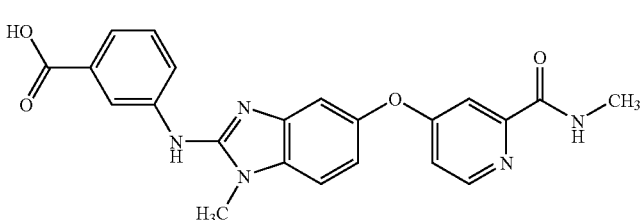 | 3-{[1-methyl-5-({2-[(methyl-amino)carbonyl]pyridin-4-yl}-oxy)-1H-benzimidazol-2-yl]-amino}benzoic acid | 418.4 |
| 224 | 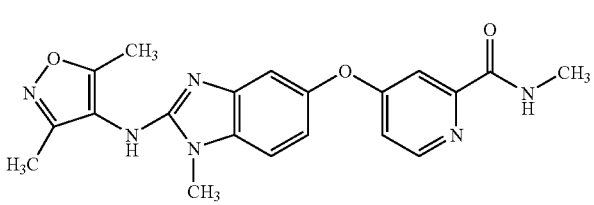 | 4-({2-[(3,5-dimethylisoxazol-4-yl)amino]-1-methyl-1H-benzimidazol-5-yl}oxy)-N-methyl-pyridine-2-carboxamide | 393.4 |
| 225 | 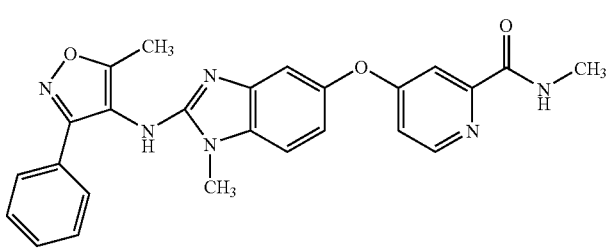 | N-methyl-4-({1-methyl-2-[(5-methyl-3-phenylisoxazol-4-yl)-amino]-1H-benzimidazol-5-yl}-oxy)pyridine-2-carboxamide | 455.5 |
| 226 | 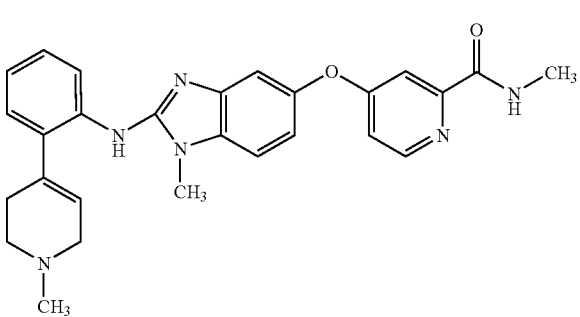 | N-methyl-4-[(1-methyl-2-{[2-(1-methyl-1,2,3,6-tetrahydro-pyridin-4-yl)phenyl]amino}-1H-benzimidazol-5-yl)oxy]pyridine-2-carboxamide | 469.6 |

TABLE 3-continued

| Example | Structure | Name | MH+ |
|---|---|---|---|
| 227 | 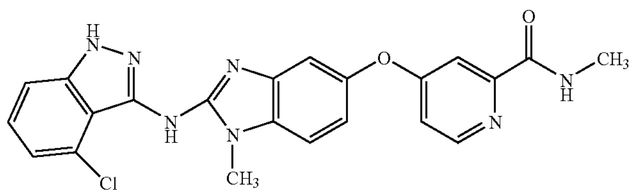 | 4-({2-[(4-chloro-1H-indazol-3-yl)amino]-1-methyl-1H-benzimidazol-5-yl}oxy)-N-methylpyridine-2-carboxamide | 448.9 |
| 228 | 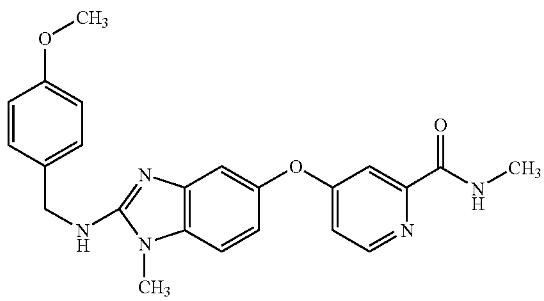 | N-methyl-4-{[1-methyl-2-({[4-(methyloxy)phenyl]methyl}amino)-1H-benzimidazol-5-yl]oxy}-pyridine-2-carboxamide | 418.5 |
| 229 | 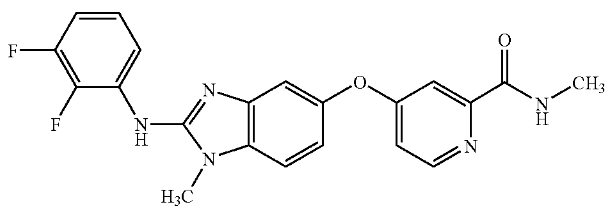 | 4-({2-[(2,3-difluorophenyl)-amino]-1-methyl-1H-benzimidazol-5-yl}oxy)-N-methylpyridine-2-carboxamide | 410.4 |
| 230 | 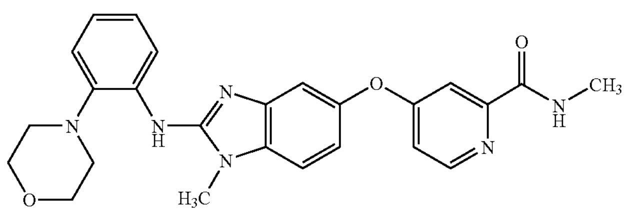 | N-methyl-4-({1-methyl-2-[(2-morpholin-4-ylphenyl)amino]-1H-benzimidazol-5-yl}oxy)-pyridine-2-carboxamide | 459.5 |
| 231 | 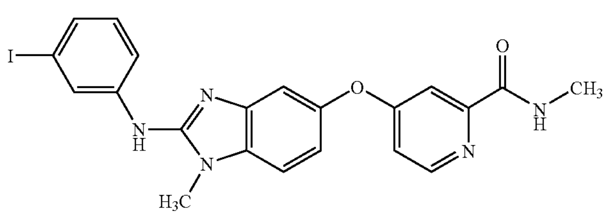 | 4-({2-[(3-iodophenyl)amino]-methyl-1H-benzimidazol-5-yl}-oxy)-N-methylpyridine-2-carboxamide | 500.3 |
| 232 | 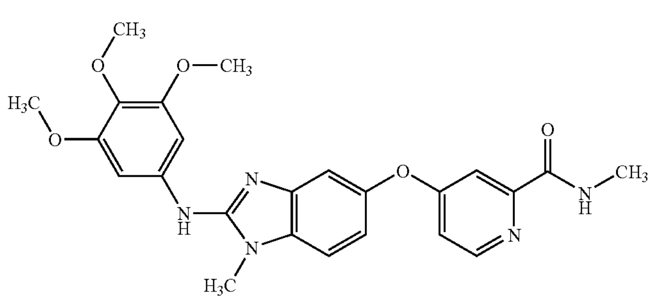 | N-methyl-4-[(1-methyl-2-{[3,4,5-tris(methyloxy)phenyl]-amino}-1H-benzimidazol-5-yl)oxy]pyridine-2-carboxamide | 464.5 |

TABLE 3-continued

| Example | Name | MH+ |
|---|---|---|
| 233 | N-methyl-4-({1-methyl-2-[(thien-2-ylmethyl)amino]-1H-benzimidazol-5-yl}oxy)pyridine-2-carboxamide | 394.5 |
| 234 | N-methyl-4-({1-methyl-2-[(3-thien-2-yl-1H-pyrazol-5-yl)-amino]-1H-benzimidazol-5-yl}oxy)pyridine-2-carboxamide | 446.5 |
| 235 | 4-{[2-(1,3-benzodioxol-5-yl-amino)-1-methyl-1H-benzimidazol-5-yl]oxy}-N-methylpyridine-2-carboxamide | 418.4 |
| 236 | 4-({2-[(2-iodophenyl)amino]-1-methyl-1H-benzimidazol-5-yl}-oxy)-N-methylpyridine-2-carboxamide | 500.3 |
| 237 | 4-({2-[(2,6-diethylphenyl)-amino]-1-methyl-1H-benzimidazol-5-yl}oxy)-N-methylpyridine-2-carboxamide | 430.5 |
| 238 | 4-[(2-{[3-(1-hydroxyethyl)-phenyl]amino}-1-methyl-1H-benzimidazol-5-yl)oxy]-N-methylpyridine-2-carboxamide | 418.5 |

TABLE 3-continued

| Example | Structure | Name | MH+ |
|---|---|---|---|
| 239 | 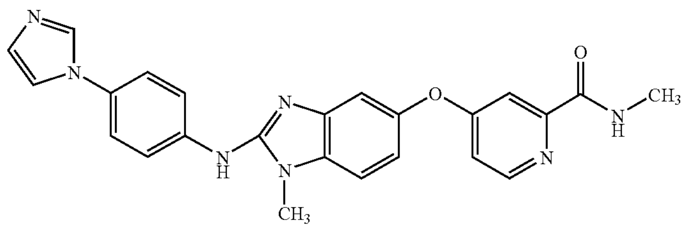 | 4-[(2-{[4-(1H-imidazol-1-yl)-phenyl]amino}-1-methyl-1H-benzimidazol-5-yl)oxy]-N-methylpyridine-2-carboxamide | 440.5 |
| 240 | 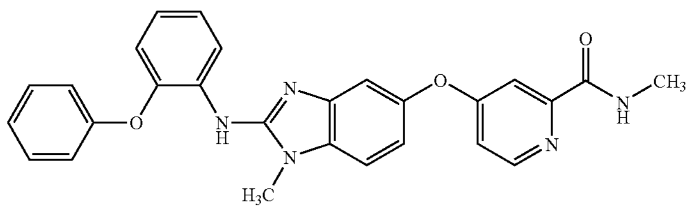 | N-methyl-4-[(1-methyl-2-{[2-(phenyloxy)phenyl]amino}-1H-benzimidazol-5-yl)oxy]pyridine-2-carboxamide | 466.5 |
| 241 | 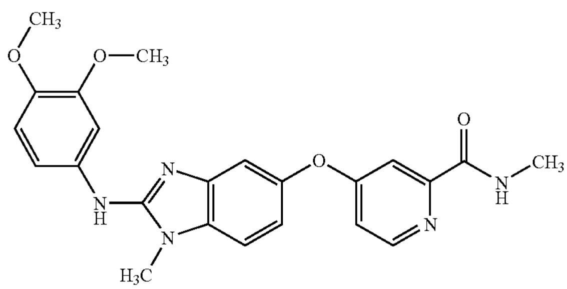 | 4-[(2-{[3,4-bis(methyloxy)-phenyl]amino}-1-methyl-1H-benzimidazol-5-yl)oxy]-N-methylpyridine-2-carboxamide | 434.5 |
| 242 | 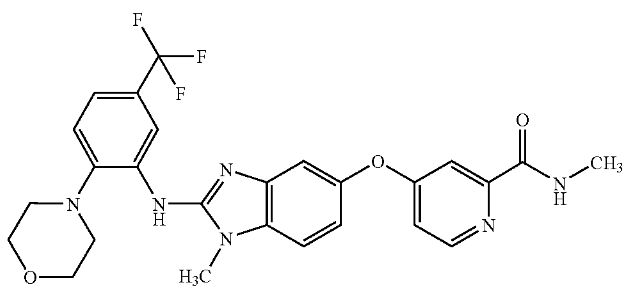 | N-methyl-4-[(1-methyl-2-{[2-morpholin-4-yl-5-(trifluoro-methyl)phenyl]amino}-1H-benzimidazol-5-yl)oxy]pyridine-2-carboxamide | 527.5 |
| 243 | 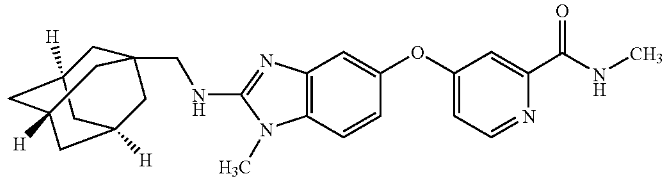 | N-methyl-4-({1-methyl-2-[(tricyclo[3.3.1.1~3,7~]dec-1-ylmethyl)amino]-1H-benzimidazol-5-yl}oxy)pyridine-2-carboxamide | 446.6 |
| 244 | 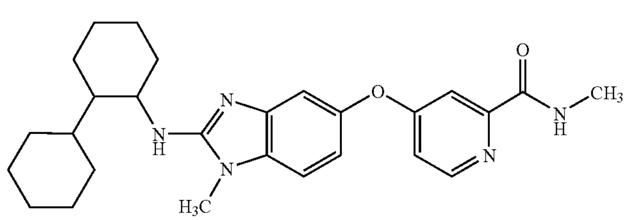 | 4-({2-[1,1'-bi(cyclohexyl)-2-ylamino]-1-methyl-1H-benzimidazol-5-yl}oxy)-N-methylpyridine-2-carboxamide | 462.6 |

TABLE 3-continued

| Example | Name | MH+ |
|---|---|---|
| 245 | 4-{[2-({[(1S,5S)-6,6-dimethyl-bicyclo[3.1.1]hept-2-yl]methyl}-amino)-1-methyl-1H-benzimidazol-5-yl]oxy}-N-methylpyridine-2-carboxamide | 434.6 |
| 246 | N-methyl-4-{[1-methyl-2-(tricyclo[3.3.1.1~3,7~]dec-1-ylamino)-1H-benzimidazol-5-yl]oxy}pyridine-2-carboxamide | 432.5 |
| 247 | N-methyl-4-({1-methyl-2-[(3-methylphenyl)amino]-1H-benzimidazol-5-yl}oxy)pyridine-2-carboxamide | 388.4 |
| 248 | 4-[2-{[5-fluoro-2-(1H-imidazol-1-yl)phenyl]amino}-1-methyl-1H-benzimidazol-5-yl)oxy]-N-methylpyridine-2-carboxamide | 458.5 |
| 249 | N-methyl-4-({1-methyl-2-[(5-phenyl-1H-pyrazol-3-yl)amino]-1H-benzimidazol-5-yl}oxy)-pyridine-2-carboxamide | 440.5 |
| 250 | 4-{[2-({4-[(4-ethylpiperazin-1-yl)methyl]phenyl}amino)-1-oxy}-N-methylpyridine-2-carboxamide | 500.6 |

TABLE 3-continued

| Example | Structure | Name | MH+ |
|---|---|---|---|
| 251 | 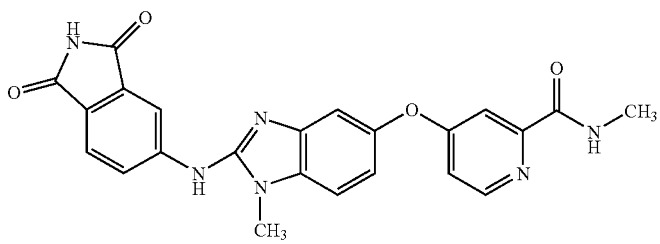 | 4-({2-[(1,3-dioxo-2,3-dihydro-1H-isoindol-5-yl)amino]-1-methyl-1H-benzimidazol-5-yl}oxy)-N-methylpyridine-2-carboxamide | 443.4 |
| 252 | 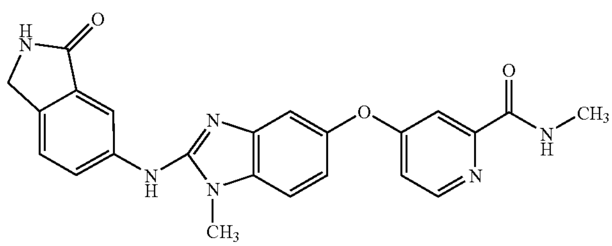 | N-methyl-4-({1-methyl-2-[(3-oxo-2,3-dihydro-1H-isoindol-5-yl)amino]-1H-benzimidazol-5-yl}oxy)pyridine-2-carboxamide | 429.4 |
| 253 | 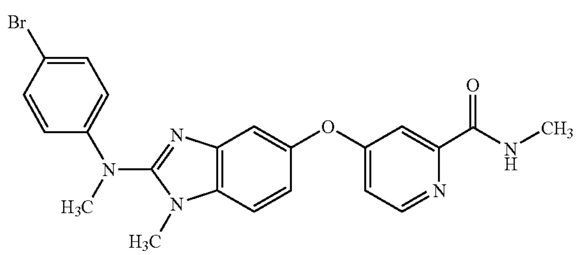 | 4-({2-[(4-bromophenyl)-(methyl)amino]-1-methyl-1H-benzimidazol-5-yl}oxy)-N-methylpyridine-2-carboxamide | 467.3 |
| 254 | 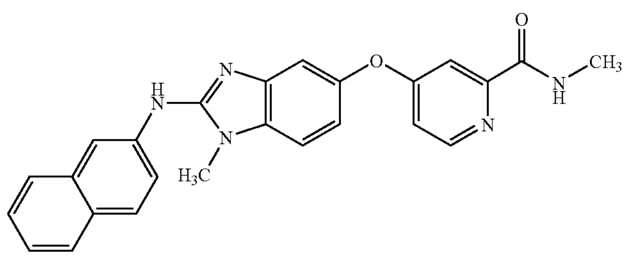 | N-methyl-4-{[1-methyl-2-(naphthalen-2-ylamino)-1H-benzimidazol-5-yl]oxy}pyridine-2-carboxamide | 424.5 |
| 255 | 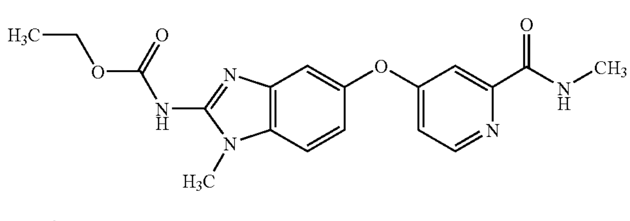 | ethyl 1-methyl-5-({2-[(methyl-amino)carbonyl]pyridin-4-yl}-oxy)-1H-benzimidazol-2-yl-carbamate | 370.4 |
| 256 | 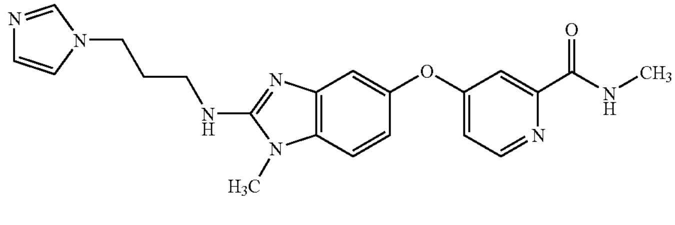 | 4-[(2-{[3-(1H-imidazol-1-yl)-propyl]amino}-1-methyl-1H-benzimidazol-5-yl)oxy]-N-methylpyridine-2-carboxamide | 406.5 |

TABLE 3-continued

| Example | Structure | Name | MH+ |
|---|---|---|---|
| 257 | 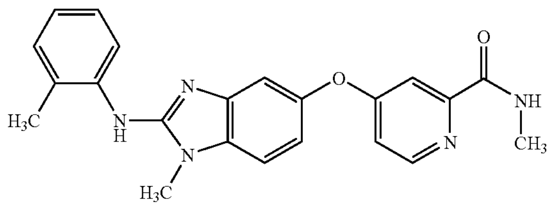 | N-methyl-4-({1-methyl-2-[(2-methylphenyl)amino]-1H-benzimidazol-5-yl}oxy)pyridine-2-carboxamide | 388.4 |
| 258 | 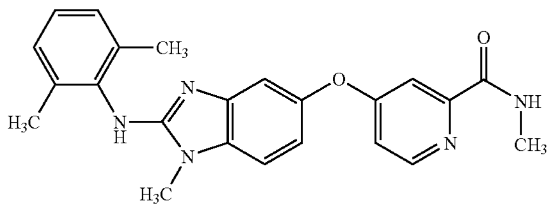 | 4-({2-[(2,6-dimethylphenyl)-amino]-1-methyl-1H-benzimidazol-5-yl}oxy)-N-methylpyridine-2-carboxamide | 402.5 |
| 259 | 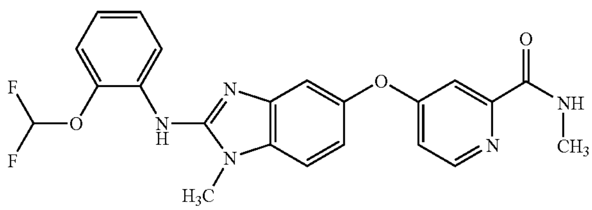 | 4-{[2-({2-[(difluoromethyl)-oxy]phenyl}amino)-1-methyl-1H-benzimidazol-5-yl]oxy}-N-methylpyridine-2-carboxamide | 440.4 |
| 260 | 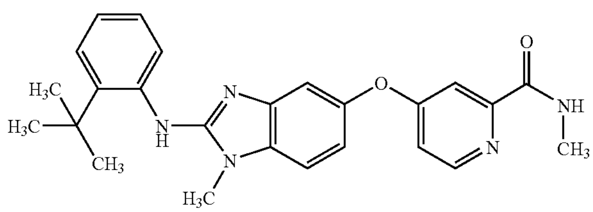 | 4-[(2-{[2-(1,1-dimethylethyl)-phenyl]amino}-1-methyl-1H-benzimidazol-5-yl)oxy]-N-methylpyridine-2-carboxamide | 430.5 |
| 261 | 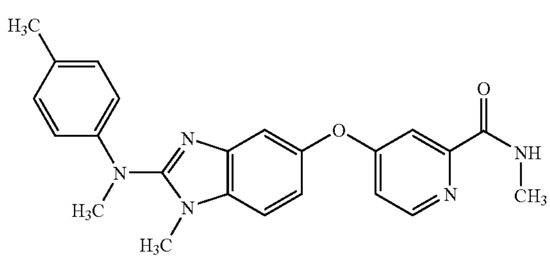 | N-methyl-4-({1-methyl-2-[methyl(4-methylphenyl)amino]-1H-benzimidazol-5-yl}oxy)-pyridine-2-carboxamide | 402.5 |
| 262 | 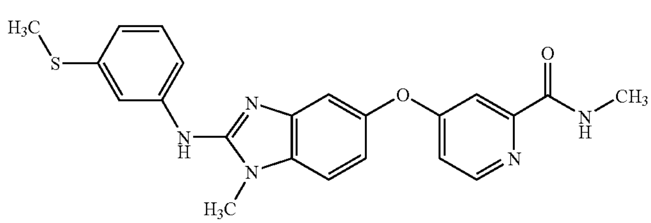 | N-methyl-4-[(1-methyl-2-{[3-(methylthio)phenyl]amino}-1H-benzimidazol-5-yl)oxy]pyridine-2-carboxamide | 420.5 |

TABLE 3-continued

| Example | Structure | Name | MH+ |
|---|---|---|---|
| 263 | 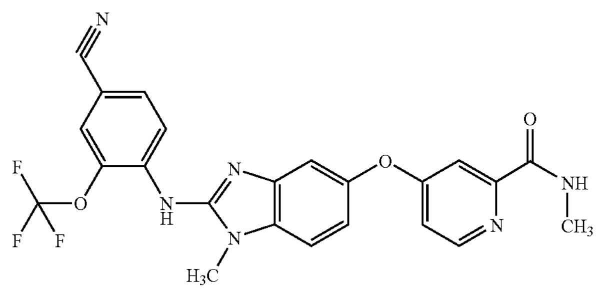 | 4-{[2-({4-cyano-2-[(trifluoro-methyl)oxy]phenyl}amino)-1-methyl-1H-benzimidazol-5-yl]oxy}-N-methylpyridine-2-carboxamide | 483.4 |
| 264 | 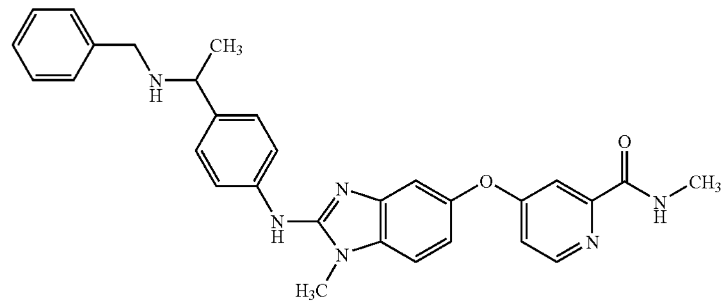 | N-methyl-4-({1-methyl-2-[(4-{1-[(phenylmethyl)amino]-ethyl}phenyl)amino]-1H-benzimidazol-5-yl}oxy)pyridine-2-carboxamide | 507.6 |
| 265 | 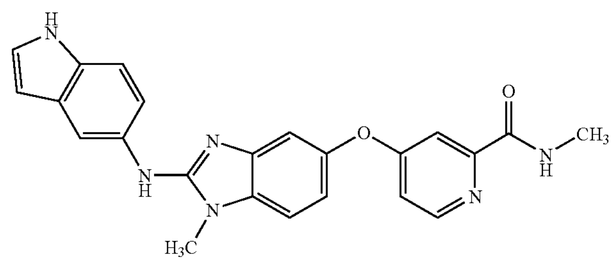 | 4-{[2-(1H-indol-5-ylamino)-1-methyl-1H-benzimidazol-5-yl]-oxy}-N-methylpyridine-2-carboxamide | 413.5 |
| 266 | 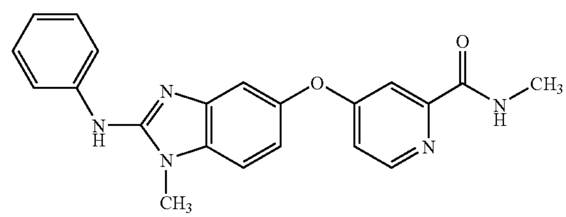 | N-methyl-4-{[1-methyl-2-(phenylamino)-1H-benzimidazol-5-yl]-oxy}pyridine-2-carboxamide | 374.4 |
| 267 | 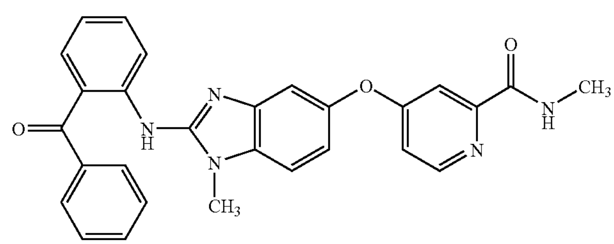 | N-methyl-4-[(1-methyl-2-{[2-(phenylcarbonyl)phenyl]amino}-1H-benzimidazol-5-yl)oxy]-pyridine-2-carboxamide | 478.5 |
| 268 | 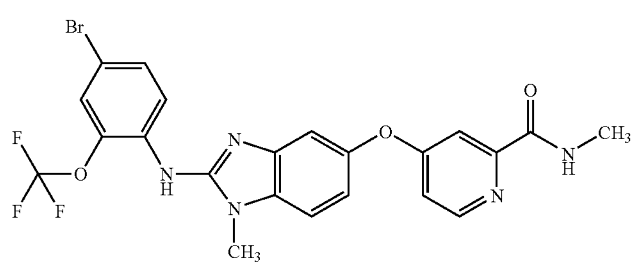 | 4-{[2-({4-bromo-2-[(trifluoro-methyl)oxy]phenyl}amino)-1-methyl-1H-benzimidazol-5-yl]oxy}-N-methylpyridine-2-carboxamide | 537.3 |

TABLE 3-continued

| Example | Name | MH+ |
|---|---|---|
| 269 | 4-({2-[(2,4-dibromo-6-fluoro-phenyl)amino]-1-methyl-1H-benzimidazol-5-yl}oxy)-N-methylpyridine-2-carboxamide | 550.2 |
| 270 | 4-{[2-(1,3-dihydro-2 h-isoindol-2-yl)-1-methyl-1H-benzimidazol-5-yl]oxy}-N-methylpyridine-2-carboxamide | 400.5 |
| 271 | 4-{[2-(isoquinolin-1-ylamino)-1-methyl-1H-benzimidazol-5-yl]oxy}-N-methylpyridine-2-carboxamide | 425.5 |
| 272 | N-methyl-4-[(1-methyl-2-{[2-(1H-pyrazol-1-yl)phenyl]-amino}-1H-benzimidazol-5-yl)oxy]pyridine-2-carboxamide | 440.5 |
| 273 | 4-{[2-(1H-indol-6-ylamino)-1-methyl-1H-benzimidazol-5-yl]oxy}-N-methylpyridine-2-carboxamide | 413.5 |
| 274 | methyl 4-{[1-methyl-5-({2-[(methylamino)carbonyl]pyridin-4-yl}oxy)-1H-benzimidazol-2-yl]amino}-3-[(trifluoromethyl)-oxy]benzoate | 516.4 |

TABLE 3-continued

| Example | Name | MH+ |
|---|---|---|
| 275 | 4-({2-[(2-cyanophenyl)amino]-1-methyl-1H-benzimidazol-5-yl}oxy)-N-methylpyridine-2-carboxamide | 399.4 |
| 276 | N-methyl-4-[(1-methyl-2-{[2-(phenylthio)phenyl]amino}-1H-benzimidazol-5-yl)oxy]pyridine-2-carboxamide | 482.6 |
| 277 | 4-[(2-{[2-[(4-chlorophenyl)oxy]-5-(trifluoromethyl)phenyl]-amino}-1-methyl-1H-benzimidazol-5-yl)oxy]-N-methylpyridine-2-carboxamide | 569.0 |
| 278 | N-methyl-4-[(1-methyl-2-{[2-[(4-methylphenyl)oxy]-5-(trifluoromethyl)phenyl]amino}-1H-benzimidazol-5-yl)oxy]-pyridine-2-carboxamide | 548.5 |
| 279 | 4-({2-[(4-chlorophenyl)amino]-1,7-dimethyl-1H-benzimidazol-5-yl}oxy)-N-methylpyridine-2-carboxamide | 422.9 |
| 280 | 4-[(2-{[3-(1,1-dimethylethyl)-phenyl]amino}-1-methyl-1H-benzimidazol-5-yl)oxy]-N-methylpyridine-2-carboxamide | 430.5 |

TABLE 3-continued

| Example | Structure | Name | MH+ |
|---|---|---|---|
| 281 | 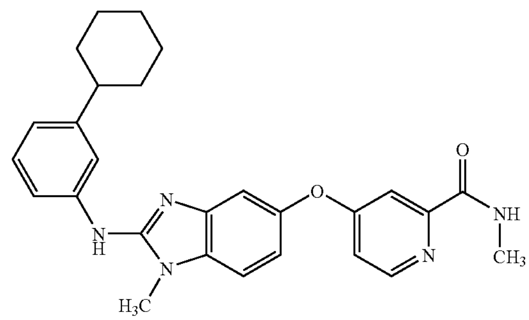 | 4-({2-[(3-cyclohexylphenyl)-amino]-1-methyl-1H-benzimidazol-5-yl}oxy)-N-methylpyridine-2-carboxamide | 456.6 |
| 282 | 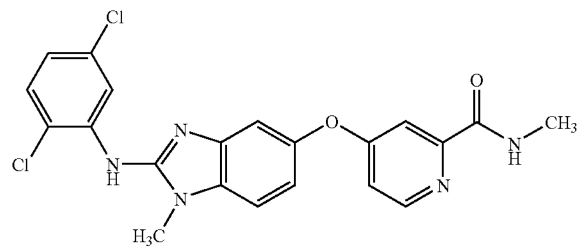 | 4-({2-[(2,5-dichlorophenyl)-amino]-1-methyl-1H-benzimidazol-5-yl}oxy)-N-methylpyridine-2-carboxamide | 443.3 |
| 283 | 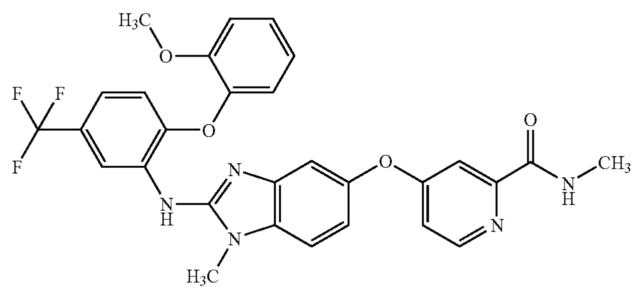 | N-methyl-4-[(1-methyl-2-{[2-{[2-(methloxy)phenyl]oxy}-5-(trifluoromethyl)phenyl]amino}-1H-benzimidazol-5-yl)oxy]pyridine-2-carboxamide | 564.5 |
| 284 | 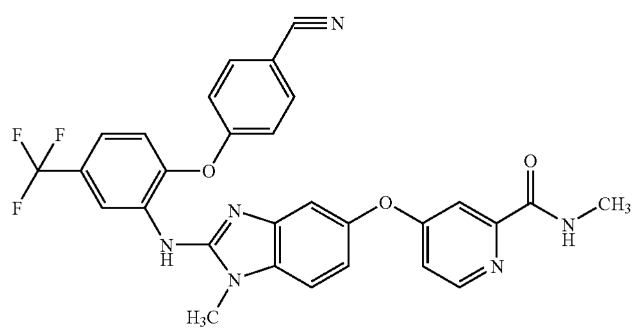 | 4-[(2-{[2-[(4-cyanophenyl)oxy]-5-(trifluoromethyl)phenyl]-amino}-1-methyl-1H-benzimidazol-5-yl)oxy]-N-methylpyridine-2-carboxamide | 559.5 |
| 285 | 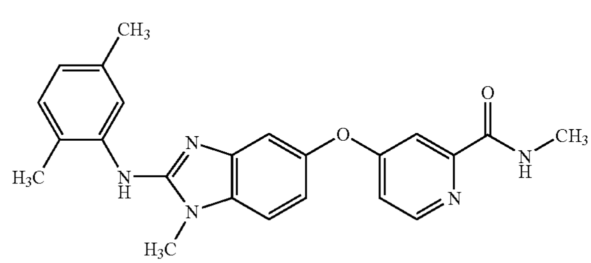 | 4-({2-[(2,5-dimethylphenyl)-amino]-1-methyl-1H-benzimidazol-5-yl}oxy)-N-methylpyridine-2-carboxamide | 402.5 |

TABLE 3-continued

| Example | Structure | Name | MH+ |
|---|---|---|---|
| 286 | 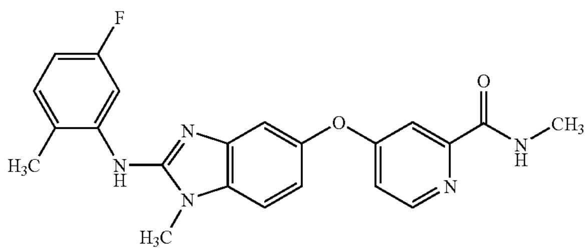 | 4-({2-[(5-fluoro-2-methyl-phenyl)amino]-1-methyl-1H-benzimidazol-5-yl}oxy)-N-methylpyridine-2-carboxamide | 406.4 |
| 287 | 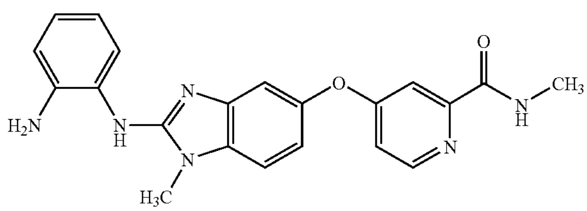 | 4-({2-[(2-aminophenyl)amino]-1-methyl-1H-benzimidazol-5-yl}oxy)-N-methylpyridine-2-carboxamide | 389.4 |
| 288 | 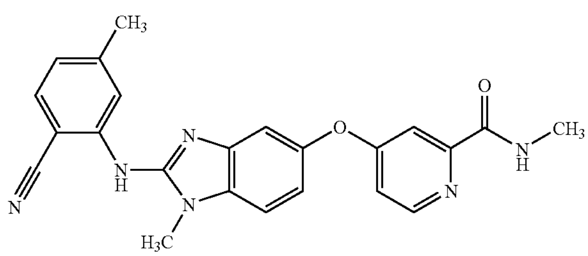 | 4-({2-[(2-cyano-5-methyl-phenyl)amino]-1-methyl-1H-benzimidazol-5-yl}oxy)-N-methylpyridine-2-carboxamide | 413.5 |
| 289 | 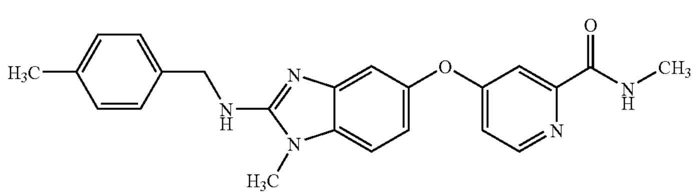 | N-methyl-4-[(1-methyl-2-{[(4-methylphenyl)methyl]amino}-1H-benzimidazol-5-yl)oxy]-pyridine-2-carboxamide | 402.5 |
| 290 | 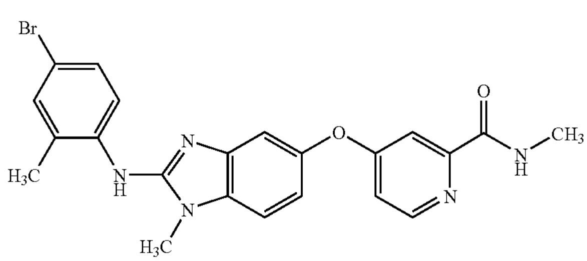 | 4-({2-[(4-bromo-2-methyl-phenyl)amino]-1-methyl-1H-benzimidazol-5-yl}oxy)-N-methylpyridine-2-carboxamide | 467.3 |
| 291 | 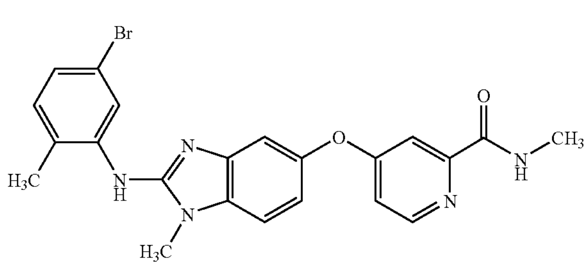 | 4-({2-[(5-bromo-2-methyl-phenyl)amino]-1-methyl-1H-benzimidazol-5-yl}oxy)-N-methylpyridine-2-carboxamide | 467.3 |

TABLE 3-continued

| Example | Structure | Name | MH+ |
| --- | --- | --- | --- |
| 292 | 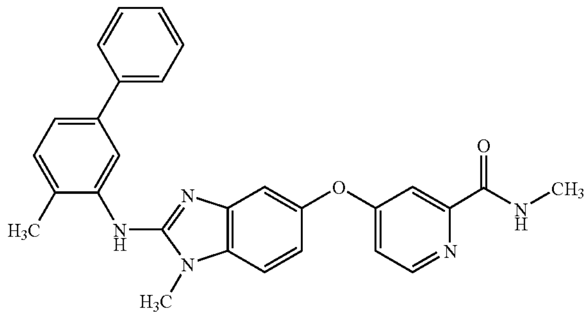 | N-methyl-4-({1-methyl-2-[(4-methyl-1,1'-biphenyl-3-yl)-amino]-1H-benzimidazol-5-yl}-oxy)pyridine-2-carboxamide | 464.5 |
| 293 | 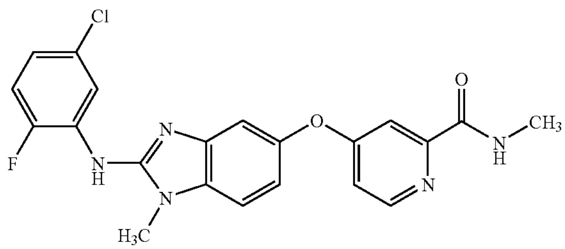 | 4-({2-[(5-chloro-2-fluoro-phenyl)amino]-1-methyl-1H-benzimidazol-5-yl}oxy)-N-methylpyridine-2-carboxamide | 426.8 |
| 294 | 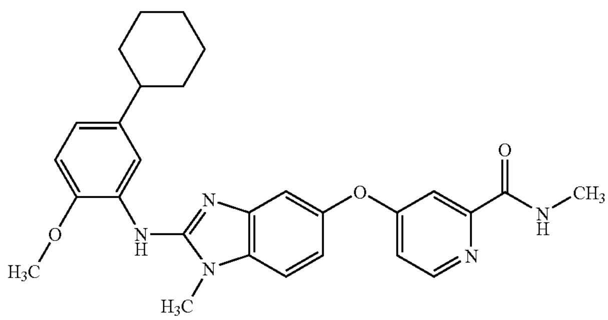 | 4-[(2-{[5-cyclohexyl-2-(methyl-oxy)phenyl]amino}-1-methyl-1H-benzimidazol-5-yl)oxy]-N-methylpyridine-2-carboxamide | 486.6 |
| 295 | 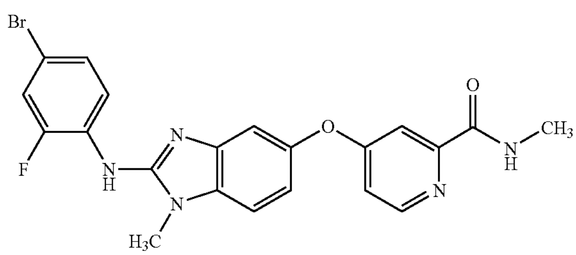 | 4-({2-[(4-bromo-2-fluoro-phenyl)amino]-1-methyl-1H-benzimidazol-5-yl}oxy)-N-methylpyridine-2-carboxamide | 471.3 |
| 296 | 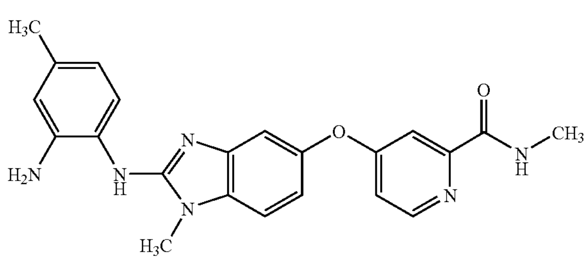 | 4-({2-[(2-amino-4-methyl-phenyl)amino]-1-methyl-1H-benzimidazol-5-yl}oxy)-N-methylpyridine-2-carboxamide | 403.5 |

TABLE 3-continued

| Example | Name | MH+ |
|---|---|---|
| 297 | N-methyl-4-{[1-methyl-2-(5,6,7,8-tetrahydronaphthalen-1-ylamino)-1H-benzimidazol-5-yl]oxy}pyridine-2-carboxamide | 428.5 |
| 298 | N-methyl-4-[(1-methyl-2-{[4-(methylsulfonyl)phenyl]amino}-1H-benzimidazol-5-yl)oxy]-pyridine-2-carboxamide | 452.5 |
| 299 | N-methyl-4-{[1-methyl-2-({3-[(trifluoromethyl)thio]phenyl}amino)-1H-benzimidazol-5-yl]-oxy}pyridine-2-carboxamide | 474.5 |
| 300 | N-methyl-4-{[1-methyl-2-({4-[(trifluoromethyl)thio]phenyl}amino)-1H-benzimidazol-5-yl]-oxy}pyridine-2-carboxamide | 474.5 |
| 301 | 4-{[2-(1,1'-biphenyl-3-ylamino)-1-methyl-1H-benzimidazol-5-yl]oxy}-N-methylpyridine-2-carboxamide | 450.5 |
| 302 | 4-({2-[(2-chloro-4-methyl-phenyl)amino]-1-methyl-1H-benzimidazol-5-yl}oxy)-N-methylpyridine-2-carboxamide | 422.9 |

TABLE 3-continued

| Example | Structure | Name | MH+ |
|---|---|---|---|
| 303 | 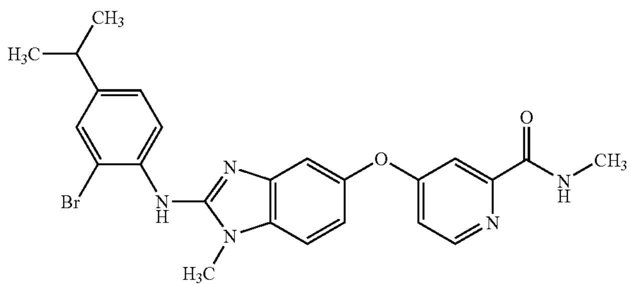 | 4-[(2-{[2-bromo-4-(1-methylethyl)phenyl]amino}-1-methyl-1H-benzimidazol-5-yl)oxy]-N-methylpyridine-2-carboxamide | 495.4 |
| 304 | 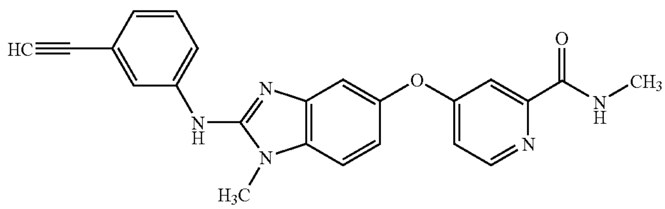 | 4-({2-[(3-ethynylphenyl)amino]-1-methyl-1H-benzimidazol-5-yl}oxy)-N-methylpyridine-2-carboxamide | 398.4 |
| 305 | 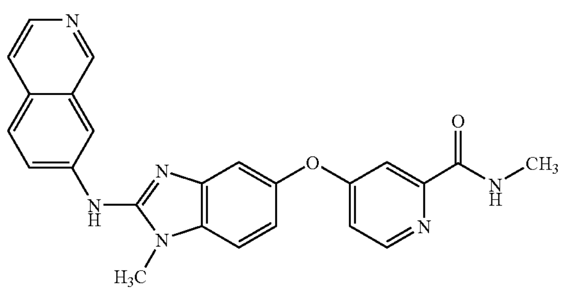 | 4-{[2-(isoquinolin-7-ylamino)-1-methyl-1H-benzimidazol-5-yl]oxy}-N-methylpyridine-2-carboxamide | 425.5 |
| 306 | 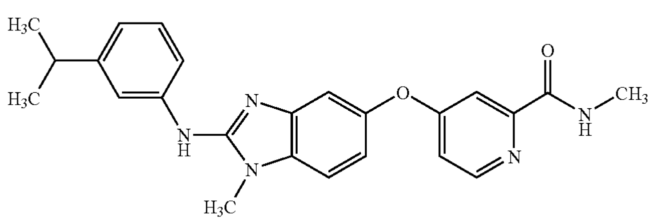 | N-methyl-4-[(1-methyl-2-{[3-(1-methylethyl)phenyl]amino}-1H-benzimidazol-5-yl)oxy]pyridine-2-carboxamide | 416.5 |
| 307 | 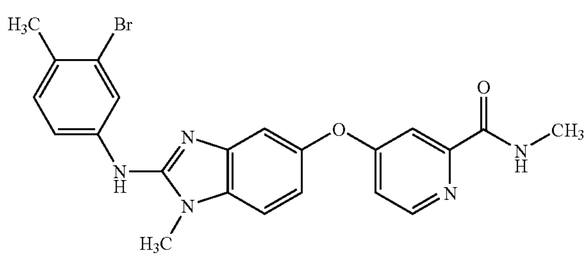 | 4-({2-[(3-bromo-4-methylphenyl)amino]-1-methyl-1H-benzimidazol-5-yl}oxy)-N-methylpyridine-2-carboxamide | 467.3 |
| 308 | 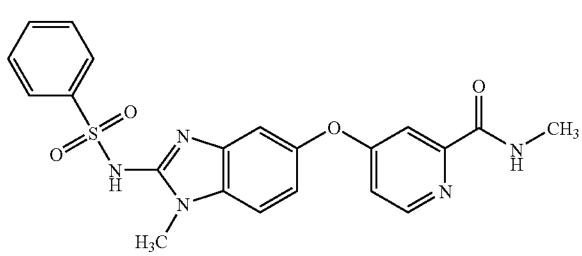 | N-methyl-4-({1-methyl-2-[(phenylsulfonyl)amino]-1H-benzimidazol-5-yl}oxy)pyridine-2-carboxamide | 438.5 |

TABLE 3-continued

| Example | Name | MH+ |
|---|---|---|
| 309 | 4-{[2-(9H-fluoren-1-ylamino)-1-methyl-1H-benzimidazol-5-yl]-oxy}-N-methylpyridine-2-carboxamide | 462.5 |
| 310 | 4-{[2-(9H-fluoren-2-ylamino)-1-methyl-1H-benzimidazol-5-yl]-oxy}-N-methylpyridine-2-carboxamide | 462.5 |
| 311 | 4-({2-[(2,2-difluoro-1,3-benzodioxol-5-yl)amino]-1-methyl-1H-benzimidazol-5-yl}-oxy)-N-methylpyridine-2-carboxamide | 454.4 |
| 312 | N-methyl-4-{[1-methyl-2-({3-[(trifluoromethyl)oxy]phenyl}amino)-1H-benzimidazol-5-yl]-oxy}pyridine-2-carboxamide | 458.4 |
| 313 | N-methyl-4-({1-methyl-2-[(1-methylethyl)amino]-1H-benzimidazol-5-yl}oxy)pyridine-2-carboxamide | 340.4 |

TABLE 3-continued

| Example | Structure | Name | MH+ |
|---|---|---|---|
| 314 | 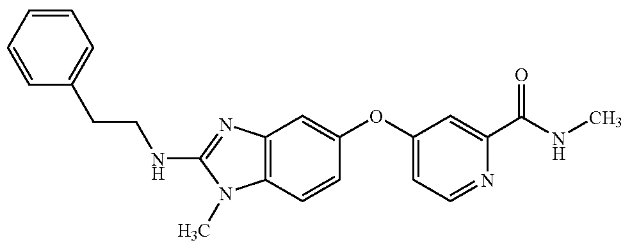 | N-methyl-4-({1-methyl-2-[(2-phenylethyl)amino]-1H-benzimidazol-5-yl}oxy)pyridine-2-carboxamide | 402.5 |
| 315 | 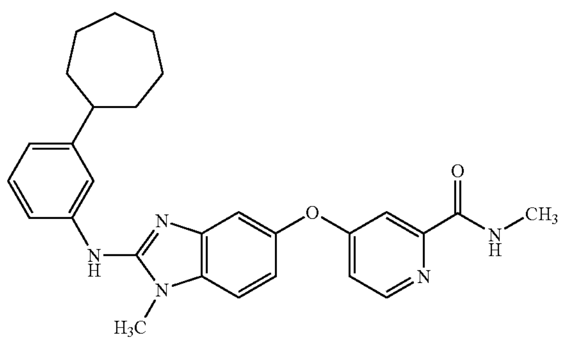 | 4-({2-[(3-cycloheptylphenyl)-amino]-1-methyl-1H-benzimidazol-5-yl}oxy)-N-methylpyridine-2-carboxamide | 470.6 |
| 316 | 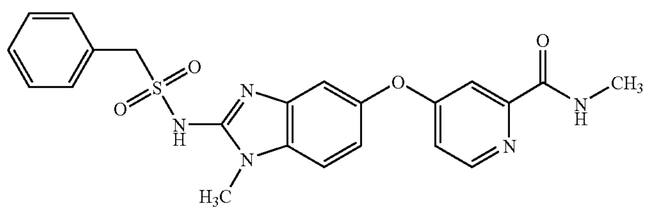 | N-methyl-4-[(1-methyl-2-{[(phenylmethyl)sulfonyl]amino}-1H-benzimidazol-5-yl)oxy]-pyridine-2-carboxamide | 452.5 |
| 317 | 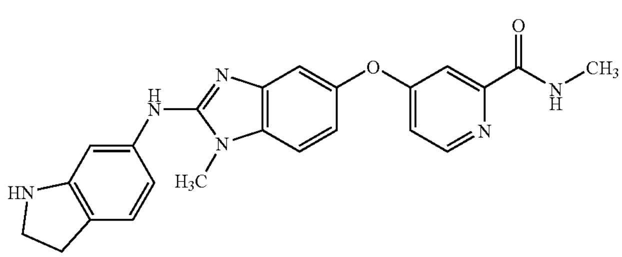 | 4-{[2-(2,3-dihydro-1H-indol-6-ylamino)-1-methyl-1H-benzimidazol-5-yl]oxy}-N-methylpyridine-2-carboxamide | 415.5 |
| 318 | 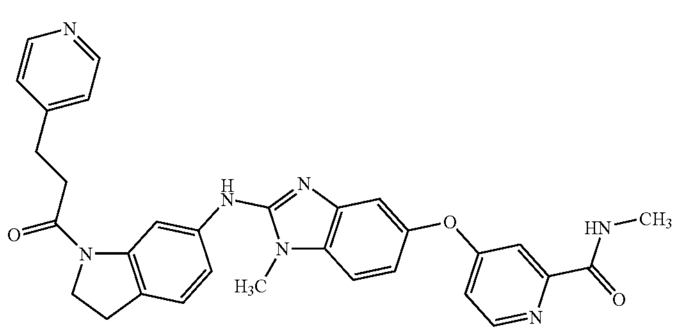 | N-methyl-4-[(1-methyl-2-{[1-(3-pyridin-4-ylpropanoyl)-2,3-dihydro-1H-indol-6-yl]amino}-1H-benzimidazol-5-yl)oxy]-pyridine-2-carboxamide | 548.6 |

TABLE 3-continued

| Example | Structure | Name | MH+ |
|---|---|---|---|
| 319 | 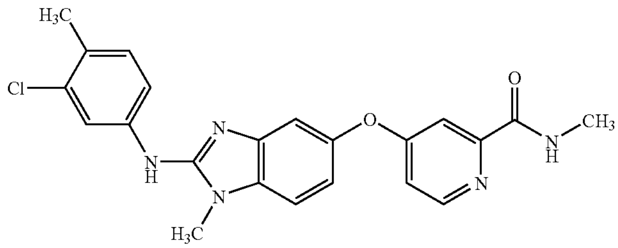 | 4-({2-[3-chloro-4-methyl-phenyl)amino]-1-methyl-1H-benzimidazol-5-yl}oxy)-N-methylpyridine-2-carboxamide | 422.9 |
| 320 | 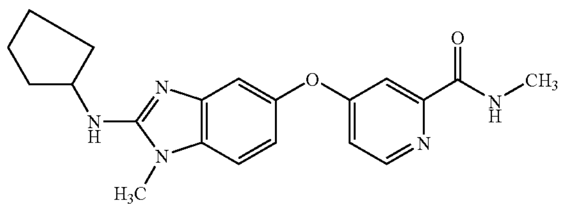 | 4-{[2-(cyclopentylamino)-1-methyl-1H-benzimidazol-5-yl]oxy}-N-methylpyridine-2-carboxamide | 366.4 |
| 321 (synthesis as in Ex 1) | 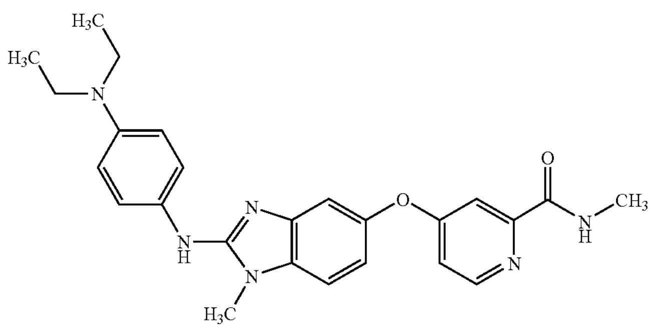 | 4-[(2-{[4-(diethylamino)phenyl]-amino}-1-methyl-1H-benzimidazol-5-yl)oxy]-N-methylpyridine-2-carboxamide | 445.5 |
| 322 | 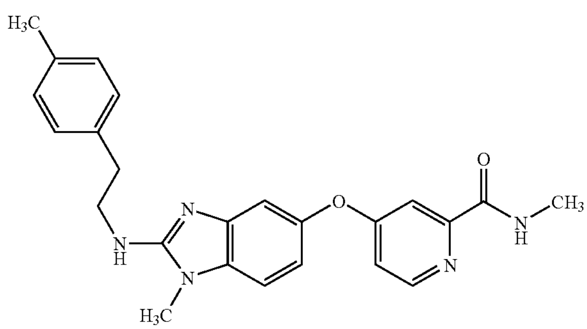 | N-methyl-4-[(1-methyl-2-{[2-(4-methylphenyl)ethyl]amino}-1H-benzimidazol-5-yl)oxy]pyridine-2-carboxamide | 416.5 |
| 323 | 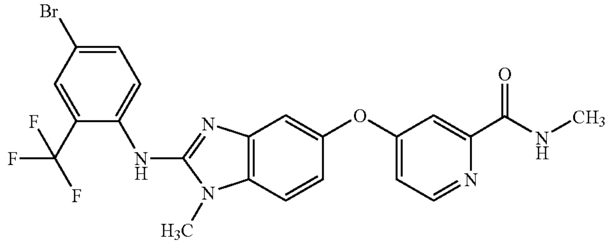 | 4-[(2-{[4-bromo-2-(trifluoro-methyl)phenyl]amino}-1-methyl-1H-benzimidazol-5-yl)-oxy]-N-methylpyridine-2-carboxamide | 521.3 |

TABLE 3-continued

| Example | Structure | Name | MH+ |
|---|---|---|---|
| 324 | 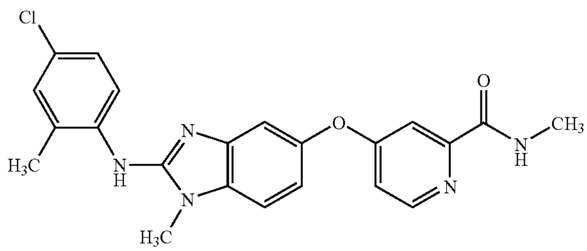 | 4-({2-[(4-chloro-2-methyl-phenyl)amino]-1-methyl-1H-benzimidazol-5-yl}oxy)-N-methylpyridine-2-carboxamide | 422.9 |
| 325 | 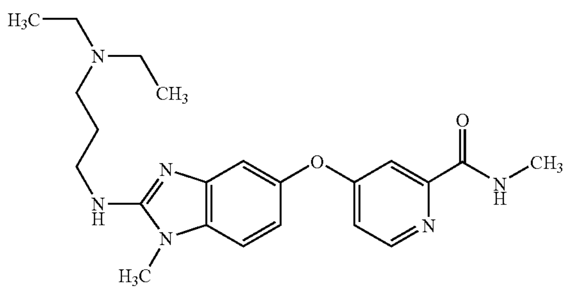 | 4-[(2-{[3-(diethylamino)-propyl]amino}-1-methyl-1H-benzimidazol-5-yl)oxy]-N-methylpyridine-2-carboxamide | 411.5 |
| 326 | 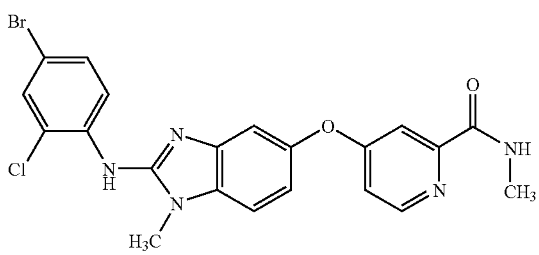 | 4-({2-[(4-bromo-2-chloro-phenyl)amino]-1-methyl-1H-benzimidazol-5-yl}oxy)-N-methylpyridine-2-carboxamide | 487.8 |
| 327 | 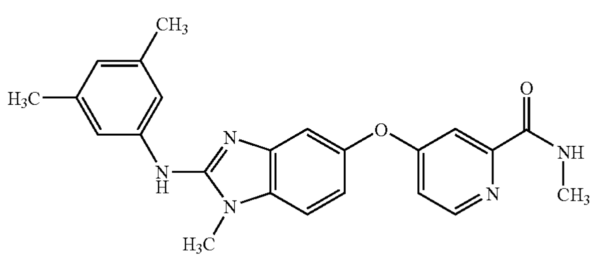 | 4-({2-[(3,5-dimethylphenyl)-amino]-1-methyl-1H-benzimidazol-5-yl}oxy)-N-methylpyridine-2-carboxamide | 402.5 |
| 328 | 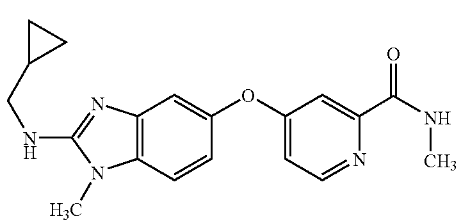 | 4-({2-[(cyclopropylmethyl)-amino]-1-methyl-1H-benzimidazol-5-yl}oxy)-N-methylpyridine-2-carboxamide | 352.4 |
| 329 | 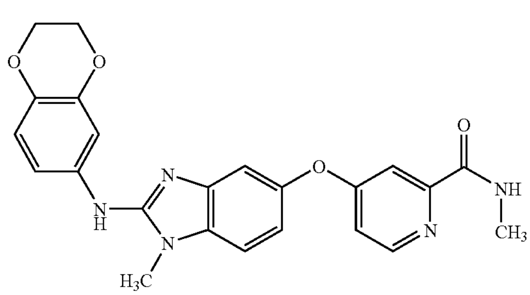 | 4-{[2-(2,3-dihydro-1,4-benzodioxin-6-ylamino)-1-methyl-1H-benzimidazol-5-yl]-oxy}-N-methylpyridine-2-carboxamide | 432.4 |

TABLE 3-continued

| Example | Structure | Name | MH+ |
|---|---|---|---|
| 330 | 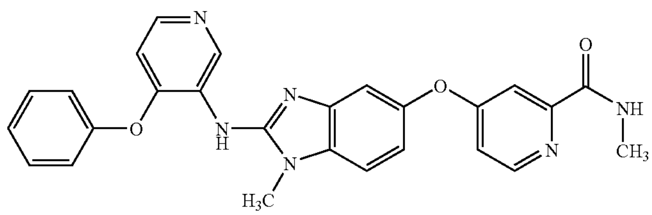 | N-methyl-4-[(1-methyl-2-{[4-(phenyloxy)pyridin-3-yl]-amino}-1H-benzimidazol-5-yl)-oxy]pyridine-2-carboxamide | 467.5 |
| 331 | 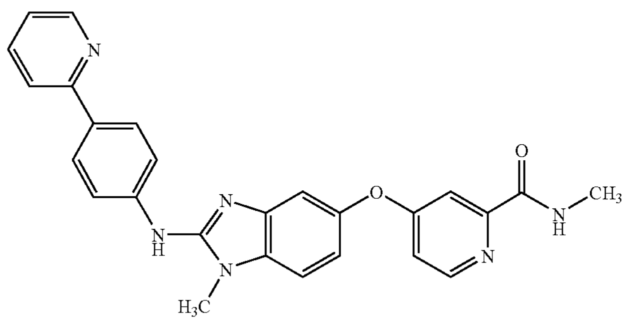 | N-methyl-4-({1-methyl-2-[(4-pyridin-2-ylphenyl)amino]-1H-benzimidazol-5-yl}oxy)pyridine-2-carboxamide | 451.5 |
| 332 | 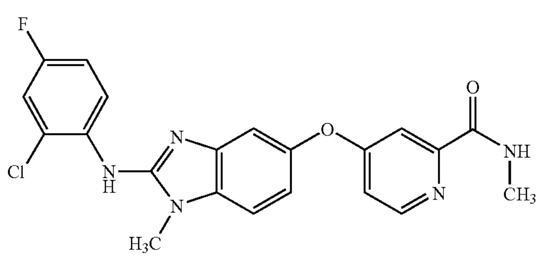 | 4-({2-[(2-chloro-4-fluoro-phenyl)amino]-1-methyl-1H-benzimidazol-5-yl}oxy)-N-methylpyridine-2-carboxamide | 426.8 |
| 333 | 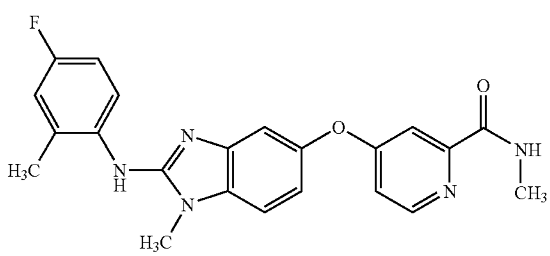 | 4-({2-[(4-fluoro-2-methyl-phenyl)amino]-1-methyl-1H-benzimidazol-5-yl}oxy)-N-methylpyridine-2-carboxamide | 406.4 |
| 334 | 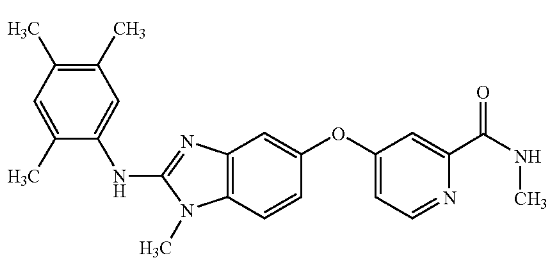 | N-methyl-4-({1-methyl-2-[(2,4,5-trimethylphenyl)amino]-1H-benzimidazol-5-yl}oxy)-pyridine-2-carboxamide | 416.5 |

TABLE 3-continued

| Example | Structure | Name | MH+ |
|---|---|---|---|
| 335 | 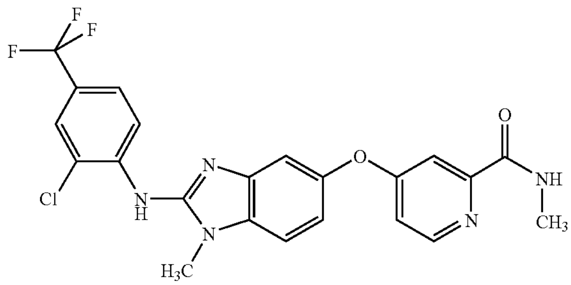 | 4-[(2-{[2-chloro-4-(trifluoro-methyl)phenyl]amino}-1-methyl-1H-benzimidazol-5-yl)-oxy]-N-methylpyridine-2-carboxamide | 476.9 |
| 336 | 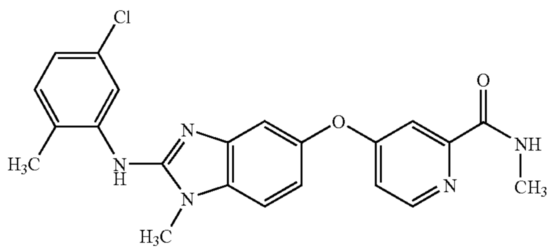 | 4-({2-[(5-chloro-2-methyl-phenyl)amino]-1-methyl-1H-benzimidazol-5-yl}oxy)-N-methylpyridine-2-carboxamide | 422.9 |
| 337 | 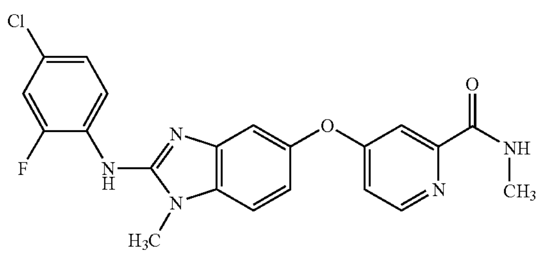 | 4-({2-[(4-chloro-2-fluoro-phenyl)amino]-1-methyl-1H-benzimidazol-5-yl}oxy)-N-methylpyridine-2-carboxamide | 426.8 |
| 338 | 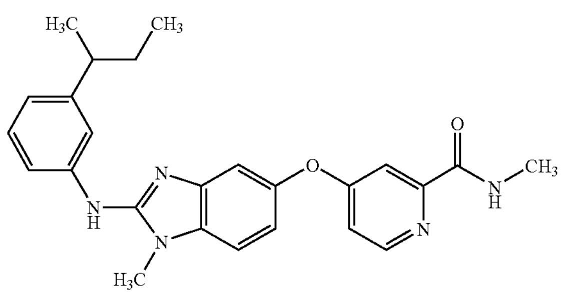 | N-methyl-4-[(1-methyl-2-{[3-(1-methylpropyl)phenyl]amino}-1H-benzimidazol-5-yl)oxy]-pyridine-2-carboxamide | 430.5 |
| 339 | 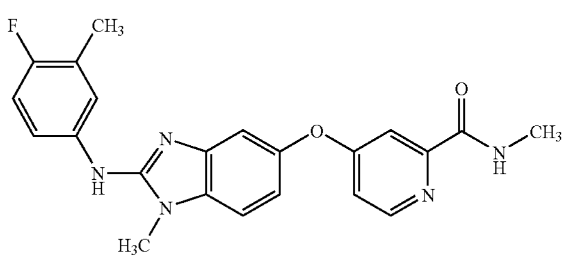 | 4-({2-[(4-fluoro-3-methyl-phenyl)amino]-1-methyl-1H-benzimidazol-5-yl}oxy)-N-methylpyridine-2-carboxamide | 406.4 |

TABLE 3-continued

| Example | Structure | Name | MH+ |
|---|---|---|---|
| 340 | 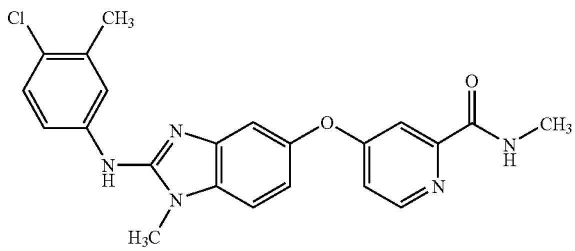 | 4-({2-[(4-chloro-3-methyl-phenyl)amino]-1-methyl-1H-benzimidazol-5-yl}oxy)-N-methylpyridine-2-carboxamide | 422.9 |
| 341 | 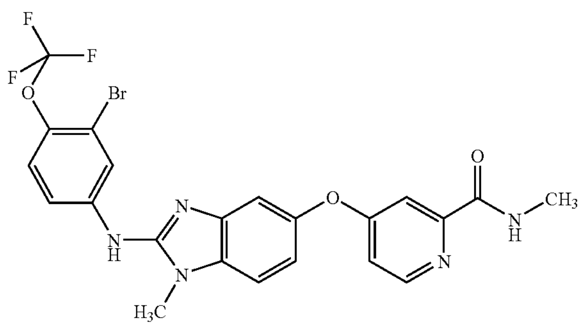 | 4-{[2-({3-bromo-4-[(trifluoro-methyl)oxy]phenyl}amino)-1-methyl-1H-benzimidazol-5-yl]oxy}-N-methylpyridine-2-carboxamide | 537.3 |
| 342 | 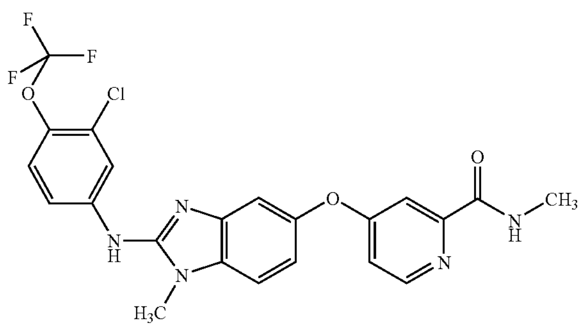 | 4-{[2-({3-chloro-4-[(trifluoro-methyl)oxy]phenyl}amino)-1-methyl-1H-benzimidazol-5-yl]-oxy}-N-methylpyridine-2-carboxamide | 492.9 |
| 343 | 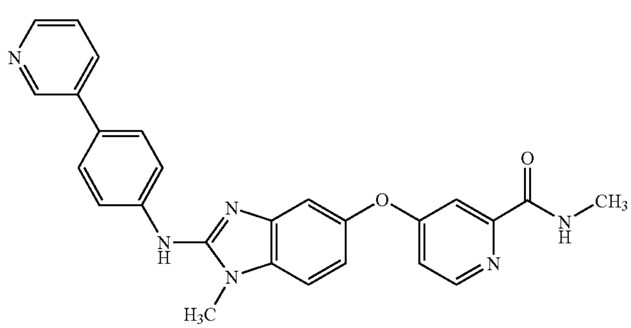 | N-methyl-4-({1-methyl-2-[(4-pyridin-3-ylphenyl)amino]-1H-benzimidazol-5-yl}oxy)pyridine-2-carboxamide | 451.5 |
| 344 | 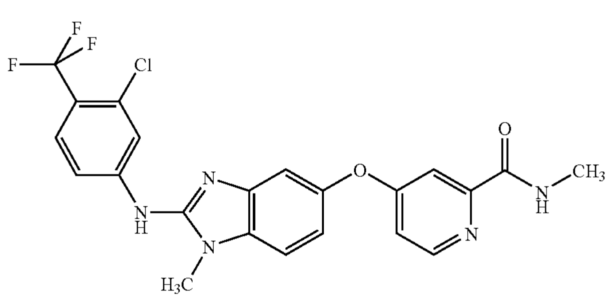 | 4-[(2-{[3-chloro-4-(trifluoro-methyl)phenyl]amino}-1-methyl-1H-benzimidazol-5-yl)-oxy]-N-methylpyridine-2-carboxamide | 476.9 |

TABLE 3-continued

| Example | Structure | Name | MH+ |
|---|---|---|---|
| 345 | 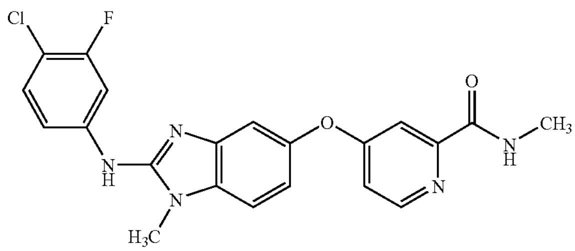 | 4-({2-[(4-chloro-3-fluoro-phenyl)amino]-1-methyl-1H-benzimidazol-5-yl}oxy)-N-methylpyridine-2-carboxamide | 426.8 |
| 346 | 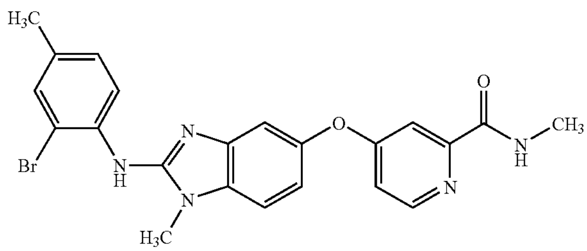 | 4-({2-[(2-bromo-4-methyl-phenyl)amino]-1-methyl-1H-benzimidazol-5-yl}oxy)-N-methylpyridine-2-carboxamide | 467.3 |
| 347 | 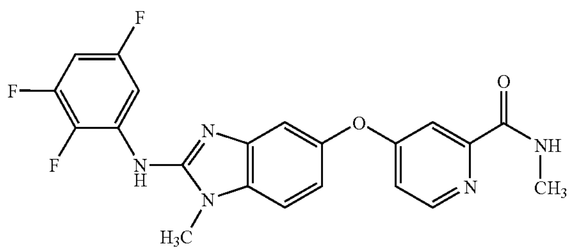 | N-methyl-4-({1-methyl-2-[(2,3,5-trifluorophenyl)amino]-1H-benzimidazol-5-yl}oxy)-pyridine-2-carboxamide | 428.4 |
| 348 | 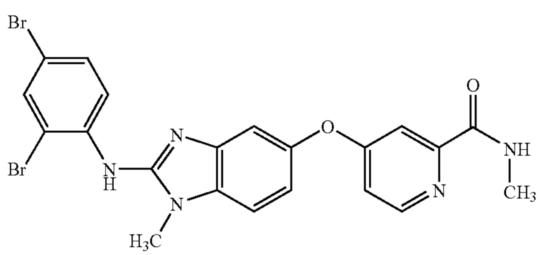 | 4-({2-[(2,4-dibromophenyl)-amino]-1-methyl-1H-benzimidazol-5-yl}oxy)-N-methylpyridine-2-carboxamide | 532.2 |
| 349 | 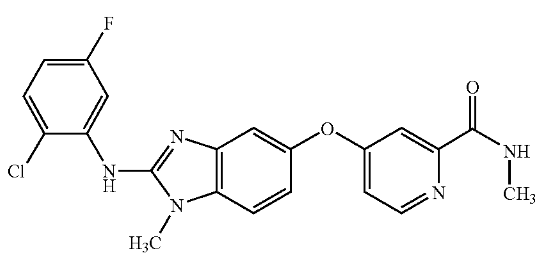 | 4-({2-[(2-chloro-5-fluoro-phenyl)amino]-1-methyl-1H-benzimidazol-5-yl}oxy)-N-methylpyridine-2-carboxamide | 426.8 |
| 350 | 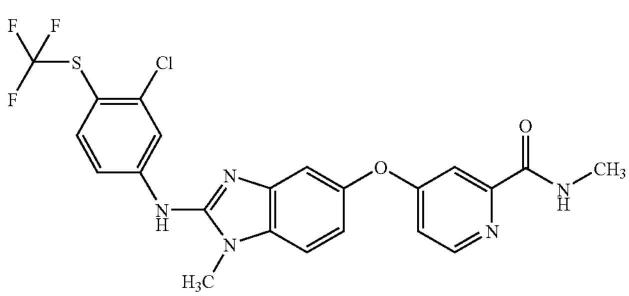 | 4-{[2-({3-chloro-4-[(trifluoro-methyl)thio]phenyl}amino)-1-methyl-1H-benzimidazol-5-yl]-oxy}-N-methypyridine-2-carboxamide | 508.9 |

TABLE 3-continued

| Example | Structure | Name | MH+ |
|---|---|---|---|
| 351 | 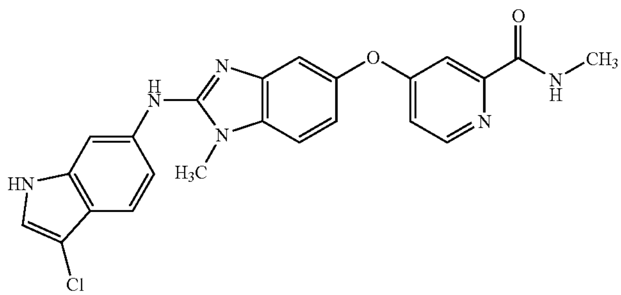 | 4-({2-[(3-chloro-1H-indol-6-yl)amino]-1-methyl-1H-benzimidazol-5-yl}oxy)-N-methylpyridine-2-carboxamide | 447.9 |
| 352 | 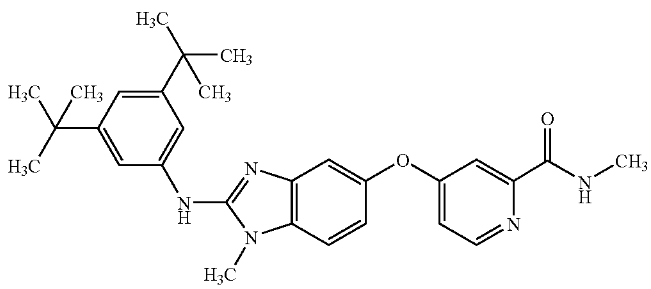 | 4-[(2-{[3,5-bis(1,1-dimethylethyl)phenyl]amino}-1-methyl-1H-benzimidazol-5-yl)oxy]-N-methylpyridine-2-carboxamide | 486.6 |
| 353 | 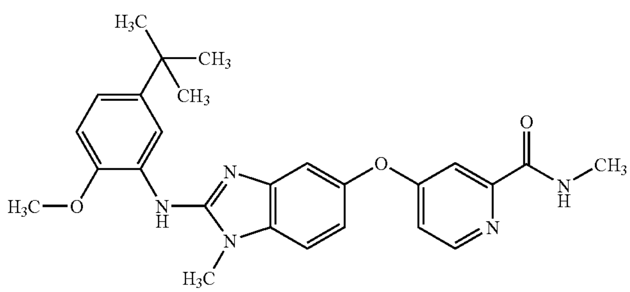 | 4-[(2-{[5-(1,1-dimethylethyl)-2-(methyloxy)phenyl]amino}-1-methyl-1H-benzimidazol-5-yl)-oxy]-N-methylpyridine-2-carboxamide | 460.5 |
| 354 | 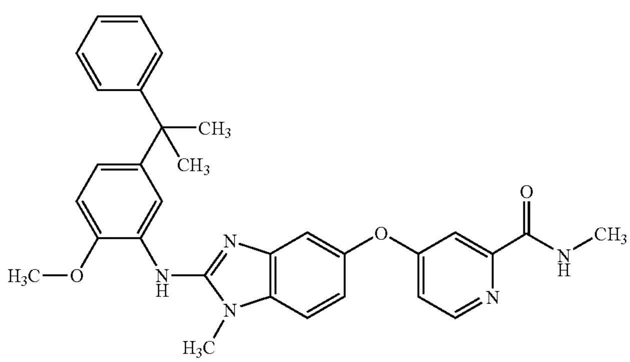 | N-methyl-4-[(1-methyl-2-{[2-(methyloxy)-5-(1-methyl-1-phenylethyl)phenyl]amino}-1H-benzimidazol-5-yl)oxy]pyridine-2-carboxamide | 522.6 |
| 355 | 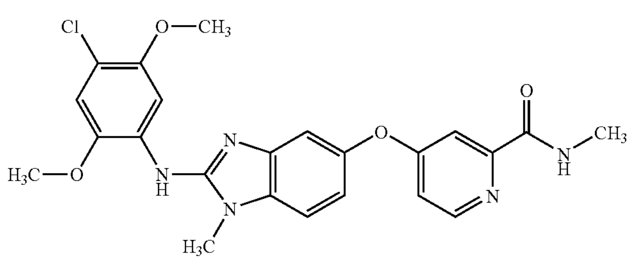 | 4-[(2-{[4-chloro-2,5-bis(methyloxy)phenyl]amino}-1-methyl-1H-benzimidazol-5-yl)oxy]-N-methylpyridine-2-carboxamide | 468.9 |

TABLE 3-continued

| Example | Structure | Name | MH+ |
|---|---|---|---|
| 356 | 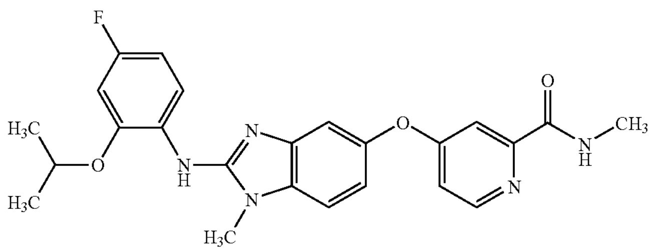 | 4-{[2-({4-fluoro-2-[(1-methyl-ethyl)oxy]phenyl}amino)-1-methyl-1H-benzimidazol-5-yl]-oxy}-N-methylpyridine-2-carboxamide | 450.5 |
| 357 | 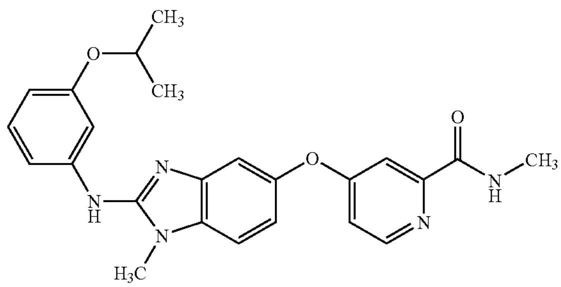 | N-methyl-4-{[1-methyl-2-({3-[(1-methylethyl)oxy]phenyl}-amino)-1H-benzimidazol-5-yl]-oxy}pyridine-2-carboxamide | 432.5 |
| 358 (synthesis as in Ex 769) | 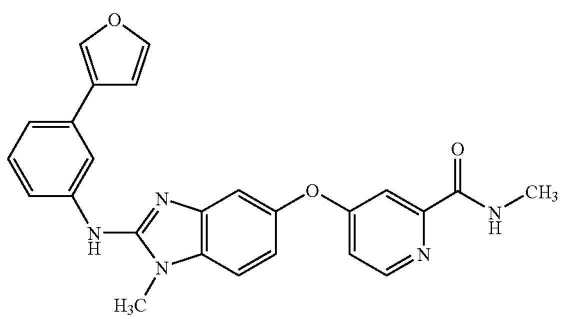 | 4-({2-[(3-furan-3-ylphenyl)-amino]-1-methyl-1H-benzimidazol-5-yl}oxy)-N-methylpyridine-2-carboxamide | 440.5 |
| 359 | 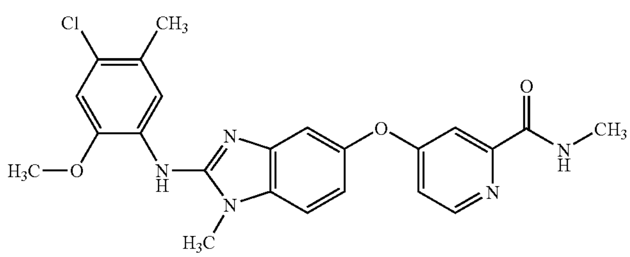 | 4-[(2-{[4-chloro-5-methyl-2-(methyloxy)phenyl]amino}-1-methyl-1H-benzimidazol-5-yl)oxy]-N-methylpyridine-2-carboxamide | 452.9 |
| 360 | 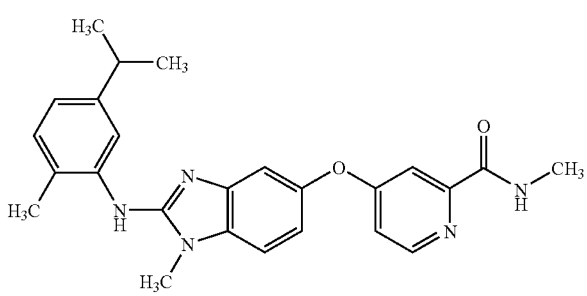 | N-methyl-4-[(1-methyl-2-{[2-methyl-5-(1-methylethyl)-phenyl]amino}-1H-benzimidazol-5-yl)oxy]pyridine-1-carboxamide | 430.5 |

TABLE 3-continued

| Example | Structure | Name | MH+ |
|---|---|---|---|
| 361 | 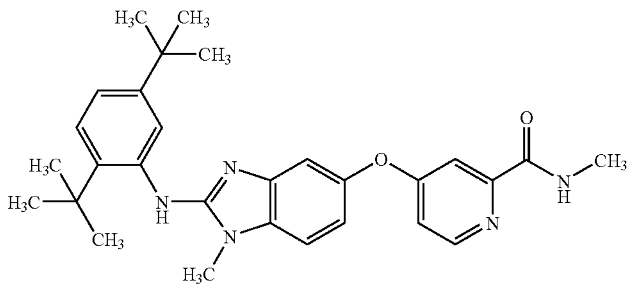 | 4-[(2-{[2,5-bis(1,1-dimethyl-ethyl)phenyl]amino}-1-methyl-1H-benzimidazol-5-yl)oxy]-N-methylpyridine-2-carboxamide | 486.6 |
| 362 | 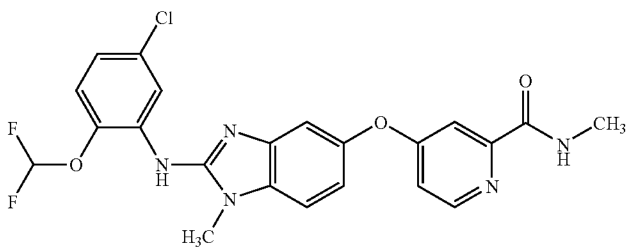 | 4-{[2-({5-chloro-2-[(difluoro-methyl)oxy]phenyl}amino)-1-methyl-1H-benzimidazol-5-yl]-oxy}-N-methylpyridine-2-carboxamide | 474.9 |
| 363 | 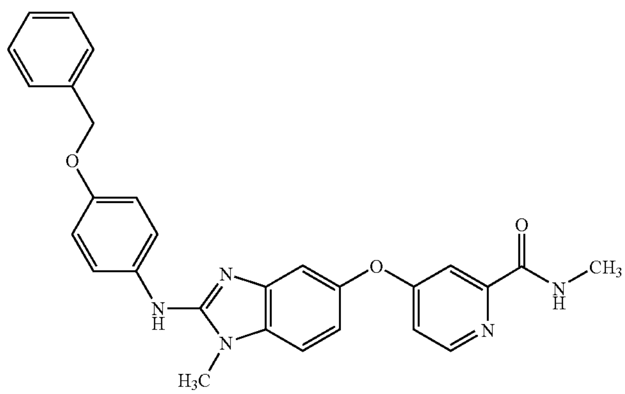 | N-methyl-4-{[1-methyl-2-({4-[(phenylmethyl)oxy]phenyl}amino)-1H-benzimidazol-5-yl]oxy}-pyridine-2-carboxamide | 480.5 |
| 364 | 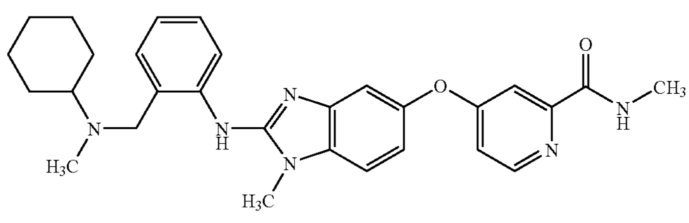 | 4-({2-[(2-{[cyclohexyl(methyl)-amino]methyl}phenyl)amino]-1-methyl-1H-benzimidazol-5-yl}-oxy)-N-methylpyridine-2-carboxamide | 499.6 |
| 365 | 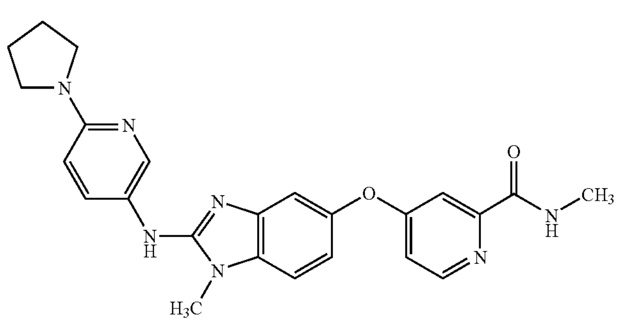 | N-methyl-4-({1-methyl-2-[(6-pyrrolidin-1-ylpyridin-3-yl)-amino]-1H-benzimidazol-5-yl}-oxy)pyridine-2-carboxamide | 444.5 |

TABLE 3-continued

| Example | Structure | Name | MH+ |
|---|---|---|---|
| 366 | 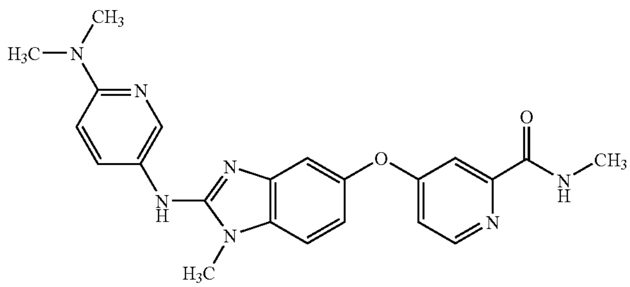 | 4-[(2-{[6-(dimethylamino)-pyridin-3-yl]amino}-1-methyl-1H-benzimidazol-5-yl)oxy]-N-methylpyridine-2-carboxamide | 418.4 |
| 367 | 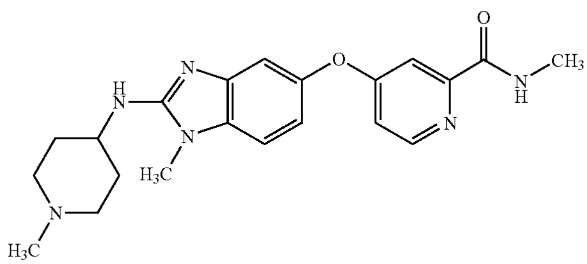 | N-methyl-4-({1-methyl-2-[(1-methylpiperidin-4-yl)amino]-1H-benzimidazol-5-yl}oxy)-pyridine-2-carboxamide | 395.4 |
| 368 | 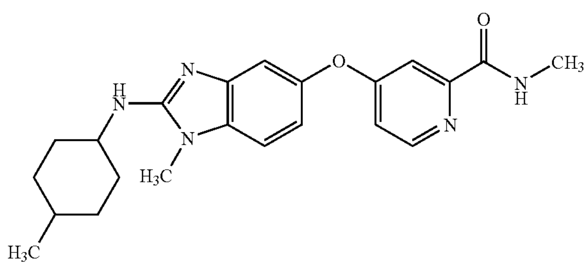 | N-methyl-4-({1-methyl-2-[(4-methylcyclohexyl)amino]-1H-benzimidazol-5-yl}oxy)pyridine-2-carboxamide | 394.4 |
| 369 | 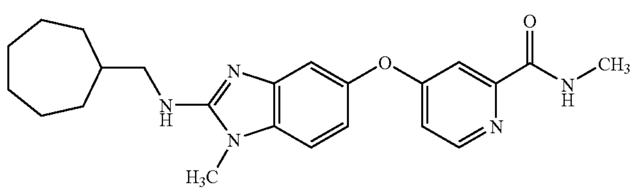 | 4-({2-[(cycloheptylmethyl)-amino]-1-methyl-1H-benzimidazol-5-yl}oxy)-N-methylpyridine-2-carboxamide | 408.5 |
| 370 | 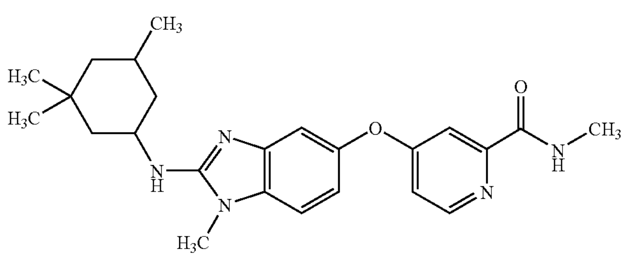 | N-methyl-4-({1-methyl-2-[(3,3,5-trimethylcyclohexyl)-amino]-1H-benzimidazol-5-yl}-oxy)pyridine-2-carboxamide | 422.5 |
| 371 | 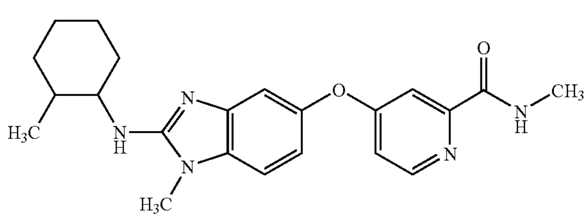 | N-methyl-4-({1-methyl-2-[(2-methylcyclohexyl)amino]-1H-benzimidazol-5-yl}oxy)pyridine-2-carboxamide | 394.4 |

Example 372

Synthesis of 4-({2-[(4-bromophenyl)amino]-1-methyl-1H-benzimidazol-5-yl}oxy)-N-ethylpyridine-2-carboxamide The compound 4-({2-[(4-bromophenyl)amino]-1-methyl-1H-benzimidazol-5-yl}oxy)-N-ethylpyridine-2-carboxamide was synthesized as follows:

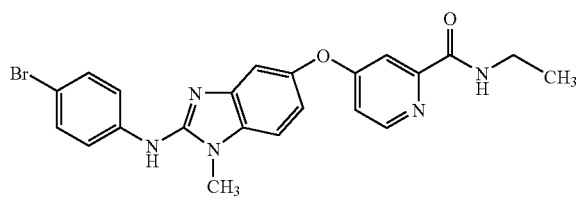

Step 1. Synthesis of tert-butyl 4-chloropyridine-2-carboxylate 4-chloropyridine-2-carbonyl chloride (1 eq) was suspended in anhydrous tetrahydrofuran. Then 2 equivalents of a solution of 1 M potassium tert-butoxide was added dropwise to the reaction slowly as the reaction was stirring under nitrogen. After 3-4 hours or when the reaction was determined to be complete by HPLC, the reaction was evaporated under reduced pressure and diluted with ethyl acetate. The organic layer was washed with water followed by brine and dried over anhydrous sodium sulfate. The organic extracts were evaporated under reduced pressure to yield the tert-butyl ester as a yellow oil. MS: MH+=214.0

Step 2. Synthesis of tert-butyl 4-(4-amino-3-nitrophenoxy)pyridine-2-carboxylate Solid anhydrous white powdered KHMDS (2 eq) was suspended in a solution of dimethylformamide. Red crystalline 4-amino-3-nitrophenol (1 eq) was charged to the rapidly stirring solution under an inert atmosphere and the heterogeneous solution was allowed to stir for 2 hours. Then a dimethylformamide solution of tert-butyl 4-chloropyridine-2-carboxylate (1 eq) was added dropwise. Anhydrous powdered potassium carbonate (1.2 eq) was charged to the reaction as an acid scavenger. The purple colored viscous mixture was heated to 80° C. for 12-15 hours until when it was determined to be complete by HPLC. The reaction was evaporated under reduced pressure and diluted with excess ethyl acetate and water. An extraction of the aqueous layer was made with ethyl acetate. The organic layers were combined and washed 4 times with water followed by brine. The organic layer was dried over anhydrous sodium sulfate and evaporated under reduced pressure. The crude material was purified by flash silica gel chromatography using an eluent of 1:1 mixture of hexanes to ethyl acetate to give the desired product. MS: MH+=332.

Step 3. Synthesis of tert-butyl 4-[3-nitro-4-(2,2,2-trifluoroacetylamino)phenoxy]pyridine-2-carboxylate Trifluoroacetic anhydride (1 eq) was slowly added dropwise to a solution of the above amine in anhydrous methylene chloride under nitrogen. After 10-15 minutes or until the reaction was complete as determined by HPLC, the reaction was quenched with excess saturated aqueous sodium bicarbonate. The product was extracted with methylene chloride from the aqueous layer and washed with water and brine. The extracts were dried over anhydrous sodium sulfate and evaporated under reduced pressure to afford the title product as a yellow solid. MS: MH+=428.

Step 4. Synthesis of tert-butyl 4-[3-nitro-4-(2,2,2-trifluoro-N-methylacetylamino)phenoxy]pyridine-2-carboxylate A solution of tert-butyl 4-[3-nitro-4-(2,2,2-trifluoroacetylamino)phenoxy]pyridine-2-carboxylate (1 eq) and sodium carbonate (4 eq) in dimethylformamide was stirred at 20° C. under nitrogen for thirty minutes before 2 equivalents of iodomethane (2 eq) was charged slowly dropwise to the reaction. After 2-3 hours or until it was determined to be complete by HPLC, the reaction was evaporated under reduced pressure. The crude mixture was diluted with ethyl acetate and washed with water. The organic layer was dried over anhydrous sodium sulfate and evaporated under reduced pressure to afford the title product as an orange solid. MS: MH+=442.

Step 5. Synthesis of tert-butyl 4-[4-(methylamino)-3-nitrophenoxy]pyridine-2-carboxylate A solution of tert-butyl 4-[3-nitro-4-(2,2,2-trifluoro-N-methylacetylamino)phenoxy]pyridine-2-carboxylate in ethanol was stirred at room temperature. 1N sodium hydroxide was slowly dropped into the reaction until the conversion was complete by HPLC. The reaction was evaporated under reduced conditions and then extracted with ethyl acetate and washed with a saturated aqueous solution of ammonium chloride followed by water and brine. The organic extracts were dried over anhydrous sodium sulfate and evaporated under reduced pressure to afford the product as an orange solid. MS: MH+=346

Step 6. Synthesis of tert-butyl 4-[3-amino-4-(methylamino)phenoxy]pyridine-2-carboxylate A solution of tert-butyl 4-[4-(methylamino)-3-nitrophenoxy]pyridine-2-carboxylate (1 eq) and 10% palladium on carbon (0.1 eq) in methanol was stirred at room temperature and flushed with nitrogen. Hydrogen was flushed through the reaction for 1-2 hours or until the reaction was determined to be complete by HPLC. Nitrogen was flushed through the reaction for 15 minutes before the reaction was filtered through a celite pad. The celite pad was washed with excess methanol followed by concentration under reduced pressure to afford the product as a light yellow solid. MS: MH+=316.

Step 7. Synthesis of tert-butyl 4-{2-[(4-bromophenyl)amino]-1-methylbenzimidazol-5-yloxy}pyridine-2-carboxylate A solution of the diamine from step 6 (1 eq) and 4-bromophenyl isothiocyanate (1 eq) in anhydrous tetrahydrofuran under nitrogen was stirred at 20° C. for 2-3 hours or when determined to be complete by HPLC. The solution was treated with 3 equivalents of 1-ethyl-(3-dimethylaminopropyl)carbodiimide HCl. The stirred solution was heated to 50° C. under nitrogen for 2-3 hrs or until the reaction is determined to be complete by HPLC. The reaction was evaporated under reduced pressure and then diluted with ethyl acetate and water. The aqueous layer was back extracted with ethyl acetate. The combined organic layers were washed with water and brine. The organic layer was dried over anhydrous sodium sulfate and later evaporated under reduced pressure. The crude material was purified by reverse high-pressure liquid chromatography to afford the product as a brown powder after lyophlization. MS: MH$^+$=495.

Step 8. Synthesis of 4-{2-[(4-bromophenyl)amino]-1-methylbenzimidazol-5-yloxy}pyridine-2-carboxylic acid A solution of the product of step 7 in trifluoroacetic acid was treated with two drops of water at room temperature for 3-4 hours or until the reaction was determined to be complete by HPLC. The reaction was evaporated under reduced pressure to afford the product as a red-orange oil in quantitative yield. MS: MH$^+$=439.

Step 9. Synthesis of 4-({2-[(4-bromophenyl)amino]-1-methyl-1H-benzimidazol-5-yl}oxy)-N-ethylpyridine-2-carboxamide A solution of above (1 eq) in anhydrous tetrahydrofuran (0.5 ml) was treated with O-benzotriazol-1-yl N,N,N',N'-tetramethyl uronium hexafluorophosphate (2 eq), excess diisopropylethyl amine, and ethyl amine (1 eq). The reaction was left stirring under nitrogen for 12-15 hours. The reaction was evaporated under reduced pressure and diluted with ethyl acetate. The ethyl acetate layer was washed once with water and then evaporated under reduced pressure. The crude material was purified by reverse high-pressure liquid chromatography and recovered as TFA salt after lyophilization. MS: MH$^+$=466.

Examples 373-447

The compounds shown in the following Table 4 (Examples 373-447) were prepared from following the procedure described for Example 372.

TABLE 4

| Example | Structure | Name | MH+ |
|---|---|---|---|
| 373 | 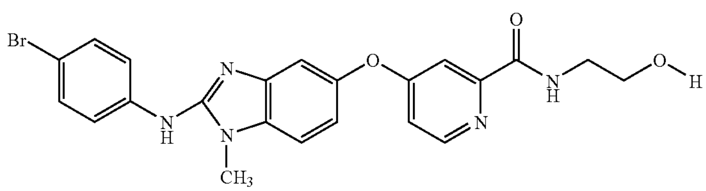 | 4-({2-[(4-bromophenyl)amino]-1-methyl-1H-benzimidazol-5-yl}-oxy)-N-(2-hydroxyethyl)pyridine-2-carboxamide | 482 |
| 374 | 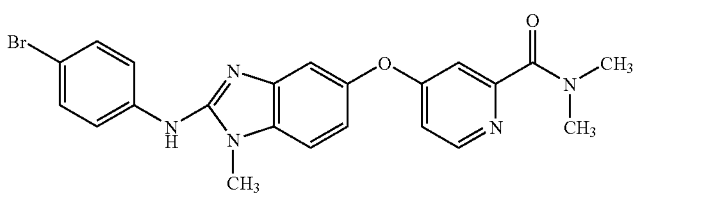 | 4-({2-[(4-bromophenyl)amino]-1-methyl-1H-benzimidazol-5-yl}-oxy)-N,N-dimethylpyridine-2-carboxamide | 466 |
| 375 | 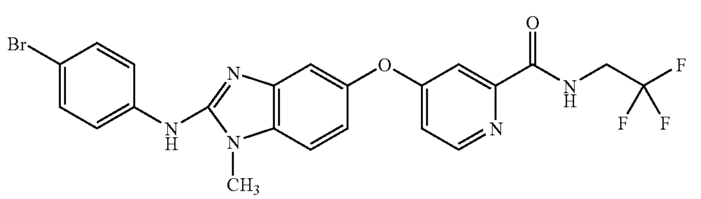 | 4-({2-[(4-bromophenyl)amino]-1-methyl-1H-benzimidazol-5-yl}-oxy)-N-(2,2,2-trifluoroethyl)-pyridine-2-carboxamide | 521 |
| 376 | 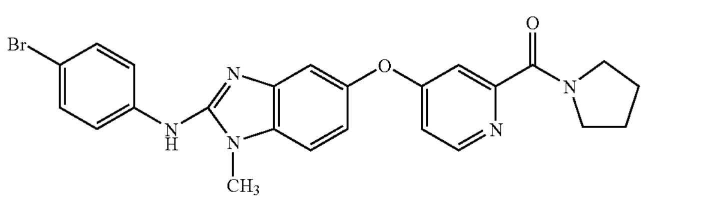 | N-(4-bromophenyl)-1-methyl-5-{[2-(pyrrolidin-1-ylcarbonyl)-pyridin-4-yl]oxy}-1H-benzimidazol-2-amine | 492 |
| 377 | 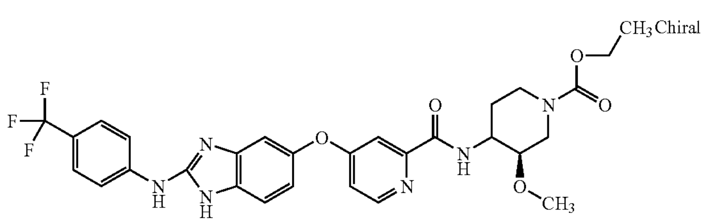 | ethyl(3R)-3-(methyloxy)-4-[({4-[(2-{[4-(trifluoromethyl)phenyl]-amino}-1H-benzimidazol-5-yl)oxy]pyridin-2-yl}carbonyl)-amino]piperidine-1-carboxylate | 599 |

TABLE 4-continued

| Example | Structure | Name | MH+ |
|---|---|---|---|
| 378 | 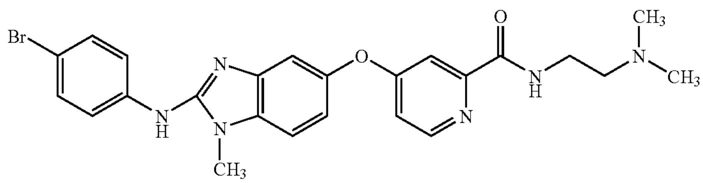 | 4-({2-[(4-bromophenyl)amino]-1-methyl-1 H-benzimidazol-5-yl}oxy)-N-[2-(dimethylamino)-ethyl]pyridine-2-carboxamide | 509 |
| 379 | 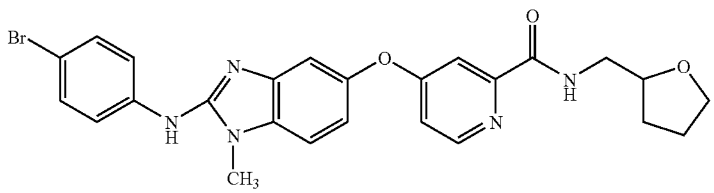 | 4-({2-[(4-bromophenyl)amino]-1-methyl-1 H-benzimidazol-5-yl}-oxy)-N-(tetrahydrofuran-2-yl-methyl)pyridine-2-carboxamide | 522 |
| 380 | 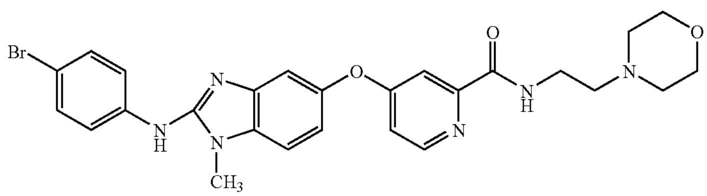 | 4-({2-[(4-bromophenyl)amino]-1-methyl-1 H-benzimidazol-5-yl}-oxy)-N-(2-morpholin-4-ylethyl)-pyridine-2-carboxamide | 551 |
| 381 | 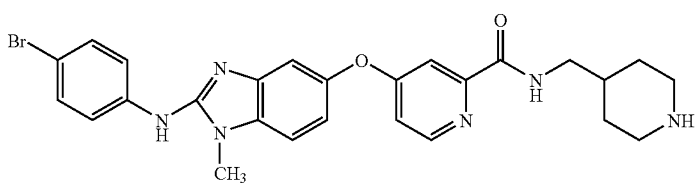 | 4-({2-[(4-bromophenyl)amino]-1-methyl-1 H-benzimidazol-5-yl}-oxy)-N-(piperidin-4-ylmethyl)-pyridine-2-carboxamide | 535 |
| 382 | 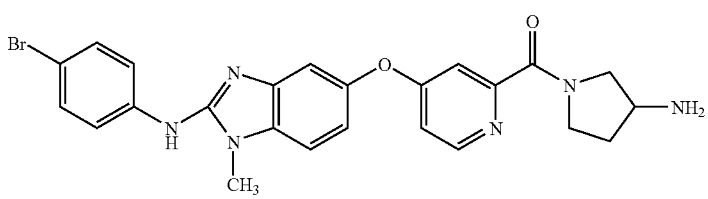 | 5-({2-[(3-aminopyrrolidin-1-yl)-carbonyl]pyridin-4-yl}oxy)-N-(4-bromophenyl)-1-methyl-1 H-benzimidazol-2-amine | 507 |
| 383 | 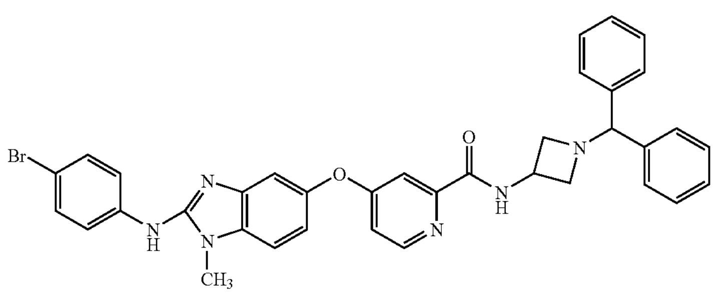 | 4-({2-[(4-bromophenyl)amino]-1-methyl-1 H-benzimidazol-5-yl}-oxy)-N-[1-diphenylmethyl)-azetidin-3-yl]pyridine-2-carboxamide | 659 |
| 384 | Chiral | N-((3S)pyrrolidin-3-yl)(4-{2-[(4-bromophenyl)amino]-1-methyl-benzimidazol-5-yloxy}(2-pyridyl)carboxamide | 507.0 |

TABLE 4-continued

| Example | Structure | Name | MH+ |
|---|---|---|---|
| 385 | 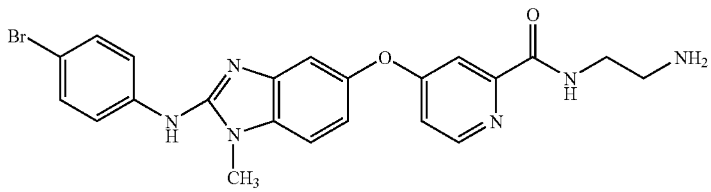 | N-(2-aminoethyl)(4-{2-[(4-bromo-phenyl)amino]-1-methyl-benzimidazol-5-yloxy}(2-pyridyl))carboxamide | 481.0 |
| 386 | Chiral | N-((3R)pyrrolidin-3-yl)(4-{2-[(4-bromophenyl)amino]-1-methyl-benzimidazol-5-yloxy}(2-pyridyl))carboxamide | 507.0 |
| 387 | 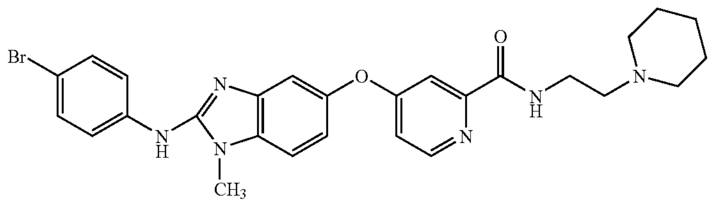 | (4-{2-[(4-bromophenyl)amino]-1-methylbenzimidazol-5-yloxy}(2-pyridyl))-N-(2-piperidylethyl)-carboxamide | 549.1 |
| 388 | 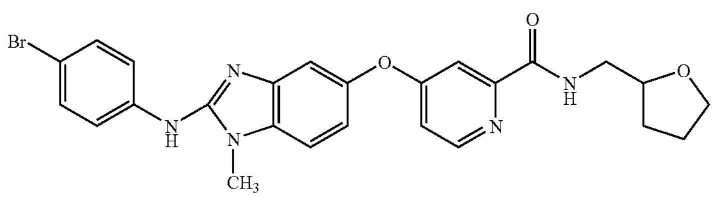 | (4-{2-[(4-bromophenyl)amino]-1-methylbenzimidazol-5-yloxy}(2-pyridyl))-N-(oxolan-2-ylmethyl)-carboxamide | 522.0 |
| 389 | 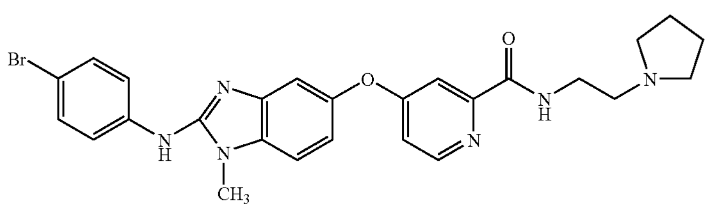 | (4-{2-[(4-bromophenyl)amino]-1-methylbenzimidazol-5-yloxy}(2-pyridyl))-N-(2-pyrrolidinylethyl)-carboxamide | 535.1 |
| 390 | 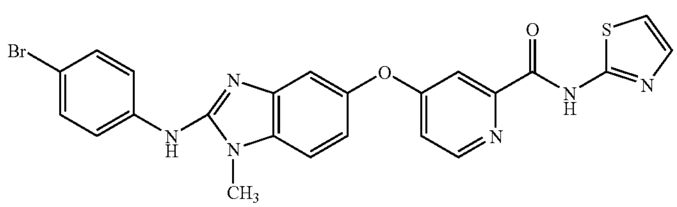 | (4-{2-[(4-bromophenyl)amino]-1-methylbenzimidazol-5-yloxy}(2-pyridyl))-N-(1,3-thiazol-2-yl)-carboxamide | 521.0 |
| 391 | 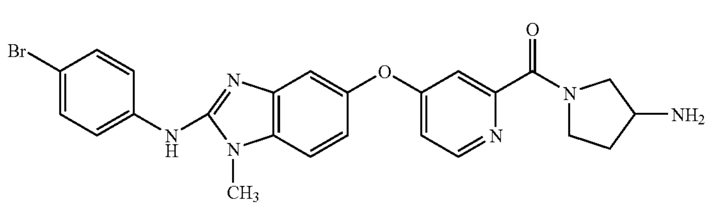 | 3-aminopyrrolidinyl 4-{2-[(4-bromophenyl)amino]-1-methyl-benzimidazol-5-yloxy}(2-pyridyl) ketone | 507.0 |

TABLE 4-continued

| Example | Structure | Name | MH+ |
|---|---|---|---|
| 392 | Chiral | N-[(3R,5R)-5-(methoxymethyl)-pyrrolidin-3-yl](4-{2-[(4-bromo-phenyl)amino]-1-methyl-benzimidazol-5-yloxy}(2-pyridyl))carboxamide | 551.1 |
| 393 | 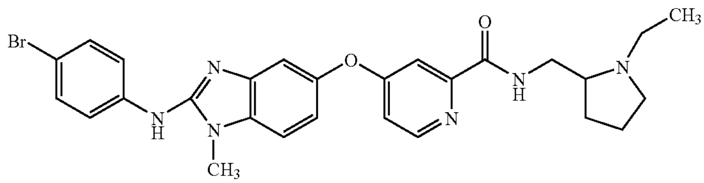 | (4-{2-[(4-bromophenyl)amino]-1-methylbenzimidazol-5-yloxy}(2-pyridyl))-N-[(1-ethylpyrrolidin-2-yl)methyl]carboxamide | 549.2 |
| 394 | 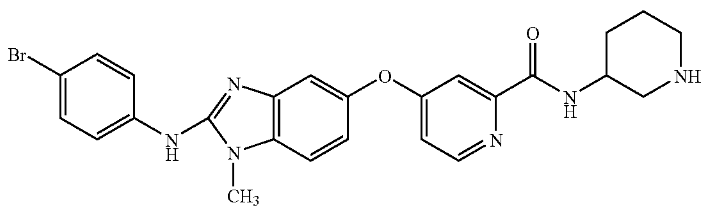 | (4-{2-[(4-bromophenyl)amino]-1-methylbenzimidazol-5-yloxy}(2-pyridyl))-N-(3-piperidyl)-carboxamide | 521.0 |
| 395 | 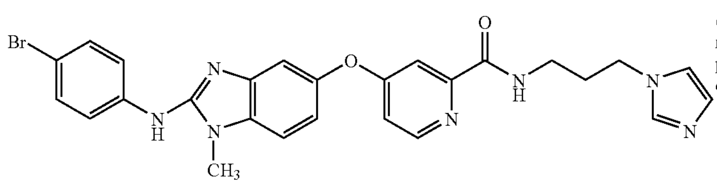 | (4-{2-[(4-bromophenyl)amino]-1-methylbenzimidazol-5-yloxy}(2-pyridyl))-N-(3-imidazolylpropyl)-carboxamide | 546.4 |
| 396 | 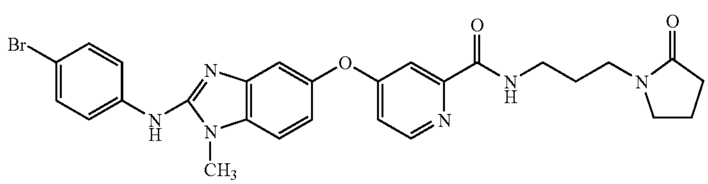 | (4-{2-[(4-bromophenyl)amino]-1-methylbenzimidazol-5-yloxy}(2-pyridyl))-N-[3-(2-oxo-pyrrolidinyl)propyl]carboxamide | 563.4 |
| 397 | 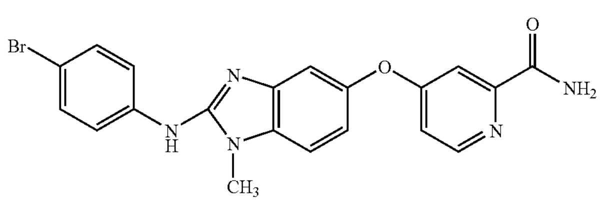 | 4-{2-[(4-bromophenyl)amino]-1-methylbenzimidazol-5-yloxy}-pyridine-2-carboxamide | 438.1 |
| 398 | 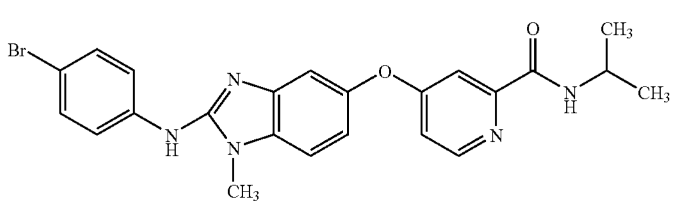 | (4-{2-[(4-bromophenyl)amino]-1-methylbenzimidazol-5-yloxy}(2-pyridyl))-N-(methylethyl)-carboxamide | 480.3 |

TABLE 4-continued

| Example | Name | MH+ |
|---|---|---|
| 399 | (4-{2-[(4-bromophenyl)amino]-1-methylbenzimidazol-5-yloxy}(2-pyridyl))-N-(4-hydroxy-cyclohexyl)carboxamide | 536.4 |
| 400 | (4-{2-[(4-bromophenyl)amino]-1-methylbenzimidazol-5-yloxy}(2-pyridyl))-N-(2-methoxyethyl)-carboxamide | 496.3 |
| 401 | N-(2 h-benzo[d]1,3-dioxolen-5-ylmethyl)(4-{2-[(4-bromophenyl)-amino]-1-methylbenzimidazol-5-yloxy}(2-pyridyl))carboxamide | 572.4 |
| 402 | (4-{2-[(4-bromophenyl)amino]-1-methylbenzimidazol-5-yloxy}(2-pyridyl))-N-(4-pyridylmethyl)-carboxamide | 529.3 |
| 403 | (4-{2-[(4-bromophenyl)amino]-1-methylbenzimidazol-5-yloxy}(2-pyridyl))-N-(2-(4-pyridyl)ethyl)-carboxamide | 543.4 |
| 404 | (4-{2-[(4-bromophenyl)amino]-1-methylbenzimidazol-5-yloxy}(2-pyridyl))-N-[3-(4-methyl-piperazinyl)propyl]carboxamide | 578.5 |
| 405 | 4-{2-[(4-bromophenyl)amino]-1-methylbenzimidazol-5-yloxy}(2-pyridyl) 4-(2-oxyethyl)piperazinyl ketone | 551.4 |
| 406 | (4-{2-[(4-bromophenyl)amino]-1-methylbenzimidazol-5-yloxy}(2-pyridyl))-N-(2-imidazol-4-ylethyl)carboxamide | 532.4 |

TABLE 4-continued

| Example | Structure | Name | MH+ |
|---|---|---|---|
| 407 | 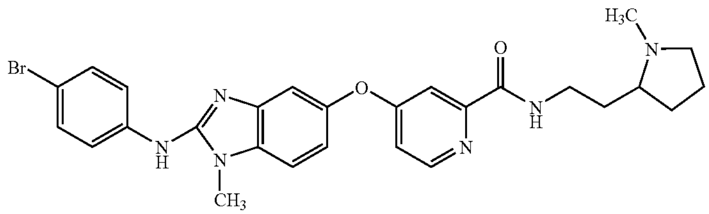 | (4-{2-[(4-bromophenyl)amino]-1-methylbenzimidazol-5-yloxy}(2-pyridyl))-N-[2-(1-methyl-pyrrolidin-2-yl)ethyl]carboxamide | 549.1 |
| 408 | 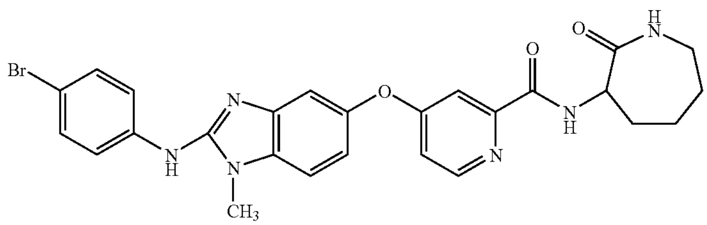 | (4-{2-[(4-bromophenyl)amino]-1-methylbenzimidazol-5-yloxy}(2-pyridyl))-N-(2-oxoazaperhydro-epin-3-yl)carboxamide | 549.1 |
| 409 | 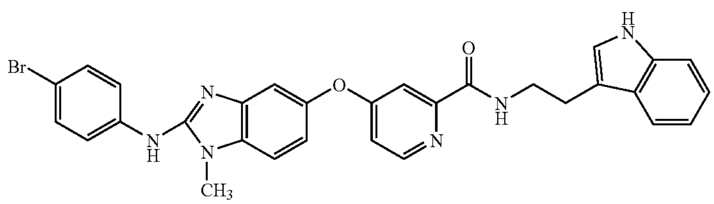 | (4-{2-[(4-bromophenyl)amino]-1-methylbenzimidazol-5-yloxy}(2-pyridyl))-N-(2-indol-3-ylethyl)-carboxamide | 581.4 |
| 410 | 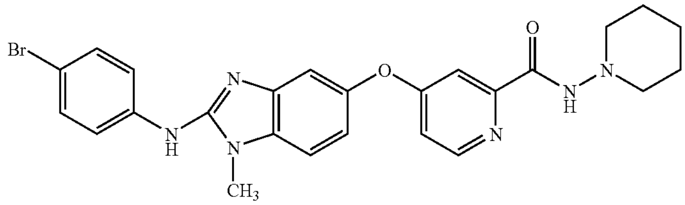 | (4-{2-[(4-bromophenyl)amino]-1-methylbenzimidazol-5-yloxy}(2-pyridyl))-N-piperidylcarboxamide | 521.1 |
| 411 | 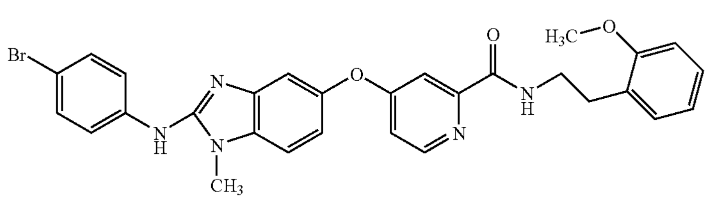 | (4-{2-[(4-bromophenyl)amino]-1-methylbenzimidazol-5-yloxy}(2-pyridyl))-N-[2-(2-methoxyphenyl)-ethyl]carboxamide | 572.1 |
| 412 | 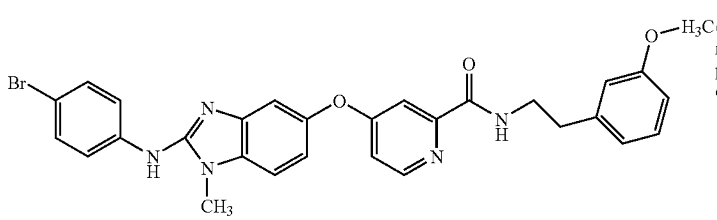 | (4-{2-[(4-bromophenyl)amino]-1-methylbenzimidazol-5-yloxy}(2-pyridyl))-N-[2-(3-methoxyphenyl)-ethyl]carboxamide | 572.4 |
| 413 | 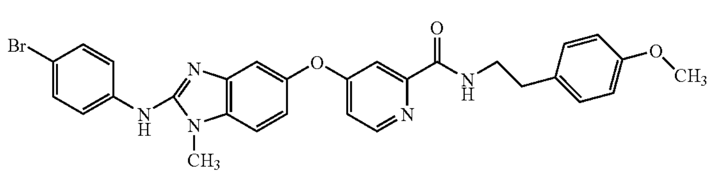 | (4-{2-[(4-bromophenyl)amino]-1-methylbenzimidazol-5-yloxy}(2-pyridyl))-N-[2-(4-methoxyphenyl)-ethyl]carboxamide | 572.4 |

TABLE 4-continued

| Example | Structure | Name | MH+ |
|---|---|---|---|
| 414 | 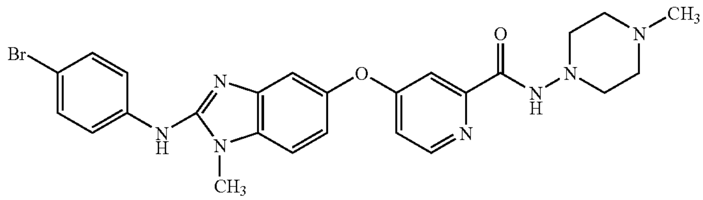 | (4-{2-[(4-bromophenyl)amino]-1-methylbenzimidazol-5-yloxy}(2-pyridyl))-N-(4-methylpiperazinyl)-carboxamide | 536.1 |
| 415 | 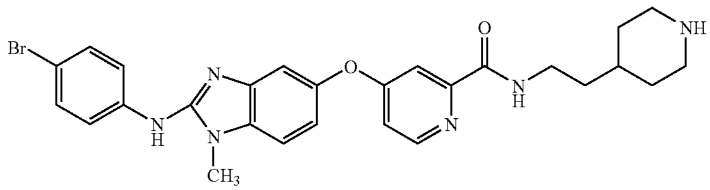 | (4-{2-[(4-bromophenyl)amino]-1-methylbenzimidazol-5-yloxy}(2-pyridyl))-N-(2-(4-piperidyl)ethyl)-carboxamide | 549.4 |
| 416 | 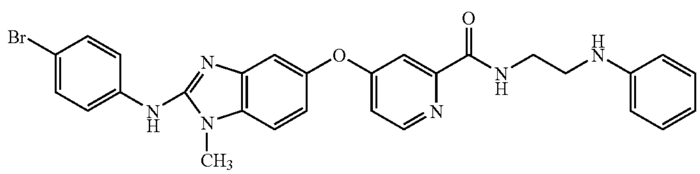 | (4-{2-[(4-bromophenyl)amino]-1-methylbenzimidazol-5-yloxy}(2-pyridyl))-N-(2-(phenylamino)-ethyl]carboxamide | 557.4 |
| 417 | 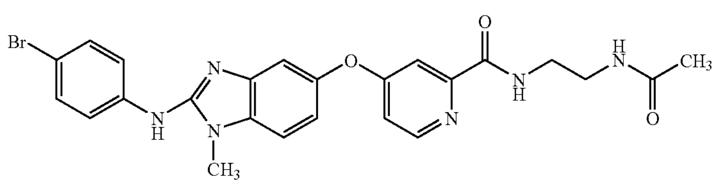 | N-{2-[(4-{2-[(4-bromophenyl)-amino]-1-methylbenzimidazol-5-yloxy}-2-pyridyl)carbonylamino]-ethyl}acetamide | 523.4 |
| 418 | 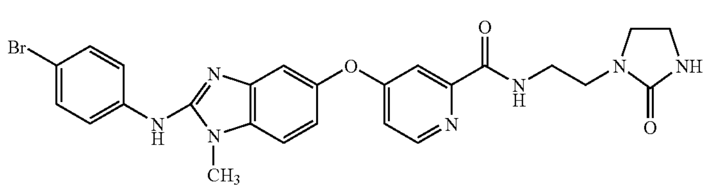 | (4-{2-[(4-bromophenyl)amino]-1-methylbenzimidazol-5-yloxy}(2-pyridyl))-N-[2-(2-oxo-imidazolidinyl)ethyl]carboxamide | 550.4 |
| 419 | 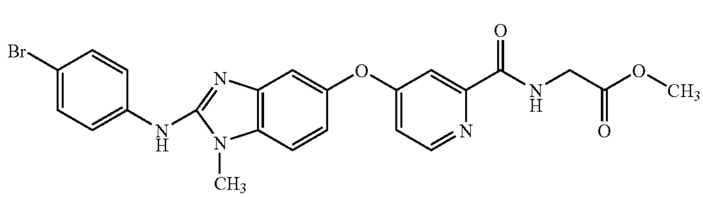 | methyl 2-[(4-{2-[(4-bromophenyl)-amino]-1-methylbenzimidazol-5-yloxy}-2-pyridyl)carbonylamino]-acetate | 510.3 |
| 420 | Chiral | methyl (2S)-2-[(4-{2-[(4-bromo-phenyl)amino]-1-methyl-benzimidazol-5-yloxy}(2-pyridyl))carbonylamino]-3-methylbutanoate | 552.4 |

TABLE 4-continued

| Example | Name | MH+ |
|---|---|---|
| 421 | Chiral (2S)-2-[(4-{2-[(4-bromophenyl)amino]-1-methyl-benzimidazol-5-yloxy}(2-pyridyl))carbonylamino]-3-carbamoylpropanoic acid | 553.3 |
| 422 | methyl 3-[(4-{2-[(4-bromophenyl)amino]-1-methyl-benzimidazol-5-yloxy}-2-pyridyl)-carbonylamino]propanoate | 524.3 |
| 423 | Chiral N-((2S)-2-aminopropyl)(4-{2-[(4-bromophenyl)amino]-1-methyl-benzimidazol-5-yloxy}(2-pyridyl))carboxamide | 495.3 |
| 424 | Chiral N-((2R)-2-aminopropyl)(4-{2-[(4-bromophenyl)amino]-1-methyl-benzimidazol-5-yloxy}(2-pyridyl))carboxamide | 495.3 |
| 425 | (4-{2-[(4-bromophenyl)amino]-1-methylbenzimidazol-5-yloxy}(2-pyridyl))-N-(pyrrolidin-2-ylmethyl)carboxamide | 521.4 |
| 426 | (4-{2-[(4-bromophenyl)amino]-1-methylbenzimidazol-5-yloxy}(2-pyridyl))-N-propylcarboxamide | 480.3 |
| 427 | (4-{2-[(4-bromophenyl)amino]-1-methylbenzimidazol-6-yloxy}(2-pyridyl))-N-methylcarboxamide | 452.1 |

TABLE 4-continued

| Example | Structure | Name | MH+ |
|---|---|---|---|
| 428 | 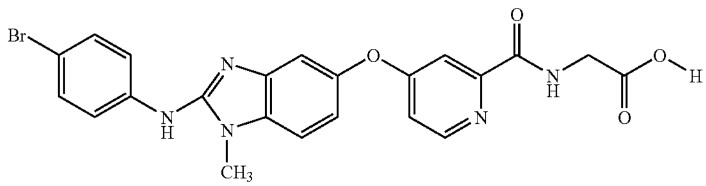 | 2-[(4-{2-[(4-bromophenyl)amino]-1-methylbenzimidazol-5-yloxy}(2-pyridyl)carbonylamino]acetic acid | 496.31 |
| 429 | Chiral | (2S)-2-[(4-{2-[(4-bromophenyl)-amino]-1-methylbenzimidazol-5-yloxy}(2-pyridyl))carbonylamino]-3-methylbutanoic acid | 538.1 |
| 430 | 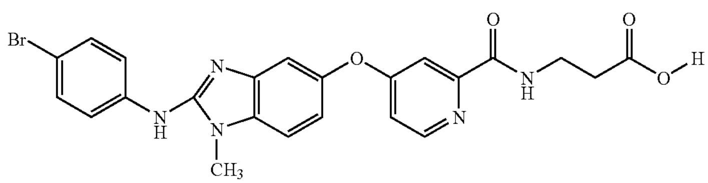 | 3-[(4-{2-[(4-bromophenyl)amino]-1-methylbenzimidazol-5-yloxy}-2-pyridyl)carbonylamino]propanoic acid | 510.1 |
| 431 | 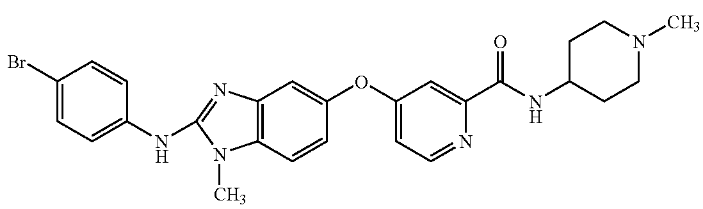 | (4-{2-[(4-bromophenyl)amino]-1-methylbenzimidazol-5-yloxy}(2-pyridyl))-N-[1-methyl(4-piperidyl))carboxamide | 535.1 |
| 432 | 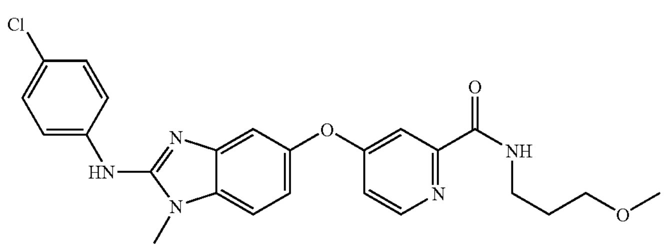 | (4-{2-[(4-chlorophenyl)amino]-1-methylbenzimidazol-5-yloxy}(2-pyridyl))-N-[3-methoxypropyl]-carboxamide | 466.1 |
| 433 | 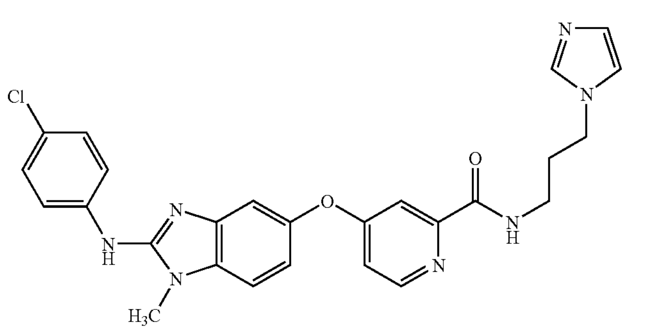 | (4-{2-[(4-chlorophenyl)amino]-1-methylbenzimidazol-5-yloxy}(2-pyridyl))-N-[3-imidazolylpropyl]-carboxamide | 502.1 |

TABLE 4-continued

| Example | Structure | Name | MH+ |
|---|---|---|---|
| 434 | 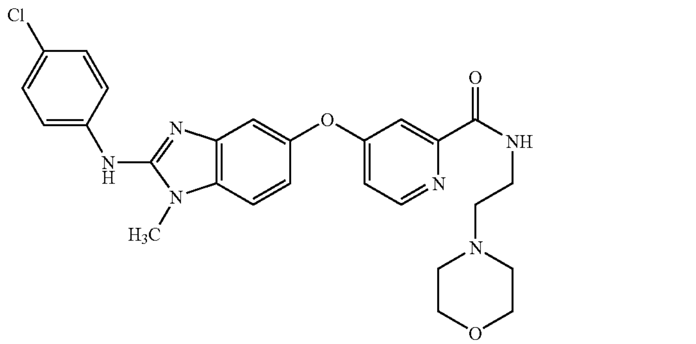 | (4-{2-[(4-chlorophenyl)amino]-1-methylbenzimidazol-5-yloxy}(2-pyridyl))-N-(2-morpholin-4-yl-ethyl)carboxamide | 507.2 |
| 435 | 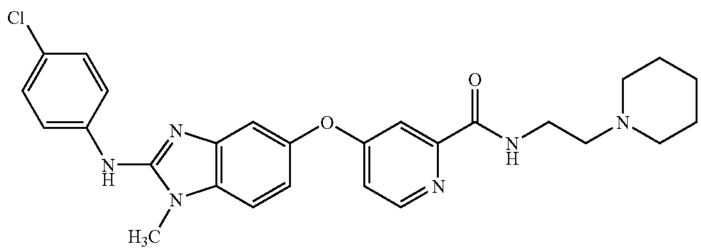 | (4-{2-[(4-chlorophenyl)amino]-1-methylbenzimidazol-5-yloxy}(2-pyridyl))-N-(2-piperidylethyl)-carboxamide | 505.2 |
| 436 | 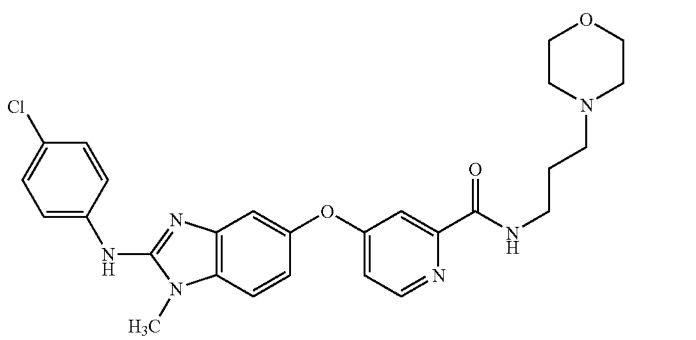 | (4-{2-[(4-chlorophenyl)amino]-1-methylbenzimidazol-5-yloxy}(2-pyridyl))-N-(3-morpholin-4-yl-propyl)carboxamide | 521.2 |
| 437 | 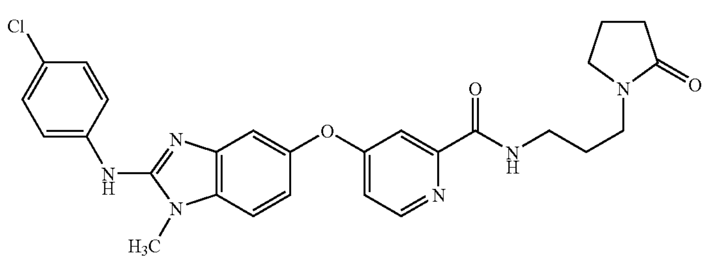 | (4-{2-[(4-chlorophenyl)amino]-1-methylbenzimidazol-5-yloxy}(2-pyridyl))-N-[3-(2-oxo-pyrrolidinyl)propyl]carboxamide | 519.2 |
| 438 | 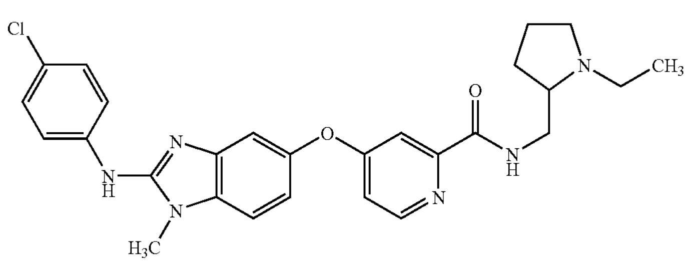 | (4-{2-[(4-chlorophenyl)amino]-1-methylbenzimidazol-5-yloxy}(2-pyridyl))-N-[(1-ethylpyrrolidin-2-yl)methyl]carboxamide | 505.2 |

TABLE 4-continued

| Example | Structure | Name | MH+ |
|---|---|---|---|
| 439 | Chiral | N-((3R)pyrrolidin-3-yl)(4-{2-[(4-chlorophenyl)amino]-1-methyl-benzimidazol-5-yloxy}(2-pyridyl))carboxamide | 463.2 |
| 440 | 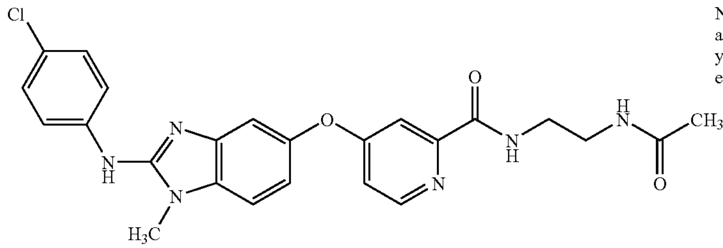 | N-{2-[(4-{2-[(4-chlorophenyl)-amino]-1-methylbenzimidazol-5-yloxy}-2-pyridyl)carbonylamino]-ethyl}acetamide | 479.2 |
| 441 | 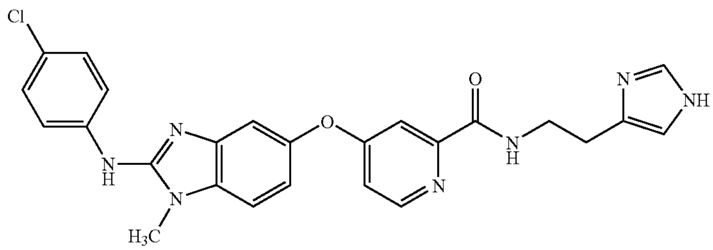 | (4-{2-[(4-chlorophenyl)amino]-1-methylbenzimidazol-5-yloxy}(2-pyridyl))-N-(2-imidazol-4-yl-ethyl)carboxamide | 488.2 |
| 442 | 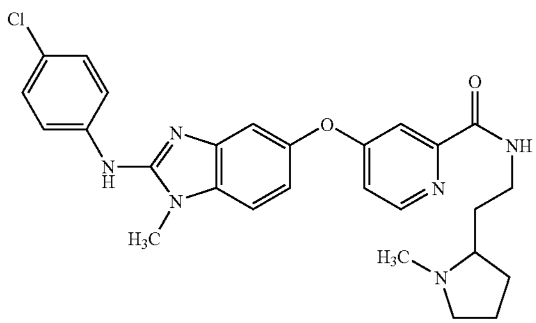 | (4-{2-[(4-chlorophenyl)amino]-1-methylbenzimidazol-5-yloxy}(2-pyridyl))-N-[2-(1-methyl-pyrrolidin-2-yl)ethyl]carboxamide | 505.2 |
| 443 | Chiral | N-[(3R,5R)-5-(methoxymethyl)-pyrrolidin-3-yl](4-{2-[(4-chloro-phenyl)amino]-1-methyl-benzimidazol-5-yloxy}(2-pyridyl))carboxamide | 507.2 |

TABLE 4-continued

| Example | Structure | Name | MH+ |
|---|---|---|---|
| 444 | Chiral | (2S)-2-[(4-{2-[{4-chlorophenyl)-amino]-1-methylbenzimidazol-5-yloxy}(2-pyridyl))carbonylamino]-propanoic acid | 466.1 |
| 445 | 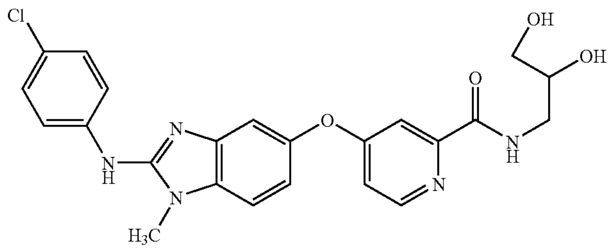 | N-(2,3-dihydroxypropyl)(4-{2-[(4-chlorophenyl)amino]-1-methyl-benzimidazol-5-yloxy}(2-pyridyl))carboxamide | 468.1 |
| 446 | Chiral | N-((3S)pyrrolidin-3-yl)(4-{2-[(4-chlorophenyl)amino]-1-methyl-benzimidazol-5-yloxy}(2-pyridyl))carboxamide | 463.2 |
| 447 (synthesis as in Ex 120a) | 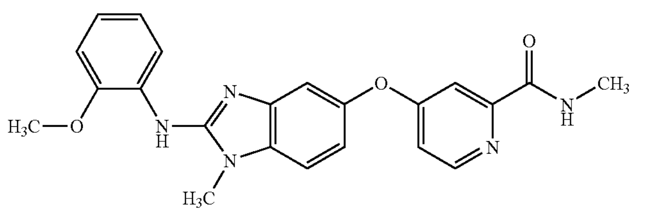 | (4-{2-[(2-methoxyphenyl)amino]-1-methylbenzimidazol-5-yloxy}(2-pyridyl))-N-methylcarboxamide | 404.1 |
| 448 (synthesis as in Ex 483) | | 4-[(2-{[3-(2-fluoropyridin-4-yl)-4-methylphenyl]amino}-1-methyl-1H-benzimidazol-5-yl)oxy]-N-[2-(4-methylpiperazin-1-yl)ethyl]-pyridine-2-carboxamide | 595.7 |
| 448 (synthesis as in Ex 483) | | 4-[(2-{[3-(2-fluoropyridin-4-yl)-4-methylphenyl]amino}-1-methyl-1H-benzimidazol-5-yl)oxy]-N-(2-pyrrolidin-1-ylethyl)pyridine-2-carboxamide | 566.7 |

Example 450

Preparation of (4-Chloro-phenyl)-{5-[2-(4,5-dihydro-1H-imidazol-2-yl)-1-pyridin-4-yloxy]-1-methyl-1H-benzoimidazol-2-yl}-amine)

Step 1. Synthesis of 4-(4-Amino-3-nitro-phenoxy)=puridine-2-carbonitrile

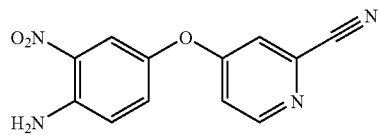

Potassium carbonate (9.00 g) was dried in vacuo with heating, cooled to RT under nitrogen. 4-amino-3-nitrophenol (3.355 g), 4-chloro-2-cyanopyridine (3.60 g) and DMSAO (30 mL, anhydrous) were added. The system was stirred under nitrogen as it was heated to 103° C., and held at this temperature 1 hr. The reaction was then cooled to RT, poured onto ice/H₂O (500 mL) the precipitate was collected, washed (H₂O), dissolved (EtOAc), dried (Na₂SO₄), filtered and stripped to a solid. This was suspended (Et₂O), collected, air-dried 4.1015 g (73.5%) a second crop was collected (0.5467 gm, 10%). M/z=257 (M+1)

Step 2. Synthesis of N-[4-(2-Cyano-pyridin-4-yloxy)-2-nitro-phenyl]-2,2,2-trifluoro-N-methyl-acetamide

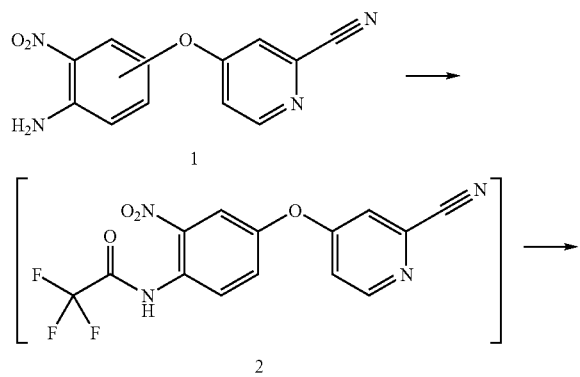

-continued

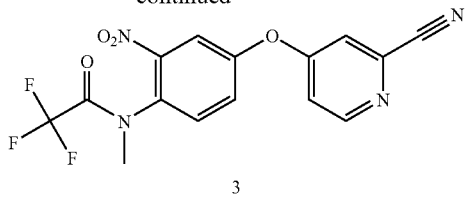

Potassium carbonate (1.6 g) was dried in vacuo with heating, cooled to RT and suspended in dichloromethane (30 mL) with 4-(4-amino-3-nitro-phenoxy)=puridine-2-carbonitrile (2.005 gm) under nitrogen. This was cooled to 0° C. and TFAA (2.2 mL) was added, neat. The starting material goes into solution rapidly as addition is made. After 10 min at 0° C., the mixture was diluted with dichloromethane, washed (H₂O, aq NaCl), dried (K₂CO₃), filtered and stripped to a yellow foam. M/z=353 (M+1) The product was used without purification.

Iodomethane (0.53 mL) was added to a suspension of potassium carbonate (1.858 g) in DMF (30 mL containing compound 2 (~7.8 mmole) under nitrogen. The suspension stirred at RT overnight, then poured onto H₂O (300 mL), extracted (Et₂O, 3×150 mL), the combined extracts were washed (H₂O, aq. NaCl), dried (potassium carbonate), filtered and stripped to an orange oil (7.4922 g). M/z=367 (M+1)

Step 3. Synthesis of 4-(4-Methylamino-3-nitro-phenoxy)-pyridine-2-carbonitrile

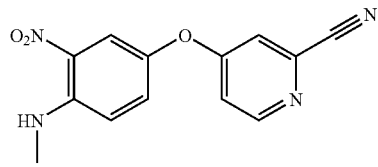

NaOH (1 mL, 1N aq) was added dropwise to a solution of N-[4-(2-cyano-pyridin-4-yloxy)-2-nitro-phenyl]-2,2,2-trifluoro-N-methyl-acetamide (440 mg) in ethanol (6 mL) at RT. After 40 min, the mixture was diluted with H₂O (20 mL) and cooled to 0° C. Bright orange crystals were collected, washed (H₂O) and air-dried 311.1 mg (94%). M/z=271 (M+1)

Step 4. Synthesis of 4-[2-(4-Chloro-phenylamino)-1-methyl-1H-benzoimidazol-5-yloxy]-pyridine-2-carbonitrile

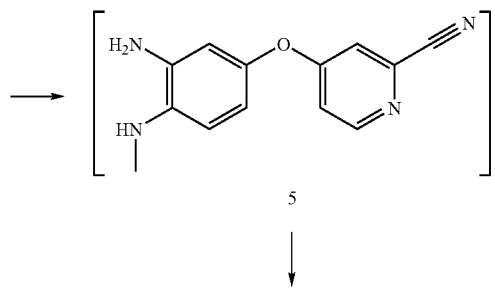

-continued

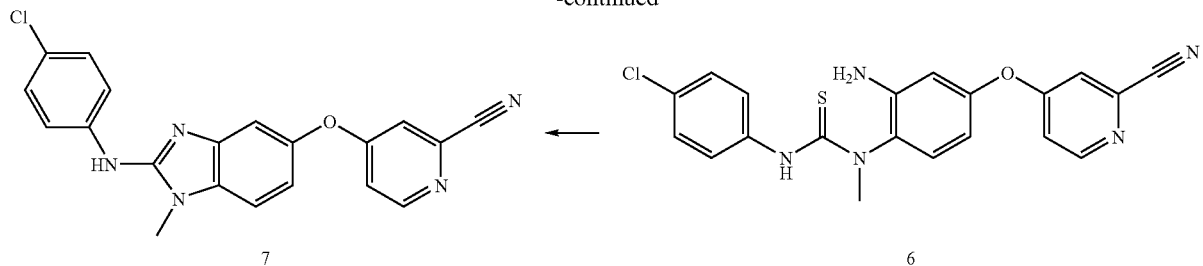

Palladium on carbon (46 mg 10% w/w) was suspended in MeOH (2 mL) under nitrogen. The resulting suspension was added, under nitrogen, to a suspension of 4-(4-methylamino-3-nitro-phenoxy)-pyridine-2-carbonitrile (311 mg) in MeOH (3 mL) at RT. The atmosphere was exchanged with hydrogen, and the system stirred vigorously under 1 atm hydrogen for 1 hr. The atmosphere was then exchanged for nitrogen, the mixture was filtered (celite) and the filtrate was used without further purification in the next reaction. M/z=2421 (M+1).

4-chlorophenylisothiocyanate (200 mg) was added to a solution of compound 5 in MeOH (10 mL). The solution was stirred at reflux for 2 hrs. Iodomethane (71 microliters) was added, and stirring continued at 67° C., overnight. The mixture was then cooled to RT evaporated to dryness, and the residue chromatographed (0.5% NH$_4$OH, 5% MeOH, 94.5% dichloromethane on silica gel) to isolate a compound of Rf=0.29 (325 mg). This was crystallized from dichloromethane/ether to give 127 mg. M/z=376 (M+1)

| 1 HNMR (MeOH-d4) | | | |
|---|---|---|---|
| 9.40 ppm | s(b) | | (1 H) |
| 8.55 ppm | d, d | H = 5.7, 0.6 Hz | (1 H) |
| 7.62 ppm | m | | (2 h) |
| 7.42 ppm | d, d | J = 2.5, 0.6 Hz | (1 H) |
| 7.43 ppm | d | | (1 H) |
| 7.37 ppm | m | | (2 h) |
| 7.21 ppm | d | J = 2.0 Hz | (1 H) |
| 7.15 ppm | d, d | J = 5.9, 2.5 Hz | (1 H) |
| 6.97 ppm | d, d | J = 8.4, 2.2 hz | (1 H) |
| 3.80 ppm | s | | (3 H) |

Step 5. Synthesis of (4-Chloro-phenyl)-{5-[2-(4,5-dihydro-1H-imidazol-2-yl)pyridin-4-yloxy]-1-methyl-1H-benzoimidazol-2-yl}-amine

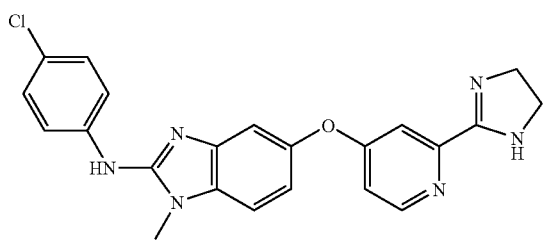

H$_2$SO$_4$ (454 mg) was added cautiously to a suspension of 4-[2-(4-chlorophenylamino)-1-methyl-1H-benzoimidazol-5-yloxy]-pyridine-2-carbonitrile (60.0 mg) in ethylenediamine (0.50 mL). The system was shaken at room temperature for 72 hrs, then poured onto ice/NaHCO$_3$. The solid product was collected, washed (H$_2$O) air-dried 59.8 mg. M/z=419 (M+1).

Example 451

Synthesis of (4-{2-[(4-bromophenyl)amino]benzoxazol-5-yloxy}-(2-pyridyl))-N-methylcarboxamide Step 1. Synthesis of 2-amino-4-methoxyphenol The mixture containing 4-methoxy-2-nitrophenol in methanol with catalytic amount of 10% Pd/C was hydrogenated until disappearance of yellow color to yield 2-amino-4-methoxyphenol. MS: MH+=140.

Step 2. Synthesis of 5-methoxybenzoxazole-2-thiol

The mixture containing 2-amino-4-methoxyphenol (1 eq) and O-ethylxanthic acid, potassium salt (1.1 eq) in pyridine was refluxed for two hours. The resultant mixture was poured in to ice/water containing hydrochloric acid to yield a 5-methoxybenzoxazole-2-thiol as a tan solid. MS: MH+=182

Step 3. Synthesis of 2-chloro-5-methoxybenzoxazole

The mixture containing 5-methoxybenzoxazole-2-thiol was heated in thionyl chloride with a drop of DMF. The resultant mixture was concentrated and partitioned between ethyl acetate and water. The organic layer was washed with brine and dried and concentrated. Purification on a silica gel column gave 2-chloro-5-methoxybenzoxazole as a white solid. MS: MH+=184.

Step 4. Synthesis of (4-bromophenyl)(5-methoxybenzoxazol-2-yl)amine

The mixture containing 2-chloro-5-methoxybenzoxazole (1 eq), 4-bromoaniline (2 eq) and diisopropylethylamine was refluxed in dimethylformamide. The resultant mixture was concentrated and partitioned between ethyl acetate and water. The organic layer was washed with brine and dried. Purification on silica gel gave (4-bromophenyl)(5-methoxybenzoxazol-2-yl)amine. MS: MH+=318

Step 5. Synthesis of 2-[(4-bromophenyl)amino]benzoxazol-5-ol

The mixture of (4-bromophenyl)(5-methoxybenzoxazol-2-yl)amine and hydrobromic acid (48%) was subjected to the microwave at 150° C. for 6 mins to yield 2-[(4-bromophenyl)amino]benzoxazol-5-ol. MS: MH+=305

Step 6. Synthesis of (4-{2-[(4-bromophenyl)amino]benzoxazol-5-yloxy}-(2-pyridyl))-N-methylcarboxamide The mixture containing 2-[(4-bromophenyl)amino]benzoxazol-5-ol (1 eq), potassium bis(trimethylsilyl)amide (4 eq), was stirred in dimethylformamide for 30 min at room temperature. To this mixture was added (4-chloro(2-pyridyl)-N-methylcarboxamide (1 eq) and Potassium carbonate (1.2 eq) and microwaved for 6 mins at 150° C. The reaction mixture was then concentrated and partitioned between ethyl acetate and water. The organic layer was separated and washed with brine, dried, filtered and concentrated. Purification on Prep LC yielded the desired product. MS: MH+=439.

The compounds shown in the following Table 5 (Examples 452-481) were prepared from following the procedure described for Examples 449-451.

TABLE 5

| Example | Structure | Name | MH+ |
|---|---|---|---|
| 452 | 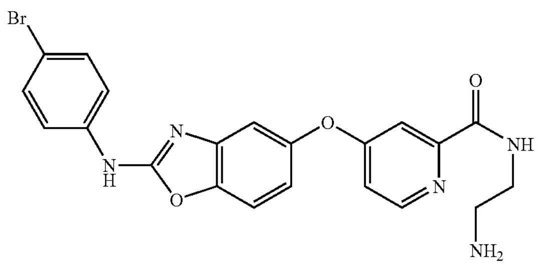 | N-(2-aminoethyl)-4-({2-[(4-bromophenyl)amino]-1,3-benzoxazol-5-yl}oxy)pyridine-2-carboxamide | 469.3 |
| 453 | 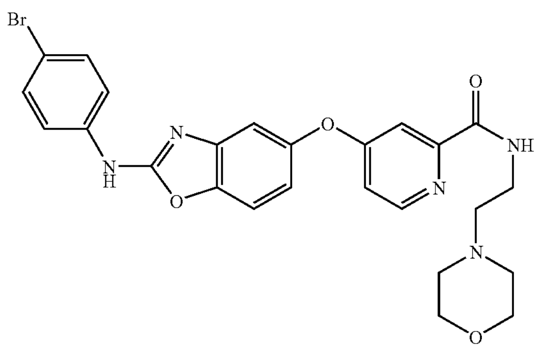 | 4-({2-[(4-bromophenyl)amino]-1,3-benzoxazol-5-yl}oxy)-N-(2-morpholin-4-ylethyl)pyridine-2-carboxamide | 539.4 |
| 454 | Chiral | 4-({2-[(4-bromophenyl)amino]-1,3-benzoxazol-5-yl}oxy)-N-[(3R)-pyrrolidin-3-yl]pyridine-2-carboxamide | 495.3 |
| 455 | Chiral | 4-({2-[(4-bromophenyl)amino]-1,3-benzoxazol-5-yl}oxy)-N-{(3R,5R)-5-[(methyloxy)methyl]pyrrolidin-3-yl}pyridine-2-carboxamide | 539.4 |

TABLE 5-continued

| Example | Structure | Name | MH+ |
|---|---|---|---|
| 456 | 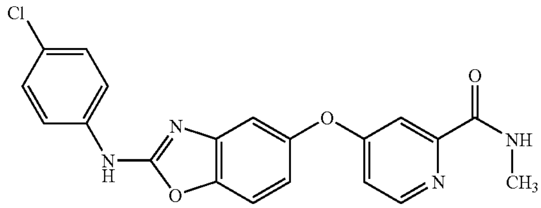 | 4-({2-[(4-chlorophenyl)amino]-1,3-benzoxazol-5-yl}oxy)-N-methyl-pyridine-2-carboxamide | 395.8 |
| 457 | 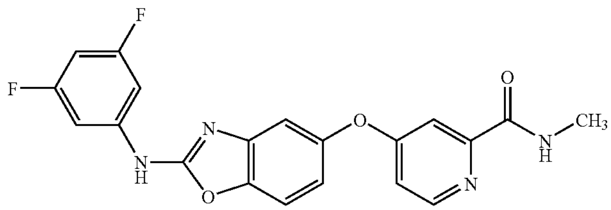 | 4-({2-[(3,5-difluorophenyl)amino]-1,3-benzoxazol-5-yl}oxy)-N-methylpyridine-2-carboxamide | 397.4 |
| 458 | 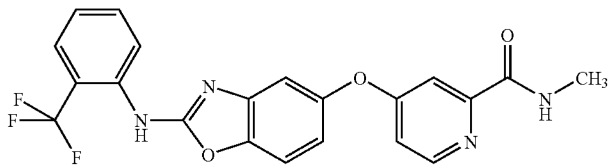 | N-methyl-4-[(2{[2-(trifluoro-methyl)phenyl]amino}-1,3-benzoxazol-5-yl)oxy]pyridine-2-carboxamide | 429.4 |
| 459 | 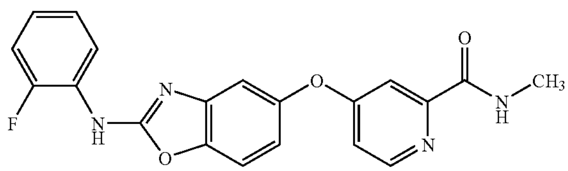 | 4-({2-[(2-fluorophenyl)amino]-1,3-benzoxazol-5-yl}oxy)-N-methyl-pyridine-2-carboxamide | 379.4 |
| 460 | 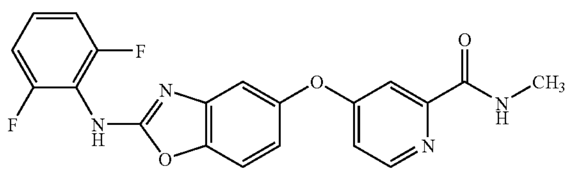 | 4-({2-[(2,6-difluorophenyl)amino]-1,3-benzoxazol-5-yl}oxy)-N-methylpyridine-2-carboxamide | 397.4 |
| 461 | 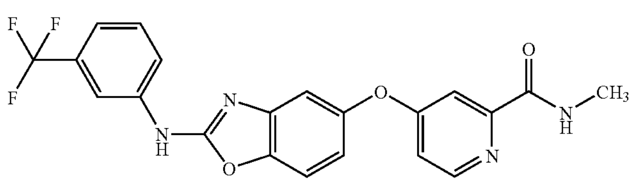 | N-methyl-4-[(2-{[3-trifluoro-methyl)phenyl]amino}-1,3-benzoxazol-5-yl)oxy]pyridine-2-carboxamide | 429.4 |
| 462 | 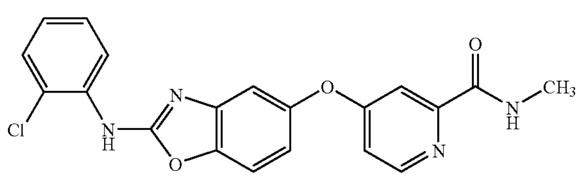 | 4-({2-[(2-chlorophenyl)amino]-1,3-benzoxazol-5-yl}oxy)-N-methyl-pyridine-2-carboxamide | 395.8 |
| 463 | 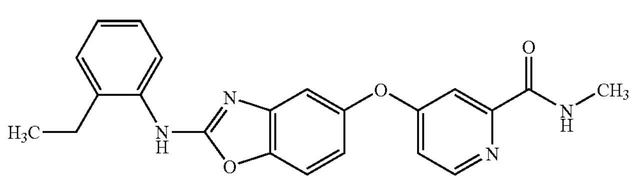 | 4-({2-[(2-ethylphenyl)amino]-1,3-benzoxazol-5-yl}oxy)-N-methyl-pyridine-2-carboxamide | 389.4 |

TABLE 5-continued

| Example | Structure | Name | MH+ |
|---|---|---|---|
| 464 | 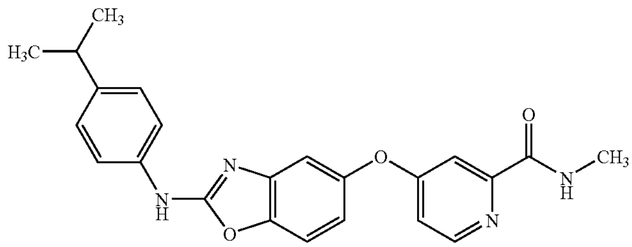 | N-methyl-4-[(2-{[4-(1-methyl-ethyl)phenyl]amino}-1,3-benzoxazol-5-yl)oxy]pyridine-2-carboxamide | 403.5 |
| 465 | 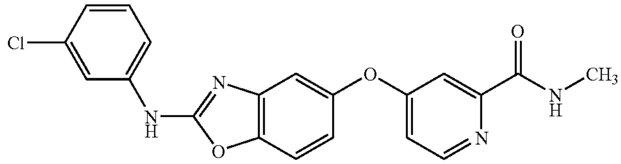 | 4-({2-[(3-chlorophenyl)amino]-1,3-benzoxazol-5-yl}oxy)-N-methyl-pyridine-2-carboxamide | 395.8 |
| 466 | 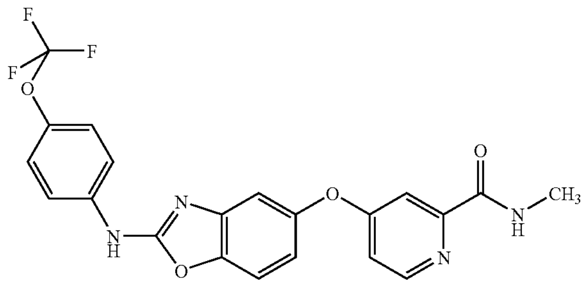 | N-methyl-4-{[2-({4-[(trifluoro-methyl)oxy]phenyl}amino)-1,3-benzoxazol-5-yl]oxy}pyridine-2-carboxamide | 445.4 |
| 467 | 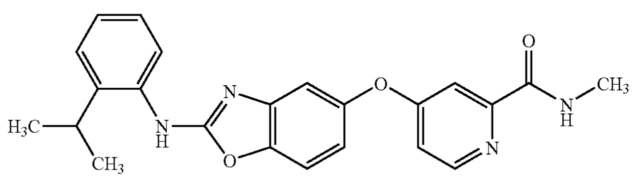 | N-methyl-4-[(2-{[2-(1-methyl-ethyl)phenyl]amino}-1,3-benzoxazol-5-yl)oxy]pyridine-2-carboxamide | 403.5 |
| 468 | 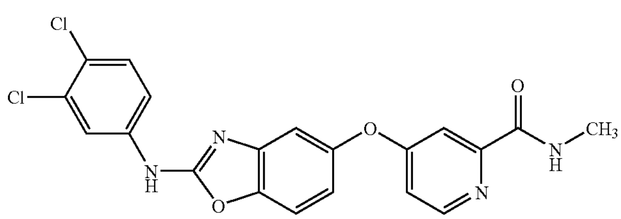 | 4-({2-[(3,4-dichlorophenyl)amino]-1,3-benzoxazol-5-yl}oxy)-N-methylpyridine-2-carboxamide | 430.3 |
| 469 | 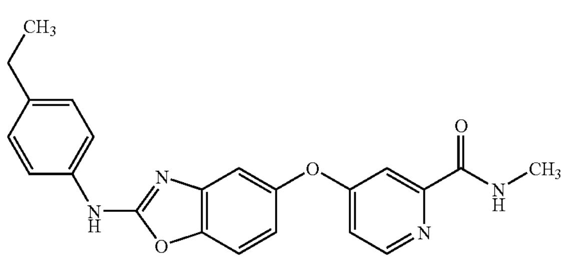 | 4-({2-[(4-ethylphenyl)amino]-1,3-benzoxazol-5-yl}oxy)-N-methyl-pyridine-2-carboxamide | 389.4 |

TABLE 5-continued

| Example | Name | MH+ |
|---|---|---|
| 470 | 4-[(2-{[4-(1-methylethyl)phenyl]-amino}-1,3-benzoxazol-5-yl)oxy]-N-[(3R)-pyrrolidin-3-yl]pyridine-2-carboxamide | 458.5 |
| 471 | 4-({2-[(2,5-dimethylphenyl)amino]-1,3-benzoxazol-5-yl}oxy)-N-methylpyridine-2-carboxamide | 389.4 |
| 472 | 4-({2-[(4-bromophenyl)(methyl)-amino]-1,3-benzoxazol-5-yl}oxy)-N-methylpyridine-2-carboxamide | 454.3 |
| 473 | N-methyl-4-{[2-(phenylamino)-1,3-benzoxazol-5-yl]oxy}pyridine-2-carboxamide | 361.4 |
| 474 | 4-[(2-{[4-dimethylamino)phenyl]-amino}-1,3-benzoxazol-5-yl)oxy]-N-methylpyridine-2-carboxamide | 404.4 |
| 475 | 4-[(2-{[4-(4-ethylpiperazin-1-yl)-phenyl]amino}-1,3-benzoxazol-5-yl)oxy]-N-methylpyridine-2-carboxamide | 473.5 |

Example 470 is Chiral.

TABLE 5-continued

| Example | Structure | Name | MH+ |
|---|---|---|---|
| 476 | 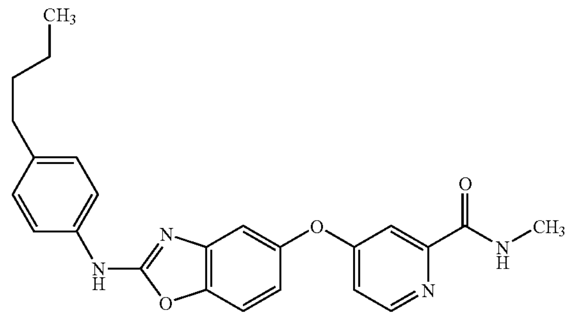 | 4-({2-[(4-butylphenyl)amino]-1,3-benzoxazol-5-yl}oxy)-N-methyl-pyridine-2-carboxamide | 417.5 |
| 477 | 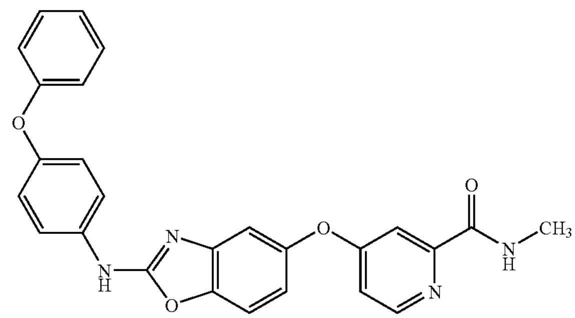 | N-methyl-4-[(2-{[4-(phenyloxy)phenyl]amino}-1,3-benzoxazol-5-yl)oxy]pyridine-2-carboxamide | 453.5 |
| 478 | 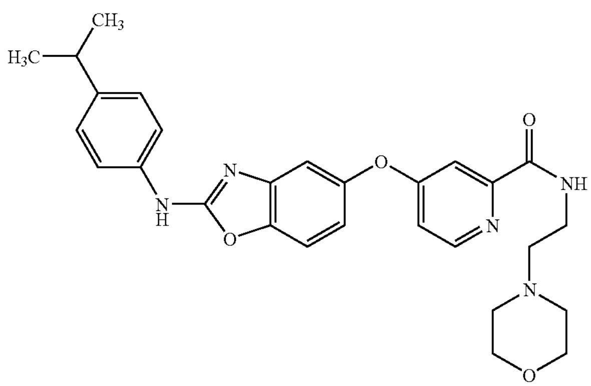 | 4-[(2-{[4-(1-methylethyl)phenyl]amino}-1,3-benzoxazol-5-yl)oxy]-N-(2-morpholin-4-ylethyl)pyridine-2-carboxamide | 502.6 |
| 479 | 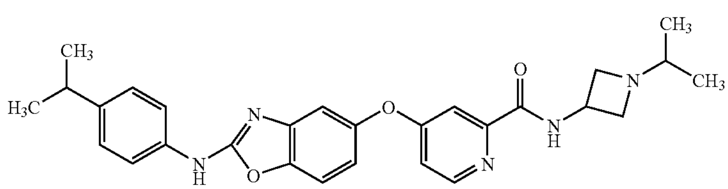 | N-[1-(1-methylethyl)azetidin-3-yl]-4-[(2-{[4-(1-methylethyl)phenyl]amino}-1,3-benzoxazol-5-yl)oxy]pyridine-2-carboxamide | 486.6 |
| 480 | 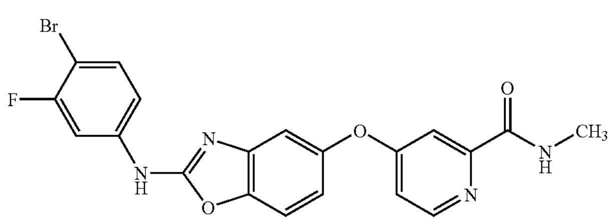 | 4-({2-[(4-bromo-3-fluorophenyl)amino]-1,3-benzoxazol-5-yl}oxy)-N-methylpyridine-2-carboxamide | 458.3 |

TABLE 5-continued

| Example | Structure | Name | MH+ |
|---|---|---|---|
| 481 | 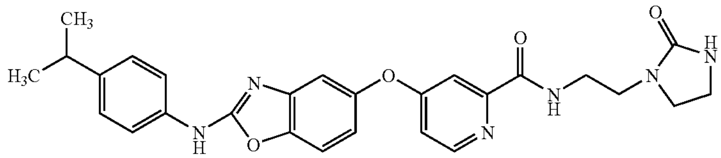 | 4-[(2-{[4-(1-methylethyl)phenyl]-amino}-1,3-benzoxazol-5-yl)oxy]-N-[2-(2-oxoimidazolidin-1-yl)-ethyl]pyridine-2-carboxamide | 501.6 |

Example 482

Synthesis of [4-(2-{[4-(dimethylamino)phenyl]amino-1-methyl benzimidazol-5-yloxy)(2-pyridyl)]-N-(2-pyrrolidinylethyl)carboxamide

Step 1. Synthesis of 4-(2-{[4-(dimethylamino)phenylamino)-1-methylbenzimidazol-5-yloxy)pyridin-2-carboxylic acid To tert-butyl4-[3-amino-4-(methylamino)phenoxy]pyridine-2-carboxylate (1 eq) in methanol was added 4-(dimethylamino)benzeneisothiocyanate (1 eq) and stir at ambient temperature for 16 h. Formation of the corresponding thiourea was followed by LC/MS. The mixture was then concentrated and to it was added tetrahydrofuran and 1-ethyl-(3-dimethylaminopropyl)carbodiimidehydrochloride (2 eq) and stir at ambient temperature for 16 h. tert-butyl4-(2-{[4-dimethylamino)phenyl]amino)-1-methylbenzimidazol-5-yloxy)pyridine-2-carboxylate crashes out of the reaction mixture. To it in methylene chloride was added trifluoroacetic acid and stirred at ambient temperature overnight. Resulting 4-(2-{[4-dimethylamino)phenylamino)-1-methylbenzimidazol-5-yloxy)pyridine-2-carboxylic acid was purified by preparative chromatography. MS: MH+=403.

Step 2. Synthesis of [4-(2-{[4-(dimethylamino)phenylamino-1-methylbenzimidazol-5-yloxy)(2-pyridyl)]-N-(2-pyrrolidinylethyl)carboxamide To 4-(2-{[4-(dimethylamino)phenylamino)-1-methylbenzimidazol-5-yloxy)pyridine-2-carboxylic acid (1 eq) in tetrahydrofuran was added 2-pyrrolidinylethylamine (2 eq), HBTU (2 eq) and N,N-diisopropylethylamine (4 eq) and stir at ambient temperature for 16 h. The mixture was then concentrated and partitioned between ethyl acetate and water. The organic layer was concentrated and preparative chromatography yielded [4-(2-{[4-(dimethylamino)phenyl]amino-1-methylbenzimidazol-5-yloxy)(2-pyridyl)]-N-(2-pyrrolidinylethyl)carboxamide. MS: MH+=498.

Example 483

Synthesis of [4-(2-{[4-bromo-3-methylphenyl)amino-1-methyl benzimidazol-5-yloxy)(2-pyridyl)]-N-(2-pyrrolidinylethyl)carboxamide

Step 1. Synthesis of 4-{2-[(4-bromo-3-methylphenyl)amino]-1-methylbenzimidazol-5-yloxy)pyridine-2-carboxylic acid To tert-butyl4-[3-amino-4-(methylamino)phenoxy]pyridine-2-carboxylate (1 eq) in methanol was added 4-bromo-3-methylbenzeneisothiocyanate (1 eq) and stir at ambient temperature for 16 h. Formation of the corresponding thiourea was followed by LC/MS. To it was then added iodomethane (1 eq) and heated to 60° C. for 2 h. Formation of tert-butyl4-(2-{[4-bromo-3-methylphenyl]amino)-1-methylbenzimidazol-5-yloxy)pyridine-2-carboxylate was followed by LC/MS. To it in methylene chloride was added trifluoroacetic acid and stirred at ambient temperature overnight. Resulting 4-(2-{[4-bromo-3-methylphenyl]amino)-1-methylbenzimidazol-5-yloxy)pyridine-2-carboxylic acid was purified by preparative chromatography. MS: MH+=452

Step 2. Synthesis of [4-(2-{[4-bromo-3-methylphenyl)amino-1-methylbenzimidazol-5-yloxy)(2-pyridyl)]-N-(2-pyrrolidinylethyl)carboxamide To 4-(2-{[4-bromo-3-methylpheylamino)-1-methylbenzimidazol-5-yloxy)pyridine-2-carboxylic acid (1 eq) in tetrahydrofuran was added 2-pyrrolidinylethylamine (2 eq), HBTU (2 eq) and N,N-diisopropylethylamine (4 eq) and stir at ambient temperature for 16 h. The mixture was then concentrated and partitioned between ethyl acetate and water. The organic layer was concentrated and preparative chromatography yielded [4-(2-{[4bromo-3-methylphenyl]amino-1-methylbenzimidazol-5-yloxy)(2-pyridyl)]-N-(2-pyrrolidinylethyl)carboxamide. MS: MH+=549.

Example 484

Synthesis of [4-(2-{[2-fluoro-5-(trifluoromethyl)phenyl)amino-1-methylbenzimidazol-5-yloxy)(2-pyridyl)]-N-(2-pyrrolidinylethyl)carboxamide

Step 1. Synthesis of 4-{2-[(2-fluoro-5-(trifluoromethyl)phenyl)amino]-1-methylbenzimidazol-5-yloxy)pyridine-2-carboxylic acid To tert-butyl4-[3-amino-4-(methylamino)phenoxy]pyridine-2-carboxylate (1 eq) in methanol was added 2-fluoro-5-(trifluoromethyl)benzeneisothiocyanate (1 eq) and stir at ambient temperature for 16 h. Formation of the corresponding thiourea was followed by LC/MS. To it was then added iodomethane (1 eq) and heated to 60° C. for 2 h. Formation of tert-butyl4-(2-{[2-fluoro-5-(trifluoromethyl)phenyl]amino)-1-methylbenzimidazol-5-yloxy)pyridine-2-carboxylate was followed by LC/MS. To it in methylene chloride was added trifluoroacetic acid and stirred at ambient temperature overnight. Resulting 4-(2-{[2-fluoro-5-(trifluoromethyl)phenylamino)-1-methylbenzimidazol-5-yloxy)pyridine-2-carboxylic acid was purified by preparative chromatography. MS: MH+=446.

Step 2. Synthesis of [4-(2-{[2-fluoro-5-(trifluoromethyl)phenyl)amino-1-methylbenzimidazol-5-yloxy)(2-pyridyl)]-N-(2-pyrrolidinylethyl)carboxamide To 4-(2-{[2-fluoro-5-(trifluoromethyl)phenylamino)-1-methylbenzimidazol-5-yloxy)pyridine-2-carboxylic acid (1 eq) in tetrahydrofuran was added 2-pyrrolidinylethylamine (2 eq), HBTU (2 eq) and N,N-diisopropylethylamine (4 eq) and stir at ambient temperature for 16 h. The mixture was then concentrated and partitioned between ethyl acetate and water. The organic layer was concentrated and preparative chromatography yielded [4-(2-{[2-fluoro-5-(trifluoromethyl)phenyl]amino-1-methylbenzimidazol-5-yloxy)-(2-pyridyl)]-N-(2-pyrrolidinylethyl)carboxamide. MS: MH$^+$=542.

Example 485

Synthesis of [4-(2-{[4-bromo-3-fluorophenyl)amino-1-methylbenzimidazol-5-yloxy)(2-pyridyl)]-N-(2-piperidylethyl)carboxamide

Step 1. Synthesis of 4-{2-[(4-bromo-3-fluorophenyl)amino]-1-methylbenzimidazol-5-yloxy)pyridine-2-carboxylic acid To tert-butyl4-[3-amino-4-(methylamino)phenoxy]pyridine-2-carboxylate (1 eq) in methanol was added 4-bromo-3-fluorobenzeneisothiocyanate (1 eq) and stir at ambient temperature for 16 h. Formation of the corresponding thiourea was followed by LC/MS. To it was then added iodomethane (1 eq) and heated to 60° C. for 2 h. Formation of tert-butyl4-(2-{[4-bromo-3-fluorophenyl]amino)-1-methylbenzimidazol-5-yloxy)pyridine-2-carboxylate was followed by LC/MS. To it in methylene chloride was added trifluoroacetic acid and stirred at ambient temperature overnight. Resulting 4-(2-{[4-bromo-3-fluorophenylamino)-1-methylbenzimidazol-5-yloxy)pyridine-2-carboxylic acid was purified by preparative chromatography. MS: MH$^+$=456.

Step 2. Synthesis of [4-(2-{[4-bromo-3-fluorophenyl)amino-1-methylbenzimidazol-5-yloxy)(2-pyridyl)]-N-(2-piperidylethyl)carboxamide To 4-(2-{[4-bromo-3-fluorophenylamino)-1-methylbenzimidazol-5-yloxy)pyridine-2-carboxylic acid (1 eq) in tetrahydrofuran was added 2-piperidylethylamine (2 eq), HBTU (2 eq) and N,N-diisopropylethylamine (4 eq) and stir at ambient temperature for 16 h. The mixture was then concentrated and partitioned between ethyl acetate and water. The organic layer was concentrated and preparative chromatography yielded [4-(2-{[4-bromo-3-fluorophenyl]amino-1-methylbenzimidazol-5-yloxy)(2-pyridyl)]-N-(2-piperidylethyl)carboxamide. MS: MH$^+$=567.

Example 486

Synthesis of 4-{1-methyl-2-[(4-methylphenyl)amino-1-methylbenzimidazol-5-yloxy)(2-pyridyl)]-N-(2-pyrrolidinylethyl)carboxamide

Step 1. Synthesis of 4-{1-methyl-2-[(4-methylphenyl)amino]benzimidazol-5-yloxy)pyridine-2-carboxylic acid To tert-butyl-4-[3-amino-4-(methylamino)phenoxy]pyridine-2-carboxylate (1 eq) in methanol was added 4-methylbenzeneisothiocyanate (1 eq) and stir at ambient temperature for 16 h. Formation of the corresponding thiourea was followed by LC/MS. To it was then added iodomethane (1 eq) and heated to 60° C. for 2 h. Formation of tert-butyl-4-{1-methyl-2-[(4-methylphenyl)amino)benzimidazol-5-yloxy)pyridine-2-carboxylate was followed by LC/MS. To it in methylene chloride was added trifluoroacetic acid and stirred at ambient temperature overnight. Resulting 4-{1-methyl-2-[(4-methylphenyl)amino]benzimidazol-5-yloxy)pyridine-2-carboxylic acid was purified by preparative chromatography. MS: MH$^+$=374.

Step 2. Synthesis of 4-{1-methyl-2-[(4-methylphenyl)amino-1-methylbenzimidazol-5-yloxy)(2-pyridyl)]-N-(2-pyrrolidinylethyl)carboxamide To 4-{1-methyl-2-[(4-methylphenyl)amino]benzimidazol-5-yloxy)pyridine-2-carboxylic acid (1 eq) in tetrahydrofuran was added 2-pyrrolidinylethylamine (2 eq), HBTU (2 eq) and N,N-diisopropylethylamine (4 eq) and stir at ambient temperature for 16 h. The mixture was then concentrated and partitioned between ethyl acetate and water. The organic layer was concentrated and preparative chromatography yielded 4-{1-methyl-2-[(4-methylphenyl)amino-1-methylbenzimidazol-5-yloxy)(2-pyridyl)]-N-2(2-pyrrolidinylethyl)carboxamide. MS: MH$^+$=470.

Example 487

Synthesis of [4-(2-{[4-ethylphenyl)amino-1-methyl benzimidazol-5-yloxy)(2-pyridyl)]-N-(2-pyrrolidinylethyl)carboxamide

Step 1. Synthesis of 4-{2-[(4-ethylphenyl)amino]-1-methylbenzimidazol-5-yloxy)pyridine-2-carboxylic acid To tert-butyl4-[3-amino-4-(methylamino)phenoxy]pyridine-2-carboxylate (1 eq) in methanol was added 4-ethylbenzeneisothiocyanate (1 eq) and stir at ambient temperature for 16 h. Formation of the corresponding thiourea was followed by LC/MS. To it was then added iodomethane (1 eq) and heated to 60° C. for 2 h. Formation of tert-butyl4-(2-{[4-ethylphenyl]amino)-1-methylbenzimidazol-5-yloxy)pyridine-2-carboxylate was followed by LC/MS. To it in methylene chloride was added trifluoroacetic acid and stirred at ambient temperature overnight. Resulting 4-(2-{[4-ethylphenylamino)-1-methylbenzimidazol-5-yloxy)pyridine-2-carboxylic acid was purified by preparative chromatography. MS: MH$^+$=388.

Step 2. Synthesis of [4-(2-{[4-ethylphenyl)amino-1-methylbenzimidazol-5-yloxy)(2-pyridyl)]-N-(2-pyrrolidinylethyl)carboxamide To 4-(2-{[4-ethylphenylamino)-1-methylbenzimidazol-5-yloxy)pyridine-2-carboxylic acid (1 eq) in tetrahydrofuran was added 2-pyrrolidinylethylamine (2 eq), HBTU (2 eq) and N,N-diisopropylethylamine (4 eq) and stir at ambient temperature for 16 h. The mixture was then concentrated and partitioned between ethyl acetate and water. The organic layer was concentrated and preparative chromatography yielded [4-(2-{[4-ethylphenyl]amino-1-methylbenzimidazol-5-yloxy)(2-pyridyl)]-N-(2-pyrrolidinylethyl)carboxamide. MS: MH$^+$=484.

Example 488

Synthesis of [4-(2-{[3-(tert-butyl)phenyl)amino-1-methylbenzimidazol-5-yloxy)(2-pyridyl)]-N-(2-piperidylethyl)carboxamide

Step 1. Synthesis of 4-{2-[(3-(tert-butyl)phenyl)amino]-1-methylbenzimidazol-5-yloxy)pyridine-2-carboxylic acid To tert-butyl4-[3-amino-4-(methylamino)phenoxy]pyridine-2-carboxylate (1 eq) in methanol was added 3-(tert-butyl)benzeneisothiocyanate (1 eq) and stir at ambient temperature for 16 h. Formation of the corresponding thiourea was followed by LC/MS. To it was then added iodomethane (1 eq) and heated to 60° C. for 2 h. Formation of tert-butyl4-(2-{[3-(tert-butyl)phenyl]amino)-1-methylbenzimidazol-5-yloxy)pyridine-2-carboxylate was followed by LC/MS. To it in methylene chloride was added trifluoroacetic acid and stirred at ambient temperature overnight. Resulting 4-(2-{[3-(tert-butyl)phenylamino)-1-methylbenzimidazol-5-yloxy)pyridine-2-carboxylic acid was purified by preparative chromatography. MS: MH$^+$=416.

Step 2. Synthesis of [4-(2-{[3-(tert-butyl)phenyl)amino-1-methylbenzimidazol-5-yloxy)(2-pyridyl)]-N-(2-piperidylethyl)carboxamide To 4-(2-{[3-(tert-butyl)phenylamino)-1-methylbenzimidazol-5-yloxy)pyridine-2-carboxylic acid (1 eq) in tetrahydrofuran was added 2-piperidylethylamine (2 eq), HBTU (2 eq) and N,N-diisopropylethylamine (4 eq) and stir at ambient temperature for 16 h. The mixture was then concentrated and partitioned between ethyl acetate and water. The organic layer was concentrated and preparative chromatography yielded [4-(2-{[3-(tert-butyl)phenyl]amino-1-methylbenzimidazol-5-yloxy)(2-pyridyl)]-N-(2-piperidylethyl)carboxamide. MS: MH$^+$=512.

Example 489

Synthesis of [4-(2-{[4-chloro-3-(trifluoromethyl)phenyl)amino-1-methylbenzimidazol-5-yloxy)(2-pyridyl)]-N-(2-piperidylethyl)carboxamide

Step 1. Synthesis of 4-{2-[(4-chloro-3-(trifluoromethyl)phenyl)amino]-1-methylbenzimidazol-5-yloxy)pyridine-2-carboxylic acid To tert-butyl4-[3-amino-4-(methylamino)phenoxy]pyridine-2-carboxylate (1 eq) in methanol was added 4-chloro-3-(trifluoromethyl)benzeneisothiocyanate (1 eq) and stir at ambient temperature for 16 h. Formation of the corresponding thiourea was followed by LC/MS. To it was then added iodomethane (1 eq) and heated to 60° C. for 2 h. Formation of tert-butyl4-(2-{[4-chloro-3-(trifluoromethyl)phenyl]amino)-1-methylbenzimidazol-5-yloxy)pyridine-2-carboxylate was followed by LC/MS. To it in methylene chloride was added trifluoroacetic acid and stirred at ambient temperature overnight. Resulting 4-(2-{[4-chloro-3-(trifluoromethyl)phenylamino)-1-methylbenzimidazol-5-yloxy)pyridine-2-carboxylic acid was purified by preparative chromatography. MS: MH$^+$=462.

Step 2. Synthesis of [4-(2-{[4-chloro-3-(trifluoromethyl)phenyl)amino-1-methylbenzimidazol-5-yloxy)(2-pyridyl)]-N-(2-piperidylethyl)carboxamide To 4-(2-{[4-chloro-3-(trifluoromethyl)phenylamino)-1-methylbenzimidazol-5-yloxy)pyridine-2-carboxylic acid (1 eq) in tetrahydrofuran was added 2-piperidylethylamine (2 eq), HBTU (2 eq) and N,N-diisopropylethylamine (4 eq) and stir at ambient temperature for 16 h. The mixture was then concentrated and partitioned between ethyl acetate and water. The organic layer was concentrated and preparative chromatography yielded [4-(2-{[4-chloro-3-trifluoromethylphenyl]amino-1-methylbenzimidazol-5-yloxy)(2-pyridyl)]-N-(2-piperidylethyl)carboxamide. MS: MH$^+$=558.

Each of the compounds 490-626 listed below in Table 6, were synthesized as indicated in the right hand column by the method described in one of the Examples 482-489.

TABLE 6

| Example | Molecular Structure | Name | MH+ | Synthesized as in Example: |
|---|---|---|---|---|
| 490 | 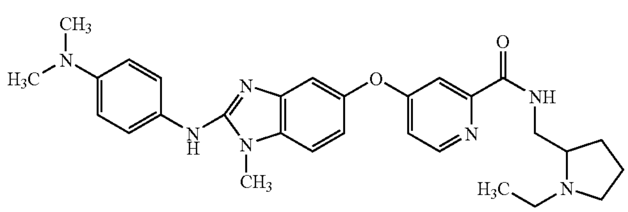 | 4-[(2-{[4-(dimethylamino)phenyl]amino}-1-methyl-1 H-benzimidazol-5-yl)oxy]-N-[(1-ethylpyrrolidin-2-yl)methyl]pyridine-2-carboxamide | 514.6 | 482 |
| 491 | 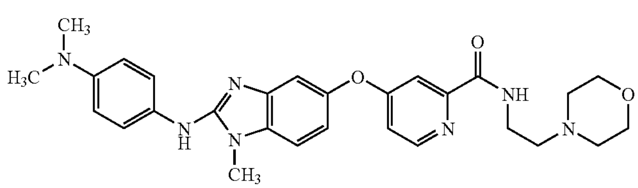 | 4-[(2-{[4-(dimethylamino)phenyl]amino}-1-methyl-1 H-benzimidazol-5-yl)oxy]-N-(2-morpholin-4-ylethyl)-pyridine-2-carboxamide | 516.6 | 482 |

TABLE 6-continued

| Example | Molecular Structure | Name | MH+ | Synthesized as in Example: |
|---|---|---|---|---|
| 492 | 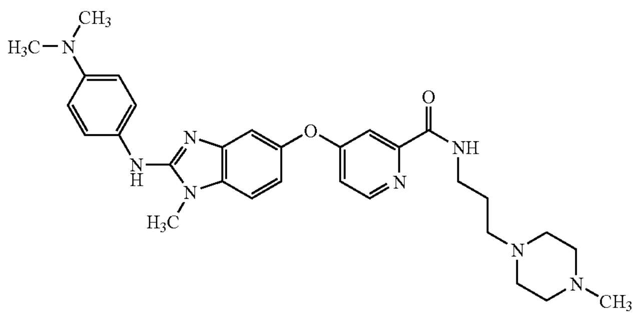 | 4-[(2-{[4-(dimethylamino)-phenyl]amino}-1-methyl-1H-benzimidazol-5-yl)oxy]-N-[3-(4-methylpiperazin-1-yl)propyl]pyridine-2-carboxamide | 543.7 | 482 |
| 493 | 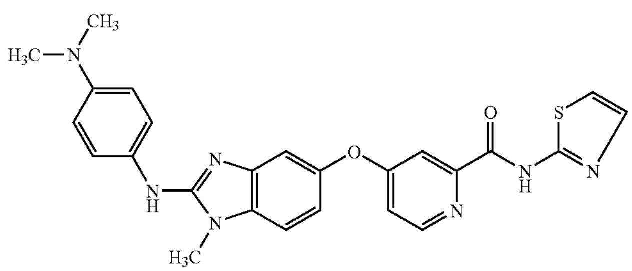 | 4-[(2-{[4-(dimethylamino)-phenyl]amino}-1-methyl-1H-benzimidazol-5-yl)oxy]-N-1,3-thiazol-2-ylpyridine-2-carboxamide | 486.6 | 482 |
| 494 | 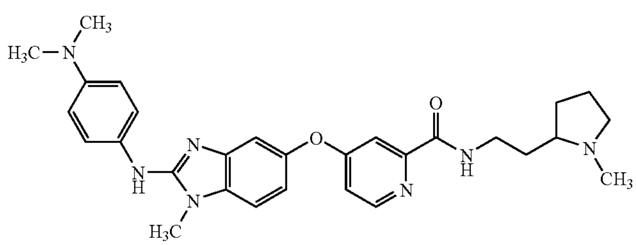 | 4-[(2-{[4-(dimethylamino)-phenyl]amino}-1-methyl-1H-benzimidazol-5-yl)oxy]-N-[2-(1-methylpyrrolidin-2-yl)ethyl]pyridine-2-carboxamide | 514.6 | 482 |
| 495 | 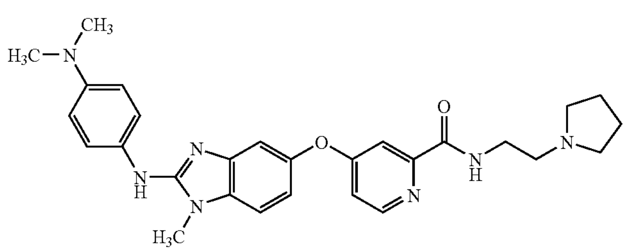 | 4-[(2-{[4-(dimethylamino)-phenyl]amino}-1-methyl-1H-benzimidazol-5-yl)oxy]-N-(2-pyrrolidin-1-ylethyl)-pyridine-2-carboxamide | 500.6 | 482 |
| 496 | 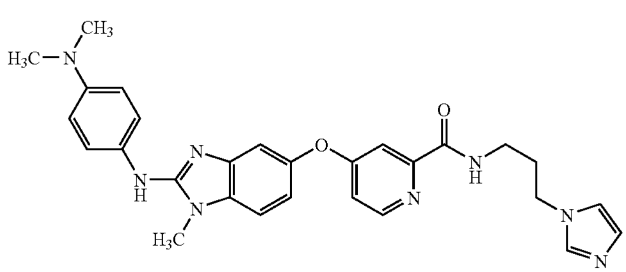 | 4-[(2-{[4-(dimethylamino)-phenyl]amino}-1-methyl-1H-benzimidazol-5-yl)oxy]-N-[3-(1H-imidazol-1-yl)-propyl]pyridine-2-carboxamide | 511.6 | 482 |

TABLE 6-continued

| Example | Molecular Structure | Name | MH+ | Synthesized as in Example: |
|---|---|---|---|---|
| 497 | 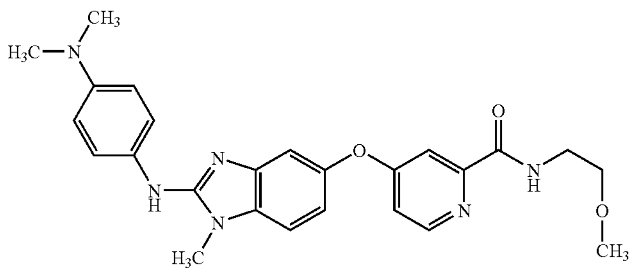 | 4-[(2-{[4-(dimethylamino)-phenyl]amino}-1-methyl-1H-benzimidazol-5-yl)oxy]-N-[2-(methyloxy)ethyl]-pyridine-2-carboxamide | 461.5 | 482 |
| 498 | 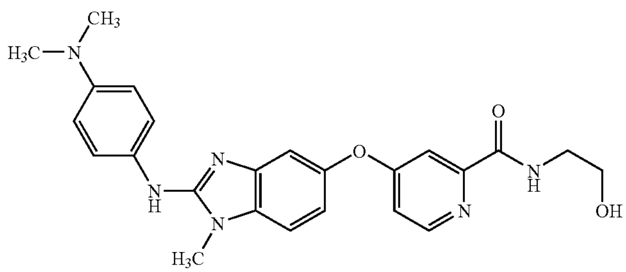 | 4-[(2-{[4-(dimethylamino)-phenyl]amino}-1-methyl-1H-benzimidazol-5-yl)oxy]-N-(2-hydroxyethyl)-pyridine-2-carboxamide | 447.5 | 482 |
| 499 | 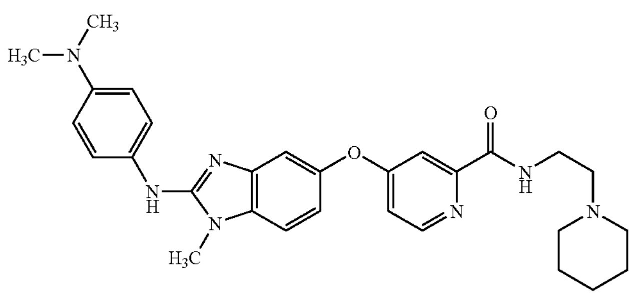 | 4-[(2-{[4-(dimethylamino)-phenyl]amino}-1-methyl-1H-benzimidazol-5-yl)oxy]-N-(2-piperidin-1-ylethyl)-pyridine-2-carboxamide | 514.6 | 482 |
| 500 | 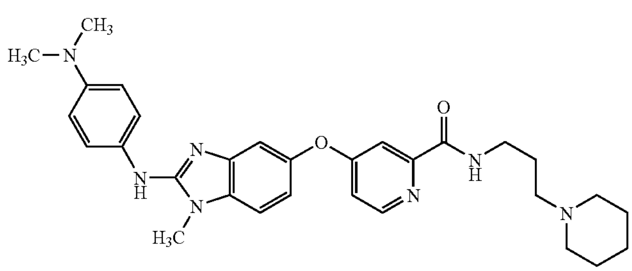 | 4-[(2-{[4-(dimethylamino)-phenyl]amino}-1-methyl-1H-benzimidazol-5-yl)oxy]-N-(3-piperidin-1-ylpropyl)-pyridine-2-carboxamide | 528.7 | 482 |
| 501 | 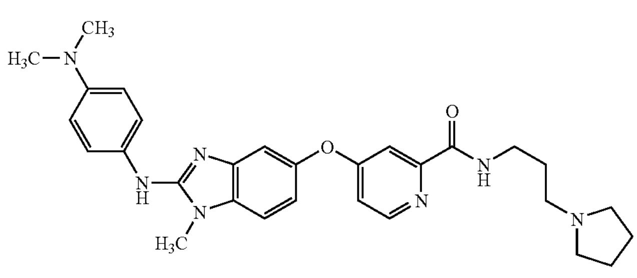 | 4-[(2-{[4-(dimethylamino)-phenyl]amino}-1-methyl-1H-benzimidazol-5-yl)oxy]-N-(3-pyrrolidin-1-ylpropyl)-pyridine-2-carboxamide | 514.6 | 482 |

TABLE 6-continued

| Example | Name | MH+ | Synthesized as in Example: |
|---|---|---|---|
| 502 | 4-[(2-{[4-(dimethylamino)-phenyl]amino}-1-methyl-1H-benzimidazol-5-yl)oxy]-N-(2-pyridin-4-ylethyl)-pyridine-2-carboxamide | 508.6 | 482 |
| 503 | 4-[(2-{[4-(dimethylamino)-phenyl]amino}-1-methyl-1H-benzimidazol-5-yl)oxy]-N-propylpyridine-2-carboxamide | 445.5 | 482 |
| 504 | 4-[(2-{[4-(dimethylamino)-phenyl]amino}-1-methyl-1H-benzimidazol-5-yl)oxy]-N-(2-piperazin-1-ylethyl)-pyridine-2-carboxamide | 515.6 | 482 |
| 505 | 4-[(2-{[4-(dimethylamino)-phenyl]amino}-1-methyl-1H-benzimidazol-5-yl)oxy]-N-[3-(methyloxy)propyl]-pyridine-2-carboxamide | 475.6 | 482 |
| 506 | 4-[(2-{[4-(dimethylamino)-phenyl]amino}-1-methyl-1H-benzimidazol-5-yl)oxy]-N-ethylpyridine-2-carboxamide | 431.5 | 482 |

TABLE 6-continued

| Example | Name | MH+ | Synthesized as in Example: |
|---|---|---|---|
| 507 | N-[2-(acetylamino)ethyl]-4-[(2-{[4-(dimethylamino)-phenyl]amino}-1-methyl-1H-benzimidazol-5-yl)oxy]-pyridine-2-carboxamide | 488.6 | 482 |
| 508 | 4-[(2-{[4-(dimethylamino)-phenyl]amino}-1-methyl-1H-benzimidazol-5-yl)oxy]-N-[2-(2-oxoimidazolidin-1-yl)ethyl]pyridine-2-carboxamide | 515.6 | 482 |
| 509 | 4-[(2-{[4-(dimethylamino)-phenyl]amino}-1-methyl-1H-benzimidazol-5-yl)oxy]-N-[(3R)-pyrrolidin-3-yl]-pyridine-2-carboxamide | 472.6 | 482 |
| 510 | 4-[(2-{[4-(dimethylamino)-phenyl]amino}-1-methyl-1H-benzimidazol-5-yl)oxy]-N-[3-(2-oxopyrrolidin-1-yl)propyl]pyridine-2-carboxamide | 528.6 | 482 |
| 511 | 4-({2-[(4-bromo-3-methylphenyl)amino]-1-methyl-1H-benzimidazol-5-yl}oxy)-N-[3-(2-oxopyrrolidin-1-yl)propyl]pyridine-2-carboxamide | 578.5 | 482 |

TABLE 6-continued

| Example | Molecular Structure | Name | MH+ | Synthesized as in Example: |
|---|---|---|---|---|
| 512 | 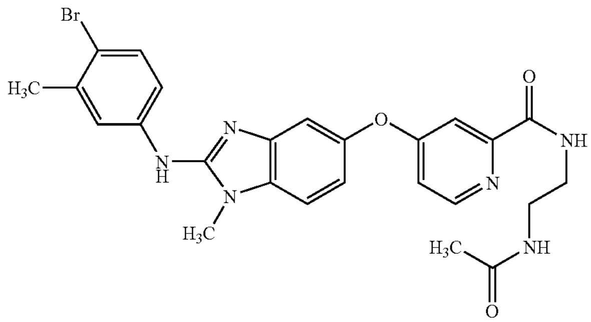 | N-[2-(acetylamino)ethyl]-4-({2-[(4-bromo-3-methylphenyl)amino]-1-methyl-1H-benzimidazol-5-yl}oxy)pyridine-2-carboxamide | 538.4 | 483 |
| 513 | 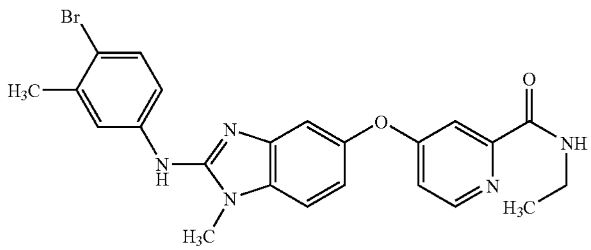 | 4-({2-[(4-bromo-3-methylphenyl)amino]-1-methyl-1H-benzimidazol-5-yl}oxy)-N-ethylpyridine-2-carboxamide | 481.4 | 483 |
| 514 | 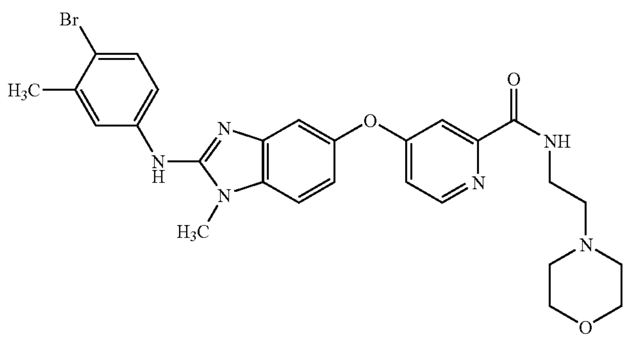 | 4-({2-[(4-bromo-3-methyl-phenyl)amino]-1-methyl-1H-benzimidazol-5-yl}oxy)-N-(2-morpholin-4-ylethyl)pyridine-2-carboxamide | 566.5 | 483 |
| 515 | 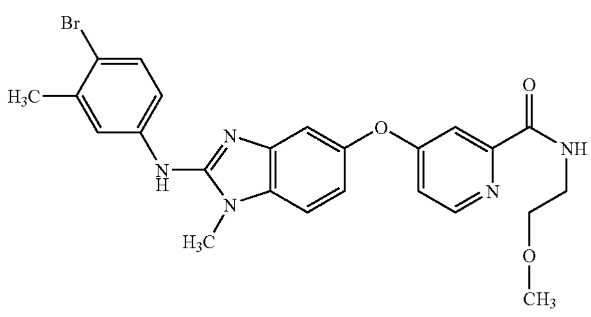 | 4-({2-[(4-bromo-3-methyl-phenyl)amino]-1-methyl-1H-benzimidazol-5-yl}oxy)-N-[2-(methyloxy)ethyl]pyridine-2-carboxamide | 511.4 | 483 |
| 516 | 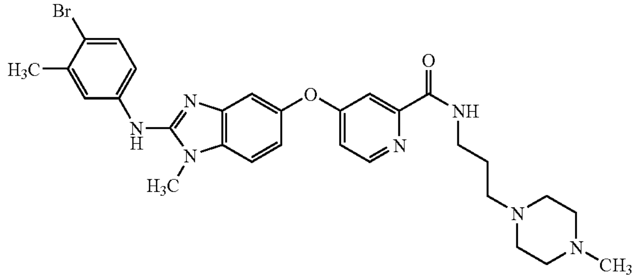 | 4-({2-[(4-bromo-3-methylphenyl)amino]-1-methyl-1H-benzimidazol-5-yl}oxy)-N-[3-(4-methylpiperazin-1-yl)propyl]pyridine-2-carboxamide | 593.5 | 483 |

TABLE 6-continued

| Example | Molecular Structure | Name | MH+ | Synthesized as in Example: |
|---|---|---|---|---|
| 517 | Chiral | 4-({2-[(4-bromo-3-methylphenyl)amino]-1-methyl-1 H-benzimidazol-5-yl}oxy)-N-[(3R)-pyrrolidin-3-yl]pyridine-2-carboxamide | 522.4 | 483 |
| 518 | 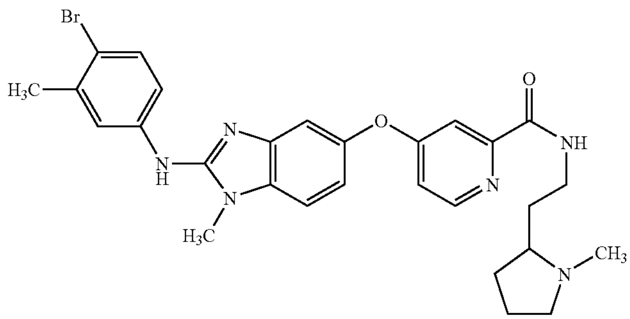 | 4-({2-[(4-bromo-3-methylphenyl)amino]-1-methyl-1 H-benzimidazol-5-yl}oxy)-N-[2-(1-methyl-pyrrolidin-2-yl)ethyl]-pyridine-2-carboxamide | 564.5 | 483 |
| 519 | 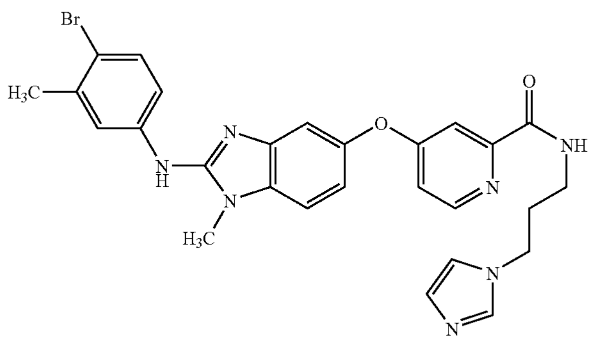 | 4-({2-[(4-bromo-3-methylphenyl)amino]-1-methyl-1 H-benzimidazol-5-yl}oxy)-N-[3-(1 H-imidazol-1-yl)propyl]pyridine-2-carboxamide | 561.5 | 483 |
| 520 | 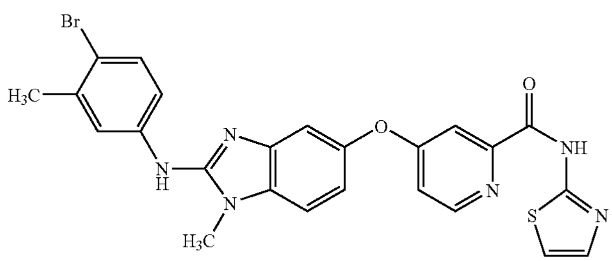 | 4-({2-[(4-bromo-3-methylphenyl)amino]-1-methyl-1 H-benzimidazol-5-yl}oxy)-N-1,3-thiazol-2-yl-pyridine-2-carboxamide | 536.4 | 483 |
| 521 | 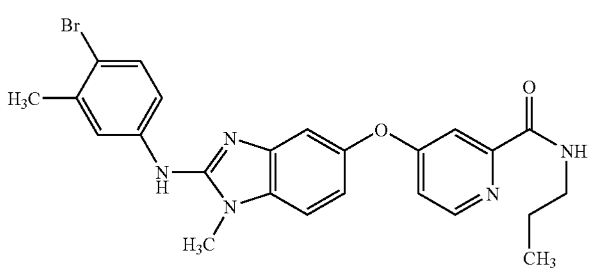 | 4-({2-[(4-bromo-3-methylphenyl)amino]-1-methyl-1 H-benzimidazol-5-yl}oxy)-N-propylpyridine-2-carboxamide | 495.4 | 483 |

TABLE 6-continued

| Example | Molecular Structure | Name | MH+ | Synthesized as in Example: |
|---|---|---|---|---|
| 522 | 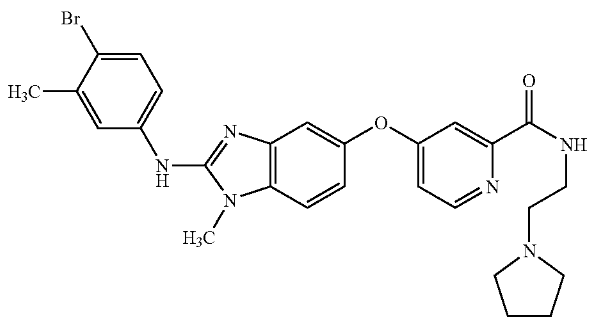 | 4-({2-[(4-bromo-3-methylphenyl)amino]-1-methyl-1 H-benzimidazol-5-yl}oxy)-N-(2-pyrrolidin-1-ylethyl)pyridine-2-carboxamide | 550.5 | 483 |
| 523 | 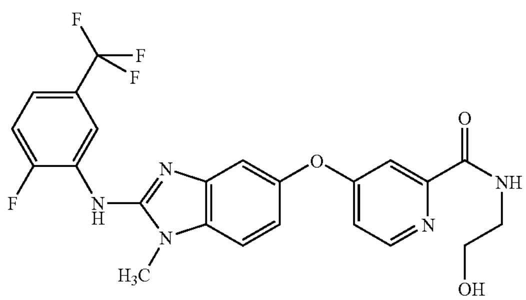 | 4-[(2-{[2-fluoro-5-(tri-fluoromethyl)phenyl]amino}-1-methyl-1 H-benzimidazol-5-yl)oxy]-N-(2-hydroxyethyl)pyridine-2-carboxamide | 490.4 | 484 |
| 524 | 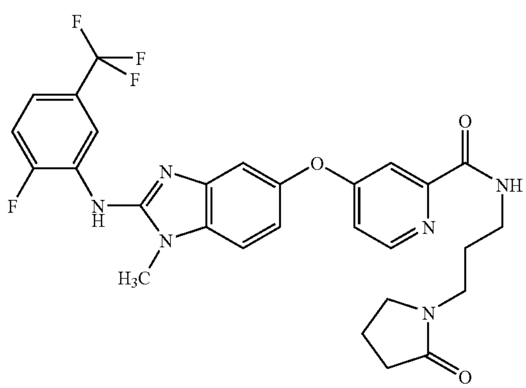 | 4-[(2-{[2-fluoro-5-(tri-fluoromethyl)phenyl]amino}-1-methyl-1 H-benzimidazol-5-yl)oxy]-N-[3-(2-oxopyrrolidin-1-yl)propyl]pyridine-2-carboxamide | 571.5 | 484 |
| 525 | 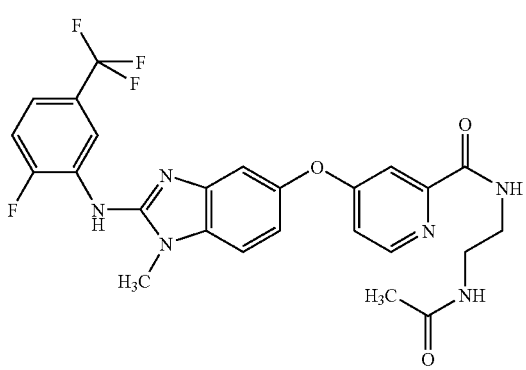 | N-[2-(acetylamino)ethyl]-4-[(2-{[2-fluoro-5-(trifluoromethyl)-phenyl]amino}-1-methyl-1 H-benzimidazol-5-yl)oxy]-pyridine-2-carboxamide | 531.5 | 484 |

TABLE 6-continued

| Example | Molecular Structure | Name | MH+ | Synthesized as in Example: |
|---|---|---|---|---|
| 526 | 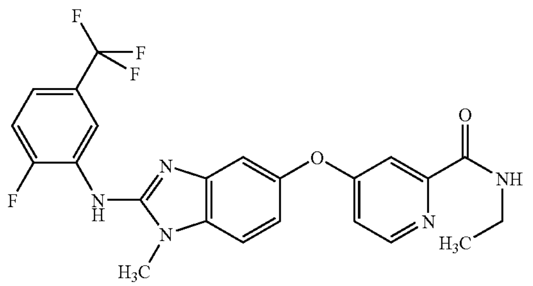 | N-ethyl-4-[(2-{[2-fluoro-5-(trifluoromethyl)-phenyl]amino}-1-methyl-1H-benzimidazol-5-yl)oxy]-pyridine-2-carboxamide | 474.4 | 484 |
| 527 | 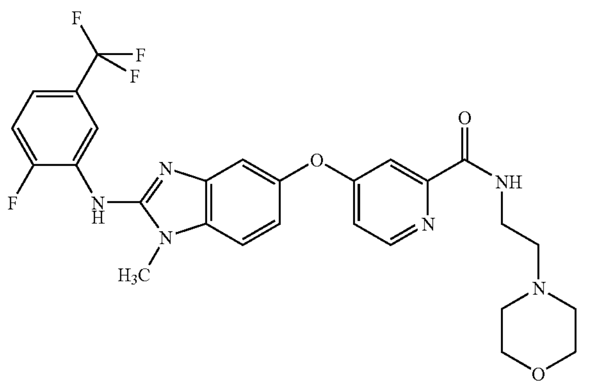 | 4-[(2-{[2-fluoro-5-(trifluoromethyl)phenyl]amino}-1-methyl-1H-benzimidazol-5-yl)oxy]-N-(2-morpholin-4-yl-ethyl)pyridine-2-carboxamide | 559.5 | 484 |
| 528 | 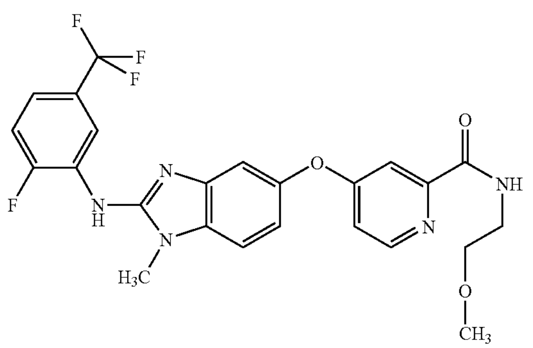 | 4-[(2-{[2-fluoro-5-(trifluoromethyl)phenyl]amino}-1-methyl-1H-benzimidazol-5-yl)oxy]-N-[2-(methyloxy)ethyl]-pyridine-2-carboxamide | 504.5 | 484 |
| 529 | 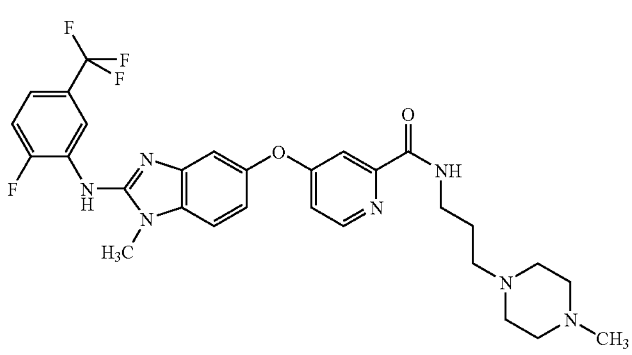 | 4-[(2-{[2-fluoro-5-(trifluoromethyl)phenyl]amino}-1-methyl-1H-benzimidazol-5-yl)oxy]-N-[3-(4-methylpiperazin-1-yl)propyl]pyridine-2-carboxamide | 586.6 | 484 |

TABLE 6-continued

| Example | Molecular Structure | Name | MH+ | Synthesized as in Example: |
|---|---|---|---|---|
| 530 | 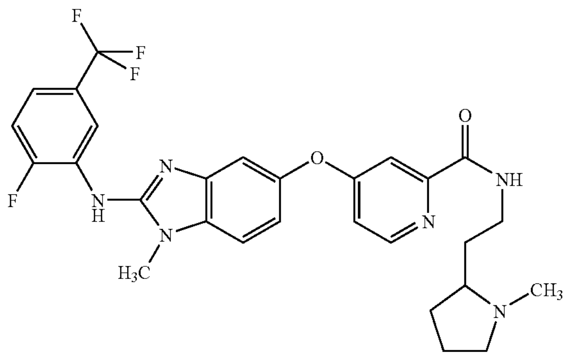 | 4-[(2-{[2-fluoro-5-(tri-fluoromethyl)phenyl]amino}-1-methyl-1 H-benzimidazol-5-yl)oxy]-N-[2-(1-methyl-pyrrolidin-2-yl)ethyl]pyridine-2-carboxamide | 557.6 | 484 |
| 531 | 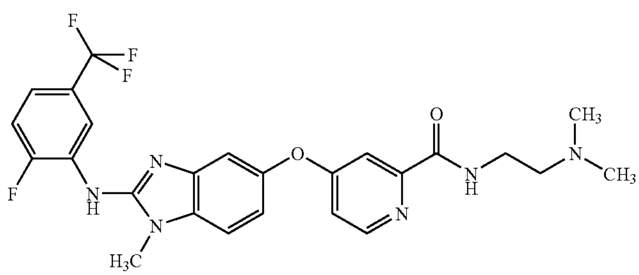 | N-[2-(dimethylamino)-ethyl]-4-[(2-{[2-fluoro-5-(trifluoromethyl)-phenyl]amino}-1-methyl-1 H-benzimidazol-5-yl)oxy]-pyridine-2-carboxamide | 517.5 | 484 |
| 532 | 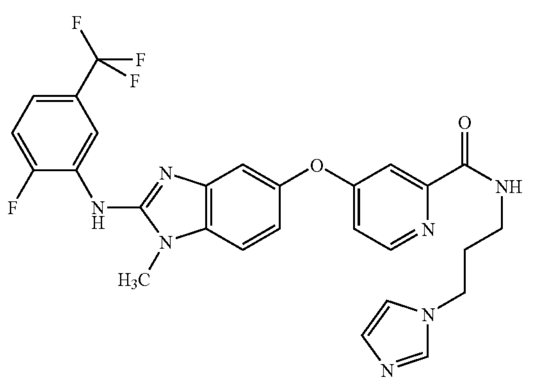 | 4-[(2-{[2-fluoro-5-(tri-fluoromethyl)phenyl]amino}-1-methyl-1 H-benzimidazol-5-yl)oxy]-N-[3-(1 H-imidazol-1-yl)-propyl]pyridine-2-carboxamide | 554.5 | 484 |
| 533 | 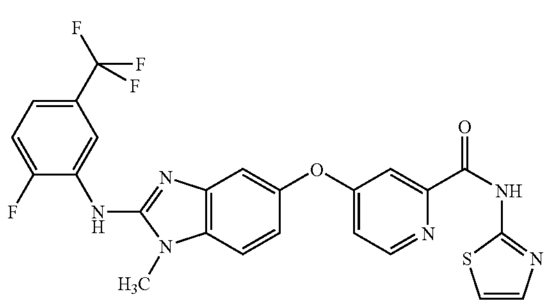 | 4-[(2-{[2-fluoro-5-(tri-fluoromethyl)phenyl]amino}-1-methyl-1 H-benzimidazol-5-yl)oxy]-N-1,3-thiazol-2-ylpyridine-2-carboxamide | 529.5 | 484 |

TABLE 6-continued

| Example | Name | MH+ | Synthesized as in Example: |
|---|---|---|---|
| 534 | 4-[(2-{[2-fluoro-5-(tri-fluoromethyl)phenyl]amino}-1-methyl-1H-benzimidazol-5-yl)oxy]-N-[2-pyridin-4-ylethyl)-pyridine-2-carboxamide | 551.5 | 484 |
| 535 | 4-[(2-{[2-fluoro-5-(tri-fluoromethyl)phenyl]amino}-1-methyl-1H-benzimidazol-5-yl)oxy]-N-propylpyridine-2-carboxamide | 488.5 | 484 |
| 536 | 4-[(2-{[2-fluoro-5-(tri-fluoromethyl)phenyl]amino}-1-methyl-1H-benzimidazol-5-yl)oxy]-N-(2-pyrrolidin-1-ylethyl)-pyridine-2-carboxamide | 543.5 | 484 |
| 537 | 4-({2-[(4-bromo-3-fluorophenyl)amino]-1-methyl-1H-benzimidazol-5-yl}oxy)-N-[(1-ethylpyrrolidin-2-yl)methyl]pyridine-2-carboxamide | 568.5 | 485 |

TABLE 6-continued

| Example | Molecular Structure | Name | MH+ | Synthesized as in Example: |
|---|---|---|---|---|
| 538 | 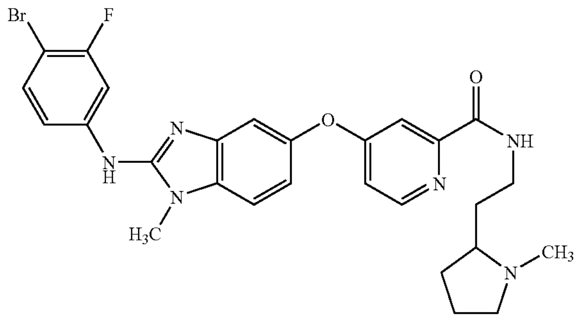 | 4-({2-[(4-bromo-3-fluorophenyl)amino]-1-methyl-1H-benzimidazol-5-yl}oxy)-N-[2-(1-methyl-pyrrolidin-2-yl)ethyl]-pyridine-2-carboxamide | 568.5 | 485 |
| 539 | 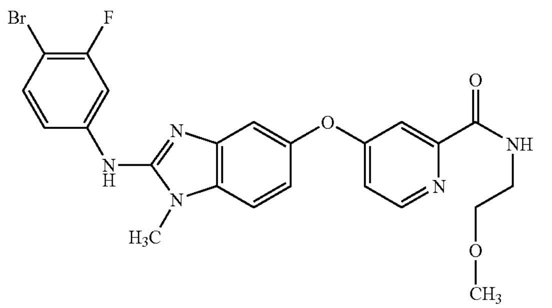 | 4-({2-[(4-bromo-3-fluorophenyl)amino]-1-methyl-1H-benzimidazol-5-yl}oxy)-N-[2-(methyloxy)ethyl]pyridine-2-carboxamide | 515.4 | 485 |
| 540 | 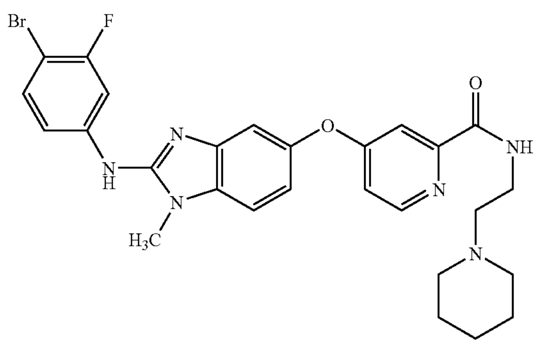 | 4-({2-[(4-bromo-3-fluorophenyl)amino]-1-methyl-1H-benzimidazol-5-yl}oxy)-N-(2-piperidin-1-ylethyl)pyridine-2-carboxamide | 568.5 | 485 |
| 541 | 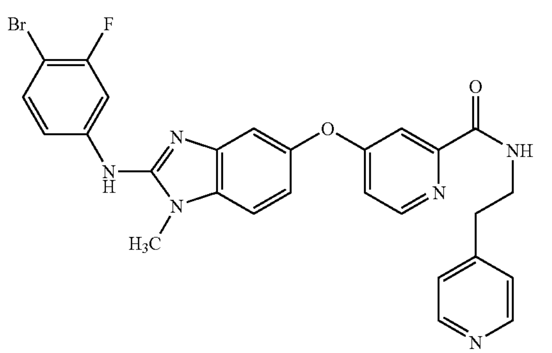 | 4-({2-[(4-bromo-3-fluorophenyl)amino]-1-methyl-1H-benzimidazol-5-yl}oxy)-N-(2-pyridin-4-ylethyl)pyridine-2-carboxamide | 562.4 | 485 |

TABLE 6-continued

| Example | Name | MH+ | Synthesized as in Example: |
|---|---|---|---|
| 542 | 4-({2-[(4-bromo-3-fluorophenyl)amino]-1-methyl-1 H-benzimidazol-5-yl}oxy)-N-[3-(methyloxy)-propyl]pyridine-2-carboxamide | 529.4 | 485 |
| 543 | 4-({2-[(4-bromo-3-fluorophenyl)amino]-1-methyl-1 H-benzimidazol-5-yl}oxy)-N-propylpyridine-2-carboxamide | 499.4 | 485 |
| 544 | 4-({2-[(4-bromo-3-fluorophenyl)amino]-1-methyl-1 H-benzimidazol-5-yl}oxy)-N-ethylpyridine-2-carboxamide | 485.3 | 485 |
| 545 | 4-({2-[(4-bromo-3-fluorophenyl)amino]-1-methyl-1 H-benzimidazol-5-yl}oxy)-N-[(3R)-pyrrolidin-3-yl]pyridine-2-carboxamide | 526.4 | 485 |
| 546 | 4-({2-[(4-bromo-3-fluorophenyl)amino]-1-methyl-1 H-benzimidazol-5-yl}oxy)-N-[3-2-oxopyrrolidin-1-yl)propyl]pyridine-2-carboxamide | 582.4 | 485 |

TABLE 6-continued

| Example | Molecular Structure | Name | MH+ | Synthesized as in Example: |
|---------|---------------------|------|-----|----------------------------|
| 547 | 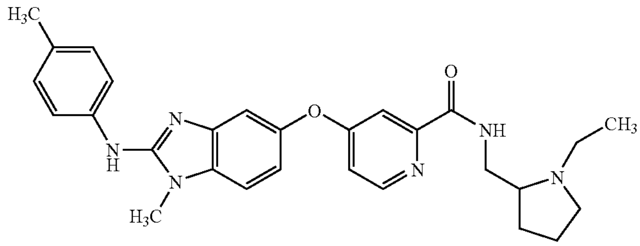 | N-[(1-ethylpyrrolidin-2-yl)methyl]-4-({1-methyl-2-[(4-methylphenyl)amino]-1 H-benzimidazol-5-yl}-oxy)pyridine-2-carboxamide | 485.6 | 486 |
| 548 | 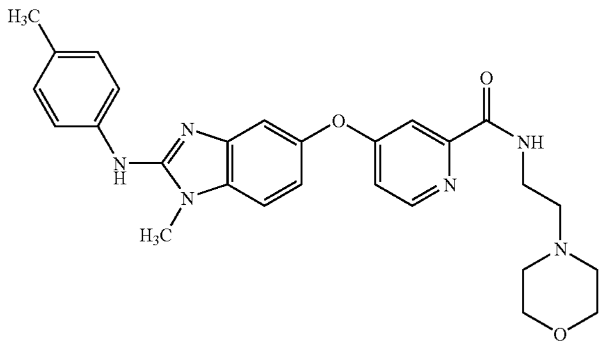 | 4-({1-methyl-2-[(4-methylphenyl)amino]-1 H-benzimidazol-5-yl}oxy)-N-(2-morpholin-4-ylethyl)pyridine-2-carboxamide | 487.6 | 486 |
| 549 | 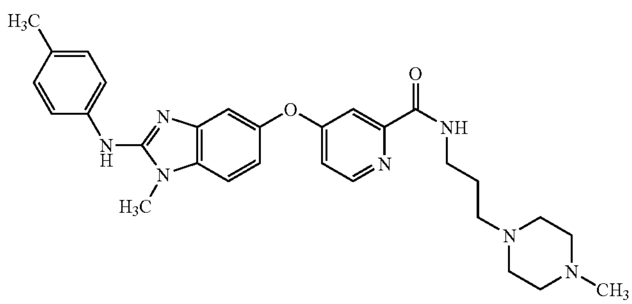 | 4-({1-methyl-2-[(4-methylphenyl)amino]-1 H-benzimidazol-5-yl}oxy)-N-[3-(4-methylpiperazin-1-yl)propyl]pyridine-2-carboxamide | 514.6 | 486 |
| 550 | 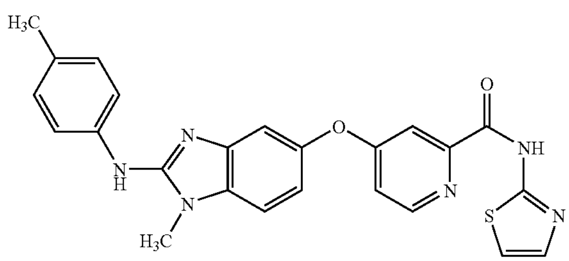 | 4-({1-methyl-2-[(4-methylphenyl)amino]-1 H-benzimidazol-5-yl}oxy)-N-1,3-thiazol-2-ylpyridine-2-carboxamide | 457.5 | 486 |
| 551 | 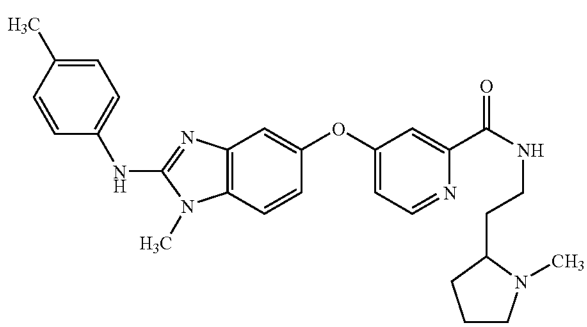 | 4-({1-methyl-2-[(4-methylphenyl)amino]-1 H-benzimidazol-5-yl}oxy)-N-[2-(1-methylpyrrolidin-2-yl)ethyl]pyridine-2-carboxamide | 485.6 | 486 |

TABLE 6-continued

| Example | Molecular Structure | Name | MH+ | Synthesized as in Example: |
|---|---|---|---|---|
| 552 | 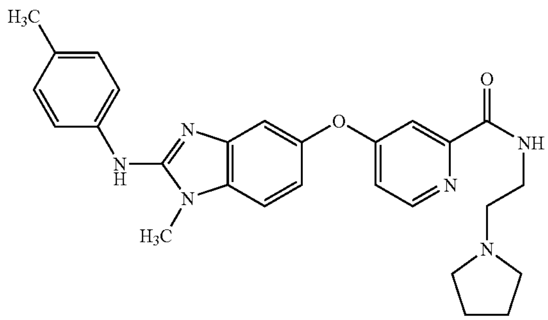 | 4-({1-methyl-2-[(4-methylphenyl)amino]-1 H-benzimidazol-5-yl}oxy)-N-(2-pyrrolidin-1-ylethyl)pyridine-2-carboxamide | 471.6 | 486 |
| 553 | 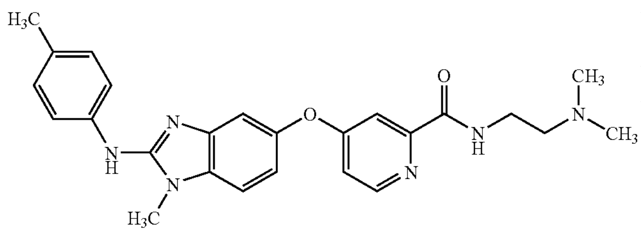 | N-[2-(dimethylamino)-ethyl]4-({1-methyl-2-[(4-methylphenyl)amino]-1 H-benzimidazol-5-yl}oxy)pyridine-2-carboxamide | 445.5 | 486 |
| 554 | 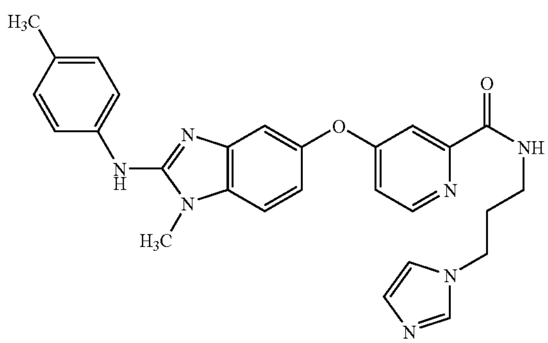 | N-[3-(1 H-imidazol-1-yl)propyl]-4-({1-methyl-2-[(4-methylphenyl)amino]-1 H-benzimidazol-5-yl}oxy)pyridine-2-carboxamide | 482.6 | 486 |
| 555 | 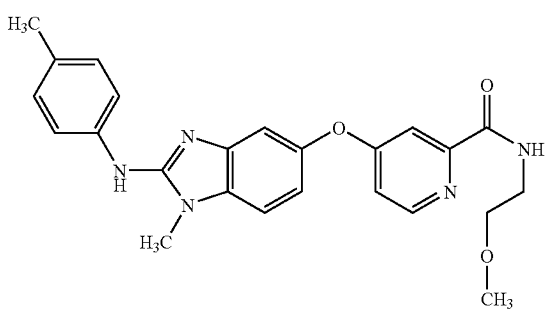 | 4-({1-methyl-2-[(4-methyl-phenyl)amino]-1 H-benzimidazol-5-yl}oxy)-N-[2-(methyloxy)ethyl]-pyridine-2-carboxamide | 432.5 | 486 |
| 556 | 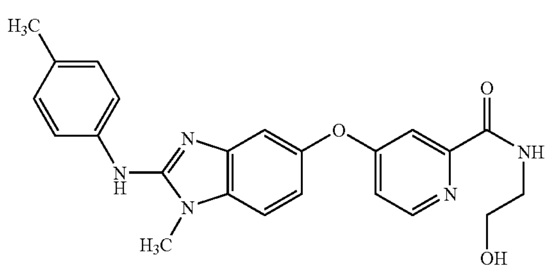 | N-(2-hydroxyethyl)-4-({1-methyl-2-[(4-methyl-phenyl)amino]-1 H-benzimidazol-5-yl}oxy)-pyridine-2-carboxamide | 418.5 | 486 |

TABLE 6-continued

| Example | Molecular Structure | Name | MH+ | Synthesized as in Example: |
|---|---|---|---|---|
| 557 | 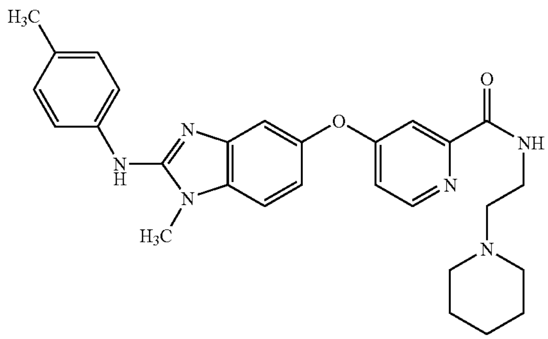 | 4-({1-methyl-2-[(4-methylphenyl)amino]-1 H-benzimidazol-5-yl}oxy)-N-(2-piperidin-1-ylethyl)pyridine-2-carboxamide | 485.6 | 486 |
| 558 | 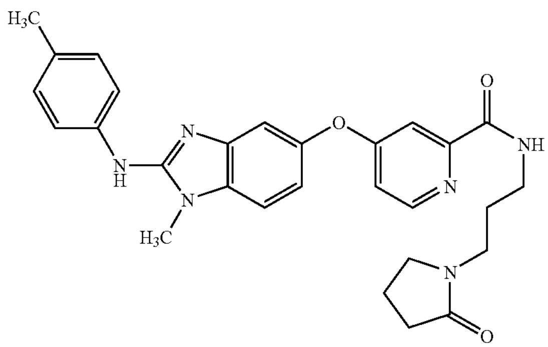 | 4-({1-methyl-2-[(4-methylphenyl)amino]-1 H-benzimidazol-5-yl}oxy)-N-[3-(2-oxopyrrolidin-1-yl)propyl]pyridine-2-carboxamide | 499.6 | 486 |
| 559 | 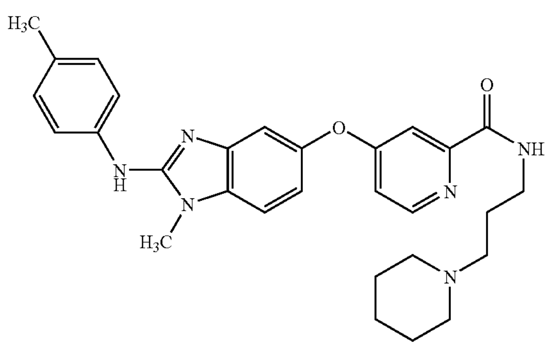 | 4-({1-methyl-2-[(4-methyl-phenyl)amino]-1 H-benzimidazol-5-yl}oxy)-N-(3-piperidin-1-ylpropyl)pyridine-2-carboxamide | 499.6 | 486 |
| 560 | 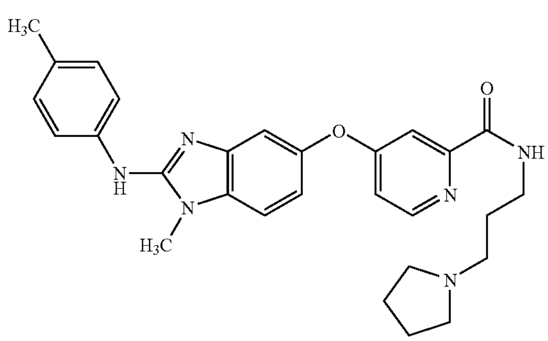 | 4-({1-methyl-2-[(4-methyl-phenyl)amino]-1 H-benzimidazol-5-yl}oxy)-N-(3-pyrrolidin-1-ylpropyl)pyridine-2-carboxamide | 485.6 | 486 |

TABLE 6-continued

| Example | Molecular Structure | Name | MH+ | Synthesized as in Example: |
|---|---|---|---|---|
| 561 | 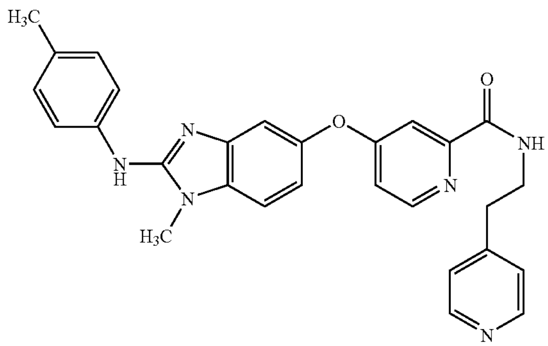 | 4-({1-methyl-2-[(4-methylphenyl)amino]-1 H-benzimidazol-5-yl}oxy)-N-(2-pyridin-4-yl-ethyl)pyridine-2-carboxamide | 479.6 | 486 |
| 562 | 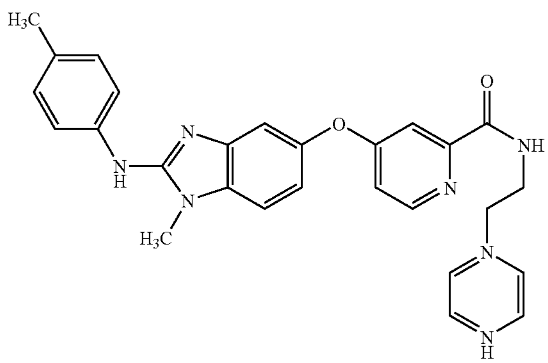 | 4-({1-methyl-2-[(4-methylphenyl)amino]-1 H-benzimidazol-5-yl}oxy)-N-(2-piperazin-1-yl-ethyl)pyridine-2-carboxamide | 486.6 | 486 |
| 563 | 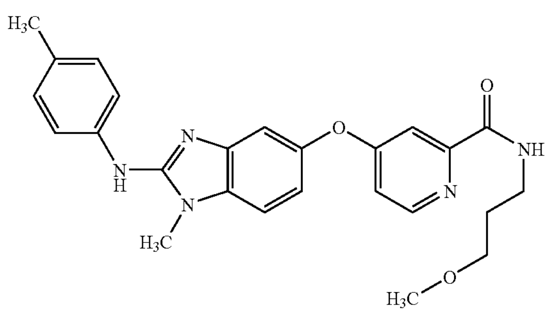 | 4-({1-methyl-2-[(4-methylphenyl)amino]-1 H-benzimidazol-5-yl}oxy)-N-[3-(methyloxy)-propyl]pyridine-2-carboxamide | 446.5 | 486 |
| 564 | 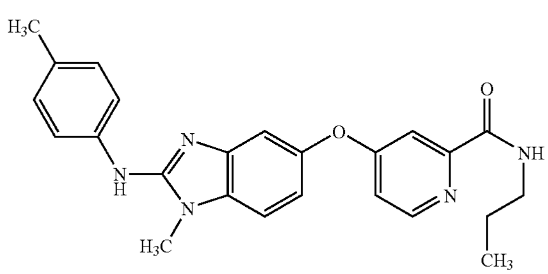 | 4-({1-methyl-2-[(4-methylphenyl)amino]-1 H-benzimidazol-5-yl}oxy)-N-propylpyridine-2-carboxamide | 416.5 | 486 |
| 565 | 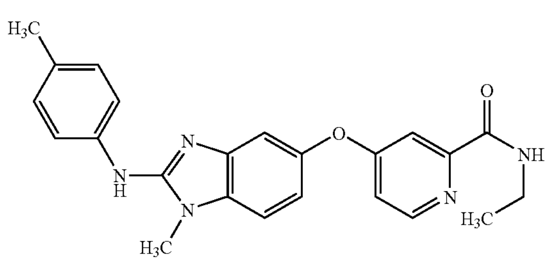 | N-ethyl-4-({1-methyl-2-[(4-methylphenyl)amino]-1 H-benzimidazol-5-yl}oxy)-pyridine-2-carboxamide | 402.5 | 486 |

TABLE 6-continued

| Example | Name | MH+ | Synthesized as in Example: |
|---|---|---|---|
| 566 | N-[2-(acetylamino)ethyl]-4-({1-methyl-2-[(4-methylphenyl)amino]-1 H-benzimidazol-5-yl}oxy)-pyridine-2-carboxamide | 459.5 | 486 |
| 567 | 4-({1-methyl-2-[(4-methylphenyl)amino]-1 H-benzimidazol-5-yl}oxy)-N-[2-(2-oxoimidazolidin-1-yl)ethyl]pyridine-2-carboxamide | 486.5 | 486 |
| 568 | 4-({1-methyl-2-[(4-methylphenyl)amino]-1 H-benzimidazol-5-yl}oxy)-N-[(3R)-pyrrolidin-3-yl]pyridine-2-carboxamide | 443.5 | 486 |
| 569 | 4-({2-[(4-ethylphenyl)amino]-1-methyl-1 H-benzimidazol-5-yl}oxy)-N-[(1-ethylpyrrolidin-2-yl)methyl]pyridine-2-carboxamide | 499.6 | 487 |

TABLE 6-continued

| Example | Molecular Structure | Name | MH+ | Synthesized as in Example: |
|---|---|---|---|---|
| 570 | 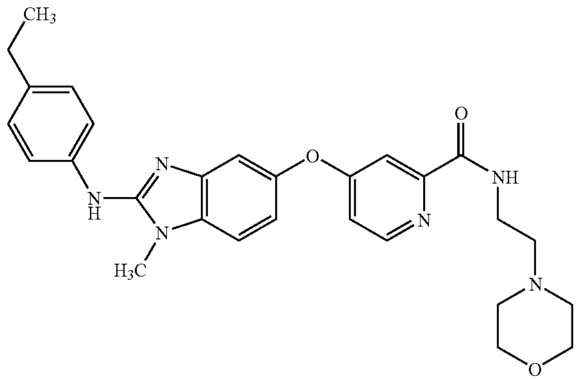 | 4-({2-[(4-ethylphenyl)-amino]-1-methyl-1 H-benzimidazol-5-yl}oxy)-N-(2-morpholin-4-ylethyl)-pyridine-2-carboxamide | 501.6 | 487 |
| 571 | 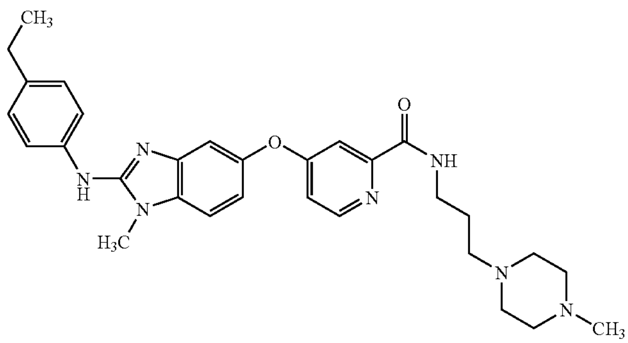 | 4-({2-[(4-ethylphenyl)-amino]-1-methyl-1 H-benzimidazol-5-yl}oxy)-N-[3-(4-methylpiperazin-1-yl)propyl]pyridine-2-carboxamide | 528.7 | 487 |
| 572 | 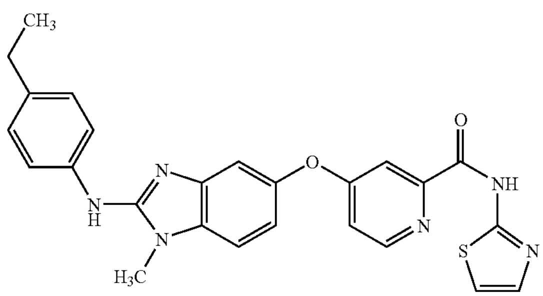 | 4-({2-[(4-ethylphenyl)-amino]-1-methyl-1 H-benzimidazol-5-yl}oxy)-N-1,3-thiazol-2-ylpyridine-2-carboxamide | 471.6 | 487 |
| 573 | 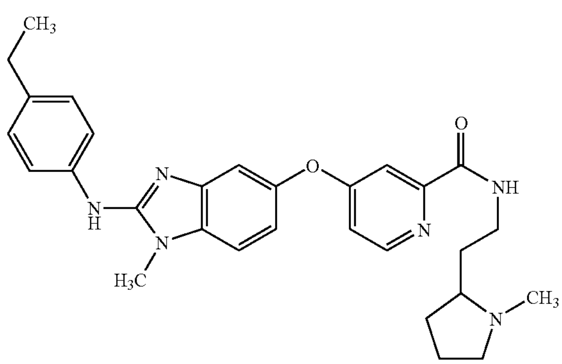 | 4-({2-[(4-ethylphenyl)-amino]-1-methyl-1 H-benzimidazol-5-yl}oxy)-N-[2-(1-methylpyrrolidin-2-yl)ethyl]pyridine-2-carboxamide | 499.6 | 487 |

TABLE 6-continued

| Example | Molecular Structure | Name | MH+ | Synthesized as in Example: |
|---|---|---|---|---|
| 574 | 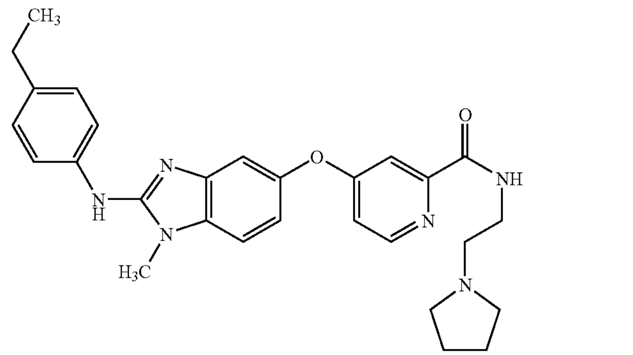 | 4-({2-[(4-ethylphenyl)-amino]-1-methyl-1 H-benzimidazol-5-yl}oxy)-N-(2-pyrrolidin-1-ylethyl)-pyridine-2-carboxamide | 485.6 | 487 |
| 575 | 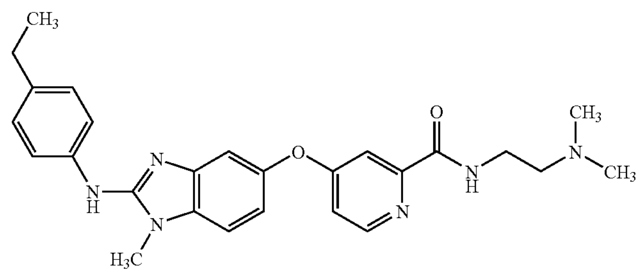 | N-[2-(dimethylamino)-ethyl]-4-({2-[(4-ethyl-phenyl)amino]-1-methyl-1 H-benzimidazol-5-yl}-oxy)pyridine-2-carboxamide | 459.6 | 487 |
| 576 | 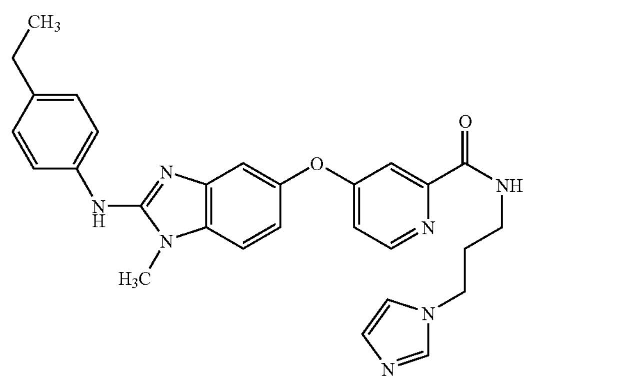 | 4-({2-[(4-ethylphenyl)-amino]-1-methyl-1 H-benzimidazol-5-yl}oxy)-N-[3-(1 H-imidazol-1-yl)-propyl]pyridine-2-carboxamide | 496.6 | 487 |
| 577 | 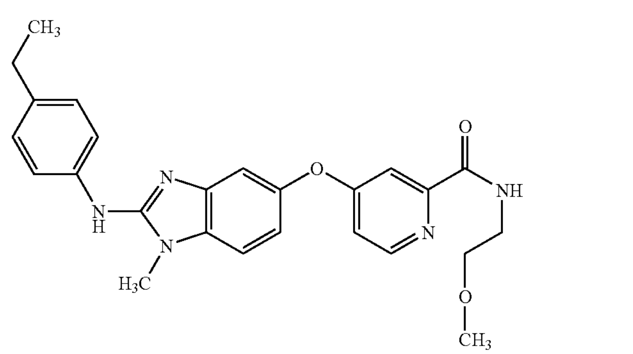 | 4-({2-[(4-ethylphenyl)-amino]-1-methyl-1 H-benzimidazol-5-yl}oxy)-N-[2-(methyloxy)ethyl]-pyridine-2-carboxamide | 446.5 | 487 |

TABLE 6-continued

| Example | Molecular Structure | Name | MH+ | Synthesized as in Example: |
|---|---|---|---|---|
| 578 | 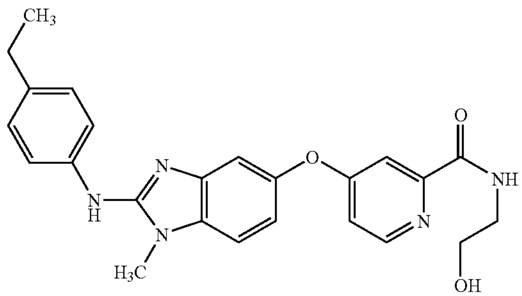 | 4-({2-[(4-ethylphenyl)-amino]-1-methyl-1 H-benzimidazol-5-yl}oxy)-N-(2-hydroxyethyl)pyridine-2-carboxamide | 432.5 | 487 |
| 579 | 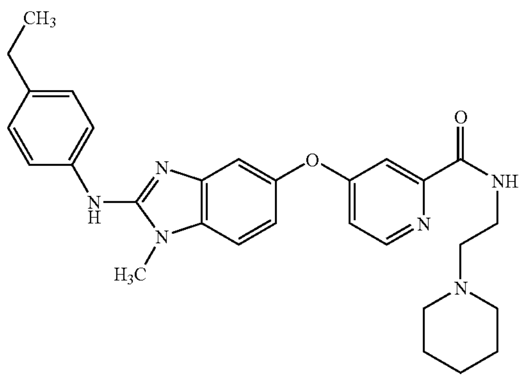 | 4-({2-[(4-ethylphenyl)-amino]-1-methyl-1 H-benzimidazol-5-yl}oxy)-N-(2-piperidin-1-ylethyl)-pyridine-2-carboxamide | 499.6 | 487 |
| 580 | 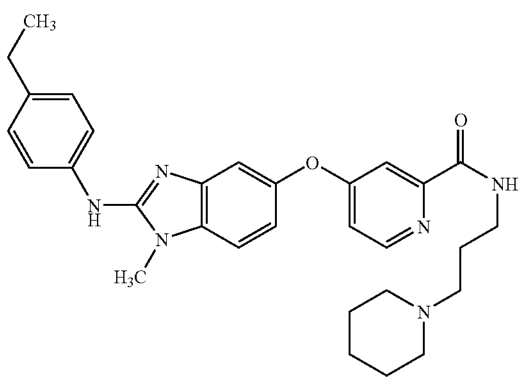 | 4-({2-[(4-ethylphenyl)-amino]-1-methyl-1 H-benzimidazol-5-yl}oxy)-N-(3-piperidin-2-ylpropyl)-pyridine-2-carboxamide | 513.7 | 487 |
| 581 | 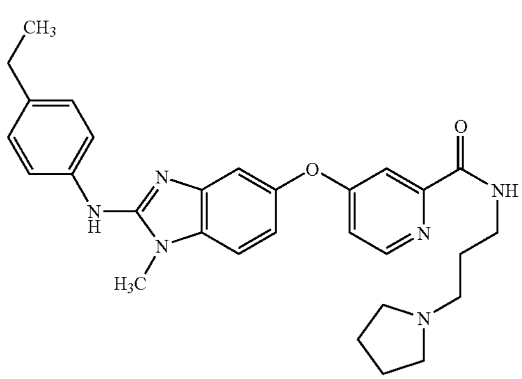 | 4-({2-[(4-ethylphenyl)-amino]-1-methyl-1 H-benzimidazol-5-yl}oxy)-N-(3-pyrrolidin-1-yl-propyl)pyridine-2-carboxamide | 499.6 | 487 |

TABLE 6-continued

| Example | Molecular Structure | Name | MH+ | Synthesized as in Example: |
|---|---|---|---|---|
| 582 | 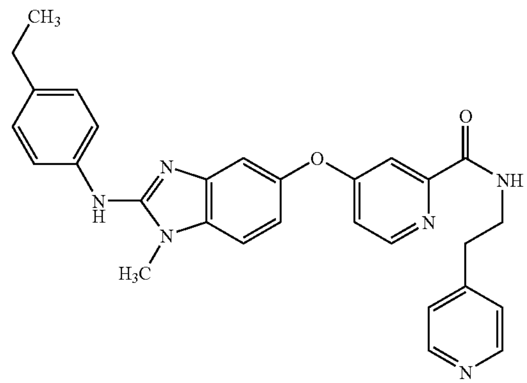 | 4-({2-[(4-ethylphenyl)-amino]-1-methyl-1 H-benzimidazol-5-yl}oxy)-N-(2-pyridine-4-ylethyl)-pyridine-2-carboxamide | 493.6 | 487 |
| 583 | 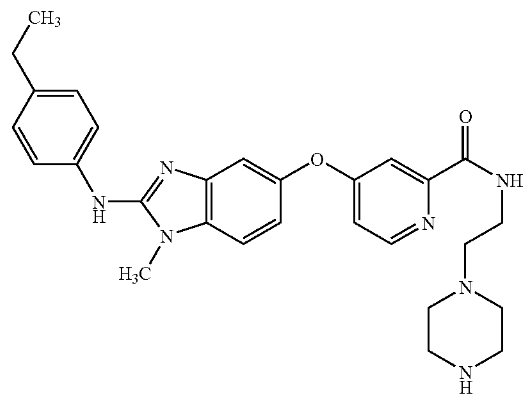 | 4-({2-[(4-ethylphenyl)-amino]-1-methyl-1 H-benzimidazol-5-yl}oxy)-N-(2-piperazin-1-ylethyl)-pyridine-2-carboxamide | 500.6 | 487 |
| 584 | 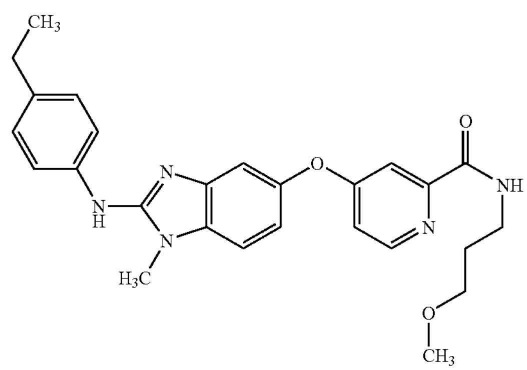 | 4-({2-[(4-ethylphenyl)-amino]-1-methyl-1 H-benzimidazol-5-yl}oxy)-N-[3-(methyloxy)propyl]-pyridine-2-carboxamide | 460.5 | 487 |
| 585 | 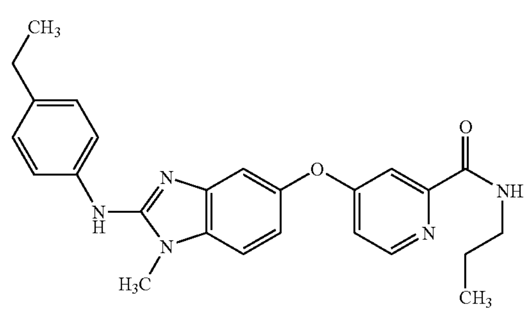 | 4-({2-[(4-ethylphenyl)-amino]-1-methyl-1 H-benzimidazol-5-yl}oxy)-N-propylpyridine-2-carboxamide | 430.5 | 487 |

TABLE 6-continued

| Example | Molecular Structure | Name | MH+ | Synthesized as in Example: |
|---|---|---|---|---|
| 586 | 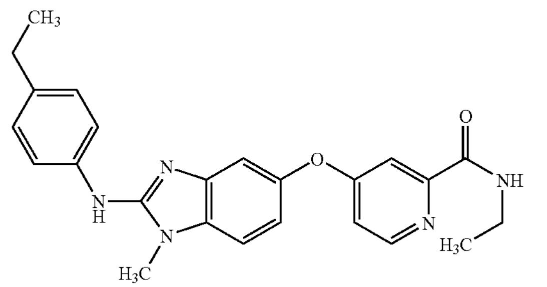 | N-ethyl-4-({2-[(4-ethyl-phenyl)-amino]-1-methyl-1H-benzimidazol-5-yl}-oxy)pyridine-2-carboxamide | 416.5 | 487 |
| 587 | 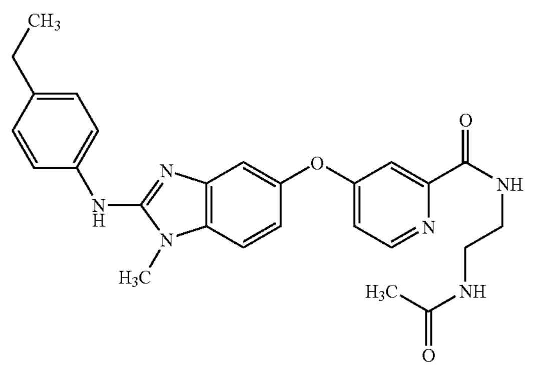 | N-[2-(acetylamino)ethyl]-4-({2-[(4-ethylphenyl)amino]-1-methyl-1H-benzimidazol-5-yl}oxy)pyridine-2-carboxamide | 473.5 | 487 |
| 588 | 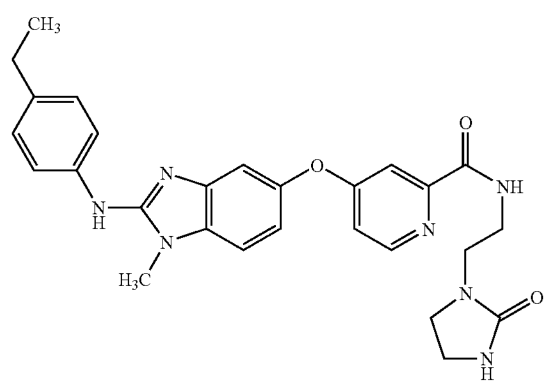 | 4-({2-[(4-ethylphenyl)-amino]-1-methyl-1H-benzimidazol-5-yl}oxy)-N-[2-(2-oxoimidazolidin-1-yl)ethyl]pyridine-2-carboxamide | 500.6 | 487 |
| 589 | 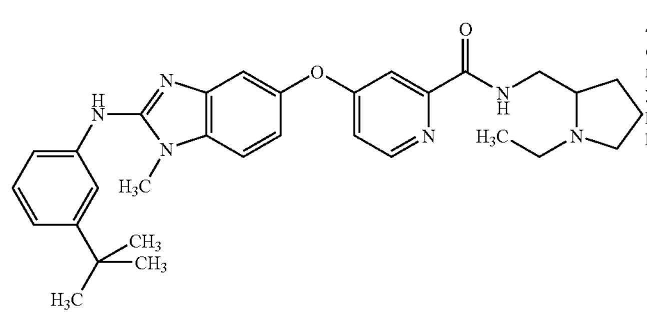 | 4-[(2-{[3-(1,1-dimethyl-ethyl)phenyl]amino}-1-methyl-1H-benzimidazol-5-yl)oxy]-N-[(1-ethyl-pyrrolidin-2-yl)methyl]-pyridine-2-carboxamide | 527.7 | 488 |

TABLE 6-continued

| Example | Molecular Structure | Name | MH+ | Synthesized as in Example: |
|---|---|---|---|---|
| 590 | 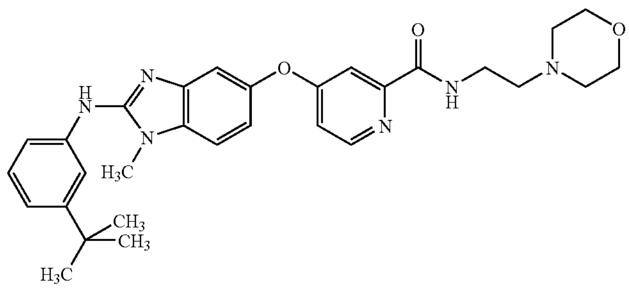 | 4-[(2-{[3-(1,1-dimethyl-ethyl)phenyl]amino}-1-methyl-1H-benzimidazol-5-yl)oxy]-N-(2-morpholin-4-ylethyl)pyridine-2-carboxamide | 529.7 | 488 |
| 591 | 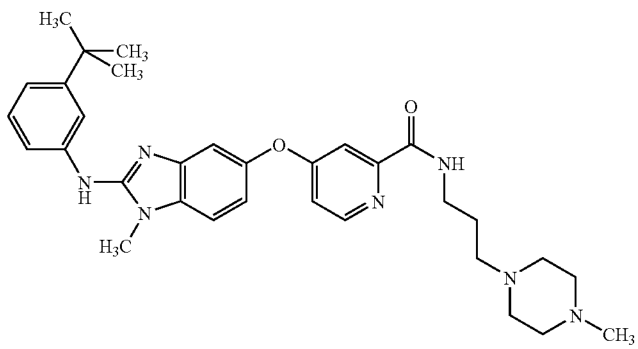 | 4-[(2-{[3-(1,1-dimethyl-ethyl)phenyl]amino}-1-methyl-1H-benzimidazol-5-yl)oxy]-N-[3-(4-methylpiperazin-1-yl)propyl]pyridine-2-carboxamide | 556.7 | 488 |
| 592 | 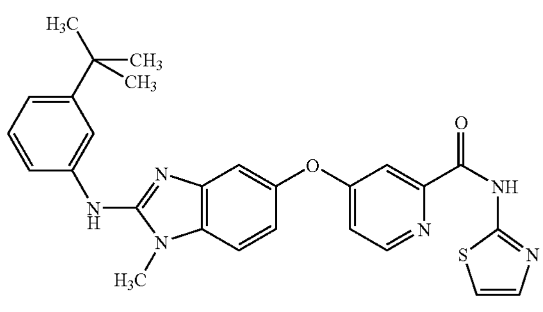 | 4-[(2-{[3-(1,1-dimethyl-ethyl)phenyl]amino}-1-methyl-1H-benzimidazol-5-yl)oxy]-N-1,3-thiazol-2-yl-pyridine-2-carboxamide | 499.6 | 488 |
| 593 | 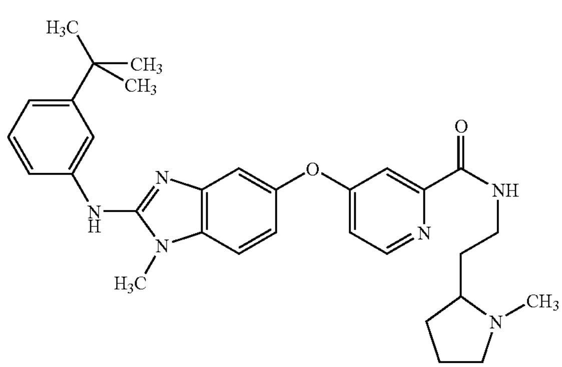 | 4-[(2-{[3-(1,1-dimethyl-ethyl)phenyl]amino}-1-methyl-1H-benzimidazol-5-yl)oxy]-N-[2-(1-methyl-pyrrolidin-2-yl)ethyl]-pyridine-2-carboxamide | 527.7 | 488 |

TABLE 6-continued

| Example | Molecular Structure | Name | MH+ | Synthesized as in Example: |
|---|---|---|---|---|
| 594 | 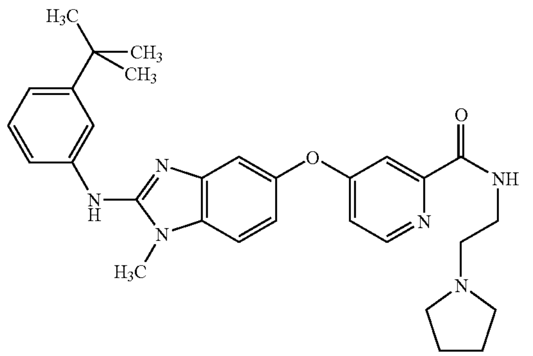 | 4-[(2-{[3-(1,1-dimethyl-ethyl)phenyl]amino}-1-methyl 1 H-benzimidazol-5-yl)oxy]-N-(2-pyrrolidin-1-ylethyl)pyridine-2-carboxamide | 513.7 | 488 |
| 595 | 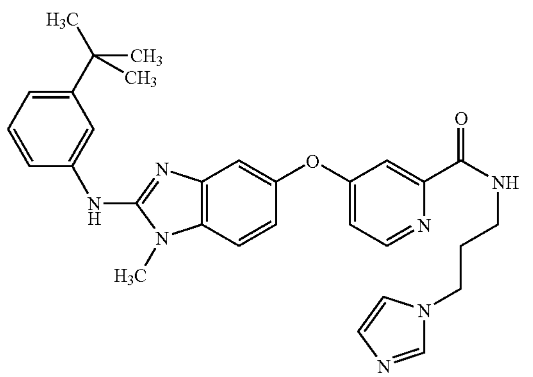 | 4-[(2-{[3-(1,1-dimethyl-ethyl)phenyl]amino}-1-methyl-1 H-benzimidazol-5-yl)oxy]-N-[3-(1 H-imidazol-1-yl)propyl]pyridine-2-carboxamide | 524.6 | 488 |
| 596 | 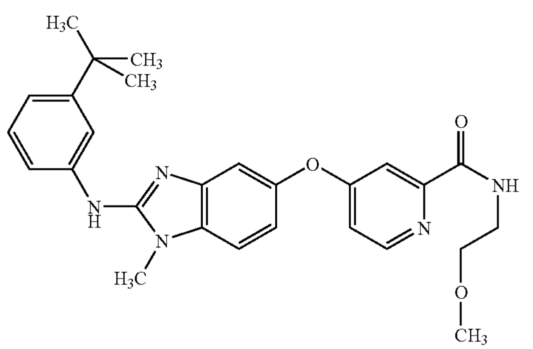 | 4-[(2-{[3-(1,1-dimethyl-ethyl)phenyl]amino}-1-methyl-1 H-benzimidazol-5-yl)oxy]-N-[2-(methyloxy)ethyl]pyridine-2-carboxamide | 474.6 | 488 |
| 597 | 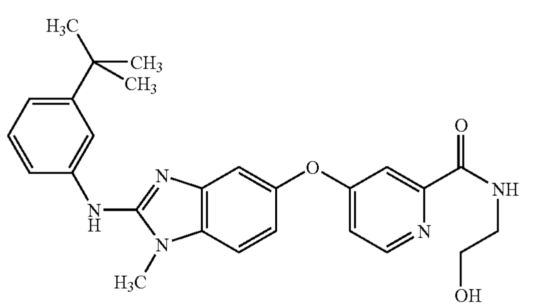 | 4-[(2-{[3-(1,1-dimethyl-ethyl)phenyl]amino}-1-methyl-1 H-benzimidazol-5-yl)oxy]-N-(2-hydroxyethyl)pyridine-2-carboxamide | 460.5 | 488 |

TABLE 6-continued

| Example | Molecular Structure | Name | MH+ | Synthesized as in Example: |
|---|---|---|---|---|
| 598 | 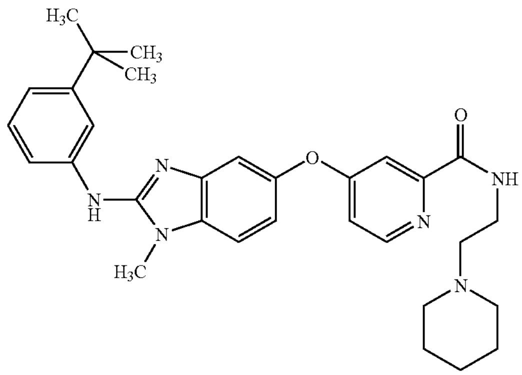 | 4-[(2-{[3-(1,1-dimethyl-ethyl)phenyl]amino}-1-methyl 1 H-benzimidazol-5-yl)oxy]-N-(2-piperidin-1-yl-ethyl)pyridine-2-carboxamide | 527.7 | 488 |
| 599 | 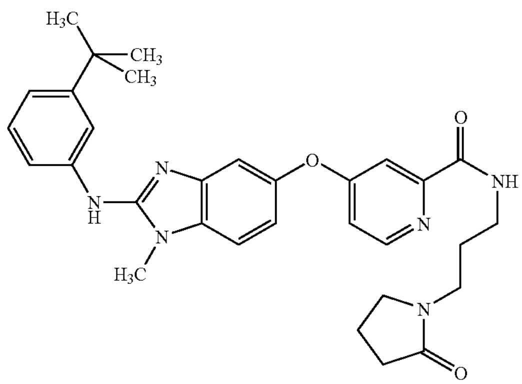 | 4-[(2-{[3-(1,1-dimethyl-ethyl)phenyl]amino}-1-methyl 1 H-benzimidazol-5-yl)oxy]-N-[3-(2-oxopyrrolidin-1-yl)propyl]pyridine-2-carboxamide | 541.7 | 488 |
| 600 | 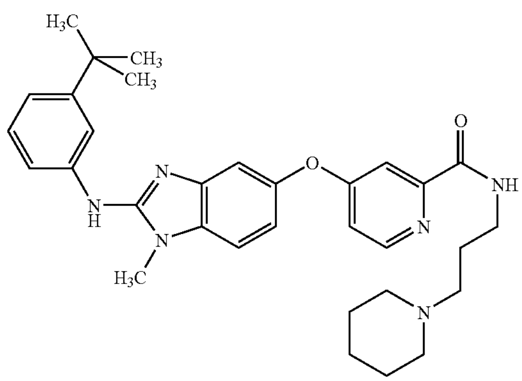 | 4-[(2-{[3-(1,1-dimethyl-ethyl)phenyl]amino}-1-methyl 1 H-benzimidazol-5-yl)oxy]-N-(3-piperidin-1-yl-propyl)pyridine-2-carboxamide | 541.7 | 488 |
| 601 | 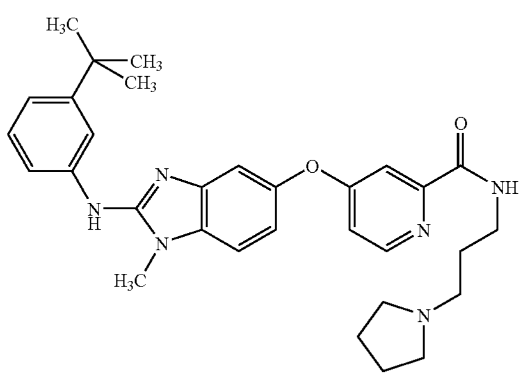 | 4-[(2-{[3-(1,1-dimethyl-ethyl)phenyl]amino}-1-methyl 1 H-benzimidazol-5-yl)oxy]-N-(3-pyrrolidin-1-ylpropyl)pyridine-2-carboxamide | 527.7 | 488 |

TABLE 6-continued

| Example | Molecular Structure | Name | MH+ | Synthesized as in Example: |
|---|---|---|---|---|
| 602 | 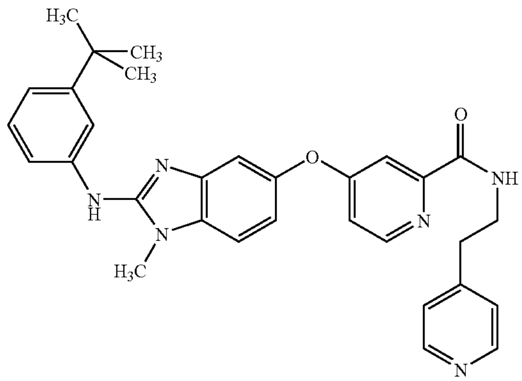 | 4-[(2-{[3-(1,1-dimethyl-ethyl)phenyl]amino}-1-methyl-1H-benzimidazol-5-yl)oxy]-N-(2-pyridin-4-ylethyl)pyridine-2-carboxamide | 521.6 | 488 |
| 603 | 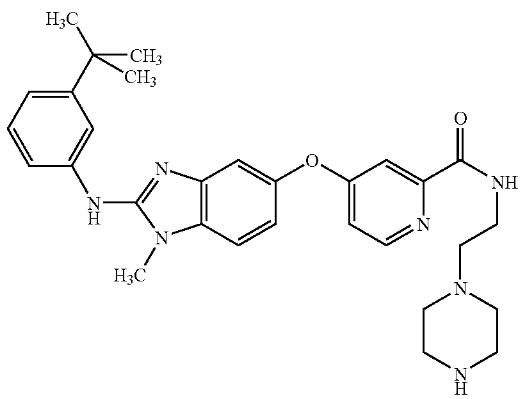 | 4-[(2-{[3-(1,1-dimethyl-ethyl)phenyl]amino}-1-methyl-1H-benzimidazol-5-yl)oxy]-N-(2-piperazin-1-ylethyl)pyridine-2-carboxamide | 528.7 | 488 |
| 604 | 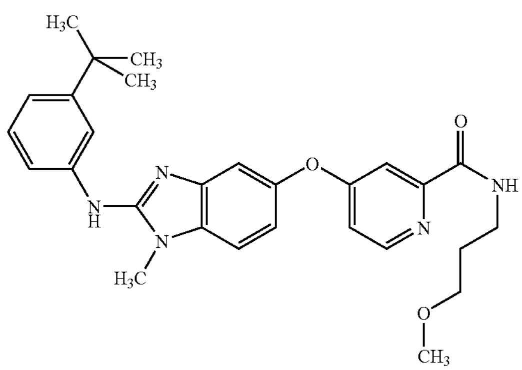 | 4-[(2-{[3-(1,1-dimethyl-ethyl)phenyl]amino}-1-methyl-1H-benzimidazol-5-yl)oxy]-N-[3-(methyloxy)-propyl]pyridine-2-carboxamide | 488.6 | 488 |
| 605 | 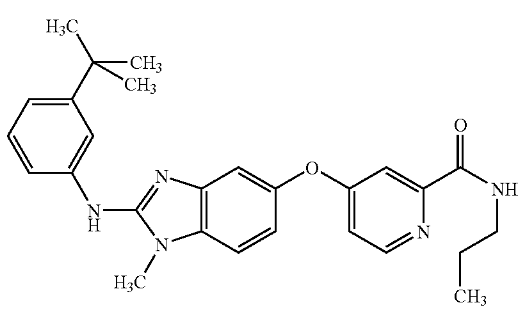 | 4-[(2-{[3-(1,1-dimethyl-ethyl)phenyl]amino}-1-methyl-1H-benzimidazol-5-yl)oxy]-N-propylpyridine-2-carboxamide | 458.6 | 488 |

TABLE 6-continued

| Example | Molecular Structure | Name | MH+ | Synthesized as in Example: |
|---|---|---|---|---|
| 606 | 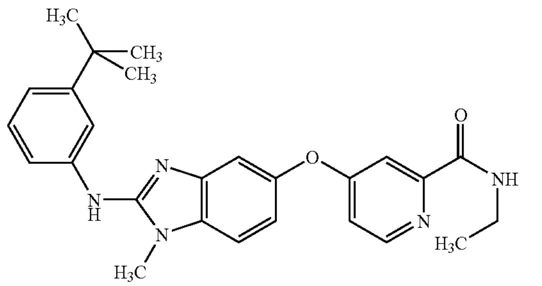 | 4-[(2-{[3-(1,1-dimethyl-ethyl)phenyl]amino}-1-methyl-1 H-benzimidazol-5-yl)oxy]-N-ethylpyridine-2-carboxamide | 444.5 | 488 |
| 607 | 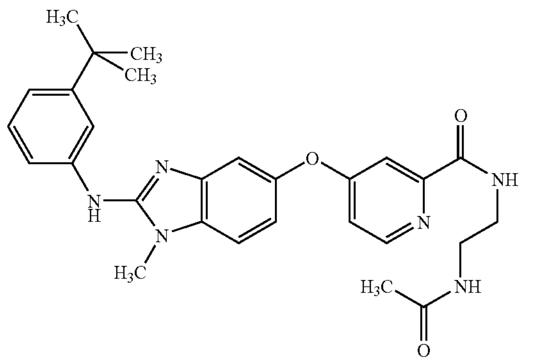 | N-[2-(acetylamino)ethyl]-4-[(2-{[3-(1,1-di-methylethyl)phenyl]-amino}-1-methyl-1 H-benzimidazol-5-yl)oxy]-pyridine-2-carboxamide | 501.6 | 488 |
| 608 | 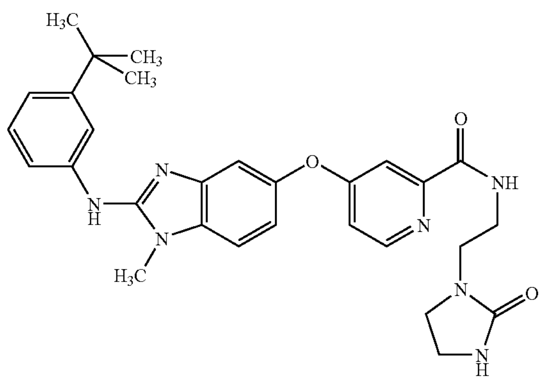 | 4-[(2-{[3-(1,1-dimethyl-ethyl)phenyl]-amino}-1-methyl-1 H-benzimidazol-5-yl)oxy]-N-[2-(2-oxo-imidazolidin-1-yl)ethyl]-pyridine-2-carboxamide | 528.6 | 488 |
| 609 | 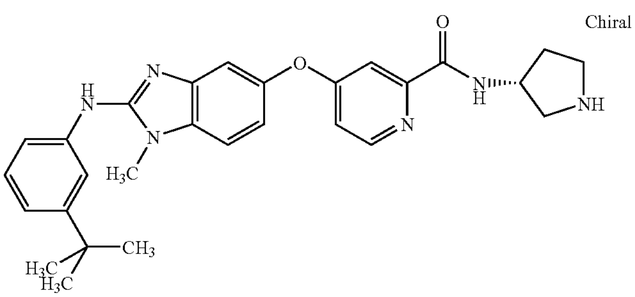 | Chiral 4-[(2-{[3-(1,1-dimethyl-ethyl)phenyl]amino}-1-methyl-1 H-benzimidazol-5-yl)oxy]-N-[(3R)-pyrrolidin-3-yl]pyridine-2-carboxamide | 485.6 | 489 |

TABLE 6-continued

| Example | Molecular Structure | Name | MH+ | Synthesized as in Example: |
|---|---|---|---|---|
| 610 | 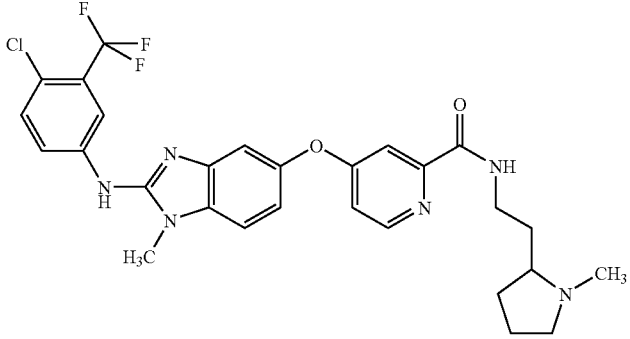 | 4-[(2-{[4-chloro-3-(tri-fluoromethyl)phenyl]amino}-1-methyl-1 H-benzimidazol-5-yl)oxy]-N-[2-(1-methylpyrrolidin-2-yl)ethyl]pyridine-2-carboxamide | 574.0 | 489 |
| 611 | 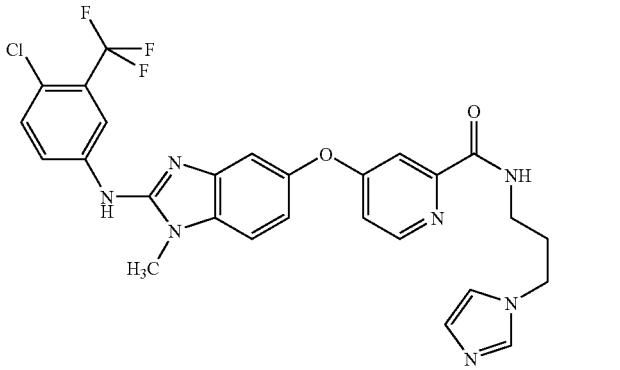 | 4-[(2-{[4-chloro-3-(trifluoromethyl)phenyl]amino}-1-methyl-1 H-benzimidazol-5-yl)oxy]-N-[3-(1 H-imidazol-1-yl)propyl]pyridine-2-carboxamide | 571.0 | 489 |
| 612 | 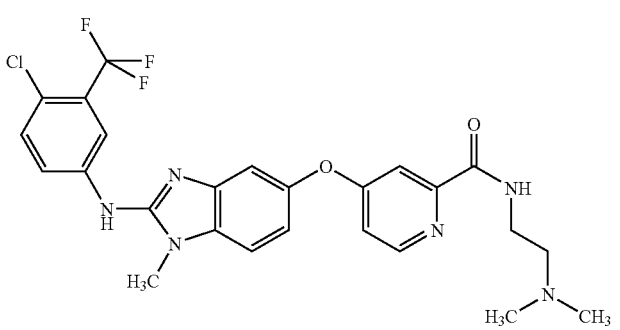 | 4-[(2-{[4-chloro-3-(trifluoromethyl)phenyl]amino}-1-methyl-1 H-benzimidazol-5-yl)oxy]-N-[2-(dimethylamino)-ethyl]pyridine-2-carboxamide | 534.0 | 489 |
| 613 | 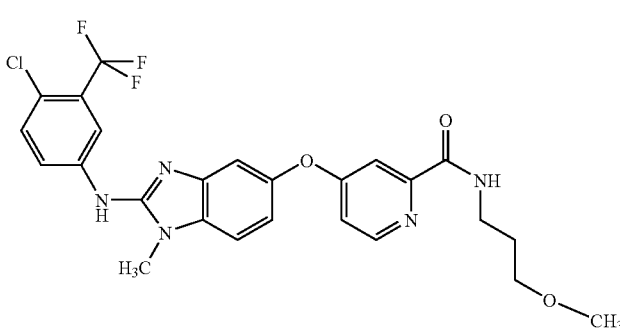 | 4-[(2-{[4-chloro-3-(trifluoromethyl)phenyl]amino}-1-methyl-1 H-benzimidazol-5-yl)oxy]-N-[3-(methyloxy)propyl]-pyridine-2-carboxamide | 534.9 | 489 |

TABLE 6-continued

| Example | Name | MH+ | Synthesized as in Example: |
|---|---|---|---|
| 614 | 4-[(2-{[4-chloro-3-(tri-fluoromethyl)phenyl]amino}-1-methyl-1 H-benzimidazol-5-yl)oxy]-N-propylpyridine-2-carboxamide | 504.9 | 489 |
| 615 | 4-[(2-{[4-chloro-3-(tri fluoromethyl)phenyl]amino}-1-methyl-1 H-benzimidazol-5-yl)oxy]-N-ethylpyridine-2-carboxamide | 490.9 | 489 |
| 616 | N-[2-(acetylamino)ethyl]-4-[(2-{[4-chloro-3-(trifluoromethyl)-phenyl]amino}-1-methyl-1 H-benzimidazol-5-yl)oxy]-pyridine-2-carboxamide | 547.9 | 489 |
| 617 | 4-[(2-{[4-chloro-3-(tri-fluoromethyl)phenyl]-amino}-1-methyl-1 H-benzimidazol-5-yl)oxy]-N-(2-morpholin-4-yl-ethyl)pyridine-2-carboxamide | 576.0 | 489 |
| 618 | 4-[(2-{[4-chloro-3-(tri-fluoromethyl)phenyl]amino}-1-methyl-1 H-benzimidazol-5-yl)oxy]-N-[3-(4-methylpiperazin-1-yl)propyl]pyridine-2-carboxamide | 603.1 | 489 |

TABLE 6-continued

| Example | Molecular Structure | Name | MH+ | Synthesized as in Example: |
|---|---|---|---|---|
| 619 | 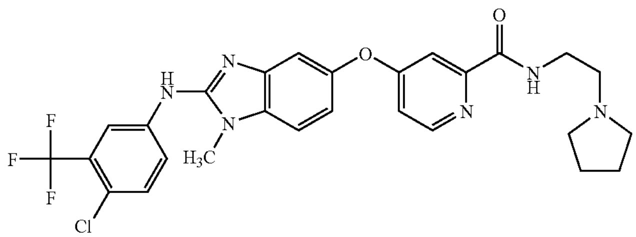 | 4-[(2-{[4-chloro-3-(trifluoromethyl)phenyl]amino}-1-methyl-1H-benzimidazol-5-yl)oxy]-N-(2-pyrrolidin-1-ylethyl)pyridine-2-carboxamide | 560.0 | 489 |
| 620 | 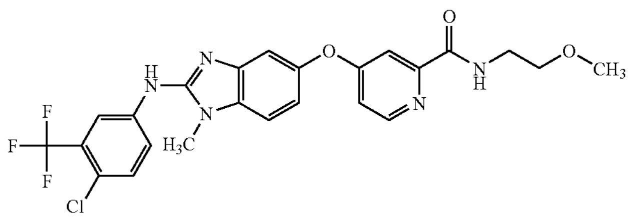 | 4-[(2-{[4-chloro-3-(trifluoromethyl)phenyl]amino}-1-methyl-1H-benzimidazol-5-yl)oxy]-N-[2-(methyloxy)ethyl]-pyridine-2-carboxamide | 520.9 | 489 |
| 621 | 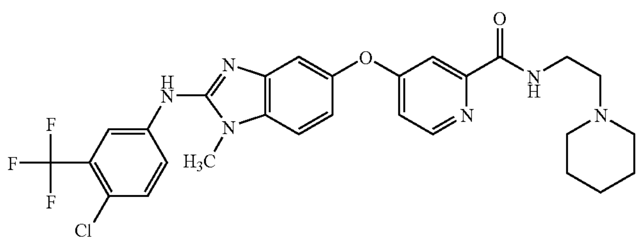 | 4-[(2-{[4-chloro-3-(trifluoromethyl)phenyl]amino}-1-methyl-1H-benzimidazol-5-yl)oxy]-N-(2-piperidin-1-ylethyl)-pyridine-2-carboxamide | 574.0 | 489 |
| 622 | 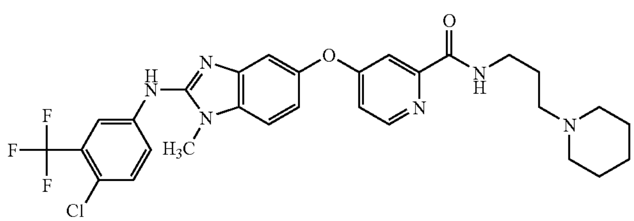 | 4-[(2-{[4-chloro-3-(trifluoromethyl)phenyl]amino}-1-methyl-1H-benzimidazol-5-yl)oxy]-N-(3-piperidin-1-yl-propyl)pyridine-2-carboxamide | 588.0 | 489 |
| 623 | 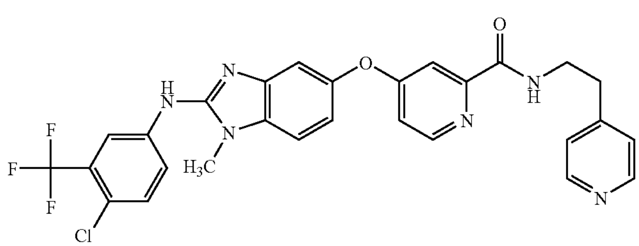 | 4-[(2-{[4-chloro-3-(tri-fluoromethyl)phenyl]-amino}-1-methyl-1H-benzimidazol-5-yl)oxy]-N-(2-pyridin-4-ylethyl)-pyridine-2-carboxamide | 568.0 | 489 |
| 624 | 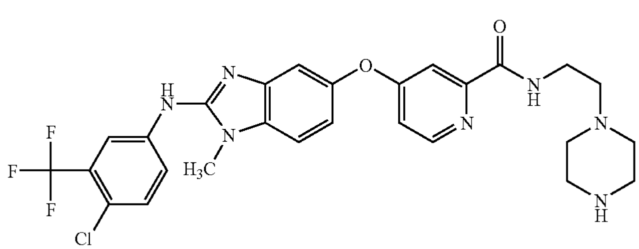 | 4-[(2-{[4-chloro-3-(trifluoromethyl)phenyl]amino}-1-methyl-1H-benzimidazol-5-yl)oxy]-N-(2-piperazin-1-ylethyl)-pyridine-2-carboxamide | 575.0 | 489 |

TABLE 6-continued

| Example | Molecular Structure | Name | MH+ | Synthesized as in Example: |
|---|---|---|---|---|
| 625 | Chiral | 4-[(2-{[4-chloro-3-(trifluoromethyl)phenyl]amino}-1-methyl-1 H-benzimidazol-5-yl)oxy]-N-[(3R)-pyrrolidin-3-yl]-pyridine-2-carboxamide | 531.9 | 489 |
| 626 | 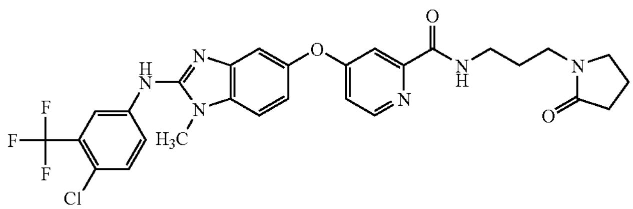 | 4-[(2-{[4-chloro-3-(trifluoromethyl)phenyl]amino}-1-methyl-1 H-benzimidazol-5-yl)oxy]-N-[3-(2-oxopyrrolidin-1-yl)propyl]pyridine-2-carboxamide | 588.0 | 489 |

Example 627

Step 1. Synthesis of [4-(2-{[4-(chloromethyl)phenyl]carbonylamino)-1-methylbenzimidazol-5-yloxy)(2-pyridyl)]-N-methylcarboxamide A solution of sodium thiocyanate (1 eq) in acetone was added slowly in to a solution of 4-(chloromethyl)benzoyl-chloride (1 eq) in acetone at 0° C. The mixture was then filtered in to a solution of {4-[3-amino-4-(methylamino)phenoxy](2-pyridyl)}-N-methylcarboxamide (1 eq) in acetone. Formation of N-acylthiourea was followed by LC/MS. The mixture was concentrated and taken in tetrahydrofuran and to it was added 1-ethyl-(3-dimethylaminopropyl)carbodiimide-hydrochloride (2 eq) and stirred at ambient temperature for 16 h. The mixture was concentrated and partitioned between ethyl acetate and water. The organic layer was then dried and concentrated to yield [4-(2-{[4-(chloromethyl)phenyl]carbonylamino)-1-methylbenzimidazol-5-yloxy)(2-pyridyl)]-N-methylcarboxamide. MS: MH+=449.

Step 2. Synthesis of N-methyl {4-[1-methyl-2-({4-[(4-methylpiperazinyl)methyl]phenyl}carbonylamino)benzimidazol-5-yloxy](2-pyridyl)}carboxamide

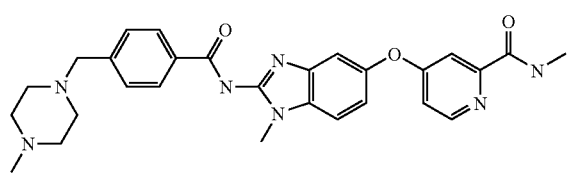

To a solution of [4-(2-{[4-(chloromethyl)phenyl]carbonylamino)-1-methylbenzimidazol-5-yloxy)(2-pyridyl)]-N-methylcarboxamide[4-(2-{[4-(chloromethyl)phenyl]carbonylamino}-1-methylbenzimidazol-5-yloxy)(2-pyridyl)]-N-methylcarboxamide (1 eq) in tetrahydrofuran was added methylpiperazine (4 eq) and stirred at ambient temperature for 16 h. The reaction mixture was concentrated and purified on preparative chromatography to yield N-methyl {4-[1-methyl-2-({4-[(4-methylpiperazinyl)methyl]phenyl}carbonylamino)benzimidazol-5-yloxy](2-pyridyl)}carboxamide. MS: MH+=512.

Example 628

Step 1. Synthesis of N-methyl[4-(1-methyl-2-{2-{4-[(4-methylpiperazinyl)methylphenyl}-benzimidazol-5-yloxy)(2-pyridyl)]carboxamide To a solution of {4-[3-amino-4-(methylamino)phenoxy](2-pyridyl)}-N-methylcarboxamide (1 eq) in tetrhydrofuran was added 4-(chloromethyl)benzoylchloride (1 eq) and triethylamine (2 eq). N-acylation is completed in 0.5 h. The reaction mixture was concentrated and partitioned between ethyl acetate and water. The organic layer was concentrated and to the crude product was added methylpiperazine (4 eq) and tetrahydrofuran and stir for 16 h at ambient temperature. The reaction mixture was concentrated and partitioned between ethyl acetate and water. The organic layer was concentrated and taken in acetic acid and heated to 60° C. for 3 h. Preparative chromatography yielded N-methyl[4-(1-methyl-2-{2-{4-[(4-methylpiperazinyl)methylphenyl}-benzimidazol-5-yloxy)(2-pyridyl)]carboxamide. MS: MH+=470.

Example 629

Step 1. Synthesis of 2-chloro-4-(3-pyridyl)pyrimidine

Nitrogen was bubbled through a solution of 2,4-dichloropyrimidine (1 eq) in tetrahydrofuran and water (3:1) for 0.5 h. Bis(diphenylphosphino)ferrocene Palladium(II)chloride (0.05 eq) followed by pyridine-3-boronic acid (1 eq) and sodium carbonate (3 eq) was added and the mixture was heated to 60° C. for 16 h under nitrogen. The reaction mixture was concentrated and partitioned between ethyl acetate and water. The organic layer was washed with brine and dried with sodium sulfate and concentrated. Purification on silica gel gave 2-chloro-4-(3-pyridyl)pyrimidine. MS: MH$^+$=190.

Step 2. Synthesis of 2-nitro-4-(4-(3-pyridyl)pyrimidin-2-yloxy)phenylamine

A solution of 4-amino-3-nitro-phenol (1 eq) and 2-chloro-4-(3-pyridyl)pyrimidine (1 eq) in N,N-dimethylformamide was microwaved at 150° C. for 10 mins. The reaction mixture was partitioned between ethyl acetate and water. The organic layer was concentrated and purified on silica gel to yield 2-nitro-4-(4-(3-pyridyl)pyrimidin-2-yloxy)phenylamine. MS: MH$^+$=309.

Step 3. Synthesis of 4-(4-(3-pyridyl)pyrimidin-2-yloxy)benzene-1,2-diamine

The mixture containing 2-nitro-4-(4-(3-pyridyl)pyrimidin-2-yloxy)phenylamine in methanol with catalytic amount of 10% Pd/C was hydrogenated until disappearance of yellow color to yield 4-(4-(3-pyridyl)pyrimidin-2-yloxy)benzene-1,2-diamine. MS: MH$^+$=279.

Step 4. Synthesis of {4-[(4-methylpiperazinyl)methyl]phenyl}-N-[5-(4-(3-pyridyl)pyrimidin-2-yloxy)benzimidazol-2-yl]carboxamide

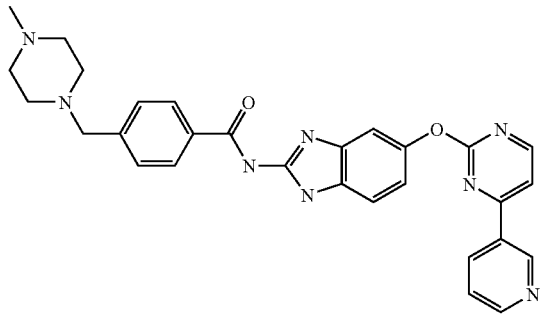

A solution of sodium thiocyanate (1 eq) in acetone was added slowly in to a solution of 4-(chloromethyl)benzoylchloride (1 eq) in acetone at 0° C. The mixture was then filtered in to a solution of 4-(4-(3-pyridyl)pyrimidin-2-yloxy)benzene-1,2-diamine (1 eq) in acetone. Formation of N-acylthiourea was followed by LC/MS. The mixture was concentrated and taken in tetrahydrofuran and to it was added 1-ethyl-(3-dimethylaminopropyl)carbodimidehydrochloride (2 eq) and stirred at ambient temperature for 16 h. The mixture was concentrated and partitioned between ethyl acetate and water. The organic layer was then dried and concentrated to yield [4-(chloromethyl)phenyl]-N-[5-(4-(3-pyridyl)pyrimidin-2-yloxy)benzimidazol-2-yl]carboxamide. It was taken in tetrahydrofuran and added methylpiperazine (4 eq) and stirred at ambient temperature for 16 h. The reaction mixture was concentrated and purified on preparative chromatography to yield {4-[(4-methylpiperazinyl)methyl]phenyl}-N-[5-(4-(3-pyridyl)pyrimidin-2-yloxy)benzimidazol-2-yl]carboxamide. MS: MH$^{30}$=520.

Example 630

Step 1. Synthesis of 4-ethyl-1-[(4-nitrophenyl)methylpiperazine

To 4-(chloromethyl)-1-nitrobenzene (1 eq) in tetrahydrofuran was added Ethylpiperazine (3 eq) and stir for 16 h at ambient temperature. Concentrating and passing through a plug of silica gave 4-ethyl-1-[(4-nitrophenyl)methylpiperazine. MS: MH$^+$=249

Step 2. Synthesis of 4-[(4-ethylpiperazinyl)methyl]phenylamine

The mixture containing 4-ethyl-1-[(nitrophenyl)methylpiperazine in methanol with catalytic amount of 10% Pd/C was hydrogenated to yield 4-[(4-ethylpiperazinyl)methyl]phenylamine. MS: MH$^+$=219.

Step 3. Synthesis of 4-[(4-ethylpiperazinyl)methyl]benzeneisothiocyanate

To 4-[(4-ethylpiperazinyl)methyl]phenylamine in acetone at 0° C. was added sodium bicarbonate (2 eq) and thiophosgene (2 eq). The mixture was brought to ambient temperature and concentrated and partitioned between ethyl acetate and water. The organic layer was dried with sodium bicarbonate and sodium sulfate and concentrated to yield 4-[(4-ethylpiperazinyl)methyl]benzeneisothiocyanate. MS: MH$^+$=261.

Step 4. Synthesis of [4-[(2-{[4-ethylpiperazinyl)methyl]phenyl]amino)-1-methylbenzimidazol-5-yloxy)(2-pyridyl)]-N-methylcarboxamide To 4-[(4-ethylpiperazinyl)methyl]benzeneisothiocyanate (1 eq) in methanol was added {4-[3-amino-4-(methylamino)phenoxy](2-pyridyl)}-N-methylcarboxamide (1 eq) and heated to 60° C. for 16 h. Preparative chromatography yielded [4-[(2-{[4-ethylpiperazinyl)methyl]phenyl]amino)-1-methylbenzimidazol-5-yloxy)(2-pyridyl)]-N-methylcarboxamide. MS: MH$^+$=499.

Example 631

Step 1. Synthesis of 4-Ethyl-1-(4-nitrophenyl)piperazine

To 4-fluoro-1-nitrobenzene (1 eq) in N,N-dimethylformamide was added Ethyl piperazine (2 eq) and N,N-diisopropylethyl amine (2 eq) and heated at 80° C. for 16 h. Concentrated the resultant mixture and partitioned between ethyl acetate and water. The organic layer was then washed with brine and dried with sodium sulfate and concentrated. Passed through a plug of silica to yield 4-Ethyl-1-(4-nitrophenyl)piperazine. MS: MH$^+$=235.

Step 2. Synthesis of 4-(4-ethylpiperazinyl)phenylamine

The mixture containing 4-ethyl-1-(4-nitrophenyl)piperazine in methanol with catalytic amount of 10% Pd/C was hydrogenated to yield 4-(4-ethylpiperazinyl)phenylamine. MS: MH$^+$=205.

Step 3. Synthesis of 4-(4-ethylpiperazinyl)benzeneisothiocyanate

To 4-(4-ethylpiperazinyl)phenylamine in acetone at 0° C. was added sodium bicarbonate (2 eq) and thiophosgene (2 eq). The mixture was brought to ambient temperature and concentrated and partitioned between ethyl acetate and water. The organic layer was dried with sodium bicarbonate and sodium sulfate and concentrated to yield 4-(4-ethylpiperazinyl)benzeneisothiocyanate. MS: MH+=247.

Step 3. Synthesis of [4-(2-{[4-ethylpiperazinyl)phenyl]amino)-1-methylbenzimidazol-5-yloxy)(2-pyridyl)]-N-methylcarboxamide To 4-(4-ethylpiperazinyl)benzeneisothiocyanate (1 eq) in methanol was added {4-[3-amino-4-(methylamino)phenoxy](2-pyridyl)}-N-methylcarboxamide (1 eq) and heated to 60° C. for 16 h. Preparative purification yielded [4-(2-{[4-ethylpiperazinyl)phenyl]-amino)-1-methylbenzimidazol-5-yloxy)(2-pyridyl)]-N-methylcarboxamide. MS: MH+=485.

Example 632

Step 1. Synthesis of 4-(2-bromoethyl)-1-nitrobenzene

To 4-(2-bromoethyl)-1-nitrobenzene (1 eq) in tetrahydrofuran was added morpholine (3 eq) and stir for 16 h at ambient temperature. Concentrating and passing through a plug of silica gave 4-[2-(4-nitrophenyl)ethylmorpholine. MS: MH+=236.

Step 2. Synthesis of 4-(2-morpholin-4-ylethyl)phenylamine

The mixture containing 4-[2-(4-nitrophenyl)ethyl]morpholine in methanol with catalytic amount of 10% Pd/C was hydrogenated to yield 4-(2-morpholin-4-ylethyl)phenylamine. MS: MH+=206.

Step 3. Synthesis of 4-(2-morpholin-4-ylethyl)benzeneisothiocyanate

To 4-(2-morpholin-4-ylethyl)phenylamine in acetone at 0° C. was added sodium bicarbonate (2 eq) and thiophosgene (2 eq). The mixture was brought to ambient temperature and concentrated and partitioned between ethyl acetate and water. The organic layer was dried with sodium bicarbonate and sodium sulfate and concentrated to yield 4(2-morpholin-4-ylethyl)benzeneisothiocyanate. MS: MH+=252.

Step 4. Synthesis of N-methyl[4-(1-methyl-2-{[4-(2-morpholin-4-ylethyl)phenyl]amino}-benzimidazol-5-oxy)(2-pyridyl)]carboxamide

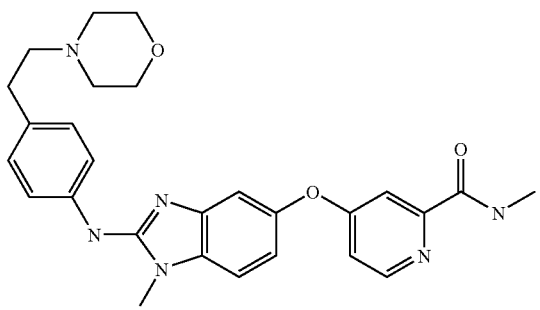

To 4(2-morpholin-4-ylethyl)benzeneisothiocyanate (1 eq) in methanol was added {4-[3-amino-4-(methylamino)phenoxy](2-pyridyl)}-N-methylcarboxamide (1 eq) and stirred at ambient temperature for 16 h. The corresponding thiourea formation was followed by LC/MS. To it was the added iodomethane (1 eq) and heated to 60° C. for 3 h. Concentration followed by preparative chromatography yielded N-methyl[4-(1-methyl-2-{[4-(2-morpholin-4-ylethyl)phenyl]amino}-benzimidazol-5-oxy)(2-pyridyl)]carboxamide. MS: MH+=486.

Example 633

Step 1. Synthesis of [(4-nitrophenyl)ethyl]benzylamine

To a solution of 1-(4-nitrophenyl)ethan-1-one (1 eq) and phenylmethylamine (1 eq) in methanol was added sodium triacetoxyborohydride (1.2 eq). The resulting mixture was stirred at ambient temperature for 16 h. The mixture was concentrated and partitioned between ethyl acetate and water. The organic layer was concentrated and preparative purification yielded [(4-nitrophenyl)ethyl]benzylamine. MS: MH+=256.

Step 2. Synthesis of [(4-aminophenyl)ethyl]benzylamine

The mixture containing [(4-nitrophenyl)ethyl]benzylamine in methanol with catalytic amount of 10% Pd/C was hydrogenated until disappearance of yellow color to yield [(4-aminophenyl)ethyl]benzylamine. MS: MH+=226.

Step 3. Synthesis of 4-{[benzylamino]ethyl}benzeneisothiocyanate

To [(4-nitrophenyl)ethyl]benzylamine in acetone at 0° C. was added sodium bicarbonate (2 eq) and thiophosgene (2 eq). The mixture was brought to ambient temperature and concentrated and partitioned between ethyl acetate and water. The organic layer was dried with sodium bicarbonate and sodium sulfate and concentrated to yield 4-{[benzylamino]ethyl}benzeneisothiocyanate. MS: MH+=268.

Step 4. Synthesis of N-methyl(4-{1-methyl-2-2[(4-{[benzylamino]ethyl}-phenyl)amino)benzimidazol-5-yloxy)-(2-pyridyl))carboxamide To a solution of [4-(3,4-diaminophenoxy)(2-pyridyl))]-N-methylcarboxamide (1 eq) in methanol was added 4-{[benzylamino]ethyl}benzeneisothiocyanate (1 eq) and heated to 60° C. for 3 h. Preparative chromatography yielded N-methyl(4-{1-methyl-2-2-[(4-{[benzylamino]ethyl}phenyl)amino)benzimidazol-5-yloxy)-(2-pyridyl))carboxamide. MS: MH+=506.

Example 634

Step 1. Synthesis of (5-fluoro-2-nitrophenyl)methylamine

A solution of 5-fluoro-2-nitrophenylamine (1 eq) in methylenechloride was treated with trifluoroacetic anhydride (1 eq) and stirred for 10 minutes at 0° C. The mixture was quenched with saturated sodium bicarbonate solution. The organic layer was separated and washed with water, brine, dried and evaporated. To the solution of the trifluoroacetamide (1 eq) in a mixture of toluene, acetonitrile and sodium hydroxide solution (50%) was added benzyltrimethylammonium chloride (1 eq) and dimethyl sulfate (1.2 eq). The biphasic mixture was stirred overnight at room temperature and evaporated. The mixture was taken up in ethyl acetate, washed with water, brine, dried and evaporated. The crude was purified by column chromatography eluting with 1:1 hexanes and ethyl acetate to afford (5-fluoro-2-nitrophenyl)methylamine. MS: MH+=170.

Step 2. Synthesis of {4-[4-amino-3-(methylamino)phenoxy](2-pyridyl)}-N-methylcarboxamide The mixture containing 5-fluoro-2-nitrophenylamine (1 eq), Potassium bis(trimethylsilyl)amide (2 eq) was stirred in dimethylformamide for 2 hours at room temperature. To this mixture was added (3-hydroxyphenyl)-N-methylcarboxamide (1 eq) and Potassium carbonate (1.2 eq) and stirred at 90° C. for 16 h. The reaction mixture was then concentrated and partitioned between ethyl acetate and water. The organic layer was separated and washed with brine, dried, filtered and concentrated in vacuum to give brown solid. Purification on silica gel gave N-methyl{4-[3-(methylamino)-4-nitro-phenoxy](2-pyridyl))carboxamide. It was taken in methanol and hydrogenated with catalytic amount of 10% Pd/C to give {4-[4-amino-3-(methylamino)phenoxy](2-pyridyl)}-N-methylcarboxamide. MS: MH+=272.

Step 3. Synthesis of (4-{2-[(4-bromophenyl)amino]-1-methylbenzimidazol-6-yloxy)-(2-pyridyl)-N-methylcarboxamide

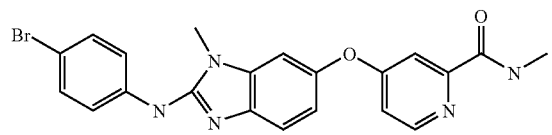

A solution of the {4-[4-amino-3-(methylamino)phenoxy](2-pyridyl)}-N-methylcarboxamide (1 eq) in methanol was treated with 4-bromophenylisothiocyanate (1 eq) and stirred at 60° C. for 2 hours. The reaction mixture was cooled down to room temperature and iodomethane (1 eq) was added and stirred overnight at 60° C. The reaction was concentrated and preparative chromatography gave (4-{2-[(4-bromophenyl)amino]-1-methylbenzimidazol-6-yloxy)-(2-pyridyl)-N-methylcarboxamide. MS: MH+=452.

Example 635

Step 1. Synthesis of ((5-aminobenzimidazol-2-yl)(4-bromophenylamine)

A solution of the 4-nitrobenzene-1,2-diamine in methanol was treated with 4-bromo phenyl isothiocyanate (1 eq) and stirred at 60° C. for 2 hours. The reaction mixture was cooled down to room temperature and iodomethane (1 eq) was added and stirred overnight at 60° C. The reaction was concentrated and purified on silica gel to yield (4-bromophenyl)(5-nitrobenzimidazol-2-yl)amine. The product was taken in methanol and hydrogenated with catalytic amount of 10% Pd/C to give ((5-aminobenzimidazol-2-yl)(4-bromophenylamine). MS: MH+=302.

Step 2. Synthesis of [4-({2-[(4-bromophenyl)amino}benzimidazol-5-yl}amino)(2-pyridyl-N-methylcarboxamide

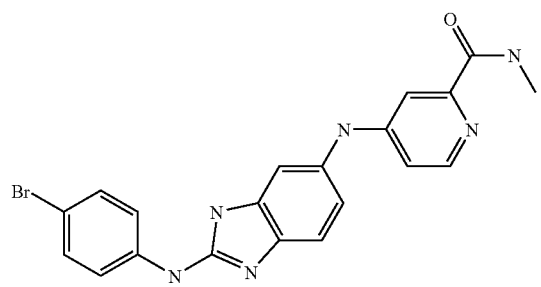

To a solution of ((5-aminobenzimidazol-2-yl)(4-bromophenylamine (1 eq) in N,N-dimethylformamide was added sodium hydride (2 eq) and the mixture was microwaved for 8 mins at 220° C. The reaction mixture was partitioned between ethyl acetate and water and the organic layer was dried with sodium sulfate and concentrated. Preparative chromatography yielded [4-({2-[(4-bromophenyl)amino}benzimidazol-5-yl}amino)(2-pyridyl-N-methylcarboxamide. MS: MH+=437.

Example 636

Step 1. Synthesis of (4-{2-[(4-bromophenyl)methyl]-1-methylbenzimidazol-5-yloxy)-(2-pyridyl))-N-methylcarboxamide

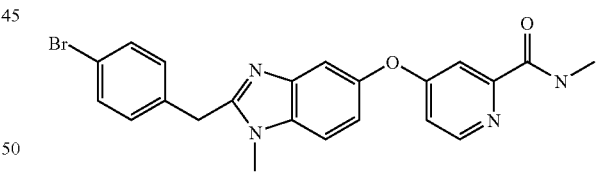

To 4-bromophenyl acetic acid (1 eq) in dichoromethane containing a drop of N,N-dimethyl formamide at 0° C. was added oxalyl chloride (1.2 eq). The resulting mixture was then brought to ambient temperature and stirred for 2 h. The mixture was concentrated and to it was added tetrahydrofuran and [4-(3,4-diaminophenoxy)(2-pyridyl)]-N-methylcarboxamide (1 eq) and triethyl amine (1 eq) and stirred for 2 h. Formation of the N-acylated product was followed by LC/MS. The mixture was concentrated and partitioned between ethyl acetate and water. The organic layer was dried with sodium sulfate and concentrated and taken in acetic acid and heated to 60° C. for 2 h. Preparative chromatography yielded (4-{2-[(4-bromophenyl)methyl]-1-methylbenzimidazol-5-yloxy)-(2-pyridyl))-N-methylcarboxamide. MS: MH+=451.

Example 637

Step 1. Synthesis of 4-({1-methyl-5-[2-(N-methyl-carbamoyl)(4-pyridyloxy))]benzimidazol-2-yl}amino)benzoic acid To {4-[3-amino-4-(methylamino)phenoxy](2-pyridyl)}-N-methylcarboxamide (1 eq) in methanol was added 4-isothiocyanatobenzoic acid (1 eq) and stirred at 60° C. for 3 h. To it was then added iodomethane (1 eq) and heated to 60° C. for 3 h. and concentrated the solvent and purified on silica gel to yield 4-({1-methyl-5-[2-(N-methylcarbamoyl)(4-pyridyloxy))]benzimidazol-2-yl}amino)benzoic acid. MS: MH$^+$=417.

Step 2. Synthesis of N-methyl[4-(1-methyl-2-{[4-(2-morpholin-4-ylethyl)phenyl]-amino-benzimidazol-5-oxy)(2-pyridyl)]carboxamide CHIR-164277

To 4-({1-methyl-5-[2-(N-methylcarbamoyl)(4-pyridyloxy))]benzimidazol-2-yl}-amino)benzoic acid (1 eq) in tetrahydrofuran was added morpholine (2 eq) and N,N-diisopropylethylamine (4 eq) and HBTU (2 eq) and stir at ambient temperature for 16 h. The mixture was then concentrated and partitioned between ethyl acetate and water. The organic layer was washed with brine and dried with sodium sulfate. Preparative chromatography gave N-methyl[4-(1-methyl-2-{[4-(2-morpholin-4-ylethyl)phenyl]-amino-benzimidazol-5-oxy)(2-pyridyl)]carboxamide. MS: MH$^+$=529.

Example 638

Step 1. Synthesis of 3-({1-methyl-5-[2-(N-methyl-carbamoyl)(4-pyridyloxy))]benzimidazol-2-yl}amino)benzoic acid To 4-[3-amino-4-(methylamino)phenoxy](2-pyridyl)}-N-methylcarboxamide (1 eq) in methanol was added 3-isothiocyanatobenzoic acid (1 eq) and stirred at 60° C. for 3 h. To it was then added iodomethane (1 eq) and heated to 60° C. for 3 h and concentrated the solvent and purified on silica gel to yield 3-({1-methyl-5-[2-(N-methylcarbamoyl)(4-pyridyloxy))]benzimidazol-2-yl}amino)benzoic acid. MS: MH+=417.

Step 2. Synthesis of N-methyl[3-(1-methyl-2-{[4-(2-morpholin-4-ylethyl)phenyl]-amino-benzimidazol-5-oxy)(2-pyridyl)]carboxamide To 3-({1-methyl-5-[2-(N-methylcarbamoyl)(4-pyridyloxy))]benzimidazol-2-yl}-amino)benzoic acid (1 eq) in tetrahydrofuran was added morpholine (2 eq) and N,N-diisopropylethylamine (4 eq), EDCI (2 eq), HOAT (1.2 eq) and stir at ambient temperature for 16 h. The mixture was then concentrated and partitioned between ethyl acetate and water. The organic layer was washed with brine and dried with sodium sulfate. Preparative chromatography gave N-methyl [3-(1-methyl-2-{[4-(2-morpholin-4-ylethyl)-phenyl]amino-benzimidazol-5-oxy)(2-pyridyl)]carboxamide. MS: MH+=529.

Each of the compounds 639-698, listed in Table 7 were synthesized as indicated in the right hand column by the method described in one of the Examples 627-638 or as otherwise indicated.

TABLE 7

| Example | Structure | Name | MH+ | Synthesis as in Example: |
|---|---|---|---|---|
| 639 | 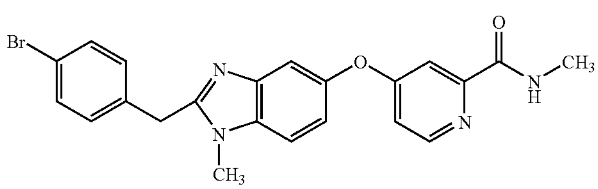 | 4-({2-[(4-bromophenyl)-methyl]-1-methyl-1H-benzimidazol-5-yl}oxy)-N-methylpyridine-2-carboxamide | 452.3 | 636 |
| 640 | 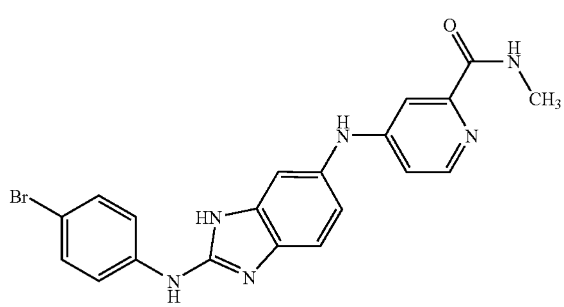 | 4-({2-[(4-bromophenyl)-amino]-1H-benzimidazol-6-yl}amino)-N-methylpyridine-carboxamide | 438.3 | 635 |
| 641 | 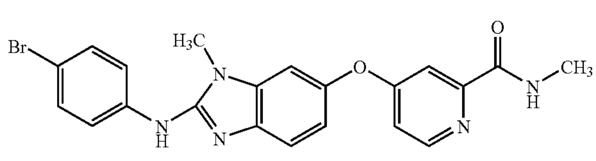 | 4-({2-[(4-bromophenyl)-amino]-1-methyl-1H-benzimidazol-6-yl}oxy)-N-methylpyridine-2-carboxamide | 453.3 | 634 |

TABLE 7-continued

| Example | Structure | Name | MH+ | Synthesis as in Example: |
|---|---|---|---|---|
| 642 | 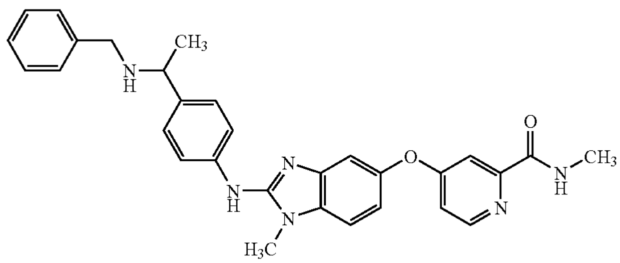 | N-methyl-4-({1-methyl-2-[(4-{1-[(phenylmethyl)-amino]ethyl}phenyl)amino]-1H-benzimidazol-5-yl}oxy)-pyridine-2-carboxamide | 507.6 | 633 |
| 643 | 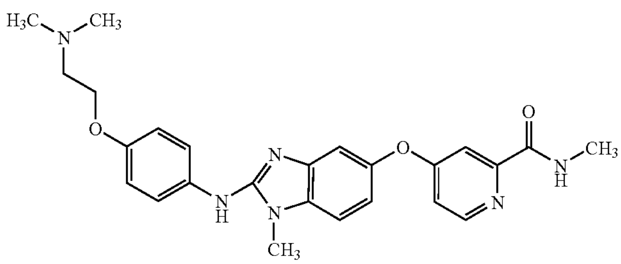 | 4-({2-[(4-{[2-(dimethyl-amino)ethyl]oxy}phenyl)-amino]-1-methyl-1H-benzimidazol-5-yl}oxy)-N-methylpyridine-2-carbox-amide | 461.5 | 631 |
| 644 | 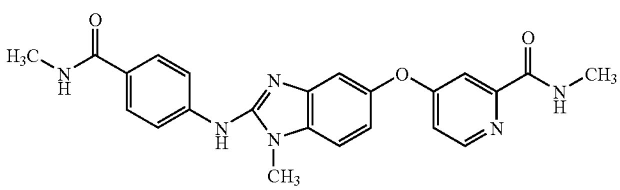 | N-methyl-4-{[1-methyl-2-({4-[(methylamino)-carbonyl]phenyl}amino)-1H-benzimidazol-5-yl]oxy}-pyridine-2-carboxamide | 431.5 | 637 |
| 645 | 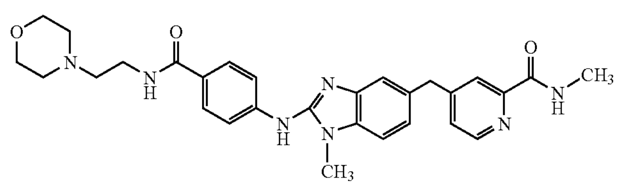 | N-methyl-4-({1-methyl-2-[(4-{[(2-morpholin-4-yl-ethyl)amino]carbonyl}-phenyl)amino]-1H-benzimidazol-5-yl}oxy)-pyridine-2-carboxamide | 530.6 | 637 |
| 646 | 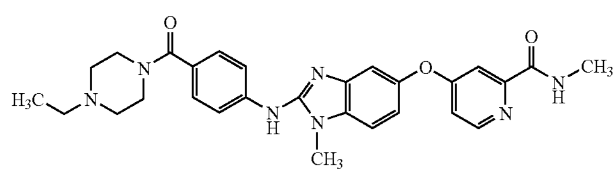 | 4-{[2-({4-[(4-ethylpiperazin-1-yl)carbonyl]phenyl}-amino)-1-methyl-1H-benzimidazol-5-yl]oxy}-N-methylpyridine-2-carbox-amide | 514.6 | 637 |
| 647 | 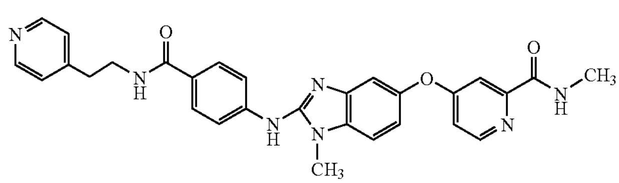 | N-methyl-4-({1-methyl-2-[(4-{[(2-pyridin-4-ylethyl)-amino]carbonyl}phenyl)amino]-1H-benzimidazol-5-yl}-oxy)pyridine-2-carboxamide | 522.6 | 637 |
| 648 | 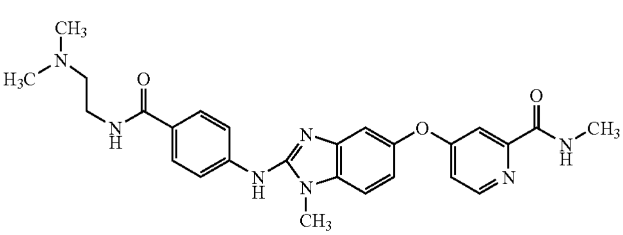 | 4-[(2-{[4-({[2-(dimethyl-amino)ethyl]amino}-carbonyl)phenyl]amino}-1-methyl-1H-benzimidazol-5-yl)oxy]-N-methylpyridine-2-carboxamide | 488.6 | 637 |

TABLE 7-continued

| Example | Structure | Name | MH+ | Synthesis as in Example: |
|---|---|---|---|---|
| 649 | 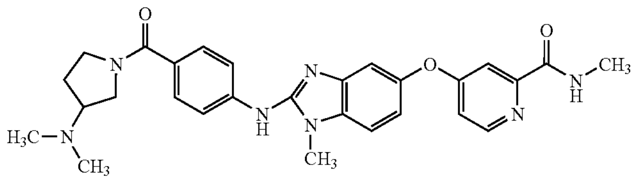 | 4-({2-[(4-{[3-(dimethyl-amino)pyrrolidin-1-yl]-carbonyl}phenyl)amino]-1-methyl-1H-benzimidazol-5-yl}oxy)-N-methylpyridine-2-carboxamide | 514.6 | 637 |
| 650 | 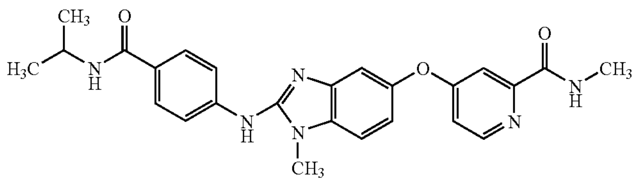 | N-methyl-4-({1-methyl-2-[(4-{[(1-methylethyl)amino]-carbonyl}phenyl)amino]-1H-benzimidazol-5-yl}oxy)-pyridine-2-carboxamide | 459.5 | 637 |
| 651 | 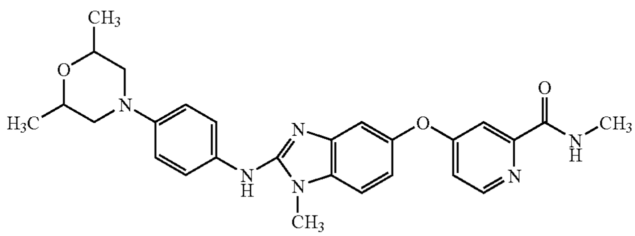 | 4-[(2-{[4-(2,6-dimethyl-morpholin-4-yl)phenyl]-amino}-1-methyl-1H-benzimidazol-5-yl)oxy]-N-methylpyridine-2-carbox-amide | 487.6 | 120a |
| 652 | 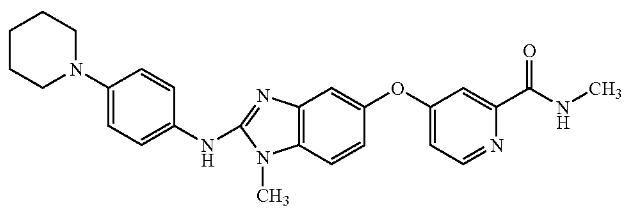 | N-methyl-4-({1-methyl-2-[(4-piperidin-1-ylphenyl)-amino]-1H-benzimidazol-5-yl}oxy)pyridine-2-carbox-amide | 457.5 | 120a |
| 653 | 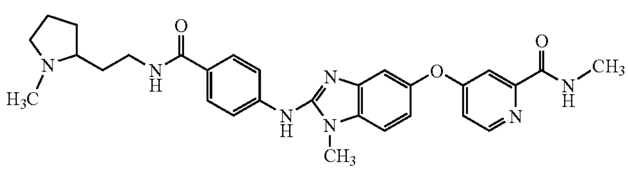 | N-methyl-4-[(1-methyl-2-{4-({[2-(1-methylpyrrolidin-2-yl)ethyl]amino}carbonyl)-phenyl]amino}-1H-benzimidazol-5-yl)oxy]-pyridine-2-carboxamide | 528.6 | 637 |
| 654 | 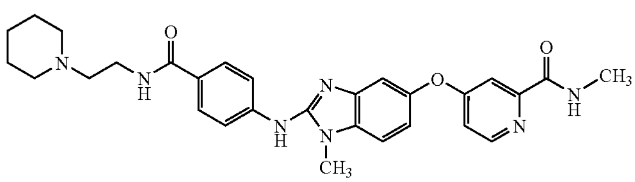 | N-methyl-4-({1-methyl-2-[(4-{[(2-piperidin-1-ylethyl)-amino]carbonyl}phenyl)amino]-1H-benzimidazol-5-yl}-oxy)pyridine-2-carboxamide | 528.6 | 637 |
| 655 | 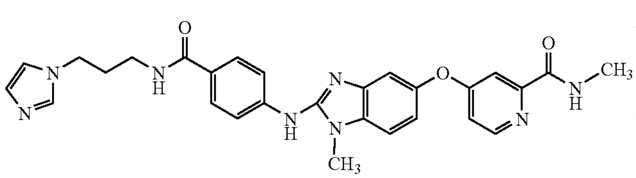 | 4-[(2-{[4-({[3-(1H-imidazol-1-yl)propyl]amino}carbonyl)-phenyl]amino}-1-methyl-1H-benzimidazol-5-yl)oxy]-N-methylpyridine-2-carbox-amide | 525.6 | 637 |
| 656 | 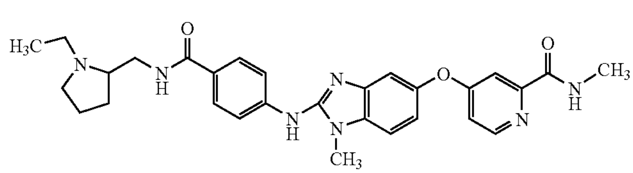 | 4-[(2-{[4-({[(1-ethyl-pyrrolidin-2-yl)methyl]-amino}carbonyl)phenyl]-amino}-1-methyl-1H-benzimidazol-5-yl)oxy]-N-methylpyridine-2-carbox-amide | 528.6 | 637 |

TABLE 7-continued

| Example | Structure | Name | MH+ | Synthesis as in Example: |
|---|---|---|---|---|
| 657 | 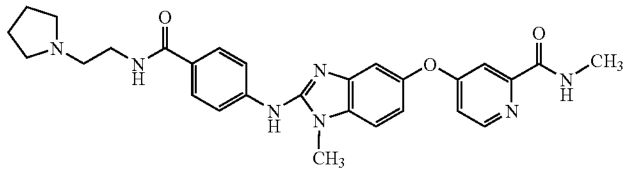 | N-methyl-4-({1-methyl-2-[(4-{[(2-pyrrolidin-1-yl-ethyl)amino]carbonyl}-phenyl)amino]-1H-benzimidazol-5-yl}oxy)-pyridine-2-carboxamide | 514.6 | 637 |
| 658 | 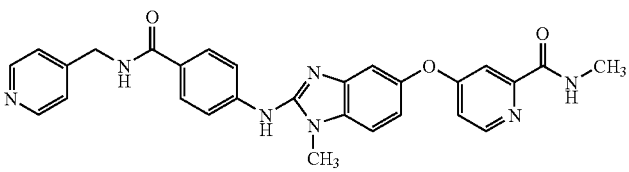 | N-methyl-4-({1-methyl-2-[(4-{[(pyridin-4-ylmethyl)-amino]carbonyl}phenyl)-amino]-1H-benzimidazol-5-yl}oxy)pyridine-2-carboxamide | 508.6 | 637 |
| 659 | 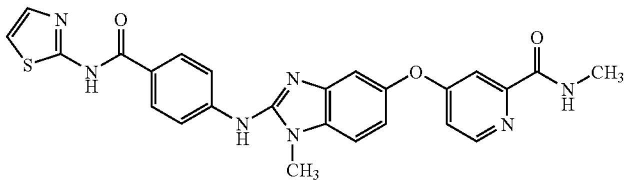 | N-methyl-4-{[1-methyl-2-({4-[(1,3-thiazol-2-yl-amino)carbonyl]phenyl}amino)-1H-benzimidazol-5-yl]-oxy}pyridine-2-carboxamide | 500.6 | 637 |
| 660 | 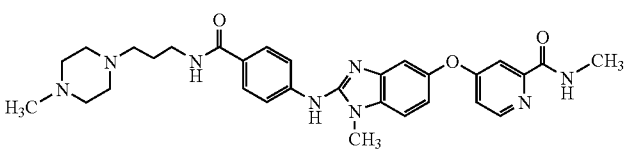 | N-methyl-4-[(1-methyl-2-{[4-({[3-(4-methylpiperazin-1-yl)propyl]amino}carbonyl)-phenyl]amino}-1H-benzimidazol-5-yl)oxy]-pyridine-2-carboxamide | 557.7 | 637 |
| 661 | 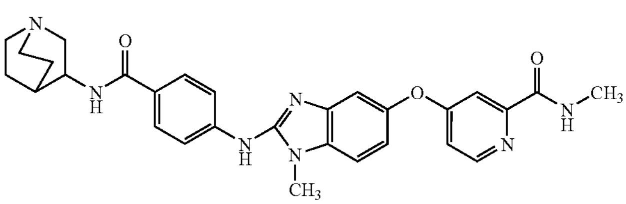 | 4-{[2-({4-[(1-aza-bicyclo[2.2.2]oct-3-ylamino)-carbonyl]phenyl}amino)-1-methyl-1H-benzimidazol-5-yl]oxy}-N-methylpyridine-2-carboxamide | 526.6 | 637 |
| 662 | Chiral | 4-({2-[(4-{[(3S)-1-azabicyclo[2.2.2]oct-3-ylamino]carbonyl}phenyl)amino]-1-methyl-1H-benzimidazol-5-yl}oxy)-N-methylpyridine-2-carbox-amide | 526.6 | 637 |
| 663 | 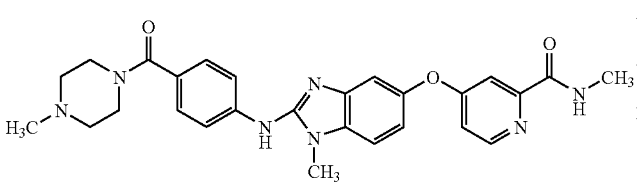 | N-methyl-4-{[1-methyl-2-{4-[(4-methylpiperazin-1-yl)carbonyl]phenyl}amino)-1H-benzimidazol-5-yl]oxy}-pyridine-2-carboxamide | 500.6 | 637 |
| 664 | 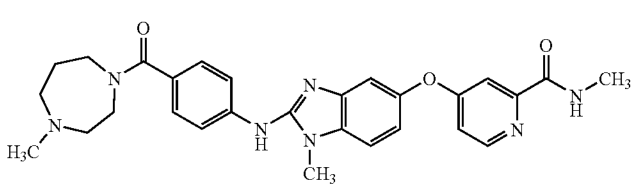 | N-methyl-4-{[1-methyl-2-({4-[(4-methyl-1,4-diazepan-1-yl)carbonyl]phenyl}-amino)-1H-benzimidazol-5-yl]oxy}pyridine-2-carbox-amide | 514.6 | 637 |

TABLE 7-continued

| Example | Structure | Name | MH+ | Synthesis as in Example: |
|---|---|---|---|---|
| 665 | 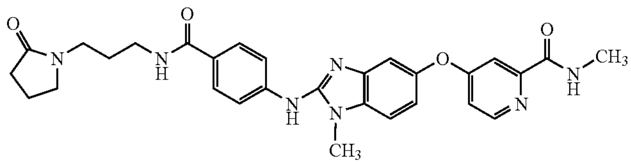 | N-methyl-4-[(1-methyl-2-{[4-({[3-(2-oxopyrrolidin-1-yl)propyl]amino}carbonyl)phenyl]amino}-1H-benzimidazol-5-yl)oxy]-pyridine-2-carboxamide | 542.6 | 637 |
| 666 | Chiral | 4-({2-[(4-{[(3R)-3-hydroxy-pyrrolidin-1-yl]carbonyl}-phenyl)amino]-1-methyl-1H-benzimidazol-5-yl}oxy)-N-methylpyridine-2-carbox-amide | 487.5 | 637 |
| 667 | Chiral | 4-({2-[(4-{[(3S)-3-hydroxy-pyrrolidin-1-yl]carbonyl}-phenyl)amino]-1-methyl-1H-benzimidazol-5-yl}oxy)-N-methylpyridine-2-carbox-amide | 487.5 | 637 |
| 668 | 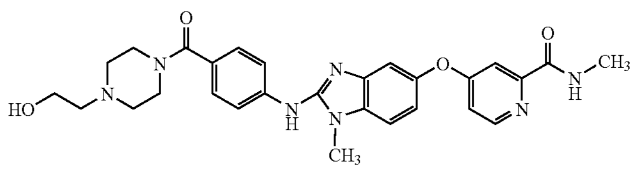 | 4-({2-[(4-{[4-(2-hydroxy-ethyl)piperazin-1-yl]-carbonyl}phenyl)amino]-1-methyl-1H-benzimidazol-5-yl}oxy)-N-methylpyridine-2-carboxamide | 530.6 | 637 |
| 669 | 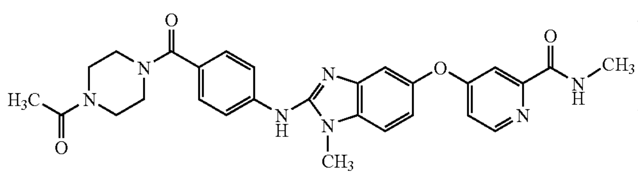 | 4-{[2-({4-[(4-acetylpiperazin-1-yl)carbonyl]phenyl}-amino)-1-methyl-1H-benzimidazol-5-yl]oxy}-N-methylpyridine-2-carbox-amide | 528.6 | 637 |
| 670 | Chiral | 4-({2-[(4-{[(3R)-3-(dimethyl-amino)pyrrolidin-1-yl]-carbonyl}phenyl)amino]-1-methyl-1H-benzimidazol-5-yl}oxy)-N-methylpyridine-2-carboxamide | 514.6 | 637 |
| 671 | Chiral | 4-({2-[(4-{[(3S)-3-(dimethyl-amino)pyrrolidin-1-yl]-carbonyl}phenyl)amino]-1-methyl-1H-benzimidazol-5-yl}oxy)-N-methylpyridine-2-carboxamide | 514.6 | 637 |
| 672 | 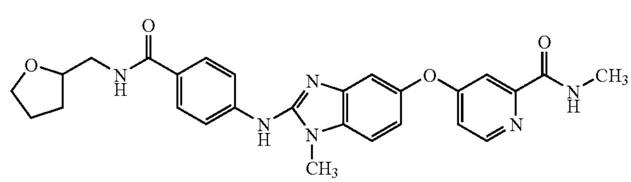 | N-methyl-4-({1-methyl-2-[(4-{[(tetrahydrofuran-2-ylmethyl)amino]carbonyl}-phenyl)amino]-1H-benzimidazol-5-yl}oxy)-pyridine-2-carboxamide | 501.6 | 637 |

TABLE 7-continued

| Example | Structure | Name | MH+ | Synthesis as in Example: |
|---|---|---|---|---|
| 673 | 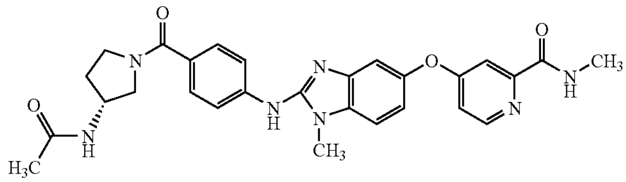 | 4-({2-[(4-{[(3R)-3-(acetyl-amino)pyrrolidin-1-yl]-carbonyl}phenyl)amino]-1-methyl-1H-benzimidazol-5-yl}oxy)-N-methylpyridine-2-carboxamide | 528.6 | 637 |
| 674 | 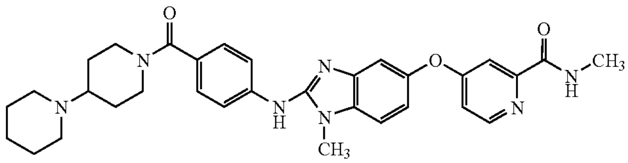 | 4-[(2-{[4-(1,4'-bipiperidin-1'-ylcarbonyl)phenyl]amino}-1-methyl-1H-benzimidazol-5-yl)oxy]-N-methylpyridine-2-carboxamide | 568.7 | 637 |
| 675 | 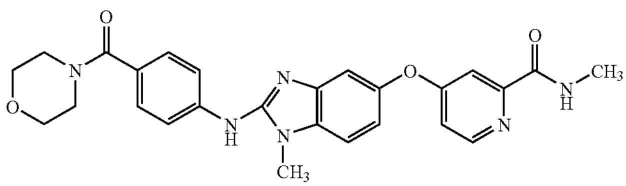 | N-methyl-4-[(1-methyl-2-{[4-(morpholin-4-yl-carbonyl)phenyl]amino}-1H-benzimidazol-5-yl)oxy]-pyridine-2-carboxamide | 487.5 | 637 |
| 676 | 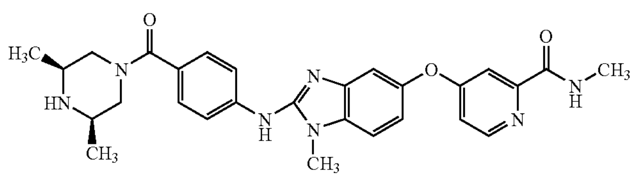 | 4-({2-[(4-{[(3R,5S)-3,5-dimethylpiperazin-1-yl]-carbonyl}phenyl)amino]-1-methyl-1H-benzimidazol-5-yl}oxy)-N-methylpyridine-2-carboxamide | 514.6 | 637 |
| 677 | 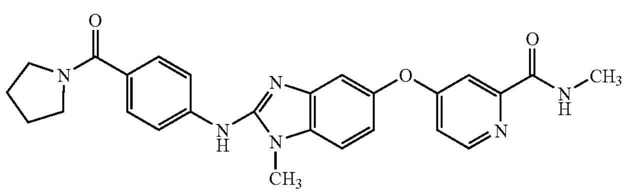 | N-methyl-4-[(1-methyl-2-{[4-(pyrrolidin-1-yl-carbonyl)phenyl]amino}-1H-benzimidazol-5-yl)oxy]-pyridine-2-carboxamide | 471.5 | 637 |
| 678 | 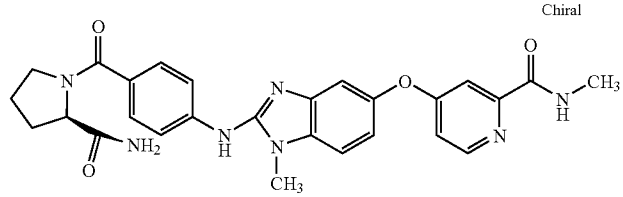 | 4-({2-[(4-{[(2R)-2-(amino-carbonyl)pyrrolidin-1-yl]-carbonyl}phenyl)amino]-1-methyl-1H-benzimidazol-5-yl}oxy)-N-methylpyridine-2-carboxamide | 514.6 | 637 |
| 679 | 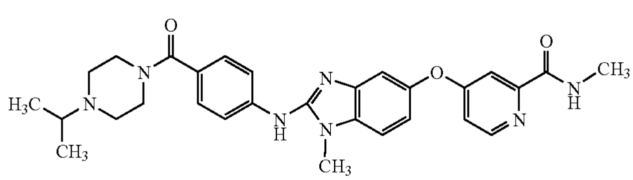 | N-methyl-4-({1-methyl-2-[(4-{[4-(1-methylethyl)-piperazin-1-yl]carbonyl}-phenyl)amino]-1H-benzimidazol-5-yl}oxy)-pyridine-2-carboxamide | 528.6 | 637 |
| 680 | 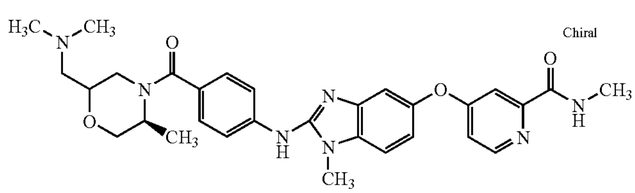 | 4-[(2-{[4-({(2R,5S)-2-[(dimethylamino)methyl]-5-methylmorpholin-4-yl}-carbonyl)phenyl]amino}-1-methyl-1H-benzimidazol-5-yl)oxy]-N-methylpyridine-2-carboxamide | 558.7 | 637 |

TABLE 7-continued

| Example | Structure | Name | MH+ | Synthesis as in Example: |
|---|---|---|---|---|
| 681 | 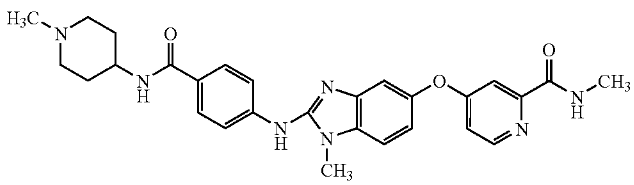 | 4-methyl-4-({1-methyl-2-[(4-{[(1-methylpiperidin-4-yl)amino]carbonyl}phenyl)amino]-1H-benzimidazol-5-yl}oxy)pyridine-2-carboxamide | 514.6 | 637 |
| 682 | 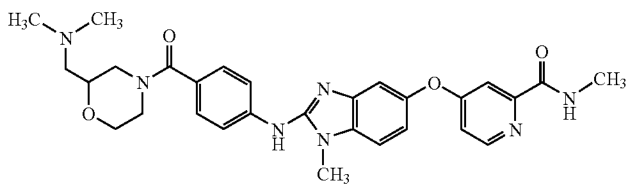 | 4-[(2-{[4-({2-[(dimethylamino)methyl]morpholin-4-yl}carbonyl)phenyl]amino}-1-methyl-1H-benzimidazol-5-yl)oxy]-N-methylpyridine-2-carboxamide | 544.6 | 637 |
| 683 | 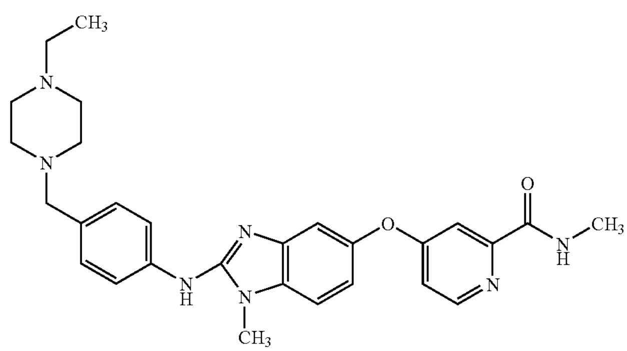 | 4-{[2-({4-[(4-ethylpiperazin-1-yl)methyl]phenyl}amino)-1-methyl-1H-benzimidazol-5-yl]oxy}-N-methylpyridine-2-carboxamide | 500.6 | 630 |
| 684 | 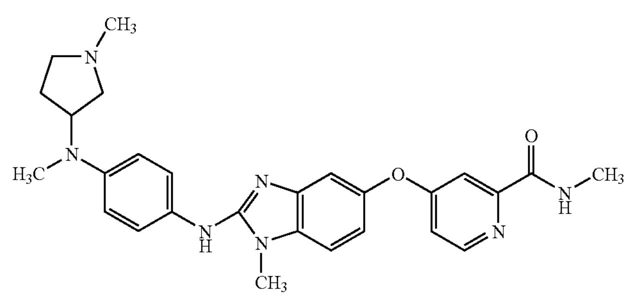 | 4-methyl-4-{[1-methyl-2-({4-[methyl(1-methyl-pyrrolidin-3-yl)amino]phenyl}amino)-1H-benzimidazol-5-yl]oxy}-pyridine-2-carboxamide | 486.6 | 631 |
| 685 | 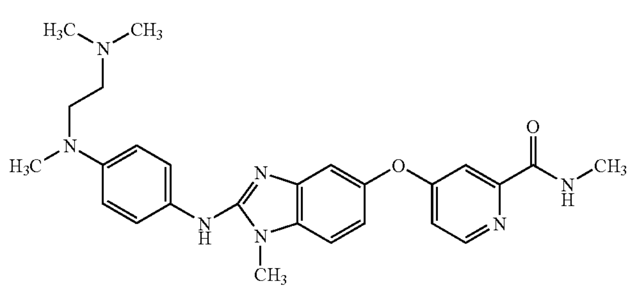 | 4-{[2-({4-[[2-(dimethylamino)ethyl](methyl)amino]phenyl}amino)-1-methyl-1H-benzimidazol-5-yl]oxy}-N-methylpyridine-2-carboxamide | 474.6 | 631 |

TABLE 7-continued

| Example | Structure | Name | MH+ | Synthesis as in Example: |
|---|---|---|---|---|
| 686 | 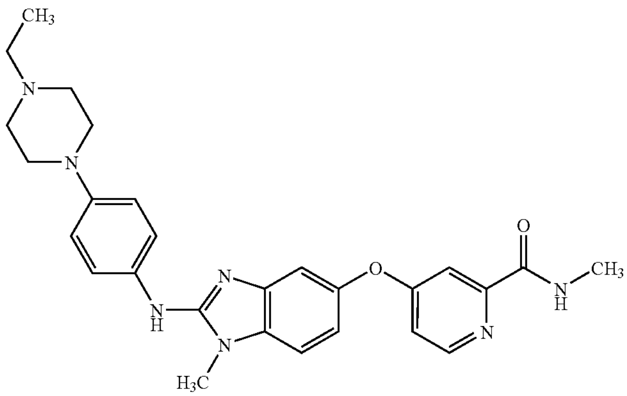 | 4-[(2-{[4-(4-ethylpiperazin-1-yl)phenyl]amino}-1-methyl-1H-benzimidazol-5-yl)oxy]-N-methylpyridine-2-carboxamide | 486.6 | 631 |
| 687 | 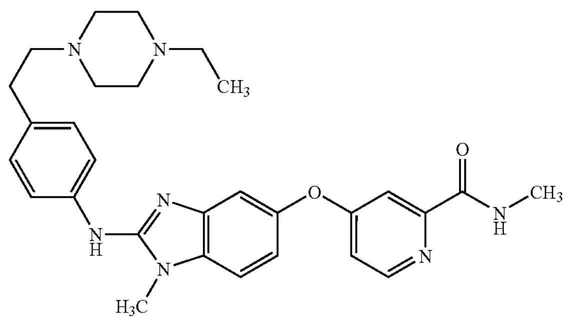 | 4-{[2-({4-[2-(4-ethylpiperazin-1-yl)ethyl]phenyl}amino)-1-yl]oxy}-N-methylpyridine-2-methyl-1H-benzimidazol-5-yl]oxy}-N-methylpyridine-2-carboxamide | 514.6 | 632 |
| 688 | 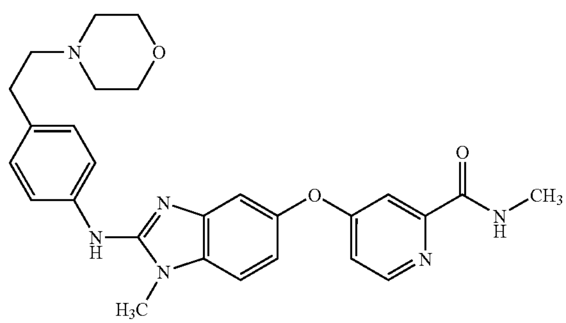 | N-methyl-4-[(1-methyl-2-{[4-(2-morpholin-4-ylethyl)phenyl]amino}-1H-benzimidazol-5-yl)oxy]pyridine-2-carboxamide | 487.6 | 632 |
| 689 | 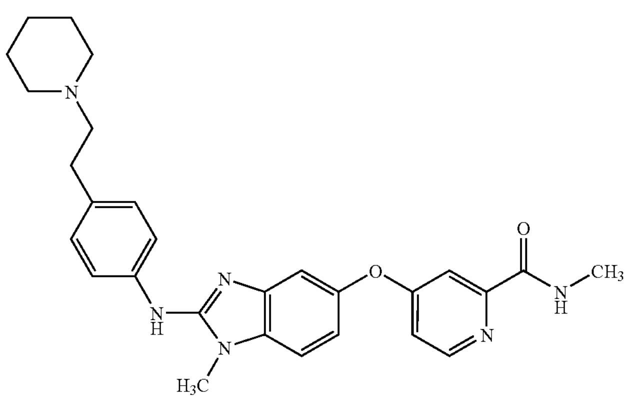 | N-methyl-4-[(1-methyl-2-{[4-(2-piperidin-1-ylethyl)phenyl]amino}-1H-benzimidazol-5-yl)oxy]pyridine-2-carboxamide | 485.6 | 632 |

TABLE 7-continued

| Example | Name | MH+ | Synthesis as in Example: |
|---|---|---|---|
| 690 | N-methyl-4-[(1-methyl-2-{4-[(4-methylpiperazin-1-yl)methyl]phenyl}-1H-benzimidazol-5-yl)oxy]pyridine-2-carboxamide | 471.6 | 628 |
| 691 | N-methyl-4-({1-methyl-2-[({4-[(4-methylpiperazin-1-yl)methyl]phenyl}carbonyl)amino]-1H-benzimidazol-5-yl}oxy)pyridine-2-carboxamide | 514.6 | 627 |
| 692 | N-methyl-4-{[1-methyl-2-({[4-(morpholin-4-ylmethyl)phenyl]carbonyl}amino)-1H-benzimidazol-5-yl]oxy}pyridine-2-carboxamide | 501.6 | 627 |
| 693 | N-methyl-4-{[1-methyl-2-{[4-(piperidin-1-ylmethyl)phenyl]carbonyl}amino)-1H-benzimidazol-5-yl]oxy}pyridine-2-carboxamide | 499.6 | 627 |
| 694 | N-methyl-4-({1-methyl-2-[4-(morpholin-4-ylmethyl)phenyl]-1H-benzimidazol-5-yl}oxy)pyridine-2-carboxamide | 458.5 | 628 |
| 695 | N-methyl-4-({1-methyl-2-[4-(piperidin-1-ylmethyl)phenyl]-1H-benzimidazol-5-yl}oxy)pyridine-2-carboxamide | 456.6 | 628 |
| 696 | 4-({2-[4-({[2-(dimethylamino)ethyl]amino}methyl)phenyl]-1-methyl-1H-benzimidazol-5-yl}oxy)-N-methylpyridine-2-carboxamide | 459.6 | 628 |

TABLE 7-continued

| Example | Structure | Name | MH+ | Synthesis as in Example: |
|---|---|---|---|---|
| 697 | 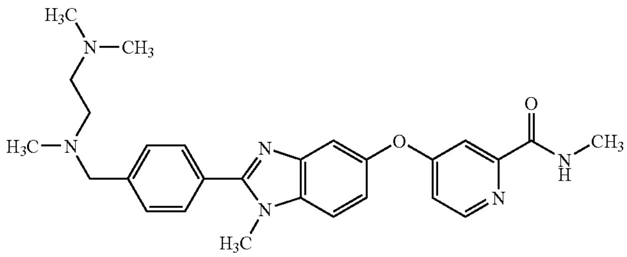 | 4-{[2-(4-{[[2-(dimethylamino)ethyl](methyl)amino]methyl}phenyl)-1-methyl-1H-benzimidazol-5-yl]oxy}-N-methylpyridine-2-carboxamide | 473.6 | 628 |
| 698 | 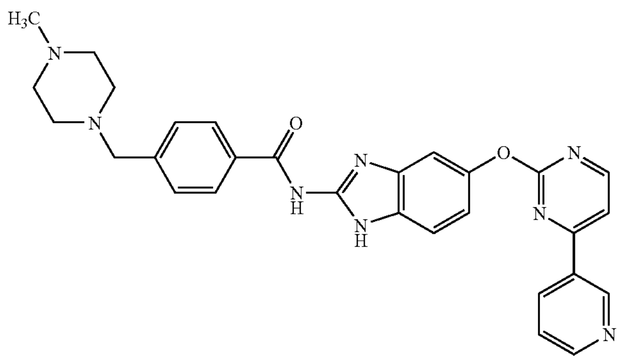 | 4-[(4-methylpiperazin-1-yl)methyl]-N-{5-[(4-pyridin-3-ylpyrimidin-2-yl)oxy]-1H-benzimidazol-2-yl}benzamide | 521.6 | 629 |

Example 699

Step 1. Synthesis of {4-[2-methoxy-4-(methylamino)-5-nitrophenoxy](2-pyridyl)}-N-methylcarboxamide To a stirred solution of concentrated nitric acid (22 eq) was added 2 h-benzo[d]1,3-dioxolane (1 eq) at 0-10° C. for 0.5 h and stirred for another 0.5 h. To this reaction mixture was then added concentrated sulfuric acid (0.06 eq) drop-wise at 0-10 C.° for 0.5 h and stirred at 20 C.° for 0.5 h. It was then poured on to crushed ice, and the separated solid was filtered washed with water and dried to give 5,6-dinitro-2 h-benzo[d]1,3-dioxalane. MS: MH+ 212

Step 2. Synthesis of methyl(6-nitro(2 h-benzo[3,4-d]1,3-dioxalan-5-yl)amine

To a stirred solution of methyl amine in ether and ethanol (1.5:1) was added 5,6-dinitro-2 h-benzo[d]1,3-dioxalane and stirred at ambient temperature for 24 h. The solvent was evaporated under vacuum and the solid was washed with water and dried to give methyl(6-nitro(2 h-benzo[3,4-d]1,3-dioxan-5-yl))amine. MS: MH+ 196

Step 3. Synthesis of 2-methoxy-4-(methylamino)-5-nitrophenol

To a stirred solution of methanol was added sodium metal (4.8 eq) slowly at ambient temperature followed by methyl (6-nitro(2 h-benzo[3,4-d]1,3-dioxalan-5-yl))amine (1 eq) and stirred for 2 h. The mixture was then refluxed for 0.5 h and diluted with water. After cooling it to ambient temperature the separated solid was filtered and dried to give 2-methoxy-4-(methylamino)-5-nitrophenol as a red solid. MS: MH+ 198

Step 4. Synthesis of {4-[2-methoxy-4-(methylamino)-5-nitrophenoxy](2-pyridyl)}-N-methylcarboxamide To a stirred solution of 2-methoxy-4-(methylamino)-5-nitrophenol (1 eq) in N,N-dimethylacetamide was added potassium-t-butoxide (1.2 eq) and continued stirring at ambient temperature utility solidified. To it was then added (3-chlorophenyl)-N-methylcarboxamide (1 eq) and anhydrous potassium carbonate (1 eq) and the resulting mixture was heated to 50° C. whereby the solid liquified. It was then heated to 110° C. for 12 h. After cooling to ambient temperature the solvent was distilled off and the resulting solid was extracted using ethyl acetate in a soxhlet apparatus for 48 h. the organic layer was cooled to 0° C., when the product crystallized from the ethyl acetate to give {4-[2-methoxy-4-(methylamino)-5-nitrophenoxy](2-pyridyl)}-N-methylcarboxamide. MS: MH+ 332

Step 5. Synthesis of 4-{2-[(4-chlorophenyl)amino]-6-methoxy-1-methylbenzimidazol-5-yloxy)pyridine-2-carboxylic acid To tert-butyl4-[3-amino-6-methoxy-4-(methylamino)phenoxy]pyridine-2-carboxylate (1 eq) in methanol was added 4-chlorobenzeneisothiocyanate (1 eq) and stir at ambient temperature for 16 h. Formation of the corresponding thiourea was followed by LC/MS. To it was then added iodomethane (1 eq) and heated to 60° C. for 2 h. Formation of tert-butyl4-(2-{[4-chlorophenyl]amino)-1-methylbenzimidazol-5-yloxy)pyridine-2-carboxylate was followed by LC/MS. To it in methylene chloride was added trifluoroacetic acid and stirred at ambient temperature overnight. Resulting 4-(2-{[4-chlorophenylamino)-6-methoxy-1-methylbenzimidazol-5-yloxy)pyridine-2-carboxylic acid was purified by preparative chromatography. MS: MH+=424.

Step 6. Synthesis of [4-(2-{[4-chlorophenyl)amino-6-methoxy-1-methylbenzimidazol-5-yloxy)(2-pyridyl)]-N-(2-pyrrolidinylethyl)carboxamide

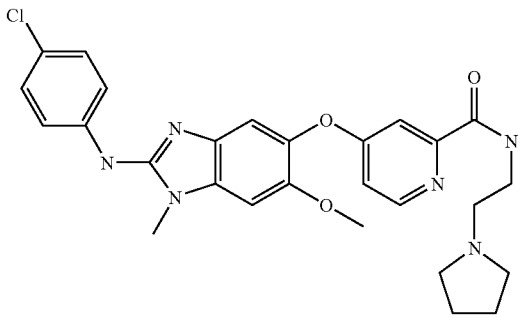

To 4-(2-{[4-chloropheylamino)-6-methoxy-1-methylbenzimidazol-5-yloxy)pyridine-2-carboxylic acid (1 eq) in tetrahydrofuran was added 2-pyrrolidinylethylamine (2 eq), HBTU (2 eq) and N,N-diisopropylethylamine (4 eq) and stir at ambient temperature for 16 h. The mixture was then concentrated and partitioned between ethyl acetate and water. The organic layer was concentrated and preparative chromatography yielded [4-(2-{[4-chlorophenyl]amino-6-methoxy-1-methylbenzimidazol-5-yloxy)(2-pyridyl)]-N-(2-pyrrolidinylethyl)carboxamide. MS: MH+=522.

Example 700

Step 1. Synthesis of 4-{2-[(4-bromo-3-methylphenyl)amino]-6-methoxy-1-methylbenzimidazol-5-yloxy)pyridine-2-carboxylic acid To tert-butyl4-[3-amino-6-methoxy-4-(methylamino)phenoxy]pyridine-2-carboxylate (1 eq) in methanol was added 4-bromo-3-methylbenzeneisothiocyanate (1 eq) and stir at ambient temperature for 16 h. Formation of the corresponding thiourea was followed by LC/MS. To it was then added iodomethane (1 eq) and heated to 60° C. for 2 h. Formation of tert-butyl4-(2-{[4-bromo-3-methylphenyl]amino)-1-methylbenzimidazol-5-yloxy)pyridine-2-carboxylate was followed by LC/MS. To it in methylene chloride was added trifluoroacetic acid and stirred at ambient temperature overnight. Resulting 4-(2-{[4-bromo-3-methylphenyl]amino)-6-methoxy-1-methylbenzimidazol-5-yloxy)pyridine-2-carboxylic acid was purified by preparative chromatography. MS: MH+=482.

Step 2. Synthesis of [4-(2-{[4-bromo-3-methylphenyl)amino-6-methoxy-1-methylbenzimidazol-5-yloxy)(2-pyridyl)]-N-(2-pyrrolidinylethyl)carboxamide

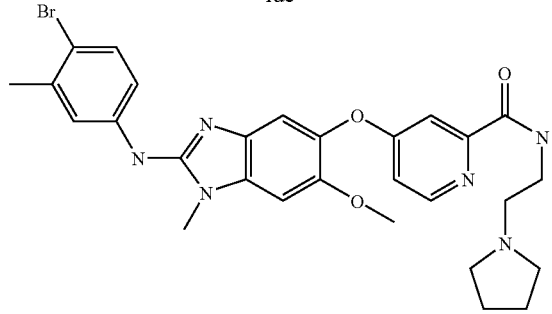

To 4-(2-{[4-bromo-3-methylpheylamino)-6-methoxy-1-methylbenzimidazol-5-yloxy)pyridine-2-carboxylic acid (1 eq) in tetrahydrofuran was added 2-pyrrolidinylethylamine (2 eq), HBTU (2 eq) and N,N-diisopropylethylamine (4 eq) and stir at ambient temperature for 16 h. The mixture was then concentrated and partitioned between ethyl acetate and water. The organic layer was concentrated and preparative chromatography yielded [4-(2-{[4-bromo-3-methylphenyl]amino-6-methoxy-1-methylbenzimidazol-5-yloxy)(2-pyridyl)]-N-(2-pyrrolidinylethyl)carboxamide. MS: MH+=579.

Example 701

Step 1. Synthesis of 4-{3-[3-(3-Isopropyl-phenyl)-thioureaido]-4-methylamino-phenoxy}-pyridine-2-carboxylic acid To tert-butyl4-[3-amino-4-(methylamino)phenoxy]pyridine-2-carboxylate (1 eq) in methanol was added 3-isopropylbenzeneisothiocyanate (1 eq) and stir at ambient temperature for 16 h. Formation of the corresponding thiourea was followed by LC/MS. To it was then added iodomethane (1 eq) and heated to 60° C. for 2 h. Formation of 4-{3-[3-(3-Isopropyl-phenyl)-thioureaido]-4-methylamino-phenoxy}-pyridine-2-carboxylate was followed by LC/MS. To it in methylene chloride was added trifluoroacetic acid and stirred at ambient temperature overnight. Resulting 4-(2-{[4-bromo-3-methylphenylamino)-1-methylbenzimidazol-5-yloxy)pyridine-2-carboxylic acid was purified by preparative chromatography. MS: MH+=437

Step 2. Synthesis of 4-[2-(3-Isopropyl-phenylamino)-1-methyl-1H-benzoimidazol-5-yloxy]-pyridine-2-carboxylicacid) 2-pyrrolidin-1-yl-ethyl)-amide To 4-{3-[3-(3-Isopropyl-phenyl)-thioureaido]-4-methylamino-phenoxy}-pyridine-2-carboxylic acid (1 eq) in tetrahydrofuran was added 2-pyrrolidinylethylamine (2 eq), EDCI (2 eq), HOAT (1.2 eq) and N,N-diisopropylethylamine (4 eq) and stir at ambient temperature for 16 h. The mixture was then concentrated and partitioned between ethyl acetate and water. The organic layer was concentrated and preparative chromatography yielded 4-[2-(3-Isopropyl-phenylamino)-1-methyl-1H-benzoimidazol-5-yloxy]-pyridine-2-carboxylicacid) 2-pyrrolidin-1-yl-ethyl)-amide. MS: MH+=499.

Example 702

Step 1. Synthesis of 3-chloro-4-(2-methyl-5-nitrophenyl)pyridine

Nitrogen was bubbled through a solution of 2-bromo-1-methyl-4-nitrobenzene (1 eq) in dimethoxyethane and water (3:1) for 0.5 h. Bis(diphenylphosphino)ferrocene Palladium (II)chloride (0.05 eq) followed by 3-chloro-4-pyridine boronic acid hydrate (1 eq) and sodium carbonate (3 eq) was added and the mixture was heated to 90° C. for 16 h under nitrogen. The reaction mixture was concentrated and partitioned between ethyl acetate and water. The organic layer was washed with brine and dried with sodium sulfate and concentrated. Purification on silica gel gave 3-chloro-4-(2-methyl-5-nitrophenyl)pyridine. MS: MH+=248.

Note: The same procedure was used for Suzuki reaction between the halopyridines and the nitrophenylboronic acids.

Boronic acids were synthesized using the following procedure if commercially unavailable.

Step 1a. Synthesis of 2-fluoropyridine boronic acid

A flame-dried flask was charged with toluene and tetrahydrofuran (4:1) and then with 4-bromo-2-fluoropyridine (1 eq) and triisopropylborate (1.2 eq) and the flask was cooled to −70° C. Then n-butyllithium (1.2 eq) was added dropwise over 0.5 h and the mixture was stirred for 0.5 h at −70° C. The reaction mixture was then brought to −20° C. and 2N hydrochloric acid was added to it. Formation of 2-fluoropyridine boronic acid was seen by LC/MS on warming the mixture to ambient temperature. The mixture was partitioned between ethyl acetate and water. The organic layer was dried with sodium sulfate and concentrated to yield 2-fluoropyridine boronic acid. MS: MH+=141.

Step 2. Synthesis of 3-(3-chloro(4-pyridyl)-4-methylphenylamine

To the mixture containing 3-chloro-4-(2-methyl-5-nitrophenyl)pyridine in acetic acid was added Fe dust (5 eq) and the resulting mixture was stirred at ambient temperature for 6 h. To it was then added saturated sodium carbonate to bring it to neutral pH and extracted with ethyl acetate. The organic layer was washed with brine and dried with sodium sulfate and concentrated and passed through a plug of silica to yield 3-(3-chloro(4-pyridyl))-4-methylphenylamine. MS: MH+=218.

Step 3. Synthesis of 3-(3-chloro(4-pyridyl))-4-methylbenzeneisothiocyanate

To 3-(3-chloro(4-pyridyl))-4-methylphenylamine in acetone at 0° C. was added sodium bicarbonate (2 eq) and thiophosgene (2 eq). The mixture was brought to ambient temperature and concentrated and partitioned between ethyl acetate and water. The organic layer was dried with sodium bicarbonate and sodium sulfate and concentrated to yield 3-(3-chloro(4-pyridyl))-4-methylbenzeneisothiocyanate. MS: MH+=260.

Step 4. Synthesis of {4-(2-{[3-(3-chloro(4-pyridyl))-4-methylphenyl]amino)-1-methylbenzimidazol-5-yloxy)(2-pyridyl)]-N-methylcarboxamide

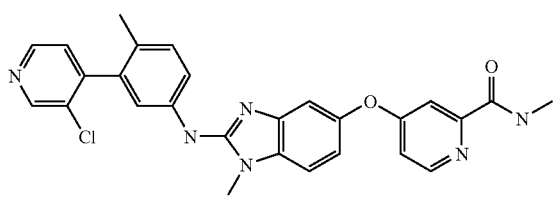

To 3-(3-chloro(4-pyridyl))-4-methylbenzeneisothiocyanate (1 eq) in methanol was added {4-[3-amino-4-(methylamino)phenoxy](2-pyridyl)}-N-methylcarboxamide (1 eq) and the resulting mixture was stirred at ambient temperature for 16 h. LC/MS shows formation of the corresponding thiourea. To it in methanol was then added anhydrous ferric chloride (1.5 eq) and stirred for 3 h. The reaction mixture was then concentrated to half its volume and brought to neutral pH with 1N sodium hydroxide. It was then extracted with ethyl acetate and the organic layer was washed with brine and dried with sodium sulfate. The crude was then titrated with hot methanol to yield {4-(2-{[3-(3-chloro(4-pyridyl))-4-methylphenyl]amino)-1-methylbenzimidazol-5-yloxy)(2-pyridyl)]-N-methylcarboxamide. MS: MH+=498.

Example 703

1. Synthesis of {4-[2-methoxy-4-(methylamino)-5-nitrophenoxy](2-pyridyl)}-N-methylcarboxamide To a stirred solution of concentrated nitric acid (22 eq) was added 2 h-benzo[d]1,3-dioxolane (1 eq) at 0-10° C. for 0.5 h and stirred for another 0.5 h. To this reaction mixture was then added concentrated sulfuric acid (0.06 eq) drop-wise at 0-10 C.° for 0.5 h and stirred at 20 C.° for 0.5 h. It was then poured on to crushed ice, and the separated solid was filtered washed with water and dried to give 5,6-dinitro-2 h-benzol[d]1,3-dioxalane. MS: MH+ 212

Step 2. Synthesis of methyl(6-nitro(2 h-benzo[3,4-d]1,3-dioxalan-5-yl)amine

To a stirred solution of methyl amine in ether and ethanol (1.5:1) was added 5,6-dinitro-2 h-benzol[d]1,3-dioxalane and stirred at ambient temperature for 24 h. The solvent was evaporated under vacuum and the solid was washed with water and dried to give methyl(6-nitro(2 h-benzo[3,4-d]1,3-dioxan-5-yl))amine. MS: MH+ 196

Step 3. Synthesis of 2-methoxy-4-(methylamino)-5-nitrophenol

To a stirred solution of methanol was added sodium metal (4.8 eq) slowly at ambient temperature followed by methyl (6-nitro(2 h-benzo[3,4-d]1,3-dioxalan-5-yl))amine (1 eq) and stirred for 2 h. The mixture was then refluxed for 0.5 h and diluted with water. After cooling it to ambient temperature the separated solid was filtered and dried to give 2-methoxy-4-(methylamino)-5-nitrophenol as a red solid. MS: MH+ 198

Step 4. Synthesis of {4-[2-methoxy-4-(methylamino)-5-nitrophenoxy](2-pyridyl)}-N-methylcarboxamide To a stirred solution of 2-methoxy-4-(methylamino)-5-nitrophenol (1 eq) in N,N-dimethylacetamide was added potassium-t-butoxide (1.2 eq) and continued stirring at ambient temperature utility solidified. To it was then added (3-chlorophenyl)-N-methylcarboxamide (1 eq) and anhydrous potassium carbonate (1 eq) and the resulting mixture was heated to 50° C. whereby the solid liquified. It was then heated to 110° C. for 12 h. After cooling to ambient temperature the solvent was distilled off and the resulting solid was extracted using ethyl acetate in a soxhlet apparatus for 48 h. The organic layer was cooled to 0° C., when the product crystallized from the ethyl acetate to give {4-[2-methoxy-4-(methylamino)-5-nitrophenoxy](2-pyridyl)}-N-methylcarboxamide. MS: MH+ 332

Step 5. Synthesis of {4-[3-amino-6-methoxy-4-(methylamino)phenoxy](2-pyridyl)}-N-methylcarboxamide A solution of {4-[2-methoxy-4-(methylamino)-5-nitrophenoxy](2-pyridyl)}-N-methylcarboxamide. In methanol was hydrogenated with 10% Pd/C. The catalyst was filtered off and the solvent was concentrated to yield {4-[3-amino-6-methoxy-4-(methylamino)phenoxy](2-pyridyl)}-N-methylcarboxamide. MS: MH+: 302.

Step 6. Synthesis of (4-{2-[(4-bromo-3-methylphenyl)amino)]-6-methoxy-1-methylbenzimidazol-5-yloxy}-(2-pyridyl))-N-methylcarboxamide

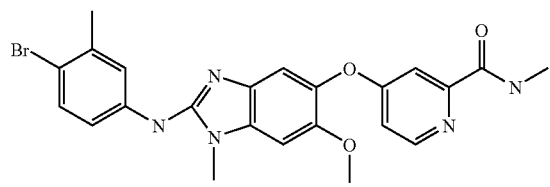

To a solution of {4-[3-amino-6-methoxy-4-(methylamino)phenoxy](2-pyridyl)}-N-methylcarboxamide (1 eq) in methanol was added 4-bromo-3-methylbenzeneisothiocyanate (1 eq) and stirred at 60° C. for 2 h. Formation of thiourea was followed by LC/MS. To it was added iodomethane (1 eq) and heated to 60° C. for 3 h. The mixture was concentrated and purified on preparative chromatography to yield (4-{2-[(4-bromo-3-methylphenyl)amino)]-6-methoxy-1-methylbenzimidazol-5-yloxy}-(2-pyridyl))-N-methylcarboxamide. MS: MH+=496.

Example 704

Synthesis of (5-{2-[(4-bromophenyl)amino]-1-methylbenzimidazol-5-yloxy)-(3-pyridyl))-N-methylcarboxamide

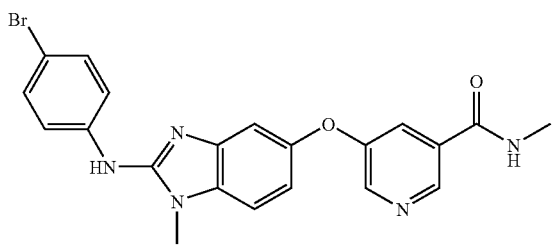

Step 1. Synthesis of methyl-5-(4-nitrophenoxy)pyridine-3-carboxylate

The mixture containing methyl-5-hydroxypyridine-3-carboxylate (1 eq), Potassium bis(trimethylsilyl)amide (1.2 eq) was stirred in N,N-dimethylformamide for 2 hours at room temperature. To this mixture was added 1-fluoro-4-nitrobenzene (1.1 eq) and Potassium carbonate (1.2 eq) and stirred at 80° C. for 16 h. The reaction mixture was then concentrated and partitioned between ethyl acetate and water. The organic layer was separated and washed with brine, dried, filtered and concentrated in vacuum to give brown solid. Purification on silica gel methyl-5-(4-nitrophenoxy)pyridine-3-carboxylate. MS: MH+=274.

Step 2. Synthesis of methyl5-[4-aminophenoxy]pyridine-3-carboxylate

The mixture containing methyl-5-(4-nitrophenoxy)pyridine-3-carboxylate in methanol with catalytic amount of 10% Pd/C was hydrogenated to yield methyl5-[4-aminophenoxy]pyridine-3-carboxylate. MS: MH+=244.

Step 3. Synthesis of methyl-5-[4-(2,2,2-trifluoroacetamino)phenoxy]pyridine-3-carboxylate A solution of methyl-5-[4-aminophenoxy]pyridine-3-carboxylate (1 eq) in methylene chloride was treated with trifluoroacetic anhydride (1 eq) and stirred for 10 minutes at 0° C. The mixture was quenched with saturated sodium bicarbonate solution. The organic layer was separated and washed with water, brine, dried and evaporated to yield methyl-5-[4-(2,2,2-trifluoroacetamino)phenoxy]pyridine-3-carboxylate. MS: MH+=340.

Step 4. Synthesis of methyl-5-[3-nitro-4-(2,2,2-trifluoroacetylamino)phenoxy]-pyridine-3-carboxylate To a solution of methyl-5-[4-(2,2,2-trifluoroacetamino)phenoxy]pyridine-3-carboxylate in acetic acid and acetic anhydride (1:1) at 0° C. was added nitric acid followed by sulfuric acid. Followed the reaction by LC and once complete it was partitioned between ethyl acetate. The organic layer was washed with brine and dried with sodium sulfate and concentrated to yield methyl5-[3-nitro-4-(2,2,2-trifluoroacetylamino)phenoxy]-pyridine-3-carboxylate. MS: MH+=385.

Step 5. Synthesis of methyl-4-[4-(methylamino)-3-nitrophenoxy]pyridine-3-carboxylate To the solution of the methyl5-[3-nitro-4-(2,2,2-trifluoroacetylamino)phenoxy]-pyridine-3-carboxylate (1 eq) in a mixture of toluene, acetonitrile and sodium hydroxide solution (50%) was added benzyltrimethylammonium chloride (1 eq) and dimethyl sulfate (1.2 eq). The biphasic mixture was stirred overnight at room temperature and evaporated. The mixture was taken up in ethyl acetate, washed with water, brine, dried and evaporated. The crude was purified by column chromatography to afford methyl-4-[4-(methylamino)-3-nitrophenoxy]pyridine-3-carboxylate. MS: MH+=303.

Step 6. Synthesis of methyl5-[3-amino-4-(methylamino)phenoxy]pyridine-3-carboxylate The mixture containing methyl-4-[4-(methylamino)-3-nitrophenoxy]pyridine-3-carboxylate was hydrogenated with 10% Pd/C to yield methyl5-[3-amino-4-(methylamino)phenoxy]pyridine-3-carboxylate. MS: MH+=273.

Step 7. Synthesis of methyl5-{2-[(4-bromophenyl)amino]-1-methylbenzimidazol-5-yloxy}pyridine-3-carboxylate A solution of the methyl5-[3-amino-4-(methylamino)phenoxy]pyridine-3-carboxylate (1 eq) in methanol (8 ml) was treated with 4-bromophenylisothiocyanate (1 eq) and stirred at 60° C.-65° C. for 2 hours. The reaction mixture was cooled down to room temperature and methyl iodide (1 eq) was added and stirred overnight at 60° C. The reaction was cooled down to room temperature, evaporated, taken up in ethyl acetate and washed with water and brine, dried, evaporated under reduced pressure. Column chromatography yielded methyl5-{2-[(4-bromophenyl)amino]-1-methylbenzimidazol-5-yloxy}pyridine-3-carboxylate. MS: MH+=452

Step 8. Synthesis of (5-{2-[(4-bromophenyl)amino]-1-methylbenzimidazol-5-yloxy)-(3-pyridyl))-N-methylcarboxamide To a solution of methyl5-{2-[(4-bromophenyl)amino]-1-methylbenzimidazol-5-yloxy}pyridine-3-carboxylate in added methylamine and the resulting mixture was stirred at ambient temperature for 16 h. It was then concentrated and purified by preparative chromatography to yield (5-{2-[(4-bromophenyl)amino]-1-methylbenzimidazol-5-yloxy)-(3-pyridyl))-N-methylcarboxamide. MS: MH+=452.

Each of the compounds 705-746, listed in Table 8 were synthesized as indicated in the right hand column by the method described in one of the Examples 699 or 700.

TABLE 8

| Example | Molecular Structure | Name | MH+ | Synthesized as in Example: |
|---------|--------------------|------|-----|---------------------------|
| 705 | 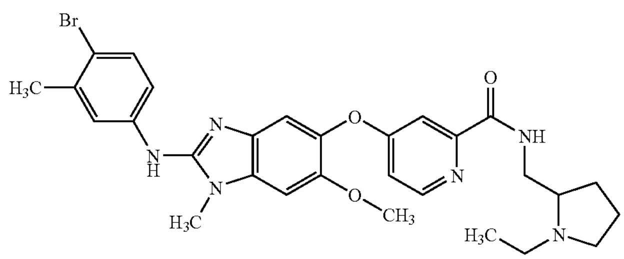 | 4-{[2-[(4-bromo-3-methyl-phenyl)amino]-1-methyl-6-(methyloxy)-1H-benzimidazol-5-yl]oxy}-N-[(1-ethyl-pyrrolidin-2-yl)methyl]-pyridine-2-carboxamide | 594.5 | 700 |
| 706 | 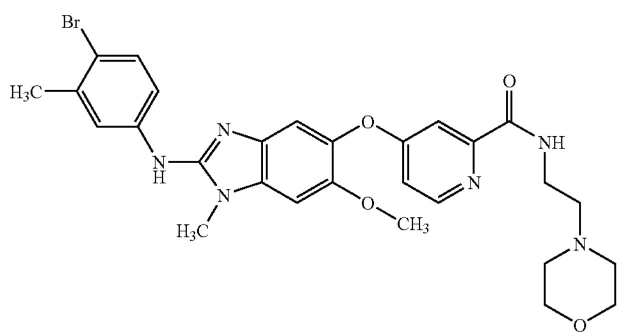 | 4-{[2-[(4-bromo-3-methyl-phenyl)amino]-1-methyl-6-(methyloxy)-1H-benzimidazol-5-yl]oxy}-N-(2-morpholin-4-ylethyl)pyridine-2-carboxamide | 596.5 | 700 |
| 707 | 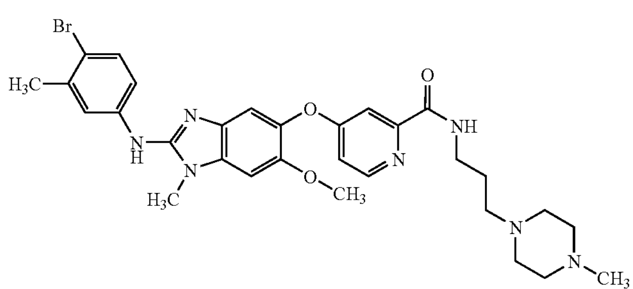 | 4-{[2-[(4-bromo-3-methyl-phenyl)amino]-1-methyl-6-(methyloxy)-1H-benzimidazol-5-yl]oxy}-N-[3-(4-methyl-piperazin-1-yl)propyl]pyridine-2-carboxamide | 623.6 | 700 |

TABLE 8-continued

| Example | Molecular Structure | Name | MH+ | Synthesized as in Example: |
|---|---|---|---|---|
| 708 | 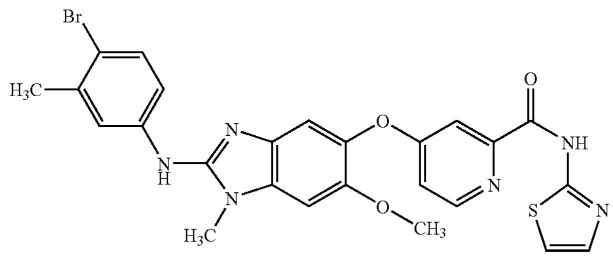 | 4-{[2-[(4-bromo-3-methyl-phenyl)amino]-1-methyl-6-(methyloxy)-1H-benzimidazol-5-yl]oxy}-N-1,3-thiazol-2-ylpyridine-2-carboxamide | 566.5 | 700 |
| 709 | 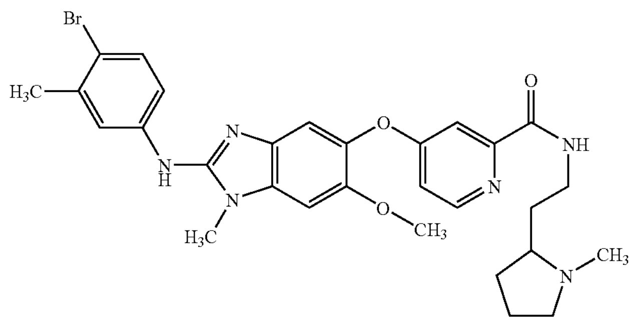 | 4-{[2-[(4-bromo-3-methyl-phenyl)amino]-1-methyl-6-(methyloxy)-1H-benzimidazol-5-yl]oxy}-N-[2-(1-methyl-pyrrolidin-2-yl)ethyl]pyridine-2-carboxamide | 594.5 | 700 |
| 710 | 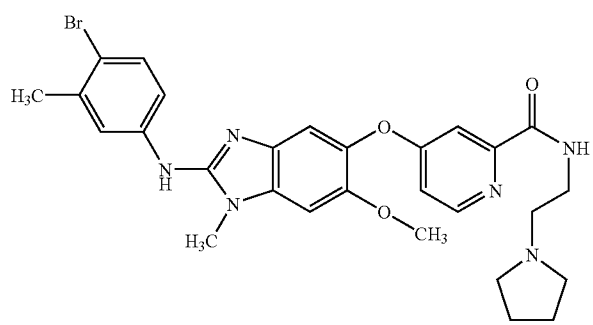 | 4-{[2-[(4-bromo-3-methyl-phenyl)amino]-1-methyl-6-(methyloxy)-1H-benzimidazol-5-yl]oxy}-N-(2-pyrrolidin-1-ylethyl)pyridine-2-carbox-amide | 580.5 | 700 |
| 711 | 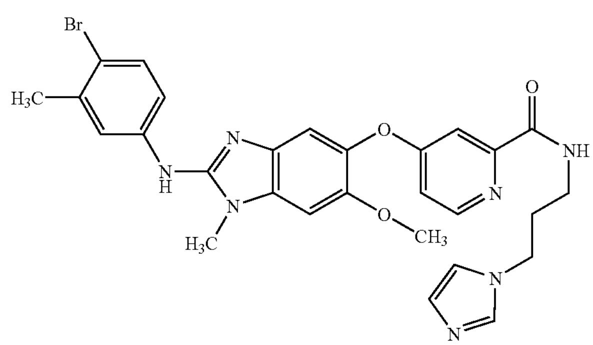 | 4-{[2-[(4-bromo-3-methyl-phenyl)amino]-1-methyl-6-(methyloxy)-1H-benzimidazol-5-yl]oxy}-N-[3-(1H-imidazol-1-yl)propyl]pyridine-2-carboxamide | 591.5 | 700 |

TABLE 8-continued

| Example | Molecular Structure | Name | MH+ | Synthesized as in Example: |
|---|---|---|---|---|
| 712 | 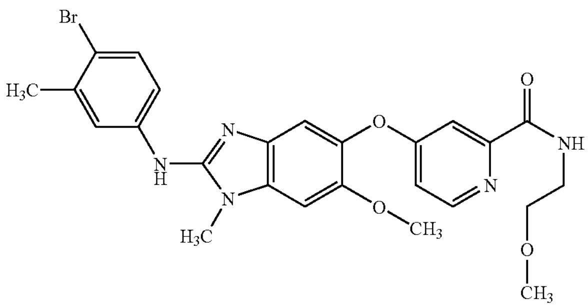 | 4-{[2-[(4-bromo-3-methyl-phenyl)amino]-1-methyl-6-(methyloxy)-1H-benzimidazol-5-yl]oxy}-N-[2-(methyloxy)-ethyl]pyridine-2-carboxamide | 541.4 | 700 |
| 713 | 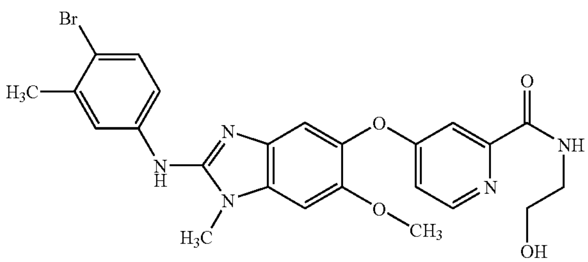 | 4-{[2-[(4-bromo-3-methyl-phenyl)amino]-1-methyl-6-(methyloxy)-1H-benzimidazol-5-yl]oxy}-N-(2-hydroxyethyl)-pyridine-2-carboxamide | 527.4 | 700 |
| 714 | 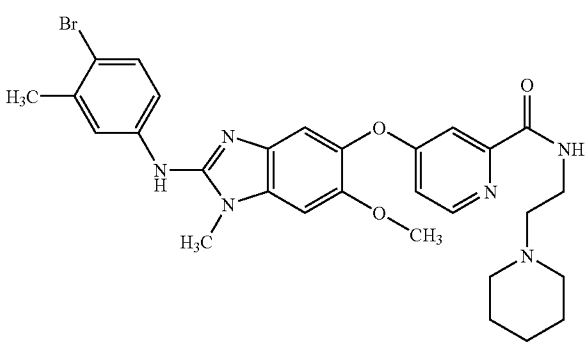 | 4-{[2-[(4-bromo-3-methyl-phenyl)amino]-1-methyl-6-(methyloxy)-1H-benzimidazol-5-yl]oxy}-N-(2-piperidin-1-ylethyl)pyridine-2-carbox-amide | 594.5 | 700 |
| 715 | 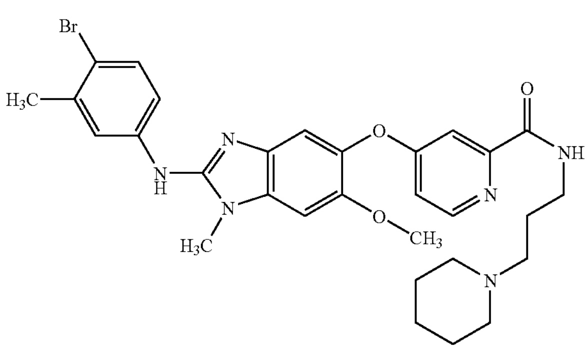 | 4-{[2-[(4-bromo-3-methyl-phenyl)amino]-1-methyl-6-(methyloxy)-1H-benzimidazol-5-yl]oxy}-N-(3-piperidin-1-ylpropyl)pyridine-2-carbox-amide | 608.5 | 700 |

TABLE 8-continued

| Example | Molecular Structure | Name | MH+ | Synthesized as in Example: |
|---|---|---|---|---|
| 716 | 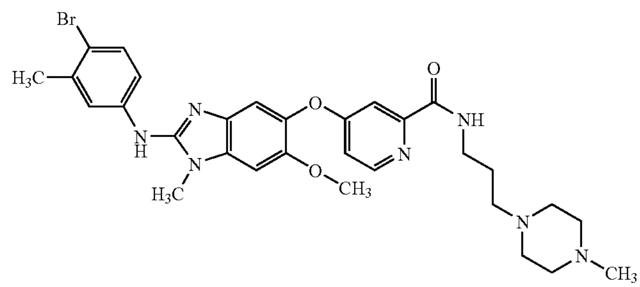 | 4-{[2-[(4-bromo-3-methyl-phenyl)amino]-1-methyl-6-(methyloxy)-1H-benzimidazol-5-yl]oxy}-N-[3-(4-methyl-piperazin-1-yl)propyl]pyridine-2-carboxamide | 623.6 | 700 |
| 717 | 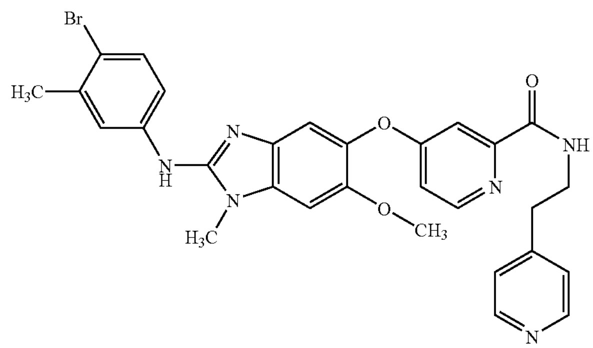 | 4-{[2-[(4-bromo-3-methyl-phenyl)amino]-1-methyl-6-(methyloxy)-1H-benzimidazol-5-yl]oxy}-N-(2-pyridin-4-yl-ethyl)pyridine-2-carboxamide | 588.5 | 700 |
| 718 | 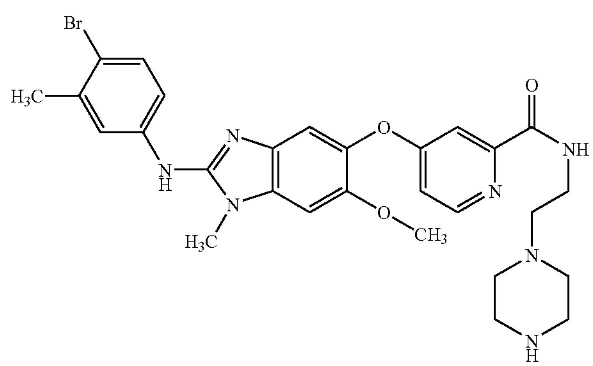 | 4-{[2-[(4-bromo-3-methyl-phenyl)amino]-1-methyl-6-(methyloxy)-1H-benzimidazol-5-yl]oxy}-N-(2-piperazin-1-yl-ethyl)pyridine-2-carboxamide | 595.5 | 700 |
| 719 | 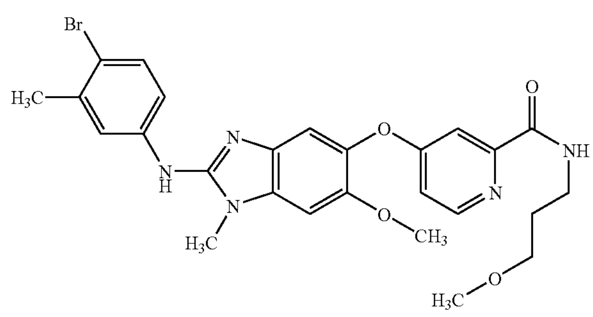 | 4-{[2-[(4-bromo-3-methyl-phenyl)amino]-1-methyl-6-(methyloxy)-1H-benzimidazol-5-yl]oxy}-N-[3-(methyloxy)-propyl]pyridine-2-carboxamide | 555.4 | 700 |

TABLE 8-continued

| Example | Molecular Structure | Name | MH+ | Synthesized as in Example: |
|---|---|---|---|---|
| 720 | 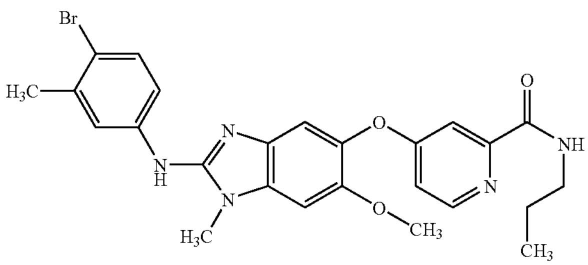 | 4-{[2-[(4-bromo-3-methyl-phenyl)amino]-1-methyl-6-(methyloxy)-1H-benzimidazol-5-yl]oxy}-N-propylpyridine-2-carboxamide | 525.4 | 700 |
| 721 | 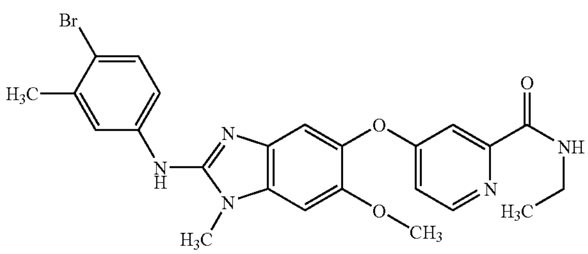 | 4-{[2-[(4-bromo-3-methyl-phenyl)amino]-1-methyl-6-(methyloxy)-1H-benzimidazol-5-yl]oxy}-N-ethylpyridine-2-carboxamide | 511.4 | 700 |
| 722 | 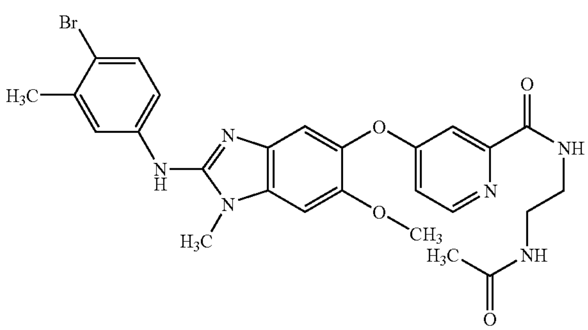 | N-[2-(acetylamino)ethyl]-4-{[2-[(4-bromo-3-methyl-phenyl)amino]-1-methyl-6-(methyloxy)-1H-benzimidazol-5-yl]oxy}pyridine-2-carboxamide | 568.4 | 700 |
| 723 | 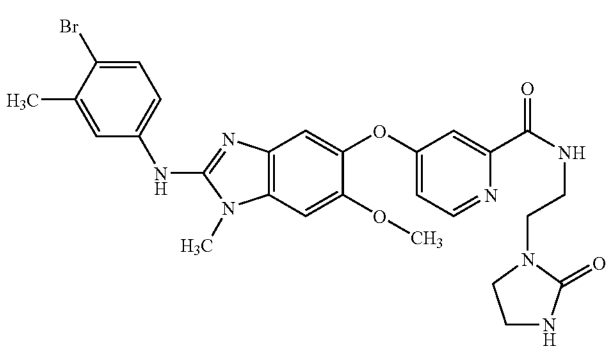 | 4-{[2-[(4-bromo-3-methyl-phenyl)amino]-1-methyl-6-(methyloxy)-1H-benzimidazol-5-yl]oxy}-N-[2-(2-oxo-imidazolidin-1-yl)ethyl]-pyridine-2-carboxamide | 595.5 | 700 |

TABLE 8-continued

| Example | Molecular Structure | Name | MH+ | Synthesized as in Example: |
|---|---|---|---|---|
| 724 | 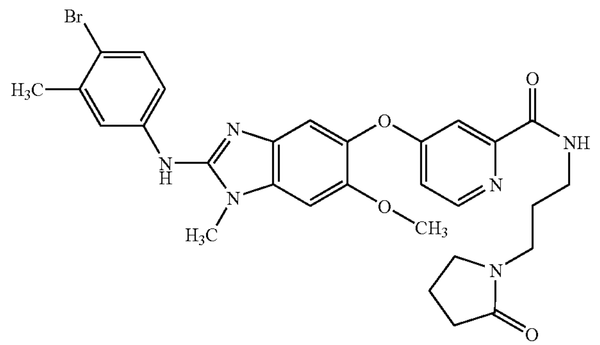 | 4-{[2-[(4-bromo-3-methyl-phenyl)amino]-1-methyl-6-(methyloxy)-1H-benzimidazol-5-yl]oxy}-N-[3-(2-oxo-pyrrolidin-1-yl)propyl]-pyridine-2-carboxamide | 608.5 | 700 |
| 725 | 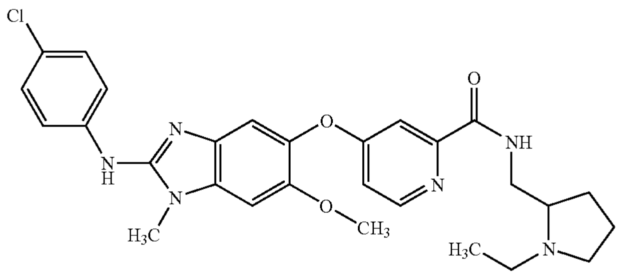 | 4-{[2-[(4-chlorophenyl)-amino]-1-methyl-6-(methyl-oxy)-1H-benzimidazol-5-yl]-oxy}-N-[(1-ethylpyrrolidin-2-yl)methyl]pyridine-2-carbox-amide | 536.0 | 699 |
| 726 | 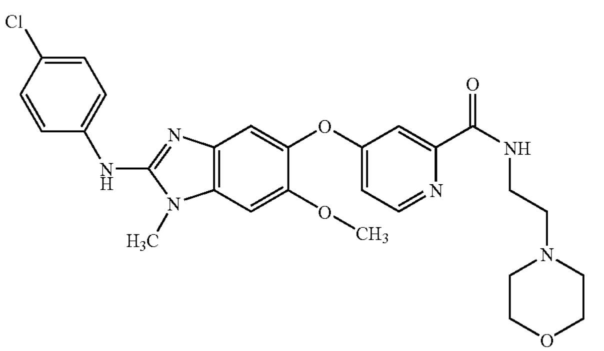 | 4-{[2-[(4-chlorophenyl)-amino]-1-methyl-6-(methyl-oxy)-1H-benzimidazol-5-yl]-oxy}-N-(2-morpholin-4-yl-ethyl)pyridine-2-carboxamide | 538.0 | 699 |
| 727 | 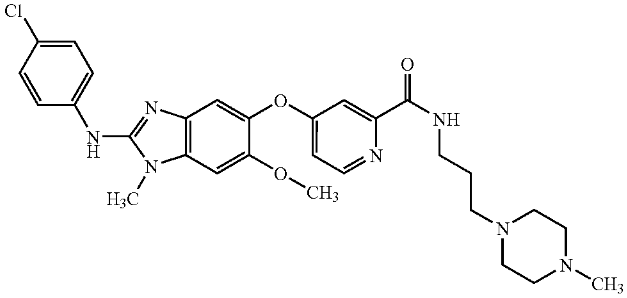 | 4-{[2-[(4-chlorophenyl)-amino]-1-methyl-6-(methyl-oxy)-1H-benzimidazol-5-yl]-oxy}-N-[3-(4-methylpiperazin-1-yl)propyl]pyridine-2-carboxamide | 565.1 | 699 |

TABLE 8-continued

| Example | Molecular Structure | Name | MH+ | Synthesized as in Example: |
|---|---|---|---|---|
| 728 | 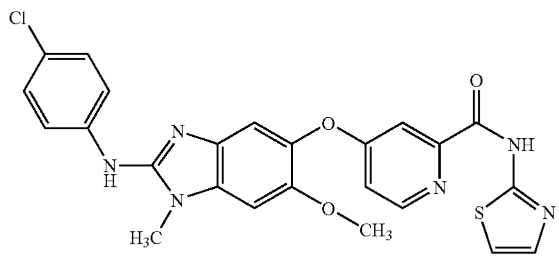 | 4-{[2-[(4-chlorophenyl)-amino]-1-methyl-6-(methyloxy)-1H-benzimidazol-5-yl]-oxy}-N-1,3-thiazol-2-yl-pyridine-2-carboxamide | 508.0 | 699 |
| 729 | 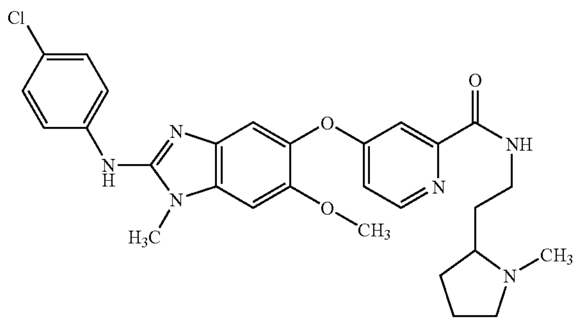 | 4-{[2-[(4-chlorophenyl)-amino]-1-methyl-6-(methyloxy)-1H-benzimidazol-5-yl]oxy}-N-[2-(1-methyl-pyrrolidin-2-yl)ethyl]pyridine-2-carboxamide | 536.0 | 699 |
| 730 | 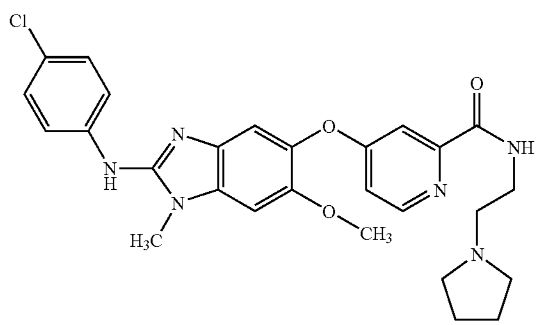 | 4-{[2-[(4-chlorophenyl)-amino]-1-methyl-6-(methyloxy)-1H-benzimidazol-5-yl]-oxy}-N-(2-pyrrolidin-1-yl-ethyl)pyridine-2-carboxamide | 522.0 | 699 |
| 731 | 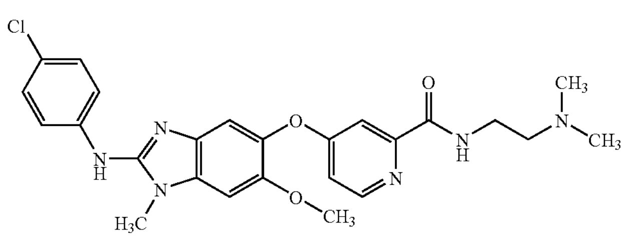 | 4-{[2-[(4-chlorophenyl)-amino]-1-methyl-6-(methyloxy)-1H-benzimidazol-5-yl]-oxy}-N-[2-(dimethylamino)-ethyl]pyridine-2-carboxamide | 496.0 | 699 |
| 732 | 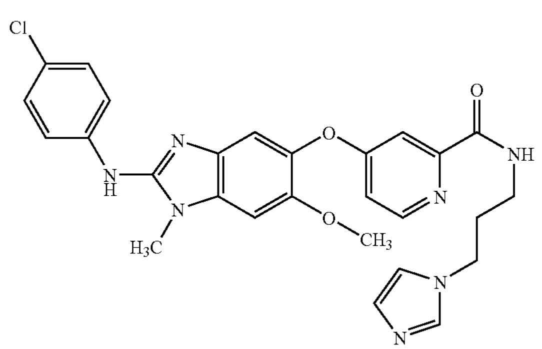 | 4-{[2-[(4-chlorophenyl)-amino]-1-methyl-6-(methyloxy)-1H-benzimidazol-5-yl]-oxy}-N-[3-(1H-imidazol-1-yl)-propyl]pyridine-2-carboxamide | 533.0 | 699 |

TABLE 8-continued

| Example | Molecular Structure | Name | MH+ | Synthesized as in Example: |
|---|---|---|---|---|
| 733 | 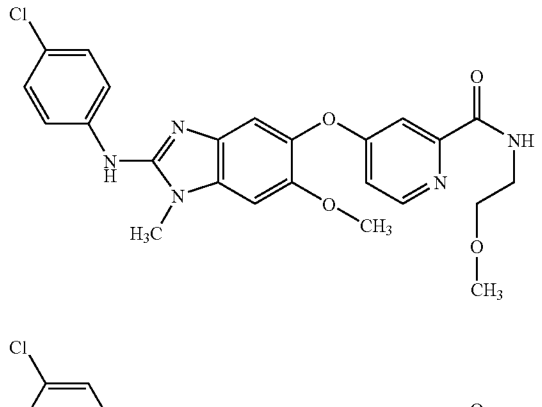 | 4-{[2-[(4-chlorophenyl)-amino]-1-methyl-6-(methyl-oxy)-1H-benzimidazol-5-yl]-oxy}-N-[2-(methyloxy)ethyl]-pyridine-2-carboxamide | 482.9 | 699 |
| 734 | 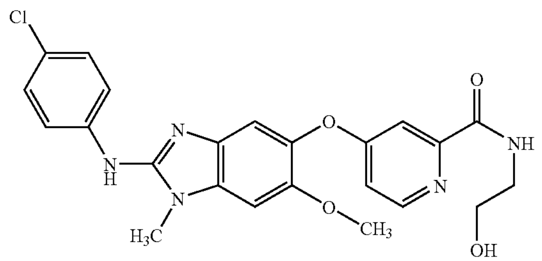 | 4-{[2-[(4-chlorophenyl)-amino]-1-methyl-6-(methyl-oxy)-1H-benzimidazol-5-yl]-oxy}-N-(2-hydroxyethyl)-pyridine-2-carboxamide | 468.9 | 699 |
| 735 | 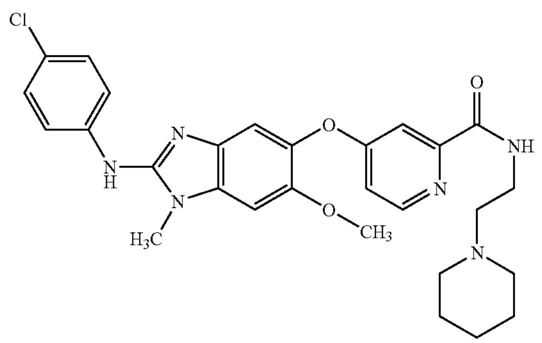 | 4-{[2-[(4-chlorophenyl)-amino]-1-methyl-6-(methyl-oxy)-1H-benzimidazol-5-yl]-oxy}-N-(2-piperidin-1-ylethyl)pyridine-2-carbox-amide | 536.0 | 699 |
| 736 | 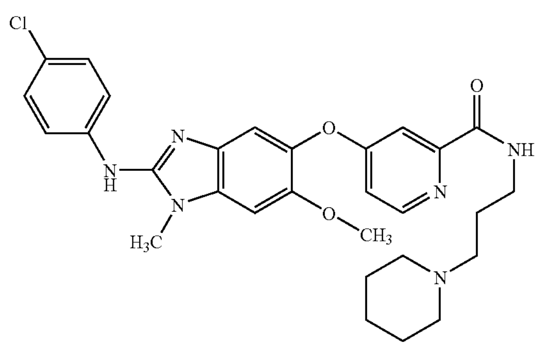 | 4-{[2-[(4-chlorophenyl)-amino]-1-methyl-6-(methyl-oxy)-1H-benzimidazol-5-yl]-oxy}-N-(3-piperidin-1-yl-propyl)pyridine-2-carboxamide | 550.1 | 699 |

TABLE 8-continued

| Example | Molecular Structure | Name | MH+ | Synthesized as in Example: |
|---|---|---|---|---|
| 737 | 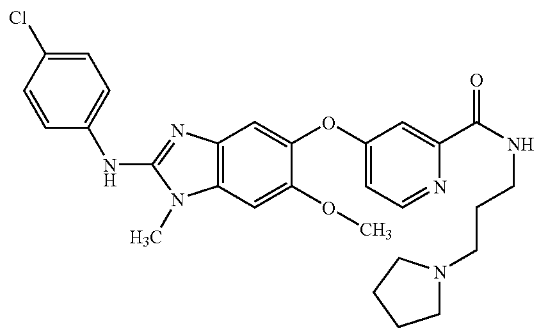 | 4-{[2-[(4-chlorophenyl)-amino]-1-methyl-6-(methyl-oxy)-1H-benzimidazol-5-yl]-oxy}-N-(3-pyrrolidin-1-yl-propyl)pyridine-2-carboxamide | 536.0 | 699 |
| 738 | 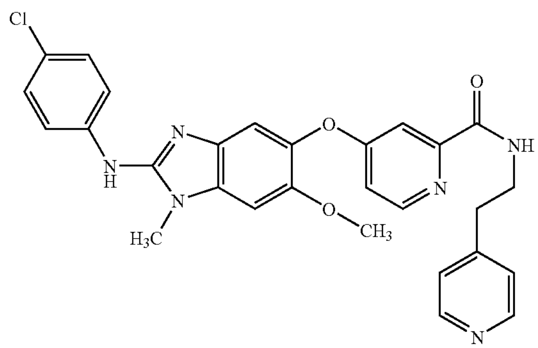 | 4-{[2-[(4-chlorophenyl)-amino]-1-methyl-6-(methyl-oxy)-1H-benziniidazol-5-yl]-oxy}-N-(2-pyridin-4-ylethyl)-pyridine-2-carboxamide | 530.0 | 699 |
| 739 | 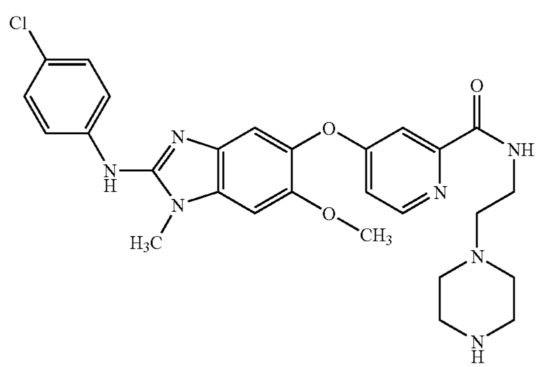 | 4-{[2-[(4-chlorophenyl)]-1-methyl-6-(methyloxy)-1H-benzimidazol-5-yl]oxy}-N-(2-piperazin-1-ylethyl)pyridine-2-carboxamide | 537.0 | 699 |
| 740 | 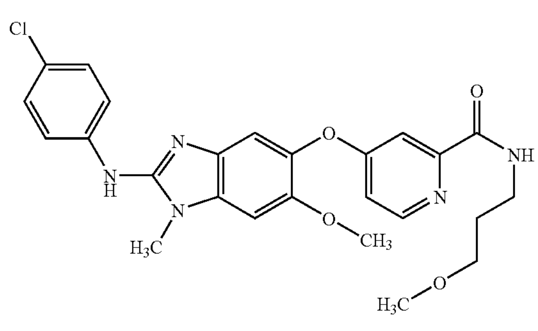 | 4-{[2-[(4-chlorophenyl)-amino]-1-methyl-6-(methyl-oxy)-1H-benzimidazol-5-yl]oxy}-N-[3-(methyloxy)-propyl]pyridine-2-carboxamide | 497.0 | 699 |

TABLE 8-continued

| Example | Molecular Structure | Name | MH+ | Synthesized as in Example: |
|---|---|---|---|---|
| 741 | 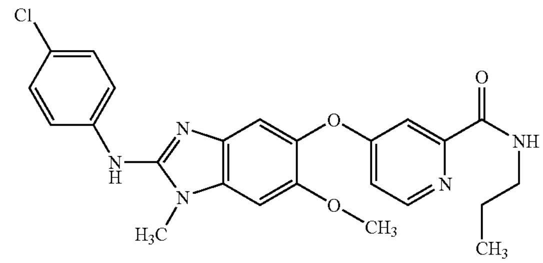 | 4-{[2-[(4-chlorophenyl)-amino]-1-methyl-6-(methyl-oxy)-1H-benzimidazol-5-yl]-oxy}-N-propylpyridine-2-carboxamide | 466.9 | 699 |
| 742 | 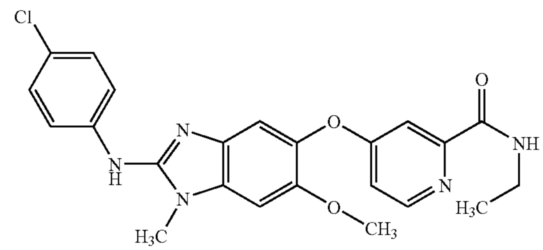 | 4-{[2-[(4-chlorophenyl)-amino]-1-methyl-6-(methyl-oxy)-1H-benzimidazol-5-yl]-oxy}-N-ethylpyridine-2-carboxamide | 452.9 | 699 |
| 743 | 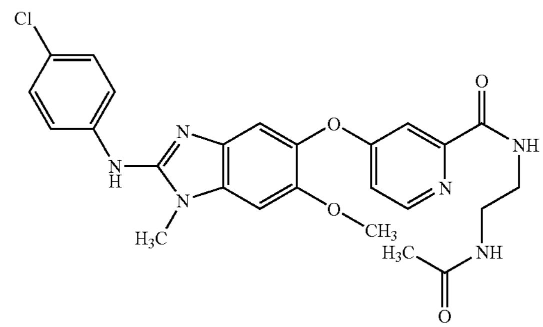 | N-[2-(acetylamino)ethyl]-4-{[2-[(4-chlorophenyl)amino]-1-methyl-6-(methyloxy)-1H-benzimidazol-5-yl]oxy}-pyridine-2-carboxamide | 510.0 | 699 |
| 744 | 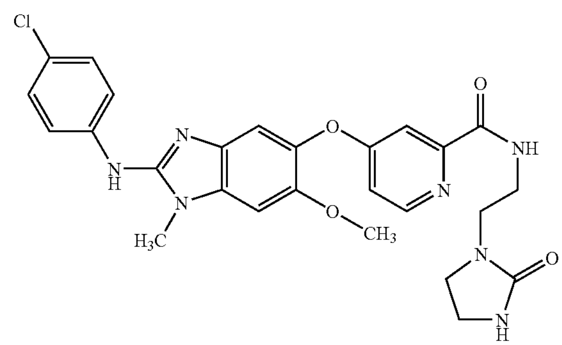 | 4-{[2-[(4-chlorophenyl)-amino]-1-methyl-6-(methyl-oxy)-1H-benzimidazol-5-yl]oxy}-N-[2-(2-oxo-imidazolidin-1-yl)ethyl]-pyridine-2-carboxamide | 537.0 | 699 |
| 745 | Chiral | 4-{[2-[(4-chlorophenyl)-amino]-1-methyl-6-(methyl-oxy)-1H-benzimidazol-5-yl]-oxy}-N-[(3R)-pyrrolidin-3-yl]pyridine-2-carboxamide | 494.0 | 699 |

TABLE 8-continued

| Example | Molecular Structure | Name | MH+ | Synthesized as in Example: |
|---|---|---|---|---|
| 746 | 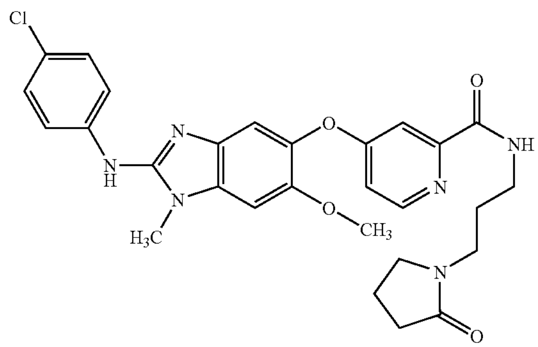 | 4-{[2-[(4-chlorophenyl)-amino]-1-methyl-6-(methyloxy)-1H-benzimidazol-5-yl]-oxy}-N-[3-(2-oxopyrrolidin-1-yl)propyl]pyridine-2-carboxamide | 550.0 | 699 |

Each of the compounds 747-782, listed in the below table were synthesized as indicated in the right hand column by the method described in one of the Examples 702 or 703 unless indicated otherwise.

TABLE 9

| Example | Structure | Name | MH+ | Synthesized as in Example: |
|---|---|---|---|---|
| 747 | 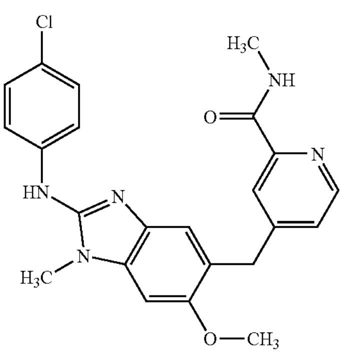 | 4-{[2-[(4-chlorophenyl)amino]-1-methyl-6-(methyloxy)-1H-benzimidazol-5-yl]oxy}-N-methylpyridine-2-carboxamide | 438.9 | 703 |
| 748 | 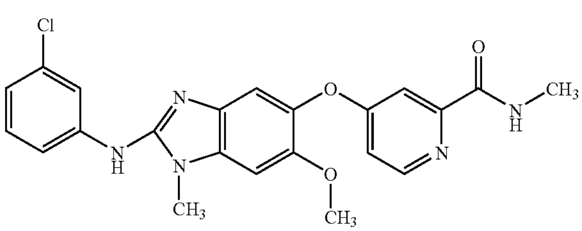 | 4-{[2-[(3-chlorophenyl)amino]-1-methyl-6-(methyloxy)-1H-benzimidazol-5-yl]oxy}-N-methylpyridine-2-carboxamide | 438.9 | 703 |
| 749 | 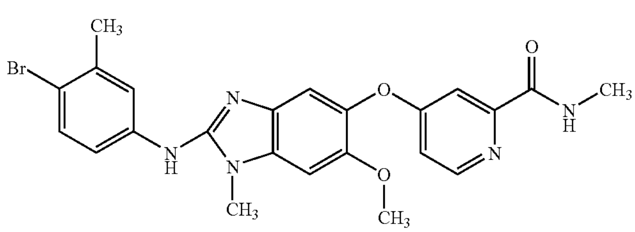 | 4-{[2-[(4-bromo-3-methylphenyl)amino]-1-methyl-6-methyloxy)-1H-benzimidazol-5-yl]oxy}-N-methylpyridine-2-carboxamide | 497.4 | 703 |

TABLE 9-continued

| Example | Structure | Name | MH+ | Synthesized as in Example: |
|---|---|---|---|---|
| 750 | 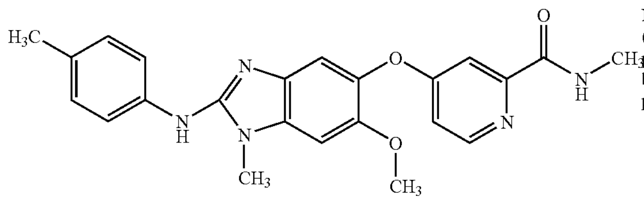 | N-methyl-4-({1-methyl-6-(methyloxy)-2-[(4-methylphenyl)amino]-1H-benzimidazol-5-yl}oxy)-pyridine-2-carboxamide | 418.5 | 703 |
| 751 | 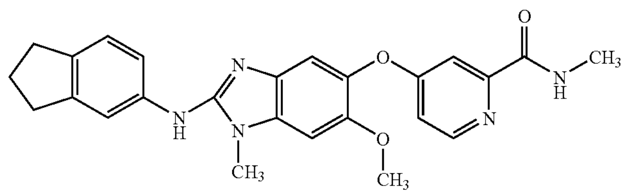 | 4-{[2-(2,3-dihydro-1H-inden-5-ylamino)-1-methyl-6-(methyloxy)-1H-benzimidazol-5-yl]oxy}-N-methylpyridine-2-carboxamide | 444.5 | 703 |
| 752 | 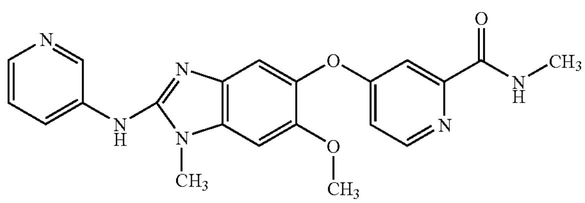 | N-methyl-4-{[1-methyl-6-(methyloxy)-2-(pyridin-3-ylamino)-1H-benzimidazol-5-yl]oxy}pyridine-2-carboxamide | 405.4 | 703 |
| 753 | 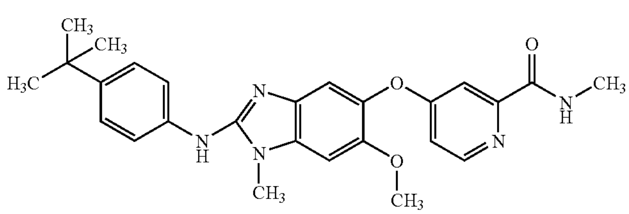 | 4-{[2-{[4-(1,1-dimethylethyl)phenyl]amino}-1-methyl-6-(methyloxy)-1H-benzimidazol-5-yl]oxy}-N-methylpyridine-2-carboxamide | 460.5 | 703 |
| 754 | 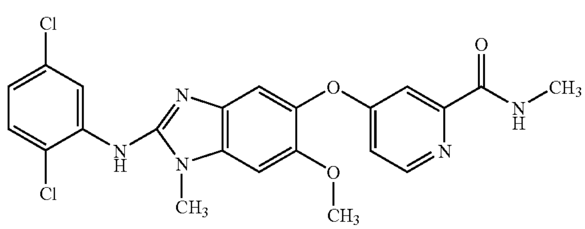 | 4-{[2-[(2,5-dichlorophenyl)amino]-1-methyl-6-(methyloxy)-1H-benzimidazol-5-yl]oxy}-N-methylpyridine-2-carboxamide | 473.3 | 703 |
| 755 | 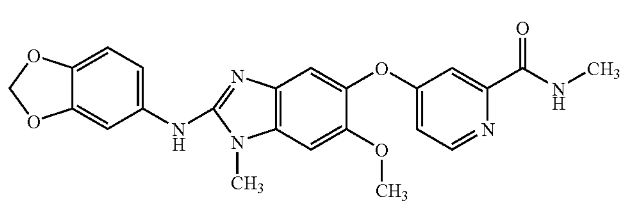 | 4-{[2-(1,3-benzodioxol-5-ylamino)-1-methyl-6-(methyloxy)-1H-benzimidazol-5-yl]oxy}-N-methylpyridine-2-carboxamide | 448.4 | 703 |
| 756 | 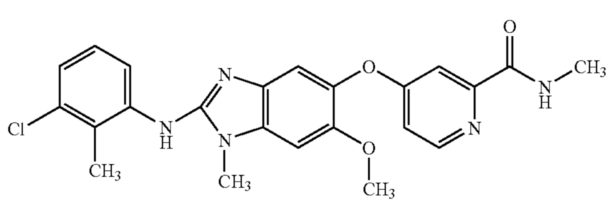 | 4-{[2-[(3-chloro-2-methylphenyl)amino]-1-methyl-6-(methyloxy)-1H-benzimidazol-5-yl]oxy}-N-methylpyridine-2-carboxamide | 452.9 | 703 |

TABLE 9-continued

| Example | Structure | Name | MH+ | Synthesized as in Example: |
|---|---|---|---|---|
| 757 | 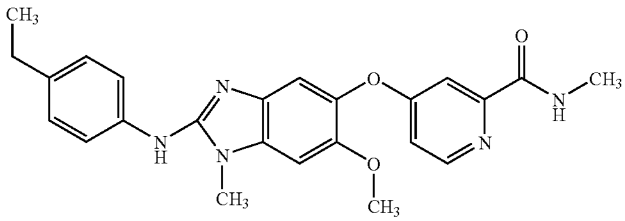 | 4-{[2-[(4-ethylphenyl)amino]-1-methyl-6-(methyloxy)-1H-benzimidazol-5-yl]oxy}-N-methylpyridine-2-carboxamide | 432.5 | 703 |
| 758 | 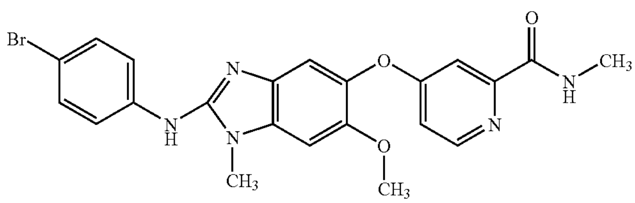 | 4-{[2-[(4-bromophenyl)amino]-1-methyl-6-(methyloxy)-1H-benzimidazol-5-yl]oxy}-N-methylpyridine-2-carboxamide | 483.3 | 703 |
| 759 | 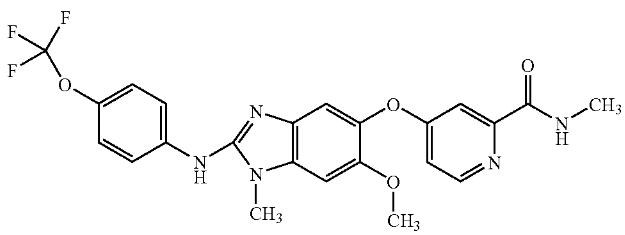 | N-methyl-4-{[1-methyl-6-(methyloxy)-2-({4-[(trifluoro-(methyl)oxy]phenyl}amino)-1H-benzimidazol-5-yl]oxy}-pyridine-2-carboxamide | 488.4 | 703 |
| 760 | 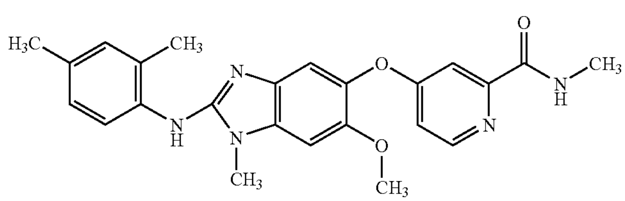 | 4-{[2-[(2,4-dimethylphenyl)-amino]-1-methyl-6-(methyl-oxy)-1H-benzimidazol-5-yl]-oxy}-N-methylpyridine-2-carboxamide | 432.5 | 703 |
| 761 | 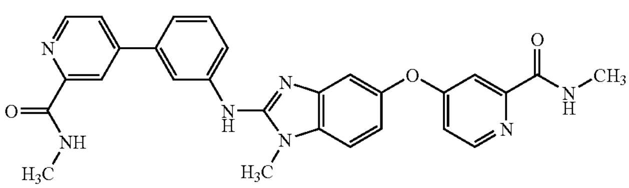 | N-methyl-4-(3-{[1-methyl-5-(-{2-[(methylamino)carbonyl]-pyridin-4-yl}oxy)-1H-benzimidazol-2-yl]amino}-phenyl)pyridine-2-carboxamide | 508.6 | 703 |
| 762 | 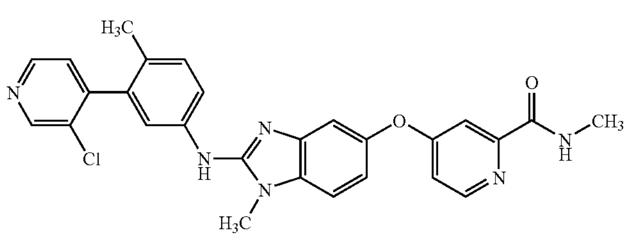 | 4-[(2-{[3-(3-chloropyridin-4-yl)-4-methylphenyl]amino}-1-methyl-1H-benzimidazol-5-yl)oxy]-N-methylpyridine-2-carboxamide | 500.0 | 702 |
| 763 | 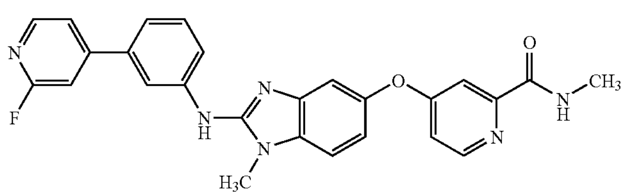 | 4-[(2-{[3-(2-fluoropyridin-4-yl)phenyl]amino}-1-methyl-1H-benzimidazol-5-yl)oxy]-N-methylpyridine-2-carboxamide | 469.5 | 702 |

TABLE 9-continued

| Example | Structure | Name | MH+ | Synthesized as in Example: |
|---|---|---|---|---|
| 764 | 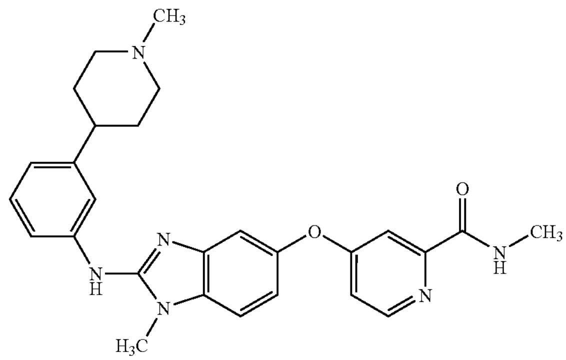 | N-methyl-4-[(1-methyl-2-{[3-(1-methylpiperidin-4-yl)-phenyl]amino}-1H-benzimidazol-5-yl)oxy]pyridine-2-carboxamide | 471.6 | 702 |
| 765 | 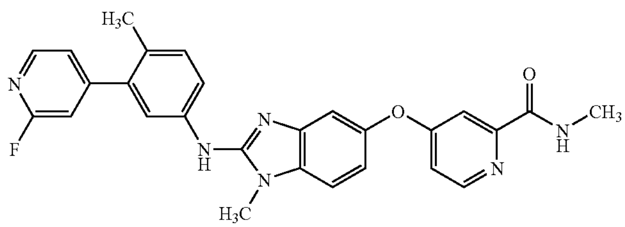 | 4-[(2-{[3-(2-fluoropyridin-4-yl)-4-methylphenyl]amino}-1-methyl-1H-benzimidazol-5-yl)-oxy]-N-methylpyridine-2-carboxamide | 483.5 | 702 |
| 766 | 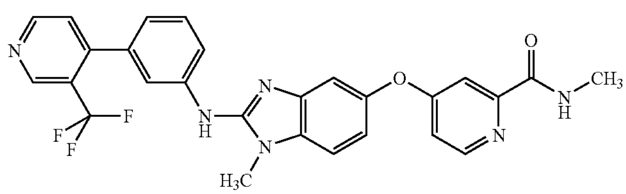 | N-methyl-4-{[1-methyl-2-({3-[3-(trifluoromethyl)pyridin-4-yl]phenyl}amino)-1H-benzimidazol-5-yl]oxy}-pyridine-2-carboxamide | 519.5 | 702 |
| 767 | 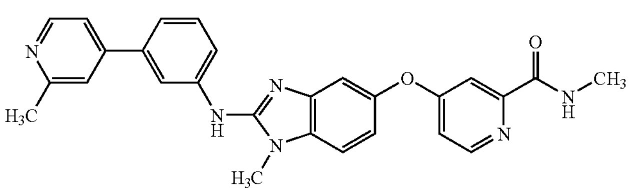 | N-methyl-4-[(1-methyl-2-{[3-(2-methylpyridin-4-yl)phenyl]-amino}-1H-benzimidazol-5-yl)oxy]pyridine-2-carboxamide | 465.5 | 702 |
| 768 | 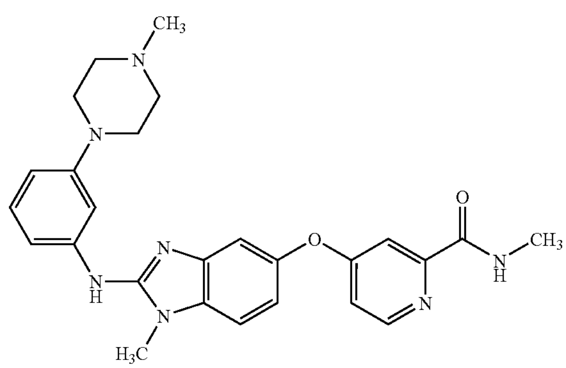 | N-methyl-4-[(1-methyl-2-{[3-(4-methylpiperazin-1-yl)phenyl]amino}-1H-benzimidazol-5-yl)oxy]pyridine-2-carboxamide | 472.6 | 702 |

TABLE 9-continued

| Example | Structure | Name | MH+ | Synthesized as in Example: |
|---|---|---|---|---|
| 769 | 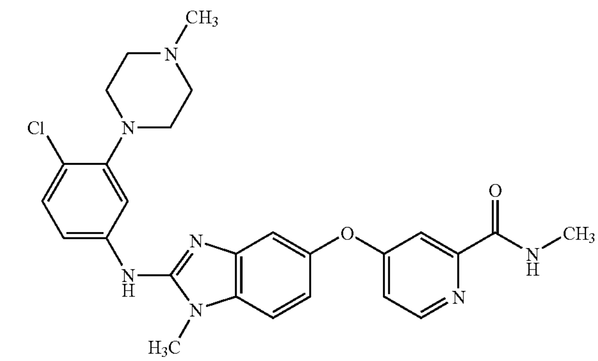 | 4-[(2-{[4-chloro-3-(4-methyl-piperazin-1-yl)phenyl]amino}-1-methyl-1H-benzimidazol-5-yl)oxy]-N-methylpyridine-2-carboxamide | 507.0 | 702 |
| 770 | 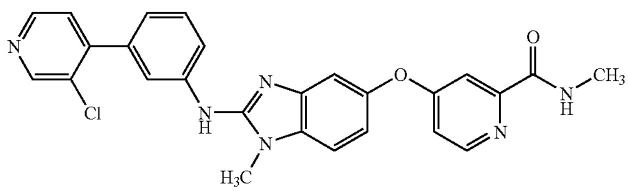 | 4-[(2-{[3-(3-chloropyridin-4-yl)phenyl]amino}-1-methyl-1H-benzimidazol-5-yl)oxy]-N-methylpyridine-2-carboxamide | 485.9 | 702 |
| 771 | 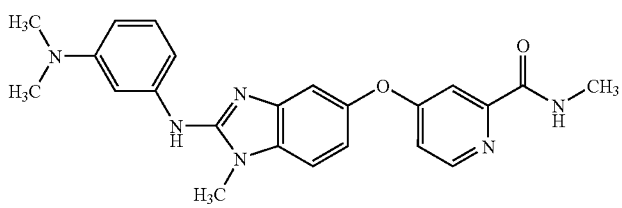 | 4-[(2-{[3-(dimethylamino)-phenyl]amino}-1-methyl-1H-benzimidazol-5-yl)oxy]-N-methylpyridine-2-carboxamide | 417.5 | 702 |
| 772 | 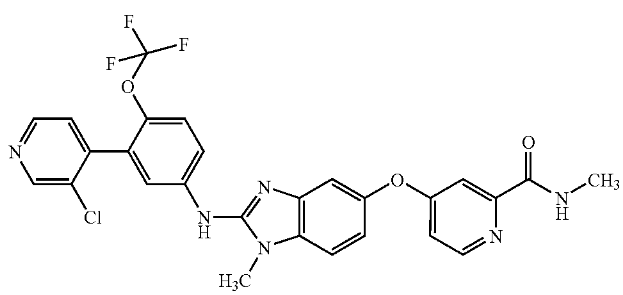 | 4-{[2-({3-(3-chloropyridin-4-yl)-4-[(trifluoromethyl)oxy]-phenyl}amino)-1-methyl-1H-benzimidazol-5-yl]oxy}-N-methylpyridine-2-carboxamide | 569.9 | 702 |
| 773 | 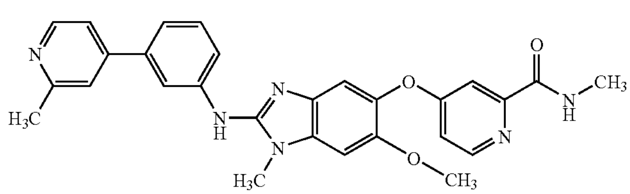 | N-methyl-4-[(1-methyl-6-(methyloxy)-2-{[3-(2-methyl-pyridin-4-yl)phenyl]amino}-1H-benzimidazol-5-yl)oxy]-pyridine-2-carboxamide | 495.6 | 702 |
| 774 | 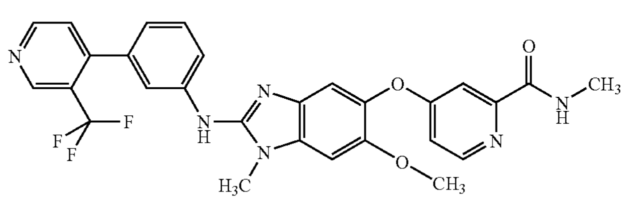 | N-methyl-4-{[1-methyl-6-(methyloxy)-2-({3-[3-(trifluoro-methyl)pyridin-4-yl]phenyl}-amino)-1H-benzimidazol-5-yl]-oxy}pyridine-2-carboxamide | 549.5 | 702 |

TABLE 9-continued

| Example | Structure | Name | MH+ | Synthesized as in Example: |
|---|---|---|---|---|
| 775 | 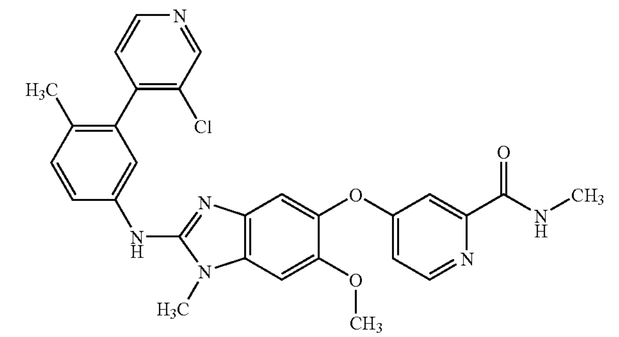 | 4-{[2-{[3-(3-chloropyridin-4-yl)-4-methylphenyl]amino}-1-methyl-6-(methyloxy)-1H-benzimidazol-5-yl]oxy}-N-methylpyridine-2-carboxamide | 530.0 | 702 |
| 776 | 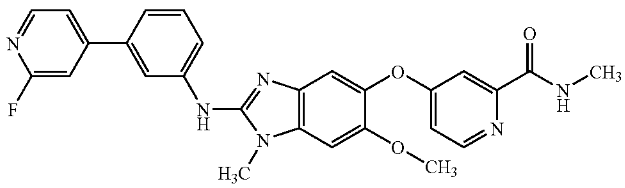 | 4-{[2-{[3-(2-fluoropyridin-4-yl)phenyl]amino}-1-methyl-6-(methyloxy)-1H-benzimidazol-5-yl]oxy}-N-methylpyridine-2-carboxamide | 499.5 | 702 |
| 777 | 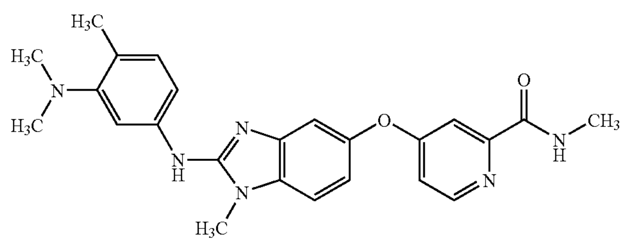 | 4-[(2-{[3-(dimethylamino)-4-methylphenyl]amino}-1-methyl-1H-benzimidazol-5-yl)oxy]-N-methylpyridine-2-carboxamide | 431.5 | 1 |
| 778 | 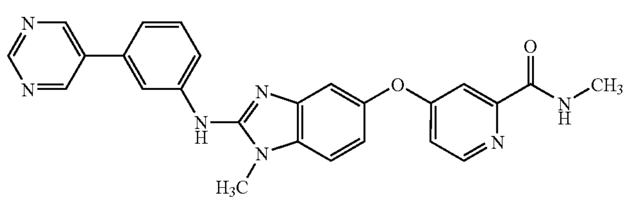 | N-methyl-4-({1-methyl-2-[(3-pyrimidin-5-ylphenyl)amino]-1H-benzimidazol-5-yl}oxy)-pyridine-2-carboxamide | 452.5 | 702 |
| 779 | 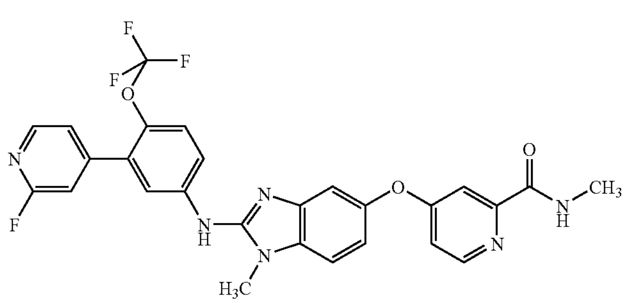 | 4-{[2-({3-(2-fluoropyridin-4-yl)-4-[(trifluoromethyl)oxy]-phenyl}amino)-1-methyl-1H-benzimidazol-5-yl]oxy}-N-methylpyridine-2-carboxamide | 553.5 | 702 |

TABLE 9-continued

| Example | Structure | Name | MH+ | Synthesized as in Example: |
|---|---|---|---|---|
| 780 | 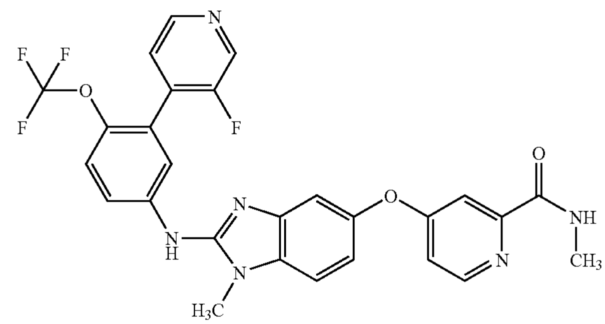 | 4-{[2-({3-(3-fluoropyridin-4-yl)-4-[(trifluoromethyl)oxy]-phenyl}amino)-1-methyl-1H-benzimidazol-5-yl]oxy}-N-methylpyridine-2-carboxamide | 553.5 | 702 |
| 781 | 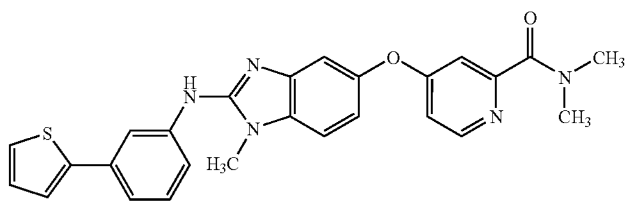 | N-methyl-4-({1-methyl-2-[(3-thien-2-ylphenyl)amino]-1H-benzimidazol-5-yl}oxy)-pyridine-2-carboxamide | 456.5 | 702 |
| 782 | 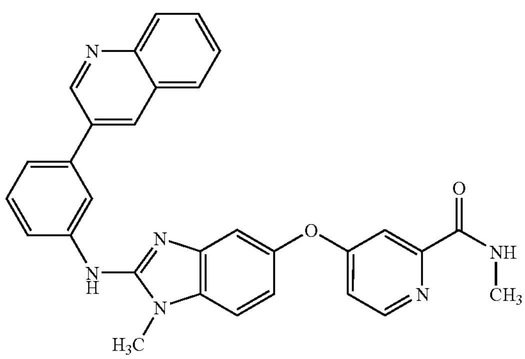 | N-methyl-4-({1-methyl-2-[(3-quinolin-3-ylphenyl)amino]-1H-benzimidazol-5-yl}oxy)-pyridine-2-carboxamide | 501.6 | 702 |

Example 783

Synthesis of [4-(2-{[6-(dimethylamino)(3-pyridyl)]amino}-1-methylbenzimidazol-5-yloxy)(2-pyridyl)]-N-methylcarboxamide

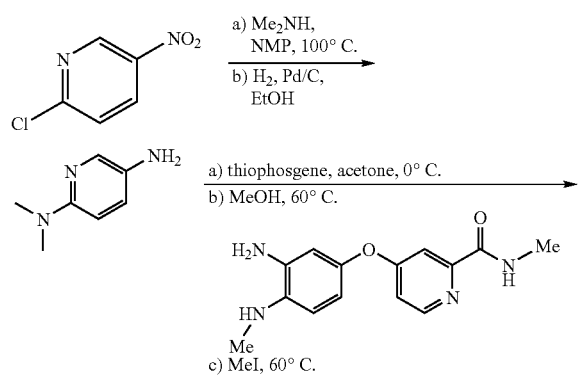

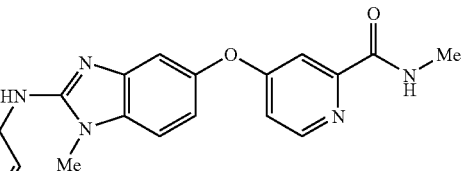

Step 1. Synthesis of 2-(Dimethylamino-5-nitropyridine

2-Chloro-5-nitropyridine (1.0 eq) and dimethylamine (2 M in EtOH, 4.6 eq) in NMP were heated for 2 h at 100° C. The solution was then poured slowly into H²O. The filtrate that formed was filtered and dried to give 2-(dimethylamino)-5-nitropyridine.

Step 2. Synthesis of
2-(Dimethylamino-5-aminopyridine

A mixture of 2-(dimethylamino)-5-nitropyridine (1 eq) and 5% palladium on carbon (0.3 eq) in ethanol was stirred at room temperature and flushed with nitrogen. The reaction vessel was evacuated and purged with hydrogen three times. The reaction mixture was left under an atmosphere of hydrogen overnight. Nitrogen was flushed through the reaction and then the reaction was filtered through a celite pad. The celite pad was washed with excess ethanol before the solvent was removed by evaporation under reduced pressure to afford 2-(dimethylamino)-5-aminopyridine.

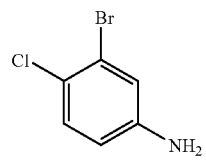

Step 3. Synthesis of
2-(Dimethylamino)-5-isothiocyanate pyridine 2-(Dimethylamino)-5-aminopyridine (1.0 eq) was taken up in acetone and cooled to 0 C. Thiophosgene (1.6 eq) was added dropwise and the reaction was stirred for 30 minutes at 0 C before the excess thiophosgene and acetone were removed by evaporation under reduced pressure.

Step 4. Synthesis of [4-(2-{[6-(dimethylamino)(3-pyridyl)]amino}-1-methylbenzimidazol-5-yloxy)(2-pyridyl)]-N-methylcarboxamide A solution of the {4-[3-amino-4-(methylamino)phenoxy] (2-pyridyl)}-N-methylcarboxamide (1.1 eq) in methanol was treated with 2-(dimethylamino)-5-isothiocyanate pyridine (1.0 eq) and stirred at 60° C. for 2 hours. Methyl iodide (1 eq) was added and stirred overnight at 60° C. The reaction was cooled down to room temperature, evaporated and purified by reverse phase HPLC. MS: MH+=418.3

Example 784

Step 1

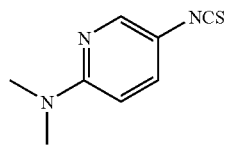

1

-continued

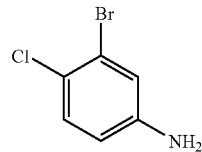

2

A solution of 1 (1 eq) and 10% palladium on carbon (0.1 eq) in ethyl acetate was stirred at room temperature and flushed with nitrogen. Hydrogen was flushed through the reaction for 2-3 hours or until the reaction was determined to be complete by HPLC. Nitrogen was flushed through the reaction for 15 minutes before the reaction was filtered through a celite pad. The celite pad was washed with excess ethyl acetate and methylene chloride before the combined organic solution was removed by evaporation under reduced pressure to afford the product as a solid 2. MS: MH+=207

Step 2

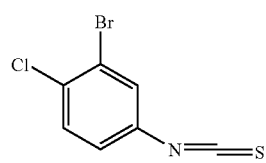

A solution of 2 (1 eq) and sodium carbonate (1.5 eq) in acetone was stirred under nitrogen in an ice bath. Thiophosgene (1.5 eq) was added drop wise over 30 minutes. The reaction was stirred for another 30 minutes in the ice bath before being removed and allowed to warm to RT. The reaction was stirred at RT for 1.5 h before the reaction solution was concentrated under vacuum. Toluene was added to the crude product and removed under vacuum to azeotrope off any residual thiophosgene and afford the product 3. MS: MH+=249

Step 3

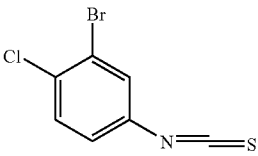

3

-continued

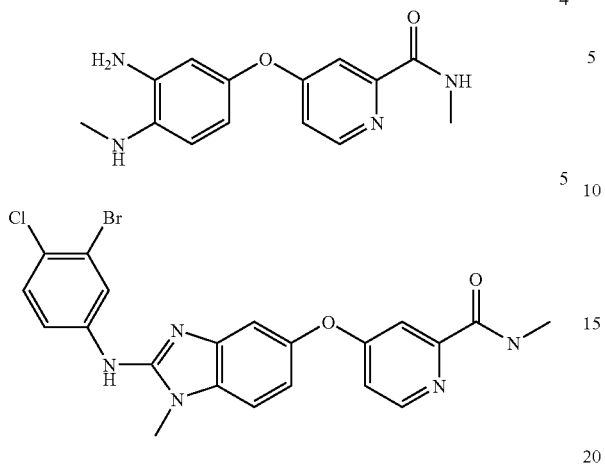

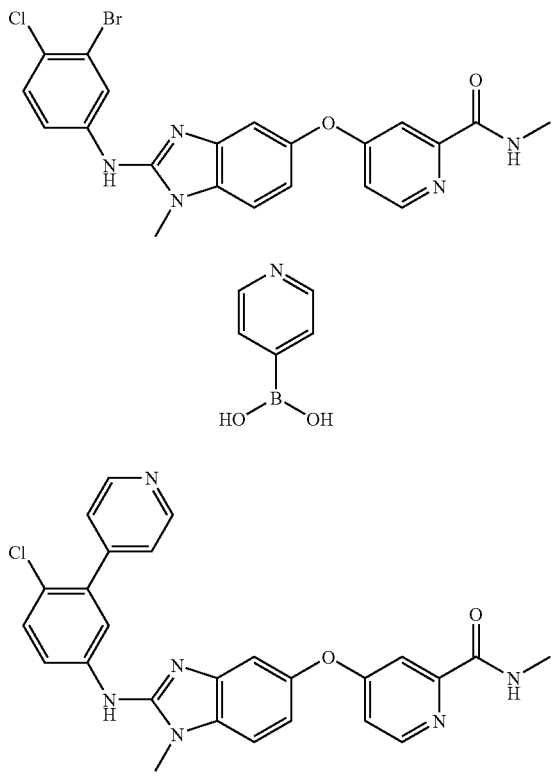

A solution of 3 (1.0 eq) and 4 (1.0 eq) in MeOH was stirred at RT overnight. Ferric chloride (1.2 eq) was added and the resulting reaction mixture was stirred overnight at RT. The reaction mixture was concentrated under vacuum. The crude product was partitioned with EtOAc and water and filtered. The layers were separated and the aqueous phase was neutralized (pH=7) with saturated Na2CO3 solution. The resulting aqueous phase was extracted with EtOAc. The combined organic layers were washed with brine, dried (Na2SO4), and concentrated to give the desired product 5. MS: MH+=487

Step 4

A solution of 5 (1 eq), 6 (1 eq), and sodium carbonate (1.2 eq) in DME/H$^2$O (3:1) was degassed by bubbling argon through the solution for 10 minutes. Pd(II)(dppf)Cl2.MeCl2 (0.1 eq) was added to the reaction solution and the reaction was sealed. The reaction was heated at 100° C. overnight. The reaction was cooled to RT and ethyl acetate and water were added. The organic layer was separated from the aqueous layer. The aqueous layer was washed once more with ethyl acetate. The organic layers were combined, dried (Na2SO4), and concentrated under vacuum to yield the desired product 7. MS: MH+=469

Step 5

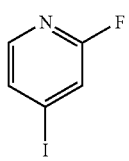

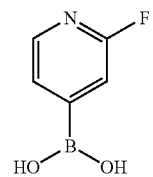

The reaction flask was flame dried and cooled under nitrogen. A solution of 8 (1.0 eq) in THF was added to the reaction flask followed by triisopropyl borate (1.2 eq). The reaction solution was placed in a dry ice/acetone bath to stir at approximately −72° C. N-butyl lithium (1.5 eq, 2.5M solution in hexane) was added drop wise over 40 minutes. The reaction solution was stirred for another 30 minutes in the dry ice/acetone bath. The reaction solution was then transferred to a saturated NaCl/dry ice bath to stir at approx. −25° C. and stirred for 20 minutes before 2N HCl (2.0 eq) was added. The reaction solution was then removed from the bath to stir and warm to RT. The organic and aqueous layers were separated. The aqueous layer was washed once with ethyl acetate. The organic layers were combined, dried (Na2SO4), and concentrated under vacuum to yield the desired product 9. MS: MH+=141

Each of the compounds 785-802, listed in the below table were synthesized as indicated in the right hand column by the method described in one of the Examples 783 or 784.

TABLE 10

| Example | Structure | Name | MH+ | Synthesized as in Example: |
|---|---|---|---|---|
| 785 | 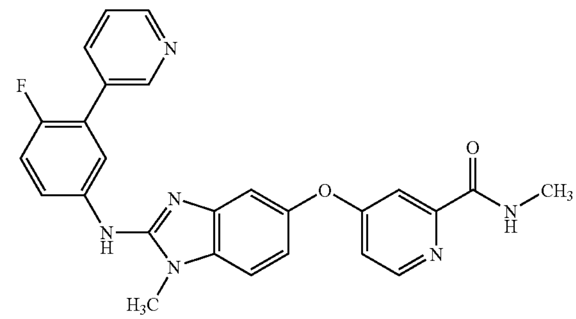 | 4-({2-[(4-fluoro-3-pyridin-3-ylphenyl)amino]-1-methyl-1H-benzimidazol-5-yl}oxy)-N-methylpyridine-2-carboxamide | 469.5 | 784 |
| 786 | 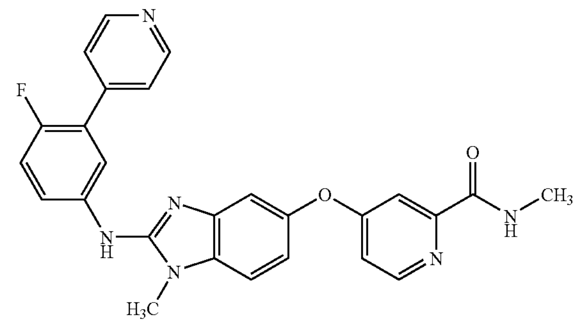 | 4-({2-[(4-fluoro-3-pyridin-4-ylphenyl)amino]-1-methyl-1H-benzimidazol-5-yl}oxy)-N-methylpyridine-2-carboxamide | 469.5 | 784 |
| 787 | 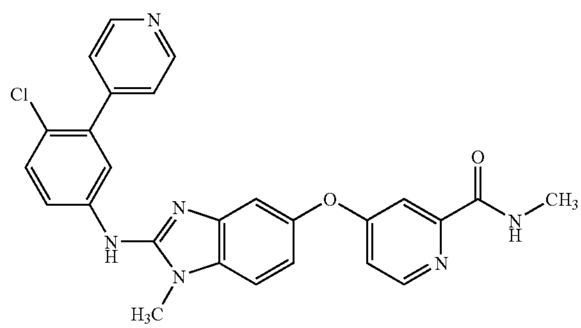 | 4-({2-[(4-chloro-3-pyridin-4-ylphenyl)amino]-1-methyl-1H-benzimidazol-5-yl}oxy)-N-methylpyridine-2-carboxamide | 485.9 | 784 |
| 788 | 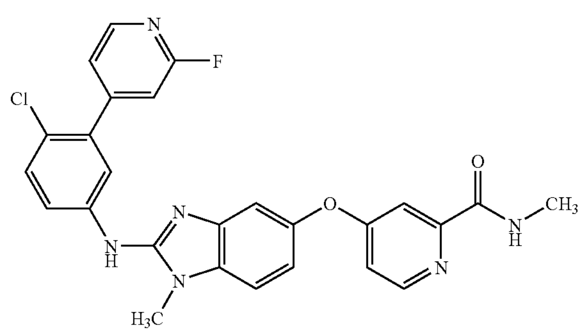 | 4-[(2-{[4-chloro-3-(2-fluoropyridin-4-yl)phenyl]-amino}-1-methyl-1H-benzimidazol-5-yl)oxy]-N-methyl-pyridine-2-carboxamide | 503.9 | 784 |

TABLE 10-continued

| Example | Structure | Name | MH+ | Synthesized as in Example: |
|---------|-----------|------|-----|---------------------------|
| 789 | 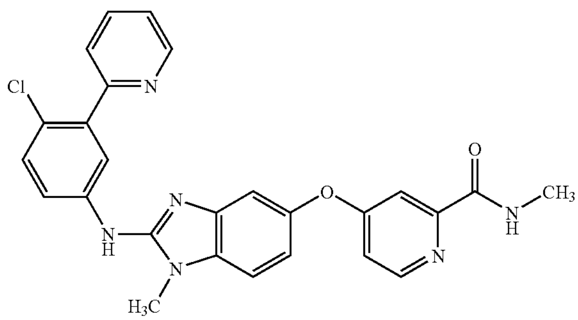 | 4-({2-[(4-chloro-3-pyridin-2-ylphenyl)amino]-1-methyl-1H-benzimidazol-5-yl}oxy)-N-methylpyridine-2-carboxamide | 485.9 | 784 |
| 790 | 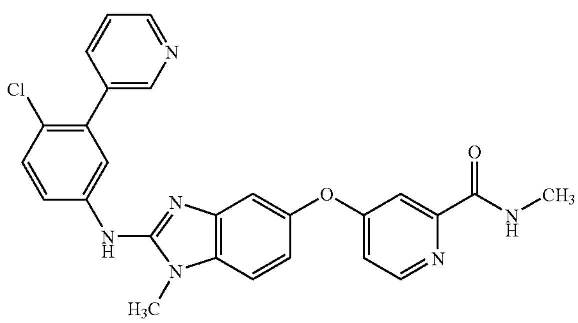 | 4-({2-[(4-chloro-3-pyridin-3-ylphenyl)amino]-1-methyl-1H-benzimidazol-5-yl}oxy)-N-methylpyridine-2-carboxamide | 485.9 | 784 |
| 791 | 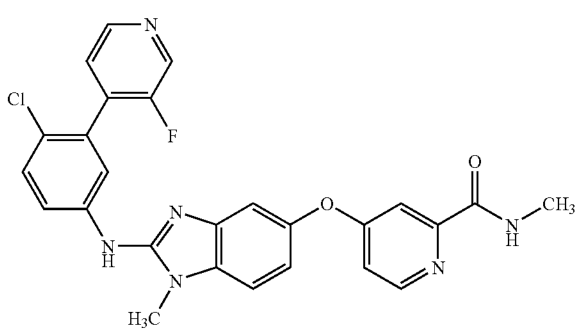 | 4-[(2-{[4-chloro-3-(3-fluoropyridin-4-yl)phenyl]-amino}-1-methyl-1H-benzimidazol-5-yl)oxy]-N-methyl-pyridine-2-carboxamide | 503.9 | 784 |
| 792 | 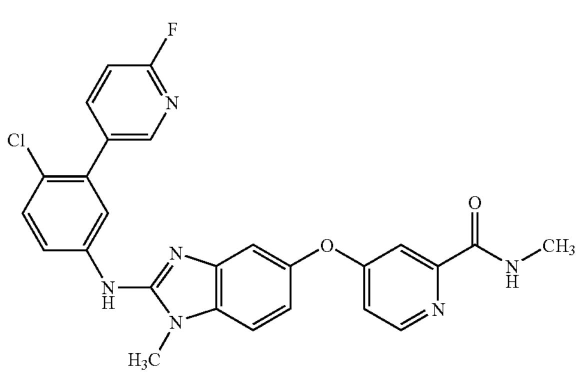 | 4-[(2-{[4-chloro-3-(6-fluoropyridin-3-yl)phenyl]-amino}-1-methyl-1H-benzimidazol-5-yl)oxy]-N-methylpyridine-2-carboxamide | 503.9 | 784 |

TABLE 10-continued

| Example | Structure | Name | MH+ | Synthesized as in Example: |
|---|---|---|---|---|
| 793 | 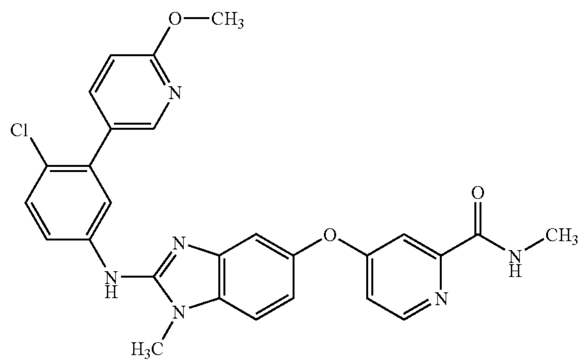 | 4-{[2-({4-chloro-3-[6-(methyloxy)pyridin-3-yl]-phenyl}amino)-1-methyl-1H-benzimidazol-5-yl]oxy}-N-methylpyridine-2-carboxamide | 516 | 784 |
| 794 | 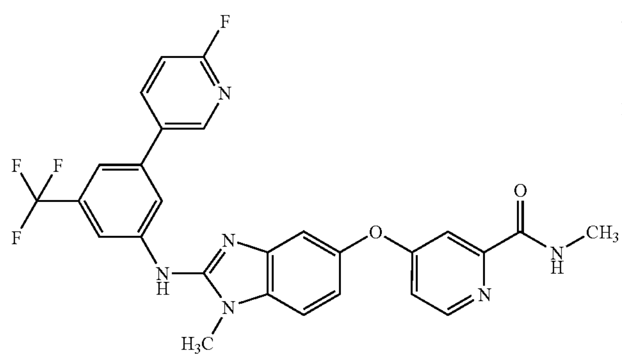 | 4-[(2-{[3-(6-fluoropyridin-3-yl)-5-(trifluoromethyl)phenyl]-amino}-1-methyl-1H-benzimidazol-5-yl)oxy]-N-methyl-pyridine-2-carboxamide | 537.5 | 784 |
| 795 | 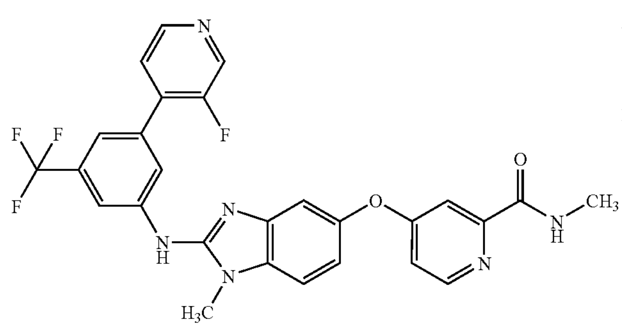 | 4-[(2-{[3-(3-fluoropyridin-4-yl)-5-(trifluoromethyl)phenyl]-amino}-1-methyl-1H-benzimidazol-5-yl)oxy]-N-methyl-pyridine-2-carboxamide | 537.5 | 784 |
| 796 | 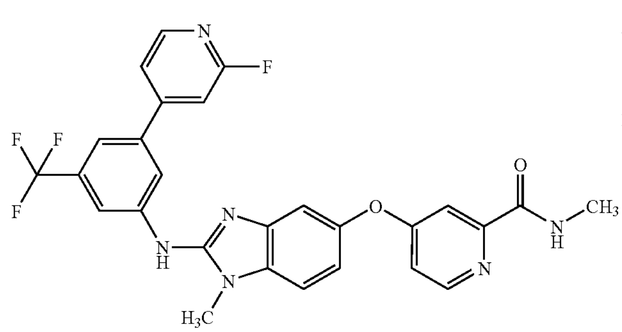 | 4-[(2-{[3-(2-fluoropyridin-4-yl)-5-(trifluoromethyl)phenyl]-amino}-1-methyl-1H-benzimidazol-5-yl)oxy]-N-methyl-pyridine-2-carboxamide | 537.5 | 784 |

TABLE 10-continued

| Example | Structure | Name | MH+ | Synthesized as in Example: |
|---|---|---|---|---|
| 797 | 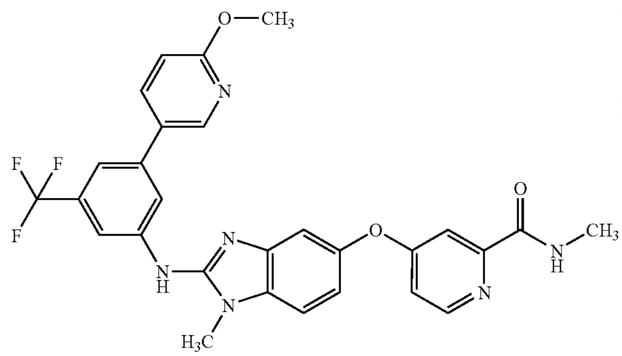 | N-methyl-4-[(1-methyl-2-{[3-[6-(methyloxy)pyridin-3-yl]-5-(trifluoromethyl)phenyl]amino}-1H-benzimidazol-5-yl)oxy]-pyridine-2-carboxamide | 549.5 | 784 |
| 798 | 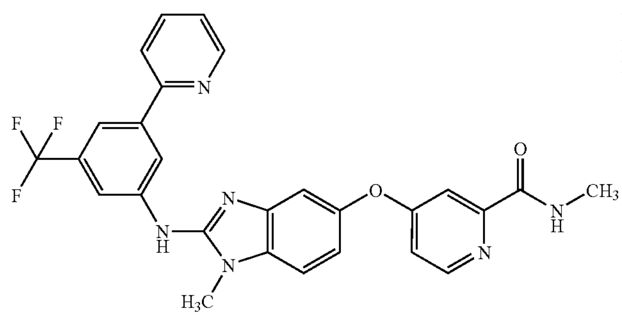 | N-methyl-4-[(1-methyl-2-{[3-pyridin-2-yl-5-(trifluoromethyl)-phenyl]amino}-1H-benzimidazol-5-yl)oxy]pyridine-2-carboxamide | 519.5 | 784 |
| 799 | 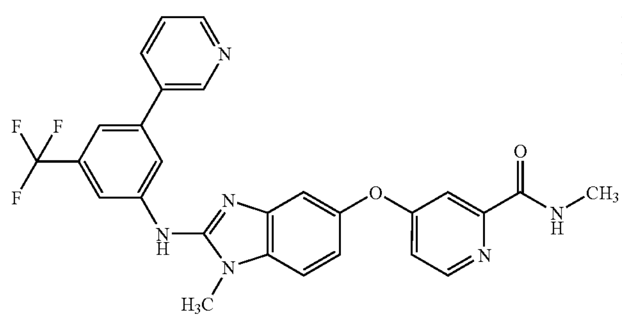 | N-methyl-4-[(1-methyl-2-{[3-pyridin-3-yl-5-(trifluoromethyl)-phenyl]amino}-1H-benzimidazol-5-yl)oxy]pyridine-2-carboxamide | 519.5 | 784 |
| 800 | 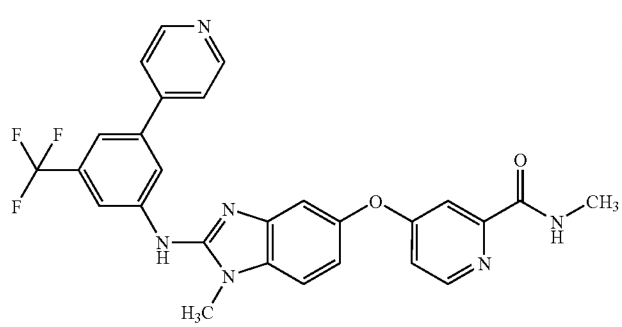 | N-methyl-4-[(1-methyl-2-{[3-pyridin-4-yl-5-(trifluoromethyl)-phenyl]amino}-1H-benzimidazol-5-yl)oxy]pyridine-2-carboxamide | 519.5 | 784 |

TABLE 10-continued
| Example | Structure | Name | MH+ | Synthesized as in Example: |
|---|---|---|---|---|
| 801 | 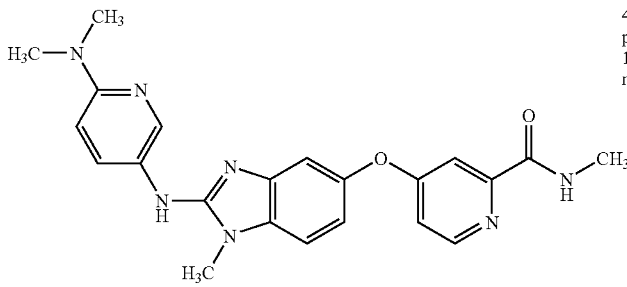 | 4-[(2-{[6-(dimethylamino)-pyridin-3-yl]amino}-1-methyl-1H-benzimidazol-5-yl)oxy]-N-methylpyridine-2-carboxamide | 418.5 | 783 |
| 802 | 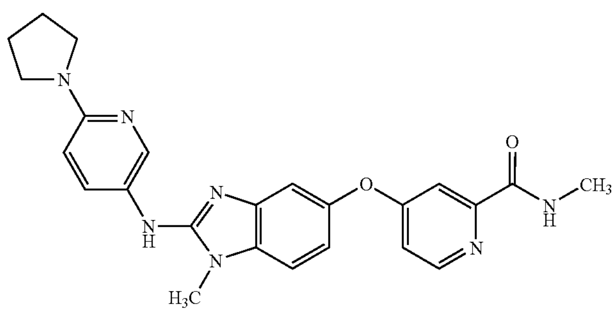 | N-methyl-4-({1-methyl-2-[(6-pyrrolidin-1-ylpyridin-3-yl)-amino]-1H-benzimidazol-5-yl}-oxy)pyridine-2-carboxamide | 444.5 | 783 |
Example 803
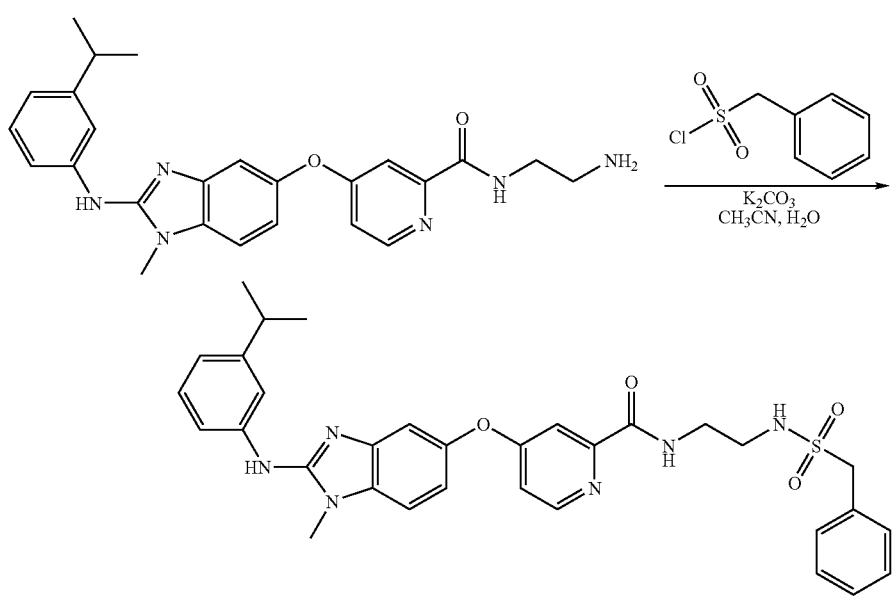

Step 1. 4-[2-(3-Isopropyl-phenylamino)-1-methyl-1H-benzoimidazol-5-yloxy]-pyridine-2-carboxylic acid (2-phenylmethanesulfonylamino-ethyl)-amide To a mixture containing 4-[2-(3-Isopropyl-phenylamino)-1-methyl-1H-benzoimidazol-5-yloxy]-pyridine-2-carboxylic acid (2-amino-ethyl)-amide (1 eq) (prepared using previously described example 3), K2CO3 (5 eq), (0.2 M in a 5:1 mixture of acetonitrile and water) were added α-toluenesulfonyl chloride (1 eq) via syringe. The resulting heterogeneous mixture was allowed to stir for 1 hour at room temperature. The mixture was then diluted with water and extracted with dichloromethane. The organics were washed with water and a saturated solution of sodium chloride, dried with sodium sulfate and concentrated in vacuo to viscous oil. Purification by chromatography yielded 4-[2-(3-Isopropyl-phenylamino)-1-methyl-1H-benzoimidazol-5-yloxy]-pyridine-2-carboxylic acid (2-phenylmethanesulfonylamino-ethyl)-amide. MS: MH+ 599

The compounds shown in the following Table (Examples 804-812) were prepared from following the procedure described for Example 803.

TABLE 11

| Example | Structure | Name | MH+ |
|---|---|---|---|
| 804 | 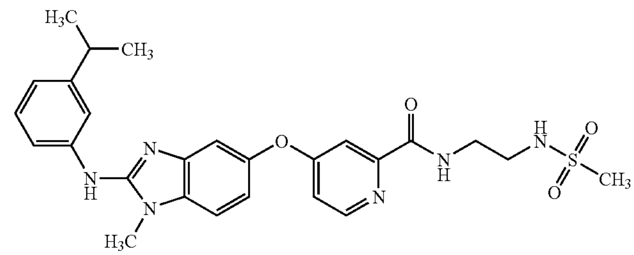 | 4-[(1-methyl-2-{[3-(1-methylethyl)phenyl]amino}-1H-benzimidazol-5-yl)oxy]-N-{2-[(methylsulfonyl)amino]ethyl}pyridine-2-carboxamide | 523.6 |
| 805 | 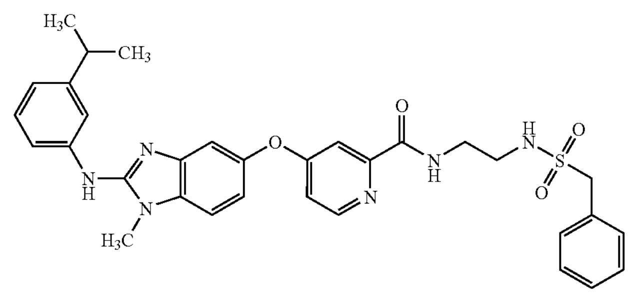 | 4-[(1-methyl-2-{[3-(1-methylethyl)phenyl]amino}-1H-benzimidazol-5-yl)oxy]-N-(2-{[(phenylmethyl)sulfonyl]amino}ethyl)pyridine-2-carboxamide | 599.7 |
| 806 | 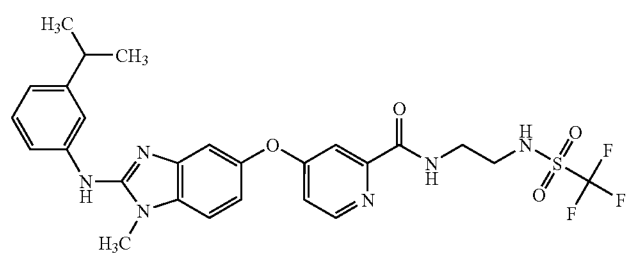 | 4-[(1-methyl-2-{[3-(1-methylethyl)phenyl]amino}-1H-benzimidazol-5-yl)oxy]-N-(2-{[(trifluoromethyl)sulfonyl]amino}ethyl)pyridine-2-carboxamide | 577.6 |
| 807 | 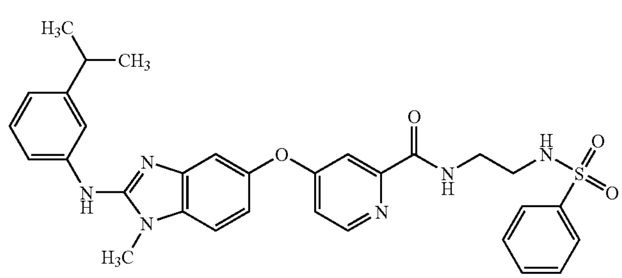 | 4-[(1-methyl-2-{[3-(1-methylethyl)phenyl]amino}-1H-benzimidazol-5-yl)oxy]-N-{2-[(phenylsulfonyl)aminoethyl}-pyridine-2-carboxamide | 585.7 |

TABLE 11-continued

| Example | Structure | Name | MH+ |
|---|---|---|---|
| 808 | 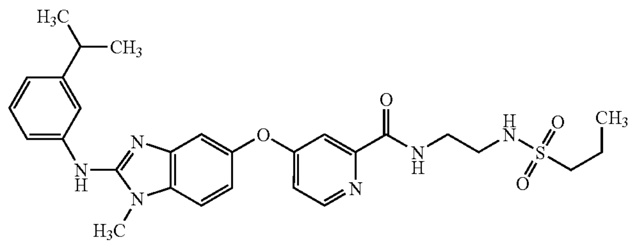 | 4-[(1-methyl-2-{[3-(1-methyl-ethyl)phenyl]amino}-1H-benzimidazol-5-yl)oxy]-N-{2-[(propylsulfonyl)amino]-ethyl}pyridine-2-carboxamide | 551.7 |
| 809 | 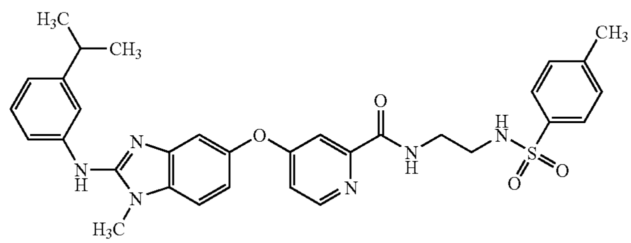 | 4-[(1-methyl-2-{[3-(1-methyl-ethyl)phenyl]amino}-1H-benzimidazol-5-yl)oxy]-N-(2-{[(4-methylphenyl)sulfonyl]-amino}ethyl)pyridine-2-carboxamide | 599.7 |
| 810 | 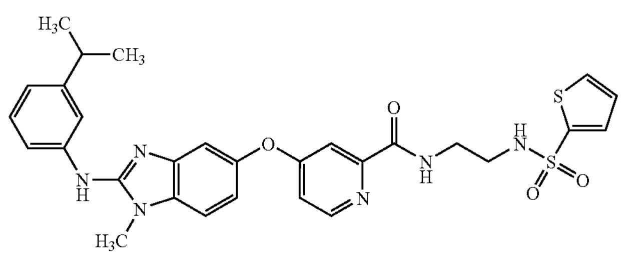 | 4-[(1-methyl-2-{[3-(1-methyl-ethyl)phenyl]amino}-1H-benzimidazol-5-yl)oxy]-N-{2-[(thien-2-ylsulfonyl)amino]-ethyl}pyridine-2-carboxamide | 591.7 |
| 811 | 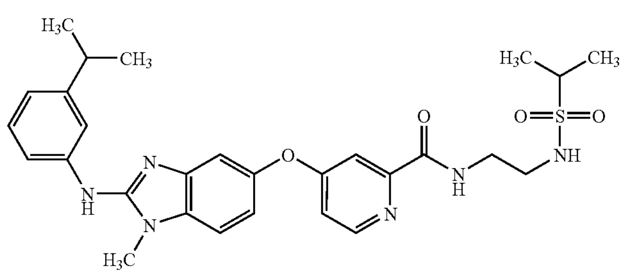 | N-(2-{[(1-methylethyl)-sulfonyl]amino}ethyl)-4-[(1-methyl-2-{[3-(1-methylethyl)-phenyl]amino}-1H-benz-imidazol-5-yl)oxy]pyridine-2-carboxamide | 551.7 |
| 812 | 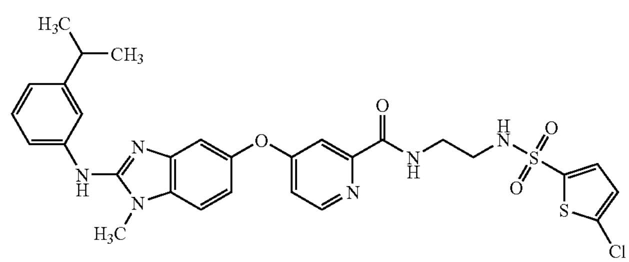 | N-(2-{[(5-chlorothien-2-yl)-sulfonyl]amino}ethyl)-4-[(1-methyl-2-{[3-(1-methylethyl)-phenyl]amino}-1H-benz-imidazol-5-yl)oxy]pyridine-2-carboxamide | 626.2 |

Example 813

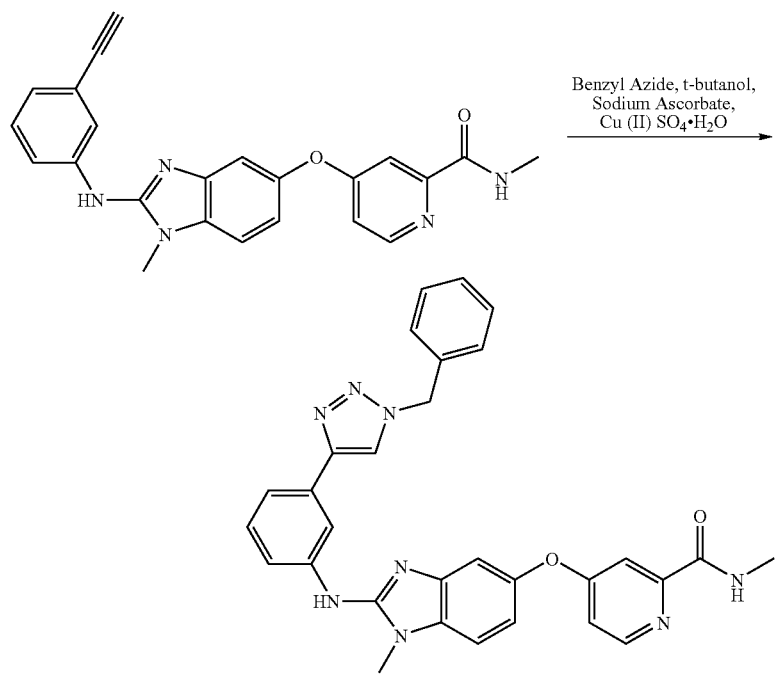

Step 1. 4-{2-(3-(1-Benzyl-1H-[1,2,3]triazol-4-yl)-phenyl amino]-1-methyl-1H-benzoimidazol-5-yloxy}-pyridine-2-carboxylic acid methyl amide To a mixture of 4-[2-(3-Ethyl-phenylamino)-1-methyl-1H-benzoimidazol-5-yloxy]-pyridine-2-carboxylic acid methylamide (1 eq) (prepared using previously described example 2), benzyl azide (1 eq) in t-butanol (0.1M) was added sodium ascorbate (0.05 eq), and copper (II) sulfate pentahydrate (0.01 eq). The resulting mixture was allowed to stir for 1 hour at room temperature. The mixture was then diluted with water and the solid collect via suction filtration. MS: MH+ 531

Example 814

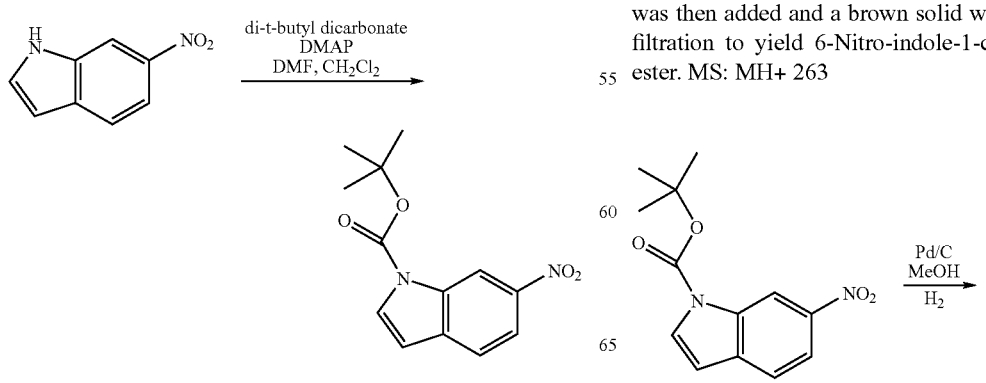

Step 1. Synthesis of 6-Nitro-indole-1-carboxylic acid t-butyl ester

To a stirring solution of 6-nitroindole (1 eq) in dichloromethane (0.3M) and DMF (3.1M), was added di-t-butyl dicarbonate (2 eq) followed by the addition of 4-(dimethylamino)pyridine (1 eq). Resulting solution was allowed to stir overnight at room temperature. The dichloromethane was then removed on a rotovap and remaining solution diluted with water and extracted with ethyl acetate. Organics were washed with 10% citric acid solution, saturated solution of sodium chloride, saturated solution of sodium bicarbonate, saturated solution of sodium chloride and dried with sodium sulfate. Ethyl acetate was then removed in vacuo. Ethyl ether was then added and a brown solid was collected by suction filtration to yield 6-Nitro-indole-1-carboxylic acid t-butyl ester. MS: MH+ 263

-continued

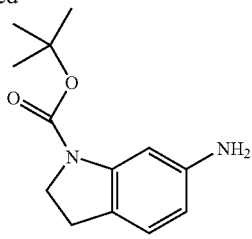

Step 2. Synthesis of 6-Amino-2,3-dihydro-indole-1-carboxylic acid t-butyl ester 6-Nitro-indole-1-carboxylic acid t-butyl ester (1 eq) was dissolved in methanol (0.1M), to this solution was added palladium on carbon (0.1 eq) in methanol under nitrogen. A hydrogen atmosphere was then inserted and resulting mixture allowed to stir for 3 hours at room temperature. The reaction mixture was then filtered through celite and solvent removed in vacuo to afford 6-Amino-2,3-dihydro-indole-1-carboxylic acid t-butyl ester as a white solid. MS: MH+ 235

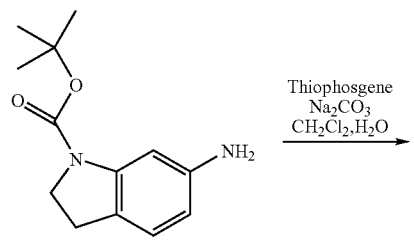

-continued

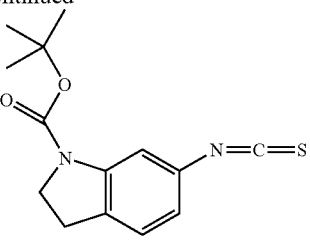

Step 3. Synthesis of 6-Isothiocyanate-2,3-dihydro-indole-1-carboxylic acid t-butyl ester Thiophosgene (1.1 eq) was added to a stirred suspension of 6-Amino-2,3-dihydro-indole-1-carboxylic acid t-butyl ester (1 eq), sodium carbonate (10 eq), and dichloromethane:water 3:1 by volume at 0° C. The resulting mixture was allowed to stir for 2 hours at 0° C. The mixture was diluted with water and organics separated and washed with water, saturated solution of sodium chloride and dried with sodium sulfate, solvent removed in vacuo to afford 6-Isothiocyanate-2,3-dihydro-indole-1-carboxylic acid t-butyl ester as orange oil.

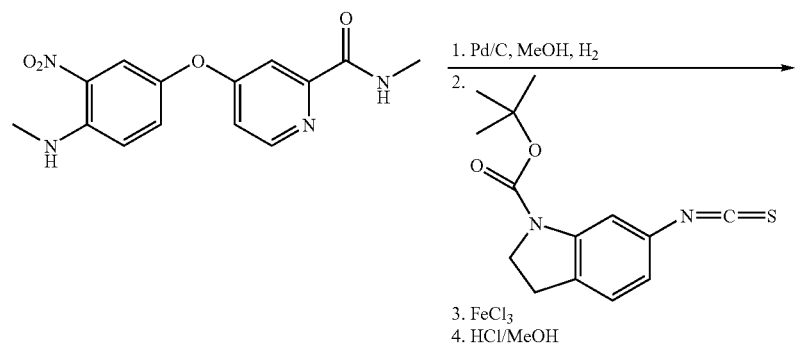

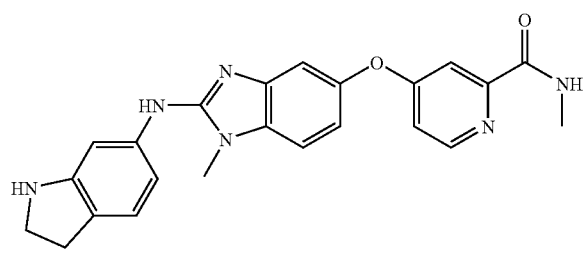

Step 4. Synthesis of 4-[2-(2,3-Dihydro-1H-indol-6-ylamino)-1-methyl-1H-benzoimidazol-5-yloxy]-pyridine-2-carboxylic acid methylamide To a solution of 4-(4-Methylamino3-nitro-phenoxy)-pyridine-2-carboxylic acid methylamide (1 eq) in methanol (0.1M) was added palladium on carbon (0.1 eq) under nitrogen. The atmosphere was exchanged for hydrogen (1 atm) and the resulting suspension allowed to stir for 2 hours at room temperature. The mixture was filtered through celite and added to 6-Isothiocyanate-2,3-dihydro-indole-1-carboxylic acid t-butyl ester (1 eq). The resulting solution was allowed to stir overnight. Iron (III) chloride (2 eq) in methanol was added and the solution turns deep red in color. This solution was allowed to stir for 3 hours at room temperature. Methanol was then removed in vacuo; the resulting oil was diluted with water and extracted with dichloromethane. Organics were washed with saturated sodium bicarbonate solution, water, and saturated sodium chloride solution and dried with sodium sulfate. Solvent was removed in vacuo. To the resulting oil was added toluene and heated to reflux, solution was cooled to room temperature and a solid was collected after 3 days by suction filtration to afford 4-[2-(2,3-Dihydro-1H-indol-6-ylamino)-1-methyl-1H-benzoimidazol-5-yloxy]-pyridine-2-carboxylic acid methylamide. MS: MH+ 415

Example 815

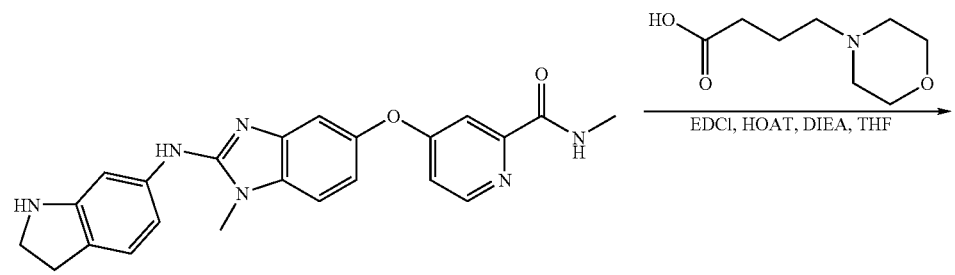

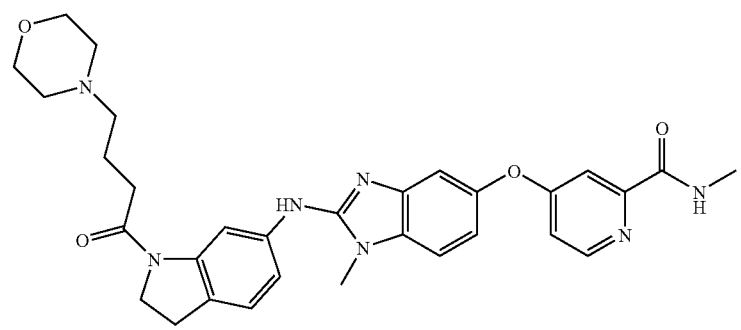

Step 1. Synthesis of 4-{1-Methyl-2-[1-(4-morpholin-4-yl-butyl)-2,3-dihydro-1H-indol-6-ylamino]-1H-benzoimidazol-5-yloxy}-pyridine-2-carboxylic acid methylamide To mixture containing 4-[2-(2,3-Dihydro-1H-indol-6-ylamino)-1-methyl-1H-benzoimidazol-5-yloxy]-pyridine-2-carboxylic acid methylamide (1 eq) (previously prepared using example 1), EDCI (2 eq), HOAT (1.2 eq), DIEA (4 eq) was added THF. The mixture was allowed to stir overnight at room temperature under nitrogen. The mixture was then diluted with water, extracted with ethyl acetate. Organics were washed with water, then saturated solution of sodium chloride and dried with sodium sulfate, filtered and the solvent was removed in vacuo. Purification by chromatography yielded 4-{1-Methyl-2-[1-(4-morpholin-4-yl-butyloyl)-2,3-dihydro-1H-indol-6-ylamino]-1H-benzoimidazol-5-yloxy}-pyridine-2-carboxylic acid methylamide. MS: MH+ 570

The compounds shown in the following table (Examples 816-819) were prepared from following the procedure described for Example 815.

TABLE 12

| Example | Structure | Name | MH+ |
|---|---|---|---|
| 816 | 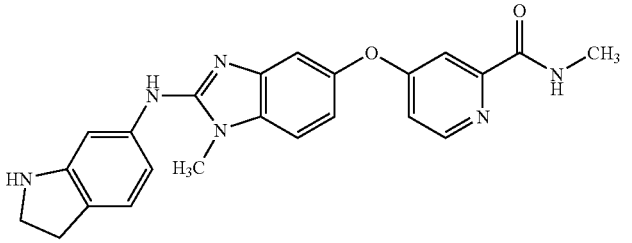 | 4-{[2-(2,3-dihydro-1H-indol-6-ylamino)-1-methyl-1H-benzimidazol-5-yl]oxy}-N-methyl-pyridine-2-carboxamide | 415.5 |
| 817 | 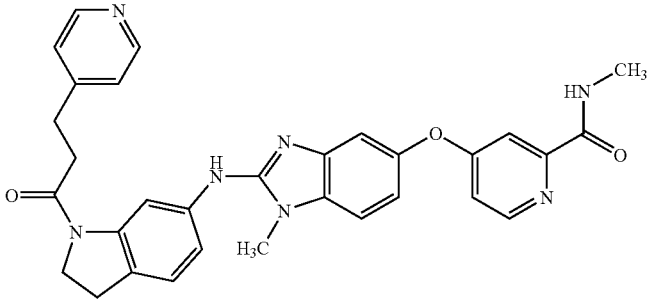 | N-methyl-4-[(1-methyl-2-{[1-(3-pyridin-4-ylpropanoyl)-2,3-dihydro-1H-indol-6-yl]amino}-1H-benzimidazol-5-yl)oxy]pyridine-2-carboxamide | 548.6 |
| 818 | 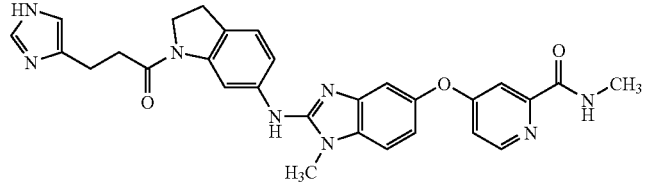 | 4-{[2-({1-[3-(1H-imidazol-4-yl)-propanoyl]-2,3-dihydro-1H-indol-6-yl}amino)-1-methyl-1H-benzimidazol-5-yl]oxy}-N-methyl-pyridine-2-carboxamide | 537.6 |
| 819 | 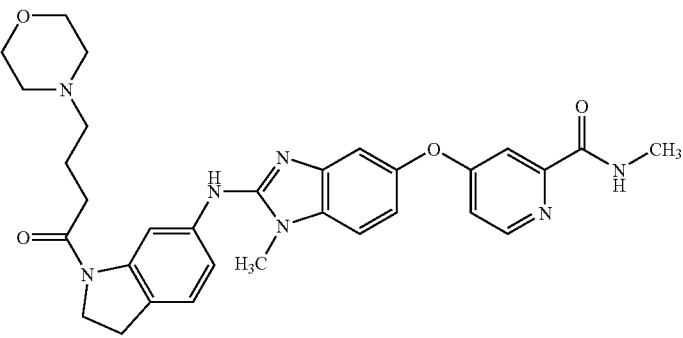 | N-methyl-4-[(1-methyl-2-{[1-(4-morpholin-4-ylbutanoyl)-2,3-dihydro-1H-indol-6-yl]amino}-1H-benzimidazol-5-yl)oxy]pyridine-2-carboxamide | 570.7 |

Example 820

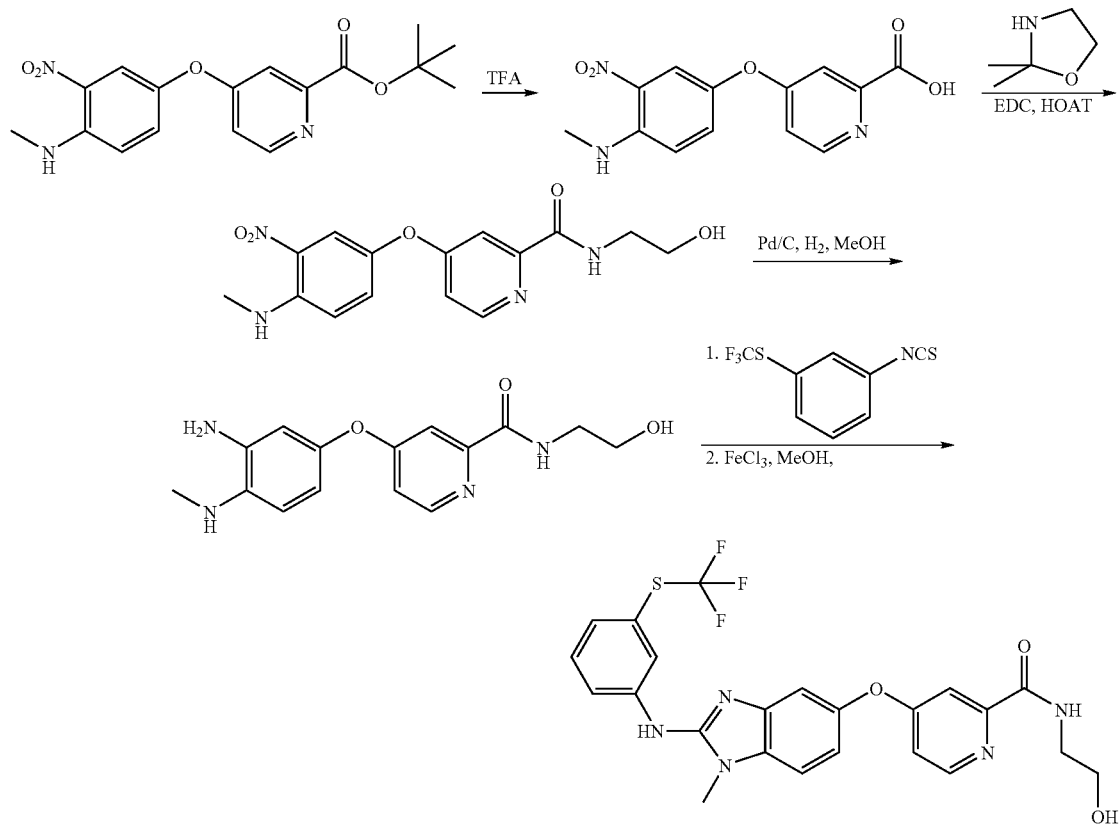

Step 1. Synthesis of 4-(4-Methylamino-3-nitro-phenoxy)-pyridine-2-carboxylic acid A stirring solution of 4-(4-Methylamino-3-nitro-phenoxy)-pyridine-2-carboxylic acid tert-butyl ester in trifluoroacetic acid was treated with two drops of water at room temperature for 3-4 hours or when the reaction was determined to be complete by HPLC. The reaction was evaporated under reduced pressure to afford the product as a red-orange oil. Addition of ethyl ether, sonication, and filtration captures the product as a light pink solid. LCMS m/z 290.1 (MH+), tR=1.71 min.

Step 2. Synthesis of 4-(4-Methylamino-3-nitro-phenoxy)-pyridine-2-carboxylic acid (2-hydroxy-ethyl)-amide To a suspension of the 4-(4-methylamino-3-nitro-phenoxy)-pyridine-2-carboxylic acid (1 eq) in dry THF, EDC-HCl (1.2 eq), HOAT (1.2 eq), and diisopropylethylamine (3 eq) were added. The suspension was stirred for 10 minutes whereupon 2,2-dimethyl-oxazolidine (1.1 eq) was added and the solution is allowed to stir overnight. The mixture was then diluted with ethyl acetate and washed with water. The aqueous layer was washed with ethyl acetate, the organic layerscombined, dried over MgSO4, filtered, and concentrated. LCMS m/z 333.2 (MH+), tR=2.1 min.

Step 3. 4-(3-Amino-4-methylamino-phenoxy)-pyridine-2-carboxylic acid (2-hydroxy-ethyl)-amide A solution of 4-(4-methylamino-3-nitro-phenoxy)-pyridine-2-carboxylic acid (2-hydroxy-ethyl)-amide (1 eq) and 10% palladium on carbon (0.1 eq) in methanol was stirred at room temperature and flushed with nitrogen. Hydrogen was flushed through the reaction for 1-2 hours or until the reaction was determined to be complete by HPLC. Nitrogen was flushed through the reaction for 15 minutes before the reaction was filtered through a celite pad. The celite pad was washed with excess methanol before it was all removed by evaporation under reduced pressure to afford the product as a light yellow solid. LCMS m/z 303.2 (MH+), tR=1.5 min.

Step 4. 4-[1-Methyl-2-(3-trifluoromethylsulfanyl-phenylamino)-1H-benzoimidazol-5-yloxy]-pyridine-2-carboxylic acid (2-hydroxy-ethyl)-amide A flask was charged with 3-(trifluoromethylthio)phenyl-isothiocyanate (1 eq), 4-(3-amino-4-methylamino-phenoxy)-pyridine-2-carboxylic acid (2-hydroxy-ethyl)-amide (1 eq), and MeOH. The reaction was maintained at rt overnight. Ferric chloride, (1.5 eq) was added and the resulting red reaction mixture was stirred overnight. The reaction was partitioned with EtOAc and water, and filtered through Celite. The layers were separated and the aqueous phase was neutralized with saturated Na2CO3 solution. The resulting aqueous phase was extracted with EtOAc and the mixture was filtered through Celite. The phases were separated and the aqueous phase was again extracted and filtered. The combined organic layers were washed with brine, dried (MgSO4), filtered, and concentrated to give a brown solid. The crude residue was purified by reverse phase HPLC. LCMS m/z 504.1 (MH+), tR=3.7 min.
Example 821
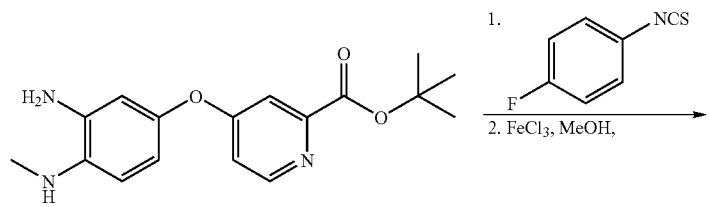
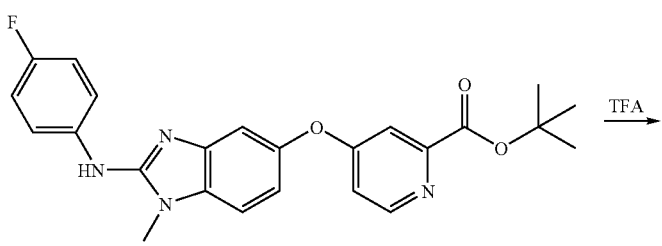
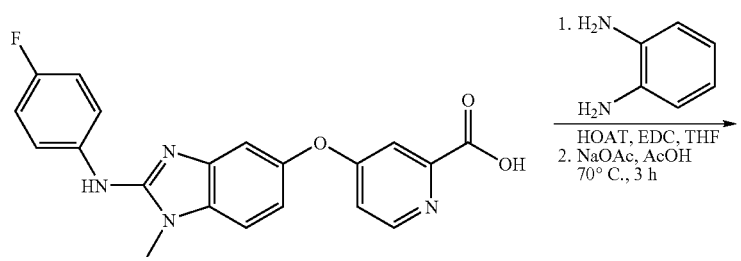
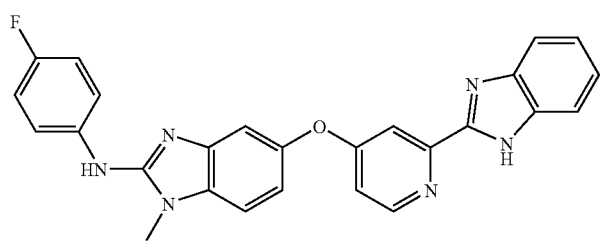

Step 1. Synthesis of 4-[2-(4-Fluoro-phenylamino)-1-methyl-1H-benzoimidazol-5-yloxy]-pyridine-2-carboxylic acid tert-butyl ester A round bottom flask was charged with 4-fluorophenyl-isothiocyanate (1 eq), 4-(3-Amino-4-methylamino-phenoxy)-pyridine-2-carboxylic acid tert-butyl ester (1 eq), and MeOH. The reaction was maintained stirring at room temperature overnight. Ferric chloride, (1.5 eq) was added and the resulting mixture was stirred overnight. The reaction was partitioned with EtOAc and water, and filtered through Celite. The layers were separated and the aqueous phase was neutralized with saturated Na2CO3 solution. The resulting aqueous phase was extracted with EtOAc and the mixture was filtered through Celite. The phases were separated and the aqueous phase was again extracted and filtered. The combined organic layers were washed with brine, dried over MgSO4, filtered, and concentrated to give a brown solid. The crude residue was purified by trituration in hot toluene to furnish the desired product. LCMS m/z 435.6 (MH+), tR=2.12 min.

Step 2. Synthesis of 4-[2-(4-Fluoro-phenylamino)-1-methyl-1H-benzoimidazol-5-yloxy]-pyridine-2-carboxylic acid A stirring solution of 4-[2-(4-Fluoro-phenylamino)-1-methyl-1H-benzoimidazol-5-yloxy]-pyridine-2-carboxylic acid tert-butyl ester in trifluoroacetic acid was treated with two drops of water at room temperature for 3-4 hours or when the reaction was determined to be complete by HPLC. The reaction was evaporated under reduced pressure and then ether was added to the residue, which was then sonicated for 30 minutes. Filtration and washing with ether yields the desired acid in quantitative yield. LCMS m/z 379.4 (MH+), tR=1.74 mm.

Step 3. Synthesis of {5-[2-(1H-Benzoimidazol-2-yl)-pyridin-4-yloxy]-1-methyl-1H-benzoimidazol-2-yl}-(4-fluoro-phenyl)-amine To a suspension of 4-[2-(4-Fluoro-phenylamino)-1-methyl-1H-benzoimidazol-5-yloxy]-pyridine-2-carboxylic acid (1 eq) in dry THF, EDC-HCl (1.2 eq), HOAT (1.2 eq), and diisopropylethylamine (3 eq) were added. The suspension was stirred for 10 minutes whereupon phenylenediamine (1.1 eq) was added and the solution is allowed to stir overnight. The mixture was then diluted with ethyl acetate and washed with water. The aqueous layer was washed with ethyl acetate, the organic layers combined, dried over MgSO4, filtered, and concentrated. Acetic acid was added to the residue followed by sodium acetate (1.1 eq). The mixture was heated for 3 hours at 70° C., whereupon the solution is concentrated and the residue purified by reverse phase HPLC to afford the desired product. LCMS m/z 451.5 (MH+), tR=1.92 min.

Synthesis of Side Chains

Ether Substituted Phenylenediamines:

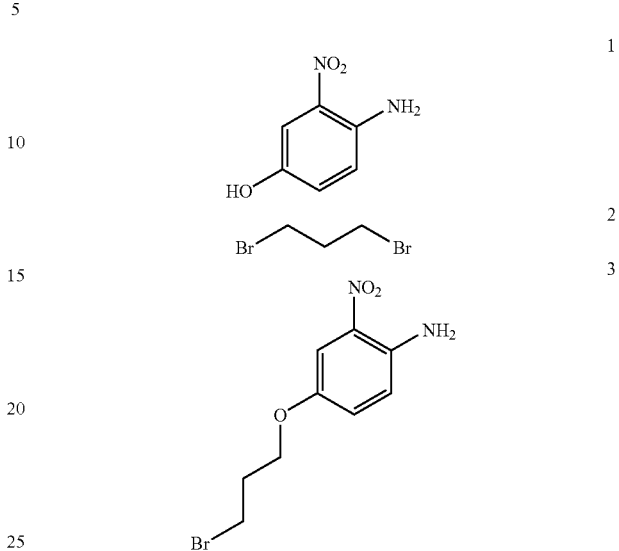

4-(3-Bromopropoxy)-2-nitrophenylamine

A flask is charged with 4-amino-3-nitrophenol 1 (1 eq), $K_2CO_3$ (2 eq), and 2-butanone. 1,3-dibromopropane 2 (1.5 eq) is added and the mixture is heated at 80° C. for 18 hours. After cooling, the mixture is filtered concentrated and water is added. The solution is then extracted with $CH_2Cl_2$ (×3), the organic layer concentrated, and the solid recovered washed with pentane to yield the desired product 3. LCMS m/z 275.1 (MH+), $R_t$ 2.74 minutes.

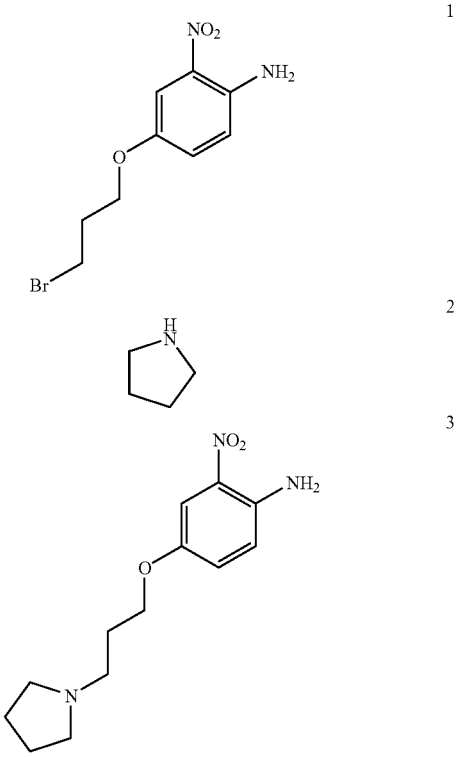

2-Nitro-4-(3-pyrrolidinylpropoxy)phenylamine 4-(3-bromopropoxy)-2-nitrophenylamine 1 (1 eq) was heated to 70° C. with pyrrolidine 2 (5 eq) in MeCN with $Cs_2CO_3$ (2 eq) and $Bu_4NI$ (0.1 eq) for 48 hours. The reaction mixture was cooled, filtered, and concentrated. The residue is dissolved in $CH_2Cl_2$, and washed with water. The organic layer is concentrated yielding the desired product 3. LCMS m/z 266.2 (MH+), $R_t$ 1.51 minutes.

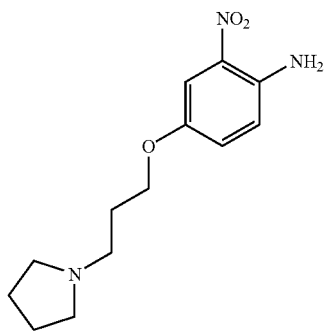

1

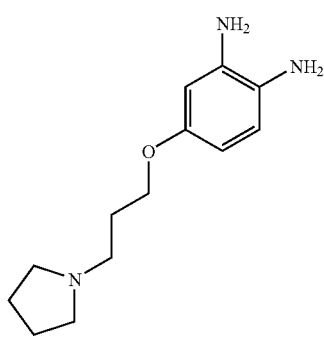

2

4-(3-Pyrrolidinylpropoxy)benzene-1,2-diamine

To a solution 2-Nitro-4-(3-pyrrolidinylpropoxy)phenylamine 1 in EtOH, Pd/C (0.1 eq) is added. The reaction vessel is repeatedly purged (×3) with nitrogen, and then stirred under a hydrogen atmosphere for 18 h. The product is filtered through a Celite plug, and the plug washed with 25 mL of EtOH, to yield 2. LCMS 236.2 $R_t$ 0.94 min.

3-Fluoro-4-amino substituted phenylenediamines

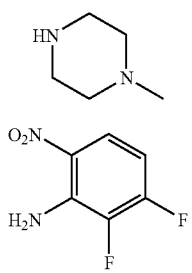

1

-continued

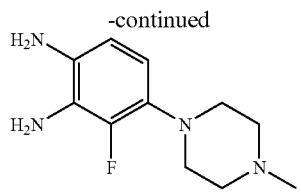

2

1. Synthesis of 2-Fluoro-3-(4-methyl-piperazin-1-yl)-6-nitro-phenylamine

A solution of N-methylpiperazine (1.0 eq), NMP, triethylamine (3.0 eq) and 5,6-difluoro-2-nitroaniline (1.0 eq) were heated at 90° C. for 1 hour. The reaction was allowed to cool to room temperature and then poured into water and let stand for 1 hour. The resulting solid was collected and dried and utilized without further purification. MH+=255.3

2. Synthesis of 3-Fluoro-4-(4-methyl-piperazin-1-yl)-benzene-1,2-diamine

To a solution Synthesis of 2-fluoro-3-(4-methyl-piperazin-1-yl)-6-nitrophenylamine in EtOH, Pd/C (0.1 eq) is added. The reaction vessel is repeatedly purged (×3) with nitrogen, and then stirred under a hydrogen atmosphere for 18 h. The product is filtered through a Celite plug, the plug washed with 25 mL of EtOH, to yield the desired diamine. LCMS 225.3 Rt 0.45 min.

4-Amino substituted phenylenediamines (a)

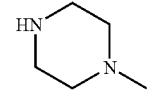

1

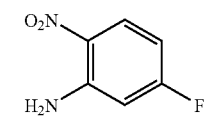

2

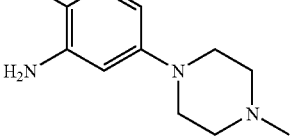

Synthesis of 5-(4-Methyl-piperazin-1-yl)-2-nitro-phenylamine

A solution of N-methylpiperazine (1.0 eq), NMP, triethylamine (3.0 eq) and 5-fluoro-2-nitrophenylamine (1.0 eq) were heated at 90° C. for 1 hours. The reaction was allowed to cool to room temperature and then poured into water and let stand for 12 hours. The resulting solid was collected and dried and utilized without further purification. MH+=237.3.

Synthesis of 4-(4-Methyl-piperazin-1-yl)-benzene-1,2-diamine

To a solution 5-(4-Methyl-piperazin-1-yl)-2-nitro-phenylamine in EtOH, Pd/C (0.1 eq) is added. The reaction vessel is repeatedly purged (×3) with nitrogen, then stirred under a hydrogen atmosphere for 18 h. The product is filtered through a Celite plug, the plug washed with 25 mL of EtOH, to yield the desired diamine. LCMS 207.3 Rt 0.25 min.

4-Amino substituted phenylenediamines (b)

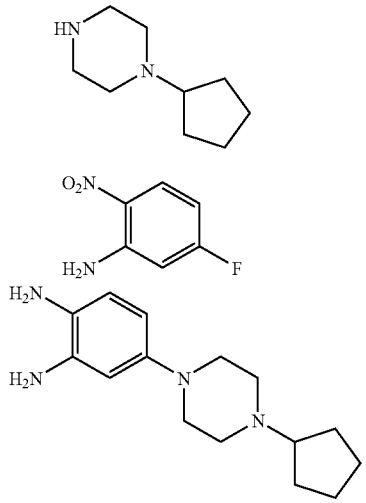

Synthesis of 5-(4-Cyclopentyl-piperazin-1-yl)-2-nitro-phenylamine

1. A solution of N-cyclopentylpiperazine (1.0 eq), NMP, triethylamine (3.0 eq) and 5-fluoro-2-nitrophenylamine (1.0 eq) were heated at 90° C. for 1 hours. The reaction was allowed to cool to room temperature and then poured into water and let stand for 12 hours. The resulting solid was collected and dried and utilized without further purification. MH+=291.4.

2. Synthesis of 4-(4-Cyclopentyl-piperazin-1-yl)-benzene-1,2-diamine:

To a solution 5-(4-Cyclopentyl-piperazin-1-yl)-2-nitro-phenylamine in EtOH, Pd/C (0.1 eq) is added. The reaction vessel is repeatedly purged (×3) with nitrogen, then stirred under a hydrogen atmosphere for 18 h. The product is filtered through a Celite plug, the plug washed with 25 mL of EtOH, to yield the desired diamine. MH+=261.3.

Example 822

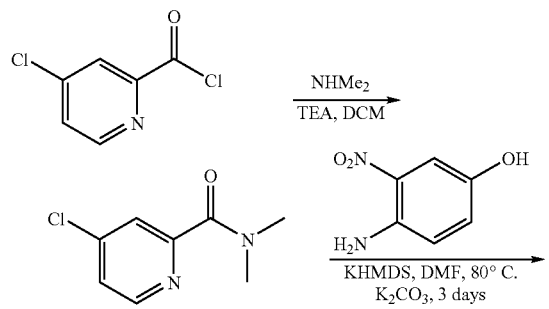

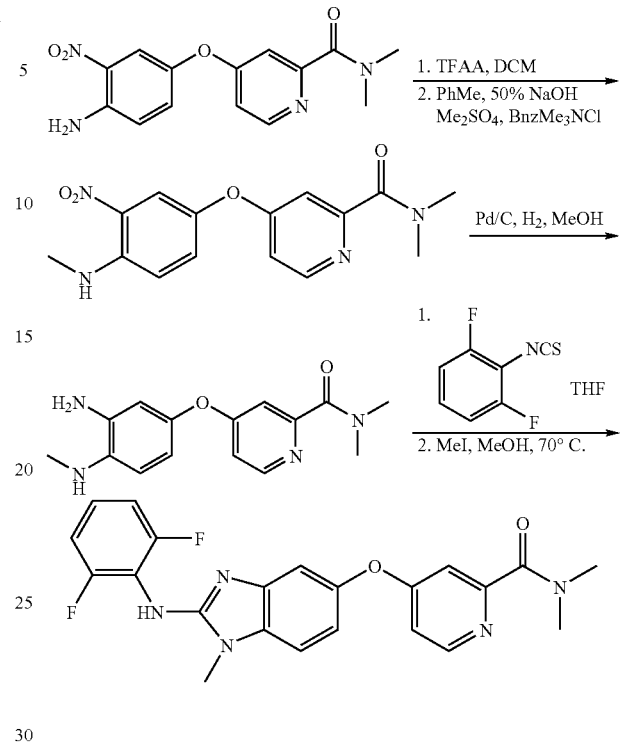

Step 1. Synthesis of 4-Chloro-pyridine-2-carboxylic acid dimethylamide

A solution of 4-chloro-pyridine-2-carbonyl chloride (1 eq) in dichloromethane was cooled to 0° C., whereupon triethylamine (2 eq) was added followed by dimethylamine (2 eq, 2M solution in THF). The solution was allowed to warm to room temperature and let stir overnight. It was then washed with 1M NaOH. The separated organic layer is dried over MgSO4, filtered, and concentrated to yield the desired product. HPLC, 1.82 min; MS: MH+=185.6

Step 2. Synthesis of 4-(4-Amino-3-nitro-phenoxy)-pyridine-2-carboxylic acid dimethylamide A mixture containing 4-amino-3-nitrophenol (1 eq) and potassium bis(trimethylsilyl)amide (2 eq) was stirred in dimethylformamide for 2 hours at room temperature. To this mixture was added 4-Chloro-pyridine-2-carboxylic acid dimethylamide (1 eq) and potassium carbonate (1.2 eq) and then it was stirred at 90° C. for 3 days. The reaction mixture was then concentrated before partitioning between ethyl acetate and water. The organic layer was separated, washed with brine, dried, filtered and concentrated in vacuum to give brown solid. Purification by flash chromatography with ethyl acetate and hexane (1:1) gave the desired product as a yellow syrup. HPLC, 1.69 min; MS: MH+=303.1.

Step 3. Synthesis of 4-(4-Methylamino-3-nitro-phenoxy)-pyridine-2-carboxylic acid dimethylamide A solution of 4-(4-Amino-3-nitro-phenoxy)-pyridine-2-carboxylic acid dimethylamide (1 eq) in methylene chloride was treated with trifluoroacetic anhydride (1 eq) and stirred for 10 minutes at 0° C. The mixture was quenched with satd.

NaHCO3 solution. The organic layer was separated and washed with water, brine, dried, filtered and evaporated. MS: MH+=399.0

To the solution of the trifluoroacetamide (1 eq) in a mixture of toluene, acetonitrile and sodium hydroxide solution (50%) was added benzyltrimethylammonium chloride (1 eq) and dimethyl sulfate (1.2 eq). The biphasic mixture was stirred overnight at room temperature. The mixture was taken up in ethyl acetate, washed with water, brine, dried and evaporated. The crude was purified by flash chromatography eluting with 5% methanol in dichloromethane to afford the desired product. HPLC, 2.14 min; MS: MH+=317.3

Step 4. Synthesis of 4-(3-Amino-4-methylamino-phenoxy)-pyridine-2-carboxylic acid dimethylamide The solution of 4-(4-Methylamino-3-nitro-phenoxy)-pyridine-2-carboxylic acid dimethylamide in methanol was treated with 10% palladium on carbon and stirred under hydrogen atmosphere for 3 hours at room temperature. The mixture was purged with nitrogen and then was filtered through celite and the filtrate was concentrated to provide the diamine. HPLC, 1.17 min; MS: MH+=287.1

Step 5. Synthesis of 4-[2-(2,6-Difluoro-phenylamino)-1-methyl-1H-benzoimidazol-5-yloxy]-pyridine-2-carboxylic acid dimethylamide A solution of the 4-(3-Amino-4-methylamino-phenoxy)-pyridine-2-carboxylic acid dimethylamide (1 eq) in methanol was treated with 2,6-difluorophenylisothiocyanate (1 eq) and stirred overnight. To the reaction mixture, methyl iodide (1 eq) was added and stirred overnight at 60° C. The reaction was cooled down to room temperature, evaporated, and the residue purified by reverse phase HPLC. HPLC, 1.66 min; MS: MH+=424.1

Each of the compounds 823-984, listed in the below table were synthesized as indicated in the right hand column by the method described herein.

TABLE 13

| Example | Structure | Name | MH+ | Synthesized as in Ex.: |
|---|---|---|---|---|
| 823 | 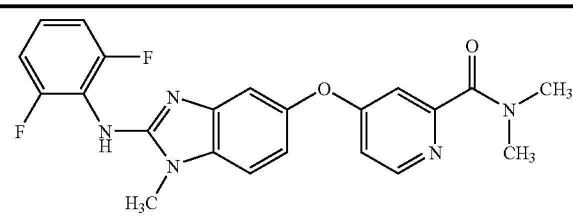 | 4-({2-[(2,6-difluorophenyl)-amino]-1-methyl-1H-benzimidazol-5-yl}oxy)-N,N-dimethylpyridine-2-carboxamide | 424.1 | 822 |
| 824 | 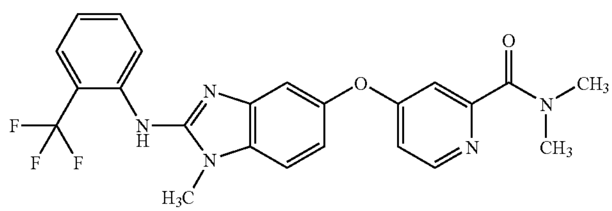 | N,N-dimethyl-4-[(1-methyl-2-{[2-(trifluoromethyl)phenyl]-amino}-1H-benzimidazol-5-yl)oxy]pyridine-2-carboxamide | 456.4 | 822 |
| 825 | 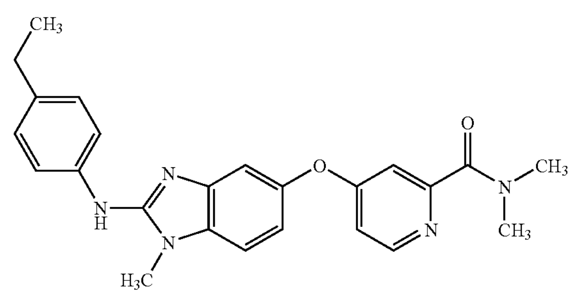 | 4-({2-[(4-ethylphenyl)amino]-1-methyl-1H-benzimidazol-5-yl}-oxy)-N,N-dimethylpyridine-2-carboxamide | 416.5 | 822 |
| 826 | 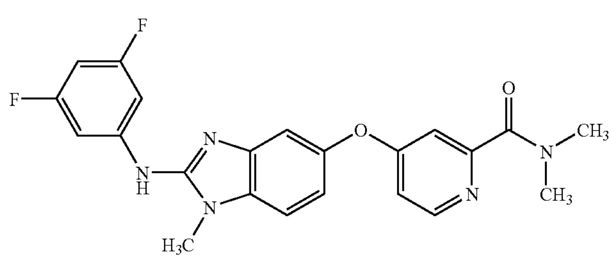 | 4-({2-[(3,5-difluorophenyl)-amino]-1-methyl-1H-benzimidazol-5-yl}oxy)-N,N-dimethylpyridine-2-carboxamide | 424.4 | 822 |

TABLE 13-continued

| Example | Structure | Name | MH+ | Synthesized as in Ex.: |
|---------|-----------|------|-----|------------------------|
| 827 | 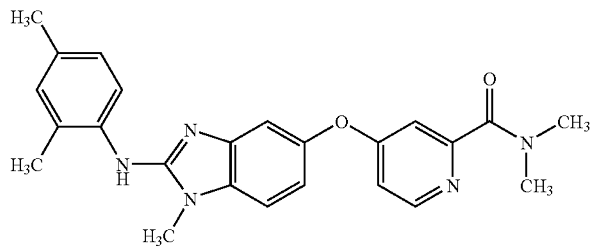 | 4-({2-[(2,4-dimethylphenyl)-amino]-1-methyl-1H-benzimidazol-5-yl}oxy)-N,N-dimethylpyridine-2-carboxamide | 416.5 | 822 |
| 828 | 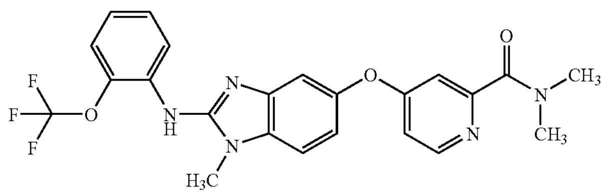 | N,N-dimethyl-4-{[1-methyl-2-({2-[(trifluoromethyl)oxy]-phenyl}amino)-1H-benzimidazol-5-yl]oxy}pyridine-2-carboxamide | 472.4 | 822 |
| 829 | 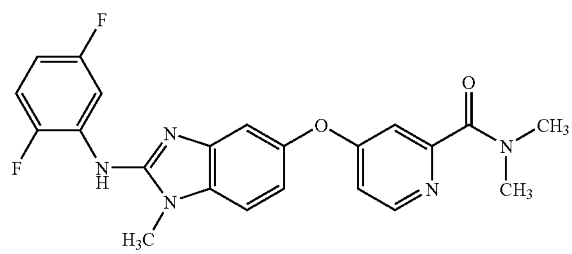 | 4-({2-[(2,5-difluorophenyl)-amino]-1-methyl-1H-benzimidazol-5-yl}oxy)-N,N-dimethylpyridine-2-carboxamide | 424.4 | 822 |
| 830 | 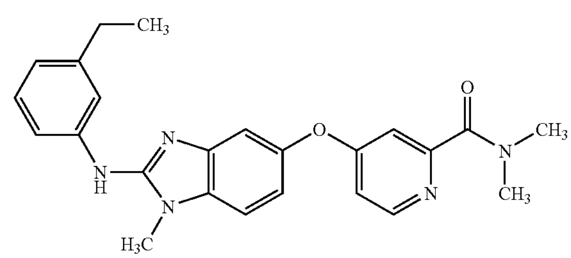 | 4-({2-[(3-ethylphenyl)amino]-1-methyl-1H-benzimidazol-5-yl}-oxy)-N,N-dimethylpyridine-2-carboxamide | 416.5 | 822 |
| 831 | 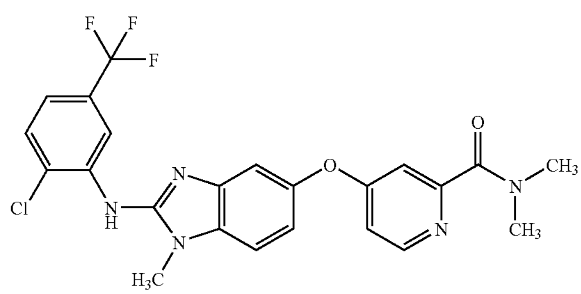 | 4-[(2-{[2-chloro-5-(trifluoromethyl)phenyl]amino}-1-methyl-1H-benzimidazol-5-yl)-oxy]-N,N-dimethylpyridine-2-oxy]-N,N-dimethylpyridine-2-carboxamide | 490.9 | 822 |
| 832 | 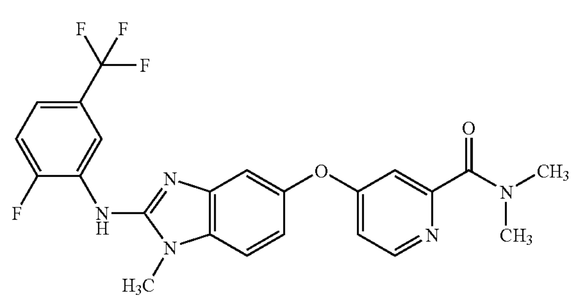 | 4-[(2-{[2-fluoro-5-(trifluoromethyl)phenyl]amino}-1-methyl-1H-benzimidazol-5-yl)-oxy]-N,N-dimethylpyridine-2-carboxamide | 474.4 | 822 |

TABLE 13-continued

| Example | Structure | Name | MH+ | Synthesized as in Ex.: |
|---|---|---|---|---|
| 833 | 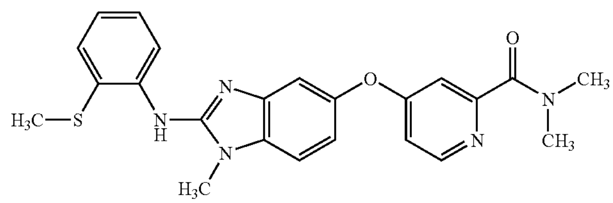 | N,N-dimethyl-4-[(1-methyl-2-{[2-(methylthio)phenyl]amino}-1H-benzimidazol-5-yl)oxy]-pyridine-2-carboxamide | 434.5 | 822 |
| 834 | 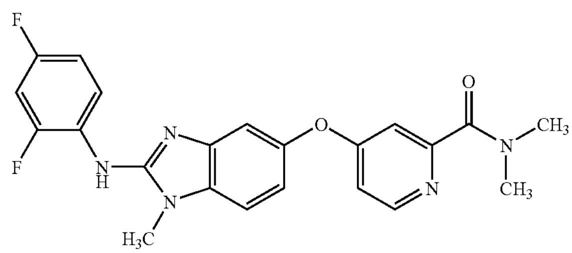 | 4-({2-[(2,4-difluorophenyl)-amino]-1-methyl-1H-benz-imidazol-5-yl}oxy)-N,N-dimethylpyridine-2-carboxamide | 424.4 | 822 |
| 835 | 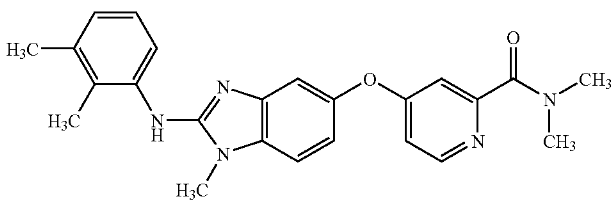 | 4-({2-[(2,3-dimethylphenyl)-amino]-1-methyl-1H-benz-imidazol-5-yl}oxy)-N,N-dimethylpyridine-2-carboxamide | 416.5 | 822 |
| 836 | 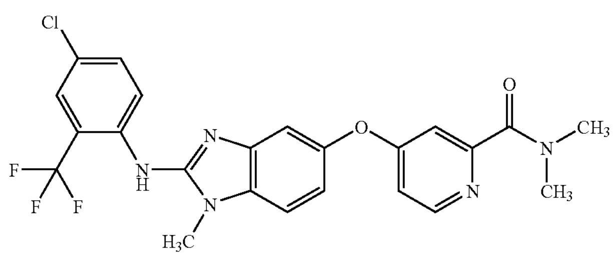 | 4-[(2-{[4-chloro-2-(trifluoro-methyl)phenyl]amino}-1-methyl-1H-benzimidazol-5-yl)-oxy]-N,N-dimethylpyridine-2-carboxamide | 490.9 | 822 |
| 837 | 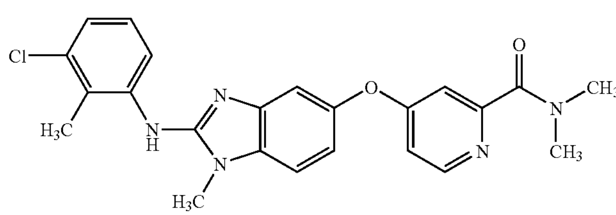 | 4-({2-[(3-chloro-2-methyl-phenyl)amino]-1-methyl-1H-benzimidazol-5-yl}oxy)-N,N-dimethylpyridine-2-carboxamide | 436.9 | 822 |
| 838 | 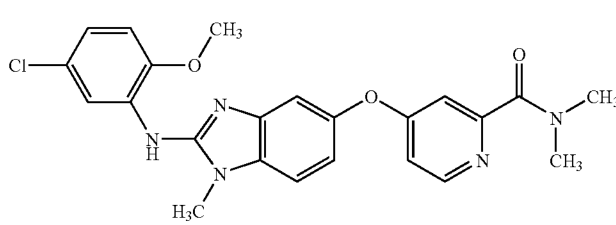 | 4-[(2-{[5-chloro-2-(methyloxy)-phenyl]amino}-1-methyl-1H-benzimidazol-5-yl)oxy]-N,N-dimethylpyridiine-2-carboxamide | 452.9 | 822 |

TABLE 13-continued

| Example | Name | MH+ | Synthesized as in Ex.: |
|---|---|---|---|
| 839 | 4-[(2-([3,5-bis(methyloxy)-phenyl]amino}-1-methyl-1H-benzimidazol-5-yl)oxy]-N,N-dimethylpyridine-2-carboxamide | 448.5 | 822 |
| 840 | N,N-dimethyl-4-[(1-methyl-2-{[5-methyl-2-(methyloxy)-phenyl]amino}-1H-benzimidazol-5-yl)oxy]pyridine-2-carboxamide | 432.5 | 822 |
| 841 | N,N-dimethyl-4-[(1-methyl-2-[4-(methyloxy)-1,1'-biphenyl-3-yl]amino}-1H-benzimidazol-5-yl)oxy]pyridine-2-carboxamide | 494.6 | 822 |
| 842 | 4-[(2-([3,4-bis(methyloxy)-phenyl]amino}-1-methyl-1H-benzimidazol-5-yl)oxy]-N,N-dimethylpyridine-2-carboxamide | 448.5 | 822 |
| 843 | N,N-dimethyl-4-[(1-methyl-2-{[2-(methyloxy)phenyl]amino}-1H-benzimidazol-5-yl)oxy]-pyridine-2-carboxamide | 418.5 | 822 |

TABLE 13-continued

| Example | Structure | Name | MH+ | Synthesized as in Ex.: |
|---|---|---|---|---|
| 844 | 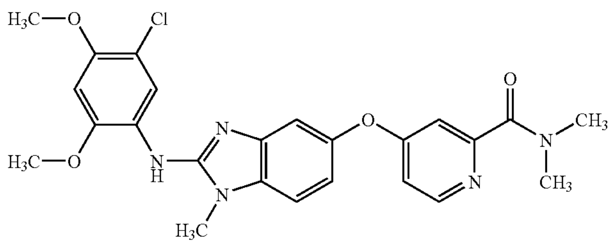 | 4-[(2-{[5-chloro-2,4-bis(methyloxy)phenyl]amino}-1-methyl-1H-benzimidazol-5-yl)oxy]-N,N-dimethylpyridine-2-carboxamide | 482.9 | 822 |
| 845 | 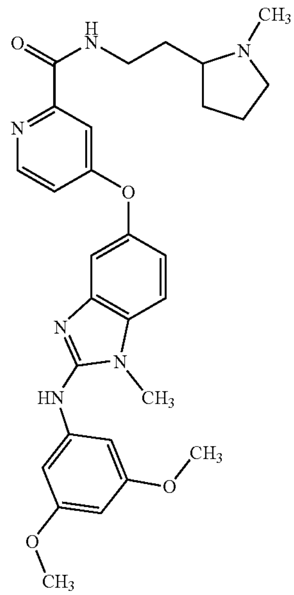 | 4-[(2-{[3,5-bis(methyloxy)phenyl]amino}-1-methyl-1H-benzimidazol-5-yl)oxy]-N-[2-(1-methylpyrrolidin-2-yl)ethyl]-pyridine-2-carboxamide | 531.6 | 372 |
| 846 | 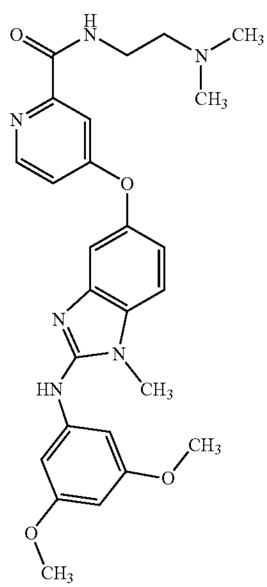 | 4-[(2-{[3,5-bis(methyloxy)phenyl]amino}-1-methyl-1H-benzimidazol-5-yl)oxy]-N-[2-(dimethylamino)ethyl]pyridine-2-carboxamide | 491.6 | 372 |

TABLE 13-continued

| Example | Structure | Name | MH+ | Synthesized as in Ex.: |
|---|---|---|---|---|
| 847 | 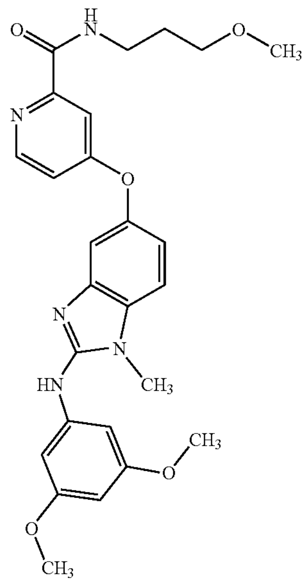 | 4-[(2-{[3,5-bis(methyloxy)-phenyl]amino}-1-methyl-1H-benzimidazol-5-yl)oxy]-N-[3-(methyloxy)propyl]pyridine-2-carboxamide | 492.5 | 372 |
| 848 | 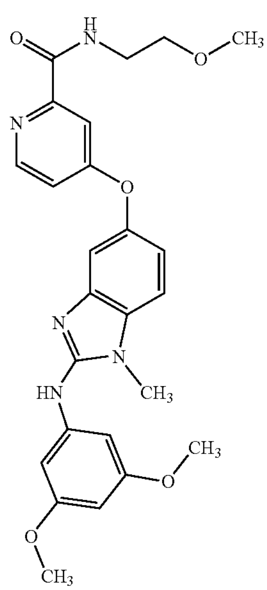 | 4-[(2-{[3,5-bis(methyloxy)-phenyl]amino}-1-methyl-1H-benzimidazol-5-yl)oxy]-N-[2-(methyloxy)ethyl]pyridine-2-carboxamide | 478.5 | 372 |

TABLE 13-continued
| Example | Structure | Name | MH+ | Synthesized as in Ex.: |
|---|---|---|---|---|
| 849 | 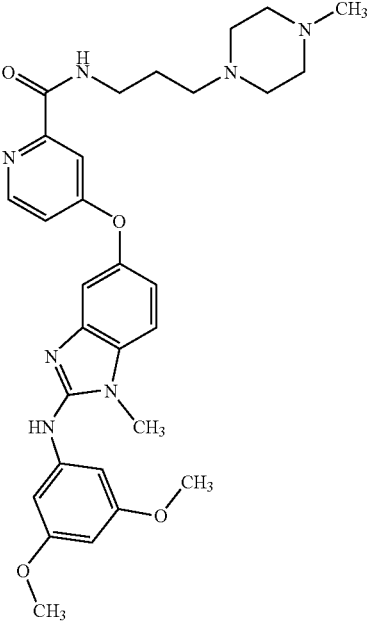 | 4-[(2-{[3,5-bis(methyloxy)-phenyl]amino}-1-methyl-1H-benzimidazol-5-yl)oxy]-N-[3-(4-methylpiperazin-1-yl)propyl]-pyridine-2-carboxamide | 560.7 | 372 |
| 850 | 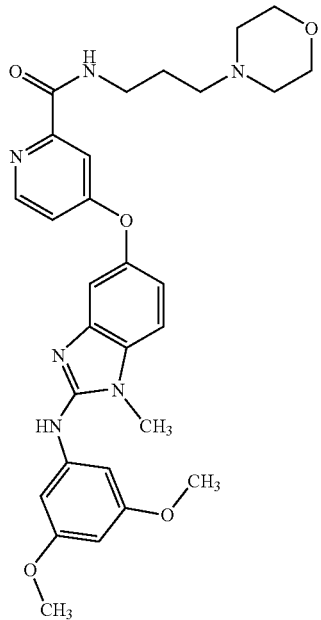 | 4-[(2-{[3,5-bis(methyloxy)-phenyl]amino}-1-methyl-1H-benzimidazol-5-yl)oxy]-N-(3-morpholin-4-ylpropyl)pyridine-2-carboxamide | 547.6 | 372 |

TABLE 13-continued
| Example | Structure | Name | MH+ | Synthesized as in Ex.: |
|---|---|---|---|---|
| 851 | 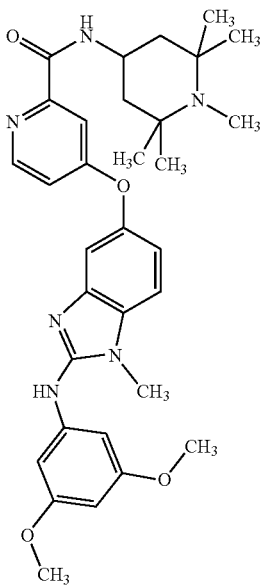 | 4-[(2-{[3,5-bis(methyloxy)-phenyl]amino}-1-methyl-1H-benzimidazol-5-yl)oxy]-N-(1,2,2,6,6-pentamethylpiperidin-4-yl)pyridine-2-carboxamide | 573.7 | 372 |
| 852 | 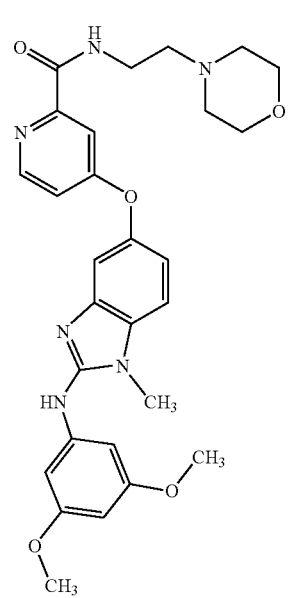 | 4-[(2-{[3,5-bis(methyloxy)-phenyl]amino}-1-methyl-1H-benzimidazol-5-yl)oxy]-N-(2-morpholin-4-ylethyl)pyridine-2-carboxamide | 533.6 | 372 |

TABLE 13-continued

| Example | Structure | Name | MH+ | Synthesized as in Ex.: |
|---|---|---|---|---|
| 853 | 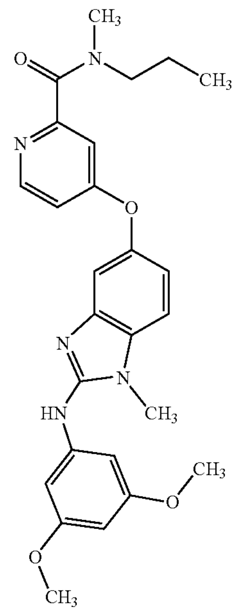 | 4-[(2-{[3,5-bis(methyloxy)-phenyl]amino}-1-methyl-1H-benzimidazol-5-yl)oxy]-N-methyl-N-propylpyridine-2-carboxamide | 476.5 | 372 |
| 854 | 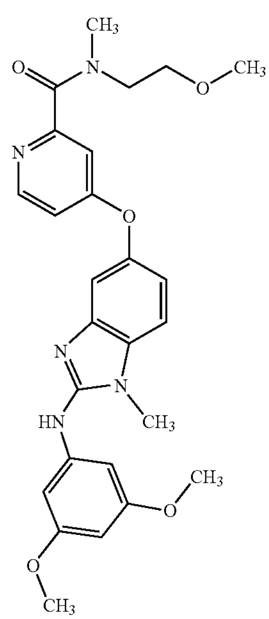 | 4-[(2-{[3,5-bis(methyloxy)-phenyl]amino}-1-methyl-1H-benzimidazol-5-yl)oxy]-N-methyl-N-[2-(methyloxy)-ethyl]pyridine-2-carboxamide | 492.5 | 372 |

TABLE 13-continued
| Example | Structure | Name | MH+ | Synthesized as in Ex.: |
|---|---|---|---|---|
| 855 | 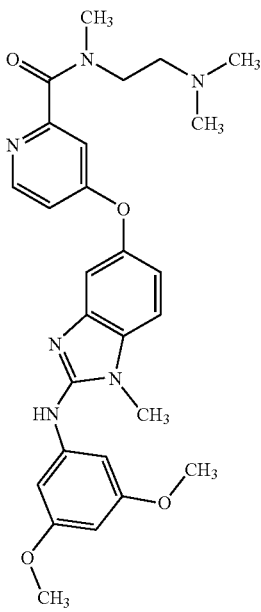 | 4-[(2-{[3,5-bis(methyloxy)-phenyl]amino}-1-methyl-1H-benzimidazol-5-yl)oxy]-N-[2-(dimethylamino)ethyl]-N-methylpyridine-2-carboxamide | 505.6 | 372 |
| 856 | 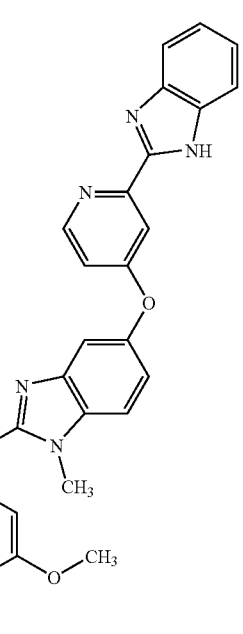 | 5-{[2-(1H-benzimidazol-2-yl)-pyridin-4-yl]oxy}-N-[3,5-bis-(methyloxy)phenyl]-1-methyl-1H-benzimidazol-2-amine | 493.5 | 821 |

TABLE 13-continued

| Example | Structure | Name | MH+ | Synthesized as in Ex.: |
|---------|-----------|------|-----|------------------------|
| 857 | 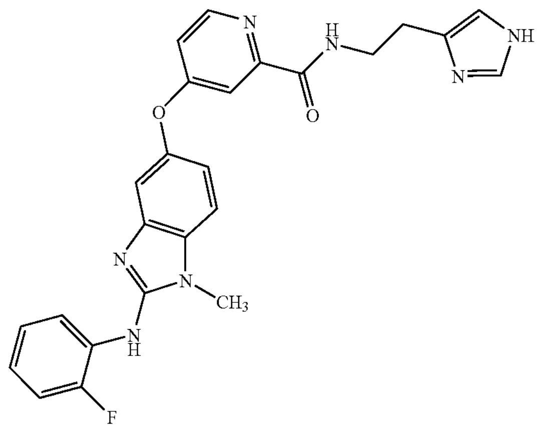 | 4-({2-[(2-fluorophenyl)amino]-1-methyl-1H-benzimidazol-5-yl}oxy)-N-[2-(1H-imidazol-4-yl)ethyl]pyridine-2-carboxamide | 472.5 | 372 |
| 858 | 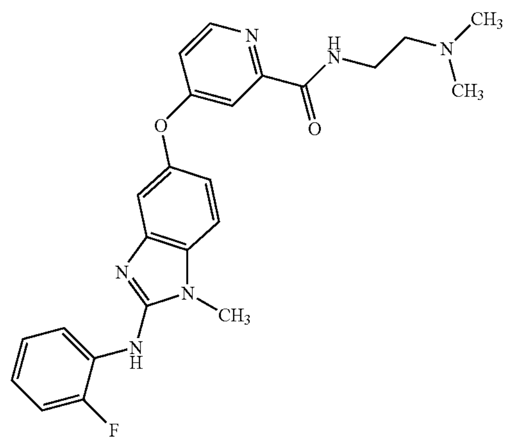 | N-[2-(dimethylamino)ethyl]-4-({2-[(2-fluorophenyl)amino]-1-methyl-1H-benzimidazol-5-yl}oxy)pyridine-2-carboxamide | 449.5 | 372 |
| 859 | 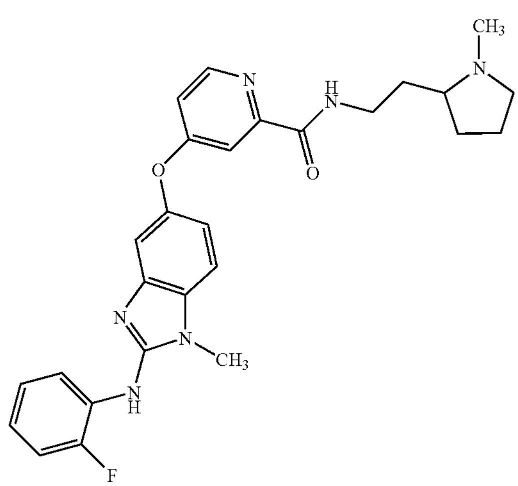 | 4-({2-[(2-fluorophenyl)amino]-1-methyl-1H-benzimidazol-5-yl}oxy)-N-[2-(1-methyl-pyrrolidin-2-yl)ethyl]pyridine-2-carboxamide | 489.6 | 372 |

TABLE 13-continued

| Example | Structure | Name | MH+ | Synthesized as in Ex.: |
|---------|-----------|------|-----|------------------------|
| 860 | 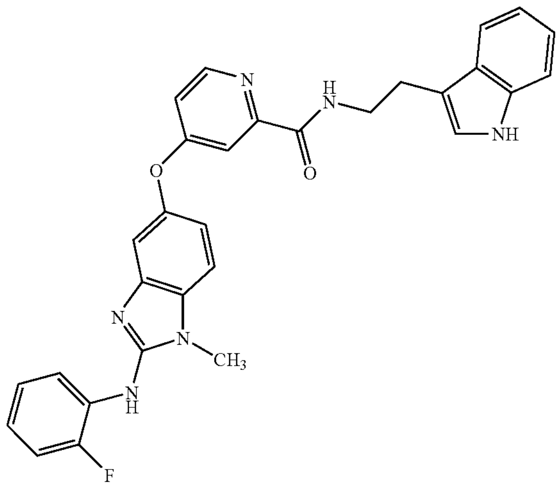 | 4-({2-[(2-fluorophenyl)amino]-1-methyl-1H-benzimidazol-5-yl}oxy)-N-[2-(1H-indol-3-yl)-ethyl]pyridine-2-carboxamide | 521.6 | 372 |
| 861 | 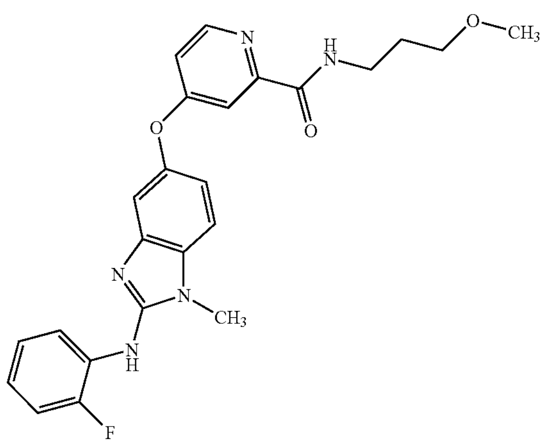 | 4-({2-[(2-fluorophenyl)amino]-1-methyl-1H-benzimidazol-5-yl}oxy)-N-[3-(methyloxy)-propyl]pyridine-2-carboxamide | 450.5 | 372 |
| 862 | 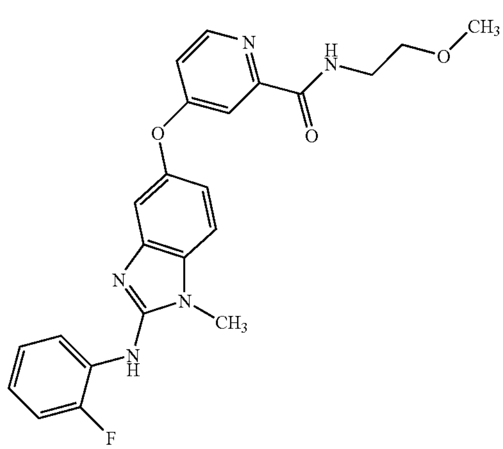 | 4-({2-[(2-fluorophenyl)amino]-1-methyl-1H-benzimidazol-5-yl}oxy)-N-[2-(methyloxy)-ethyl]pyridine-2-carboxamide | 436.5 | 372 |

TABLE 13-continued

| Example | Structure | Name | MH+ | Synthesized as in Ex.: |
|---|---|---|---|---|
| 863 | 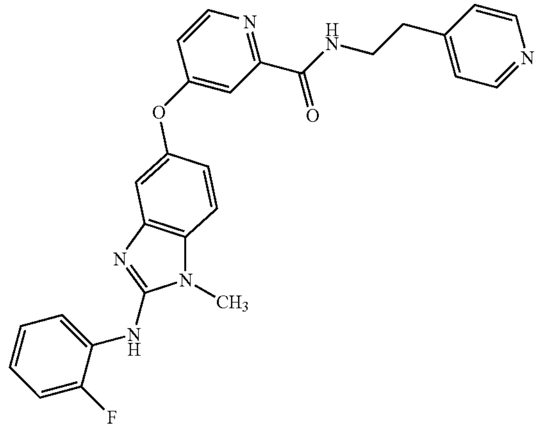 | 4-({2-[(2-fluorophenyl)amino]-1-methyl-1H-benzimidazol-5-yl}oxy)-N-(2-pyridin-4-ylethyl)-pyridine-2-carboxamide | 483.5 | 372 |
| 864 | 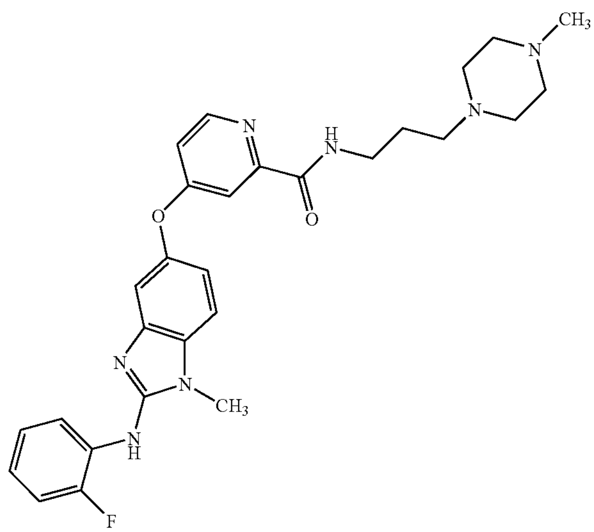 | 4-({2-[(2-fluorophenyl)amino]-1-methyl-1H-benzimidazol-5-yl}oxy)-N-[3-(4-methyl-piperazin-1-yl)propyl]pyridine-2-carboxamide | 518.6 | 372 |
| 865 | 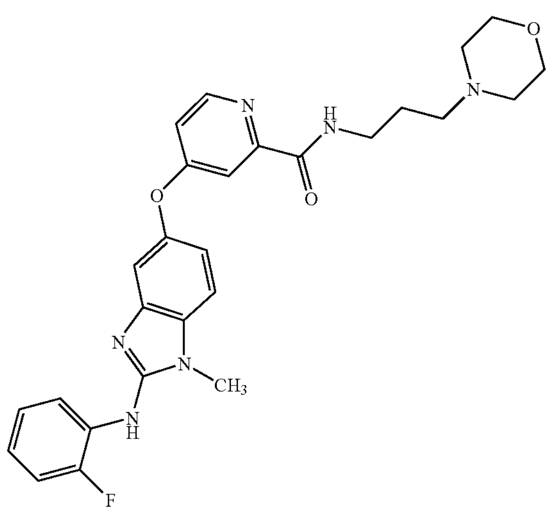 | 4-({2-[(2-fluorophenyl)amino]-1-methyl-1H-benzimidazol-5-yl}oxy)-N-(3-morpholin-4-yl-propyl)pyridine-2-carboxamide | 505.6 | 372 |

TABLE 13-continued

| Example | Structure | Name | MH+ | Synthesized as in Ex.: |
|---------|-----------|------|-----|------------------------|
| 866 | 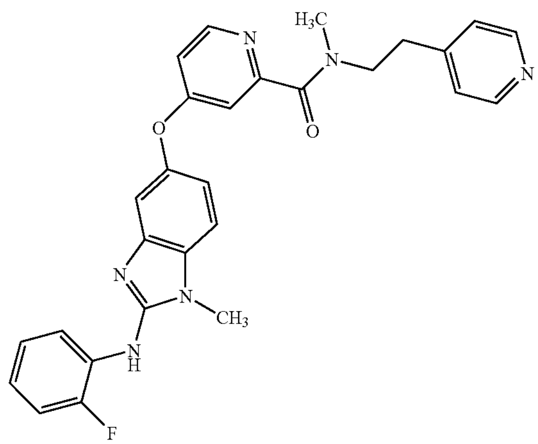 | 4-({2-[(2-fluorophenyl)amino]-1-methyl-1H-benzimidazol-5-yl}oxy)-N-methyl-N-(2-pyridin-4-ylethyl)pyridine-2-carboxamide | 497.5 | 372 |
| 867 | 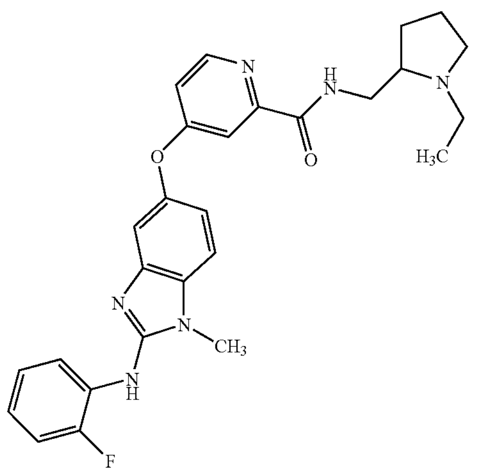 | N-[(1-ethylpyrrolidin-2-yl)methyl]-4-({2-[(2-fluorophenyl)amino]-1-methyl-1H-benzimidazol-5-yl}oxy)pyridine-2-carboxamide | 489.6 | 372 |
| 868 | 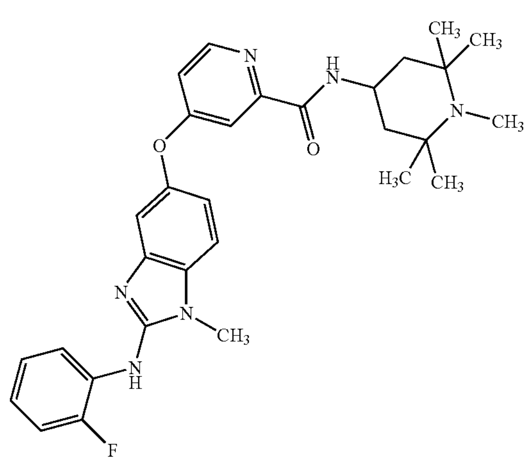 | 4-({2-[(2-fluorophenyl)amino]-1-methyl-1H-benzimidazol-5-yl}oxy)-N-(1,2,2,6,6-pentamethylpiperidin-4-yl)pyridine-2-carboxamide | 531.6 | 372 |

TABLE 13-continued

| Example | Structure | Name | MH+ | Synthesized as in Ex.: |
|---|---|---|---|---|
| 869 | 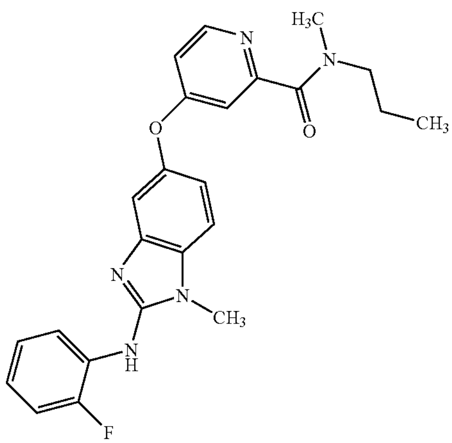 | 4-({2-[(2-fluorophenyl)amino]-1-methyl-1H-benzimidazol-5-yl}oxy)-N-methyl-N-propyl-pyridine-2-carboxamide | 434.5 | 372 |
| 870 | 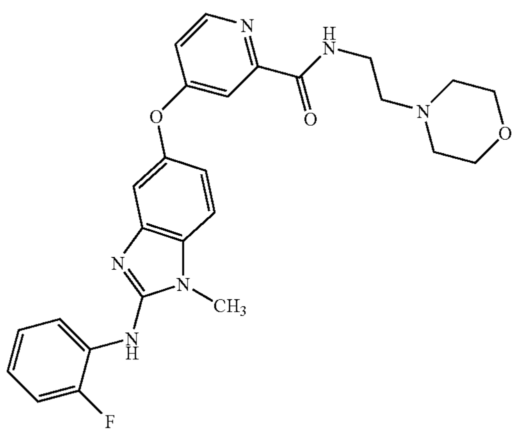 | 4-({2-{(2-fluorophenyl)amino]-1-methyl-1H-benzimidazol-5-yl}oxy)-N-(2-morpholin-4-yl-ethyl)pyridine-2-carboxamide | 491.5 | 372 |
| 871 | 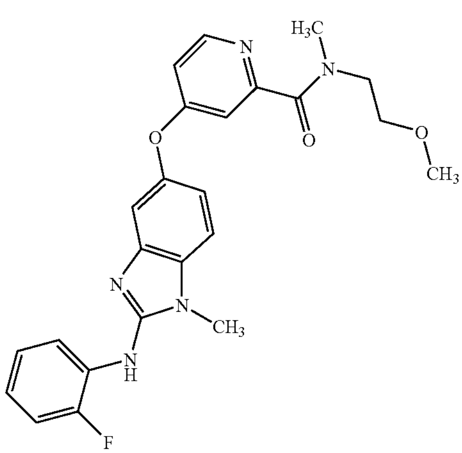 | 4-({2-[(2-fluorophenyl)amino]-1-methyl-1H-benzimidazol-5-yl}oxy)-N-methyl-N-[2-(methyloxy)ethyl]pyridine-2-carboxamide | 450.5 | 372 |

TABLE 13-continued

| Example | Structure | Name | MH+ | Synthesized as in Ex.: |
|---|---|---|---|---|
| 872 | 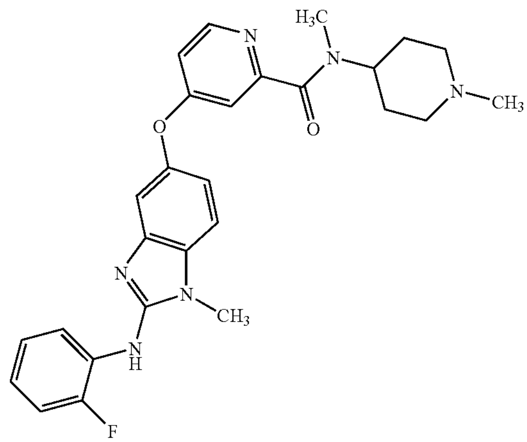 | 4-({2-[(2-fluorophenyl)amino]-1-methyl-1H-benzimidazol-5-yl}oxy)-N-methyl-N-(1-methyl-piperidin-4-yl)pyridine-2-carboxamide | 489.6 | 372 |
| 873 | 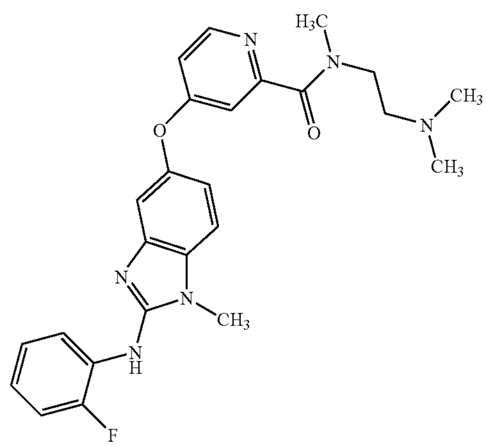 | N-[2-(dimethylamino)ethyl]-4-({2-[(2-fluorophenyl)amino]-1-methyl-1H-benzimidazol-5-yl}-oxy)-N-methylpyridine-2-carboxamide | 463.5 | 372 |
| 874 | 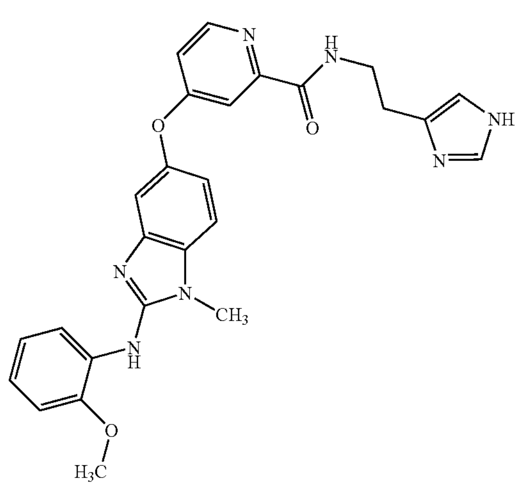 | N-[2-(1H-imidazol-4-yl)ethyl]-4-[(1-methyl-2-{[2-(methyloxy)-phenyl]amino}-1H-benzimidazol-5-yl)oxy]pyridine-2-carboxamide | 484.5 | 372 |

TABLE 13-continued

| Example | Structure | Name | MH+ | Synthesized as in Ex.: |
|---|---|---|---|---|
| 875 | 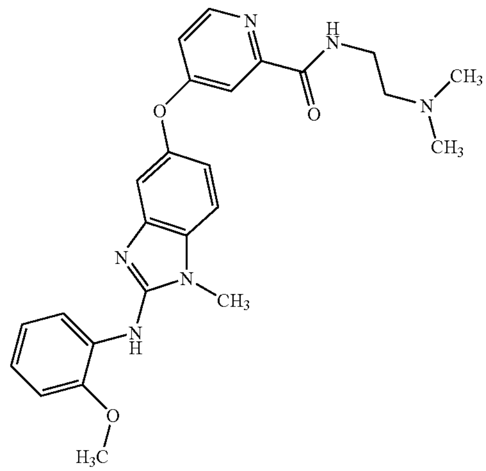 | N-[2-(dimethylamino)ethyl]-4-[(1-methyl-2-{[2-(methyloxy)-phenyl]amino}-1H-benzimidazol-5-yl)oxy]pyridine-2-carboxamide | 461.5 | 372 |
| 876 | 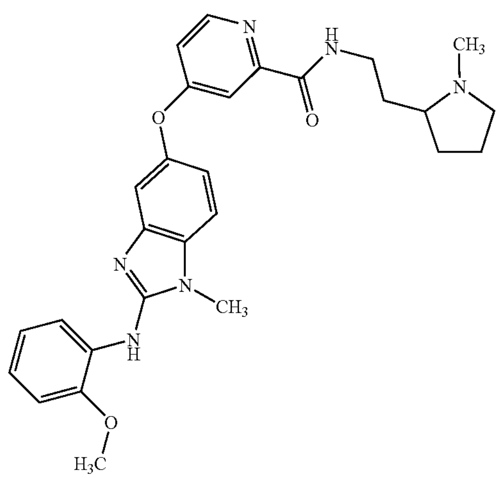 | 4-[(1-methyl-2-{[2-(methyloxy)-phenyl]amino}-1H-benzimidazol-5-yl)oxy]-N-[2-(1-methylpyrrolidin-2-yl)ethyl]-pyridine-2-carboxamide | 501.6 | 372 |
| 877 | 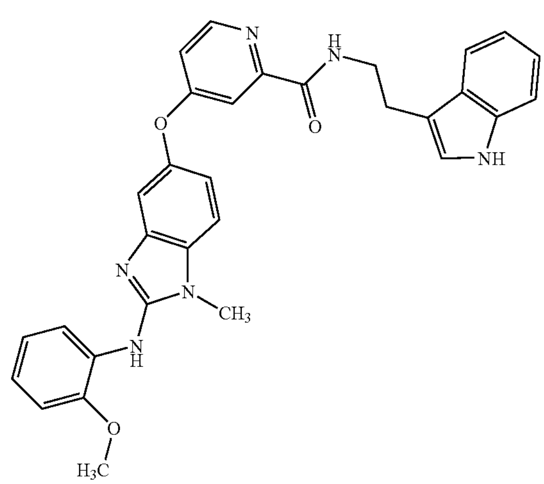 | N-[2-(1H-indol-3-yl)ethyl]-4-[(1-methyl-2-{[2-(methyloxy)-phenyl]amino}-1H-benzimidazol-5-yl)oxy]pyridine-2-carboxamide | 533.6 | 372 |

TABLE 13-continued

| Example | Structure | Name | MH+ | Synthesized as in Ex.: |
|---|---|---|---|---|
| 878 | 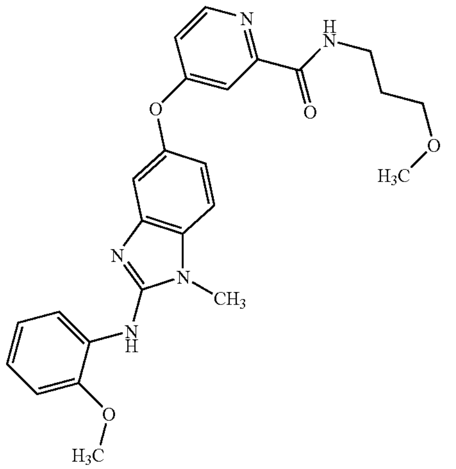 | 4-[(1-methyl-2-{[2-(methyloxy)phenyl]amino}-1H-benzimidazol-5-yl)oxy]-N-[3-(methyloxy)propyl]pyridine-2-carboxamide | 462.5 | 372 |
| 879 | 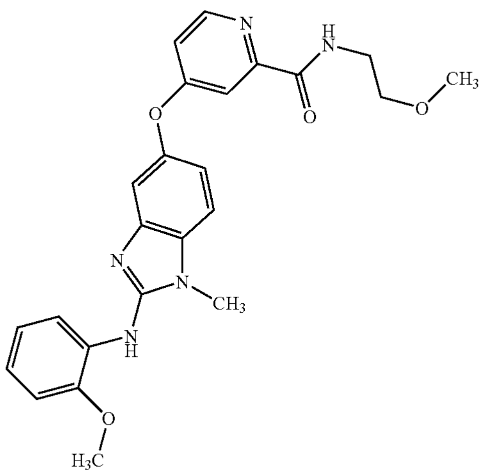 | 4-[(1-methyl-2-{[2-(methyloxy)phenyl]amino}-1H-benzimidazol-5-yl)oxy]-N-[2-(methyloxy)ethyl]pyridine-2-carboxamide | 448.5 | 372 |
| 880 | 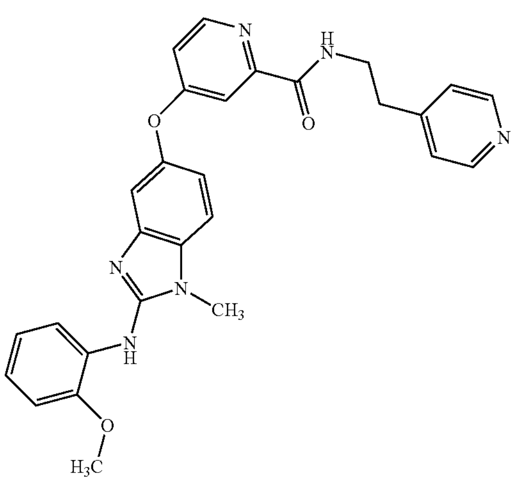 | 4-[(1-methyl-2-{[2-(methyloxy)phenyl]amino}-1H-benzimidazol-5-yl)oxy]-N-(2-pyridin-4-ylethyl)pyridine-2-carboxamide | 495.6 | 372 |

TABLE 13-continued

| Example | Structure | Name | MH+ | Synthesized as in Ex.: |
|---|---|---|---|---|
| 881 | 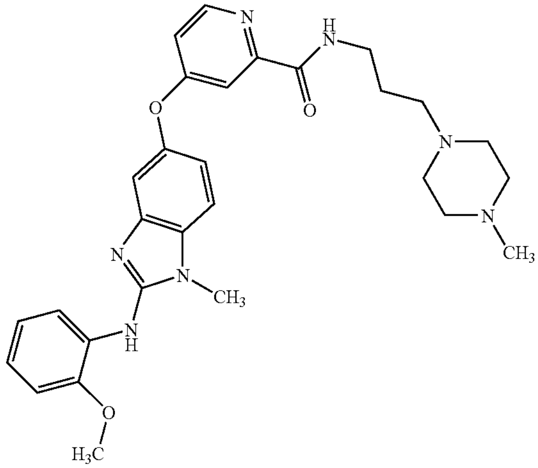 | 4-[(1-methyl-2-{[2-(methyl-oxy)phenyl]amino}-1H-benz-imidazol-5-yl)oxy]-N-[3-(4-methylpiperazin-1-yl)propyl]-pyridine-2-carboxamide | 530.6 | 372 |
| 882 | 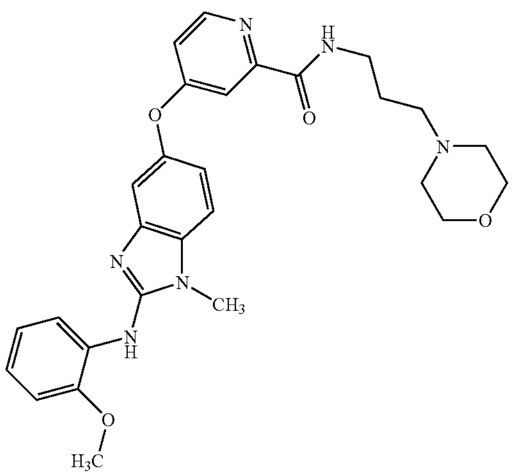 | 4-[(1-methyl-2-{[2-(methyloxy)-phenyl]amino}-1H-benz-imidazol-5-yl)oxy]-N-(3-morpholin-4-ylpropyl)pyridine-2-carboxamide | 517.6 | 372 |
| 883 | 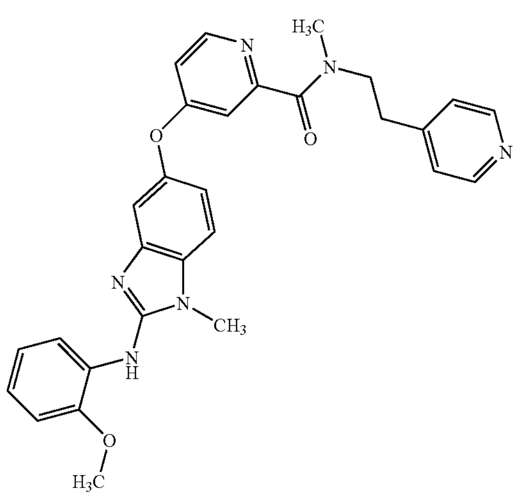 | N-methyl-4-[(1-methyl-2-{[2-(methyloxy)phenyl]amino}-1H-benzimidazol-5-yl)oxy]-N-(2-pyridin-4-ylethyl)pyridine-2-carboxamide | 509.6 | 372 |

TABLE 13-continued

| Example | Structure | Name | MH+ | Synthesized as in Ex.: |
|---|---|---|---|---|
| 884 | 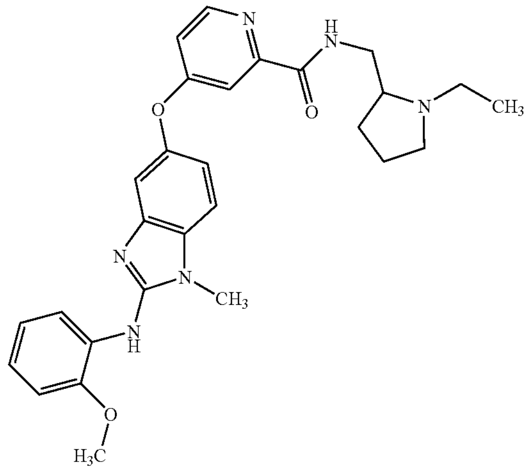 | N-[(1-ethylpyrrolidin-2-yl)methyl]-4-[(1-methyl-2-{[2-(methyloxy)phenyl]amino}-1H-benzimidazol-5-yl)oxy]pyridine-2-carboxamide | 501.6 | 372 |
| 885 | 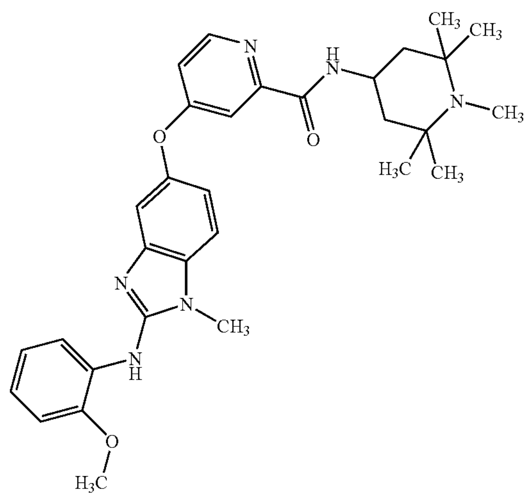 | 4-[(1-methyl-2-{[2-(methyloxy)phenyl]amino}-1H-benzimidazol-5-yl)oxy]-N-(1,2,2,6,6-pentamethylpiperidin-4-yl)pyridine-2-carboxamide | 543.7 | 372 |
| 886 | 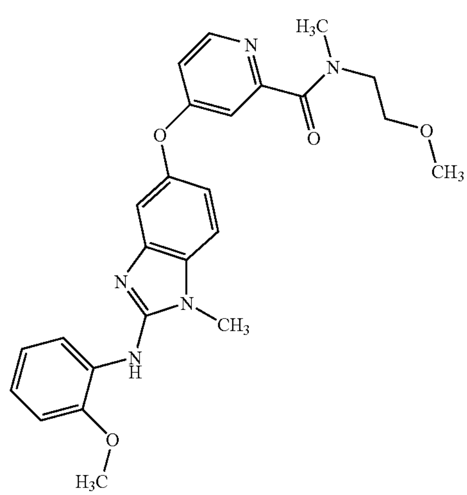 | N-methyl-4-[(1-methyl-2-{[2-(methyloxy)phenyl]amino}-1H-benzimidazol-5-yl)oxy]-N-[2-(methyloxy)ethyl]pyridine-2-carboxamide | 462.5 | 372 |

TABLE 13-continued

| Example | Structure | Name | MH+ | Synthesized as in Ex.: |
|---|---|---|---|---|
| 887 | 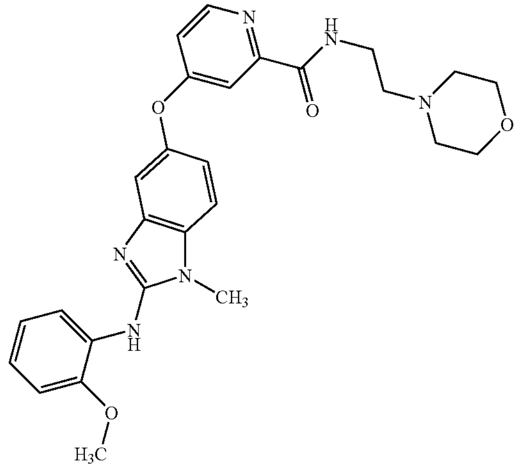 | 4-[(1-methyl-2-{[2-(methyloxy)phenyl]amino}-1H-benzimidazol-5-yl)oxy]-N-(2-morpholin-4-ylethyl)pyridine-2-carboxamide | 503.6 | 372 |
| 888 | 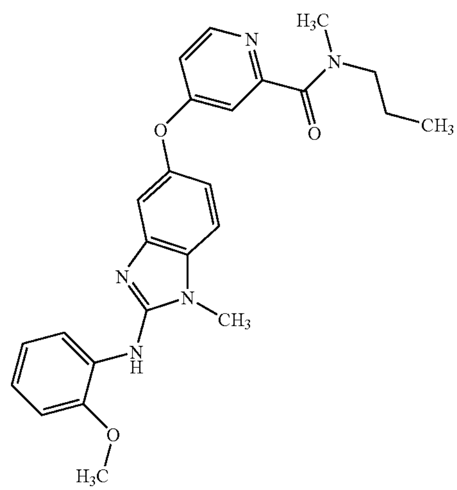 | N-methyl-4-[(1-methyl-2-{[2-(methyloxy)phenyl]amino}-1H-benzimidazol-5-yl)oxy]-N-propylpyridine-2-carboxamide | 446.5 | 372 |
| 889 | 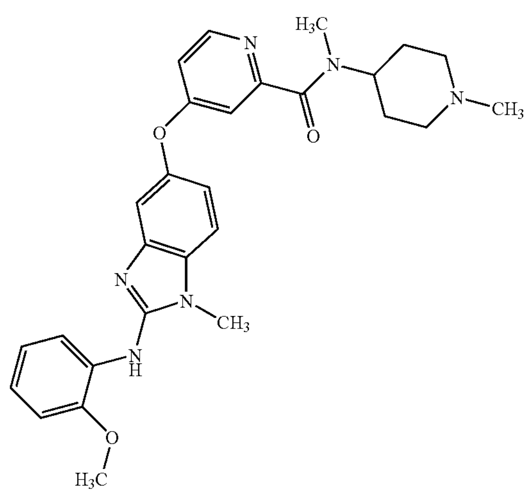 | N-methyl-4-[(1-methyl-2-{[2-(methyloxy)phenyl]amino}-1H-benzimidazol-5-yl)oxy]-N-(1-methylpiperidin-4-yl)pyridine-2-carboxamide | 501.6 | 372 |

TABLE 13-continued
| Example | Structure | Name | MH+ | Synthesized as in Ex.: |
|---|---|---|---|---|
| 890 | 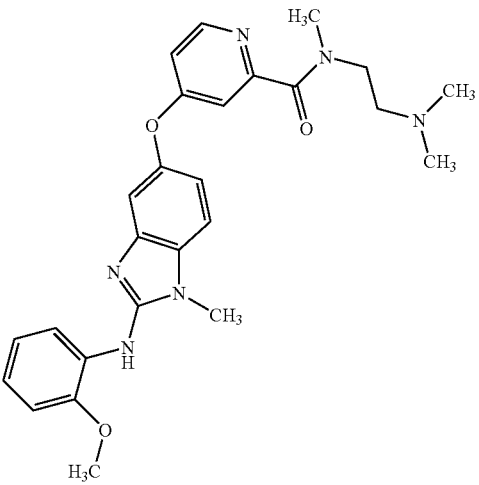 | N-[2-(dimethylamino)ethyl]-N-methyl-4-[(1-methyl-2-{[2-(methyloxy)phenyl]amino}-1H-benzimidazol-5-yl)oxy]pyridine-2-carboxamide | 475.6 | 372 |
| 891 | 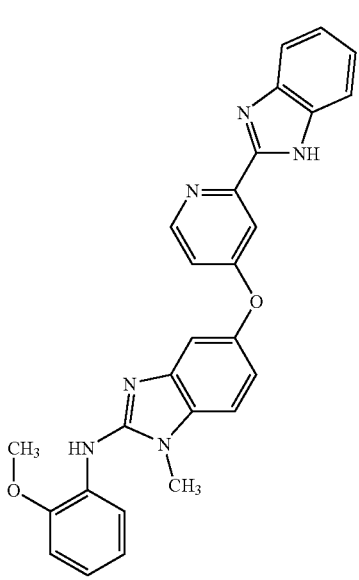 | 5-{[2-(1H-benzimidazol-2-yl)pyridin-4-yl]oxy}-1-methyl-N-[2-(methyloxy)phenyl]-1H-benzimidazol-2-amine | 463.5 | 372 |

TABLE 13-continued
| Example | Structure | Name | MH+ | Synthesized as in Ex.: |
|---|---|---|---|---|
| 892 | 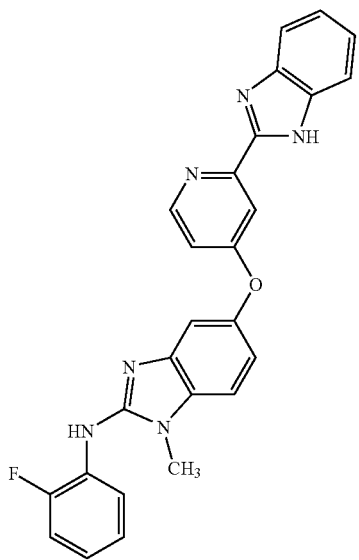 | 5-{[2-(1H-benzimidazol-2-yl)pyridin-4-yl]oxy}-N-(2-fluorophenyl)-1-methyl-1H-benzimidazol-2-amine | 451.5 | 372 |
| 893 | 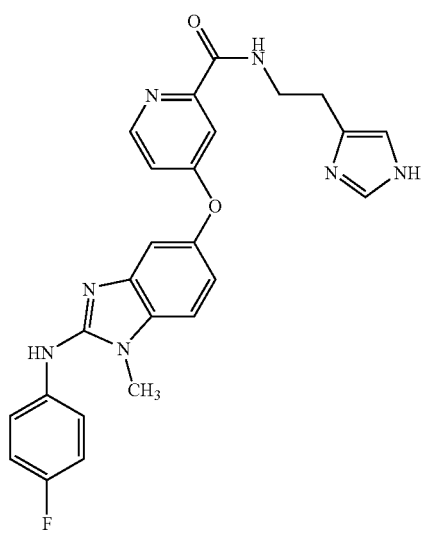 | 4-({2-[(4-fluorophenyl)amino]-1-methyl-1H-benzimidazol-5-yl}oxy)-N-[2-(1H-imidazol-4-yl)ethyl]pyridine-2-carboxamide | 472.5 | 372 |

TABLE 13-continued
| Example | Structure | Name | MH+ | Synthesized as in Ex.: |
|---|---|---|---|---|
| 894 | 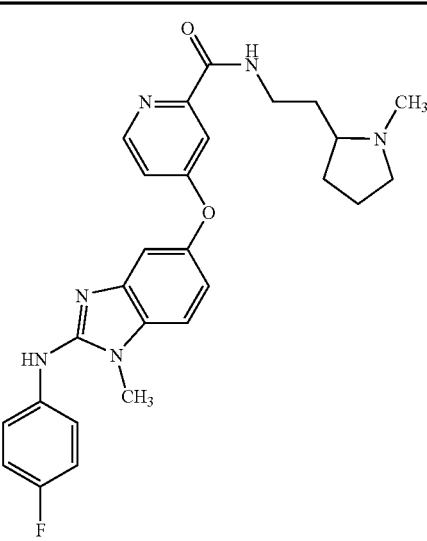 | 4-({2-[(4-fluorophenyl)amino]-1-methyl-1H-benzimidazol-5-yl}oxy)-N-[2-(1-methyl-pyrrolidin-2-yl)ethyl]pyridine-2-carboxamide | 489.6 | 372 |
| 895 | 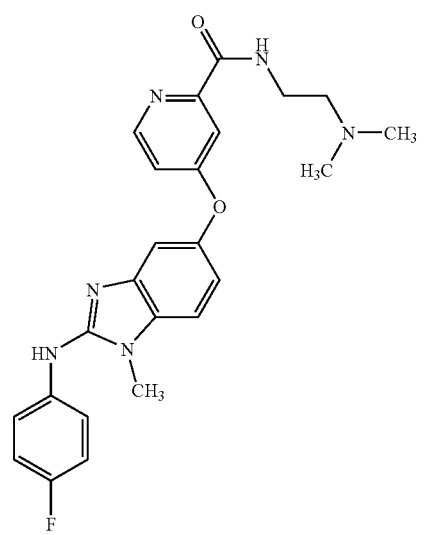 | N-[2-(dimethylamino)ethyl]-4-({2-[(4-fluorophenyl)amino]-1-methyl-1H-benzimidazol-5-yl}-oxy)pyridine-2-carboxamide | 449.6 | 372 |

TABLE 13-continued
| Example | Structure | Name | MH+ | Synthesized as in Ex.: |
|---|---|---|---|---|
| 896 | 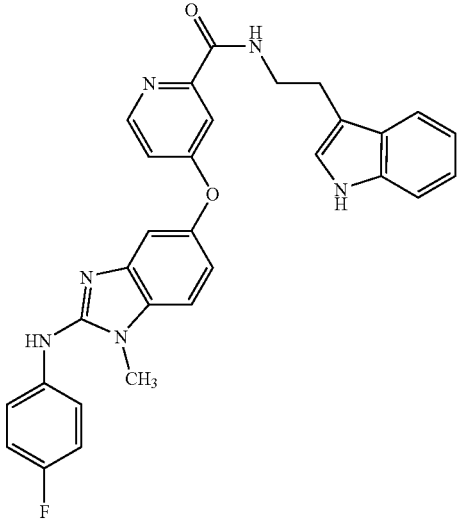 | 4-({2-[(4-fluorophenyl)amino]-1-methyl-1H-benzimidazol-5-yl}oxy)-N-[2-(1H-indol-3-yl)-ethyl]pyridine-2-carboxamide | 521.6 | 372 |
| 897 | 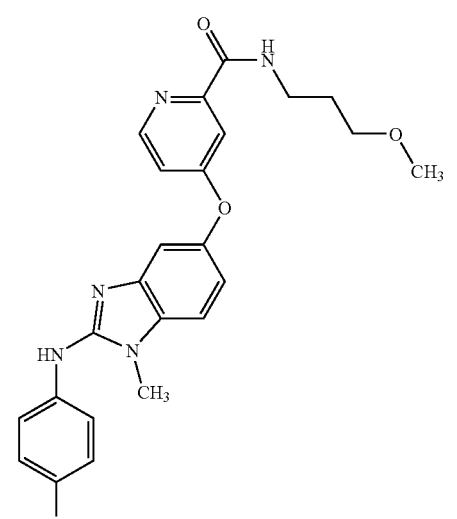 | 4-({2-[(4-fluorophenyl)amino]-1-methyl-1H-benzimidazol-5-yl}oxy)-N-[3-(methyloxy)-propyl]pyridine-2-carboxamide | 450.5 | 372 |

TABLE 13-continued
| Example | Structure | Name | MH+ | Synthesized as in Ex.: |
|---|---|---|---|---|
| 898 | 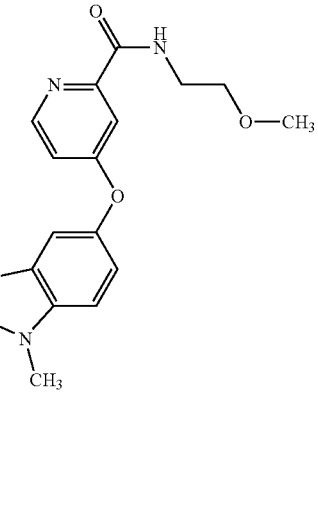 | 4-({2-[(4-fluorophenyl)amino]-1-methyl-1H-benzimidazol-5-yl}oxy)-N-[2-(methyloxy)-ethyl]pyridine-2-carboxamide | 436.5 | 372 |
| 899 | 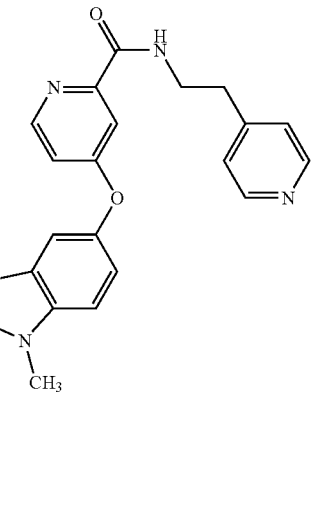 | 4-({2-[(4-fluorophenyl)amino]-1-methyl-1H-benzimidazol-5-yl}oxy)-N-(2-pyridin-4-ylethyl)-pyridine-2-carboxamide | 483.6 | 372 |

TABLE 13-continued
| Example | Structure | Name | MH+ | Synthesized as in Ex.: |
|---|---|---|---|---|
| 900 | 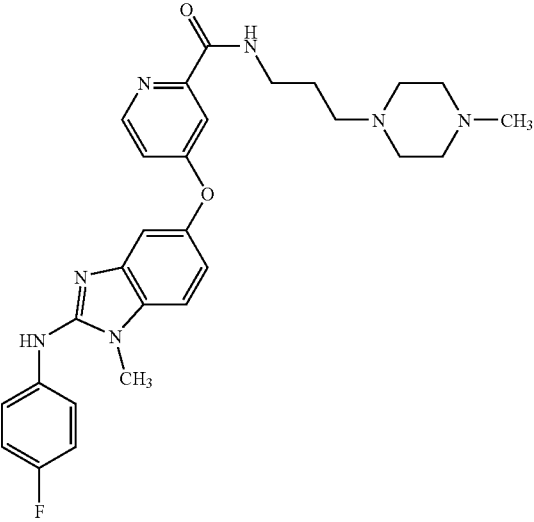 | 4-({2-[(4-fluorophenyl)amino]-1-methyl-1H-benzimidazol-5-yl}oxy)-N-[3-(4-methyl-piperazin-i-yl)propyl]pyridine-2-carboxamide | 518.6 | 372 |
| 901 | 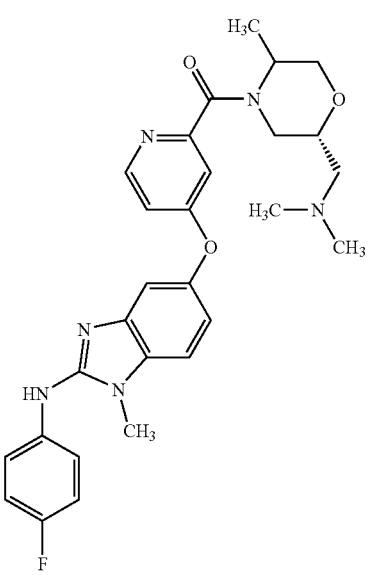 | 5-{[2-({(2R,5R)-2-[(dimethyl-amino)methyl]-5-methyl-morpholin-4-yl}carbonyl)-pyridin-4-yl]oxy}-N-(4-fluoro-phenyl)-1-methyl-1H-benz-imidazol-2-amine | 519.6 | 372 |

TABLE 13-continued
| Example | Structure | Name | MH+ | Synthesized as in Ex.: |
|---|---|---|---|---|
| 902 | 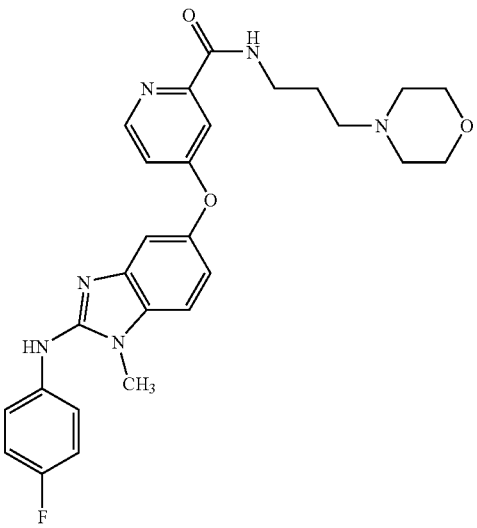 | 4-({2-[(4-fluorophenyl)amino]-1-methyl-1H-benzimidazol-5-yl}oxy)-N-(3-morpholin-4-yl-propyl)pyridine-2-carboxamide | 505.6 | 372 |
| 903 | 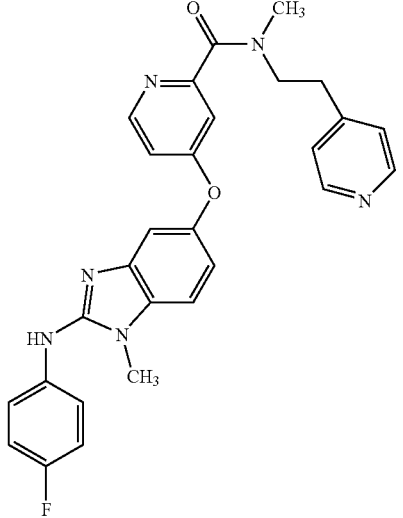 | 4-({2-[(4-fluorophenyl)amino]-1-methyl-1H-benzimidazol-5-yl}oxy)-N-methyl-N-(2-pyridin-4-ylethyl)pyridine-2-carboxamide | 497.6 | 372 |

TABLE 13-continued
| Example | Structure | Name | MH+ | Synthesized as in Ex.: |
|---|---|---|---|---|
| 904 | 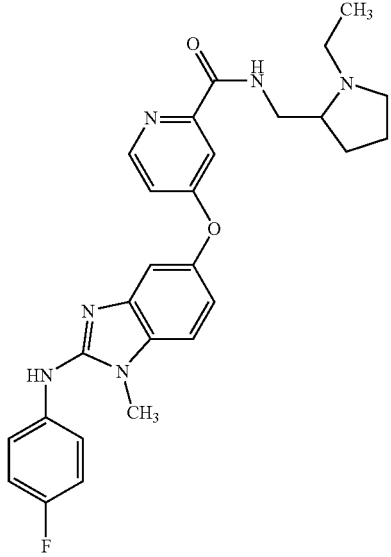 | N-[(1-ethylpyrrolidin-2-yl)methyl]-4-({2-[(4-fluorophenyl)amino]-1-methyl-1H-benzimidazol-5-yl}oxy)-pyridine-2-carboxamide | 489.6 | 372 |
| 905 | 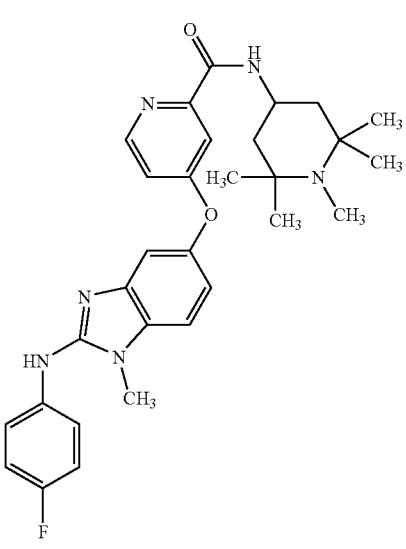 | 4-({2-[(4-fluorophenyl)amino]-1-methyl-1H-benzimidazol-5-yl}oxy)-N-(1,2,2,6,6-pentamethylpiperidin-4-yl)pyridine-2-carboxamide | 531.7 | 372 |

TABLE 13-continued
| Example | Structure | Name | MH+ | Synthesized as in Ex.: |
|---|---|---|---|---|
| 906 | 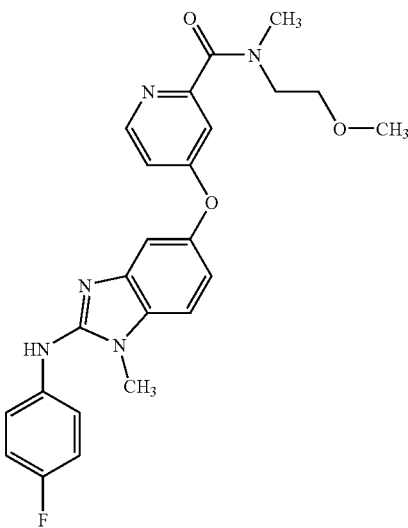 | 4-({2-[(4-fluorophenyl)amino]-1-methyl-1H-benzimidazol-5-yl}oxy)-N-methyl-N-[2-(methyloxy)ethyl]pyridine-2-carboxamide | 450.6 | 372 |
| 907 | 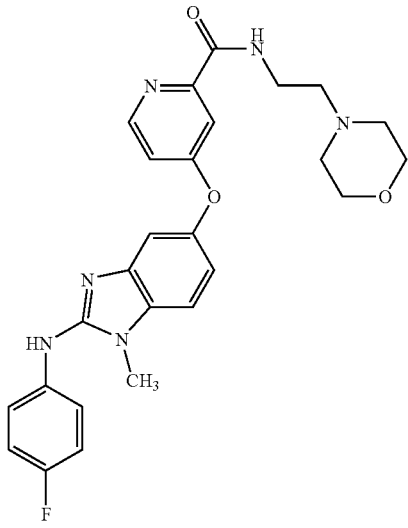 | 4-({2-[(4-fluorophenyl)amino]-1-methyl-1H-benzimidazol-5-yl}oxy)-N-(2-morpholin-4-yl-ethyl)pyridine-2-carboxamide | 491.6 | 372 |

TABLE 13-continued
| Example | Structure | Name | MH+ | Synthesized as in Ex.: |
|---|---|---|---|---|
| 908 | 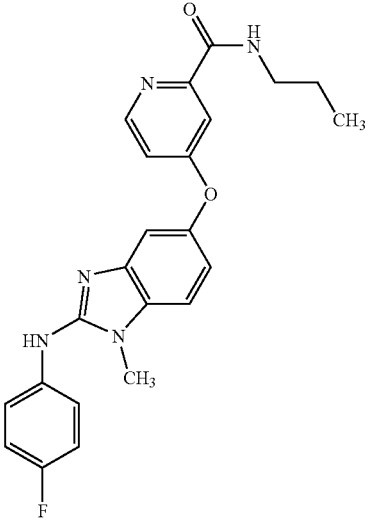 | 4-({2-[(4-fluorophenyl)amino]-1-methyl-1H-benzimidazol-5-yl}oxy)-N-propylpyridine-2-carboxamide | 434.6 | 372 |
| 909 | 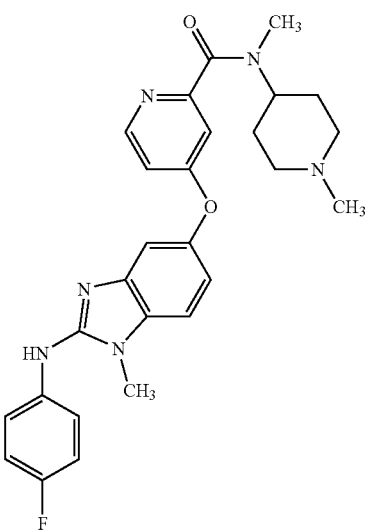 | 4-({2-[(4-fluorophenyl)amino]-1-methyl-1H-benzimidazol-5-yl}oxy)-N-methyl-N-(1-methyl-piperidin-4-yl)pyridine-2-carboxamide | 489.6 | 372 |

TABLE 13-continued
| Example | Structure | Name | MH+ | Synthesized as in Ex.: |
|---|---|---|---|---|
| 910 | 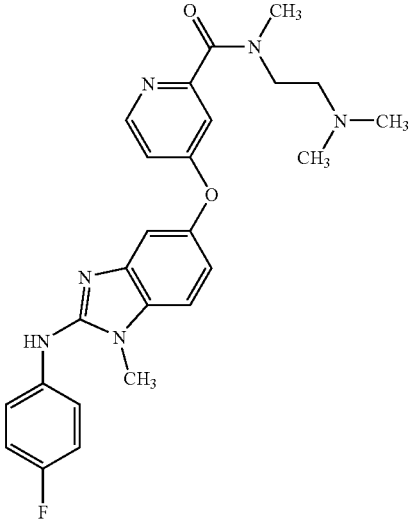 | N-[2-(dimethylamino)ethyl]-4-({2-[(4-fluorophenyl)amino]-1-methyl-1H-benzimidazol-5-yl}-oxy)-N-methylpyridine-2-carboxamide | 463.6 | 372 |
| 911 | 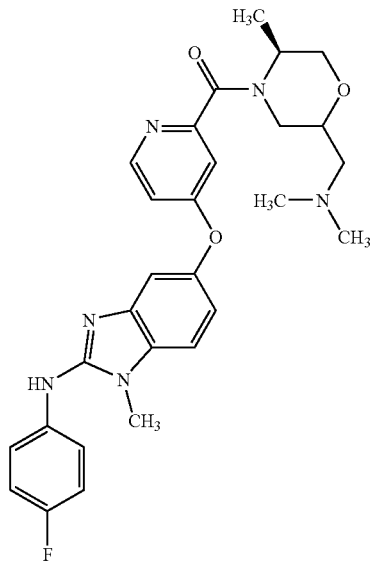 | 5-{[2-({(2R,5S)-2-[(dimethyl-amino)methyl]-5-methyl-morpholin-4-yl}carbonyl)-pyridin-4-yl]oxy}-N-(4-fluoro-phenyl)-1-methyl-1H-benz-imidazol-2-amine | 519.6 | 372 |

TABLE 13-continued

| Example | Structure | Name | MH+ | Synthesized as in Ex.: |
|---|---|---|---|---|
| 912 | 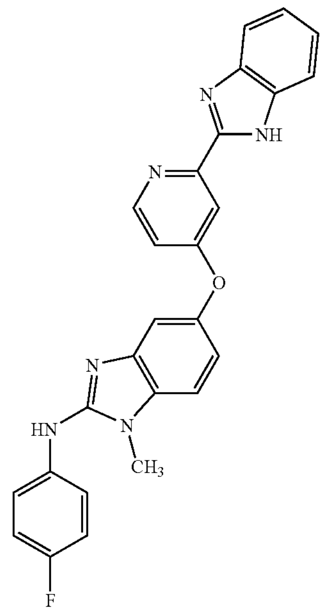 | 5-{[2-(1H-benzimidazol-2-yl)-pyridin-4-yl]oxy}-N-(4-fluorophenyl)-1-methyl-1H-benzimidazol-2-amine | 451.5 | 821 |
| 913 | 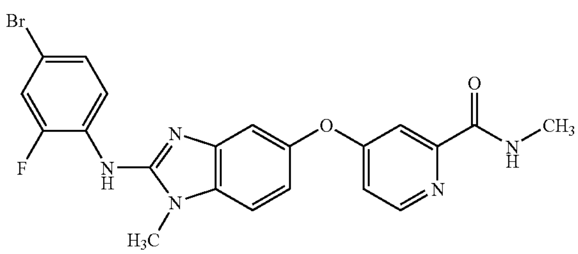 | 4-({2-[(4-bromo-2-fluorophenyl)amino]-1-methyl-1H-benzimidazol-5-yl}oxy)-N-methylpyridine-2-carboxamide | 471.3 | 120a |
| 914 | 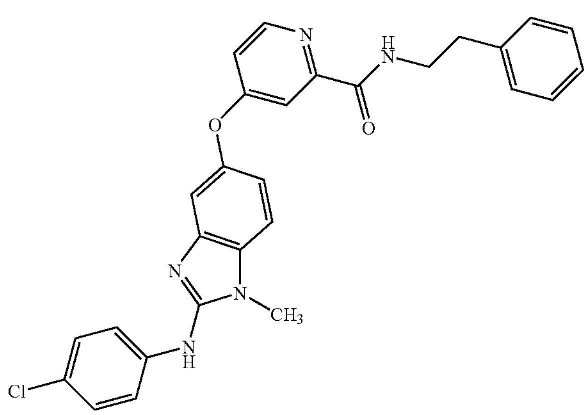 | 4-({2-[(4-chlorophenyl)amino]-1-methyl-1H-benzimidazol-5-yl}oxy)-N-(2-phenylethyl)-pyridine-2-carboxamide | 499.0 | 372 |

TABLE 13-continued

| Example | Structure | Name | MH+ | Synthesized as in Ex.: |
|---|---|---|---|---|
| 915 | 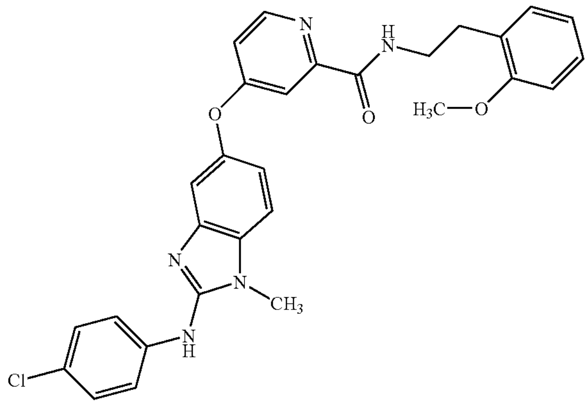 | 4-({2-[(4-chlorophenyl)amino]-1-methyl-1H-benzimidazol-5-yl}oxy)-N-{2-[2-(methyloxy)-phenyl]ethyl}pyridine-2-carboxamide | 529.0 | 372 |
| 916 | 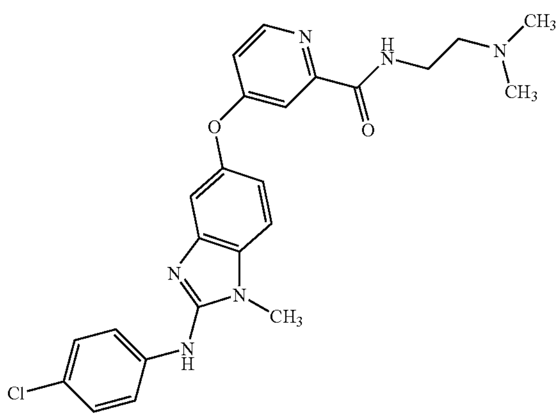 | 4-({2-[(4-chlorophenyl)amino]-1-methyl-1H-benzimidazol-5-yl}oxy)-N-[2-(dimethylamino)-ethyl]pyridine-2-carboxamide | 466.0 | 372 |
| 917 | 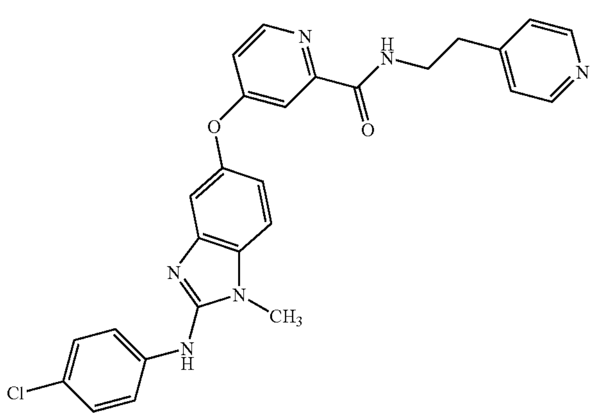 | 4-({2-[(4-chlorophenyl)amino]-1-methyl-1H-benzimidazol-5-yl}oxy)-N-(2-pyridin-4-ylethyl)-pyridine-2-carboxamide | 500.0 | 372 |

TABLE 13-continued

| Example | Structure | Name | MH+ | Synthesized as in Ex.: |
|---|---|---|---|---|
| 918 | 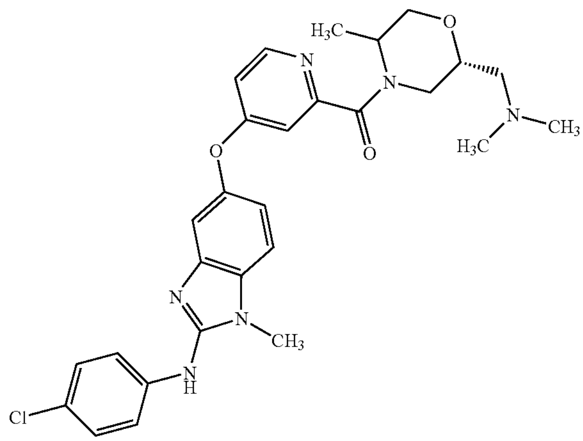 | N-(4-chlorophenyl)-5-({(2R,5R)-2-[(dimethylamino)-methyl]-5-methylmorpholin-4-yl}carbonyl)pyridin-4-yl]oxy}-1-methyl-1H-benzimidazol-2-amine | 536.0 | 372 |
| 919 | 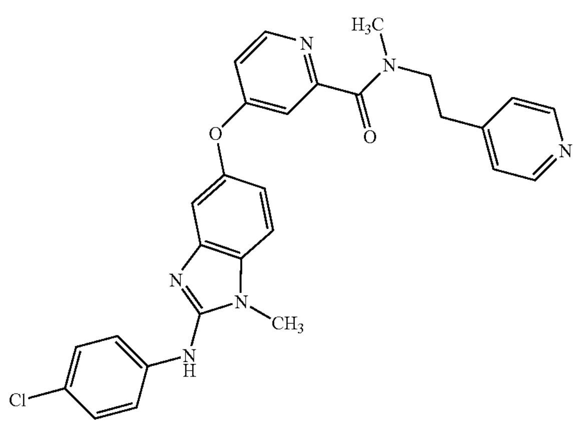 | 4-({2-[(4-chlorophenyl)amino]-1-methyl-1H-benzimidazol-5-yl}oxy)-N-methyl-N-(2-pyridin-4-ylethyl)pyridine-2-carboxamide | 514.0 | 372 |
| 920 | 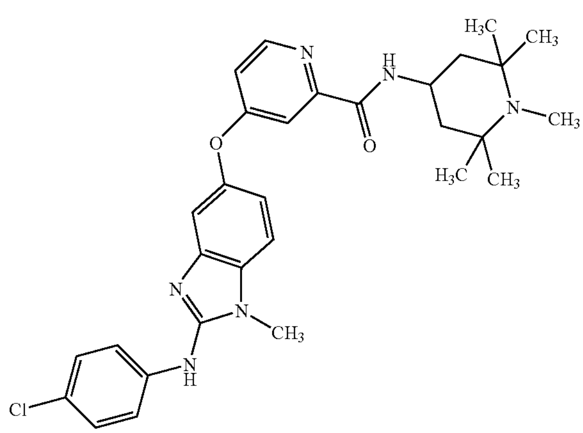 | 4-({2-[(4-chlorophenyl)amino]-1-methyl-1H-benzimidazol-5-yl}oxy)-N-(1,2,2,6,6-pentamethylpiperidin-4-yl)pyridine-2-carboxamide | 548.1 | 372 |

TABLE 13-continued

| Example | Structure | Name | MH+ | Synthesized as in Ex.: |
|---|---|---|---|---|
| 921 | 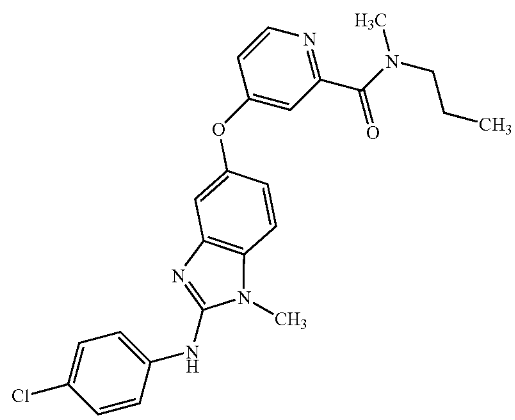 | 4-({2-[(4-chlorophenyl)amino]-1-methyl-1H-benzimidazol-5-yl}oxy)-N-methyl-N-propyl-pyridine-2-carboxamide | 450.9 | 372 |
| 922 | 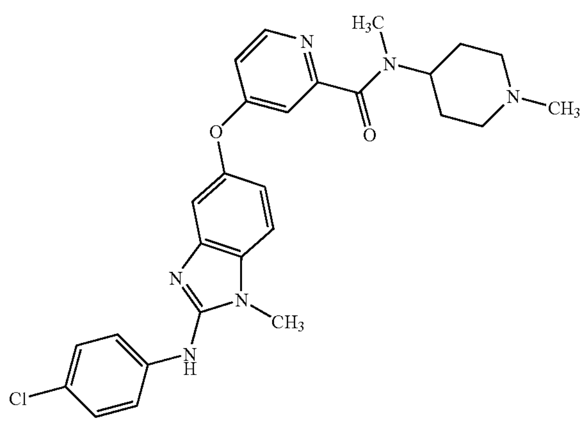 | 4-({2-[(4-chlorophenyl)amino]-1-methyl-1H-benzimidazol-5-yl}oxy)-N-methyl-N-(1-methyl-piperidin-4-yl)pyridine-2-carboxamide | 506.0 | 372 |
| 923 | 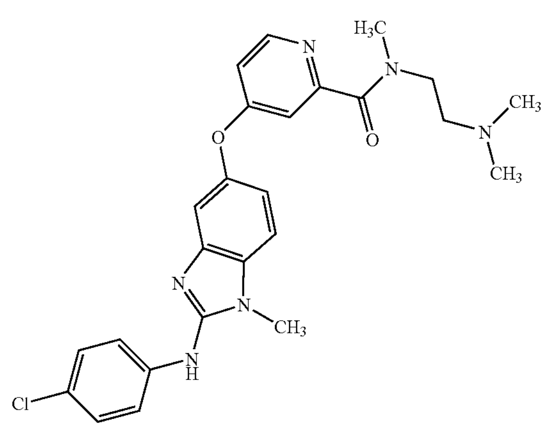 | 4-({2-[(4-chlorophenyl)amino]-1-methyl-1H-benzimidazol-5-yl}oxy)-N-[2-(dimethylamino)-ethyl]-N-methylpyridine-2-carboxamide | 480.0 | 372 |

TABLE 13-continued

| Example | Structure | Name | MH+ | Synthesized as in Ex.: |
|---|---|---|---|---|
| 924 | 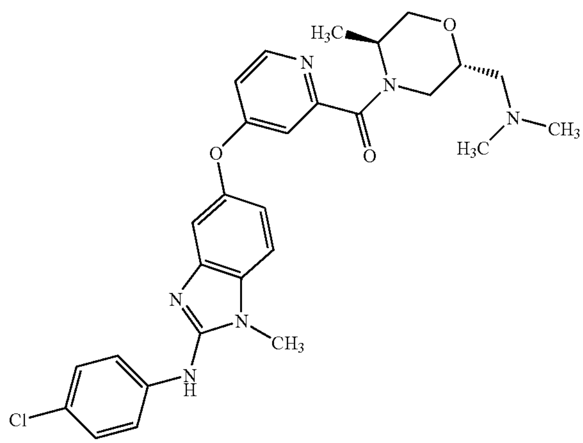 | N-(4-chlorophenyl)-5-{[2-({(2R,5S)-2-[(dimethylamino)-methyl]-5-methylmorpholin-4-yl}carbonyl)pyridin-4-yl]oxy}-1-methyl-1H-benzimidazol-2-amine | 536.0 | 372 |
| 925 | 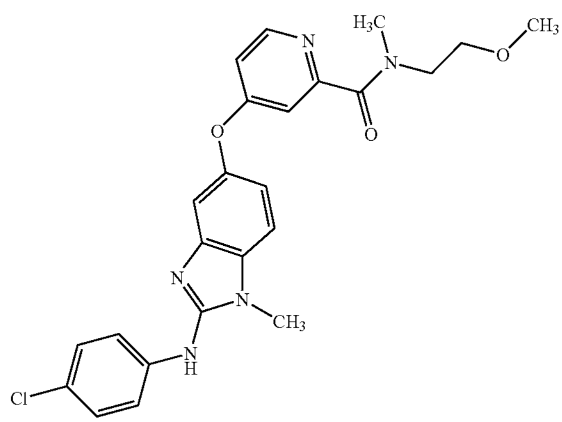 | 4-({2-[(4-chlorophenyl)amino]-1-methyl-1H-benzimidazol-5-yl}oxy)-N-methyl-N-[2-(methyloxy)ethyl]pyridine-2-carboxamide | 466.9 | 372 |
| 926 | 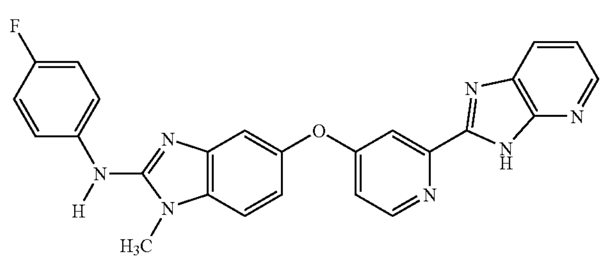 | N-(4-fluorophenyl)-5-{[2-(3H-imidazo[4,5-b]pyridin-2-yl)-pyridin-4-yl]oxy}-1-methyl-1H-benzimidazol-2-amine | 452.5 | 821 |
| 927 | 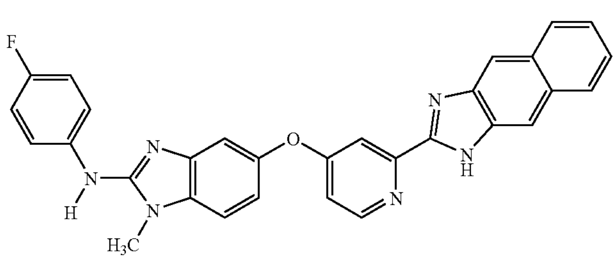 | N-(4-fluorophenyl)-1-methyl-5-{[2-(1H-naphtho[2,3-d]-imidazol-2-yl)pyridin-4-yl]oxy}-1H-benzimidazol-2-amine | 501.5 | 821 |

TABLE 13-continued

| Example | Name | MH+ | Synthesized as in Ex.: |
|---|---|---|---|
| 928 | N-(4-fluorophenyl)-1-methyl-5-{[2-(5-methyl-1H-benzimidazol-2-yl)pyridin-4-yl]oxy}-1H-benzimidazol-2-amine | 465.5 | 821 |
| 929 | N-(4-fluorophenyl)-1-methyl-5-({2-[5-(4-methylpiperazin-1-yl)-1H-benzimidazol-2-yl]pyridin-4-yl}oxy)-1H-benzimidazol-2-amide | 549.6 | 821 |
| 930 | N-(4-fluorophenyl)-1-methyl-5-{[2-(1-methyl-1H-benzimidazol-2-yl)pyridin-4-yl]oxy}-1H-benzimidazol-2-amine | 465.5 | 821 |
| 931 | 5-({2-[5-(1,1-dimethylethyl)-1H-benzimidazol-2-yl]pyridin-4-yl}oxy)-N-(4-fluorophenyl)-1-methyl-1H-benzimidazol-2-amine | 507.6 | 821 |
| 932 | N-[(1-ethylpyrrolidin-2-yl)methyl]-4-[(1-methyl-2-{[3-(trifluoromethyl)phenyl]amino}-1H-benzimidazol-5-yl)oxy]-pyridine-2-carboxamide | 539.3 | 372 |

TABLE 13-continued

| Example | Structure | Name | MH+ | Synthesized as in Ex.: |
|---|---|---|---|---|
| 933 | 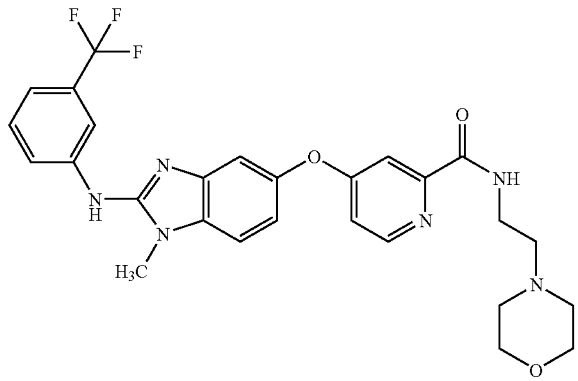 | 4-[(1-methyl-2-{[3-(trifluoromethyl)phenyl]amino}-1H-benzimidazol-5-yl)oxy]-N-(2-morpholin-4-ylethyl)pyridine-2-carboxamide | 541.3 | 372 |
| 934 | 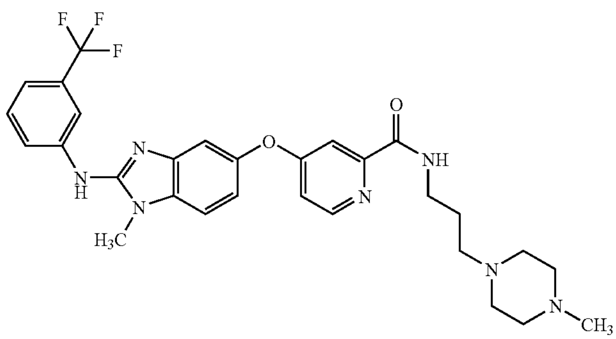 | N-[3-(4-methylpiperazin-1-yl)propyl]-4-[(1-methyl-2-{[3-(trifluoromethyl)phenyl]amino}-1H-benzimidazol-5-yl)oxy]-pyridine-2-carboxamide | 568.4 | 372 |
| 935 | 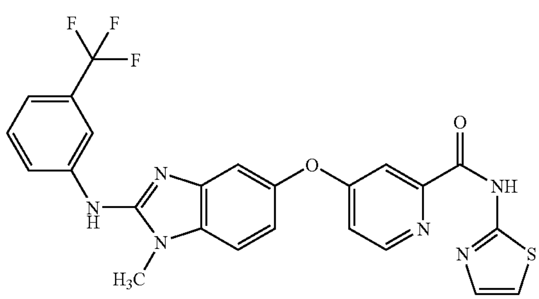 | 4-[(1-methyl-2-{[3-(trifluoromethyl)phenyl]amino}-1H-benzimidazol-5-yl)oxy]-N-1,3-thiazol-2-ylpyridine-2-carboxamide | 511.2 | 372 |
| 936 | 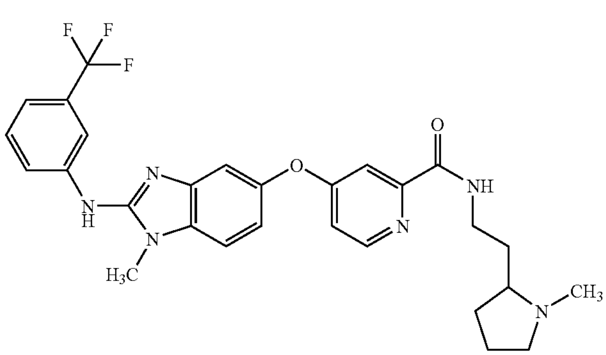 | N-[2-(1-methylpyrrolidin-2-yl)ethyl]-4-[(1-methyl-2-{[3-(trifluoromethyl)phenyl]amino}-1H-benzimidazol-5-yl)oxy]-pyridine-2-carboxamide | 539.3 | 372 |

TABLE 13-continued

| Example | Structure | Name | MH+ | Synthesized as in Ex.: |
|---|---|---|---|---|
| 937 | 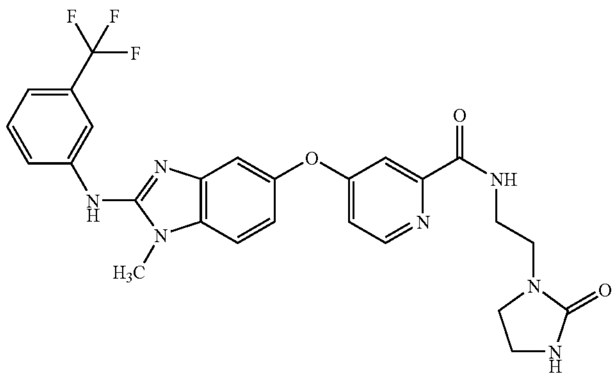 | 4-[(1-methyl-2-{[3-(trifluoromethyl)phenyl]amino}-1H-benzimidazol-5-yl)oxy]-N-[2-(2-oxoimidazolidin-1-yl)ethyl]-pyridine-2-carboxamide | 540.3 | 372 |
| 938 | 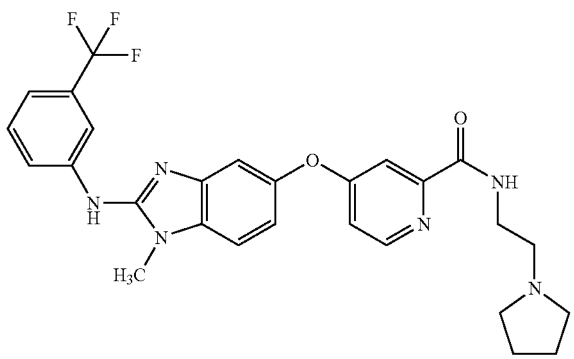 | 4-[(1-methyl-2-{[3-(trifluoromethyl)phenyl]amino}-1H-benzimidazol-5-yl)oxy]-N-(2-pyrrolidin-1-ylethyl)pyridine-2-carboxamide | 525.3 | 372 |
| 939 | 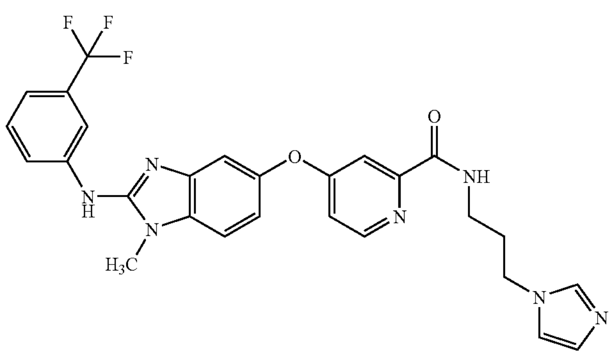 | N-[3-(1H-imidazol-1-yl)propyl]-4-[(1-methyl-2-{[3-(trifluoromethyl)phenyl]amino}-1H-benzimidazol-5-yl)oxy]pyridine-2-carboxamide | 536.3 | 372 |
| 940 | 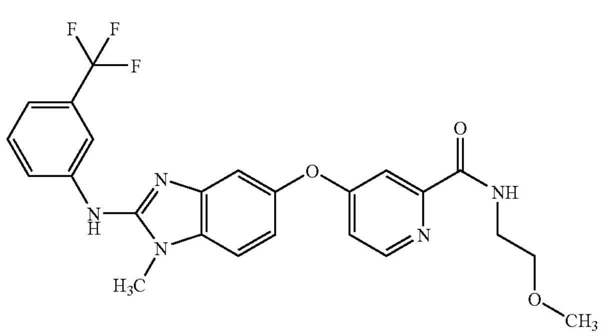 | N-[2-(methyloxy)ethyl]-4-[(1-methyl-2-{[3-(trifluoromethyl)phenyl]amino}-1H-benzimidazol-5-yl)oxy]pyridine-2-carboxamide | 486.3 | 372 |

TABLE 13-continued

| Example | Structure | Name | MH+ | Synthesized as in Ex.: |
|---------|-----------|------|-----|------------------------|
| 941 | 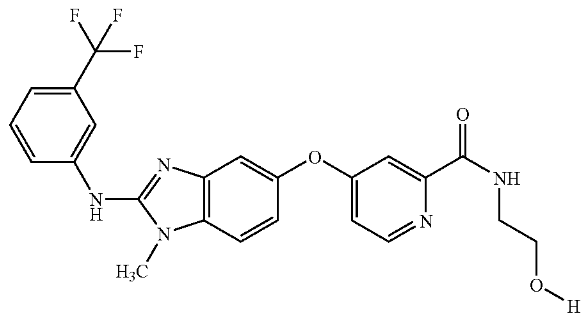 | N-(2-hydroxyethyl)-4-[(1-methyl-2-{[3-(trifluoromethyl)phenyl]amino}-1H-benzimidazol-5-yl)oxy]pyridine-2-carboxamide | 472.2 | 372 |
| 942 | 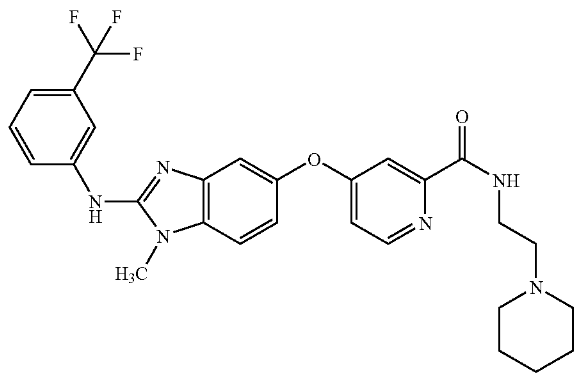 | 4-[(1-methyl-2-{[3-(trifluoromethyl)phenyl]amino}-1H-benzimidazol-5-yl)oxy]-N-(2-piperidin-1-ylethyl)pyridine-2-carboxamide | 539.3 | 372 |
| 943 | 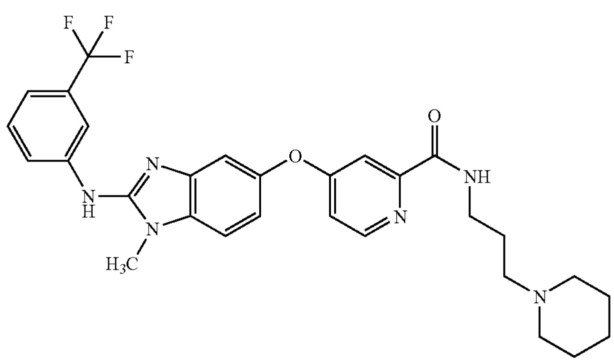 | 4-[(1-methyl-2-{[3-(trifluoromethyl)phenyl]amino}-1H-benzimidazol-5-yl)oxy]-N-(3-piperidin-1-ylpropyl)pyridine-2-carboxamide | 553.3 | 372 |
| 944 | 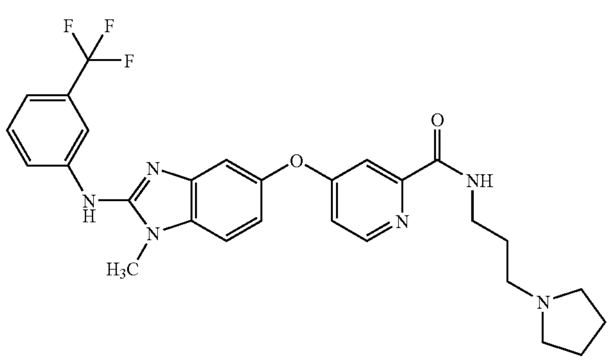 | 4-[(1-methyl-2-{[3-(trifluoromethyl)phenyl]amino}-1H-benzimidazol-5-yl)oxy]-N-(3-pyrrolidin-1-ylpropyl)pyridine-2-carboxamide | 539.3 | 372 |

TABLE 13-continued

| Example | Structure | Name | MH+ | Synthesized as in Ex.: |
|---------|-----------|------|-----|------------------------|
| 945 | 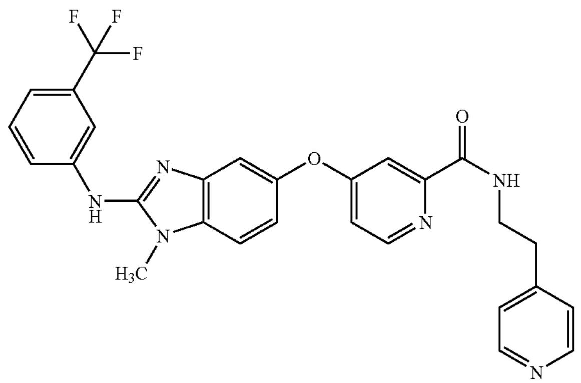 | 4-[(1-methyl-2-{[3-(trifluoromethyl)phenyl]amino}-1H-benzimidazol-5-yl)oxy]-N-(2-pyridin-4-ylethyl)pyridine-2-carboxamide | 533.3 | 372 |
| 946 | 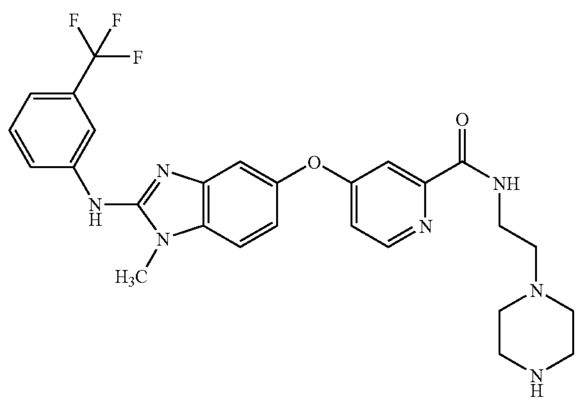 | 4-[(1-methyl-2-{[3-(trifluoromethyl)phenyl]amino}-1H-benzimidazol-5-yl)oxy]-N-(2-piperazin-1-ylethyl)pyridine-2-carboxamide | 540.2 | 372 |
| 947 | 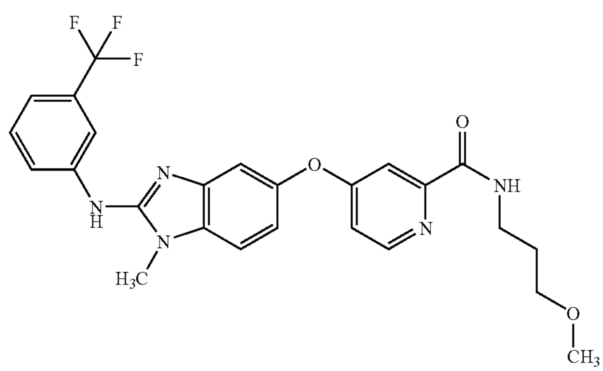 | N-[3-(methyloxy)propyl]-4-[(1-methyl-2-{[3-(trifluoromethyl)phenyl]amino}-1H-benzimidazol-5-yl)oxy]pyridine-2-carboxamide | 500.2 | 372 |
| 948 | 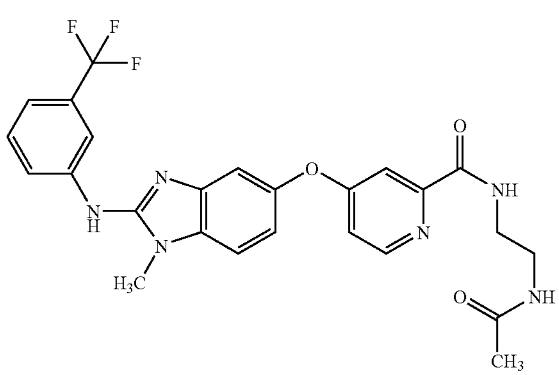 | N-[2-(acetylamino)ethyl]-4-[(1-methyl-2-{[3-(trifluoromethyl)phenyl]amino}-1H-benzimidazol-5-yl)oxy]pyridine-2-carboxamide | 513.3 | 372 |

TABLE 13-continued

| Example | Structure | Name | MH+ | Synthesized as in Ex.: |
|---|---|---|---|---|
| 949 | 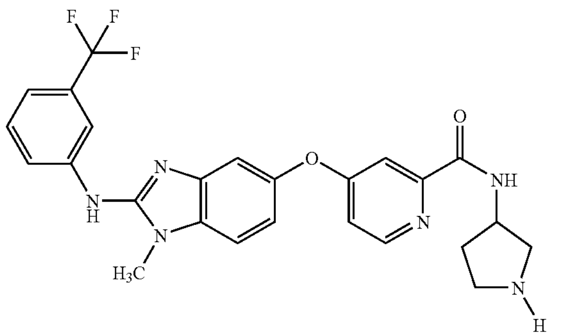 | 4-[(1-methyl-2-{[3-(trifluoromethyl)phenyl]amino}-1H-benzimidazol-5-yl)oxy]-N-pyrrolidin-3-ylpyridine-2-carboxamide | 497.2 | 372 |
| 950 | 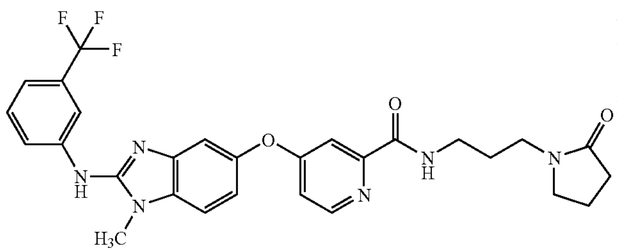 | 4-[(1-methyl-2-{[3-(trifluoromethyl)phenyl]amino}-1H-benzimidazol-5-yl)oxy]-N-[3-(2-oxopyrrolidin-1-yl)propyl]-pyridine-2-carboxamide | 553.3 | 372 |
| 951 | 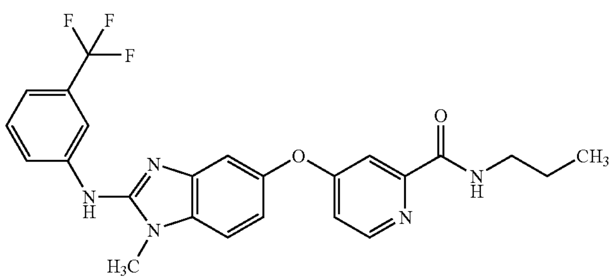 | 4-[(1-methyl-2-{[3-(trifluoromethyl)phenyl]amino}-1H-benzimidazol-5-yl)oxy]-N-propylpyridine-2-carboxamide | 470.3 | 372 |
| 952 | 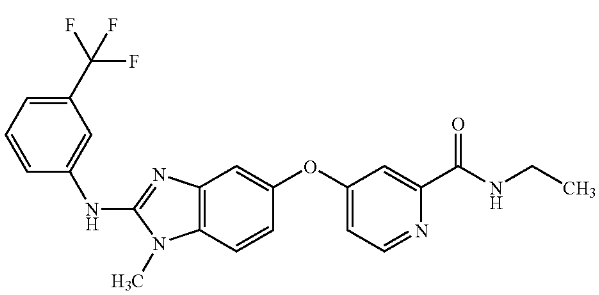 | N-ethyl-4-[(1-methyl-2-{[3-(trifluoromethyl)phenyl]amino}-1H-benzimidazol-5-yl)oxy]-pyridine-2-carboxamide | 456.2 | 372 |
| 953 | 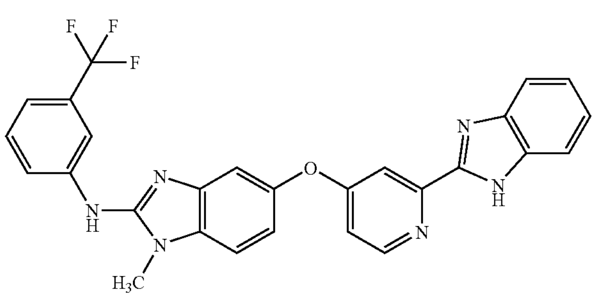 | 5-{[2-(1H-benzimidazol-2-yl)pyridin-4-yl]oxy}-1-methyl-N-[3-(trifluoromethyl)phenyl]-1H-benzimidazol-2-amine | 501.2 | 821 |

TABLE 13-continued

| Example | Structure | Name | MH+ | Synthesized as in Ex.: |
|---|---|---|---|---|
| 954 | 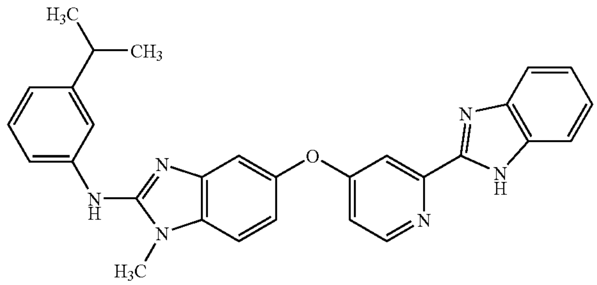 | 5-{[2-(1H-benzimidazol-2-yl)pyridin-4-yl]oxy}-1-methyl-N-[3-(1-methylethyl)phenyl]-1H-benzimidazol-2-amine | abran | 821 |
| 955 | 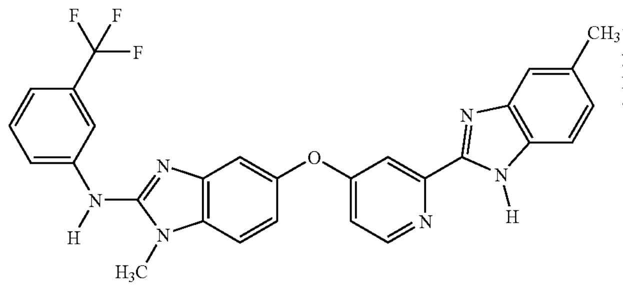 | 1-methyl-5-{[2-(5-methyl-1H-benzimidazol-2-yl)pyridin-4-yl]oxy}-N-[3-(trifluoromethyl)phenyl]-1H-benzimidazol-2-amine | 515.2 | 821 |
| 956 | 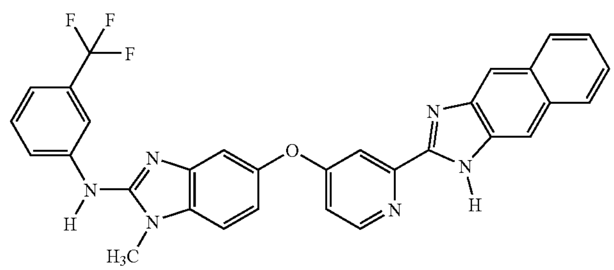 | 1-methyl-5-{[2-(1H-naphtho[2,3-d]imidazol-2-yl)-pyridin-4-yl]oxy}-N-[3-(trifluoromethyl)phenyl]-1H-benzimidazol-2-amine | 551.3 | 821 |
| 957 | 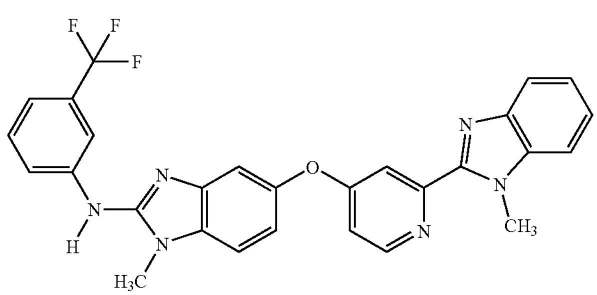 | 1-methyl-5-{[2-(1-methyl-1H-benzimidazol-2-yl)pyridin-4-yl]oxy}-N-[3-(trifluoromethyl)phenyl]-1H-benzimidazol-2-amine | 515.2 | 821 |
| 958 | 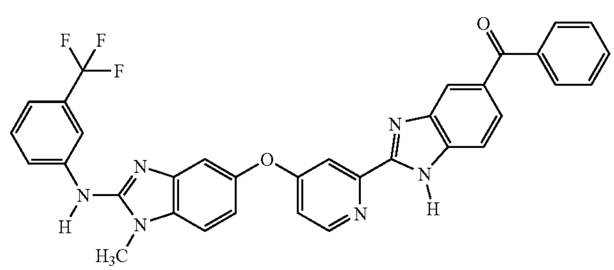 | (2-{4-[(1-methyl-2-{[3-(trifluoromethyl)phenyl]amino}-1H-benzimidazol-5-yl)oxy]-pyridin-2-yl}-1H-benzimidazol-5-yl)(phenyl)methanone | 605.2 | 821 |

TABLE 13-continued

| Example | Structure | Name | MH+ | Synthesized as in Ex.: |
|---|---|---|---|---|
| 959 | 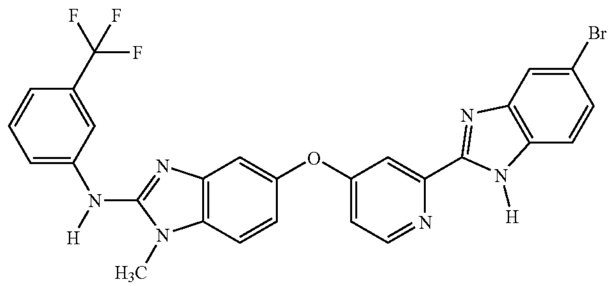 | 5-{[2-(5-bromo-1H-benzimidazol-2-yl)pyridin-4-yl]oxy}-1-methyl-N-[3-(trifluoromethyl)phenyl]-1H-benzimidazol-2-amine | 579.1 | 821 |
| 960 | 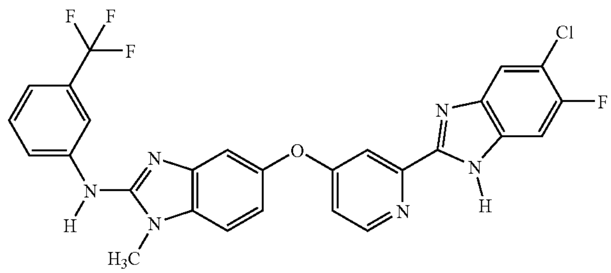 | 5-{[2-(5-chloro-6-fluoro-1H-benzimidazol-2-yl)pyridin-4-yl]oxy}-1-methyl-N-[3-(trifluoromethyl)phenyl]-1H-benzimidazol-2-amine | 553.2 | 821 |
| 961 | 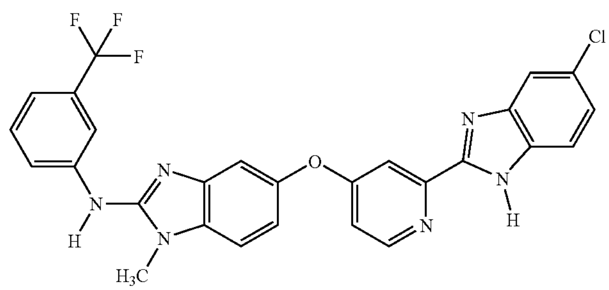 | 5-{[2-(5-chloro-1H-benzimidazol-2-yl)pyridin-4-yl]oxy}-1-methyl-N-[3-(trifluoromethyl)phenyl]-1H-benzimidazol-2-amine | 535.2 | 821 |
| 962 | 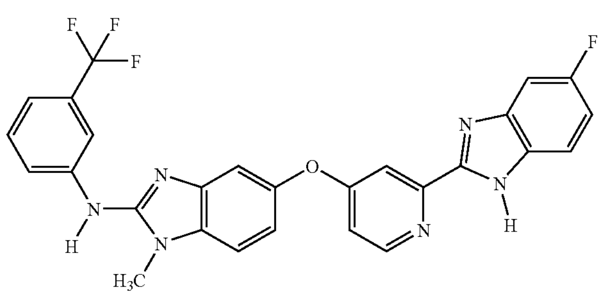 | 5-{[2-(5-fluoro-1H-benzimidazol-2-yl)pyridin-4-yl]oxy}-1-methyl-N-[3-(trifluoromethyl)phenyl]-1H-benzimidazol-2-amine | 519.4 | 821 |
| 963 | 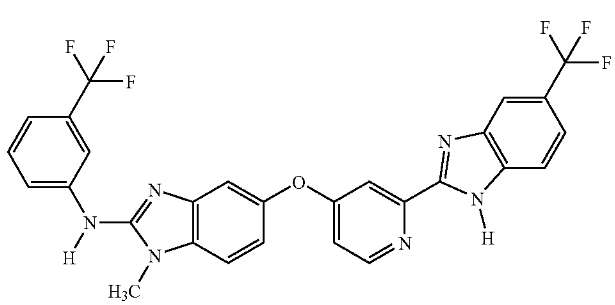 | 1-methyl-5-({2-[5-(trifluoromethyl)-1H-benzimidazol-2-yl]pyridin-4-yl}oxy)-N-[3-(trifluoromethyl)phenyl]-1H-benzimidazol-2-amine | 569.2 | 821 |

TABLE 13-continued

| Example | Structure | Name | MH+ | Synthesized as in Ex.: |
|---|---|---|---|---|
| 964 | 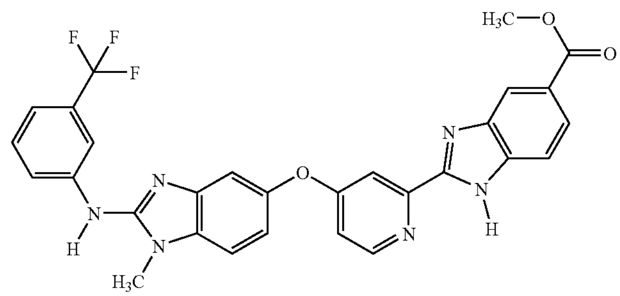 | methyl 2-{4-[(1-methyl-2-{[3-(trifluoromethyl)phenyl]amino}-1H-benzimidazol-5-yl)oxy]pyridin-2-yl}-1H-benzimidazole-5-carboxylate | 559.2 | 821 |
| 965 | 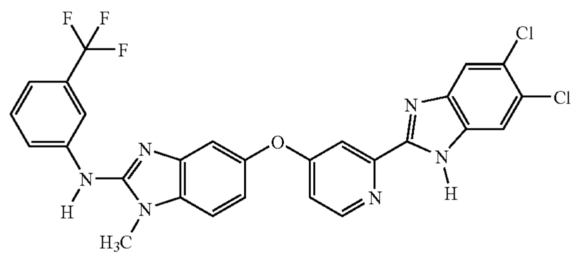 | 5-{[2-(5,6-dichloro-1H-benzimidazol-2-yl)pyridin-4-yl]oxy}-1-methyl-N-[3-trifluoromethyl)phenyl]-1H-benzimidazol-2-amine | 569.1 | 821 |
| 966 | 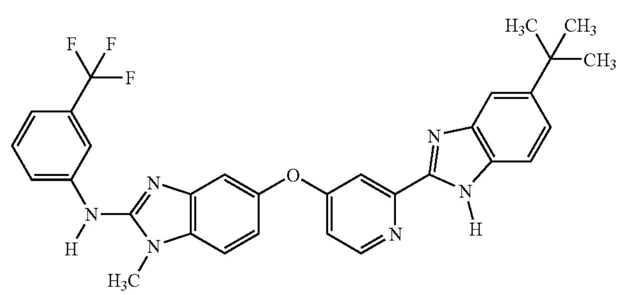 | 5-({2-[5-(1,1-dimethylethyl)-1H-benzimidazol-2-yl]pyridin-4-yl}oxy)-1-methyl-N-[3-(trifluoromethyl)phenyl]-1H-benzimidazol-2-amine | 557.3 | 821 |
| 967 | 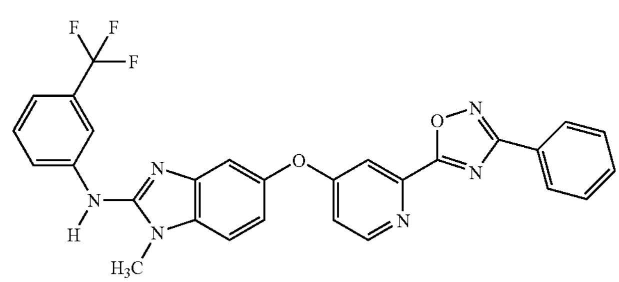 | 1-methyl-5-{[2-(3-phenyl-1,2,4-oxadiazol-5-yl)pyridin-4-yl]oxy}-N-[3-(trifluoromethyl)phenyl]-1H-benzimidazol-2-amine | 529.2 | 821 |
| 968 | 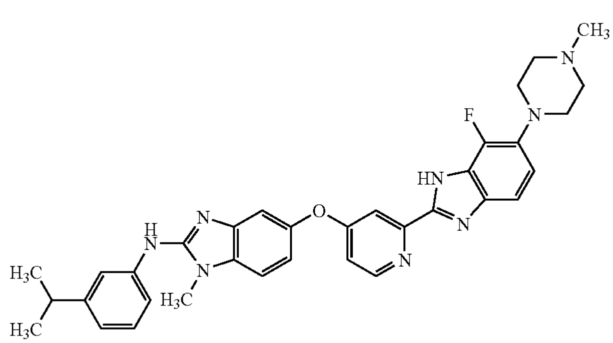 | 5-({2-[7-fluoro-6-(4-methyl-piperazin-1-yl)-1H-benzimidazol-2-yl]pyridin-4-yl}oxy)-1-methyl-N-[3-(1-methylethyl)phenyl]-1H-benzimidazol-2-amine | 591.3 | 821 |

TABLE 13-continued

| Example | Structure | Name | MH+ | Synthesized as in Ex.: |
|---|---|---|---|---|
| 969 | 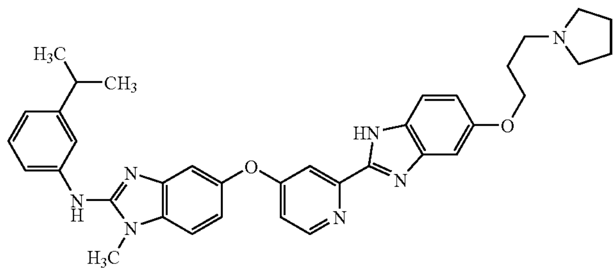 | 1-methyl-N-[3-(1-methylethyl)phenyl]-5-[(2-{5-[(3-pyrrolidin-1-ylpropyl)oxy]-1H-benzimidazol-2-yl}pyridin-4-yl)oxy]-1H-benzimidazol-2-amine | 602.7 | 821 |
| 970 | 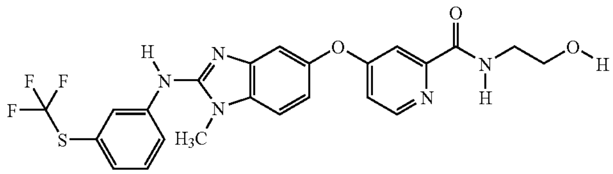 | N-(2-hydroxyethyl)-4-{[1-methyl-2-({3-[(trifluoromethyl)thio]phenyl}amino)-1H-benzimidazol-5-yl]oxy}-pyridine-2-carboxamide | 504.1 | 820 |
| 971 | 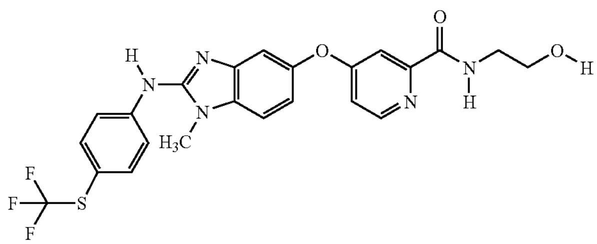 | N-(2-hydroxyethyl)-4-{[1-methyl-2-({4-[(trifluoromethyl)thio]phenyl}amino)-1H-benzimidazol-5-yl]oxy}-pyridine-2-carboxamide | 504.1 | 820 |
| 972 | 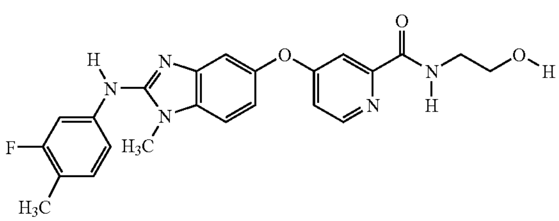 | 4-({2-[(3-fluoro-4-methylphenyl)amino]-1-methyl-1H-benzimidazol-5-yl}oxy)-N-(2-hydroxyethyl)pyridine-2-carboxamide | 436.2 | 820 |
| 973 | 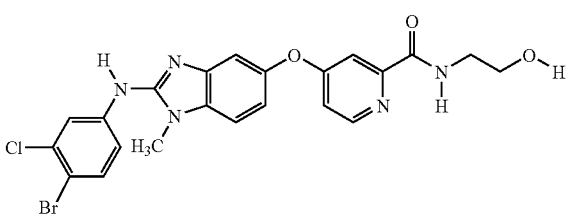 | 4-({2-[(4-bromo-3-chlorophenyl)amino]-1-methyl-1H-benzimidazol-5-yl}oxy)-N-(2-hydroxyethyl)pyridine-2-carboxamide | 516 | 820 |
| 974 | 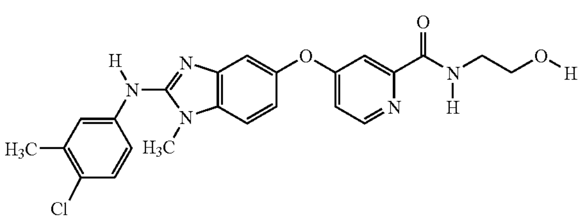 | 4-({2-[(4-chloro-3-methylphenyl)amino]-1-methyl-1H-benzimidazol-5-yl}oxy)-N-(2-hydroxyethyl)pyridine-2-carboxamide | 452.2 | 820 |

TABLE 13-continued

| Example | Structure | Name | MH+ | Synthesized as in Ex.: |
|---|---|---|---|---|
| 975 | 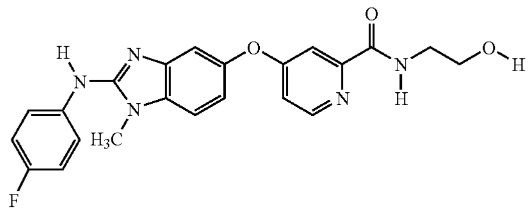 | 4-({2-[(4-fluorophenyl)amino]-1-methyl-1H-benzimidazol-5-yl}oxy)-N-(2-hydroxyethyl)-pyridine-2-carboxamide | 422.2 | 820 |
| 976 | 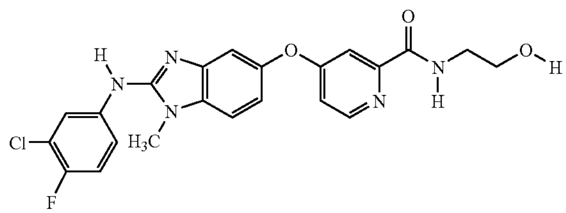 | 4-({2-[(3-chloro-4-fluoro-phenyl)amino]-1-methyl-1H-benzimidazol-5-yl}oxy)-N-(2-hydroxyethyl)pyridine-2-carboxamide | 456.2 | 820 |
| 977 | 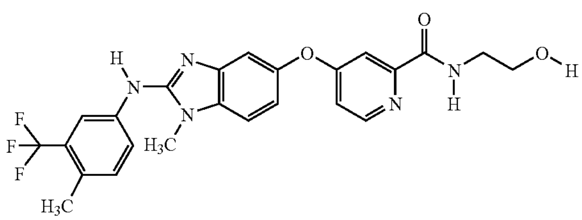 | N-(2-hydroxyethyl)-4-[(1-methyl-2-{[4-methyl-3-(trifluoromethyl)phenyl]amino}-1H-benzimidazol-5-yl)oxy]-pyridine-2-carboxamide | 486.2 | 820 |
| 978 | 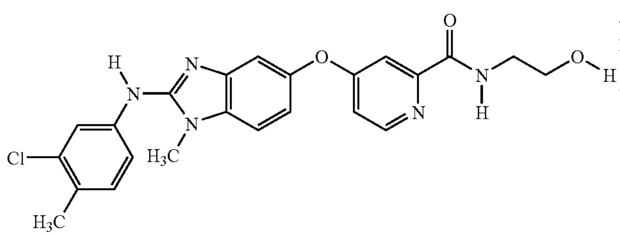 | 4-({2-[(3-chloro-4-methyl-phenyl)amino]-1-methyl-1H-benzimidazol-5-yl}oxy)-N-(2-hydroxyethyl)pyridine-2-carboxamide | 452.2 | 820 |
| 979 | 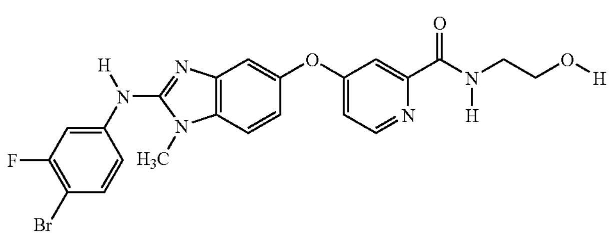 | 4-({2-[(4-bromo-3-fluoro-phenyl)amino]-1-methyl-1H-benzimidazol-5-yl}oxy)-N-(2-hydroxyethyl)pyridine-2-carboxamide | 502.1 | 820 |
| 980 | 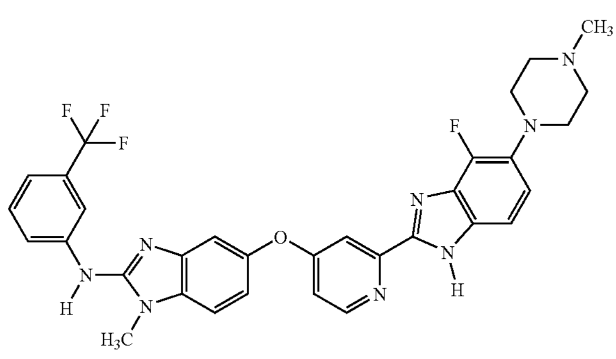 | 5-({2-[4-fluoro-5-(4-methyl-piperazin-1-yl)-1H-benz-imidazol-2-yl]pyridin-4-yl}oxy)-1-methyl-N-[3-(trifluoromethyl)-phenyl]-1H-benzimidazol-2-amine | 428.2 | 821 |

TABLE 13-continued

| Example | Structure | Name | MH+ | Synthesized as in Ex.: |
|---|---|---|---|---|
| 981 | 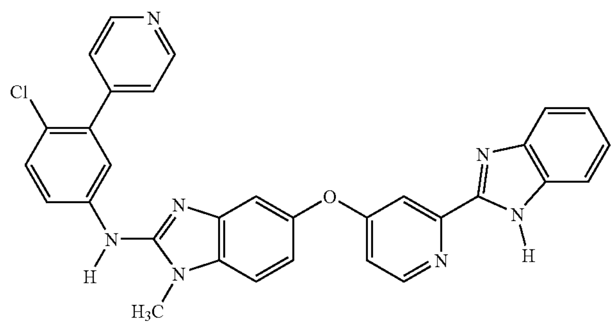 | 5-{[2-(1H-benzimidazol-2-yl)-pyridin-4-yl]oxy}-N-(4-chloro-3-pyridin-4-ylphenyl)-1-methyl-1H-benzimidazol-2-amine | 545.0 | 821 |
| 982 | 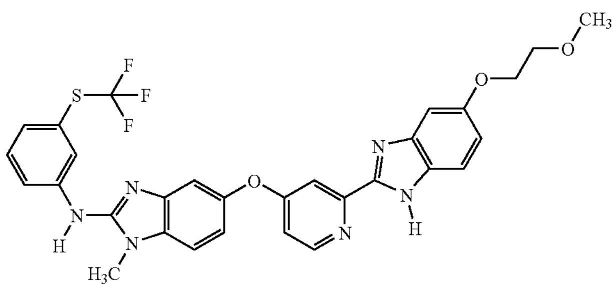 | 1-methyl-5-{[2-(5-{[2-(methyl-oxy)ethyl]oxy}-1H-benz-imidazol-2-yl)pyridin-4-yl]oxy}-N-{3-[(trifluoromethyl)thio]-phenyl}-1H-benzimidazol-2-amine | 607.2 | 821 |
| 983 | 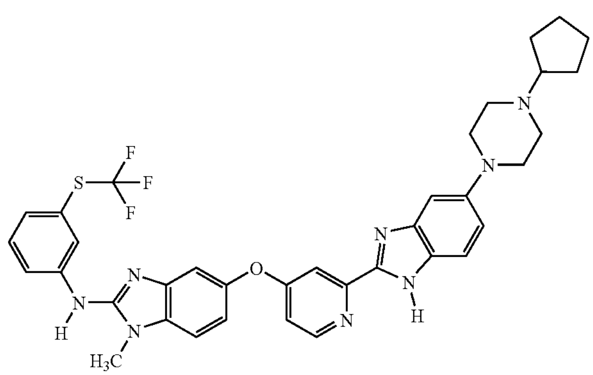 | 5-({2-[5-(4-cyclopentyl-piperazin-1-yl)-1H-benz-imidazol-2-yl]pyridin-4-yl}oxy)-1-methyl-N-{3-{(trifluoro-methyl)thio]phenyl}-1H-benzimidazol-2-amine | 685.3 | 821 |
| 984 | 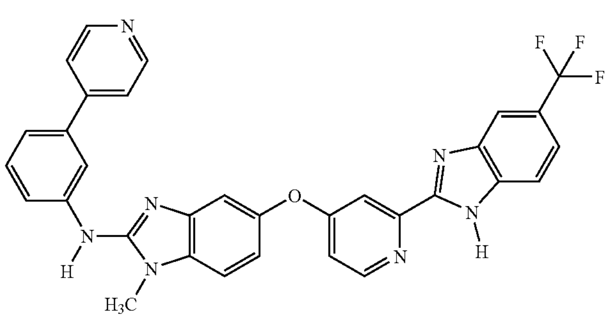 | 1-methyl-N-(3-pyridin-4-yl-phenyl)-5-({2-[5-(trifluoro-methyl)-1H-benzimidazol-2-yl]pyridin-4-yl}oxy)-1H-benzimidazol-2-amine | 578.3 | 821 |

Example 985

Synthesis of Oxime Series: 4-[2-(4-Bromo-phenylamino)-1-methyl-1H-benzoimidazol-5-yloxy]-pyridine-2-carbaldehyde oxime Step 1. Synthesis of [4-(4-Methylamino-3-nitro-phenoxy)-pyridin-2-yl]-methanol

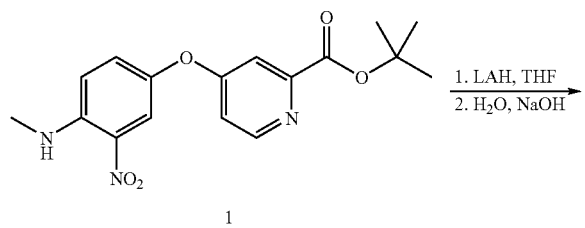

A flame dried 500 mL three-necked round bottom flask purged with N₂ was charged with LAH (2.32 g, 58.0 mmol) and dry THF (60 mL). The resulting suspension was cooled to 0° C. and a suspension of t-butyl ester 1 (10.0 g, 29.0 mmol) in dry THF (60 mL) was slowly added while keeping the internal reaction temperature under 5° C. The reaction was stirred at 0° C. for 30 min then at rt for 30 min. After the reaction was judged complete, the mixture was treated with successive dropwise addition of water (2.3 mL), 10% NaOH (2.3 mL), and water (7.2 mL). The resulting suspension was filtered through Celite, washed with ethyl acetate and methanol, and the collected organics concentrated. The crude product was absorbed onto silica gel and purified by flash chromatography (97:3 CH$_2$Cl$_2$/MeOH) to give 2 as an orange solid: $^1$H NMR (300 MHz, CDCl$_3$) δ 8.40 (d, J=5.5 Hz, 1H), 8.05 (br s, 1H), 7.96 (d, J=2.75 Hz, 1H), 7.29 (d, J=2.75 Hz, 1H), 6.92 (d, J=9.35 Hz, 1H), 6.75 (m, 2H), 4.68 (s, 2H), 3.07 (d, J=5.23 Hz, 3H).

Step 2. Synthesis of 4-(4-Methylamino-3-nitro-phenoxy)-pyridine-2-carbaldehyde

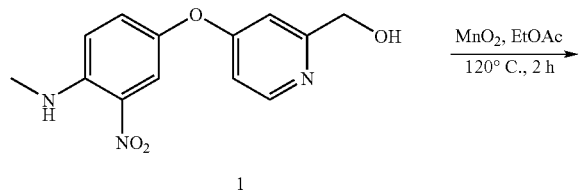

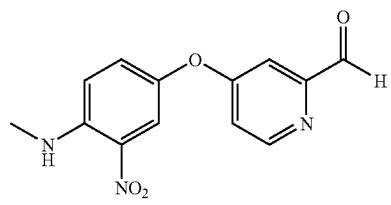

A 250 mL reaction tube was charged with benzyl alcohol 1 (1.0 g, 3.6 mmol), MnO$_2$ (4.7 g, 54 mmol) and EtOAc (20 mL). The reaction tube was sealed was heated to 120° C. with stirring for 2 h. The reaction was allowed to cool to rt, then filtered through Celite and washed successively with EtOAc, MeOH, and EtOH. The combine organics were concentrated to give 936 mg (3.4 mmol, 94%) of 2 as an orange solid: $^1$H NMR (300 MHz, CDCl$_3$) δ 10.01 (s, 1H), 8.64 (d, J=5.5 Hz, 1H), 8.09 (br s, 1H), 7.96 (d, J=2.75 Hz, 1H), 7.37 (d, J=2.48 Hz, 1H), 7.29 (d, J=2.75 Hz, 1H), 7.08 (dd, J=2.47, 5.5 Hz, 1H), 6.94 (d, J=9.35 Hz, 1H), 3.08 (d, J=5.23 Hz, 3H).

Step 3. Synthesis of 4-(4-Methylamino-3-nitro-phenoxy)-pyridine-2-carbaldehyde oxime

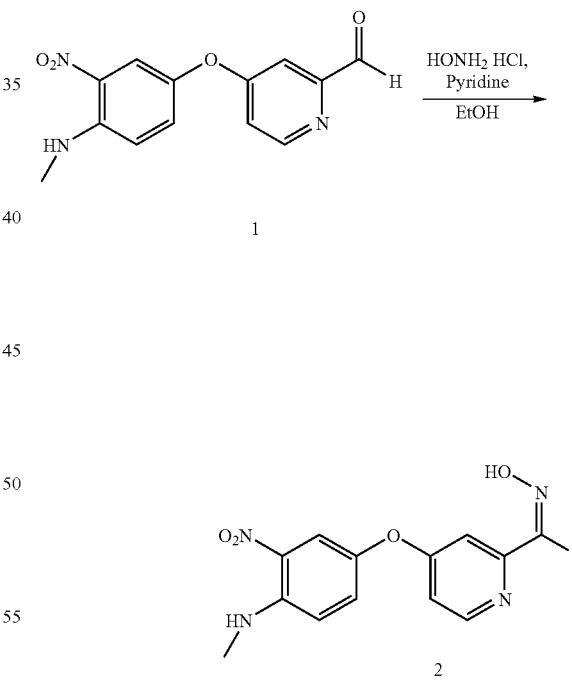

A 50 mL round bottom flask was charged with 1 (680 mg, 2.5 mmol), hydroxylamine HCl (191 mg, 2.75 mmol), pyridine (0.25 mL, 3.0 mmol) and ethanol (10 mL). The resulting reaction mixture was stirred at rt overnight. The crude product was concentrated, absorbed onto silica gel, and purified by flash chromatography (97:3 CH$_2$Cl$_2$/MeOH to give 2 as an orange solid. LCMS m/z 289.2 (MH⁺), t$_R$=2.06 min.

Step 4. Synthesis of 4-(3-Amino-4-methylamino-phenoxy)-pyridine-2-carbaldehyde oxime

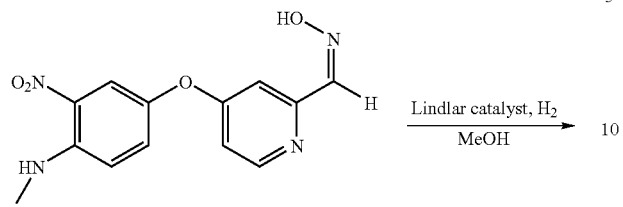

A reaction tube was charged with suspension of 1 (330 mg, 1.15 mmol) and Lindlar catalyst (245 mg, 10 mol %) in methanol (5 mL), sealed, and placed on a Parr shaker. The reaction was pressurized with $H_2$ (60 psi) and maintained for 1 h. The reaction was filtered through Celite and the remaining solids were washed with MeOH. The combined organics were concentrated to give 2 as a brown semi-solid which was taken on without further purification.

Step 5. Synthesis of 4-[2-(4-Bromo-phenylamino)-1-methyl-1H-benzoimidazol-5-yloxy]-pyridine-2-carbaldehyde oxime

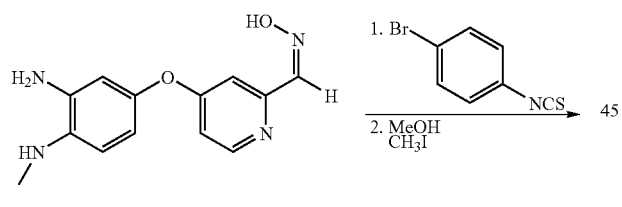

A 5 mL round bottom flask was charged with 4-bromophenylisothiocyanate (54 mg, 0.25 mmol), diamine 1 (65 mg, 0.25 mmol), and MeOH (1 mL). The resulting reaction was maintained at rt overnight. Methyl iodide (20 μL, 0.33 mmol) was added to the reaction and stirred overnight. The reaction was concentrated and the resulting residue was purified by reverse-phase HPLC. LCMS m/z 438.1 (MH$^+$), $t_R$=1.87 min.

Example 986

Synthesis of O-methyl-oxime Series: 4-[1-Methyl-2-(4-trifluoromethylsulfanyl-phenylamino)-1H-benzoimidazol-5-yloxy]-pyridine-2-carbaldehyde O-methyl-oxime

Step 1. Synthesis of 4-(4-Methylamino-3-nitro-phenoxy)-pyridine-2-carbaldehyde O-methyl-oxime

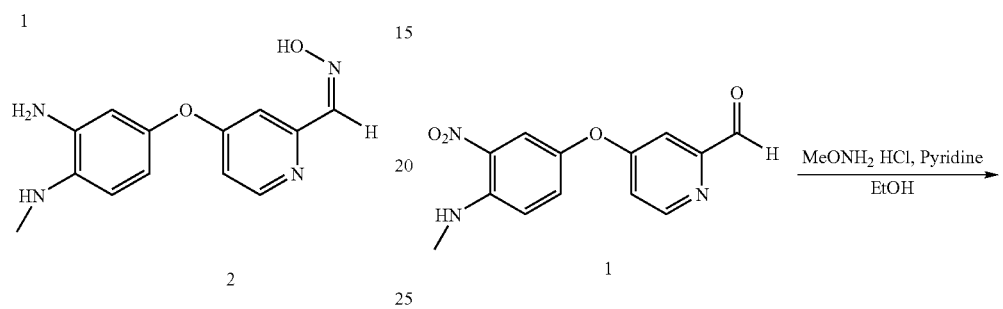

A 25 mL round bottom flask was charged with a suspension of 1 (600 mg, 2.2 mmol), methoxylamine HCl (202 mg, 2.42 mmol), and pyridine (0.22 mL, 2.6 mmol) in ethanol (9 mL). The resulting reaction mixture was stirred at rt overnight. The crude product was concentrated, absorbed onto silica gel, and purified by flash chromatography (97:3 $CH_2Cl_2$/MeOH) to give 2 as an orange solid. LCMS m/z 303.2 (MH$^+$), $t_R$=2.40 mm.

Step 2. Synthesis of 4-(3-Amino-4-methylamino-phenoxy)-pyridine-2-carbaldehyde O-methyl-oxime

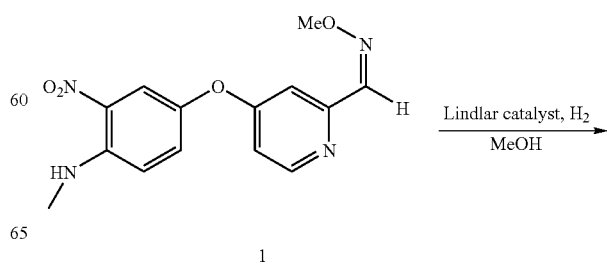

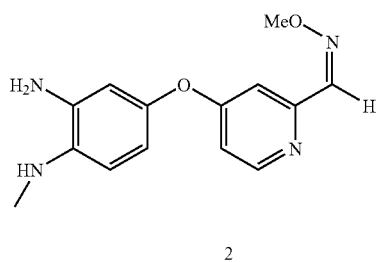

2

A reaction tube was charged with a suspension of 1 (270 mg, 0.9 mmol) and Lindlar catalyst (192 mg, 10 mol %) in methanol (5 mL), and was then placed on a Parr shaker. The was reaction pressurized with $H_2$ (60 psi) and maintained for 1 h. The reaction was filtered through Celite and the remained solids were washed with methanol. The combined organics were concentrated to give 2 as a brown semi-solid which was carried forward without further purification LCMS m/z 273.3 (MH$^+$), $t_R$=1.56 min.

Step 3. Synthesis of 4-[1-Methyl-2-(4-trifluoromethylsulfanyl-phenylamino)-1H-benzoimidazol-5-yloxy]-pyridine-2-carbaldehyde O-methyl-oxime

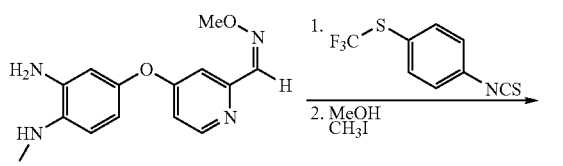

1

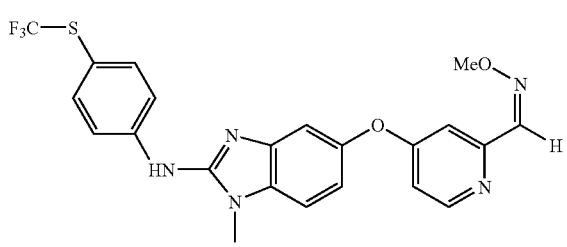

2

A 5 mL round bottom flask was charged with 4-trifluoromethylthio-phenylisothiocyanate (24 mg, 0.1 mmol), diamine 1 (27 mg, 0.1 mmol), and MeOH (0.5 mL). The reaction was maintained at rt overnight, after which methyl iodide (8 µL, 0.13 mmol) was added. After 16 h, the reaction was concentrated and the resulting residue was purified by reverse-phase HPLC. LCMS m/z 474.3 (MH$^+$), $t_R$=2.42 min.

Example 987

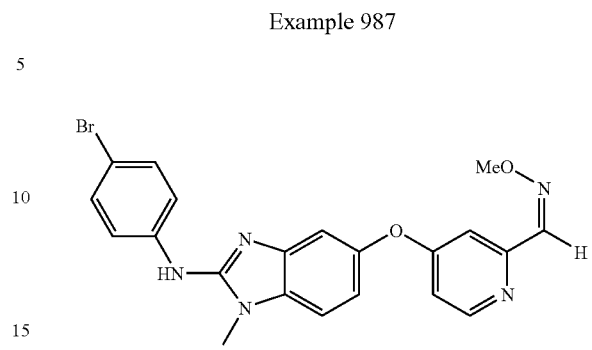

Synthesized as described in Example 986 step 3 using 4-bromophenyl isothiocyanate. LCMS m/z 402.4 (MH$^+$), $t_R$=2.15 min.

Example 988

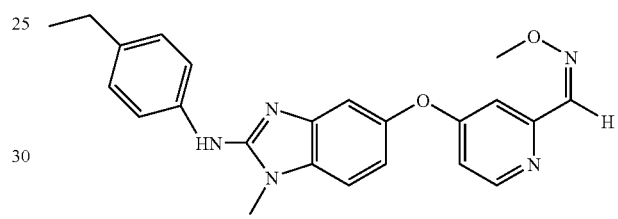

Synthesized as described in Example 986 step 3 using 4-ethylphenylisothiocyanate. LCMS m/z 402.4 (MH$^+$), $t_R$=2.15 min.

Example 989

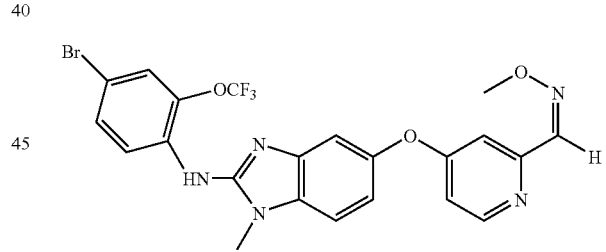

Synthesized as described in Example 986 step 3 using 4-bromo-2-trifluoro-methoxyphenylisothiocyanate. LCMS m/z 536.2 (MH$^+$), $t_R$=2.38 min.

Example 990

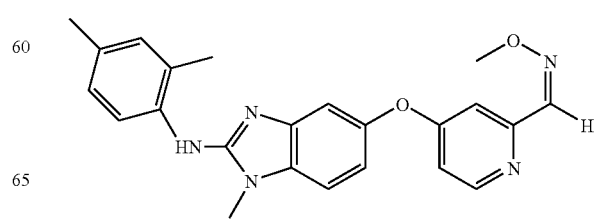

Synthesized as described in Example 986 step 3 using 2,4-dimethylphenylisothiocyanate. LCMS m/z 402, (MH+), $t_R$=2.07 min.

Example 991

Synthesis of Benzyl Alcohol Series: {4-[2-(4-Chloro-phenylamino)-1-methyl-1H-benzoimidazol-5-yloxy]-pyridin-2-yl}-methanol Step 1. Synthesis of [4-(3-Amino-4-methylamino-phenoxy)-pyridin-2-yl]-methanol

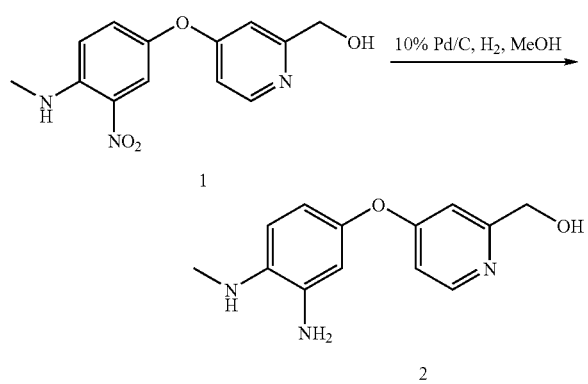

A suspension of nitroaniline 1 (550 mg, 2.0 mmol) in methanol was sparged with $N_2$ for 20 min after which 10% Pd/C (106 mg, 0.1 mmol) was added. The reaction was charged with $H_2$ and maintained under a $H_2$ atmosphere overnight at rt. The reaction was sparged with $N_2$ and filtered through Celite. The collected solids were washed with EtOAc (3×50 mL), and the combined organic layers were dried ($MgSO_4$) and concentrated to afford 2, which was taken on without further purification.

Step 2. Synthesis of {4-[2-(4-Chloro-phenylamino)-1-methyl-1H-benzoimidazol-5-yloxy]-pyridin-2-yl}-methanol

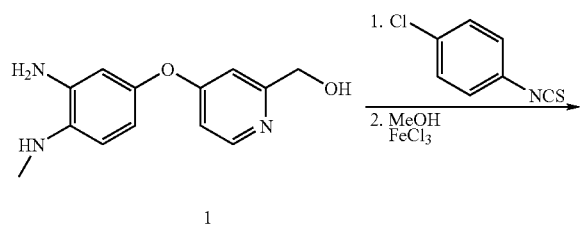

A 5 mL round bottom flask was charged with 4-chlorophenylisothiocyanate (34 g, 0.2 mmol), diamine 1 (49 mg, 0.2 mmol), and MeOH (1 mL) and the resulting reaction was maintained at rt overnight. Ferric chloride (16 mg, 0.1 mmol) was added and the red reaction mixture was stirred overnight. The reaction was partitioned with EtOAc and water, the layers were separated and the aqueous phase was neutralized (pH=7) with saturated aqueous $Na_2CO_3$ solution. The aqueous phase was extracted with EtOAc. The combined organic layers were washed with brine, dried, and concentrated to give a brown solid. The reaction was concentrated and the resulting residue purified on reverse-phase HPLC. LCMS m/z 381.3 (MH+), $t_R$=2.27 min.

Example 992

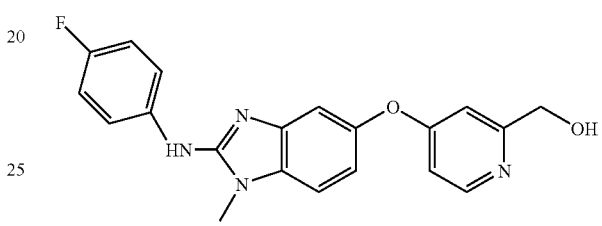

Synthesized as described in Example 1058 step 2 using 4-fluorophenylisothiocyanate. LCMS m/z 365.4 (MH+), $t_R$=2.04 min.

Example 993

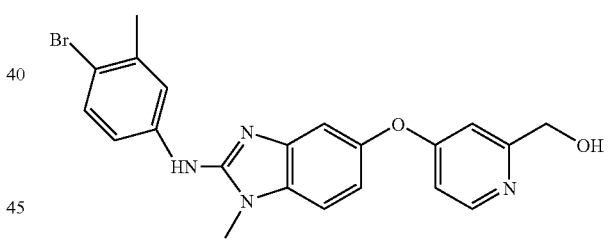

Synthesized as described in Example 991 step 2 using 4-bromo-3-methylphenylisothiocyanate. LCMS m/z 439.3 (MH+), $t_R$=2.79 min.

Example 994

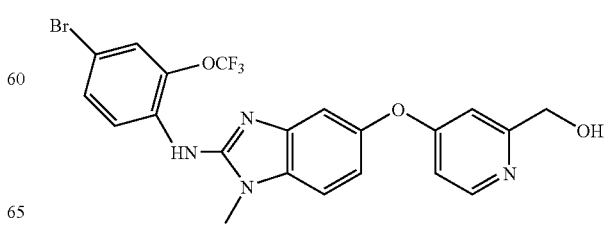

Synthesized as described in Example 991 step 2 using 4-bromo-2-trifluoromethoxyphenylisothiocyanate. LCMS m/z 511.3 (MH+), $t_R$=3.08 min.

Example 995

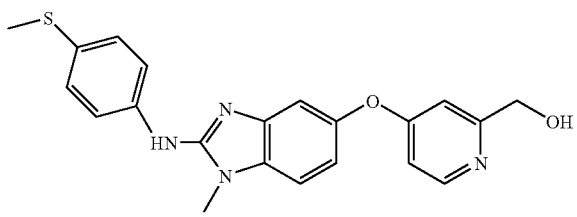

Synthesized as described in Example 991 step 2 using 4-methylthiophenylisothiocyanate. LCMS m/z 393.4 (MH+), $t_R$=2.46 min.

Example 995

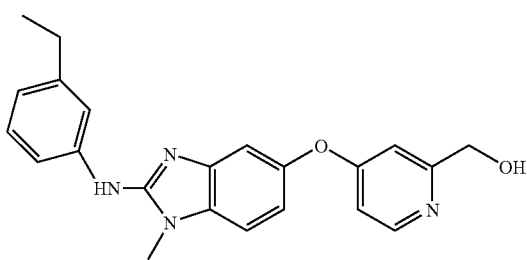

Synthesized as described in Example 991 step 2 using 3-ethylphenylisothiocyanate. LCMS m/z 375.4 (MH+), $t_R$=2.57 min.

Example 996

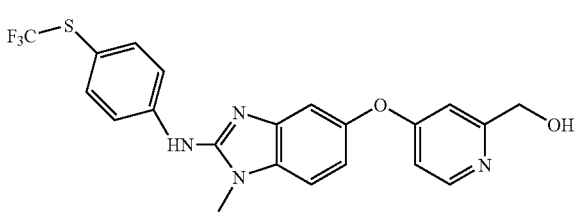

Example 997

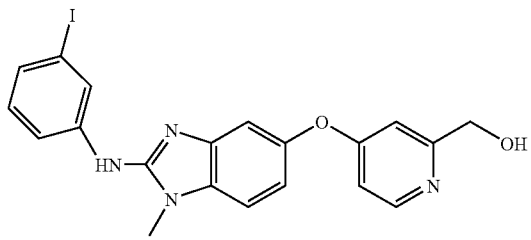

Synthesized as described in Example 991 step 2 using 3-iodophenylisothiocyanate. LCMS m/z 473.2 (MH+), $t_R$=2.57 min.

Example 998

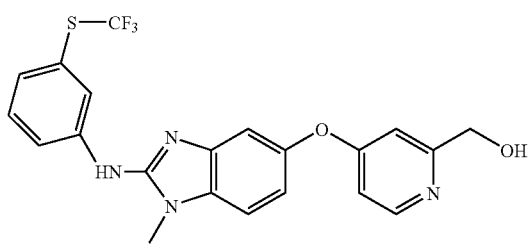

Synthesized as described in Example 991 step 2 using 3-trifluoromethylthiophenylisothiocyanate. LCMS m/z 447.3 (MH+), $t_R$=3.08 min.

Example 999

4-[2-(4-Bromo-phenylamino)-1-methyl-1H-benzoimidazol-5-yloxy]-pyridine-2-carboxylic acid phenylamide Procedure for Synthesis of Anilide Series (4-Br and 3-iPr West-Ends)

Synthesis of 4-[2-(4-Bromo-phenylamino)-1-methyl-1H-benzoimidazol-5-yloxy]-pyridine-2-carboxylic acid phenylamide

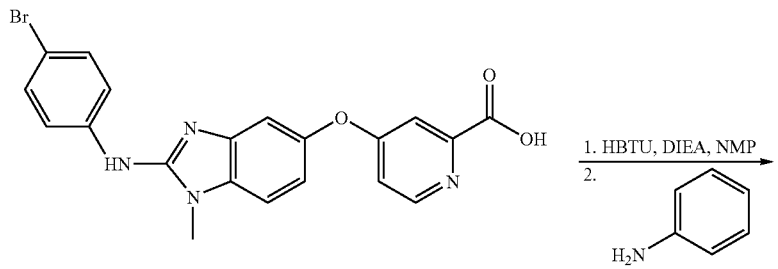

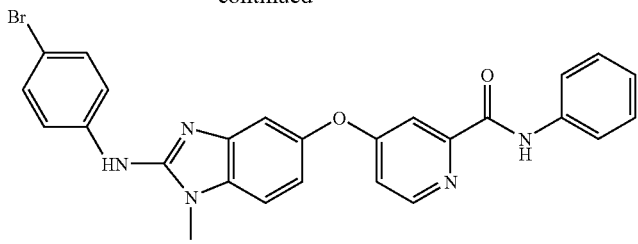

2

A suspension of 1 (44 mg, 0.1 mmol), HBTU (46 mg, 0.12 mmol), and DIEA (43 uL, 0.25 mmol) in NMP (0.5 mL) was shaken for 30 min at rt. Aniline was added and the reaction was shaken overnight. The crude product purified on reverse-phase HPLC. LCMS m/z 515.2 (MH$^+$), $t_R$=2.75 min.

Example 1000

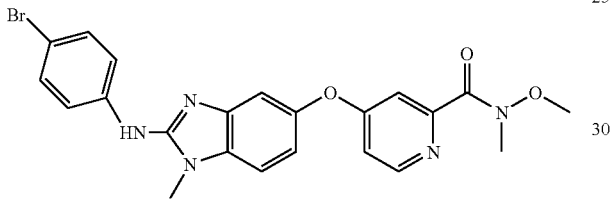

Synthesized as described in Example 999 using N,O-dimethylhydroxylamine HCl. LCMS m/z 483.3 (MH$^+$), $t_R$=2.07 min.

Example 1001

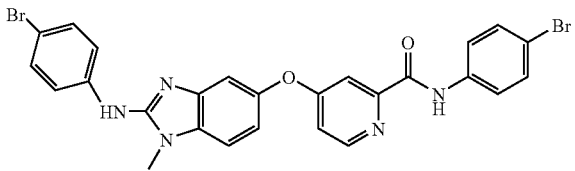

Synthesized as described in Example 999 using 4-bromoaniline. LCMS m/z 594.0 (MH$^+$), $t_R$=5.39 min.

Example 1002

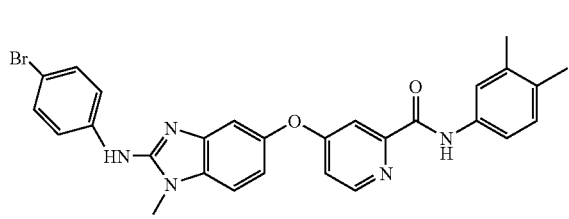

Synthesized as described in Example 999 using 3,4-dimethylaniline. LCMS m/z 543.2 (MH$^+$), $t_R$=5.39 min.

Example 1003

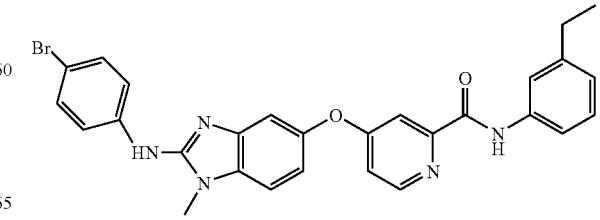

Synthesized as described in Example 999 using 3-trifluoromethylaniline. LCMS m/z 583.1 (MH$^+$), $t_R$=3.12 min.

Example 1004

Synthesized as described in Example 999 using 3-chloroaniline. LCMS m/z 550.1 (MH$^+$), $t_R$=5.28 min.

Example 1005

Synthesized as described in Example 999 using 3-ethylaniline. LCMS m/z 543.2 (MH⁺), $t_R$=3.16 min.

Example 1006

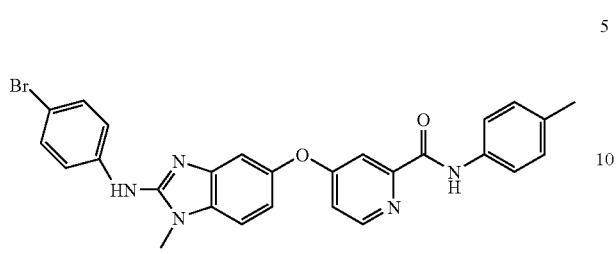

Synthesized as described in Example 1067 using 4-methylaniline. LCMS m/z 529.2 (MH⁺), $t_R$=5.15 min.

Example 1007

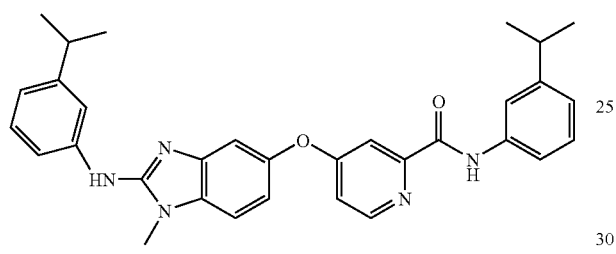

Synthesized as described in Example 999 using 3-isopropylaniline. LCMS m/z 520.3 (MH⁺), $t_R$=5.98 min.

Example 1008

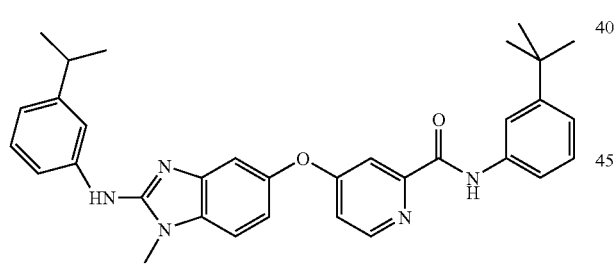

Synthesized as described in Example 999 using 3-tert-butylaniline. LCMS m/z 534.3 (MH⁺), $t_R$=3.32 min.

Example 1009

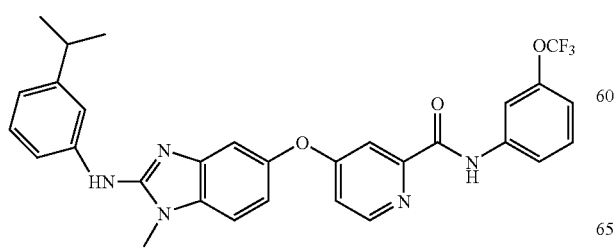

Synthesized as described in Example 999 using 3-trifluoromethoxyaniline. LCMS m/z 562.2 (MH⁺), $t_R$=3.15 min.

Example 1010

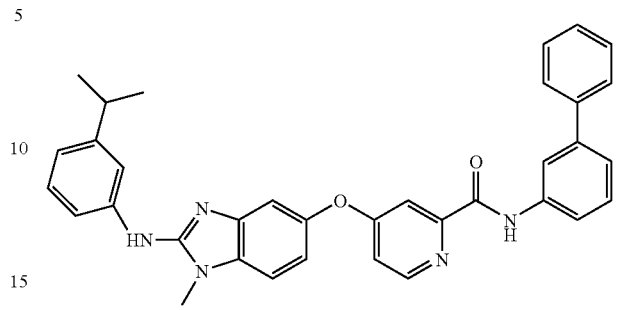

Synthesized as described in Example 999 using 3-biphenylamine. LCMS m/z 554.3 (MH⁺), $t_R$=3.28 min.

Example 1011

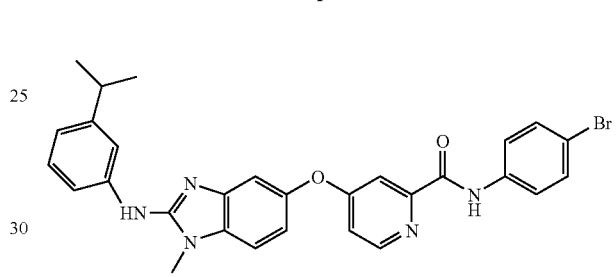

Synthesized as described in Example 999 using 4-bromoaniline. LCMS-m/z 557.2 (MH⁺), $t_R$=5.65 min.

Example 1012

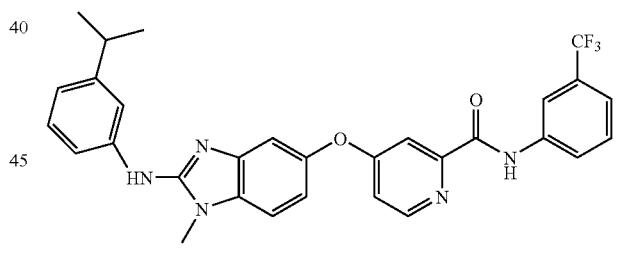

Synthesized as described in Example 999 using 3-trifluoromethylaniline. LCMS m/z 546.3 (MH⁺), $t_R$=5.74 min.

Example 1013

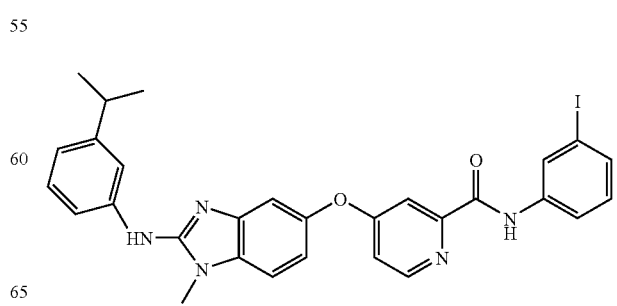

Synthesized as described above in Example 999 using 3-iodoaniline. LCMS m/z 604.2 (MH⁺), $t_R$=5.81 min.

Example 1014

4-[1-Methyl-2-(3-phenoxy-phenylamino)-1H-benzoimidazol-5-yloxy]-pyridine-2-carboxylic acid methylamide Step 1. Synthesis of 3-phenoxyphenylisothiocyanate

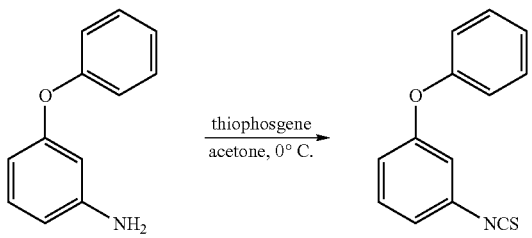

To a stirring solution of 3-phenoxyaniline (185 mg, 1.0 mmol) in acetone (4.0 mL) at 0° C. was added thiophosgene (0.23 mL, 3.0 mmol) and the resulting reaction maintained for 30 min. The reaction determined complete by TLC (4:1 hexane/EtOAc). The reaction was concentrated, azeotroped with toluene and taken on without further purification.

Step 2. Synthesis of 4-[1-Methyl-2-(3-phenoxy-phenylamino)-1H-benzoimidazol-5-yloxy]-pyridine-2-carboxylic acid methylamide

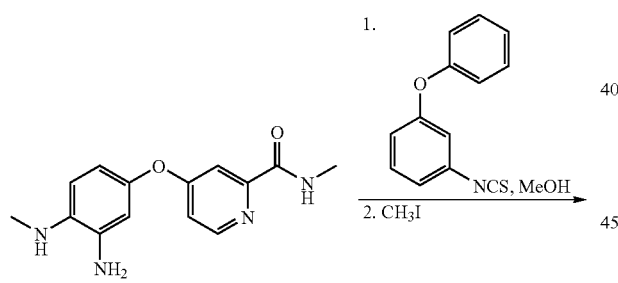

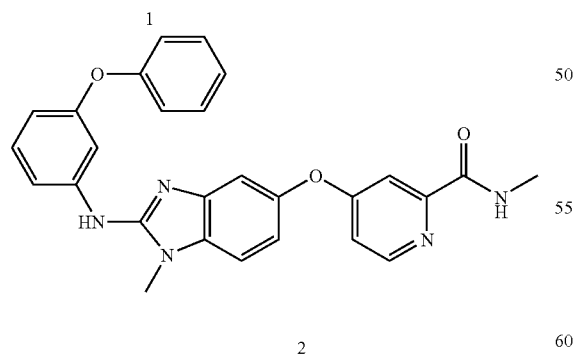

A 1 dram vial was charged with a solution of 3-phenoxyphenylisothiocyanate (23 mg, 0.1 mmol), diamine 1 (27 mg, 0.1 mmol), and MeOH (0.5 mL) and the reaction was shaken at rt overnight. Methyl iodide (8 uL, 0.13 mmol) was added and the mixture shaken overnight. The reaction was concentrated and the resulting residue purified on reverse phase HPLC. LCMS m/z 466.3 (MH⁺), $t_R$=2.40 min.

Example 1015

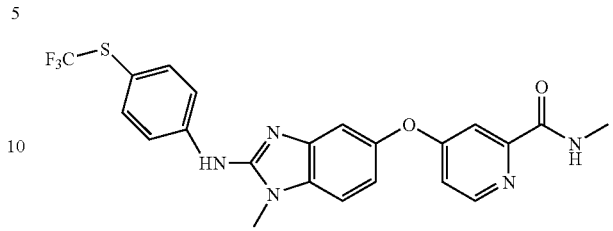

Synthesized as described in Example 1014 step 2 using 4-trifluoromethylthiophenylisothiocyanate. LCMS m/z 474.5 (MH⁺), $t_R$=3.76 min.

Example 1016

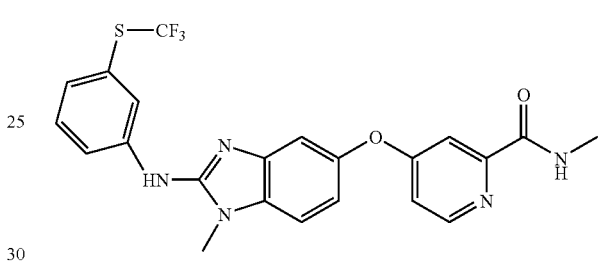

Synthesized as described in Example 1014 step 2 using 3-trifluoromethylthiophenylisothiocyanate. LCMS m/z 474.5 (MH⁺), $t_R$=3.65 min.

Example 1017

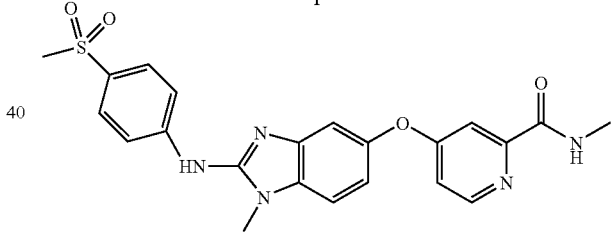

Synthesized as described in Example 1014 step 2 using 4-1-isothiocyanato-4-methanesulfonyl-benzene, prepared as in step 1. LCMS m/z 452.5 (MH⁺), $t_R$=2.86 min.

Example 1018

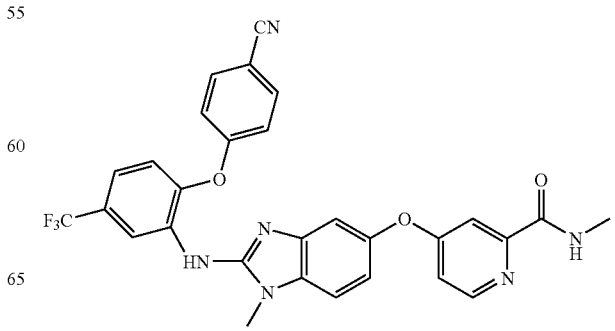

Synthesized as described in Example 1014 step 2 using 4-(2-isothiocyanato-4-trifluoromethyl-phenoxy)-benzonitrile, prepared as in step 1. LCMS m/z 559.6 (MH+), $t_R$=4.22 min.

Example 1019

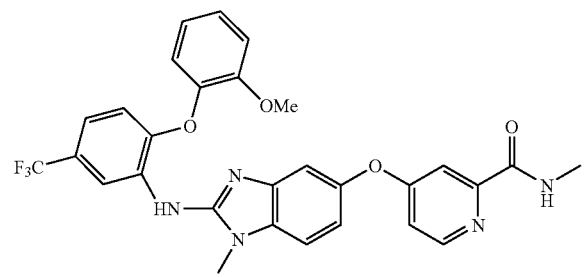

Synthesized as described in Example 1014 step 2 using 2-(2-methoxy-phenoxy)-5-trifluoromethyl-phenylisothiocyanate, prepared as in step 1. LCMS m/z 564.6 (MH+), $t_R$=4.42 min.

Example 1020

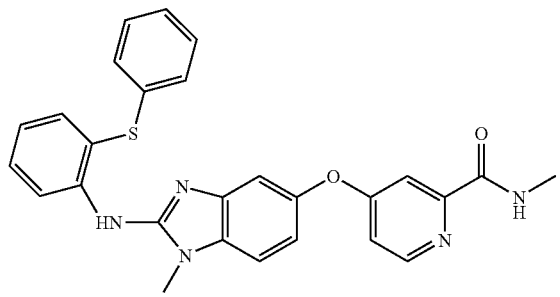

Synthesized as described in Example 1014 step 2 using 2-phenylsulfanyl-phenylisothiocyanate, prepared as in step 1. LCMS m/z 482.5 (MH+), $t_R$=3.85 ml.

Example 1021

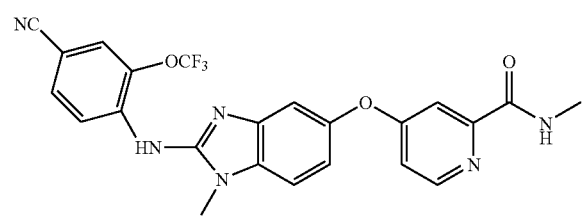

Synthesized as described in Example 1014 step 2 using 4-isothiocyanato-3-trifluoromethoxy-benzonitrile, prepared as in step 1. LCMS m/z 483.4 (MH+), $t_R$=2.35 min.

Example 1022

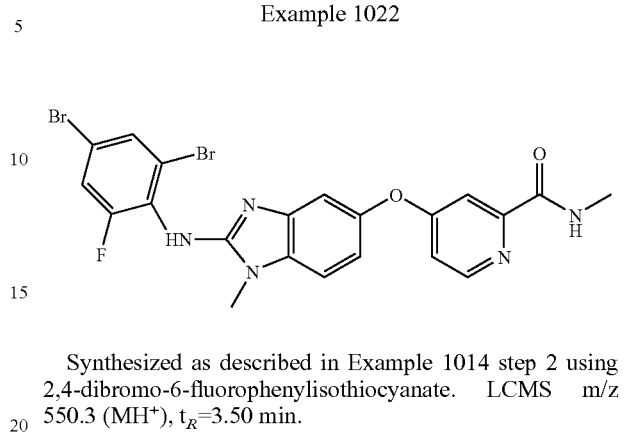

Synthesized as described in Example 1014 step 2 using 2,4-dibromo-6-fluorophenylisothiocyanate. LCMS m/z 550.3 (MH+), $t_R$=3.50 min.

Example 1023

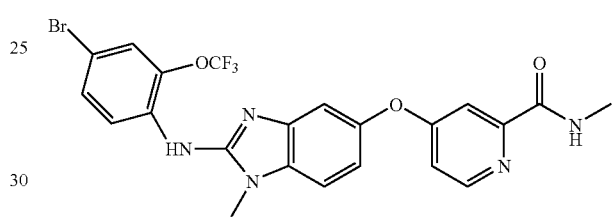

Synthesized as described in Example 1014 step 2 using 4-bromo-2-trifluoromethoxy-phenylisothiocyanate. LCMS m/z 537.3 (MH+), $t_R$=3.89 min.

Example 1024

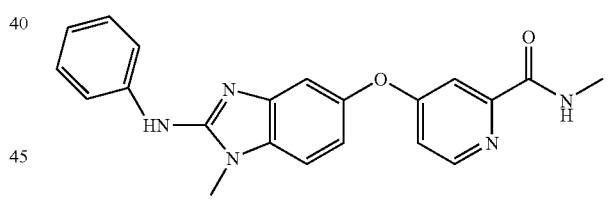

Synthesized as described in Example 1014 step 2 using phenylisothiocyanate. LCMS m/z 374.5 (MH+), $t_R$=2.84 min.

Example 1025

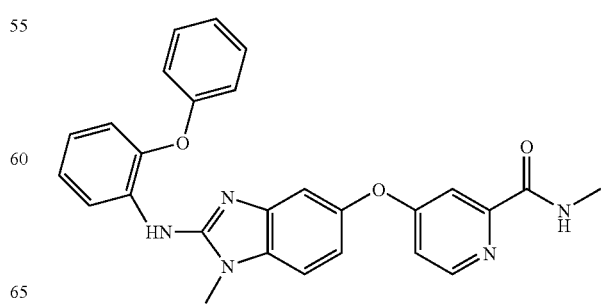

Synthesized as described in Example 1014 step 2 using 2-phenoxy-phenylisothiocyanate, prepared as in step 1. LCMS m/z 466.5 (MH+), $t_R$=2.37 min.

Example 1026

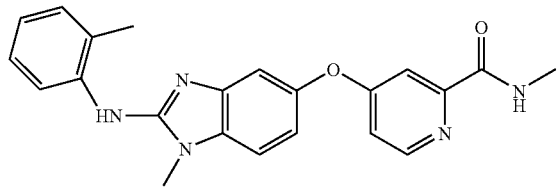

Synthesized as described in Example 1014 step 2 using 2-methyl-phenylisothiocyanate. LCMS m/z 388.5 (MH+), $t_R$=2.99 min.

Example 1027

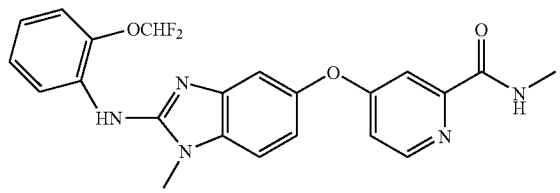

Synthesized as described in Example 1014 step 2 using 2-difluoromethoxy-phenylisothiocyanate. LCMS m/z 440.5 (MH+), $t_R$=3.13 min.

Example 1028

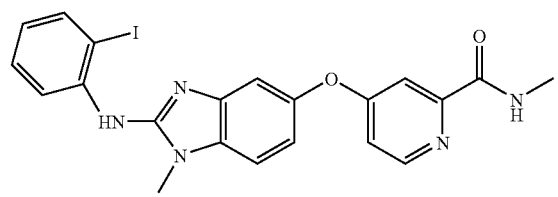

Synthesized as described in Example 1014 step 2 using 2-iodo-phenylisothiocyanate. LCMS m/z 500.4 (MH+), $t_R$=2.07 min.

Example 1029

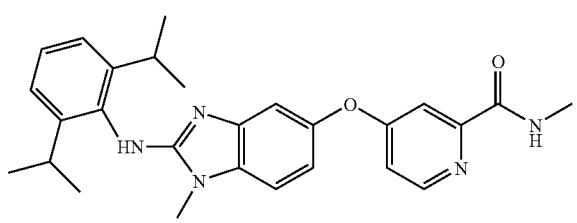

Synthesized as described in Example 1014 step 2 using 2,6-diisopropyl-phenylisothiocyanate. LCMS m/z 430.5 (MH+), $t_R$=2.27 min.

Example 1030

4-[2-(4-Bromophenyl)-1-methyl-1H-benzimidazol-5-yloxy]-pyridine-2-carboxylic acid methylamide

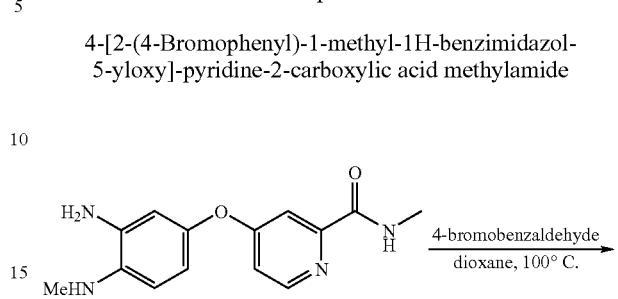

A mixture of diamine 1 (137 mg, 0.36 mmol) and 4-bromobenzaldehyde (66 mg, 0.50 mmol) in dry dioxane (2 mL) was heated to 100° C. for 16 h. The reaction mixture was allowed to cool to rt and was then concentrated. The resulting residue was purified by reverse phase HPLC to furnish 2 as the TFA salt: LCMS m/z 437.1, $t_R$=2.16 min.

Example 1031

4-[1-Methyl-2-(4-methylbenzylamino)-1H-benzoimidazol-5-yloxy]-pyridine-2-carboxylic acid methylamide

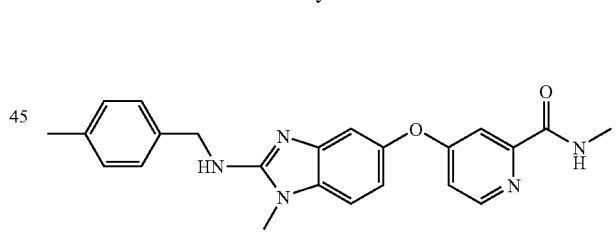

Prepared as per Example 120b using 4-methylbenzyl thioisocyanate: LCMS m/z 402.2 (MH+), $t_R$=1.91 min.

Example 1032

4-[2-(4-Bromophenylamino)-1-methyl-1H-benzoimidazol-5-yloxy]-pyridine-2-carboxylic acid (3-pyrrolidin-1-yl-propyl)-amide

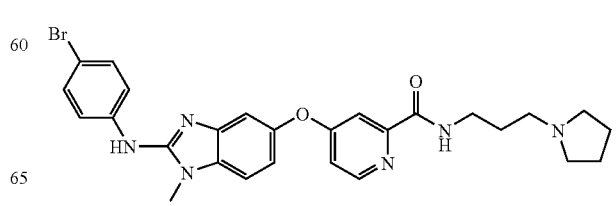

Prepared as per Example 371 using amido-1-(3-aminopropyl)pyrrolidine: LCMS m/z 549.5 (MH$^+$), $t_R$=2.97 min.

Example 1033

(4-Bromophenyl)-[1-methyl-5-(pyridin-4-yloxy)-1H-benzolimidazol-2-yl]-amine

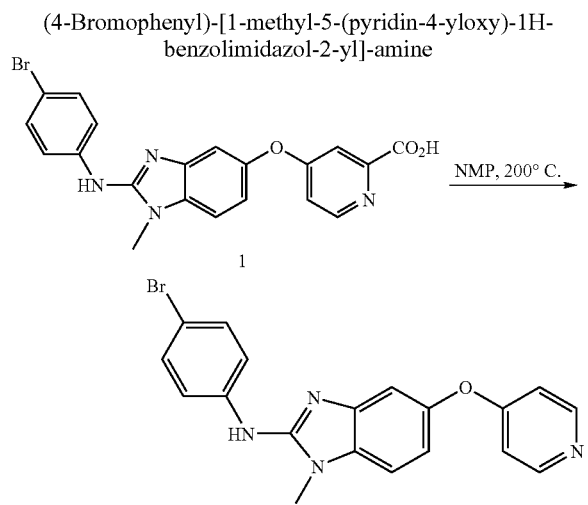

A solution of acid 1 (44 mg, 0.1 mmol) in dry NMP (1 mL) was heated at 200° C. for 20 min. The reaction was allowed to cool to rt and the crude reaction mixture was directly purified on reverse-phase HPLC to provide 2 as a TFA salt: $^1$H NMR (300 MHz, CD3OD) δ 8.67 (d, J=7.4 Hz, 2H), 7.70 (d, J=8.5 Hz, 1H), 7.68 (d, J=8.8 Hz, 2H), 7.45 (d, J=8.8 Hz, 2H), 7.42 (d, J=7.4 Hz, 2H), 7.32 (d, J=2.2 Hz, 1H), 7.26 (dd, J=2.2, 8.5 Hz, 1H), 3.86 (s, 3H); LCMS m/z 395.0 (MH$^+$), $t_R$=1.48 min.

Example 1034

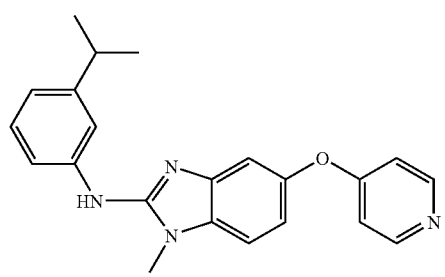

LCMS m/z 359.3 (MH$^+$), $t_R$=1.91 min.

Example 1035

{4-[2-(4-Bromophenylamino)-1-methyl-1H-benzolimidazol-5-yloxy]-pyridin-2-yl}-methanol

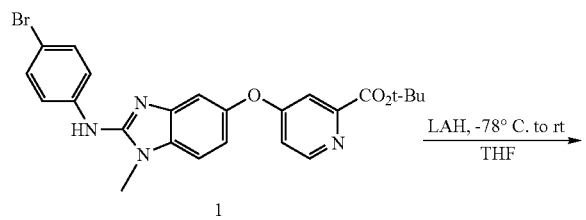

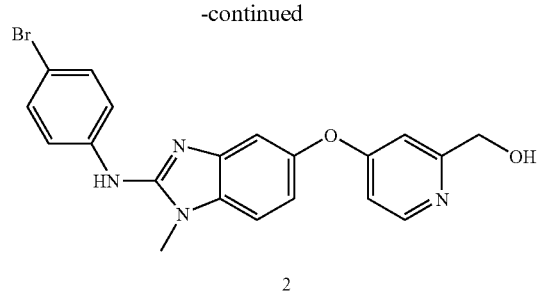

A suspension of t-butyl ester 1 (496 mg, 1.0 mmol) in dry THF (3 mL) was added to a stirring suspension of LAH (61 mg, 1.6 mmol) in dry THF (2 mL) at −78° C. The reaction was allowed to warm to rt over 3 h. After the reaction was judged complete by LCMS, water (30 ul, 1.7 mmol) and NaF (270 mg, 6.4 mmol) were added and the resulting mixture was stirred vigorously overnight at rt. The crude mixture was filtered through Celite and the remaining solids were rinsed with EtOAc. The combined organic portions were concentrated and a portion of the resulting residue was purified by reverse-phase HPLC to furnish alcohol 2 as a TFA salt: $^1$H NMR (300 MHz, CD3OD) δ 8.56 (d, J=7.2 Hz, 1H), 7.72 (d, J=8.5 Hz, 1H), 7.69 (d, J=8.8 Hz, 2H), 7.45 (d, J=8.8 Hz, 2H), 7.33 (m, 3H), 7.28 (dd, J=2.2, 8.5 Hz, 1H), 4.86 (app s, 2H), 3.87 (s, 3H); LCMS m/z 425.1, $t_R$=1.49 min.

Example 1036

(4-Bromophenyl)-[1-methyl-5-(2-methylaminomethyl-pyridin-4-yloxy)-1H benzoimidazol-2-yl]-amine General Preparation for Benzyl Amines Step 1. 4-[2-(4-Bromophenylamino)-1-methyl-1H-benzoimidazol-5-yloxy]-pyridine-2-carboxaldehyde

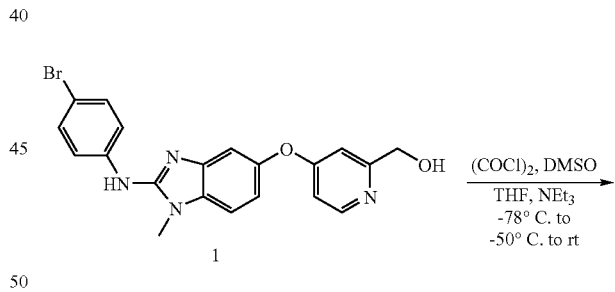

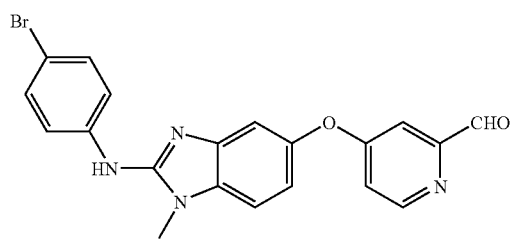

Dry DMSO (0.1 mL, 1.4 mmol) was added to a solution of oxalyl chloride (0.11 mL, 1.3 mmol) in dry THF (2 mL) at −78° C. and the resulting solution was maintained at −78° C. for 30 min. A solution of alcohol 1 in dry THF (2 mL) was then introduced and the resulting reaction was maintained at −78° C. for 30 min, then at −50° C. for 45 min. Triethylamine (0.5 mL, 3.6 mmol) was added and the reaction was allowed to warm to rt over 1 h. The reaction was quenched with water and partitioned with EtOAc. The layers were separated and the aqueous portion was extracted with EtOAc (3×). The combined organic phases were washed with brine, dried (MgSO$_4$), and concentrated. The resulting residue was carried forward without further purification.

-continued

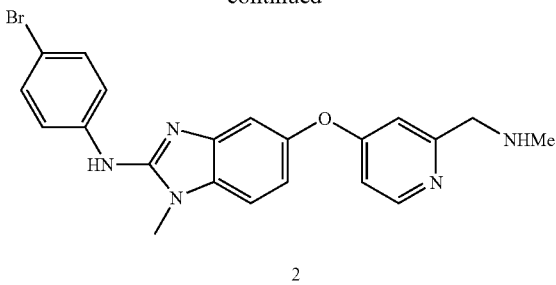

2

Methyl amine (0.3 mL, 0.6 mmol, 2.0 M in MeOH) was added to a solution of aldehyde 1 in MeOH (1 mL) and the reaction was maintained at rt for 2 d. The reaction was acidified by addition of acetic acid (pH=3-4), and an excess of NaBH$_3$CN was added. The reaction was maintained for 2 d then concentrated. The crude reaction mixture was dissolved in EtOAc and partitioned with aqueous saturated NaHCO3 solution. The layers were separated and the aqueous phase was extracted with EtOAc (3 X). The combined organic portions were washed with brine, dried (MgSO$_4$), and concentrated. The resulting residue was purified by reverse-phase HPLC to afford N-methyl amine 2 as a TFA salt: $^1$H NMR (300 MHz, CD$_3$OD) δ 8.48 (d, J=5.8 Hz, 1H), 7.72 (d, J=8.8 Hz, 2H), 7.67 (d, J=9.4 Hz, 1H), 7.43 (d, J=8.8 Hz, 2 h), 7.20 (dd, J=2.2, 9.4 Hz, 1H), 7.19 (d, J=2.2 Hz, 1H), 7.02 (d, J=2.2, 1H), 6.90 (dd, J=2.2, 5.8 Hz, 1H), 4.27 (s, 2H), 3.86 (s, 3H), 2.76 (s, 3H); LCMS m/z 438.5 (MH$^+$), t$_R$=1.85 min.

The following tabulated benzyl amines were prepared by the above method as in Example 1036 using the appropriate amine.

Step 2. (4-Bromophenyl)-[1-methyl-5-(2-methylaminomethyl-pyridin-4-yloxy)-1H benzoimidazol-2-yl]-amine

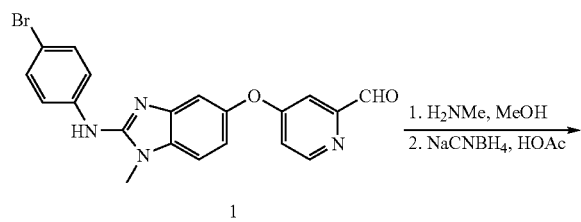

TABLE 14

| Example | Structure | LCMS (MH$^+$) m/z | TIME t$_R$ (min) |
|---|---|---|---|
| 1037 | 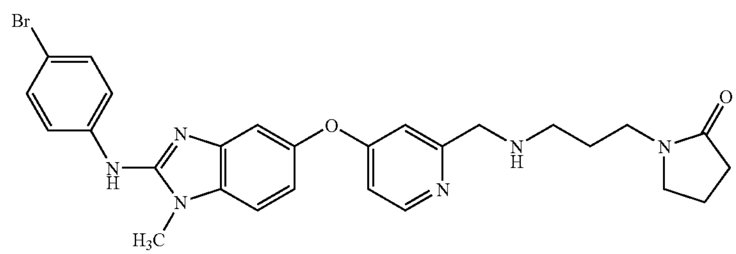 | 549.1 | 1.62 |
| 1038 | 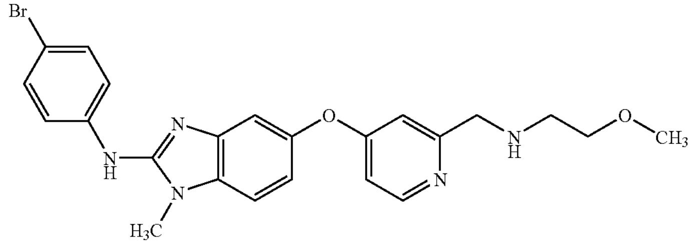 | 482.2 | 1.94 |

TABLE 14-continued

| Example | Structure | LCMS (MH+) m/z | TIME $t_R$ (min) |
|---|---|---|---|
| 1039 | 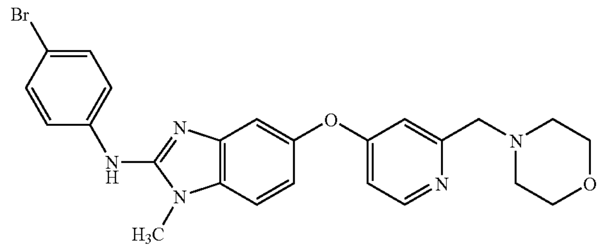 | 494.1 | 1.59 |
| 1040 | 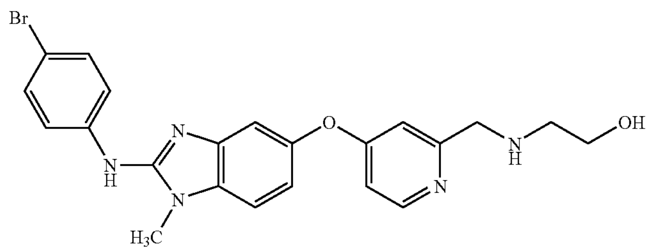 | 468.2 | 1.87 |
| 1041 | 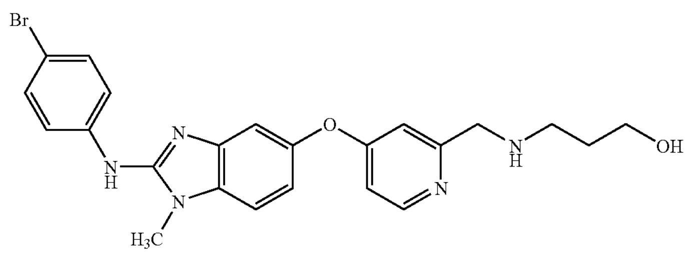 | 483.3 | 1.83 |
| 1042 | 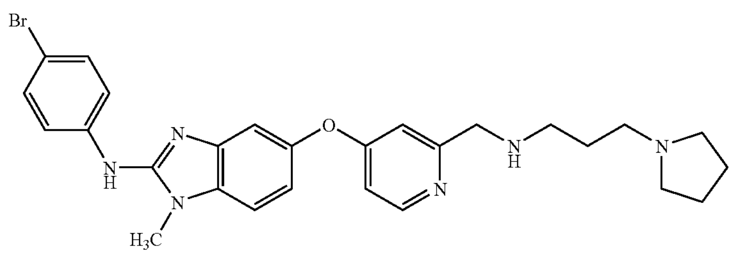 | 536.2 | 1.87 |
| 1043 | 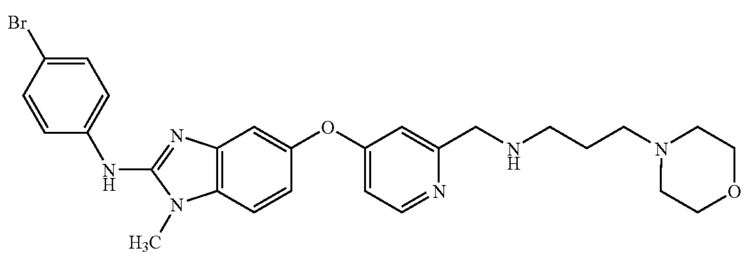 | 552.2 | 1.84 |
| 1044 | 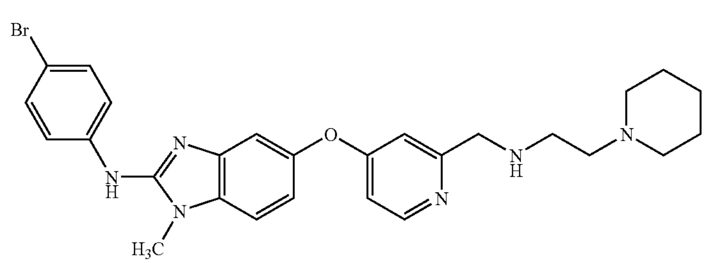 | 536.4 | 1.80 |

TABLE 14-continued
| Example | Structure | LCMS (MH+) m/z | TIME $t_R$ (min) |
|---|---|---|---|
| 1045 | 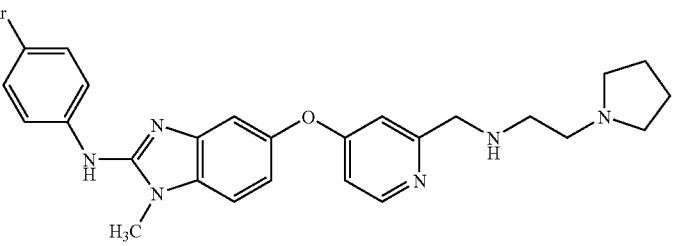 | 522.3 | 1.76 |
| 1046 | 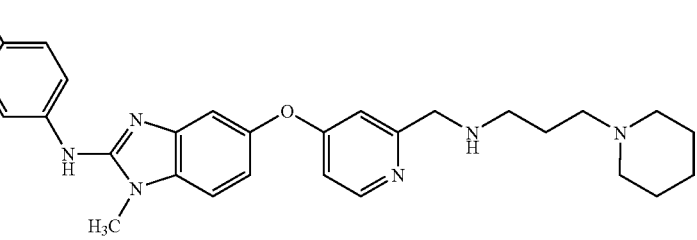 | 550.4 | 1.80 |
| 1047 | 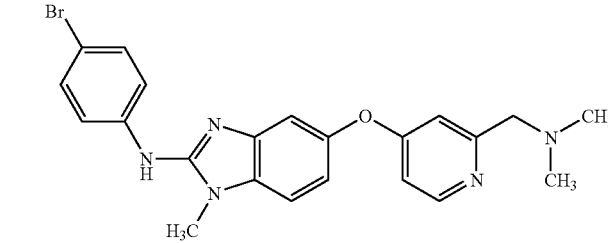 | 452.3 | 2.70* |
| 1048 | 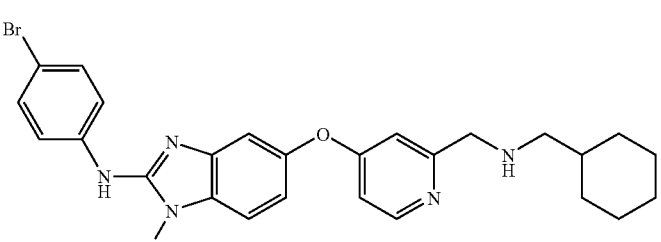 | 521.4 | 3.63* |
| 1049 | 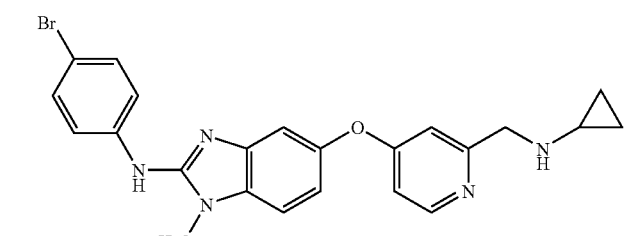 | 465.3 | 2.75* |
| 1050 | 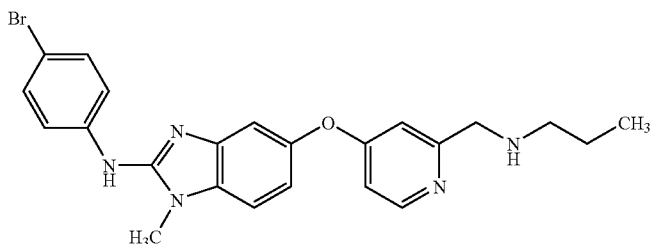 | 467.3 | 2.86* |

TABLE 14-continued

| Example | Structure | LCMS (MH+) m/z | TIME $t_R$ (min) |
|---|---|---|---|
| 1051 | 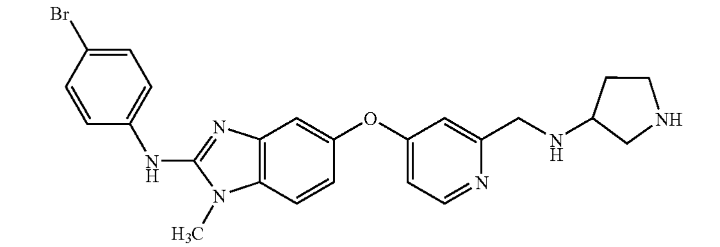 | 494.2 | 1.82 |
| 1052 | 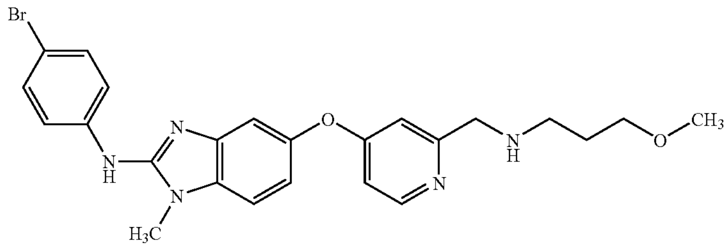 | 497.2 | 2.04 |

Example 1053

[5-(2-Aminomethyl-pyridin-4-yloxy)-1-methyl-1H-benzoimidazol-2-yl]-(4-bromophenyl)-amine

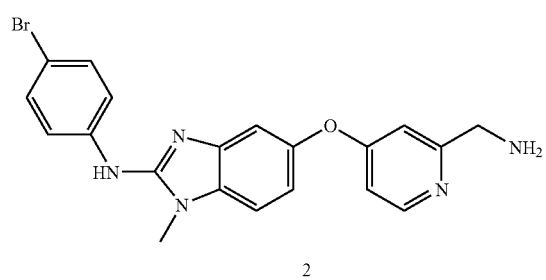

LAH (98 mg, 2.5 mmol) was added portionwise to a stirring solution of oxime 1 (225 mg, 0.5 mmol) in dry THF (3 mL) at 0° C. After addition, the cooling bath was removed and the reaction was allowed to warm to rt overnight. The reaction was quenched by addition of water (0.1 mL), 10% w/w aqueous NaOH solution (0.1 mL), and water (0.3 mL). The resulting slurry was stirred at rt for 1 h and filtered through Celite. The remaining solids were rinsed with EtOAc and the organic portions were combined and concentrated. The crude residue was purified by reverse-phase HPLC to provide benzyl amine 2 as a TFA salt: LCMS m/z 424.1 (MH+), $t_R$=1.87 min.

Example 1054

{4-[2-(4-Bromophenylamino)-1-methyl-1H-benzoimidazol-5-yloxy]-pyridin-2-yl-methyl]-carbamic acid methyl ester

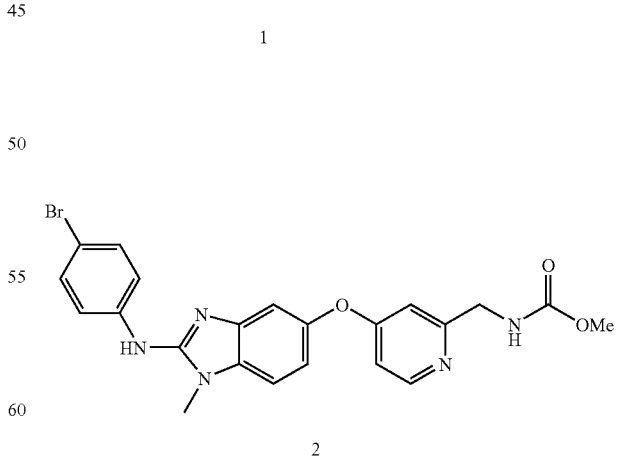

Methyl chloroformate (6 µL, 0.08 mmol) was added to a solution of benzyl amine 1 (21 mg, 0.05 mmol) and triethylamine (69 µL, 0.5 mmol) in dry THF (1 mL) at 0° C. The reaction was maintained at 0° C. for 20 min, then at rt for 2 h.

Example 1055

N-{4-[2-(4-Bromophenylamino)-1-methyl-1H-benzoimidazol-5-yloxy]-pyridin-2-ylmethyl}acetamide

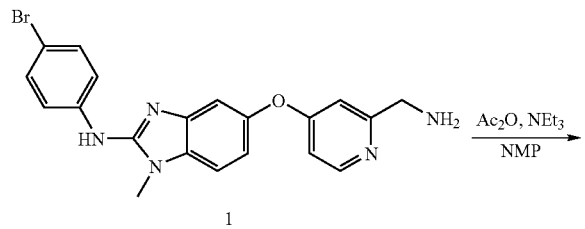

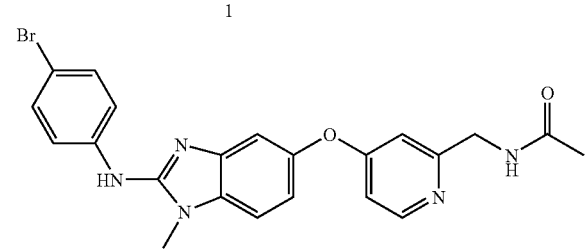

To a solution of benzyl amine 1 (17 mg, 0.04 mmol) in dry NMP (2 mL) was added triethylamine (0.06 mL, 0.4 mmol) and acetic anhydride (0.04 mL, 0.4 mmol). The resulting reaction was maintained at rt overnight and purified directly by reverse-phase HPLC to furnish acetamide 2 as a TFA salt: LCMS m/z 466.3 (MH$^+$), $t_R$=1.78 min.

Example 1056

4-[2-(3-Ethylphenylamino)-1-methyl-1H-benzoimidazol-5-yloxy]-pyridine-2-carboxylic acid [3-(2-oxo-pyrrolidin-yl)-propyl]-amide General Preparation for N-(3-Aminopropyl)-pyrrolidinone Amides Step 1: 4-Chloro-pyridine-2-carboxylic acid [3-(2-oxo-pyrrolidin-1-yl)-propyl]-amide

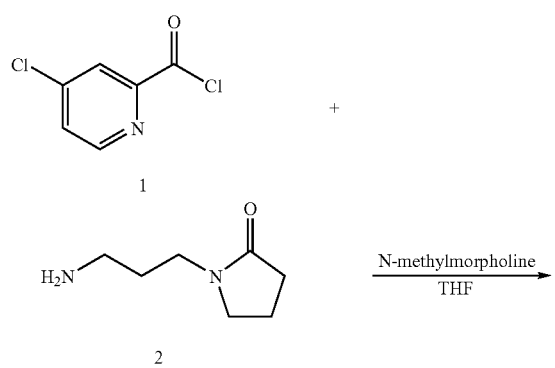

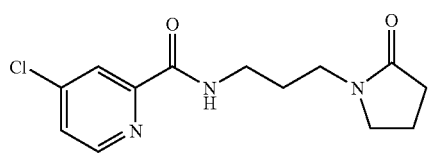

Acid chloride 1 (2.12 g, 10 mmol) was treated with N-methylmorpholine (4.5 mL, 41 mmol) and N-(3-aminopropyl)-pyrrolidinone 2 (1.6 mL, 11 mmol) in dry THF (40 mL). The reaction was maintained overnight and concentrated. The residue was dissolved in EtOAc and partitioned with water. The aqueous portion was extracted with EtOAc (3×) and the combined organic phases were washed with brine, dried (MgSO$_4$), and concentrated. The crude residue was purified by Kugelrohr distillation (0.5 mmHg, 170-200° C.) to provide 3.

Step 2: 4-(4-Methylamino-3-nitrophenoxy)-pyridine-2-carboxylic acid [3-(2-oxo-pyrrolidin-yl)-propyl]-amide

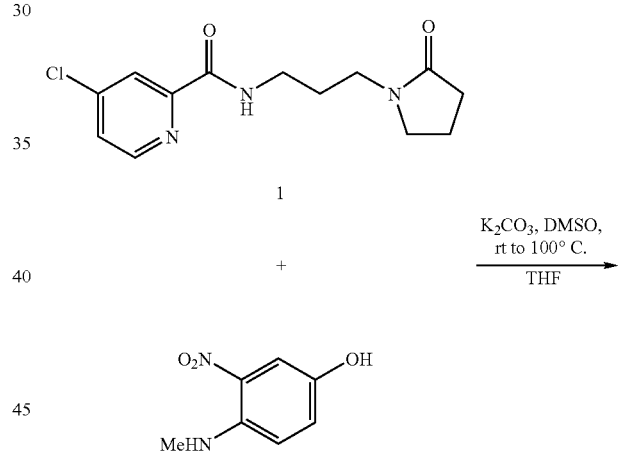

Prepared as per Example 120b with the appropriate substitutions. Amide 3 can be purified by flash chromatography (95:5 CH$_2$Cl$_2$-MeOH). It can also be further purified by recrystallization from MeCN.

Step 3: 4-(3-Amino-4-methylamino-phenoxy)-pyridine-2-carboxylic acid [3-(2-oxo-pyrrolidin-yl)-propyl]-amide
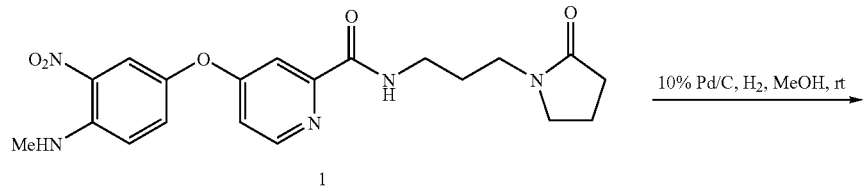
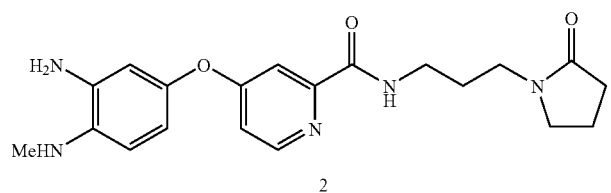
Prepared as per Example 120b.
Step 4: 4-[2-(3-Ethylphenylamino)-1-methyl-1H-benzoimidazol-5-yloxy]-pyridine-2-carboxylic acid [3-(2-oxo-pyrrolidin-yl)-propyl]-amide
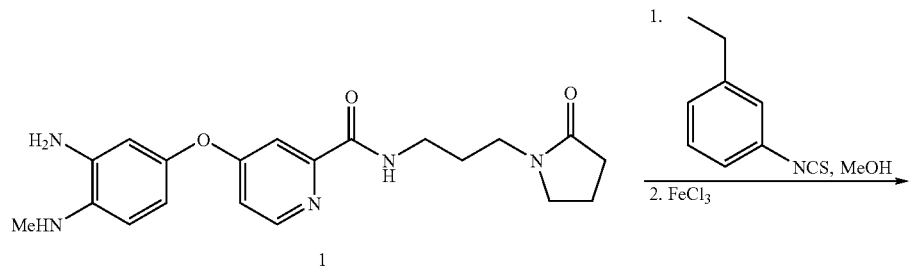
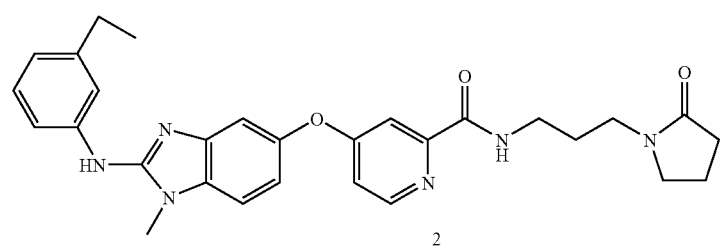

Prepared as per Example 120b to provide benzimidazole 2 as a TFA salt: LCMS m/z 513.3 (MH+), $t_R$=2.22 min.

Example 1057

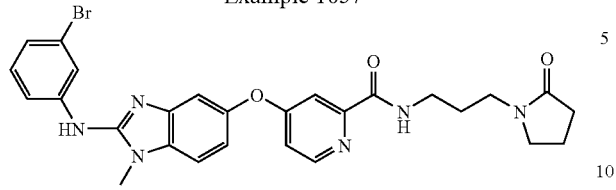

Prepared as per Example 1056: LCMS m/z 563.2 (MH+), $t_R$=2.15 min.

Example 1058

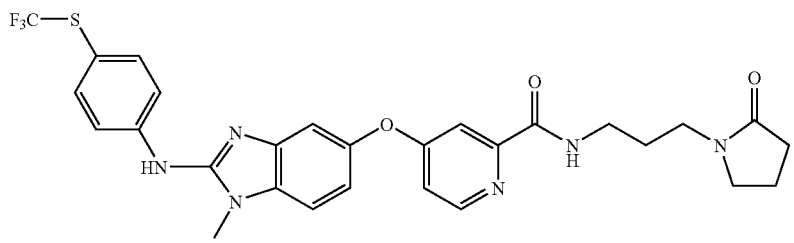

Prepared as per Example 1056: LCMS $t_R$=585.3 (MH+), $t_R$=2.55 min.

Example 1059

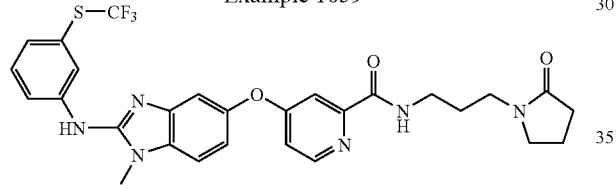

Prepared as per Example 1056: LCMS m/z 563.2 (MH+), $t_R$=2.50 min.

The following additional compounds were prepared following the procedures of the indicated Examples:

TABLE 15

| Example | Structure | Name | MH+ | Synthesized as in Ex.: |
|---|---|---|---|---|
| 1060 | 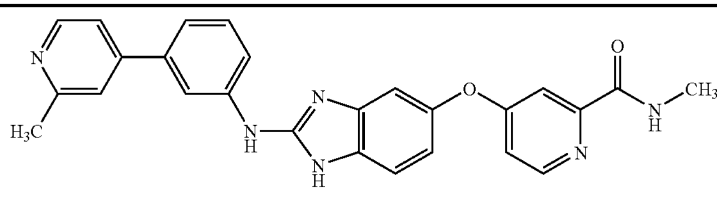 | N-methyl-4-[(2-{[3-(2-methyl-pyridin-4-yl)phenyl]amino}-1H-benzimidazol-5-yl)oxy]pyridine-2-carboxamide | 451.5 | 702 |
| 1061 | 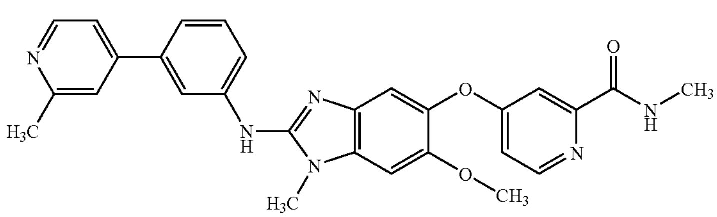 | N-methyl-4-[(1-methyl-6-(methyloxy)-2-{[3-(2-methyl-pyridin-4-yl)phenyl]amino}-1H-benzimidazol-5-yl)oxy]pyridine-2-carboxamide | 495.6 | 702 |

TABLE 15-continued

| Example | Structure | Name | MH+ | Synthesized as in Ex.: |
|---|---|---|---|---|
| 1062 | 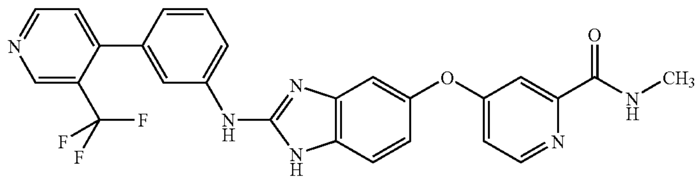 | N-methyl-4-{[2-({3-[3-(trifluoromethyl)pyridin-4-yl]phenyl}amino)-1H-benzimidazol-5-yl]oxy}pyridine-2-carboxamide | 505.5 | 702 |
| 1063 | 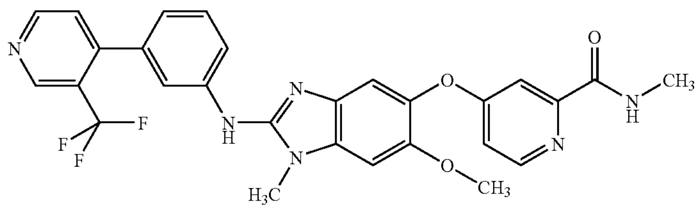 | N-methyl-4-{[1-methyl-6-(methyloxy)-2-({3-[3-(trifluoromethyl)pyridin-4-yl]phenyl}-amino)-1H-benzimidazol-5-yl]oxy}pyridine-2-carboxamide | 549.5 | 702 |
| 1064 | 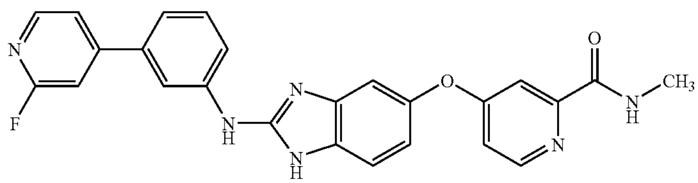 | 4-[(2-{[3-(2-fluoropyridin-4-yl)phenyl]amino}-1H-benzimidazol-5-yl)oxy]-N-methylpyridine-2-carboxamide | 455.5 | 702 |
| 1065 | 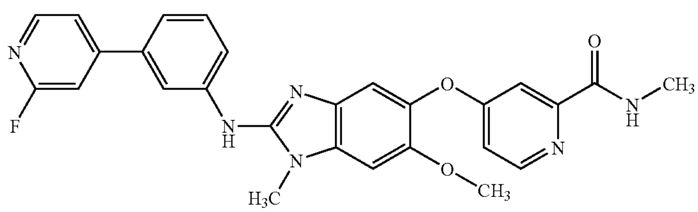 | 4-{[2-{[3-(2-fluoropyridin-4-yl)phenyl]amino}-1-methyl-6-(methyloxy)-1H-benzimidazol-5-yl]oxy}-N-methylpyridine-2-carboxamide | 499.5 | 702 |
| 1066 | 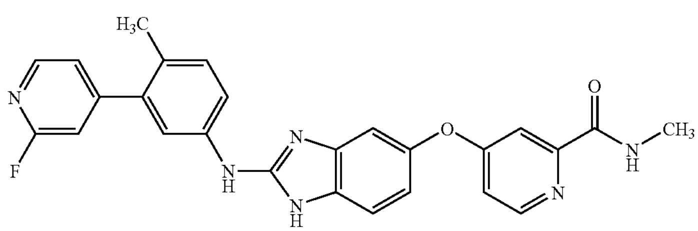 | 4-[(2-{[3-(2-fluoropyridin-4-yl)-4-methylphenyl]amino}-1H-benzimidazol-5-yl)oxy]-N-methylpyridine-2-carboxamide | 469.5 | 702 |
| 1067 | 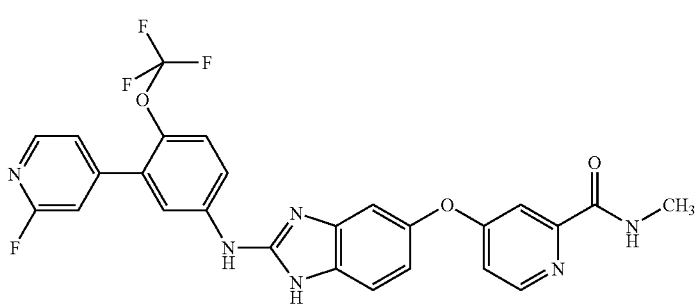 | 4-{[2-({3-(2-fluoropyridin-4-yl)-4-[(trifluoromethyl)oxy]phenyl}amino)-1H-benzimidazol-5-yl]oxy}-N-methylpyridine-2-carboxamide | 539.5 | 702 |

TABLE 15-continued

| Example | Structure | Name | MH+ | Synthesized as in Ex.: |
|---|---|---|---|---|
| 1068 | 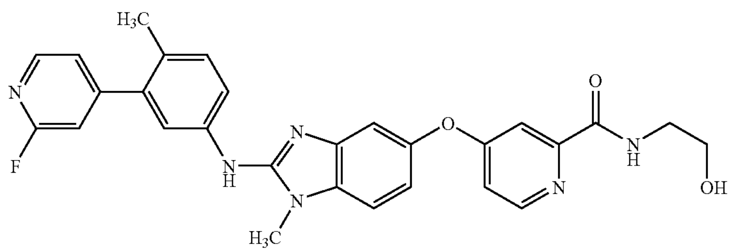 | 4-[(2-{[3-(2-fluoropyridine-4-yl)-4-methylphenyl]amino}-1-methyl-1H-benzimidazol-5-yl)oxy]-N-(2-hydroxyethyl)-pyridine-2-carboxamide | 513.5 | 483 |
| 1069 | 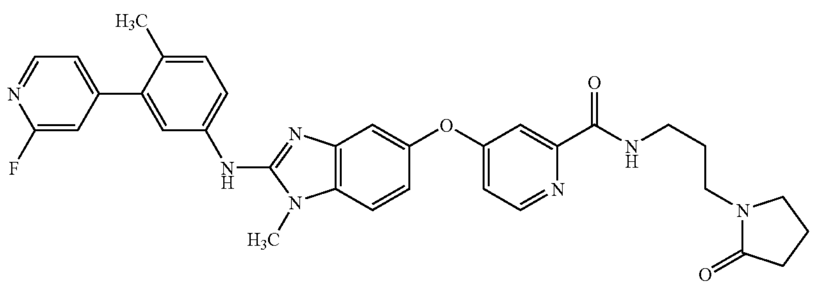 | 4-[(2-{[3-(2-fluoropyridin-4-yl)-4-methylphenyl]amino}-1-methyl-1H-benzimidazol-5-yl)oxy]-N-[3-(2-oxopyrrolidin-1-yl)propyl]pyridine-2-carbox-amide | 594.7 | 483 |
| 1070 | 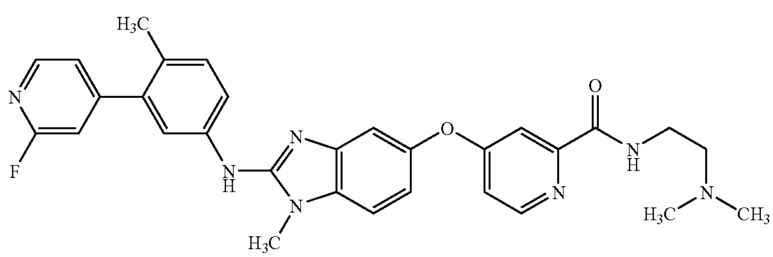 | N-[2-(dimethylamino)ethyl]-4-[(2-{[3-(2-fluoropyridin-4-yl)-4-methylphenyl]amino}-1-methyl-1H-benzimidazol-5-yl)oxy]-pyridine-2-carboxamide | 540.6 | 483 |
| 1071 | 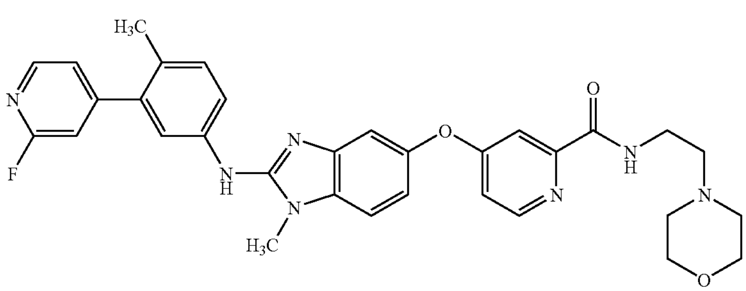 | 4-[(2-{[3-(2-fluoropyridin-4-yl)-4-methylphenyl]amino}-1-methyl-1H-benzimidazol-5-yl)oxy]-N-(2-morpholin-4-ylethyl)-pyridine-2-carboxamide | 582.6 | 483 |
| 1072 | 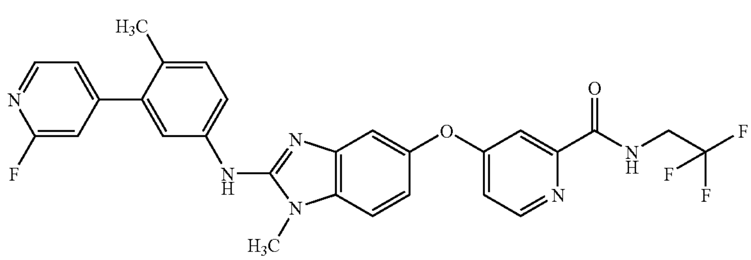 | 4-[(2-{[3-(2-fluoropyridin-4-yl)-4-methylphenyl]amino}-1-methyl-1H-benzimidazol-5-yl)oxy]-N-(2,2,2-trifluoroethyl)-pyridine-2-carboxamide | 551.5 | 483 |

TABLE 15-continued

| Example | Structure | Name | MH+ | Synthesized as in Ex.: |
|---|---|---|---|---|
| 1073 | 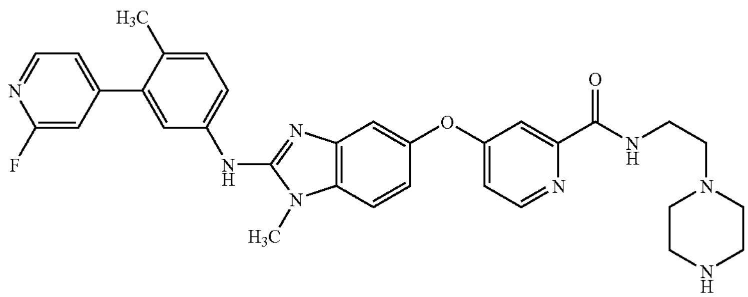 | 4-[(2-{[3-(2-fluoropyridin-4-yl)-4-methylphenyl]amino}-1-methyl-1H-benzimidazol-5-yl)oxy]-N-(2-piperazin-1-ylethyl)-pyridine-2-carboxamide | 581.7 | 483 |
| 1074 | 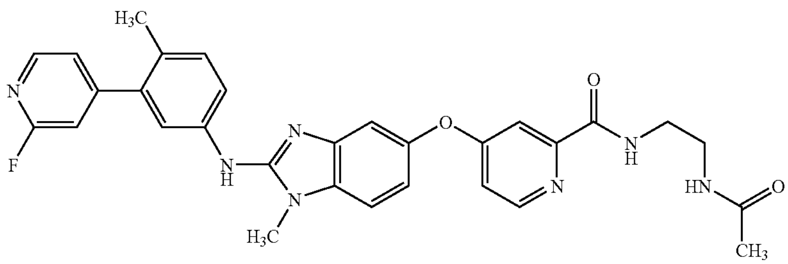 | N-[2-(acetylamino)ethyl]-4-[(2-{[3-(2-fluoropyridin-4-yl)-4-methylphenyl]amino}-1-methyl-1H-benzimidazol-5-yl)oxy]-1H-benzimidazol-5-yl)oxy]-pyridine-2-carboxamide | 554.6 | 483 |
| 1075 | 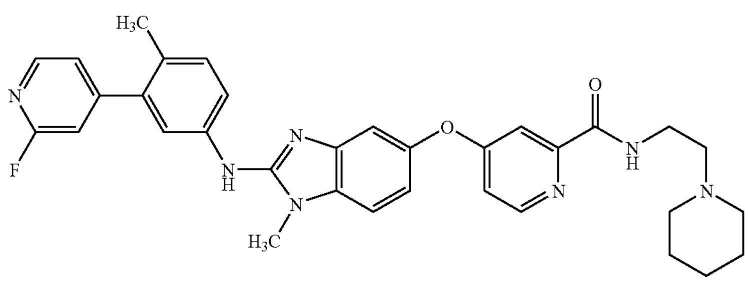 | 4-[(2-{[3-(2-fluoropyridin-4-yl)-4-methylphenyl]amino}-1-methyl-1H-benzimidazol-5-yl)oxy]-N-(2-piperidin-1-ylethyl)-pyridine-2-carboxamide | 580.7 | 483 |
| 1076 | 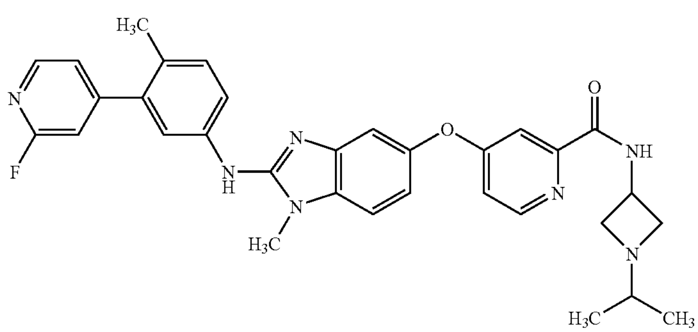 | 4-[(2-{[3-(2-fluoropyridin-4-yl)-4-methylphenyl]amino}-1-methyl-1H-benzimidazol-5-yl)oxy]-N-[1-(1-methylethyl)-azetidin-3-yl]pyridine-2-carboxamide | 566.7 | 636 |
| 1077 | 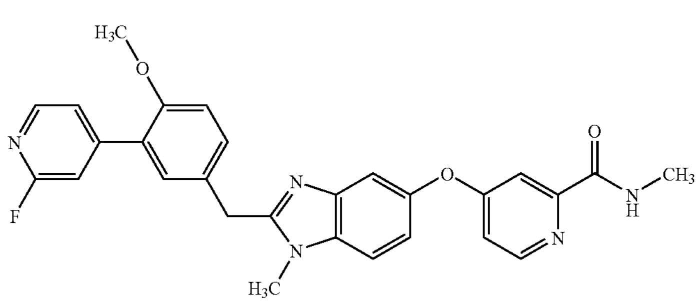 | 4-[(2-{[3-(2-fluoropyridin-4-yl)-4-(methyloxy)phenyl]methyl}-1-methyl-1H-benzimidazol-5-yl)oxy]-N-methylpyridine-2-carboxamide | 498.5 | 636 |

TABLE 15-continued

| Example | Structure | Name | MH+ | Synthesized as in Ex.: |
|---|---|---|---|---|
| 1078 | 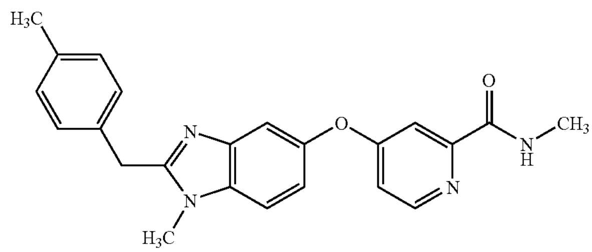 | N-methyl-4-({1-methyl-2-[(4-methylphenyl)methyl]-1H-benzimidazol-5-yl}oxy)-pyridine-2-carboxamide | 387.5 | 636 |
| 1079 | 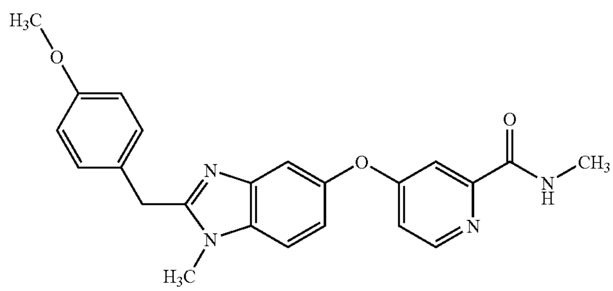 | N-methyl-4-[(1-methyl-2-{[4-(methyloxy)phenyl]methyl}-1H-benzimidazol-5-yl)oxy]pyridine-2-carboxamide | 403.5 | 636 |
| 1080 | 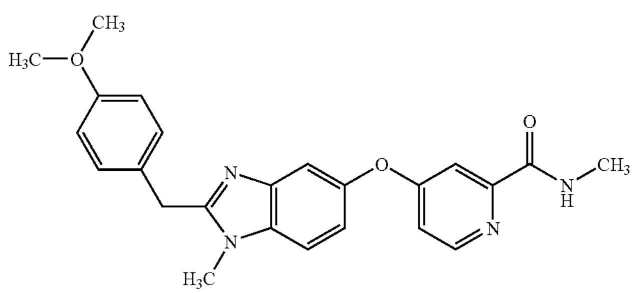 | N-methyl-4-[(1-methyl-2-{[4-(1-methylethyl)phenyl]methyl}-1H-benzimidazol-5-yl)oxy]-pyridine-2-carboxamide | 415.5 | 636 |
| 1081 | 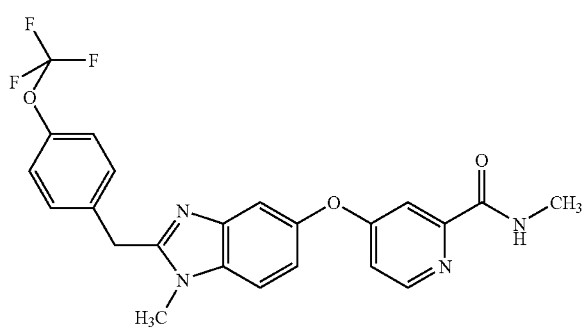 | N-methyl-4-{[1-methyl-2-({4-[(trifluoromethyl)oxy]phenyl}methyl)-1H-benzimidazol-5-yl]oxy}pyridine-2-carboxamide | 457.4 | 636 |
| 1082 | 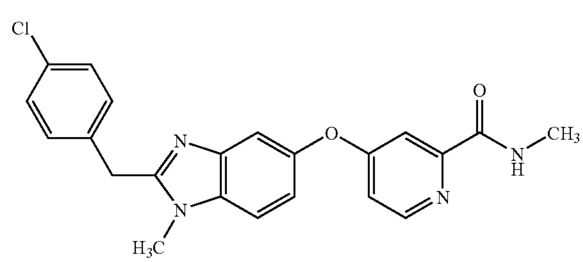 | 4-({2-[(4-chlorophenyl)methyl]-1-methyl-1H-benzimidazol-5-yl}oxy)-N-methylpyridine-2-carboxamide | 407.9 | 636 |

TABLE 15-continued

| Example | Structure | Name | MH+ | Synthesized as in Ex.: |
|---|---|---|---|---|
| 1083 | 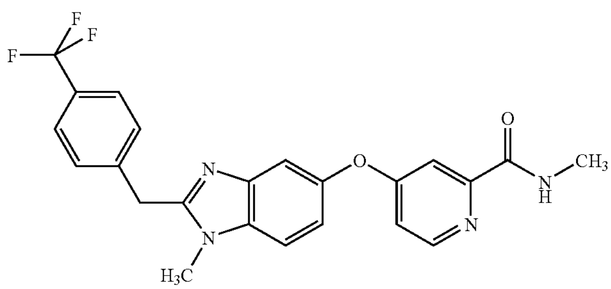 | N-methyl-4-[(1-methyl-2-{[4-(trifluoromethyl)phenyl]methyl}-1H-benzimidazol-5-yl)oxy]-pyridine-2-carboxamide | 441.4 | 636 |
| 1084 | 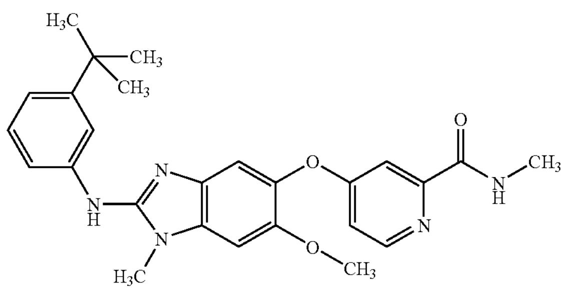 | 4-{[2-{[3-(1,1-dimethylethyl)-phenyl]amino}-1-methyl-6-(methyloxy)-1H-benzimidazol-5-yl]oxy}-N-methylpyridine-2-carboxamide | 460.5 | 703 |
| 1085 | 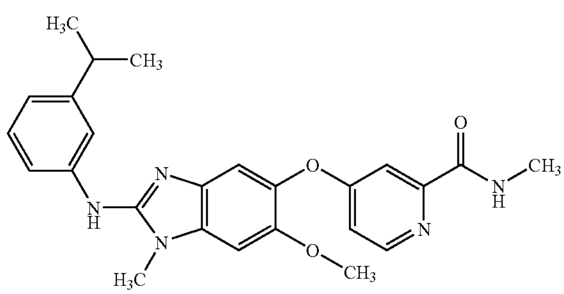 | N-methyl-4-{[1-methyl-2-{[3-(1-methylethyl)phenyl]amino}-6-(methyloxy)-1H-benzimidazol-5-yl]oxy}pyridine-2-carboxamide | 446.5 | 703 |
| 1086 | 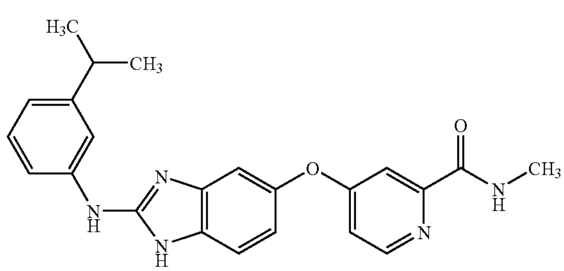 | N-methyl-4-[(2-{[3-(1-methylethyl)phenyl]amino}-1H-benzimidazol-5-yl)oxy]pyridine-2-carboxamide | 402.5 | 1 |
| 1087 | 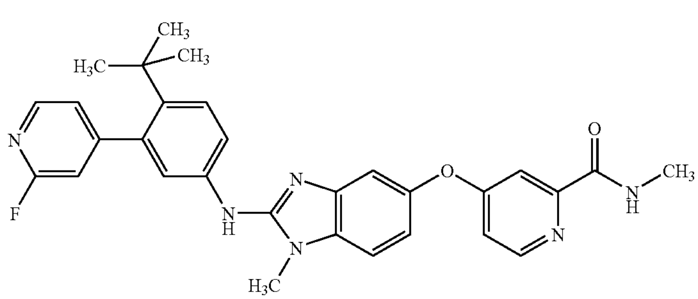 | 4-[(2-{[4-(1,1-dimethylethyl)-3-(2-fluoropyridin-4-yl)phenyl]amino}-1-methyl-1H-benzimidazol-5-yl)oxy]-N-methyl-pyridine-2-carboxamide | 525.6 | 702 |

TABLE 15-continued

| Example | Structure | Name | MH+ | Synthesized as in Ex.: |
|---|---|---|---|---|
| 1088 | 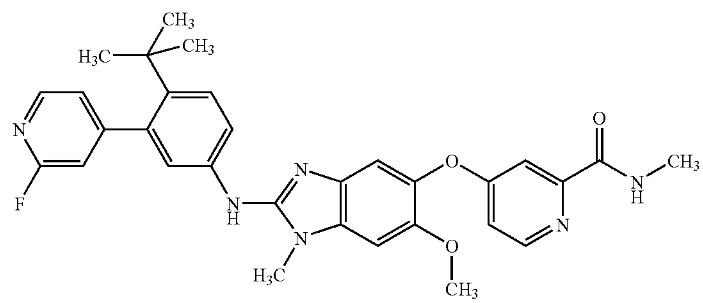 | 4-{[2-{[4-(1,1-dimethylethyl)-3-(2-fluoropyridin-4-yl)phenyl]amino}-1-methyl-6-(methyl-oxy)-1H-benzimidazol-5-yl]oxy}-N-methylpyridine-2-carboxamide | 555.6 | 702 |
| 1089 | 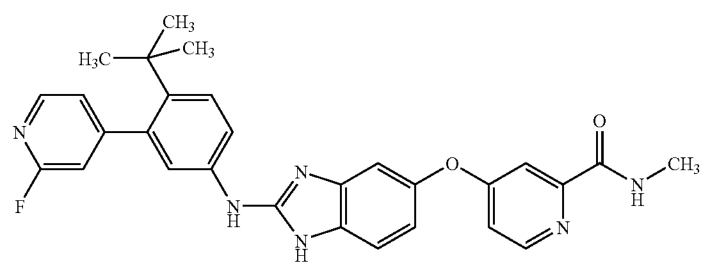 | 4-[(2-{[4-(1,1-dimethylethyl)-3-(2-fluoropyridin-4-yl)phenyl]amino}-1H-benzimidazol-5-yl)oxy]-N-methylpyridine-2-carboxamide | 511.6 | 702 |
| 1090 | 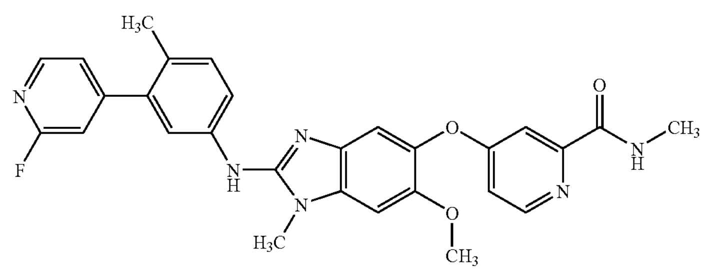 | 4-{[2-{[3-(2-fluoropyridin-4-yl)-4-methylphenyl]amino}-1-methyl-6-(methyloxy)-1H-benzimidazol-5-yl]oxy}-N-methylpyridine-2-carboxamide | 513.5 | 702 |
| 1091 | 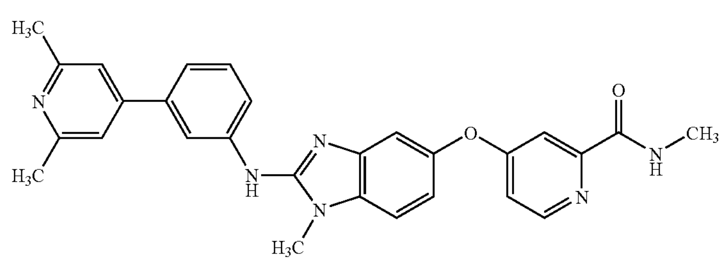 | 4-[(2-{[3-(2,6-dimethylpyridin-4-yl)phenyl]amino}-1-methyl-1H-benzimidazol-5-yl)oxy]-N-methylpyridine-2-carboxamide | 479.6 | 702 |
| 1092 | 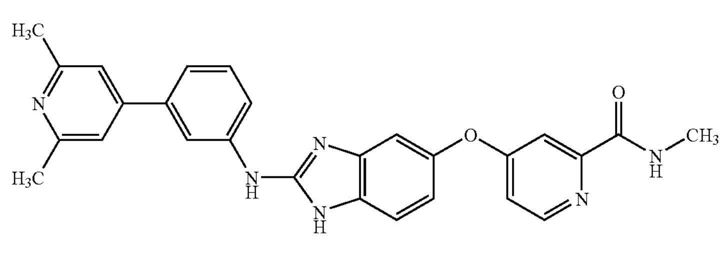 | 4-[(2-{[3-(2,6-dimethylpyridin-4-yl)phenyl]amino}-1H-benzimidazol-5-yl)oxy]-N-methyl-pyridine-2-carboxamide | 465.5 | 702 |

TABLE 15-continued

| Example | Structure | Name | MH+ | Synthesized as in Ex.: |
|---|---|---|---|---|
| 1093 | 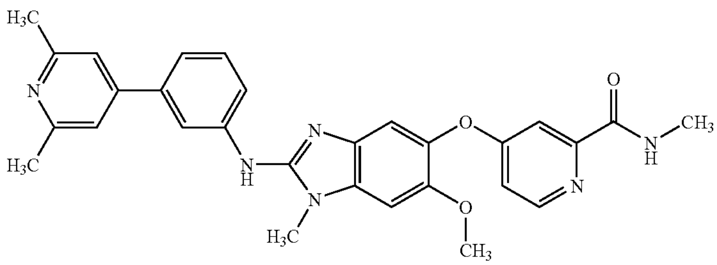 | 4-{[2-{[3-(2,6-dimethylpyridin-4-yl)phenyl]amino}-1-methyl-6-(methyloxy)-1H-benzimidazol-5-yl]oxy}-N-methylpyridine-2-carboxamide | 509.6 | 702 |
| 1094 a | 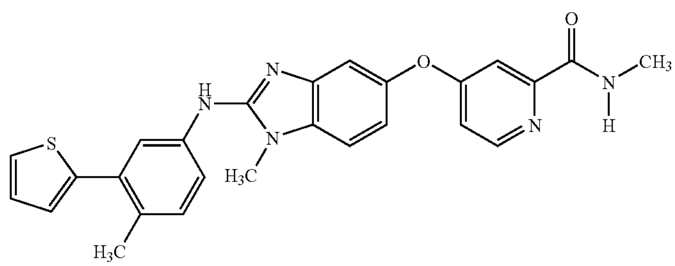 | N-methyl-4-({1-methyl-2-[(4-methyl-3-thien-2-ylphenyl)-amino]-1H-benzimidazol-5-yl}-oxy)pyridine-2-carboxamide | 470.6 | 702 |
| 1094 b | 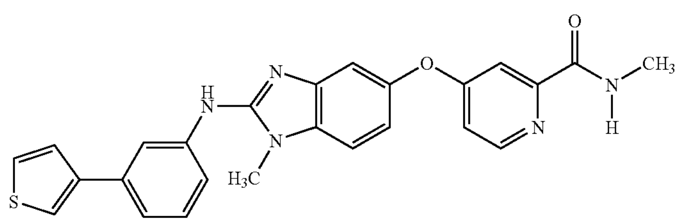 | N-methyl-4-({1-methyl-2-[(3-thien-3-ylphenyl)amino]-1H-benzimidazol-5-yl}oxy)-pyridine-2-carboxamide | 456.5 | 702 |

General Preparation for Phenolic Benzimidazoles

3-Amino-4-methylaminophenol

Diamine 2 prepared as per Example 120b from nitroaniline 1.

Example 1095

2-(3-Bromophenylamino)-1-methyl-1H-benzoimidazol-5-ol

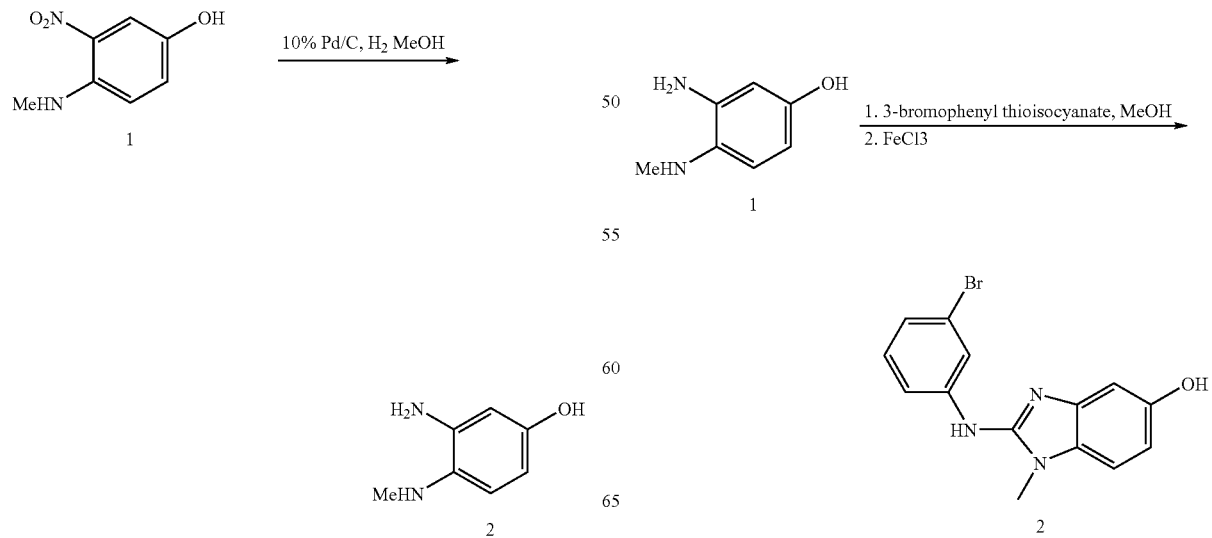

Benzimidazole 2 was prepared as per Example 120b: LCMS m/z 318.1 (MH⁺), $t_R$=2.07 min.

Example 1096

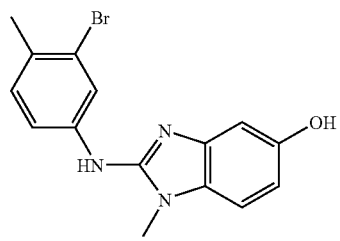

LCMS m/z 332.1 (MH⁺), $t_R$=2.22 min

Example 1097

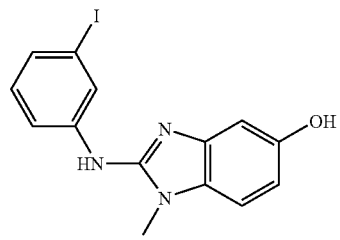

LCMS m/z 366.1 (MH⁺), $t_R$=2.13 min

Example 1098

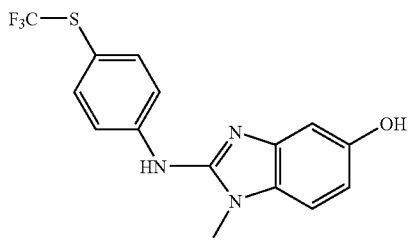

LCMS m/z 340.2 (MH⁺), $t_R$=2.39 min

Example 1099

Preparation of Symmetrical bis-Benzimidazoles

Step 1: 4,4'-dimethylamino-3,3'-dinitro diphenyl ether

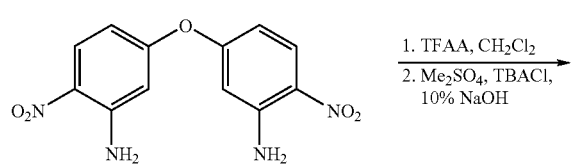

-continued

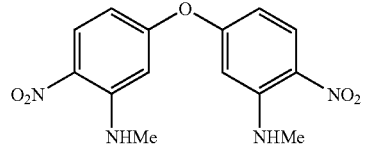

Diphenyl ether 2 was prepared using the method described in Example 120b: ¹H NMR (300 MHz, CDCl₃) δ 7.98 (br s, 2H), 7.75 (d, J=3.0 Hz, 2H), 7.29 (app d, J=3.0 Hz, 1H), 6.87 (d, J=9.5 Hz, 2H), 3.05 (d, J=5.2 Hz, 6H).

Step 2: 4,4'-dimethylamino-3,3'-diamino diphenyl ether

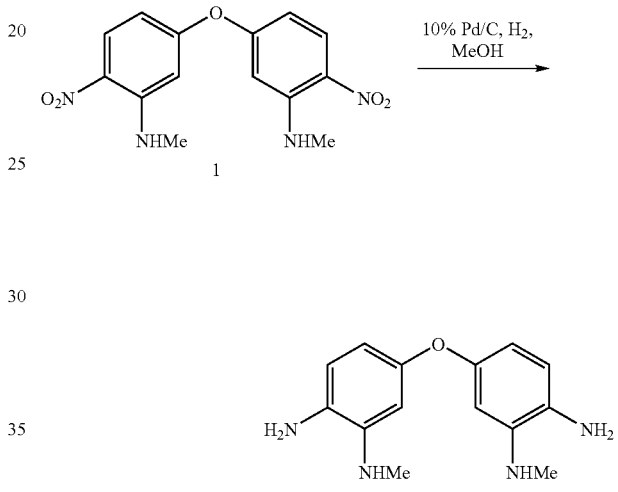

Tetramine 2 was prepared as per Example 120b: ¹H NMR (300 MHz, CDCl₃) δ 6.59 (d, J=8.5 Hz, 2H), 6.47 (dd, J=2.8, 8.5 Hz, 2H), 6.41 (d, J=2.8 Hz, 2H), 3.40 (br s, 4H), 3.06 (br s, 2H), 2.84 (d, J=5.5 Hz, 6H).

Example 1100 bis-5-[2-(3-Bromophenylamino)-1-methyl-1H-benzoimidazole]-ether

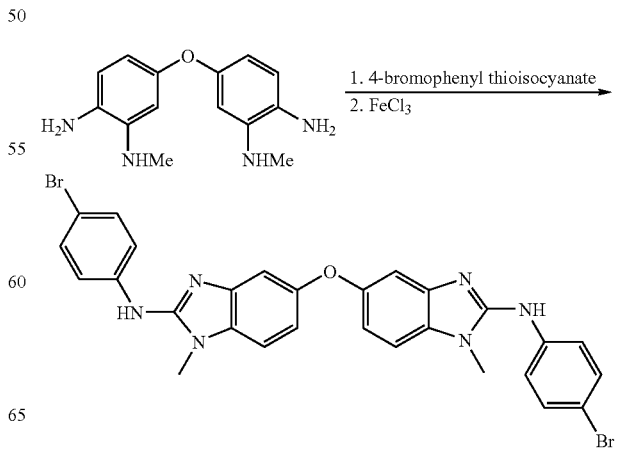

Prepared as per Example 120b: LCMS m/z 617.1 (MH⁺), $t_R$=2.27 min

Example 1101

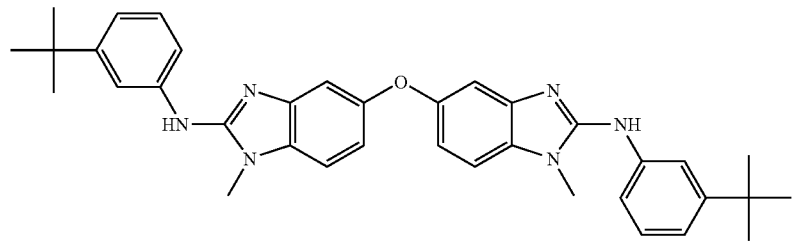

Prepared as per Example 120b: LCMS m/z 573.4 (MH⁺), $t_R$=2.78 min

Example 1102

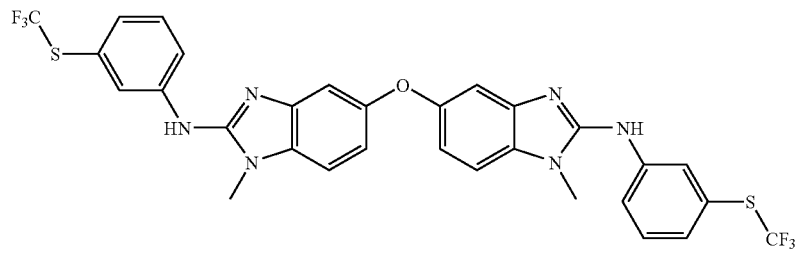

Prepared as per Example 120b: LCMS t/z 661.2 (MH⁺), $t_R$=2.83 min

Example 1103

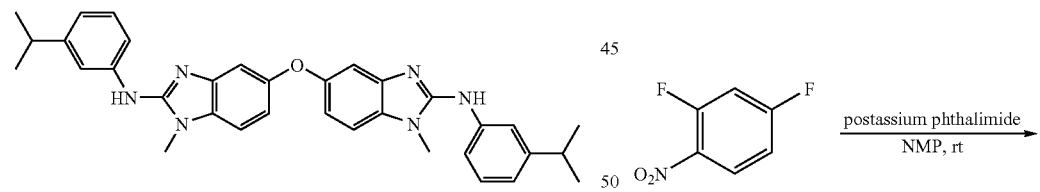

Prepared as per Example 120b: LCMS m/z 545.4 (MH⁺), $t_R$=2.73 min

Example 1104

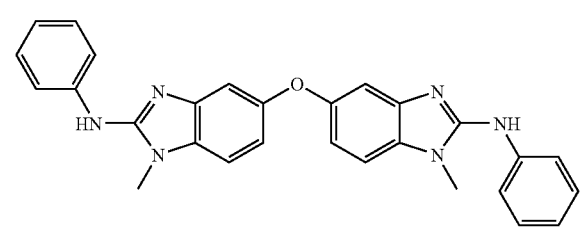

Prepared as per Example 120b: LCMS m/z 461.3 (MH⁺), $t_R$=1.98 min

Example 1105

Preparation of Benzo Derivatives 2-(N-Phthalimido)-4-fluoronitrobenzene

A suspension of 2,4 difluoronitrobenzene (15.9 g, 100 mmol) and potassium phthalimide (16.5 g, 100 mmol) was stirred in dry NMP (50 mL) for 3 d. The reaction solution was poured into MTBE and the resulting precipitate was collected by filtration. The solids were washed with MTBE (3×) and the mother liquor was extracted with MTBE (3×). The combined organic portions were washed with water (3×) and concentrated to furnish a yellow solid which was combined with the

Example 1106

2-(N-Phthalimido)-4-phenoxynitrobenzene

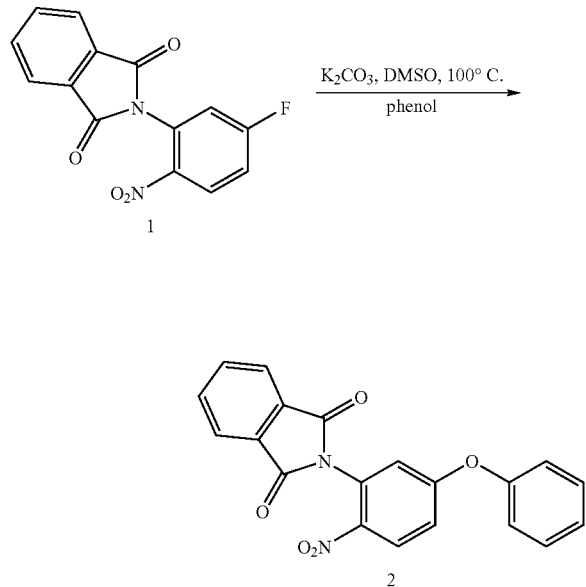

2-(N-Phthalimido)-4-phenoxynitrobenzene 2 was prepared using a similar procedure employed in Example 120b.

Example 1107

2-(N-Phthalimido)-4-phenoxyaniline

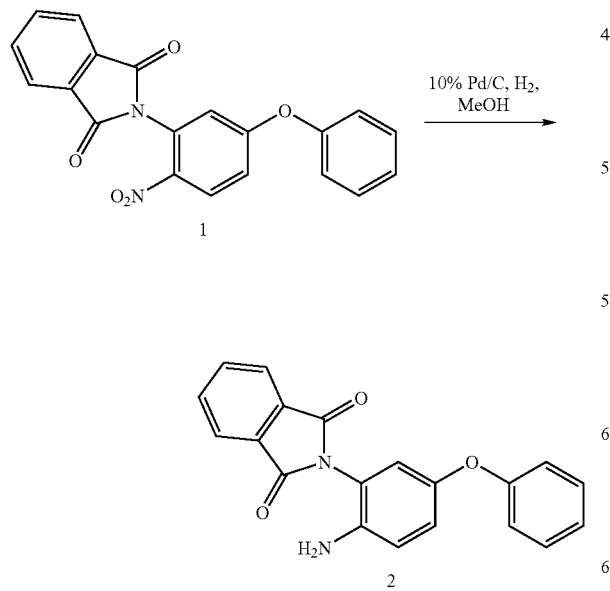

2-(N-Phthalimido)-4-phenoxyaniline 2 was obtained through the reduction of 2-(N-phthalimido)-4-phenoxynitrobenzene 1 as described in Example 120b.

Example 1108

N-[2-(N-Phthalimido)-4-phenoxy-phenyl]-formamide

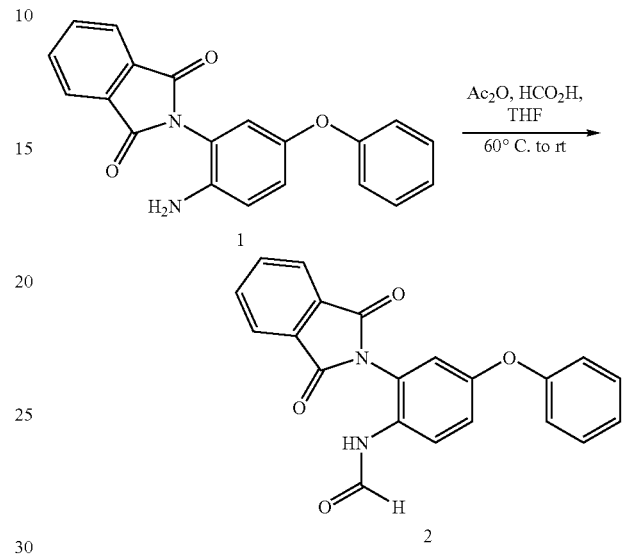

A mixture of formic acid (0.12 mL, 5.3 mmol) and acetic anhydride (0.24 mL, 2.5 mmol) was heated to 60° C. for 2 h. After allowing to cool to rt, a solution of aniline 1 (387 mg, 1.0 mmol) in dry THF (1 mL) was added and the reaction was maintained overnight. The reaction was concentrated and the resulting crude residue was directly used in the next step.

Example 1109

N-Methyl-[2-(N-phthalimido)-4-phenoxy]-aniline

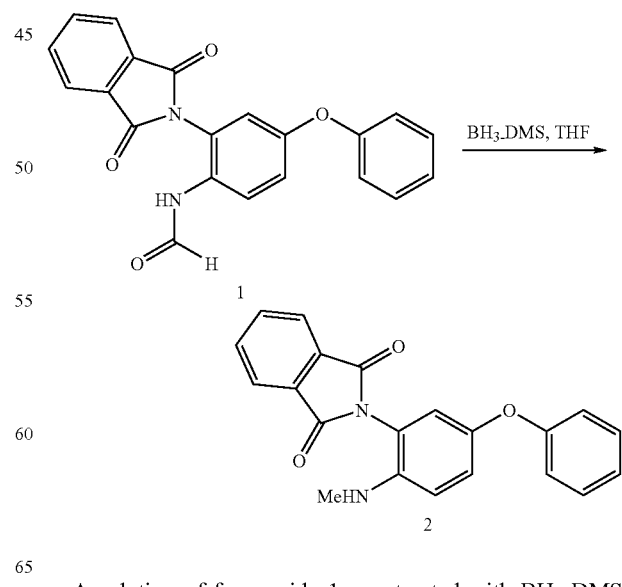

A solution of formamide 1 was treated with $BH_3$-DMS solution (2.0 M in $CH_2Cl_2$, 0.5 mL, 1.0 mL) and the reaction

--- initial crop of precipitate. The combined crude solid was purified by recrystallization from hot toluene, and the crystals were washed with cold MTBE: $^1$H NMR (300 MHz, $d^6$-DMSO) δ 8.31 (dd, J=5.2, 9.1 Hz, 1H), 7.98 (m, 4H), 7.69 (dd, J=2.8, 9.1 Hz, 1H), 7.62 (ddd, J=1.7, 2.8, 7.7 Hz, 1H).

was allowed to warm to rt overnight. The reaction was concentrated and the resulting residue was dissolved in EtOAc. The solution was partitioned with saturated aqueous NaHCO₃ solution and the layers were separated. The aqueous phase was extracted with EtOAc (3×) and the combined organics phases were washed with brine, dried (MgSO₄), adsorbed onto SiO₂ and purified by flash chromatography (4:1 hexanes-EtOAc) to furnish 2 as a colorless residue.

Example 1110

N1-Methyl-4-phenoxybenzene-1,2-diamine hydrazine monohydrate

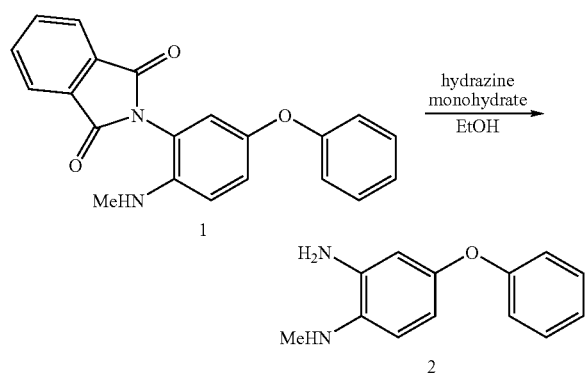

Hydrazine monohydrate (0.13 mL, 2.7 mmol) was added to a solution of phthalimide 1 (134 mg, 0.39 mmol) in ethanol (4 mL). The reaction was maintained overnight at rt and then was filtered through Celite. The filter cake was rinse with EtOAc (3×) and the organic portions were combined and concentrated to give diamine 2 which was carried forward without further purification: LCMS m/z 215.1 (MH⁺), $t_R$=1.77 min.

Example 1111

Synthesis of (4-Bromophenyl)-(1-methyl-5-phenoxy-1H-benzoimidazol-2-yl)amine

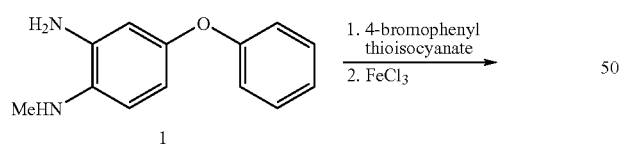

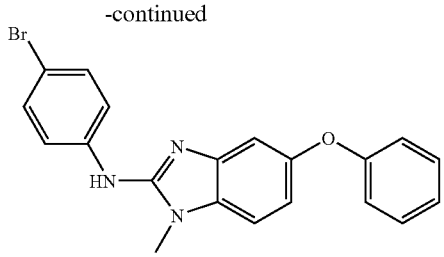

Benzimidazole 2 was prepared as per Example 120b: ¹H NMR (300 MHz, CD₃OD) δ 7.68 (app ddd, J=2.9, 4.9, 8.8 Hz, 2H), 7.53 (app d, J=8.8 Hz, 1H), 7.41 (app ddd, J=2.9, 4.9, 8.8 Hz, 2H), 7.40 (app ddd, J=1.0, 2.0, 8.5 Hz, 2 h), 7.24 (app ddd, J=1.0, 2.0, 8.5 Hz, 1H), 7.07 (app dd, J=2.2, 8.8 Hz, 1H), 7.00 (app d, J=2.2 Hz, 1H), 7.00 (app ddd, J=1.0, 2.0, 8.5 Hz, 2H), 3.82 (s, 3H); LCMS m/z 394.0 (MH⁺), $t_R$=2.36 min.

Example 1112

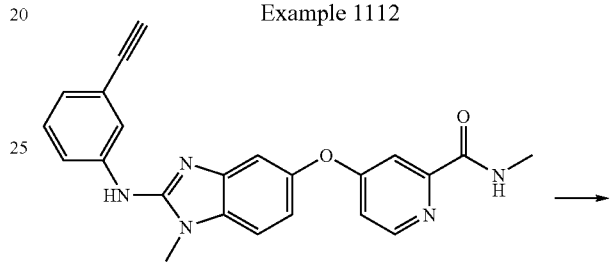

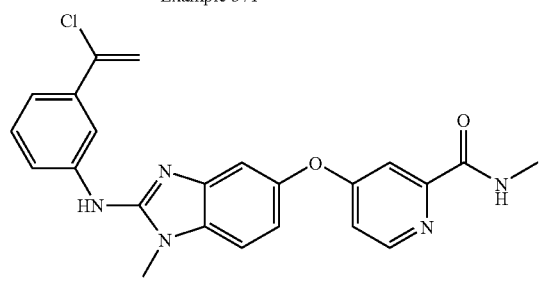

A solution of 1 in MeCN was treated with aqueous 1 N HCl and freeze dried. The resulting residue was purified by reverse-phase HPLC to provide vinyl chloride 2 as a TFA salt: LCMS m/z 434.2 (MH⁺), $t_R$=2.48 min.

Example 1113

4-[2-(3-Furan-3-yl-phenylamino)-1-methyl-1H-benzoimidazol-5-yloxy]-pyridine-2-carboxylic acid methyl amide

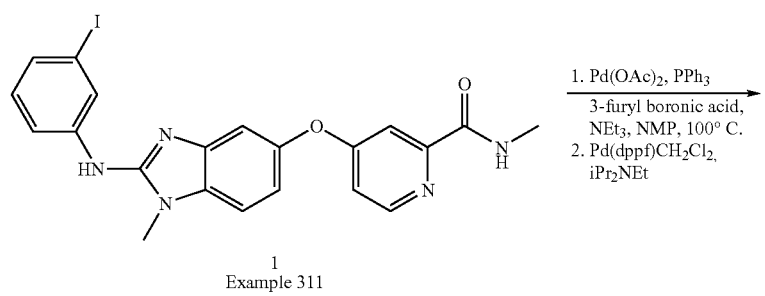

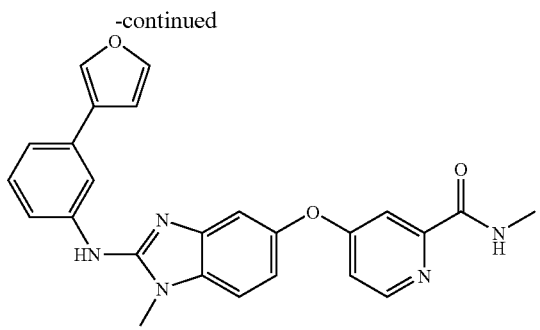

2

A solution of Pd(OAc)₂ (4.5 mg, 0.02 mmol) and triphenylphosphine (13.1 mg 0.05 mmol) in dry NMP (1 mL) was stirred at rt for 20 min. Aryl iodide 1 (100 mg, 0.2 mmol), 3-furyl boronic acid (45 mg, 0.4 mmol), and triethylamine (0.11 mL, 0.8 mmol) were added and the resulting solution was degassed and purged with Ar. The reaction was heated to 100° C. for 2 h; LCMS indicated no conversion. The reaction was allowed to cool to rt under Ar and Pd(dppf)Cl₂CH₂Cl₂ and diisopropylethylamine (0.14 mL) were added. The reaction was heated to 100° C. and maintained overnight. The reaction was allowed to cool to rt and LCMS indicated complete conversion. The reaction was partitioned between saturated aqueous NaHCO₃ solution and EtOAc and the resulting mixture filtered through Celite. The remaining solids were washed with water and EtOAc. The combined rinsings were partitioned and separated. The aqueous phase was extracted with EtOAc (3×) and the combined organic portions were washed with saturated aqueous Na₂CO₃, brine, dried (MgSO₄), and concentrated. The crude residue was purified by reverse-phase HPLC to furnish 2 as a TFA salt: LCMS m/z 440.3 (MH⁺), $t_R$=2.35 min.

Example 1114

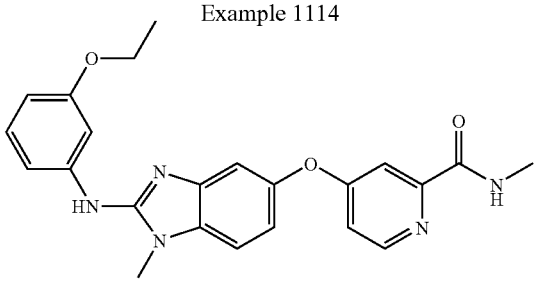

Prepared as per Example 120b.

Example 1115

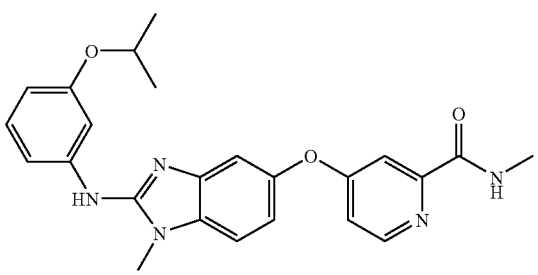

Prepared as per Example 120b.

Example 1116

Raf/Mek Filtration Assay

Buffers

Assay buffer: 50 mM Tris, pH 7.5, 15 mM MgCl₂, 0.1 mM EDTA, 1 mM DTT

Wash buffer: 25 mM Hepes, pH 7.4, 50 mM sodium pyrophosphate, 500 mM NaCl

Stop reagent: 30 mM EDTA

Materials

| | |
|---|---|
| Raf, active: | Upstate Biotech #14-352 |
| Mek, inactive: | Upstate Biotech #14-205 |
| ³³P-ATP: | NEN Perkin Elmer #NEG 602 h |
| 96 well assay plates: | Falcon U-bottom polypropylene plates #35-1190 |
| Filter apparatus: | Millipore #MAVM 096 OR |
| 96 well filtration plates: | Millipore Immobilon 1 #MAIP NOB |
| Scintillation fluid: | Wallac OptiPhase "SuperMix" #1200-439 |

Assay Conditions

Raf approximately 120 μM

Mek approximately 60 nM

³³P-ATP 100 nM

Reaction time 45-60 minutes at room temperature

Assay Protocol

Raf and Mek were combined at 2× final concentrations in assay buffer (50 mM Tris, pH 7.5, 15 mM MgCl₂. 0.1 mM EDTA and 1 mM DTT) and dispensed 15 μl per well in polypropylene assay plates (Falcon U-bottom polypropylene 96 well assay plates #35-1190. Background levels are determined in wells containing Mek and DMSO without Raf.

To the Raf/Mek containing wells was added 3 μl of 10× of a raf kinase inhibitor test compound diluted in 100% DMSO. The raf kinase activity reaction was started by the addition of 12 μl per well of 2.5× ³³P-ATP diluted in assay buffer. After 45-60 minutes, the reactions were stopped with the addition of 70 μl of stop reagent (30 mM EDTA). Filtration plates were pre-wetted for 5 min with 70% ethanol, and then rinsed by filtration with wash buffer. Samples (90 μl) from the reaction wells were then transferred to the filtration plates. The filtration plates were washed 6× with wash buffer using Millipore filtration apparatus. The plates were dried and 100 μl per well of scintillation fluid (Wallac OptiPhase "SuperMix" #1200-439) was added. The CPM is then determined using a Wallac Microbeta 1450 reader.

Example 1117

Assay 2: Biotinylated Raf Screen

In Vitro Raf Screen

The activity of various isoforms of Raf serine/threonine kinases can be measured by providing ATP, MEK substrate, and assaying the transfer of phosphate moiety to the MEK residue. Recombinant isoforms of Raf were obtained by purification from sf9 insect cells infected with a human Raf recombinant baculovirus expression vector. Recombinant kinase inactive MEK was expressed in *E. coli* and labeled with Biotin post purification. For each assay, test compounds were serially diluted in DMSO then mixed with Raf (0.50 nM) and kinase inactive biotin-MEK (50 nM) in reaction buffer plus ATP (1 uM). Reactions were subsequently incubated for 2 hours at room temperature and stopped by the addition of 0.5 M EDTA. Stopped reaction mixture was transferred to a neutradavin-coated plate (Pierce) and incubated for 1 hour. Phosphorylated product was measured with the DELFIA time-resolved fluorescence system (Wallac), using a rabbit anti-p-MEK (Cell Signaling) as the primary antibody and europium labeled anti-rabbit as the secondary antibody. Time resolved fluorescence was read on a Wallac 1232 DELFIA fluorometer. The concentration of each compound for 50% inhibition ($IC_{50}$) was calculated by non-linear regression using XL Fit data analysis software.

Using the procedures of Examples 1116 or 1117, the compounds of Examples 1-1094 were shown to have a raf kinase inhibitory activity at an $IC_{50}$ of less than 5 μM.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A compound of the formula (I):

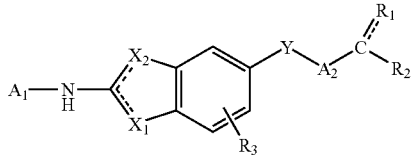

wherein, $X_1$ and $X_2$ are independently selected from =N— and —O—, provided that when $X_1$ is =N—, $X_2$ is —O—; when $X_2$ is =N—, $X_1$ is —O—; and $X_1$ and $X_2$ are not both O;

Y is O or S;

$A_1$ is substituted or unsubstituted alkyl, cycloalkyl, heterocycloalkyl, aryl, polycyclic aryl, polycyclic arylalkyl, heteroaryl, biaryl, heteroarylaryl, heteroarylheteroaryl, cycloalkylalkyl, heterocycloalkylalkyl, arylalkyl, heteroarylalkyl, biarylalkyl, or heteroarylarylalkyl;

$A_2$ is substituted or unsubstituted heteroaryl;

$R_1$ is O and $R_2$ is $NR_5R_6$ or hydroxyl; or $R_1$ is taken together with $R_2$ to form a substituted or unsubstituted heterocloalkyl or heteroaryl group; wherein, the dashed line represents a single or double bond, provided that the dashed line in

represents a double bond when $R_1$ is O;

$R_3$ is hydrogen, halogen, loweralkyl, or loweralkoxy;

$R_5$ and $R_6$ are independently selected from hydrogen, and substituted or unsubstituted alkyl, alkoxyalkyl, aminoalkyl, amidoalkyl, acyl, cycloalkyl, heterocycloalkyl, aryl, heteroaryl, alkyloxyalkylheterocyclo, and heteroarylalkyl; or $R_5$ and $R_6$ are taken together to form substituted or unsubstituted heterocyclo or heteroaryl; and the pharmaceutically acceptable salts, esters and prodrugs thereof.

2. A compound of claim 1 wherein $X_1$ is —O—, and $X_2$ is =N—.

3. A compound of claim 1 wherein Y is O.

4. A compound of claim 1 wherein $A_1$ is selected from the group consisting of substituted or unsubstituted phenyl, pyridyl, pyrimidinyl, phenylalkyl, pyridylalkyl, pyrimidinylalkyl, heterocyclylcarbonylphenyl, heterocyclylphenyl, heterocyclylalkylphenyl, chlorophenyl, fluorophenyl, bromophenyl, iodophenyl, dihalophenyl, nitrophenyl, 4-bromophenyl, 4-chlorophenyl, alkylbenzoate, alkoxyphenyl, dialkoxyphenyl, dialkylphenyl, trialkylphenyl, thiophene, thiophene-2-carboxylate, alkylthiophenyl, trifluoromethylphenyl, acetylphenyl, sulfamoylphenyl, biphenyl, cyclohexylphenyl, phenyloxyphenyl, dialkylaminophenyl, alkylbromophenyl, alkylchlorophenyl, alkylfluorophenyl, trifluoromethylchlorophenyl, trifluoromethylbromophenyl, indenyl, 2,3-dihydroindenyl, tetralinyl, trifluorophenyl, (trifluoromethyl)thiophenyl, alkoxybiphenyl, morpholinyl, N-piperazinyl, N-morpholinylalkyl, piperazinylalkyl, cyclohexylalkyl, indolyl, 2,3-dihydroindolyl, 1-aceyt1-2,3-dihydroindolyl, cycloheptyl, bicyclo[2.2.1]hept-2-yl, hydroxyphenyl, hydroxyalkylphenyl, pyrrolidinyl, pyrrolidin-1-yl, pyrrolidin-1-ylalkyl, 4-amino(imino)methylphenyl, isoxazolyl, indazolyl, adamantyl, bicyclohexyl, quinuclidinyl, imidazolyl, benzimidazolyl, imidazolylphenyl, phenylimidazolyl, pthalamido, napthyl, benzophenone, anilinyl, quinolinyl, quinolinonyl, 9H-fluoren-1-yl, piperidin-1-yl, piperidin-1-ylalkyl, cyclopropyl, cyclopropylalkyl, pyrimidin-5-ylphenyl, quinolidinyiphenyl, furanyl, furanylphenyl, N-methylpiperidin-4-yl, pyrrolidin-4-ylpyridinyl, 4-diazepan-1-yl, hydroxypyrrolidn-1-yl, dialkylaminopyrrolidin-1-yl, 1,4'-bipiperidin-1'-yl, and (1,4'-bipiperidin-1'-ylcarbonyl)phenyl.

5. A compound of claim 1 wherein $A_2$ is substituted or unsubstituted pyridyl.

6. A compound of claim 1 wherein $R_1$ is O and the dashed line in

represents a double bond.

7. A compound of claim 1 wherein $R_2$ is $NR_5R_6$, $R_5$ is hydrogen and $R_6$ is selected from hydrogen, and substituted or unsubstituted alkyl, alkoxyalkyl, aminoalkyl, amidoalkyl, acyl, cycloalkyl, heterocycloalkyl, aryl, heteroaryl, alkyloxyalkylheterocyclo, and heteroarylalkyl.

8. A compound of claim 1 wherein $R_1$ is taken together with $R_2$ to form a substituted or unsubstituted heterocycloalkyl or heteroaryl group.

9. A compound of claim 1 wherein $A_1$ is substituted or unsubstituted cycloalkyl.

10. A compound of claim 1 wherein $R_3$ is hydrogen.

11. The compound of claim 1 wherein $R_1$ is O, $R_2$ is $NR_5R_6$, $R_5$ is H, and $R_6$ is methyl.

12. A compound of the formula (IIIa):

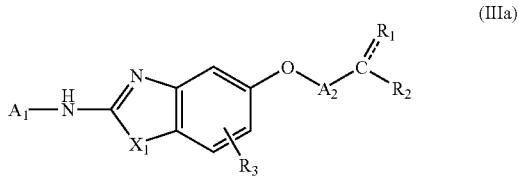

wherein:
$A_1$ is substituted or unsubstituted cycloalkyl, heterocycloalkyl, aryl, polycyclic aryl, polycyclic arylalkyl, heteroaryl, biaryl, heteroarylaryl, heteroarylheteroaryl, cycloalkylalkyl, heterocycloalkylalkyl, arylalkyl, heteroarylalkyl, biarylalkyl, or heteroarylarylalkyl;

$A_2$ is substituted or unsubstituted heteroaryl;

$R_1$ is O and $R_2$ is $NR_5R_6$; or $R_1$ is taken together with $R_2$ to form a substituted or unsubstituted heterocycloalkyl or heteroaryl group; wherein, the dashed line represents a single or double bond, provided that the dashed line in

represents a double bond when $R_1$ is O or a single bond when $R_1$ is taken together with $R_2$ to form a substituted or unsubstituted heterocycloalkyl or heteroaryl group;

$R_3$ is hydrogen, halogen, loweralkyl, or loweralkoxy;

$R_5$ and $R_6$ are independently selected from hydrogen, and substituted or unsubstituted alkyl, alkoxyalkyl, aminoalkyl, amidoalkyl, acyl, cycloalkyl, heterocycloalkyl, aryl, heteroaryl, alkyloxyalkylheterocyclo, and heteroarylalkyl; or $R_5$ and $R_6$ are taken together to form substituted or unsubstituted heterocyclo or heteroaryl; and the pharmaceutically acceptable salts, esters and prodrugs thereof.

13. A compound of claim 12 wherein $A_1$ is selected from the group consisting of substituted or unsubstituted phenyl, pyridyl, pyrimidinyl, phenylalkyl, pyridylalkyl, pyrimidinylalkyl, heterocyclylcarbonylphenyl, heterocyclylphenyl, heterocyclylalkylphenyl, chlorophenyl, fluorophenyl, bromophenyl, iodophenyl, dihalophenyl, nitrophenyl, 4-bromophenyl, 4-chlorophenyl, alkylbenzoate, alkoxyphenyl, dialkoxyphenyl, dialkylphenyl, trialkylphenyl, thiophene, thiophene-2-carboxylate, alkylthiophenyl, trifluoromethylphenyl, acetylphenyl, sulfamoylphenyl, biphenyl, cyclohexylphenyl, phenyloxyphenyl, dialkylaminophenyl, alkylbromophenyl, alkylchlorophenyl, alkylfluorophenyl, trifluoromethylchlorophenyl, trifluoromethylbromophenyl, indenyl, 2,3-dihydroindenyl, tetralinyl, trifluorophenyl, (trifluoromethyl)thiophenyl, alkoxybiphenyl, morpholinyl, N-piperazinyl, N-morpholinylalkyl, piperazinylalkyl, cyclohexylalkyl, indolyl, 2,3-dihydroindolyl, 1-aceyt1-2,3-dihydroindolyl, cycloheptyl, bicyclo[2.2.1]hept-2-yl, hydroxyphenyl, hydroxyalkylphenyl, pyrrolidinyl, pyrrolidin-1-yl, pyrrolidin-1-ylalkyl, 4-amino(imino)methylphenyl, isoxazolyl, indazolyl, adamantyl, bicyclohexyl, quinuclidinyl, imidazolyl, benzimidazolyl, imidazolylphenyl, phenylimidazolyl, pthalamido, napthyl, benzophenone, anilinyl, quinolinyl, quinolinonyl, 9H-fluoren-1-yl, piperidin-1-yl, piperidin-1-ylalkyl, cyclopropyl, cyclopropylalkyl, pyrimidin-5-ylphenyl, quinolidinylphenyl, furanyl, furanylphenyl, N-methylpiperidin-4-yl, pyrrolidin-4-ylpyridinyl, 4-diazepan-1-yl, hydroxypyrrolidn-1-yl, dialkylaminopyrrolidin-1-yl, 1,4'-bipiperidin-1'-yl, and (1,4'-bipiperidin-1'-ylcarbonyl)phenyl.

14. A compound of claim 12 wherein $A_2$ is substituted or unsubstituted pyridyl.

15. A compound of claim 12 wherein $R_1$ is O and the dashed line

represents a double bond.

16. A compound of claim 12 wherein $R_2$ is $NR_5R_6$, $R_5$ is hydrogen and $R_6$ is selected from hydrogen, and substituted or unsubstituted alkyl, alkoxyalkyl, aminoalkyl, amidoalkyl, acyl, cycloalkyl, heterocycloalkyl, aryl, heteroaryl, alkyloxyalkylheterocyclo, and heteroarylalkyl.

17. A compound of claim 12 wherein $R_1$ is taken together with $R_2$ to form a substituted or unsubstituted heterocycloalkyl or heteroaryl group.

18. A compound of claim 12 wherein $R_3$ is hydrogen.

19. A compound of claim 12 wherein $R_3$ is methoxy.

20. A compound of claim 12 wherein $R_1$ is O, $R_2$ is $NR_5R_6$, $R_5$ is H, and $R_6$ is methyl.

21. A compound of the formula (IVa):

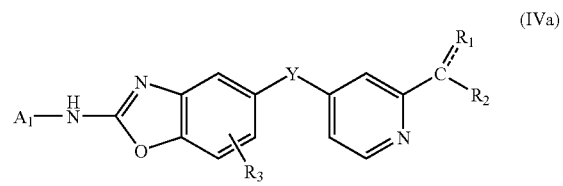

wherein Y is O or S;
$A_1$ is substituted or unsubstituted cycloalkyl, heterocycloalkyl, aryl, polycyclic aryl, polycyclic arylalkyl, heteroaryl, biaryl, heteroarylaryl, heteroarylheteroaryl, cycloalkylalkyl, heterocycloalkylalkyl, arylalkyl, heteroarylalkyl, biarylalkyl, or heteroarylarylalkyl;

$R_1$ is O and $R_2$ is $NR_5R_6$; or $R_1$ is taken together with $R_2$ to form a substituted or unsubstituted heterocycloalkyl or heteroaryl group; wherein, the dashed line represents a single or double bond, provided that the dashed line in

represents a double bond when $R_1$ is O or a single bond when $R_1$ is taken together with $R_2$ to form a substituted or unsubstituted heterocycloalkyl or heteroaryl group;

$R_3$ is hydrogen, halogen, loweralkyl, or loweralkoxy;

$R_5$ and $R_6$ are independently selected from hydrogen, and substituted or unsubstituted alkyl, alkoxyalkyl, aminoalkyl, amidoalkyl, acyl, cycloalkyl, heterocycloalkyl, aryl, heteroaryl, alkyloxyalkylheterocyclo, and heteroarylalkyl; or $R_5$ and $R_6$ are taken together to form substituted or unsubstituted heterocyclo or heteroaryl; and the pharmaceutically acceptable salts, esters and prodrugs thereof.

22. A compound of claim 21 wherein Y is O.

23. A compound of claim 21 wherein $A_1$ is selected from the group consisting of substituted or unsubstituted phenyl, pyridyl, pyrimidinyl, phenylalkyl, pyridylalkyl, pyrimidinylalkyl, heterocyclylcarbonylphenyl, heterocyclylphenyl, heterocyclylalkylphenyl, chlorophenyl, fluorophenyl, bromophenyl, iodophenyl, dihalophenyl, nitrophenyl, 4-bromophenyl, 4-chlorophenyl, alkylbenzoate, alkoxyphenyl, dialkoxyphenyl, dialkylphenyl, trialkylphenyl, thiophene, thiophene-2-carboxylate, alkylthiophenyl, trifluoromethylphenyl, acetylphenyl, sulfamoylphenyl, biphenyl, cyclohexylphenyl, phenyloxyphenyl, dialkylaminophenyl, alkylbromophenyl, alkylchlorophenyl, alkylfluorophenyl, trifluoromethylchlorophenyl, trifluoromethylbromophenyl, indenyl, 2,3-dihydroindenyl, tetralinyl, trifluorophenyl, (trifluoromethyl)thiophenyl, alkoxybiphenyl, morpholinyl, N-piperazinyl, N-morpholinylalkyl, piperazinylalkyl, cyclohexylalkyl, indolyl, 2,3-dihydroindolyl, 1-aceytl-2,3-dihydroindolyl, cycloheptyl, bicyclo[2.2.1]hept-2-yl, hydroxyphenyl, hydroxyalkylphenyl, pyrrolidinyl, pyrrolidin-1-yl, pyrrolidin-1-ylalkyl, 4-amino(imino)methylphenyl, isoxazolyl, indazolyl, adamantyl, bicyclohexyl, quinuclidinyl, imidazolyl, benzimidazolyl, imidazolylphenyl, phenylimidazolyl, pthalamido, napthyl, benzophenone, anilinyl, quinolinyl, quinolinonyl, 9H-fluoren-1-yl, piperidin-1-yl, piperidin-1-ylalkyl, cyclopropyl, cyclopropylalkyl, pyrimidin-5-ylphenyl, quinolidinyiphenyl, furanyl, furanylphenyl, N-methylpiperidin-4-yl, pyrrolidin-4-ylpyridinyl, 4-diazepan-1-yl, hydroxypyrrolidn-1-yl, dialkylaminopyrrolidin-1-yl, 1,4'-bipiperidin-1'-yl, and (1,4'-bipiperidin-1'-ylcarbonyl)phenyl.

24. A compound of claim 21 wherein $R_1$ is O and the dashed line in

represents a double bond.

25. A compound of claim 21 wherein $R_2$ is $NR_5R_6$, $R_5$ is hydrogen and $R_6$ is selected from hydrogen, and substituted or unsubstituted alkyl, alkoxyalkyl, aminoalkyl, amidoalkyl, acyl, cycloalkyl, heterocycloalkyl, aryl, heteroaryl, alkyloxyalkylheterocyclo, and heteroarylalkyl.

26. A compound of claim 21 wherein $R_1$ is taken together with $R_2$ to form a substituted or unsubstituted heterocycloalkyl or heteroaryl group.

27. A compound of claim 21 wherein $R_3$ is hydrogen.

28. A compound of claim 21 wherein $R_3$ is methoxy.

29. A compound of claim 21 wherein $R_1$ is O, $R_2$ is $NR_5R_6$, $R_5$ is H, and $R_6$ is methyl.

30. A compound of the formula (Va):

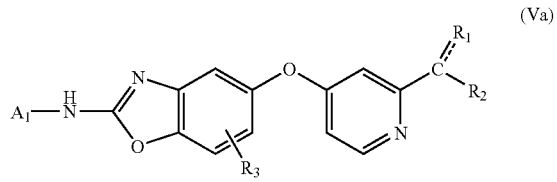

wherein $A_1$ is substituted or unsubstituted cycloalkyl, heterocycloalkyl, aryl, polycyclic aryl, polycyclic arylalkyl, heteroaryl, biaryl, heteroarylaryl, heteroarylheteroaryl, cycloalkylalkyl, heterocycloalkylalkyl, arylalkyl, heteroarylalkyl, biarylalkyl, or heteroarylarylalkyl;

$R_1$ is O and $R_2$ is $NR_5R_6$; or $R_1$ is taken together with $R_2$ to form a substituted or unsubstituted heterocycloalkyl or heteroaryl group; wherein, the dashed line represents a single or double bond, provided that the dashed line in

represents a double bond when $R_1$ is O or a single bond when $R_1$ is taken together with $R_2$ to form a substituted or unsubstituted heterocycloalkyl or heteroaryl group;

$R_3$ is hydrogen, halogen, loweralkyl, or loweralkoxy;

$R_5$ and $R_6$ are independently selected from hydrogen, and substituted or unsubstituted alkyl, alkoxyalkyl, aminoalkyl, amidoalkyl, acyl, cycloalkyl, heterocycloalkyl, aryl, heteroaryl, alkyloxyalkylheterocyclo, and heteroarylalkyl; or $R_5$ and $R_6$ are taken together to form substituted or unsubstituted heterocyclo or heteroaryl; and the pharmaceutically acceptable salts, esters and prodrugs thereof.

31. A compound of claim 30 wherein $A_1$ is selected from the group consisting of substituted or unsubstituted phenyl, pyridyl, pyrimidinyl, phenylalkyl, pyridylalkyl, pyrimidinylalkyl, heterocyclylcarbonylphenyl, heterocyclylphenyl, heterocyclylalkylphenyl, chlorophenyl, fluorophenyl, bromophenyl, iodophenyl, dihalophenyl, nitrophenyl, 4-bromophenyl, 4-chlorophenyl, alkylbenzoate, alkoxyphenyl, dialkoxyphenyl, dialkylphenyl, trialkylphenyl, thiophene, thiophene-2-carboxylate, alkylthiophenyl, trifluoromethylphenyl, acetylphenyl, sulfamoylphenyl, biphenyl, cyclohexylphenyl, phenyloxyphenyl, dialkylaminophenyl, alkylbromophenyl, alkylchlorophenyl, alkylfluorophenyl, trifluoromethylchlorophenyl, trifluoromethylbromophenyl, indenyl, 2,3-dihydroindenyl, tetralinyl, trifluorophenyl, (trifluoromethyl)thiophenyl, alkoxybiphenyl, morpholinyl, N-piperazinyl, N-morpholinylalkyl, piperazinylalkyl, cyclohexylalkyl, indolyl, 2,3-dihydroindolyl, 1-aceytl-2,3-dihydroindolyl, cycloheptyl, bicyclo[2.2.1]hept-2-yl, hydroxyphenyl, hydroxyalkylphenyl, pyrrolidinyl, pyrrolidin-1-yl, pyrrolidin-1-ylalkyl, 4-amino(imino)methylphenyl, isoxazolyl, indazolyl, adamantyl, bicyclohexyl, quinuclidinyl, imidazolyl, benzimidazolyl, imidazolylphenyl, phenylimidazolyl, pthalamido, napthyl, benzophenone, anilinyl, quinolinyl, quinolinonyl, 9H-fluoren-1-yl, piperidin-1-yl, piperidin-1-ylalkyl, cyclopropyl, cyclopropylalkyl, pyrimidin-5-ylphenyl, quinolidinyiphenyl, furanyl, furanylphenyl, N-methylpiperidin-4-yl, pyrrolidin-4-ylpyridinyl, 4-diazepan-1-yl, hydroxypyrrolidn-1-yl, dialkylaminopyrrolidin-1-yl, 1,4'-bipiperidin 1'-yl, and (1,4'-bipiperidin-1'-ylcarbonyl)phenyl.

32. A compound of claim 30 wherein $R_1$ is O and the dashed line in

represents a double bond.

33. A compound of claim 30 wherein $R_2$ is $NR_5R_6$, $R_5$ is hydrogen and $R_6$ is selected from hydrogen, and substituted or unsubstituted alkyl, alkoxyalkyl, aminoalkyl, amidoalkyl, acyl, cycloalkyl, heterocycloalkyl, aryl, heteroaryl, alkyloxyalkylheterocyclo, and heteroarylalkyl.

34. A compound of claim 30 wherein $R_1$ is taken together with $R_2$ to form a substituted or unsubstituted heterocycloalkyl or heteroaryl group.

35. A compound of claim 30 wherein $R_3$ is hydrogen.

36. A compound of claim 30 wherein $R_3$ is methoxy.

37. A compound of claim 30 wherein $R_1$ is O, $R_2$ is $NR_5R_6$, $R_5$ is H, and $R_6$ is methyl.

38. A composition comprising an amount of a compound of claim 1 effective to inhibit Raf activity in a human or animal subject when administered thereto, together with a pharmaceutically acceptable carrier.

39. A composition of claim 38 which further comprises at least one additional agent for the treatment of cancer.

40. A composition of claim 39 in which the at least one additional agent for the treatment of cancer is selected from irinotecan, topotecan, gemcitabine, 5-fluorouracil, leucovorin carboplatin, cisplatin, taxanes, tezacitabine, cyclophosphamide, vinca alkaloids, imatinib, anthracyclines, rituximab and trastuzumab.

* * * * *